(12) United States Patent
Kim et al.

(10) Patent No.: US 11,173,214 B2
(45) Date of Patent: *Nov. 16, 2021

(54) ANTIBODY-DRUG CONJUGATES COMPRISING BRANCHED LINKERS AND METHODS RELATED THERETO

(71) Applicant: LegoChem Biosciences, Inc., Daejeon (KR)

(72) Inventors: Yong Zu Kim, Daejeon (KR); Yeong Soo Oh, Daejeon (KR); Jeiwook Chae, Daejeon (KR); Ho Young Song, Daejeon (KR); Chul-Woong Chung, Daejeon (KR); Yun Hee Park, Daejeon (KR); Hyo Jung Choi, Daejeon (KR); Kyung Eun Park, Daejeon (KR); Hyoungrae Kim, Daejeon (KR); Jinyeong Kim, Daejeon (KR); Ji Young Min, Daejeon (KR); Sung Min Kim, Daejeon (KR); Byung Soo Lee, Daejeon (KR); Dong Hyun Woo, Daejeon (KR); Ji Eun Jung, Daejeon (KR); Su In Lee, Daejeon (KR)

(73) Assignee: LegoChem Biosciences, Inc., Daejeon (KR)

(\*) Notice: Subject to any disclaimer, the term of this patent is extended or adjusted under 35 U.S.C. 154(b) by 284 days.
This patent is subject to a terminal disclaimer.

(21) Appl. No.: 15/779,444

(22) PCT Filed: Nov. 23, 2016

(86) PCT No.: PCT/IB2016/001811
§ 371 (c)(1),
(2) Date: May 25, 2018

(87) PCT Pub. No.: WO2017/089895
PCT Pub. Date: Jun. 1, 2017

(65) Prior Publication Data
US 2019/0151465 A1    May 23, 2019

Related U.S. Application Data

(60) Provisional application No. 62/260,006, filed on Nov. 25, 2015.

(51) Int. Cl.
*A61K 47/68* (2017.01)
*A61K 47/60* (2017.01)
*A61P 35/00* (2006.01)

(52) U.S. Cl.
CPC .......... *A61K 47/6889* (2017.08); *A61K 47/60* (2017.08); *A61K 47/6803* (2017.08);
(Continued)

(58) Field of Classification Search
None
See application file for complete search history.

(56) References Cited

U.S. PATENT DOCUMENTS

| 5,112,739 A | 5/1992 | Meneghini et al. |
| 5,935,995 A | 8/1999 | Bosslet et al. |

(Continued)

FOREIGN PATENT DOCUMENTS

| CA | 2921707 A1 | 4/2015 |
| CN | 1185786 A | 6/1998 |

(Continued)

OTHER PUBLICATIONS

Lee et al., Angew. Chem. Int. Ed., 2015, 54, 1-6 (Year: 2015).*
(Continued)

*Primary Examiner* — Karl J Puttlitz
(74) *Attorney, Agent, or Firm* — Foley Hoag LLP; David P. Halstead; Lucas P. Watkins

(57) ABSTRACT

The present invention relates to antibody-drug conjugates (ADCs) wherein a plurality of active agents are conjugated
(Continued)

to an antibody through at least one branched linker. The branched linker may comprise a branching unit, and two active agents are coupled to the branching unit through a secondary linker and the branching unit is coupled to the antibody by a primary linker. The active agents may be the same or different. In certain such embodiments, two or more such branched linkers are conjugated to the antibody, e.g., 2-4 branched linkers, which may each be coupled to a different C-terminal cysteine of a heavy or light chain of the antibody. The branched linker may comprise one active agent coupled to the branching unit by a first branch and a second branch that comprises a polyethylene glycol moiety coupled to the branching unit. In certain such embodiments, two or more such branched linkers are conjugated to the antibody, e.g., 2-4 branched linkers, which may each be coupled to a different C-terminal cysteine of a heavy or light chain of the antibody.

22 Claims, 27 Drawing Sheets

(52) U.S. Cl.
CPC ...... *A61K 47/6817* (2017.08); *A61K 47/6849* (2017.08); *A61K 47/6855* (2017.08); *A61K 47/6883* (2017.08); *A61P 35/00* (2018.01)

(56) References Cited

U.S. PATENT DOCUMENTS

| | | | |
|---|---|---|---|
| 6,218,519 | B1 | 4/2001 | Kenten et al. |
| 6,759,509 | B1 * | 7/2004 | King .................. C07K 5/0202 424/178.1 |
| 8,039,273 | B2 | 10/2011 | Jeffrey |
| 8,568,728 | B2 | 10/2013 | Jeffrey |
| 9,919,057 | B2 | 3/2018 | Kim et al. |
| 9,993,568 | B2 | 6/2018 | Kim et al. |
| 10,118,965 | B2 | 10/2018 | Kim et al. |
| 10,183,997 | B2 | 1/2019 | Kim et al. |
| 10,383,949 | B2 | 8/2019 | Kim et al. |
| 10,980,890 | B2 | 4/2021 | Kim et al. |
| 2005/0238649 | A1 | 10/2005 | Doronina et al. |
| 2006/0088522 | A1 | 4/2006 | Boghaert et al. |
| 2012/0030858 | A1 | 2/2012 | Duffin |
| 2012/0058051 | A1 | 3/2012 | Rader et al. |
| 2012/0107332 | A1 | 5/2012 | Jeffrey |
| 2012/0308584 | A1 | 12/2012 | Kim et al. |
| 2013/0251723 | A1 | 9/2013 | Rohlff et al. |
| 2014/0031535 | A1 | 1/2014 | Jeffrey |
| 2014/0032535 | A1 | 1/2014 | Singla |
| 2014/0088292 | A1 | 3/2014 | Kim et al. |
| 2014/0161829 | A1 | 6/2014 | Kim et al. |
| 2014/0187756 | A1 | 7/2014 | Kim et al. |
| 2014/0286969 | A1 | 9/2014 | Tschoepe et al. |
| 2015/0105541 | A1 | 4/2015 | Kim et al. |
| 2016/0184451 | A1 | 6/2016 | Kim et al. |
| 2016/0256561 | A1 | 9/2016 | Howard et al. |
| 2016/0257709 | A1 | 9/2016 | Kline et al. |
| 2017/0088614 | A1 | 3/2017 | Kim et al. |
| 2017/0088621 | A1 | 3/2017 | Kim et al. |
| 2017/0095576 | A1 | 4/2017 | Kim et al. |
| 2018/0265593 | A1 | 9/2018 | Chen et al. |
| 2018/0369406 | A1 | 12/2018 | Lannutti et al. |
| 2019/0151465 | A1 | 5/2019 | Kim et al. |
| 2019/0381185 | A1 | 12/2019 | Kim et al. |
| 2020/0069816 | A1 | 3/2020 | Kim et al. |
| 2020/0095317 | A1 | 3/2020 | Song et al. |
| 2020/0297865 | A1 | 9/2020 | Kim et al. |
| 2021/0069342 | A1 | 3/2021 | Park et al. |

FOREIGN PATENT DOCUMENTS

| | | | |
|---|---|---|---|
| CN | 101287500 A | | 10/2008 |
| CN | 103648530 A | | 3/2014 |
| CN | 105358579 A | | 2/2016 |
| EP | 2913064 A1 | | 9/2015 |
| EP | 3156424 A1 | | 4/2017 |
| KR | 10-2009-0088893 A | | 8/2009 |
| KR | 10-2012-0113175 A | | 10/2012 |
| KR | 2014/0035393 A | | 3/2014 |
| KR | 10-2015-0137015 | | 6/2016 |
| KR | 10-2014-0192328 | | 7/2016 |
| KR | 10-2018-0110645 A | | 10/2018 |
| KR | 10-2019-0018400 A | | 2/2019 |
| KR | 10-2019-0028350 A | | 3/2019 |
| RU | 2191021 C2 | | 10/2002 |
| TW | 201524520 A | | 7/2015 |
| WO | WO-98/19705 A1 | | 5/1998 |
| WO | WO-2004050089 A1 | | 6/2004 |
| WO | WO-2007/011968 A2 | | 1/2007 |
| WO | WO-2008/034120 A2 | | 3/2008 |
| WO | WO-2009/016647 A1 | | 2/2009 |
| WO | WO-2009/054863 A2 | | 4/2009 |
| WO | WO-2011066418 A1 | | 6/2011 |
| WO | WO-2011/145068 A1 | | 11/2011 |
| WO | WO-2012/153193 A2 | | 11/2012 |
| WO | WO-2013055990 A1 | | 4/2013 |
| WO | WO-2013103707 A1 | | 7/2013 |
| WO | WO-2014/096368 A1 | | 6/2014 |
| WO | 2014194030 | * | 12/2014 |
| WO | WO-2014/194030 A2 | | 12/2014 |
| WO | WO-2015/057699 A2 | | 4/2015 |
| WO | 2015095755 | * | 6/2015 |
| WO | WO-2015/095755 A1 | | 6/2015 |
| WO | WO-2015/182984 A1 | | 12/2015 |
| WO | WO-2016/033570 A1 | | 3/2016 |
| WO | WO-2016/040684 A1 | | 3/2016 |
| WO | WO-2016/094517 A1 | | 6/2016 |
| WO | WO-2016108587 A1 | | 7/2016 |
| WO | WO-2017/051249 A1 | | 3/2017 |
| WO | WO-2017/051254 A1 | | 3/2017 |
| WO | WO-2017/066136 A2 | | 4/2017 |
| WO | WO-2017089890 A1 | | 6/2017 |
| WO | WO-2017089894 A1 | | 6/2017 |
| WO | WO-2017089895 A1 | | 6/2017 |
| WO | WO-2018/069490 A1 | | 4/2018 |
| WO | WO-2018/083535 A1 | | 5/2018 |
| WO | WO-2019/215510 A2 | | 11/2019 |
| WO | WO-2019/225992 A1 | | 11/2019 |
| WO | WO-2020/180121 A1 | | 9/2020 |
| WO | WO-2019/215510 A8 | | 11/2020 |
| WO | WO-2021/044208 A1 | | 3/2021 |

OTHER PUBLICATIONS

Jeffrey et al., Bioconjugate Chem. 2006, 17, 831-840 (Year: 2006).*
Extended European Search Report for EP Application No. 16868096.5 dated Jun. 21, 2019.
Extended European Search Report for EP Application No. EP 16868095 dated Jul. 29, 2019.
Extended European Search Report for EP application No. PCT/IB2016001772 dated May 17, 2019.
International Search Report and Written Opinion for International Application No. PCT/IB2019/000577 dated Nov. 28, 2019.
Jeffrey et al., "Minor groove binder antibody conjugates employing a water soluable ß-glucuronide linker," Bioorganic & Medicinal Chemistry Letters, 17:2278-2280 (2007).
Lee et al., "Enzymatic prenylation and oxime ligation for the synthesis of stable and homogeneous protein-drug conjugates for targeted therapy," Angewandte Chemie, 54(41):12020-12024 (2015).
Lu et al., "Linkers Having a Crucial Role in Antibody—Drug Conjugates," Int J Molec Sci 17(561):1-22 (2016).
Behrens et al., "Methods for Site-specific Drug Conjugation to Antibodies," MAbs, 6(1): 46-53 (2014).
Carey, FA. Organic Chemistry 6th Ed. McGraw Hill. 2006, chapter 1, p. 9.

(56) References Cited

OTHER PUBLICATIONS

Chu et al., "Antibody-drug Conjugates for the Treatment of B-cell Non-Hodgkin's Lymphoma and Leukemia," Future Oncol, 9(3): 355-368 (2013).
Connolly et al., "Discovery of Orally Active 4-amino-6-arylaminopyrimidine-5-carbaldehyde Oximes with Dual EGFR and HER2 Inhibitory Activity," AACR 104th Annual Meeting, Abstract 2456 (2013).
Desbene, S. et al. Doxorubicin prodrugs with reduced cytotoxicity suited for tumour-specific activation. Anti-Cancer Drug Design. 1998,vol. 13,p. 955.
Dunn, PJ. et al. Green Chemistry Principle #8. ACS What is Green Chemistry. Accessed from ACS Website on Jan. 8, 2016.
Extended European Search Report issued by the European Patent Office in corresponding Application No. EP 15799360.1, dated Dec. 21, 2017.
Grinda, M. et al., A Self-Immolative Dendritic Glucuronide Prodrug of Doxorubicin, Medicinal Chemistry Communications, (2012) vol. 3, No. 1, pp. 68-70.
International Search Report and Written Opinion for International Application No. PCT/IB2016/001772 dated Apr. 6, 2017.
International Search Report and Written Opinion for International Application No. PCT/IB2016/001810 dated Apr. 19, 2017.
International Search Report and Written Opinion for International Application No. PCT/IB2016/001811 dated Apr. 19, 2017.
International Search Report and Written Opinion from corresponding International Application Publication No. WO2015182984.
Jeffrey et al., Development and properties of β-glucuronide linkers for monoclonal antibody-drug conjugates, Bioconjugate Chem, 17:835 (2006).
Kim et al., "Synthesis of Bispecific Antibodies Using Genetically Encoded Unnatural Amino Acids," J Am Chem Soc, 134: 9918-9921 (2012).
Lartigue, "Antibody-Drug Conjugates: Guided Missiles Deployed Against Cancerous Cells," Oncology Live, p. 1 (2012).
Lee et al., "Enzymatic Prenylation and Oxime Ligation for the Synthesis of Stable and Homogeneous Protein-Drug Conjugates for Targeted Therapy," Angew Chem Int Edit, 54: 1-6 (2015).
Leong, KW. Biomaterials. El Sevier. Accessed on Sep. 26, 2016.
McCombs et al., "Antibody Drug Conjugates: Design and Selection of Linker, Payload and Conjugation Chemistry," AAPS J, 17(2): 339-351 (2015).
Merriam-Webster. Biomaterial Definition. Accessed on Sep. 26, 2016.
Tranoy-Opalinski et al., "ß-Glucuronidase-responsive prodrugs for selective cancer chemotherapy: an update," Eur J Med Chem, 74:302-313 (2014).
Wermuth, "Similarity in drugs: reflections on analogue design," Drug Discov Today, 11(Issues 7-8): 248-254 (2006).
Yewale et al., "Epidermal growth factor receptor targeting in cancer: A review of trends and strategies," Biomaterials, 34: 8690-8707 (2013).
U.S. Appl. No. 16/545,869, Pending.
Extended European Search Report for Application No. EP 18774896 dated Dec. 15, 2020.
Kim et al., "Protein conjugation with genetically encoded unnatural amino acids," Current Opinion in Chemical Biology, 17: 412-419 (2013).
U.S. Appl. No. 14/865,778, Issued.
U.S. Appl. No. 14/898,932, Issued.
U.S. Appl. No. 16/005,245, Issued.
U.S. Appl. No. 16/545,869, Issued.
U.S. Appl. No. 15/276,231, Issued.
U.S. Appl. No. 15/276,209, Issued.
U.S. Appl. No. 15/779,446, Pending.
U.S. Appl. No. 15/779,450, Pending.
U.S. Appl. No. 16/408,002, Pending.
U.S. Appl. No. 16/328,256, Pending.
U.S. Appl. No. 16/940,326, Pending.
U.S. Appl. No. 16/964,965, Pending.
Christie et al., "Stabilization of cysteine-linked antibody drug conjugates with N-aryl maleimides," Journal of Controlled Release, 220:660-670 (2015).
Gaertner et al., "Chemo-enzymic Backbone Engineering of Proteins ," J. Biol. Chem., 269(10):7224-7230 (1994).
Guan., "Metabolic Activation and Drug Targeting," Drug Delivery: Principles and Applications: 201-244 (2005).
International Search Report and Written Opinion for International Application Np. PCT/IB2020/000649 dated Nov. 27, 2020.
Rose et al., "Preparation of well-defined protein conjugates using enzyme-assisted reverse proteolysis," Bioconjugate Chem, 2(3):154-159 (1991).
Sagnou et al., "Design and synthesis of novel pyrrolobenzodiazepine (PBD) prodrugs for ADEPT and GDEPT," Bioorganic and Medicinal Chemistry Letters, 10(18): 2083-2086 (2000).
Schwarz et al., "[15] Enzymatic C-terminal biotinylation of proteins," Methods Enzymol 184:160-162 (1990).
Translation of International Search Report for International Application No. PCT/KR2020/003100 dated Jun. 24, 2020 (4 pages).
Varvounis, "An Update on the Synthesis of Pyrrolo[1,4]benzodiazepines," Molecules, 21(154):1-55 (2016).
Zimmerman et al., "Production of Site-Specific Antibody-Drug Conjugates Using Optimized Non-Natural Amino Acids in a Cell-Free Expression System," Bioconjugate Chem., 25(2):351-361 (2014).

\* cited by examiner part is carbamate, part is ester,

ANTIBODY-DRUG CONJUGATES COMPRISING BRANCHED LINKERS AND METHODS RELATED THERETO

CROSS-REFERENCE TO RELATED APPLICATIONS

This application is the U.S. 371(c) national stage application of PCT/IB2016/001811, filed Nov. 23, 2016, which claims the benefit of priority to U.S. Provisional Application Ser. No. 62/260,006, filed Nov. 25, 2015, each of which is hereby incorporated by reference in its entirety.

BACKGROUND

Antibody-drug conjugate (ADC) technology is a target-oriented technology, which allows for selective killing or inhibition of growth or division of cancer cells. Typically, ADCs function by targeting cancer cells using the antibody and then releasing a toxic material (i.e., the drug) in a cell, thereby triggering cell death. Since ADC technology allows a drug to be accurately delivered to a target cancer cell and released under specific conditions, while minimizing collateral damage to healthy cells, ADC technology increases the efficacy of a therapeutic antibody and decreases the risk of an adverse reaction.

A basic structure of an antibody-drug conjugate is an "antibody-linker-low molecular drug (toxin)". The linker ideally allows the drug to exhibit an effect on a target cancer cell, e.g., after being separated from the antibody (for example, by enzyme-mediated hydrolysis), after the drug reaches a target cell. The linker also plays a functional role, by connecting the antibody and the drug. The efficacy and toxicity of the antibody-drug conjugate thereby depends, in part, on the stability of the linker, and thus, the linker plays an important role in drug safety.

The linkers of antibody-drug conjugates may be roughly classified as non-cleavable or cleavable. Many non-cleavable linkers are attached to antibodies using a thioether, comprising a cysteine of the antibody. The pendant drug generally cannot dissociate from the antibody in vivo and reduced efficacy may be further encountered when ADC internalization is poor. In the case of the widely-used thiol-maleimide method, the antibody-drug conjugate is unstable, which may result in dissociation of the drug from the conjugate before or after it reaches a target cell.

Instead of chemically labile linkers that have limited stability in physiological extracellular conditions, such as hydrazone and disulfide-based linkers, there is a need for linkers that are stable in physiological extracellular conditions. Furthermore, there is a need for linkers that have high plasma stability to improve therapeutic applicability, since the drug should be released only within the cell, which is targeted by the protein, to which the drug is linked, and not outside of the cell.

Cleavable linkers may be hydrolyzed, for example, by a lysosomal enzyme. A cleavable linker may comprise a disulfide bond, e.g., including a cysteine of the antibody. A disulfide linker, which allows for dissociation via a thiol exchange reaction, relies in part on the uptake of an antibody-drug conjugate into a target cell and the exposure of the disulfide to the cytosol, which is a reducing environment. Since various types of thiols (for example, albumin, and glutathione) are present in the blood, however, a drug may dissociate from the antibody prior to reaching its target.

Recently, a new approach to making antibody-drug conjugates has been described, using protein prenylation of a C-terminal amino acid sequence to install a modified isoprenoid unit that allows for attachment of a drug or other active agent to the antibody in a mild and site-specific manner (e.g., see U.S. Patent Publication No. 2012/0308584). Further refinement is possible.

In light of the foregoing, improved linkers for antibody-drug conjugates are desirable.

SUMMARY

In some aspects, the invention relates to antibody-drug conjugates (ADCs) comprising an antibody, at least one branched linker covalently coupled to the antibody, and at least one or two active agents covalently coupled to the branched linker. A branched linker may comprise a branching unit, with at least one drug coupled to the branching unit through a secondary linker; the branching unit is coupled to the antibody by a primary linker. The primary and/or secondary linker may comprise at least one polyethylene glycol unit.

In some embodiments, the invention relates to a ligand-drug conjugate, comprising a ligand and one or more branched linkers covalently coupled to the ligand, wherein
i) each branched linker comprises a branching unit (BR) covalently coupled to the ligand by a primary linker (PL);
ii) each branched linker comprises a first branch (B1), in which a first active agent is covalently coupled to the branching unit by a secondary linker (SL) and a cleavage group (CG); and
iii) each branched linker further comprises a second branch (B2), in which either a) a second active agent is covalently coupled to the branching unit by a secondary linker (SL) and a cleavage group (CG) or b) a polyethylene glycol moiety is covalently coupled to the branching unit,
wherein each cleavage group can be hydrolyzed to release the active agent from the ligand-drug conjugate.

In some embodiments, the invention relates to a branched ligand-active agent compound, wherein
i) the branched linker comprises a branching unit (BR) covalently coupled to a reactive moiety by a primary linker (PL);
ii) the branching unit is covalently coupled to a first branch (B1), comprising a first active agent covalently coupled to a secondary linker (SL) and a cleavage group (CG); and
iii) the branching unit is covalently coupled to a second branch (B2), comprising either a) a second active agent covalently coupled to a secondary linker (SL) and a cleavage group (CG) or b) a polyethylene glycol moiety,
wherein each cleavage group can be hydrolyzed to release the active agent from the ligand-active agent compound.

In some embodiments, the cleavage group has the formula:

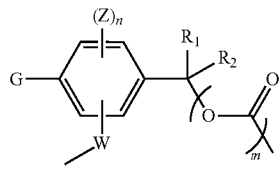

wherein:

G represents a sugar, sugar acid, or modified sugar, preferably a sugar or sugar acid, most preferably glucuronic acid;

W represents —C(O)—, —C(O)NR'—, —C(O)O—, —S(O)$_2$NR'—, —P(O)R"NR'—, —S(O)NR'—, or —PO$_2$NR'—, in each case where the C(O), S, or P is preferably directly bound to the phenyl ring, and R' and R" are each independently hydrogen, ($C_1$-$C_8$)alkyl, mono- or di-carboxyl($C_1$-$C_8$)alkyl, ($C_3$-$C_8$)cycloalkyl, ($C_1$-$C_8$)alkoxy, ($C_1$-$C_8$)alkylthio, mono- or di-($C_1$-$C_8$)alkylamino, ($C_3$-$C_{20}$)heteroaryl, or ($C_6$-$C_{20}$)aryl and W is coupled directly or indirectly to the branching unit;

each Z independently represents hydrogen, ($C_1$-$C_8$)alkyl, or an electron-withdrawing group (such as an amide, carboxylic acid, carboxylic acid ester, halogen, cyano, or nitro), preferably a hydrogen, ($C_1$-$C_8$)alkyl, halogen, cyano, or nitro, most preferably hydrogen;

n is an integer from 1 to 3;

m is 0 or 1, preferably 1; and $R_1$ and $R_2$ are each independently hydrogen, ($C_1$-$C_8$)alkyl, or ($C_3$-$C_8$)cycloalkyl, preferably hydrogen, or $R_1$ and $R_2$ taken together with the carbon atom to which they are attached form a ($C_3$-$C_8$)cycloalkyl ring.

In some embodiments, the active agent is coupled to the first branch through a cleavage group having the formula:

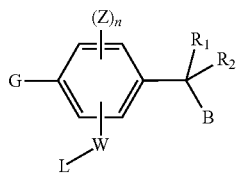

or a pharmaceutically acceptable salt thereof, wherein

G represents a sugar, sugar acid, or modified sugar, preferably a sugar or sugar acid, most preferably glucuronic acid;

B is a unit covalently attached to the active agent,

W represents —C(O)—, —C(O)NR'—, —C(O)O—, —S(O)$_2$NR'—, —P(O)R"NR'—, —S(O)NR'—, or —PO$_2$NR'—, in each case where the C(O), S, or P is directly bound to the phenyl ring, and R' and R" are each independently hydrogen, ($C_1$-$C_8$)alkyl, ($C_3$-$C_8$)cycloalkyl, ($C_1$-$C_8$)alkoxy, ($C_1$-$C_8$)alkylthio, mono- or di-($C_1$-$C_8$)alkylamino, ($C_3$-$C_{20}$)heteroaryl, or ($C_6$-$C_{20}$)aryl each Z independently represents hydrogen, ($C_1$-$C_8$)alkyl, or an electron-withdrawing group (such as an amide, carboxylic acid, carboxylic acid ester, halogen, cyano, or nitro), preferably a hydrogen, ($C_1$-$C_8$)alkyl, halogen, cyano, or nitro, most preferably hydrogen;

n is an integer from 1 to 3, preferably 3;

L represents a bond to a linker or a branching unit;

$R_1$ and $R_2$ are each independently hydrogen, ($C_1$-$C_8$)alkyl, or ($C_3$-$C_8$)cycloalkyl, preferably hydrogen, or $R_1$ and $R_2$ taken together with the carbon atom to which they are attached form a ($C_3$-$C_8$)cycloalkyl ring.

In some embodiments, the sugar or sugar acid is a monosaccharide. In some embodiments, the sugar comprises:

G is

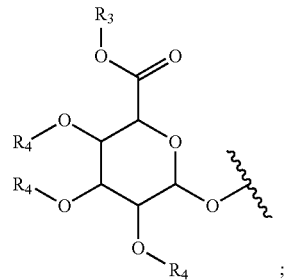

$R_3$ is hydrogen or a carboxyl protecting group; and each $R_4$ is independently hydrogen or a hydroxyl protecting group.

In some embodiments, the primary or secondary linker has the structure —(CH$_2$)$_r$(V(CH$_2$)$_p$)$_q$—, —((CH$_2$)$_p$V)$_q$—, —(CH$_2$)$_r$(V(CH$_2$)$_p$)$_q$Y—, —((CH$_2$)$_p$V)$_q$(CH$_2$)$_r$—, —Y(((CH$_2$)$_p$V)$_q$— or —(CH$_2$)$_r$(V(CH$_2$)$_p$)$_q$YCH$_2$— wherein:

r is an integer from 0 to 10;

p is an integer from 1 to 10;

q is an integer from 1 to 20;

V and Y are each independently a single bond, —O—, —S—, —NR$_{21}$—, —C(O)NR$_{22}$—, —NR$_{23}$C(O)—, —NR$_{24}$SO$_2$—, or —SO$_2$NR$_{25}$—; and $R_{21}$ to $R_{25}$ are each independently hydrogen, ($C_1$-$C_6$)alkyl, ($C_1$-$C_6$)alkyl($C_6$-$C_{20}$)aryl or ($C_1$-$C_6$)alkyl($C_3$-$C_{20}$)heteroaryl.

In some embodiments, the at least one branching unit has the structure

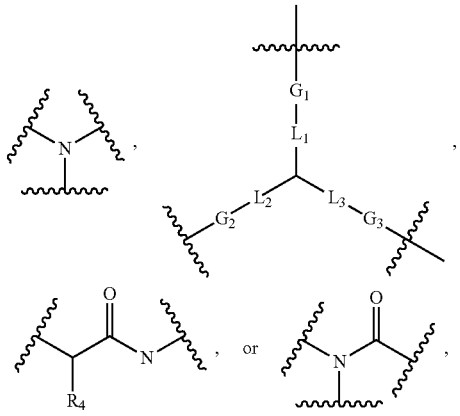

wherein $L_1$, $L_2$, $L_3$ is each independently a direct bond or —$C_nH_{2n}$— where n is a integer of 1 to 30, wherein $G_1$, $G_2$, $G_3$ is each independently a direct bond,

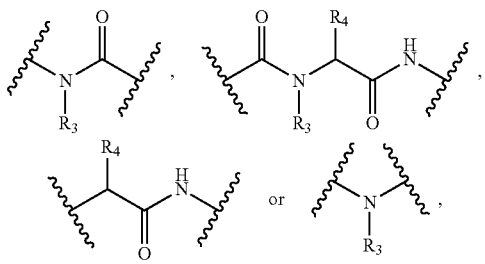

wherein $R_3$ is hydrogen or $C_1$-$C_{30}$ alkyl;

wherein $R_4$ is hydrogen or -$L_4$-COO$R_5$, wherein $L_4$ is a direct bond or —$C_nH_{2n}$— wherein n is a integer of 1 to 10, and $R_5$ is hydrogen or $C_1$-$C_{30}$ alkyl.

A secondary linker (e.g., linking an active agent to the branching unit) may comprise a binding unit formed by a 1,3-dipolar cycloaddition reaction, hetero-Diels-Alder reaction, nucleophilic substitution reaction, non-aldol type carbonyl reaction, addition to a carbon-carbon multiple bond, oxidation reaction, or click reaction. A binding unit may be formed by a reaction between an acetylene and azide, or a non-aldol type carbonyl reaction, such as a reaction between an aldehyde or ketone group and hydrazine or alkoxyamine, reactions which allow for mild coupling of active agents and/or cleavage groups to the branching unit. Such binding units may be represented by Formula (A), (B), (C), or (D).

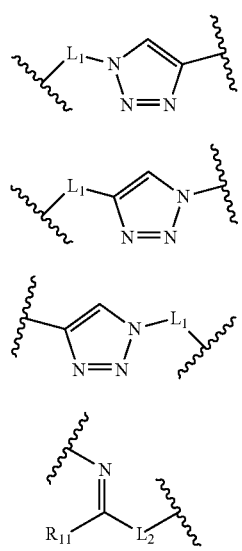

$L_1$ is a single bond or alkylene having 1 to 30 carbon atoms, preferably 10, 11, 12, 13, 14, 15, or 16 carbon atoms;

$R_{11}$ is hydrogen or an alkyl having 1 to 10 carbon atoms, preferably methyl; and $L_2$ is an alkylene having 1 to 30 carbon atoms, preferably 10, 11, 12, 13, 14, 15, or 16 carbon atoms.

In some embodiments, the ligand-drug conjugate as described above comprises a ligand, a linker, and an active agent, and has the formula:

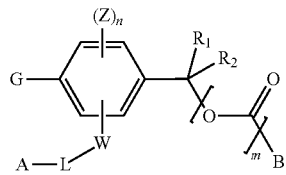

wherein:
G represents a sugar, sugar acid, or a modified sugar;
A represents the ligand;
B represents the active agent;
W represents —C(O)—, —C(O)NR'—, —C(O)O—, —S(O)$_2$NR'—, —P(O)R"NR'—, —S(O)NR'—, or —PO$_2$NR'—, in each case where the C(O), S, or P is directly bound to the phenyl ring, and R' and R" are each independently hydrogen, ($C_1$-$C_8$)alkyl, ($C_3$-$C_8$)cycloalkyl, ($C_1$-$C_8$)alkoxy, ($C_1$-$C_8$)alkylthio, mono- or di-($C_1$-$C_8$)alkylamino, ($C_3$-$C_{20}$)heteroaryl, or ($C_6$-$C_{20}$)aryl each Z independently represents hydrogen, ($C_1$-$C_8$)alkyl, or an electron-withdrawing group (such as an amide, carboxylic acid, carboxylic acid ester, halogen, cyano, or nitro), preferably a hydrogen, ($C_1$-$C_8$)alkyl, halogen, cyano, or nitro, most preferably hydrogen;

n is an integer from 1 to 3, preferably 3;

m is 0 or 1, preferably 1;

L is a linker that comprises at least one branching unit (BR) and at least one primary linker (PL);

$R_1$ and $R_2$ are each independently hydrogen, ($C_1$-$C_8$)alkyl, or ($C_3$-$C_8$)cycloalkyl, preferably hydrogen, or $R_1$ and $R_2$ taken together with the carbon atom to which they are attached form a ($C_3$-$C_8$)cycloalkyl ring.

In any of the embodiments disclosed herein, the ligand is preferably an antibody.

In some embodiments, the invention relates to an antibody-drug conjugate, comprising an antibody; at least one branched linker covalently coupled to the antibody; and at least two active agents covalently coupled to the branched linker. Preferably, at least two branched linkers are coupled to the antibody, and each branched linker is coupled to at least two active agents. Three or even four such branched linkers may be coupled to the antibody. In some embodiments, exactly one branched linker is coupled to the antibody. In certain embodiments, each branched linker is coupled to exactly two active agents. In some embodiments, all of the active agents of the antibody-drug conjugate are the same. In other embodiments, the antibody-drug conjugate comprises at least two different active agents. In some such embodiments, at least one branched linker is coupled to two different active agents.

In some embodiments, each active agent is coupled to a branched linker by a cleavable (e.g., hydrolysable) bond, such as via a self-immolative group, e.g., a cleavage group as described in greater detail below.

In preferred embodiments, each branched linker comprises a branching unit, and each active agent is coupled to the branching unit through a secondary linker and the branching unit is coupled to the antibody by a primary linker. For example, the branching unit may comprise a nitrogen atom, e.g., of an amine or an amide. In embodiments wherein the branching unit is an amide, the primary linker may comprise the carbonyl of the amide, or a secondary linker may comprise the carbonyl of the amide. In certain preferred embodiments, the branching unit is an amine. In other preferred embodiments, the branching unit is a lysine unit, e.g., such that one secondary linker extends from the α-nitrogen and the other secondary linker extends from the backbone nitrogen.

In some embodiments, one or more or even each active agent is coupled to the branched linker through a cleavage group having the formula:

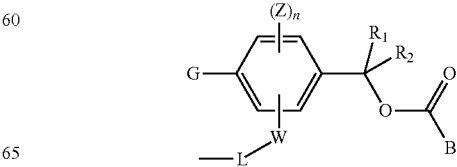

wherein:

G represents a sugar or sugar acid, preferably glucuronic acid;

B represents the active agent;

W represents an electron-withdrawing group, preferably —C(O)NR'—, where C(O) is bonded to the phenyl ring and NR' (which may be the amino group of an amino acid, preferably a hydrophilic amino acid) is bonded to L;

each Z independently represents hydrogen, $(C_1-C_8)$alkyl, or an electron-withdrawing group (such as an amide, carboxylic acid, carboxylic acid ester, halogen, cyano, or nitro), preferably a hydrogen, $(C_1-C_8)$alkyl, halogen, cyano, or nitro, most preferably hydrogen; n is an integer from 1 to 3;

L represents a linkage to the antibody;

$R_1$ and $R_2$ are each independently hydrogen, $(C_1-C_8)$alkyl, or $(C_3-C_8)$cycloalkyl, preferably hydrogen, or $R_1$ and $R_2$ taken together with the carbon atom to which they are attached form a $(C_3-C_8)$cycloalkyl ring.

Alternative cleavage groups include valine-citrulline-p-aminobenzylcarbamate (VC-PABC).

In some embodiments, W is —C(O)—, —C(O)NR'—, —C(O)O—, —S(O)$_2$NR'—, —P(O)R"NR'—, —S(O)NR'—, or —PO$_2$NR'—, in each case where the C(O), S, or P is preferably directly bound to the phenyl ring, and R' and R" are each independently hydrogen, $(C_1-C_8)$alkyl, $(C_3-C_8)$cycloalkyl, $(C_1-C_8)$alkoxy, $(C_1-C_8)$alkylthio, mono- or di-$(C_1-C_8)$alkylamino, $(C_3-C_{20})$heteroaryl, or $(C_6-C_{20})$aryl. In certain preferred embodiments, W represents —C(O)NR'—, and the nitrogen of W is a nitrogen of an amino acid, preferably a hydrophilic amino acid. In some embodiments, W is —C(O)NR'—, where C(O) is bonded to the phenyl ring and NR' is bonded to L.

In some embodiments, the sugar or sugar acid is a monosaccharide. In some embodiments, the sugar comprises:

G is

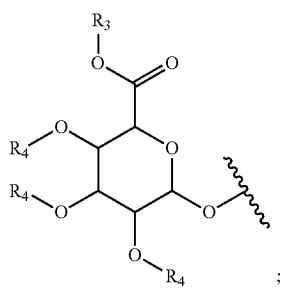

$R_3$ is hydrogen or a carboxyl protecting group; and each $R_4$ is independently hydrogen or a hydroxyl protecting group.

In some such embodiments, $R_3$ is hydrogen and each $R_4$ is hydrogen.

In some embodiments, each Z represents hydrogen and n is 3.

In certain preferred embodiments:

G is glucuronic acid;

W is —C(O)NR'—, where C(O) is bonded to the phenyl ring and NR' is bonded to L;

Z represents hydrogen;

n is 3; and $R_1$ and $R_2$ each represent hydrogen.

In some embodiments of the invention, the primary linker of the antibody-drug conjugate comprises an alkylene having 1 to 100, preferably 1-50, carbon atoms, and either:

the alkylene includes at least one unsaturated bond;

the alkylene includes at least one heteroarylene;

a carbon atom of the alkylene is replaced by one or more heteroatoms selected from nitrogen (N), oxygen (O), and sulfur (S); or the alkylene is further substituted with one or more alkyls having 1 to 20 carbon atoms.

In some such embodiments, the at least one carbon atom of the alkylene is replaced by a nitrogen, the primary linker comprises at least two atoms of a hydrophilic amino acid, and the nitrogen forms a peptide bond with the backbone carbonyl of the hydrophilic amino acid. The hydrophilic amino acid may be, for example, arginine, aspartate, asparagine, glutamate, glutamine, histidine, lysine, ornithine, proline, serine, or threonine.

In some embodiments, the branched linker of the antibody-drug conjugate comprises an amino acid having a side chain with a moiety that bears a charge at neutral pH in aqueous solution, preferably an arginine, aspartate, glutamate, lysine, or ornithine. This amino acid may be present anywhere in the branched linker. For example, it may covalently link an oxime of the branched linker to a polyethylene glycol unit of the branched linker. Alternatively or additionally, such an amino acid may by present in a secondary linker, optionally in each secondary linker.

In certain preferred embodiments, the branched linker of the antibody-drug conjugate is covalently bound to the antibody by a thioether bond, and the thioether bond comprises a sulfur atom of a cysteine of the antibody, most preferably a C-terminal cysteine, which may be part of amino acid motif that is recognized by an isoprenoid transferase.

For example, the amino acid motif may be a sequence selected from CXX, CXC, XCXC, XXCC, and CYYX;

C represents cysteine;

Y, independently for each occurrence, represents an aliphatic amino acid;

X, independently for each occurrence, represents glutamine, glutamate, serine, cysteine, methionine, alanine, or leucine; and the thioether bond comprises a sulfur atom of a cysteine of the amino acid motif.

In some embodiments, the amino acid motif is:

a sequence CYYX; and

Y, independently for each occurrence, represents alanine, isoleucine, leucine, methionine, or valine.

In certain preferred embodiments, the amino acid motif is a sequence CVIM or CVLL.

In some embodiments, at least one of the seven amino acids preceding the amino acid motif is glycine. In some embodiments, at least three of the seven amino acids preceding the amino acid motif are each independently selected from glycine and proline. In some embodiments, one to ten amino acids immediately preceding the amino acid motif are glycine. In certain preferred embodiments, at least one, two, three, four, five, six, seven, eight, nine, or ten amino acids immediately preceding the amino acid motif are glycine, most preferably at least five. In certain preferred embodiments, each of the one, two, three, four, five, six, seven, eight, nine, or ten amino acids preceding the amino acid motif is glycine. In some embodiments, a C-terminus of the antibody comprises the amino acid sequence GGGGGGGCVIM.

In some embodiments, the above-described thioether bond comprises a carbon atom of at least one isoprenyl unit, represented by

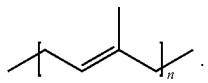

In preferred embodiments, n is 1 or 2, most preferably 2.

In some embodiments of the invention, the branched linker comprises an oxime, and the at least one isoprenyl unit covalently links the oxime to the antibody. In some embodiments, the branched linker comprises:

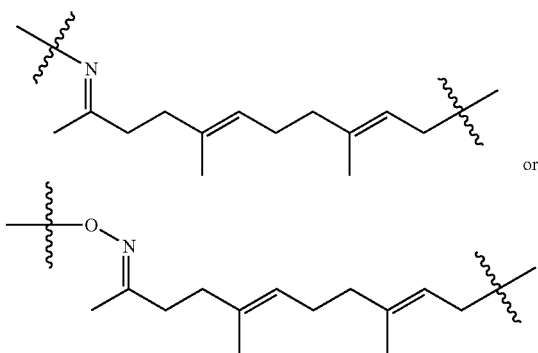

In some embodiments, the linker may comprise

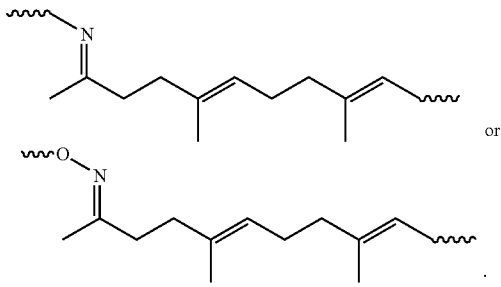

In some embodiments of the invention, the primary linker and/or secondary linker (preferably each secondary linker) comprises at least one polyethylene glycol unit, represented by either

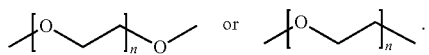

The polyethylene glycol unit may comprise 1 to 19 —OCH$_2$CH$_2$— units, preferably 4 to 20 —OCH$_2$CH$_2$— units. In some preferred embodiments, the linker may comprise 1 to 20 —OCH$_2$CH$_2$— units. In certain preferred embodiments, the linker may comprise 1 to 12 —OCH$_2$CH$_2$— units. In other preferred embodiments, the linker may comprise 3 to 12 —OCH$_2$CH$_2$— units. In some embodiments, the linker comprises an oxime, and the at least one polyethylene glycol unit covalently links the oxime to the peptide.

In some embodiments of the invention, the primary linker, the secondary linker (preferably each secondary linker), or both comprise a connection unit represented by —(CH$_2$)$_r$(V(CH$_2$)$_p$)$_q$—, wherein:
  r is an integer from 1 to 10, preferably 2;
  p is an integer from 0 to 12, preferably 2;
  q is an integer from 1 to 20;
  V is a single bond, —O—, —S—, —NR$_{21}$—, —C(O)NR$_{22}$—, —NR$_{23}$C(O)—, —NR$_{24}$SO$_2$—, or —SO$_2$NR$_{25}$—, preferably —O—; and
  R$_{21}$ to R$_{25}$ are each independently hydrogen, (C$_1$-C$_6$)alkyl, (C$_1$-C$_6$)alkyl(C$_6$-C$_{20}$)aryl, or (C$_1$-C$_6$)alkyl(C$_3$-C$_{20}$)heteroaryl.

In some embodiments, the primary linker, the secondary linker (preferably each secondary linker), or both comprise a connection unit represented by —(CH$_2$)$_r$(V(CH$_2$)$_p$)$_q$—, —((CH$_2$)$_p$V)$_q$—, —(CH$_2$)$_r$(V(CH$_2$)$_p$)$_q$Y—, —((CH$_2$)$_p$V)$_q$(CH$_2$)$_r$—, —Y(((CH$_2$)$_p$V)$_q$— or —(CH$_2$)$_r$(V(CH$_2$)$_p$)$_q$YCH$_2$—
wherein:
  r is an integer from 0 to 10;
  p is an integer from 1 to 10;
  q is an integer from 1 to 20;
  V and Y are each independently a single bond, —O—, —S—, —NR$_{21}$—, —C(O)NR$_{22}$—, —NR$_{23}$C(O)—, —NR$_{24}$SO$_2$—, or —SO$_2$NR$_{25}$—; and
  R$_{21}$ to R$_{25}$ are each independently hydrogen, (C$_1$-C$_6$)alkyl, (C$_1$-C$_6$)alkyl(C$_6$-C$_{20}$)aryl or (C$_1$-C$_6$)alkyl(C$_3$-C$_{20}$)heteroaryl.

In some embodiments of these linkers, q is an integer from 4 to 20. In some embodiments of these linkers, q is an integer from 6 to 20. In certain preferred embodiments, q is an integer from 1 to 10. In other preferred embodiments, q is 2, 5, or 11.

In some embodiments of these linkers, r is preferably 2. In some embodiments of these linkers, p is preferably 2. In some embodiments, V and Y are each independently —O—.

In some embodiments of these linkers:
  r is 2;
  p is 2;
  q is 2, 5, or 11, and
  V is —O—.

In some embodiments of the invention, the primary linker, the secondary linker (preferably each secondary linker), or both comprises a connection unit represented by —(CH$_2$CH$_2$X)$_w$—, wherein:
  X represents —O—, (C$_1$-C$_8$)alkylene, or —NR$_{21}$—, preferably —O—;
  R$_{21}$ represents hydrogen, (C$_1$-C$_6$)alkyl, (C$_1$-C$_6$)alkyl(C$_6$-C$_{20}$)aryl, or (C$_1$-C$_6$)alkyl(C$_3$-C$_{20}$)heteroaryl, preferably hydrogen; and
  w is an integer from 1 to 12, preferably 1, 3, 6, or 12.

In some embodiments X is —O— and w is an integer from 6 to 12.

In some embodiments of the invention, the primary linker comprises a binding unit formed by a 1,3-dipolar cycloaddition reaction, hetero-Diels-Alder reaction, nucleophilic substitution reaction, non-aldol type carbonyl reaction, addition to carbon-carbon multiple bond, oxidation reaction, or click reaction. In some embodiments, the binding unit is formed by a reaction between acetylene and azide, or a reaction between an aldehyde or ketone group and a hydrazine or alkoxyamine. In some embodiments, the binding unit is represented by any one of Formulas A, B, C, or D, preferably D:

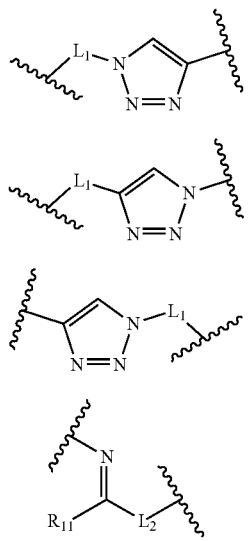

(A)

(B)

(C)

(D)

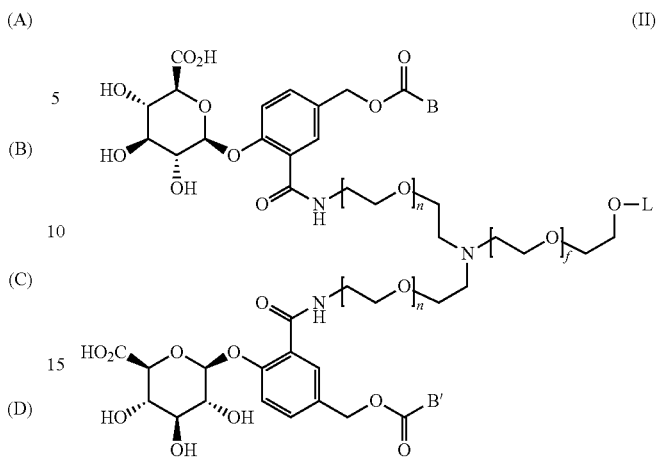

(II)

wherein:

B and B' represent active agents, which may be the same or different;

n, independently for each occurrence, represents an integer from 0 to 30;

f, independently for each occurrence, represents an integer from 0 to 30; and

L represents a linkage to the antibody.

In some embodiments, n is an integer from 1 to 10. In some embodiments, n is an integer from 4 to 20. In some embodiments, f is an integer from 1 to 10. In some embodiments, f is an integer from 4 to 20. Preferably n and f are selected such that n+f is less than 20, e.g., less than 15. In some embodiments, the linker comprises an oxime, and the at least one polyethylene glycol unit covalently links the oxime to the active agent.

In some embodiments of the invention, the antibody is a monoclonal antibody, polyclonal antibody, antibody fragment, Fab, Fab', Fab'-SH, F(ab')$_2$, Fv, single chain Fv ("scFv"), diabody, linear antibody, bispecific antibody, multispecific antibody, chimeric antibody, humanized antibody, human antibody, or fusion protein comprising the antigen-binding portion of an antibody.

In some embodiments of the invention, the antibody is selected from muromonab-CD3 abciximab, rituximab, daclizumab, palivizumab, infliximab, trastuzumab, etanercept, basiliximab, gemtuzumab, alemtuzumab, ibritumomab, adalimumab, alefacept, omalizumab, efalizumab, tositumomab, cetuximab, ABT-806, bevacizumab, natalizumab, ranibizumab, panitumumab, eculizumab, rilonacept, certolizumab, romiplostim, AMG-531, golimumab, ustekinumab, ABT-874, belatacept, belimumab, atacicept, an anti-CD20 antibody, canakinumab, tocilizumab, atlizumab, mepolizumab, pertuzumab, HuMax CD20, tremelimumab, ticilimumab, ipilimumab, IDEC-114, inotuzumab, HuMax EGFR, aflibercept, HuMax-CD4, teplizumab, otelixizumab, catumaxomab, the anti-EpCAM antibody IGN101, adecatumomab, oregovomab, dinutuximab, girentuximab, denosumab, bapineuzumab, motavizumab, efumgumab, raxibacumab, LY2469298, and veltuzumab.

In some embodiments of the invention, the active agent is independently selected from chemotherapeutic agents and toxins.

In some embodiments of the invention, the active agent is independently selected from:

(a) erlotinib, bortezomib, fulvestrant, sutent, letrozole, imatinib mesylate, PTK787/ZK 222584, oxaliplatin, 5-fluowherein:

$L_1$ is a single bond or alkylene having 1 to 30 carbon atoms, preferably 12;

$R_{11}$ is hydrogen or alkyl having 1 to 10 carbon atoms, preferably methyl; and $L_2$ is alkylene having 1 to 30 carbon atoms, preferably 11.

In some embodiments the primary linker comprises

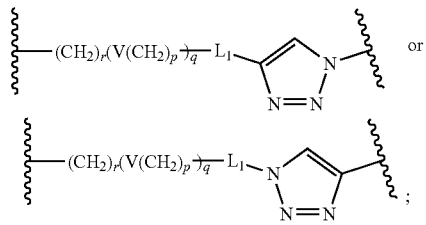

or

V is a single bond, —O—, —S—, —NR$_{21}$—, —C(O)NR$_{22}$—, —NR$_{23}$C(O)—, —NR$_{24}$SO$_2$—, or —SO$_2$NR$_{25}$—, preferably —O—;

R$_{21}$ to R$_{25}$ are each independently hydrogen, (C$_1$-C$_6$)alkyl, (C$_1$-C$_6$)alkyl(C$_6$-C$_{20}$)aryl, or (C$_1$-C$_6$)alkyl(C$_3$-C$_{20}$)heteroaryl;

r is an integer of 1 to 10, preferably 2 or 3;

p is an integer of 0 to 10, preferably 1 or 2;

q is an integer of 1 to 20, preferably 1 to 6; and $L_1$ is a single bond.

In some embodiments of the invention, the branched linker comprises an O-substituted oxime; wherein a) the oxygen atom of the oxime is substituted with a group that covalently links the oxime to the active agent, e.g., via the branching unit; and the carbon atom of the oxime is substituted with a group that covalently links the oxime to the antibody; or b) the oxygen atom of the oxime is substituted with a group that covalently links the oxime to the antibody; and the carbon atom of the oxime is substituted with a group that covalently links the oxime to the active agent, e.g., via the branching unit.

In some embodiments, the antibody-drug conjugate comprises the structure of Formula II:

rouracil, leucovorin, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethylenimine, altretamine, triethylenemelamine, trietylenephosphoramide, triethiylenethiophosphoramide, trimethylolomelamine, bullatacin, bullatacinone, camptothecin, camptothecin derivatives and metabolites (SN-38), topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, melphalan, novembichin, phenesterine, prednimustine, trofosfamide, uracil mustard, carmustine, chlorozotocin, fotemustine, lomustine, nimustine, ranimnustine, calicheamicin, calicheamicin gamma 1, calicheamicin omega 1, dynemicin, dynemicin A, clodronate, esperamicin, neocarzinostatin chromophore, aclacinomysins, actinomycin, antrmycin, azaserine, bleomycins, cactinomycin, carabicin, caminomycin, carzinophilin, chromomycins, dactinomycin, daunorubicin, detorubucin, 6-diazo-5-oxo-L-norleucine, doxorubicin, morpholino-doxorubicin, cyanomorpholino-doxorubicin, 2-pyrrolino-doxorubicin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, thiguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaziquone, 2,2',2"-trichlorotriethylamine, T-2 toxin, verracurin A, roridin A, and anguidine, urethane, vindesine, dacarbazine, mannomustine, mitobronitol, mitolactol, pipobroman, gacytosine, arabinoside, cyclophosphamide, thiotepa, paclitaxel, albumin-engineered nanoparticle formulation of paclitaxel, doxetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, xeloda, ibandronate, CPT-11, topoisomerase inhibitor RFS 2000, difluoromethylornithine, retinoic acid, capecitabine, or pharmaceutically acceptable salts, solvates or acids of any of the foregoing;

(b) monokine, a lymphokine, a traditional polypeptide hormone, parathyroid hormone, thyroxine, relaxin, prorelaxin, a glycoprotein hormone, follicle stimulating hormone, thyroid stimulating hormone, luteinizing hormone, hepatic growth factor fibroblast growth factor, prolactin, placental lactogen, tumor necrosis factor-α, tumor necrosis factor-β, mullerian-inhibiting substance, mouse gonadotropin-associated peptide, inhibin, activin, vascular endothelial growth factor, thrombopoietin, erythropoietin, an osteoinductive factor, an interferon, interferon-α, interferon-β, interferon-γ, a colony stimulating factor ("CSF"), macrophage-CSF, granulocyte-macrophage-CSF, granulocyte-CSF, an interleukin ("IL"), IL-1, IL-1α, IL-2, IL-3, IL-4, IL-5, IL-6, IL-7, IL-8, IL-9, IL-10, IL-11, IL-12, a tumor necrosis factor, TNF-α, TNF-β, a polypeptide factor, LIF, kit ligand, or a combination of any of the foregoing;

(c) diphtheria toxin, botulium toxin, tetanus toxin, dysentery toxin, cholera toxin, amanitin, amanitin derivatives, α-amanitin, pyrrolobenzodiazepine, pyrrolobenzodiazepine derivatives, tetrodotoxin, brevetoxin, ciguatoxin, ricin, AM toxin, tubulysin, geldanamycin, maytansinoid, calicheamicin, daunomycin, doxorubicin, methotrexate, vindesine, SG2285, dolastatin, a dolastatin analog, auristatin, cryptophycin, camptothecin, camptothecin derivatives and metabolites (SN-38), rhizoxin, a rhizoxin derivative, CC-1065, a CC-1065 analogue or derivative, duocarmycin, an enediyne antibiotic, esperamicin, epothilone, azoiafide, aplidine, a toxoid, or a combination of any of the foregoing;

(d) an affinity ligand, wherein the affinity ligand is a substrate, an inhibitor, a stimulating agent, a neurotransmitter, a radioisotope, or a combination of any of the foregoing;

(e) a radioactive label, $^{32}P$, $^{35}S$, a fluorescent dye, an electron dense reagent, an enzyme, biotin, streptavidin, dioxigenin, a hapten, an immunogenic protein, a nucleic acid molecule with a sequence complementary to a target, or a combination of any of the foregoing;

(f) an immunomodulatory compound, an anti-cancer agent, an anti-viral agent, an anti-bacterial agent, an anti-fungal agent, and an anti-parasitic agent, or a combination of any of the foregoing;

(g) tamoxifen, raloxifene, droloxifene, 4-hydroxytamoxifen, trioxifene, keoxifene, LY117018, onapristone, or toremifene;

(h) 4(5)-imidazoles, aminoglutethimide, megestrol, acetate, exemestane, letrozole, or anastrozole;

(i) flutamide, nilutamide, bicalutamide, leuprolide, goserelin, or troxacitabine;

(j) an aromatase inhibitor;
(k) a protein kinase inhibitor;
(l) a lipid kinase inhibitor;
(m) an antisense oligonucleotide;
(n) a ribozyme;
(o) a vaccine; and
(p) an anti-angiogenic agent.

In some embodiments of the invention, the active agent is amanitin, auristatin, calicheamicin, camptothecin, camptothecin derivatives and metabolites (SN-38), cryptophycin, daunomycin, dolastatin, doxorubicin, duocarmycin, epothilone, esperamicin, geldanamycin, maytansinoid, methotrexate, monomethyl auristatin E ("MMAE"), monomethyl auristatin F ("MMAF"), pyrrolobenzodiazepine, rhizoxin, SG2285, tubulysin, vindesine, toxoid, or a derivative of any one of the foregoing. In some embodiments, the active agent is amanitin, MMAE, or MMAF, or a derivative of any one of the foregoing.

In some embodiments of the invention, the active agent is:
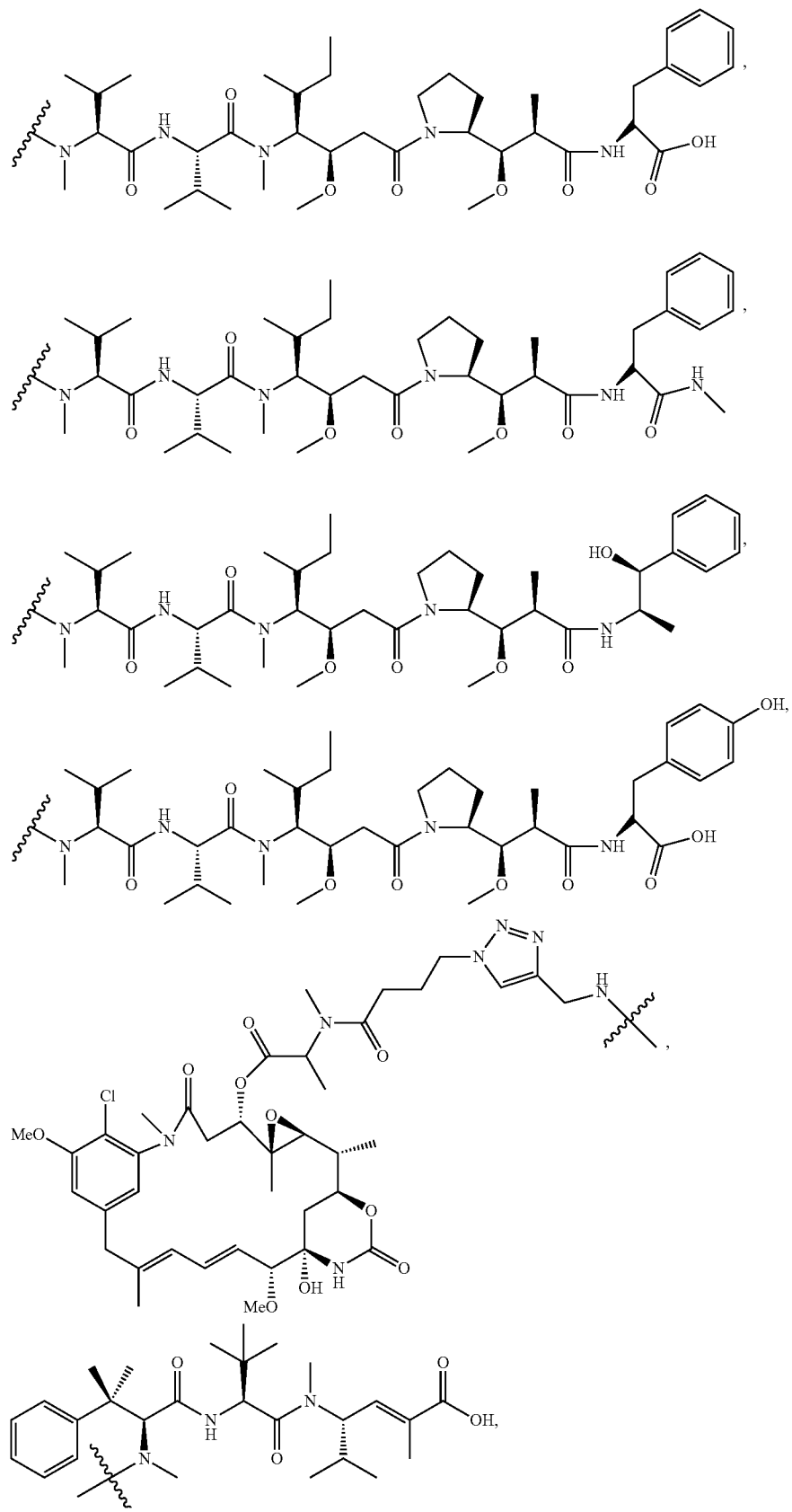

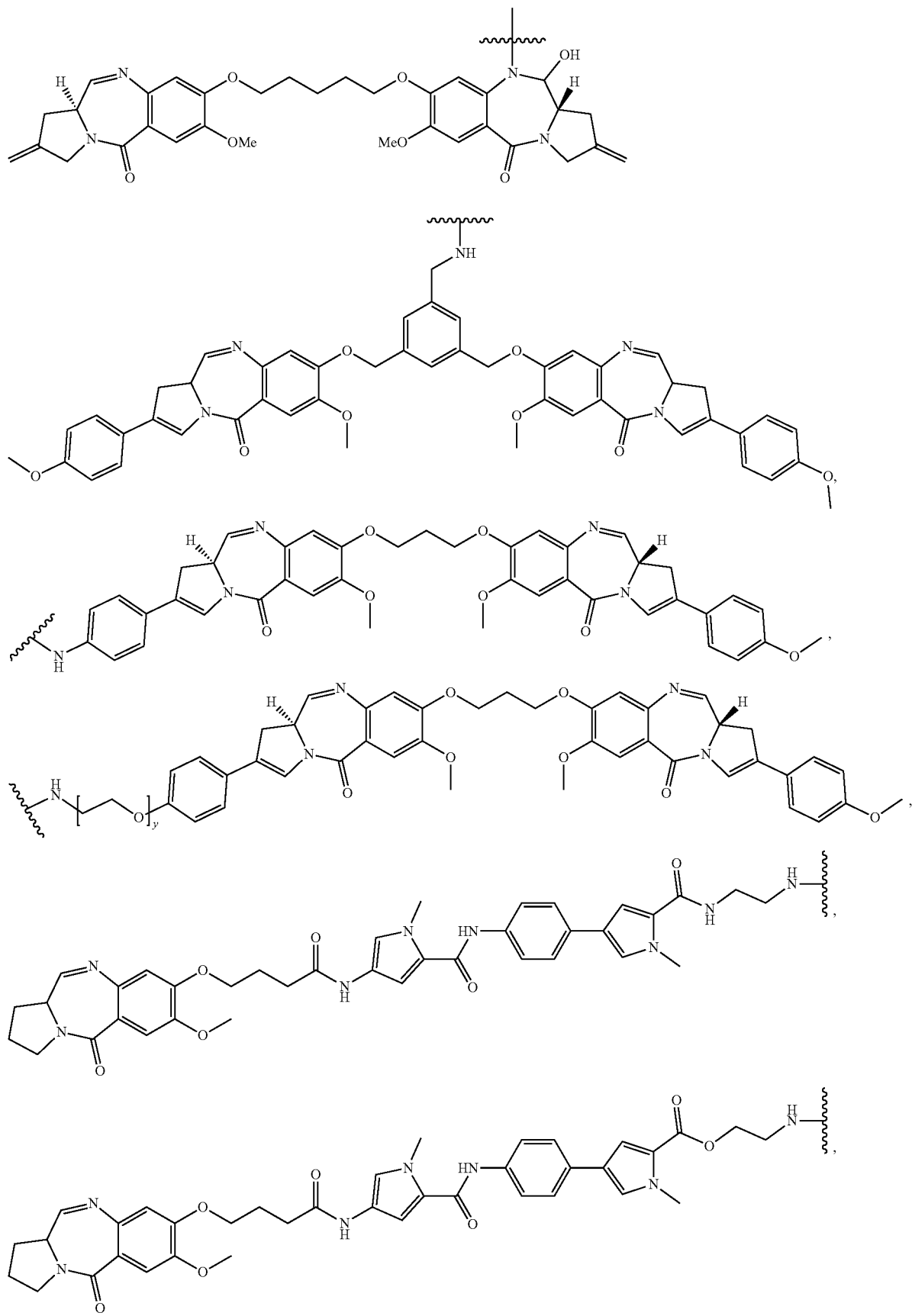

-continued

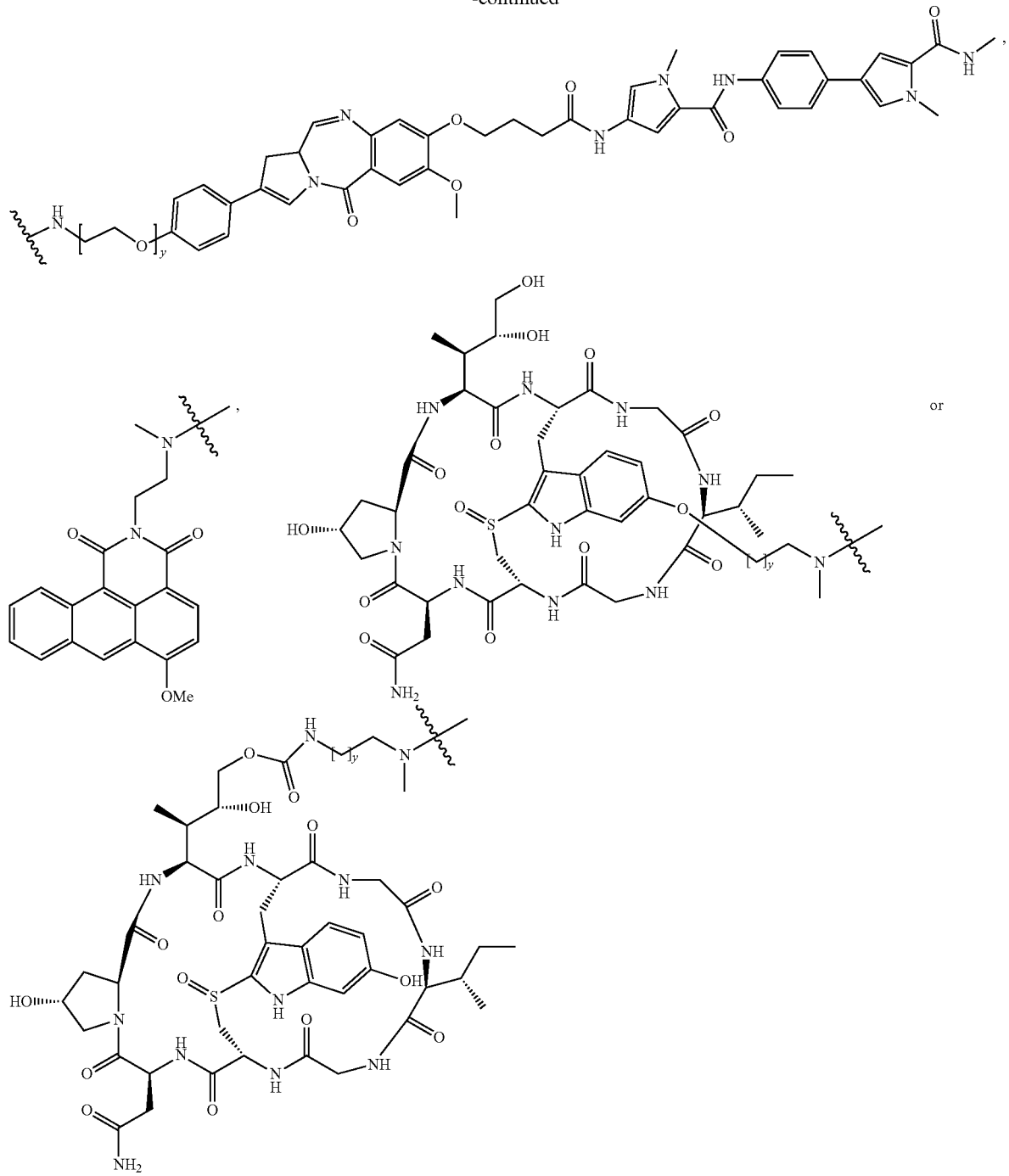

wherein y is an integer of 1 to 10.

Structures and components of related antibody-drug conjugates are disclosed in PCT/KR2015/005299, which is hereby incorporated by reference in its entirety, in particular for the chemical formulae and generic structures of antibody-drug conjugates, their component parts (e.g., linkers, cleavage groups, etc.), and their preparation and use as disclosed therein. In certain preferred embodiments, the various conjugates and other aspects of the present invention specifically exclude the various structures and methods disclosed in PCT/KR2015/005299.

In some embodiments, the invention provides a pharmaceutical composition comprising an antibody-drug conjugate as described herein. A pharmaceutical composition may further comprise a therapeutically effective amount of chemotherapeutic agent. In some embodiments, the invention provides a method of treating cancer in a subject, comprising administering such a pharmaceutical composition to the subject. In some embodiments, the subject is a mammal, e.g., selected from rodents, lagomorphs, felines, canines, porcines, ovines, bovines, equines, and primates. In some embodiments, the subject is preferably a human.

In some embodiments, the invention provides a method for making an antibody-drug conjugate as described herein, comprising reacting a biomolecule with a prodrug, wherein:

the biomolecule comprises an antibody and a ketone or aldehyde;

the prodrug comprises an alkoxyamine; and the reaction produces an oxime, thereby covalently linking the antibody to the prodrug.

In some embodiments, the method further comprises isoprenylating the antibody, thereby producing the biomolecule, wherein:

the antibody comprises an isoprenylation sequence;

isoprenylating the antibody comprises incubating the antibody with an isoprenoid transferase and an isoprenoid transferase substrate; and the substrate comprises the ketone or aldehyde.

In some embodiments, the isoprenoid transferase is farnesyltransferase or geranylgeranyltransferase.

In some embodiments, the invention provides a method for making a ligand-drug conjugate as described herein, comprising isoprenylating a ligand, wherein the ligand comprises an amino acid motif that is recognized by an isoprenoid transferase; isoprenylating the ligand comprises incubating the ligand with an isoprenoid transferase and an isoprenoid transferase substrate; and the substrate comprises the active agent.

In some embodiments, the invention provides a method for making a ligand-drug conjugate as described herein, comprising isoprenylating a ligand, wherein the ligand comprises an amino acid motif that is recognized by an isoprenoid transferase; isoprenylating the ligand comprises incubating the ligand with an isoprenoid transferase and an isoprenoid transferase substrate; and the substrate comprises the active agent.

In other embodiments, the invention relates to an antibody-drug conjugate, comprising an antibody; at least one branched linker covalently coupled to the antibody, the branched linker comprising a branching unit covalently coupled to the antibody by a primary linker; an active agent covalently coupled to the branching unit by a first branch; and a second branch that comprises a polyethylene glycol moiety covalently coupled to the branching unit. Preferably, at least two branched linkers are coupled to the antibody, each branched linker coupled to exactly one active agent. Three or even four such branched linkers may be coupled to the antibody. In some such embodiments, at least two different active agents are coupled to different branched linkers. In some embodiments, only one branched linker is coupled to the antibody. In certain preferred embodiments, each branched linker is coupled to exactly one active agent.

In some embodiments, the active agent is coupled to the first branch by a cleavable (e.g., hydrolysable) bond, such as via a self-immolative group, e.g., a cleavage group as described in greater detail below.

In some embodiments, the branching unit may comprise a nitrogen atom, e.g., of an amine or an amide. In certain preferred embodiments, the branching unit is an amine. In embodiments wherein the branching unit is an amide, the primary linker may comprise the carbonyl of the amide. In some embodiments wherein the branching unit is an amide and the first branch or the second branch may comprise the carbonyl of the amide. In other preferred embodiments, the branching unit is a lysine unit.

In some embodiments, one or more or even each active agent is coupled to the first branch through a cleavage group having the formula:

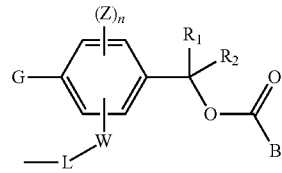

wherein:

G represents a sugar or sugar acid, preferably glucuronic acid;

B represents the active agent;

W represents an electron-withdrawing group, preferably —C(O)NR'—, where C(O) is bonded to the phenyl ring and NR' (which may be the amino group of an amino acid, preferably a hydrophilic amino acid) is bonded to L;

each Z independently represents hydrogen, $(C_1-C_8)$alkyl, or an electron-withdrawing group (such as an amide, carboxylic acid, carboxylic acid ester, halogen, cyano, or nitro), preferably a hydrogen, $(C_1-C_8)$alkyl, halogen, cyano, or nitro, most preferably hydrogen;

n is an integer from 1 to 3;

L represents a linkage to the antibody;

$R_1$ and $R_2$ are each independently hydrogen, $(C_1-C_8)$alkyl, or $(C_3-C_8)$cycloalkyl, preferably hydrogen, or $R_1$ and $R_2$ taken together with the carbon atom to which they are attached form a $(C_3-C_8)$cycloalkyl ring.

In some embodiments, the active agent is coupled to the first branch through a cleavage group having the formula:

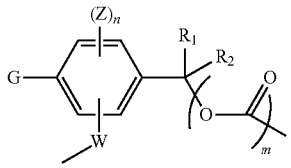

wherein:

G represents a sugar, sugar acid, or modified sugar, preferably a sugar or sugar acid, most preferably glucuronic acid;

W represents —C(O)—, —C(O)NR'—, —C(O)O—, —S(O)$_2$NR'—, —P(O)R"NR'—, —S(O)NR'—, or —PO$_2$NR'—, in each case where the C(O), S, or P is preferably directly bound to the phenyl ring, and R' and R" are each independently hydrogen, $(C_1-C_8)$alkyl, mono- or di-carboxyl$(C_1-C_8)$alkyl, $(C_3-C_8)$cycloalkyl, $(C_1-C_8)$alkoxy, $(C_1-C_8)$alkylthio, mono- or di-$(C_1-C_8)$alkylamino, $(C_3-C_{20})$heteroaryl, or $(C_6-C_{20})$aryl and W is coupled directly or indirectly to the branching unit;

each Z independently represents hydrogen, $(C_1-C_8)$alkyl, or an electron-withdrawing group (such as an amide, carboxylic acid, carboxylic acid ester, halogen, cyano, or nitro), preferably a hydrogen, $(C_1-C_8)$alkyl, halogen, cyano, or nitro, most preferably hydrogen;

n is an integer from 1 to 3;

m is 0 or 1, preferably 1; and $R_1$ and $R_2$ are each independently hydrogen, $(C_1-C_8)$alkyl, or $(C_3-C_8)$cycloalkyl, preferably hydrogen, or $R_1$ and $R_2$ taken together with the carbon atom to which they are attached form a $(C_3-C_8)$cycloalkyl ring.

In some embodiments, the active agent is coupled to the first branch through a cleavage group having the formula:

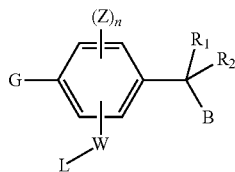

or a pharmaceutically acceptable salt thereof, wherein
G represents a sugar, sugar acid, or modified sugar, preferably a sugar or sugar acid, most preferably glucuronic acid;
B is a unit covalently attached to the active agent,
W represents —C(O)—, —C(O)NR'—, —C(O)O—, —S(O)$_2$NR'—, —P(O)R"NR'—, —S(O)NR'—, or —PO$_2$NR'—, in each case where the C(O), S, or P is directly bound to the phenyl ring, and R' and R" are each independently hydrogen, ($C_1$-$C_8$)alkyl, ($C_3$-$C_8$)cycloalkyl, ($C_1$-$C_8$)alkoxy, ($C_1$-$C_8$)alkylthio, mono- or di-($C_1$-$C_8$)alkylamino, ($C_3$-$C_{20}$)heteroaryl, or ($C_6$-$C_{20}$)aryl
each Z independently represents hydrogen, ($C_1$-$C_8$)alkyl, or an electron-withdrawing group (such as an amide, carboxylic acid, carboxylic acid ester, halogen, cyano, or nitro), preferably a hydrogen, ($C_1$-$C_8$)alkyl, halogen, cyano, or nitro, most preferably hydrogen;
n is an integer from 1 to 3, preferably 3;
L represents a bond to a linker or a branching unit;
$R_1$ and $R_2$ are each independently hydrogen, ($C_1$-$C_8$)alkyl, or ($C_3$-$C_8$)cycloalkyl, preferably hydrogen, or $R_1$ and $R_2$ taken together with the carbon atom to which they are attached form a ($C_3$-$C_5$)cycloalkyl ring.

In some embodiments, W is —C(O)—, —C(O)NR'—, —C(O)O—, —S(O)$_2$NR'—, —P(O)R"NR'—, —S(O)NR'—, or —PO$_2$NR'—, in each case where the C(O), S, or P is preferably directly bound to the phenyl ring, and R' and R" are each independently hydrogen, ($C_1$-$C_8$)alkyl, ($C_3$-$C_8$)cycloalkyl, ($C_1$-$C_8$)alkoxy, ($C_1$-$C_8$)alkylthio, mono- or di-($C_1$-$C_8$)alkylamino, ($C_3$-$C_{20}$)heteroaryl, or ($C_6$-$C_{20}$)aryl, preferably hydrogen. In certain preferred embodiments, W represents —C(O)NR'—, and the nitrogen of W is a nitrogen of an amino acid, preferably a hydrophilic amino acid. In some embodiments, W is —C(O)NR'—, where C(O) is bonded to the phenyl ring and NR' is bonded to L.

In some embodiments, the sugar or sugar acid is a monosaccharide. In some embodiments, the sugar comprises:
G is

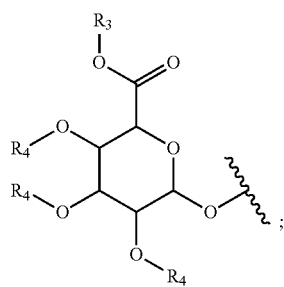

$R_3$ is hydrogen or a carboxyl protecting group; and
each $R_4$ is independently hydrogen or a hydroxyl protecting group.
In some such embodiments, $R_3$ is hydrogen and each $R_4$ is hydrogen.

In some embodiments, each Z represents hydrogen and n is 3.
In certain preferred embodiments:
G is glucuronic acid;
W is —C(O)NR'—, where C(O) is bonded to the phenyl ring and NR' is bonded to L;
Z represents hydrogen;
n is 3; and
$R_1$ and $R_2$ each represent hydrogen.

In some embodiments of the invention, the primary linker of the antibody-drug conjugate comprises an alkylene having 1 to 100, preferably 1-50, carbon atoms, and either:
the alkylene includes at least one unsaturated bond;
the alkylene includes at least one heteroarylene;
a carbon atom of the alkylene is replaced by one or more heteroatoms selected from nitrogen (N), oxygen (O), and sulfur (S); or
the alkylene is further substituted with one or more alkyls having 1 to 20 carbon atoms. In some such embodiments, the at least one carbon atom of the alkylene is replaced by a nitrogen, the primary linker comprises at least two atoms of a hydrophilic amino acid, and the nitrogen forms a peptide bond with the backbone carbonyl of the hydrophilic amino acid. The hydrophilic amino acid is arginine, aspartate, asparagine, glutamate, glutamine, histidine, lysine, ornithine, proline, serine, or threonine.

In some embodiments, the primary linker comprises an amino acid, and the amino acid comprises having a side chain with a moiety that bears a charge at neutral pH in aqueous solution, preferably an arginine, aspartate, glutamate, lysine, or ornithine. This amino acid may be present anywhere in the branched linker. For example, it may covalently link an oxime of the branched linker to a polyethylene glycol unit of the branched linker. Alternatively or additionally, such an amino acid may be present in the first branch.

In certain preferred embodiments, the primary linker of the antibody-drug conjugate is covalently bound to the antibody by a thioether bond, and the thioether bond comprises a sulfur atom of a cysteine of the antibody, most preferably a C-terminal cysteine, which may be part of the amino acid motif that is recognized by an isoprenoid transferase.

For example, the amino acid motif may be a sequence selected from CXX, CXC, XCXC, XXCC, and CYYX;
C represents cysteine;
Y, independently for each occurrence, represents an aliphatic amino acid;
X, independently for each occurrence, represents glutamine, glutamate, serine, cysteine, methionine, alanine, or leucine; and
the thioether bond comprises a sulfur atom of a cysteine of the amino acid motif.
In some embodiments, the amino acid motif is:
a sequence CYYX; and
Y, independently for each occurrence, represents alanine, isoleucine, leucine, methionine, or valine.
In certain preferred embodiments, the amino acid motif is a sequence CVIM or CVLL.

In some embodiments, at least one of the seven amino acids preceding the amino acid motif is glycine. In some embodiments, the at least three of the seven amino acids preceding the amino acid motif are each independently selected from glycine and proline. In some embodiments, one to ten amino acids immediately preceding the amino acid motif are glycine. In certain preferred embodiments, at least one, two, three, four, five, six, seven, eight, nine, or ten amino acids immediately preceding the amino acid motif are glycine, most preferably at least five. In certain preferred embodiments, each of the one, two, three, four, five, six, seven, eight, nine, or ten amino acids preceding the amino acid motif is glycine. In some embodiments, a C-terminus of the antibody comprises the amino acid sequence GGGGGGGCVIM.

In some embodiments, the above described thioether bond comprises a carbon atom of at least one isoprenyl unit, represented by

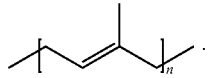

In preferred embodiments, n is 1 or 2, most preferably 2.

In some embodiments, the primary linker comprises an oxime, and the at least one isoprenyl unit covalently links the oxime to the antibody. In some embodiments, the linker comprises:

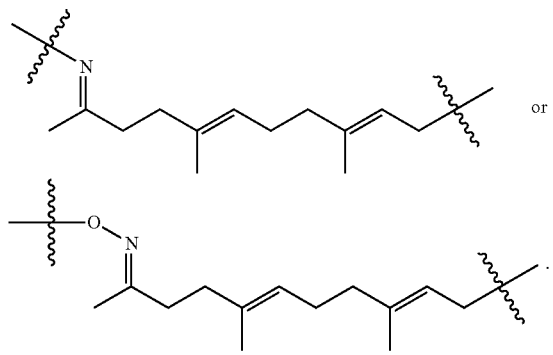

In some embodiments, the linker may comprise

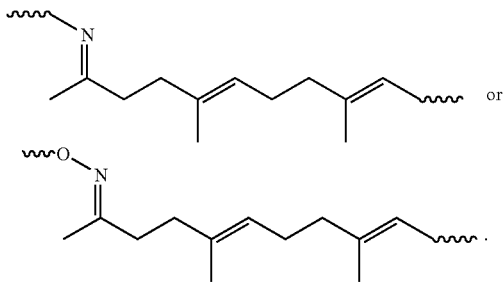

In some embodiments, the primary linker and/or the first branch comprises at least one polyethylene glycol unit, represented by either

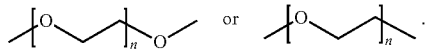

The polyethylene glycol unit may comprise 1 to 19 —OCH$_2$CH$_2$— units, preferably 4 to 20 —OCH$_2$CH$_2$— units. In some preferred embodiments, the linker may comprise 1 to 20 —OCH$_2$CH$_2$— units. In certain preferred embodiments, the linker may comprise 1 to 12 —OCH$_2$CH$_2$— units. In other preferred embodiments, the linker may comprise 3 to 12 —OCH$_2$CH$_2$— units. In some embodiments, the linker comprises an oxime, and the at least one polyethylene glycol unit covalently links the oxime to the peptide.

In some embodiments of the invention, the primary linker, the first branch, or both comprises a connection unit represented by —(CH$_2$)$_r$(V(CH$_2$)$_p$)$_q$—, wherein:
r is an integer from 1 to 10, preferably 2;
p is an integer from 0 to 12, preferably 2;
q is an integer from 1 to 20;
V is a single bond, —O—, —S—, —NR$_{21}$—, —C(O)NR$_{22}$—, —NR$_{23}$C(O)—, —NR$_{24}$SO$_2$—, or —SO$_2$NR$_{25}$—, preferably —O—; and
R$_{21}$ to R$_{25}$ are each independently hydrogen, (C$_1$-C$_6$)alkyl, (C$_1$-C$_6$)alkyl(C$_6$-C$_{20}$)aryl, or (C$_1$-C$_6$)alkyl(C$_3$-C$_{20}$)heteroaryl.

In certain preferred embodiments, q is an integer from 1 to 10. In other preferred embodiments, q is 2, 5, or 11.

In some embodiments of the invention, the primary linker, the first branch, or both comprises a connection unit represented by —(CH$_2$)$_r$(V(CH$_2$)$_p$)$_q$—, —((CH$_2$)$_p$V)$_q$—, —(CH$_2$)$_r$(V(CH$_2$)$_p$)$_q$Y—, —((CH$_2$)$_p$V)$_q$(CH$_2$)$_r$—, —Y(((CH$_2$)$_p$V)$_q$— or —(CH$_2$)$_r$(V(CH$_2$)$_p$)$_q$YCH$_2$— wherein:
r is an integer from 0 to 10;
p is an integer from 1 to 10;
q is an integer from 1 to 20;
V and Y are each independently a single bond, —O—, —S—, —NR$_{21}$—, —C(O)NR$_{22}$—, —NR$_{23}$C(O)—, —NR$_{24}$SO$_2$—, or —SO$_2$NR$_{25}$—; and
R$_{21}$ to R$_{25}$ are each independently hydrogen, (C$_1$-C$_6$)alkyl, (C$_1$-C$_6$)alkyl(C$_6$-C$_{20}$)aryl or (C$_1$-C$_6$)alkyl(C$_3$-C$_{20}$)heteroaryl.

In certain preferred embodiments of these linkers, q is an integer from 4 to 20. In some embodiments q is an integer from 6 to 20. In other preferred embodiments, q is an integer from 2 to 12. In some embodiments, q is 2, 5 or 11.

In some embodiments of these linkers, r is preferably 2. In some embodiments of these linkers, p is preferably 2. In some embodiments of these linkers, q is an integer from 6 to 20. In some embodiments, V and Y are each independently —O—.

In some embodiments:
r is 2;
p is 2;
q is 2, 5, or 11, and
V is —O—.

In some embodiments of the invention, the at least one branching unit is

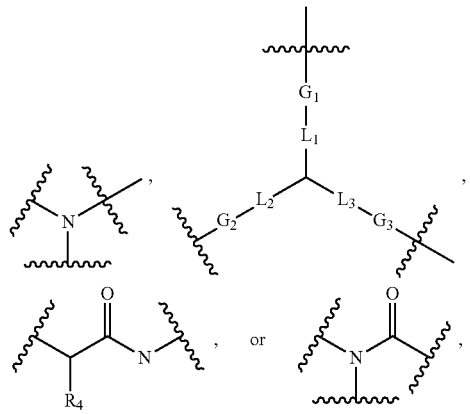

wherein $L_1$, $L_2$, $L_3$ is each independently a direct bond or $-C_nH_{2n}-$ where n is a integer of 1 to 30, wherein $G_1$, $G_2$, $G_3$ is each independently a direct bond,

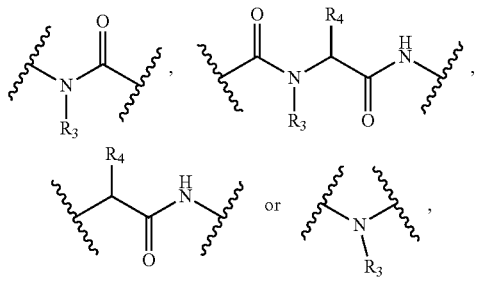

wherein $R_3$ is hydrogen or $C_1$-$C_{30}$ alkyl;

wherein $R_4$ is hydrogen or -$L_4$-COOR$_5$, wherein $L_4$ is a direct bond or $-C_nH_{2n}-$ wherein n is a integer of 1 to 10, and $R_5$ is hydrogen or $C_1$-$C_{30}$ alkyl.

A secondary linker (e.g., linking an active agent to the branching unit) may comprise a binding unit formed by a 1,3-dipolar cycloaddition reaction, hetero-Diels-Alder reaction, nucleophilic substitution reaction, non-aldol type carbonyl reaction, addition to a carbon-carbon multiple bond, oxidation reaction, or click reaction. A binding unit may be formed by a reaction between an acetylene and azide, or a non-aldol type carbonyl reaction, such as a reaction between an aldehyde or ketone group and hydrazine or alkoxyamine, reactions which allow for mild coupling of active agents and/or cleavage groups to the branching unit. Such binding units may be represented by Formula (A), (B), (C), or (D).

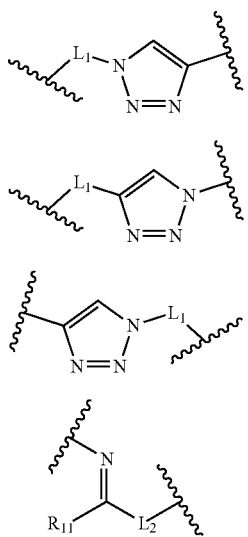

$L_1$ is a single bond or alkylene having 1 to 30 carbon atoms, preferably 10, 11, 12, 13, 14, 15, or 16 carbon atoms;

$R_{11}$ is hydrogen or an alkyl having 1 to 10 carbon atoms, preferably methyl; and $L_2$ is an alkylene having 1 to 30 carbon atoms, preferably 10, 11, 12, 13, 14, 15, or 16 carbon atoms.

In some embodiments of the invention, the primary linker, the first branch, or both comprises a connection unit represented by $-(CH_2CH_2X)_w-$, wherein:

X represents $-O-$, $(C_1$-$C_8)$alkylene, or $-NR_{21}-$, preferably $-O-$;

$R_{21}$ represents hydrogen, $(C_1$-$C_6)$alkyl, $(C_1$-$C_6)$alkyl$(C_6$-$C_{20})$aryl, or $(C_1$-$C_6)$alkyl$(C_3$-$C_{20})$heteroaryl, preferably hydrogen; and w is an integer from 1 to 12, preferably 1, 3, 6, or 12.

In some embodiments, X is $-O-$ and w is an integer from 6 to 12.

In some embodiments of the invention, the primary linker comprises a binding unit formed by a 1,3-dipolar cycloaddition reaction, hetero-Diels-Alder-reaction, nucleophilic substitution reaction, non-aldol type carbonyl reaction, addition to carbon-carbon multiple bond, oxidation reaction, or click reaction. In some embodiments, the binding unit is formed by a reaction between acetylene and azide, or a reaction between an aldehyde or ketone group and a hydrazine or alkoxyamine. In some embodiments, the binding unit is represented by any one of Formulas A, B, C, or D, preferably D:

(A)
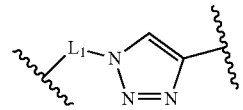

(B)
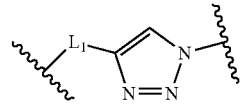

(C)
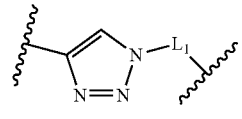

(D)
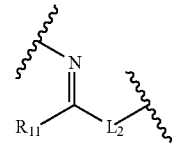

wherein:

$L_1$ is a single bond or alkylene having 1 to 30 carbon atoms, preferably 12;

$R_{11}$ is hydrogen or alkyl having 1 to 10 carbon atoms, preferably methyl; and $L_2$ is alkylene having 1 to 30 carbon atoms, preferably 11.

In some embodiments the primary linker comprises

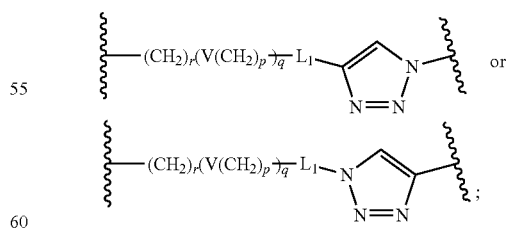

V is a single bond, $-O-$, $-S-$, $-NR_{21}-$, $-C(O)NR_{22}-$, $-NR_{23}C(O)-$, $-NR_{24}SO_2-$, or $-SO_2NR_{25}-$, preferably $-O-$;

$R_{21}$ to $R_{25}$ are each independently hydrogen, $(C_1$-$C_6)$alkyl, $(C_1$-$C_6)$alkyl$(C_6$-$C_{20})$aryl, or $(C_1$-$C_6)$alkyl$(C_3$-$C_{20})$heteroaryl;

r is an integer of 1 to 10, preferably 2 or 3;
p is an integer of 0 to 10, preferably 1 or 2;
q is an integer of 1 to 20, preferably 1 to 6; and
$L_1$ is a single bond.

In some embodiments, the primary linker comprises an O-substituted oxime; wherein
  a) the oxygen atom of the oxime is substituted with a group that covalently links the oxime to the active agent; e.g., via the branching unit; and
  the carbon atom of the oxime is substituted with a group that covalently links the oxime to the antibody; or
  b) the oxygen atom of the oxime is substituted with a group that covalently links the oxime to the antibody; and
  the carbon atom of the oxime is substituted with a group that covalently links the oxime to the active agent, e.g., via the branching unit.

In some embodiments, the antibody-drug conjugate comprises the structure of Formula III:

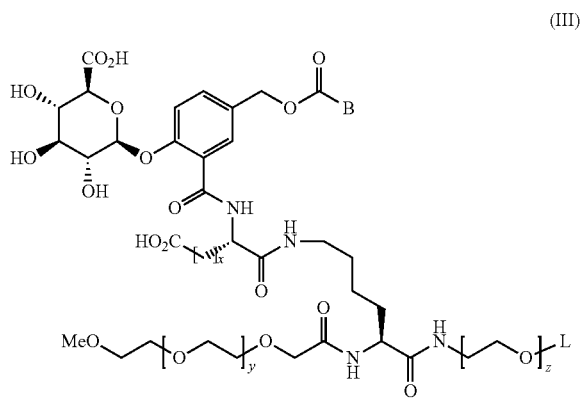

wherein:
B represents an active agent,
x represents an integer from 1 to 3;
y represents an integer from 0 to 20;
z represents an integer from 1 to 20; and
L represents a linkage to the antibody.

In some embodiments, y and z independently represent an integer from 1 to 20. In other embodiments, y and z independently represent an integer from 2 and 20. In certain preferred embodiments, y and z independently represent an integer from 1 to 19, most preferably from 4 to 20. In certain preferred embodiments, y and z independently represent an integer less than or equal to 20.

In some embodiments, the primary linker and/or the first branch comprises at least one polyethylene glycol moiety that comprises 1 to 20 —OCH$_2$CH$_2$— units, preferably 4 to 20 —OCH$_2$CH$_2$— units. In some preferred embodiments, the primary linker and/or the first branch comprises at least one polyethylene glycol moiety that comprises 3 to 12 —OCH$_2$CH$_2$— units. In some embodiments, the polyethylene glycol moiety terminates with a hydroxyl moiety, an amino group, or an alkyl ether.

In some embodiments of the invention, the antibody is a monoclonal antibody, polyclonal antibody, antibody fragment, Fab, Fab', Fab'-SH, F(ab')$_2$, Fv, single chain Fv ("scFv"), diabody, linear antibody, bispecific antibody, multispecific antibody, chimeric antibody, humanized antibody, human antibody, or fusion protein comprising the antigen-binding portion of an antibody.

In some embodiments of the invention, the antibody is selected from muromonab-CD3 abciximab, rituximab, daclizumab, palivizumab, infliximab, trastuzumab, etanercept, basiliximab, gemtuzumab, alemtuzumab, ibritumomab, adalimumab, alefacept, omalizumab, efalizumab, tositumomab, cetuximab, ABT-806, bevacizumab, natalizumab, ranibizumab, panitumumab, eculizumab, rilonacept, certolizumab, romiplostim, AMG-531, golimumab, ustekinumab, ABT-874, belatacept, belimumab, atacicept, an anti-CD20 antibody, canakinumab, tocilizumab, atlizumab, mepolizumab, pertuzumab, HuMax CD20, tremelimumab, ticilimumab, ipilimumab, IDEC-114, inotuzumab, HuMax EGFR, aflibercept, HuMax-CD4, teplizumab, otelixizumab, catumaxomab, the anti-EpCAM antibody IGN101, adecatumomab, oregovomab, dinutuximab, girentuximab, denosumab, bapineuzumab, motavizumab, efumgumab, raxibacumab, LY2469298, and veltuzumab.

In some embodiments, the one active agent is selected from chemotherapeutic agents and toxins.

In some embodiments, the active agent is selected from:
(a) erlotinib, bortezomib, fulvestrant, sutent, letrozole, imatinib mesylate, PTK787/ZK 222584, oxaliplatin, 5-fluorouracil, leucovorin, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethylenimine, altretamine, triethylenemelamine, trietylenephosphoramide, triethiylenethiophosphoramide, trimethylolomelamine, bullatacin, bullatacinone, camptothecin, camptothecin derivatives and metabolites (SN-38), topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, melphalan, novembichin, phenesterine, prednimustine, trofosfamide, uracil mustard, carmustine, chlorozotocin, fotemustine, lomustine, nimustine, ranimnustine, calicheamicin, calicheamicin gamma 1, calicheamicin omega 1, dynemicin, dynemicin A, clodronate, esperamicin, neocarzinostatin chromophore, aclacinomysins, actinomycin, antrmycin, azaserine, bleomycins, cactinomycin, carabicin, carninomycin, carzinophilin, chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, thiguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaziquone, 2,2',2''-trichlorotriethylamine, T-2 toxin, verracurin A, roridin A, and anguidine, urethane, vindesine, dacarbazine, mannomustine, mitobronitol, mitolactol, pipobroman, gacytosine, arabinoside, cyclophosphamide, thiotepa, paclitaxel, albumin-engineered nanoparticle formulation of paclitaxel, doxetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, xeloda, ibandronate, CPT-11, topoisomerase inhibitor RFS 2000, difluoromethylornithine, retinoic acid, capecitabine, or pharmaceutically acceptable salts, solvates or acids of any of the foregoing;

(b) monokine, a lymphokine, a traditional polypeptide hormone, parathyroid hormone, thyroxine, relaxin, prorelaxin, a glycoprotein hormone, follicle stimulating hormone, thyroid stimulating hormone, luteinizing hormone, hepatic growth factor fibroblast growth factor, prolactin, placental lactogen, tumor necrosis factor-α, tumor necrosis factor-β, mullerian-inhibiting substance, mouse gonadotropin-associated peptide, inhibin, activin, vascular endothelial growth factor, thrombopoietin, erythropoietin, an osteoinductive factor, an interferon, interferon-α, interferon-β, interferon-γ, a colony stimulating factor ("CSF"), macrophage-CSF, granulocyte-macrophage-CSF, granulocyte-CSF, an interleukin ("IL"), IL-1, IL-1α, IL-2, IL-3, IL-4, IL-5, IL-6, IL-7, IL-8, IL-9, IL-10, IL-11, IL-12, a tumor necrosis factor, TNF-α, TNF-β, a polypeptide factor, LIF, kit ligand, or a combination of any of the foregoing;

(c) diphtheria toxin, botulium toxin, tetanus toxin, dysentery toxin, cholera toxin, amanitin, amanitin derivatives, α-amanitin, pyrrolobenzodiazepine, pyrrolobenzodiazepine derivatives, tetrodotoxin, brevetoxin, ciguatoxin, ricin, AM toxin, tubulysin, geldanamycin, maytansinoid, calicheamicin, daunomycin, doxorubicin, methotrexate, vindesine, SG2285, dolastatin, a dolastatin analog, auristatin, cryptophycin, camptothecin, camptothecin derivatives and metabolites (SN-38), rhizoxin, a rhizoxin derivative, CC-1065, a CC-1065 analogue or derivative, duocarmycin, an enediyne antibiotic, esperamicin, epothilone, azonafide, aplidine, a toxoid, or a combination of any of the foregoing;

(d) an affinity ligand, wherein the affinity ligand is a substrate, an inhibitor, a stimulating agent, a neurotransmitter, a radioisotope, or a combination of any of the foregoing;

(e) a radioactive label, $^{32}$P, $^{35}$S, a fluorescent dye, an electron dense reagent, an enzyme, biotin, streptavidin, dioxigenin, a hapten, an immunogenic protein, a nucleic acid molecule with a sequence complementary to a target, or a combination of any of the foregoing;

(f) an immunomodulatory compound, an anti-cancer agent, an anti-viral agent, an anti-bacterial agent, an anti-fungal agent, and an anti-parasitic agent, or a combination of any of the foregoing;

(g) tamoxifen, raloxifene, droloxifene, 4-hydroxytamoxifen, trioxifene, keoxifene, LY117018, onapristone, or toremifene;

(h) 4(5)-imidazoles, aminoglutethimide, megestrol acetate, exemestane, letrozole, or anastrozole;

(i) flutamide, nilutamide, bicalutamide, leuprolide, goserelin, or troxacitabine;

(j) an aromatase inhibitor;

(k) a protein kinase inhibitor;

(l) a lipid kinase inhibitor;

(m) an antisense oligonucleotide;

(n) a ribozyme;

(o) a vaccine; and (p) an anti-angiogenic agent.

In some embodiments, the least one active agent is taltobulin or azonafide.

In some embodiments, the active agent is amanitin, auristatin, calicheamicin, camptothecin, camptothecin derivatives and metabolites (SN-38), cryptophycin, daunomycin, dolastatin, doxorubicin, duocarmycin, epothilone, esperamicin, geldanamycin, maytansinoid, methotrexate, monomethyl auristatin E ("MMAE"), monomethyl auristatin F ("MMAF"), pyrrolobenzodiazepine, rhizoxin, SG2285, tubulysin, vindesine, toxoid, or a derivative of any one of the foregoing. In certain embodiments, active agent is amanitin, MMAE, or MMAF, or a derivative of any one of the foregoing.

In some embodiments, the conjugate comprises one or more branched linkers comprising a moiety selected from:

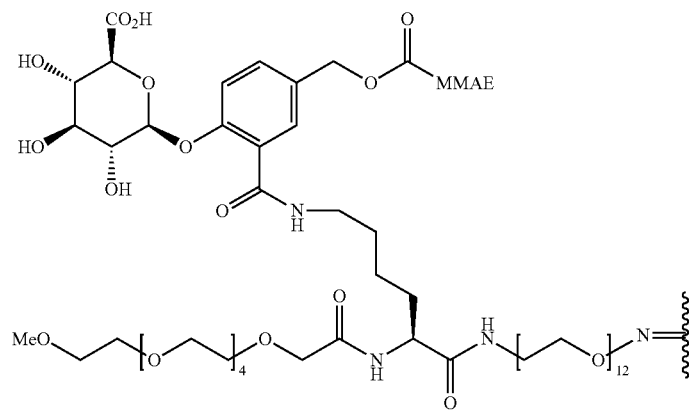

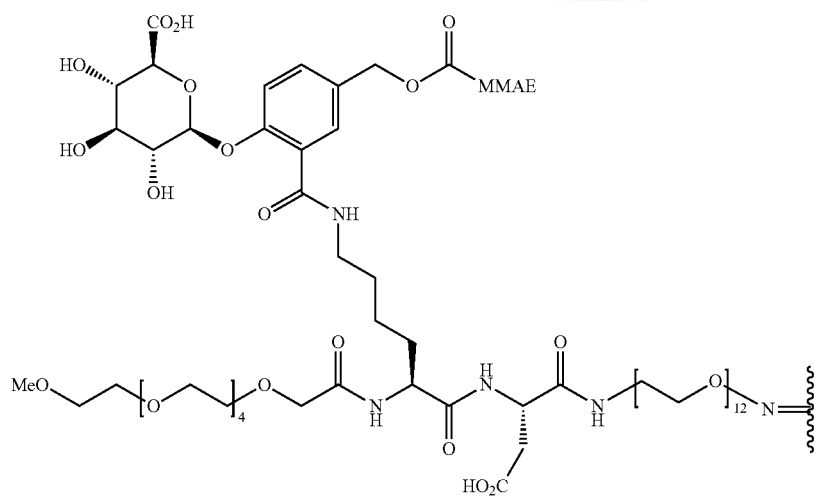
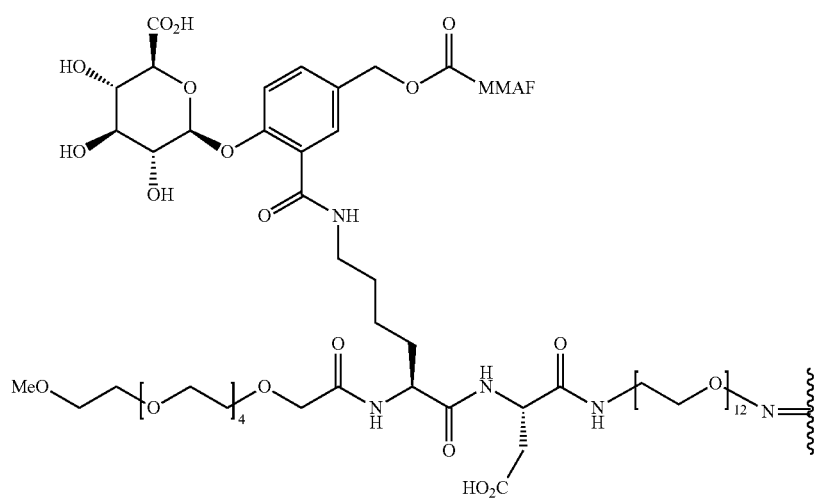
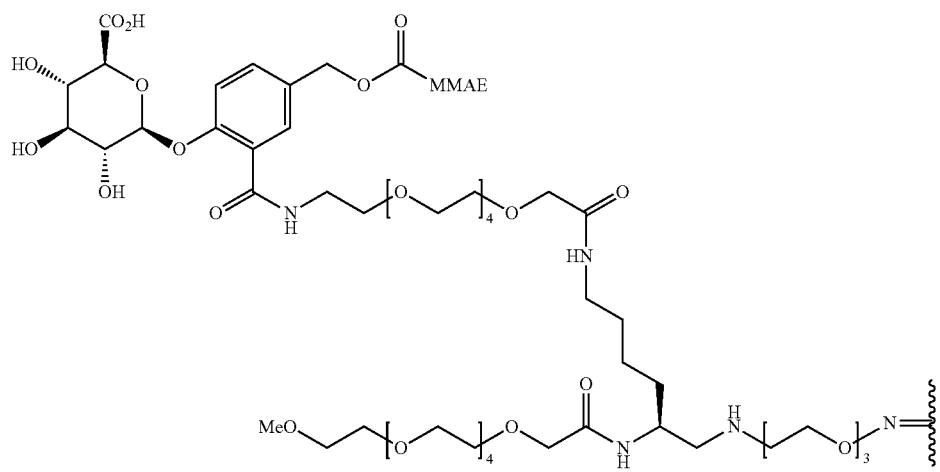

-continued
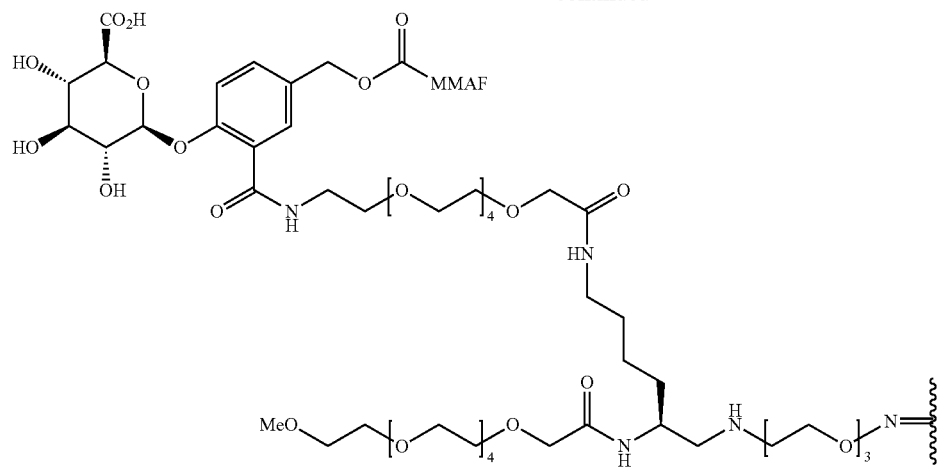
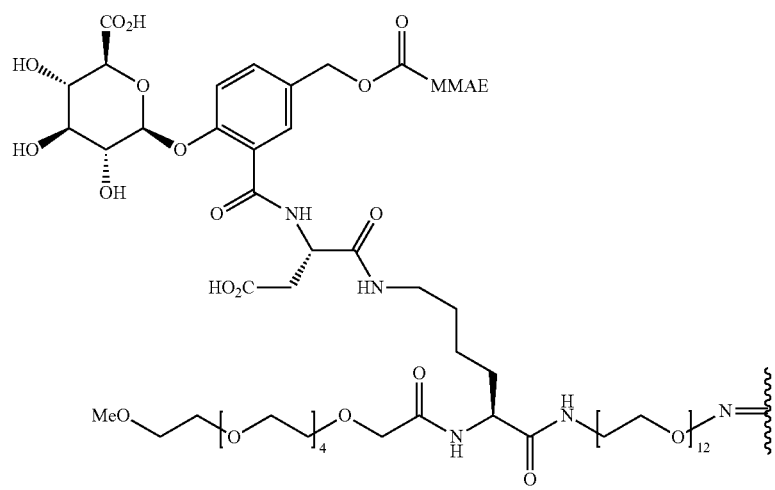
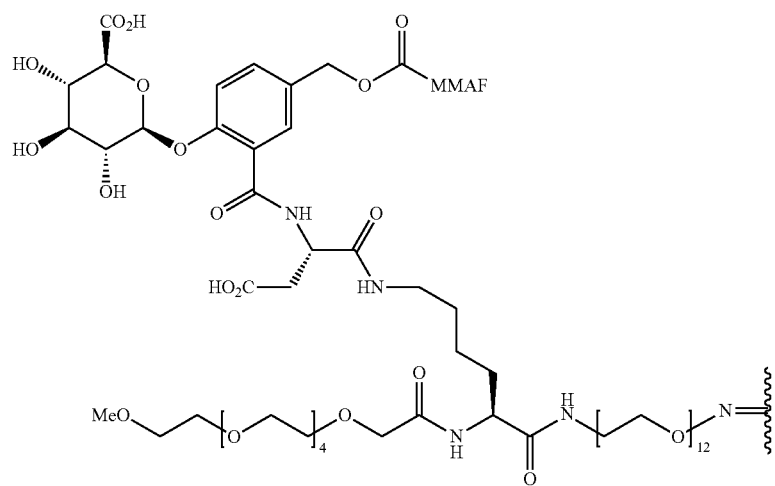

-continued
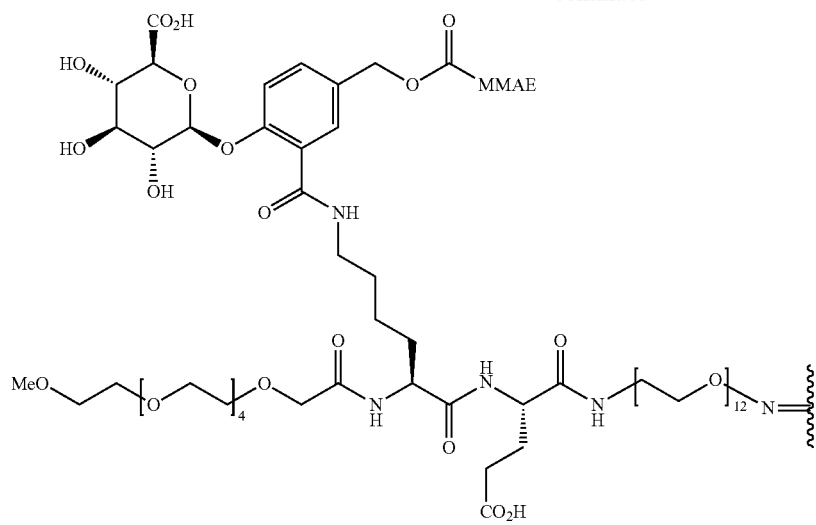
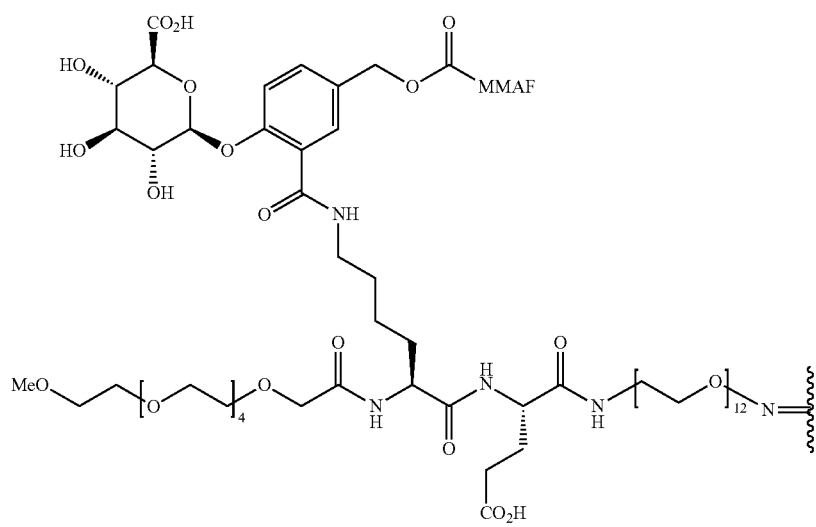
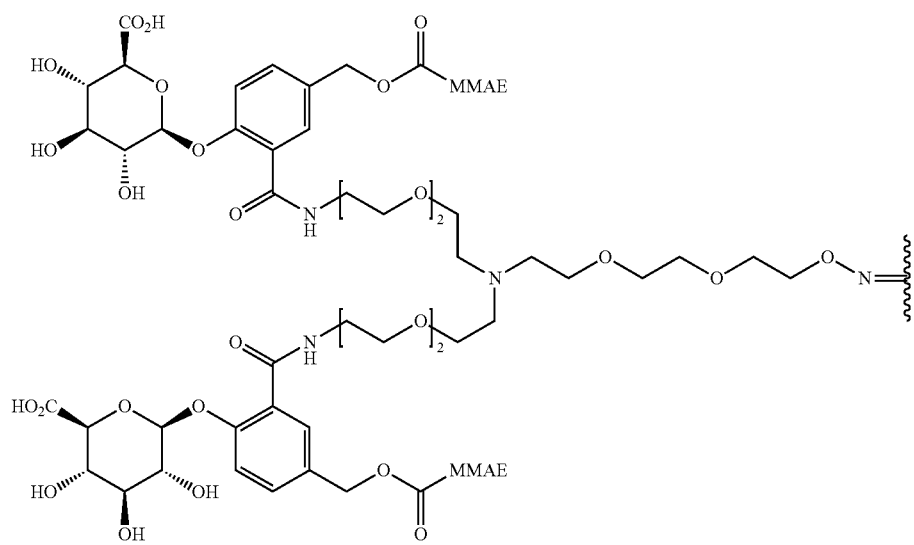

-continued
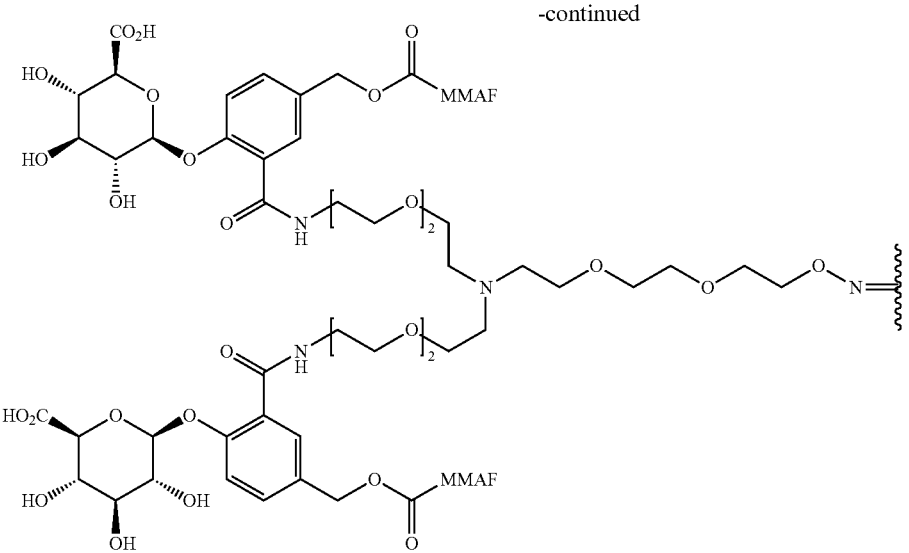
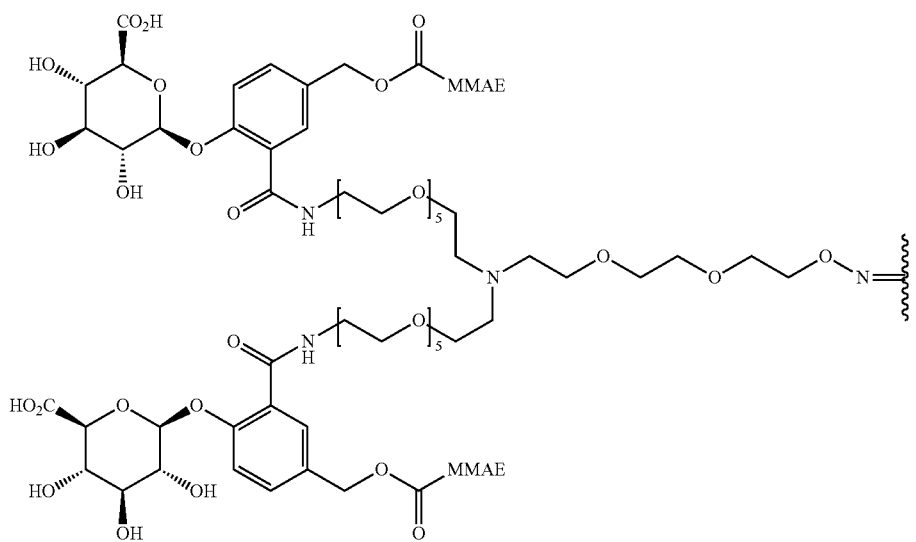
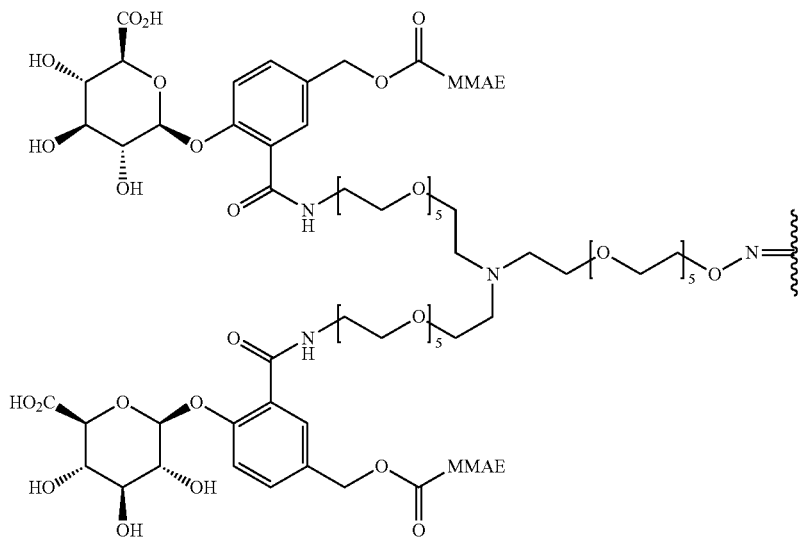

-continued
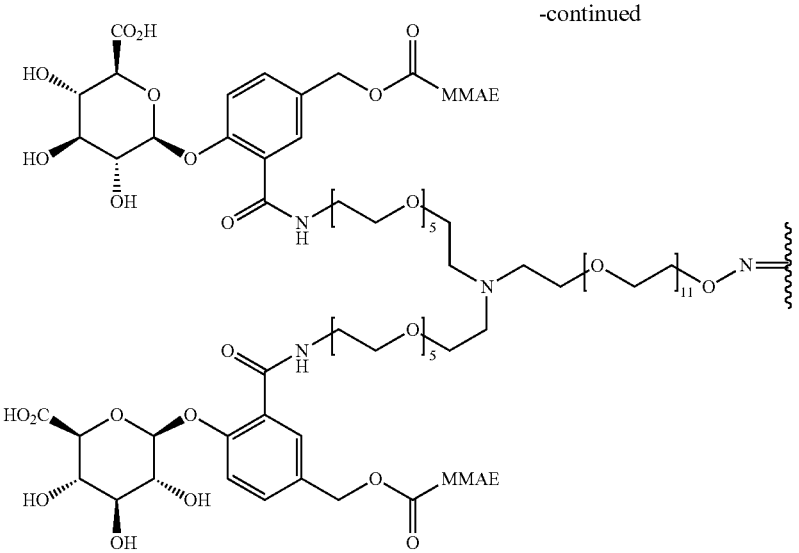
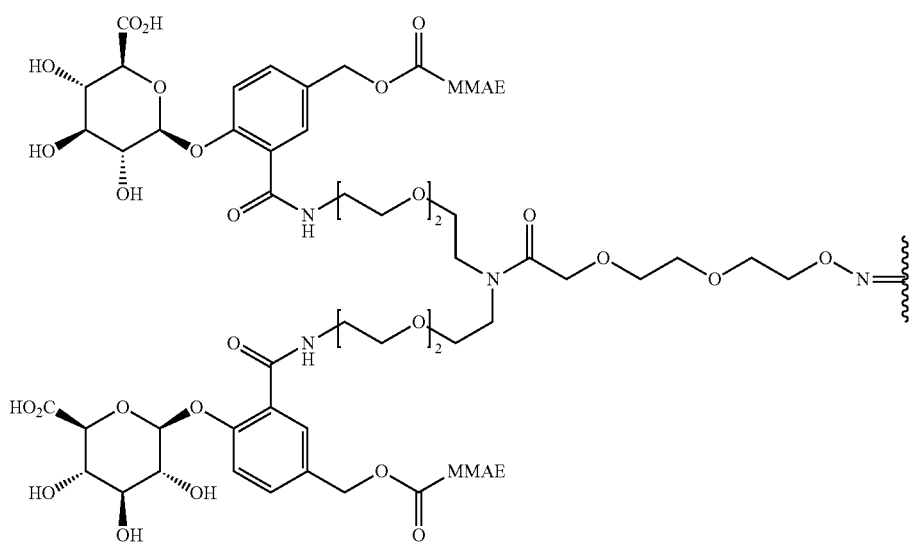
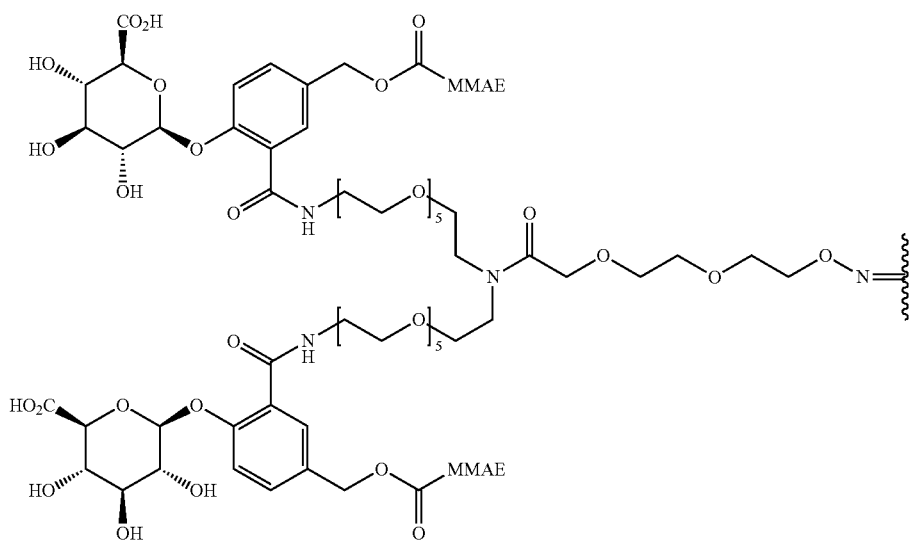

-continued
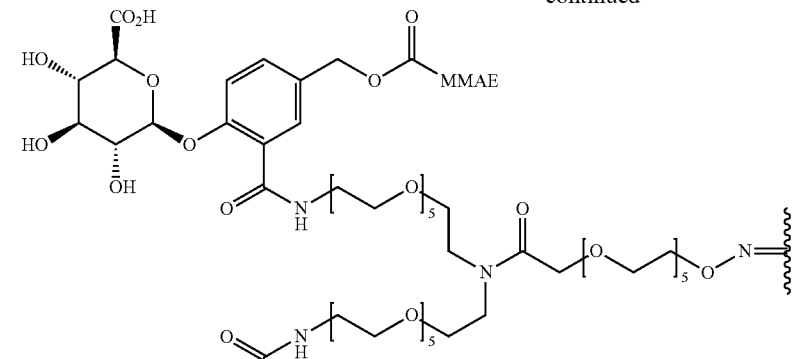
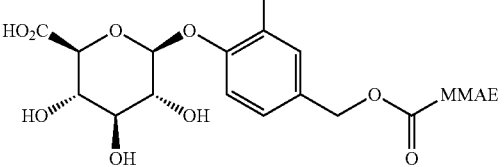
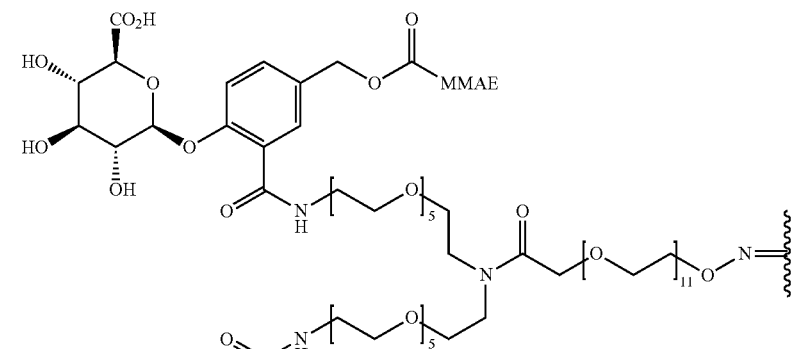
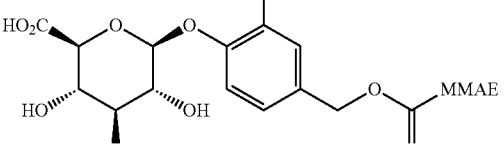
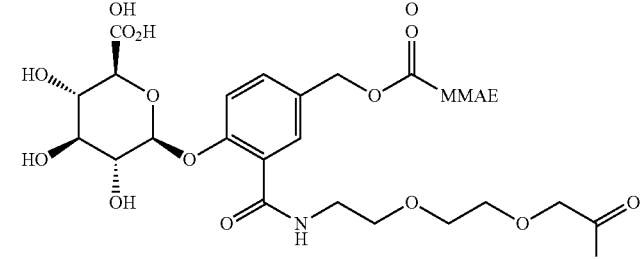
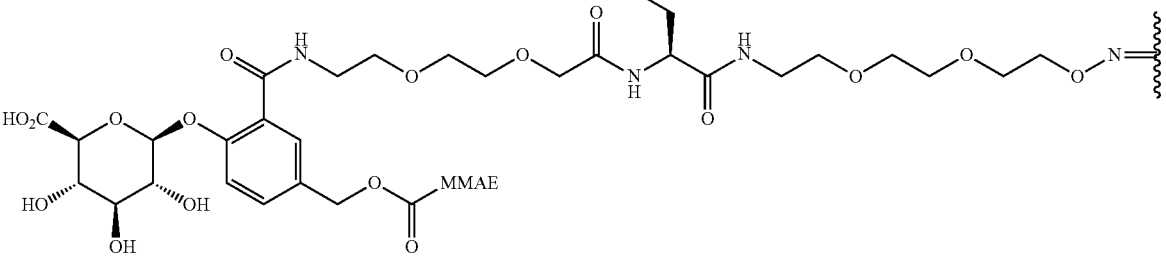

-continued
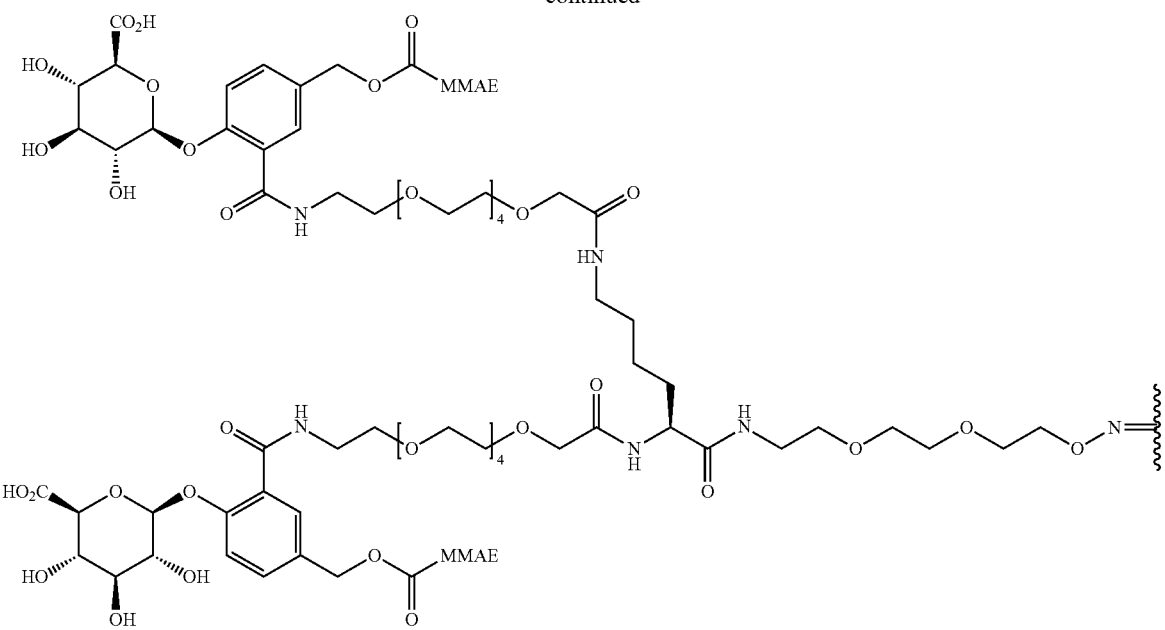
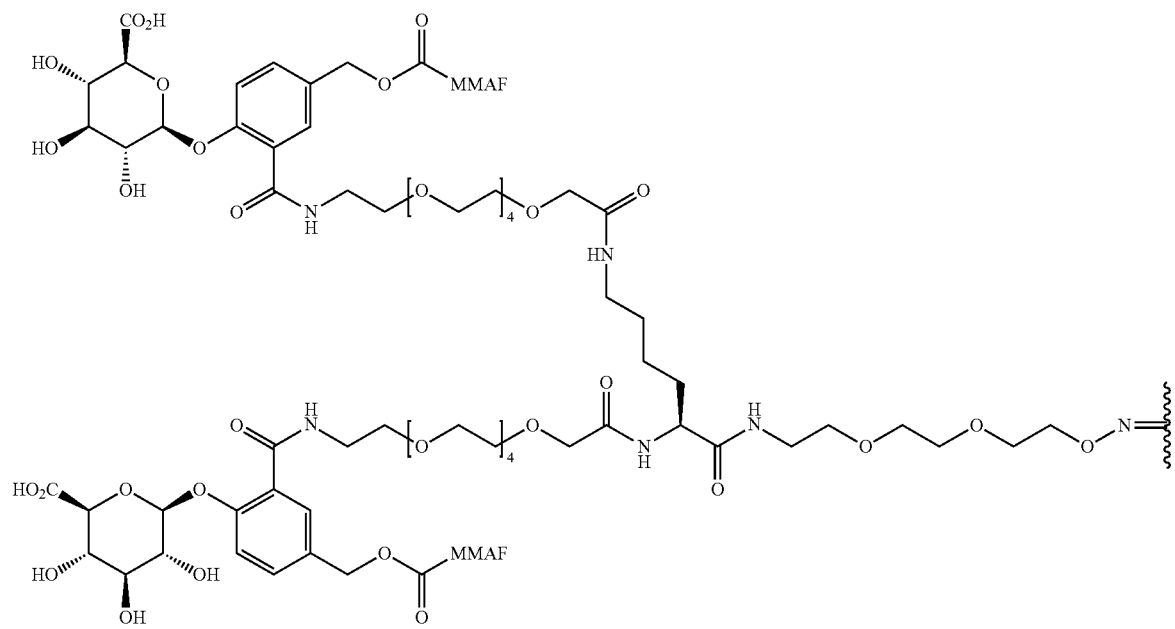

-continued
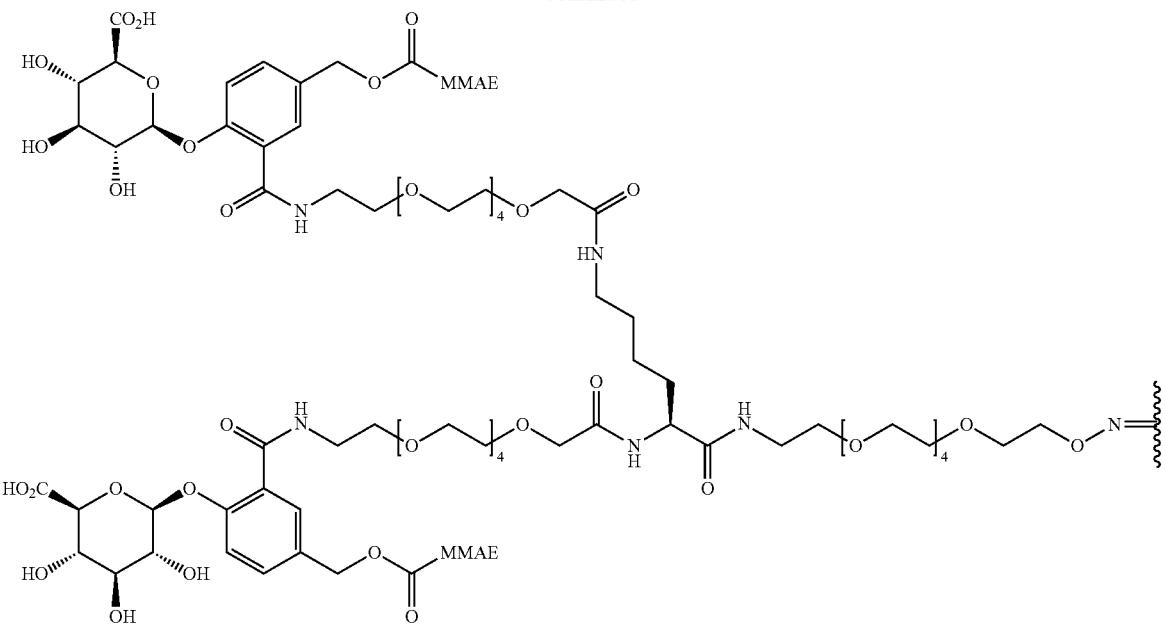
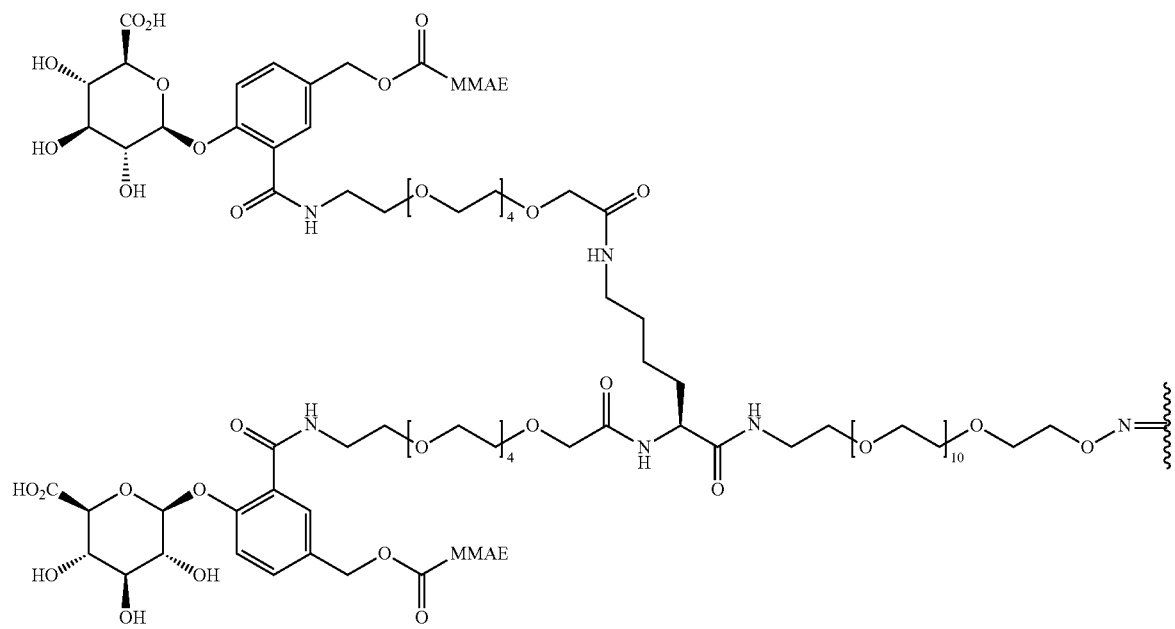

-continued
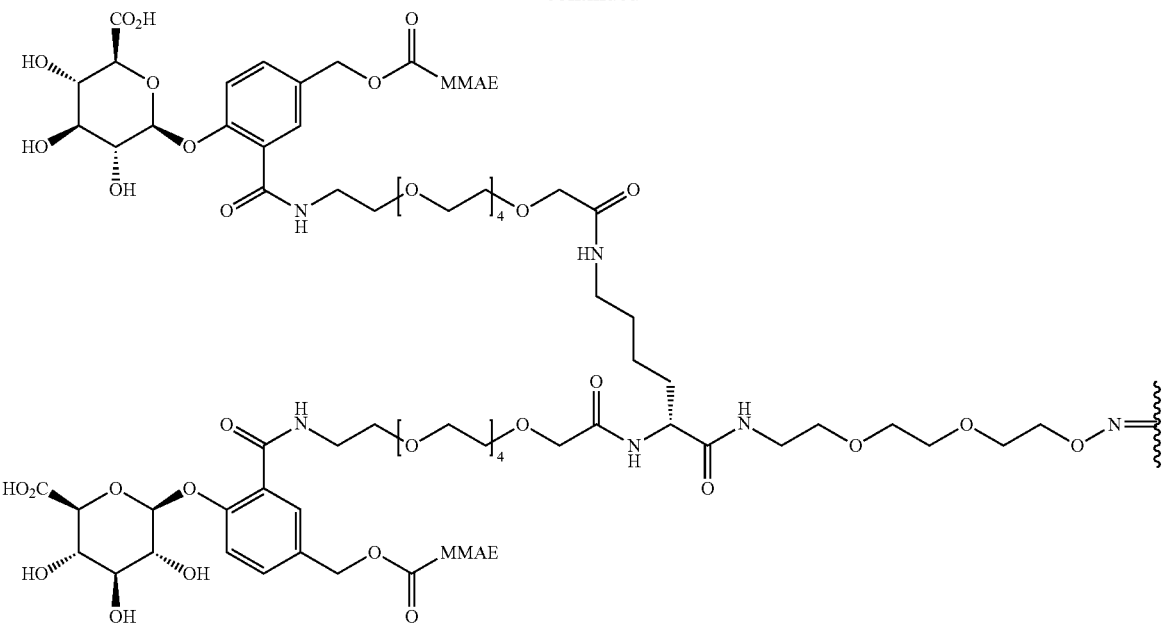
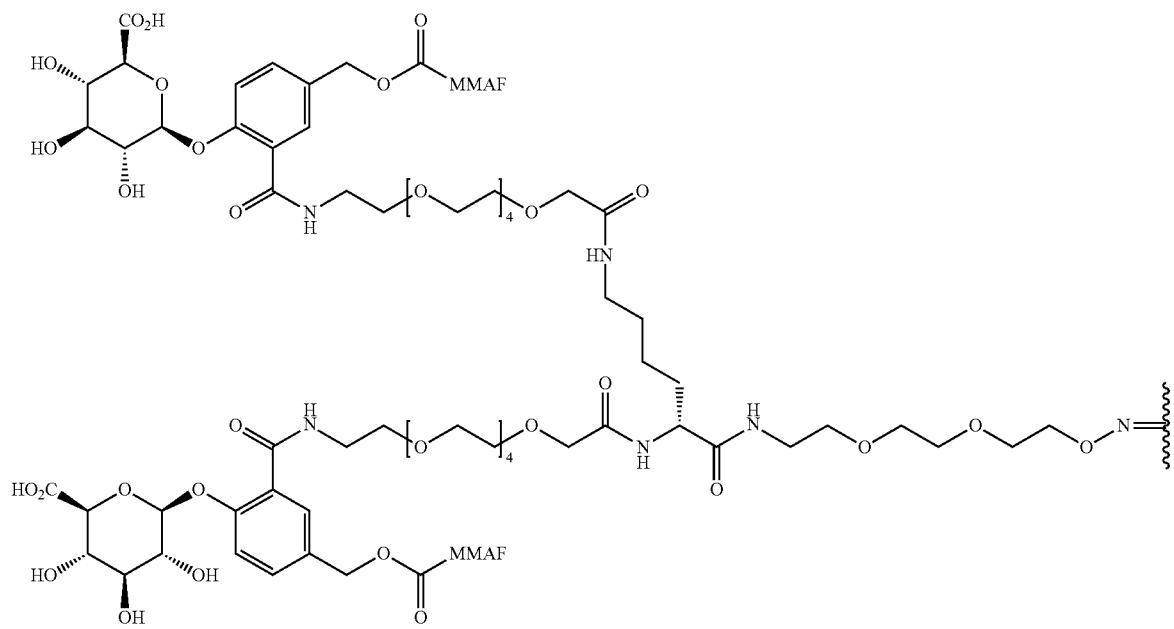

-continued
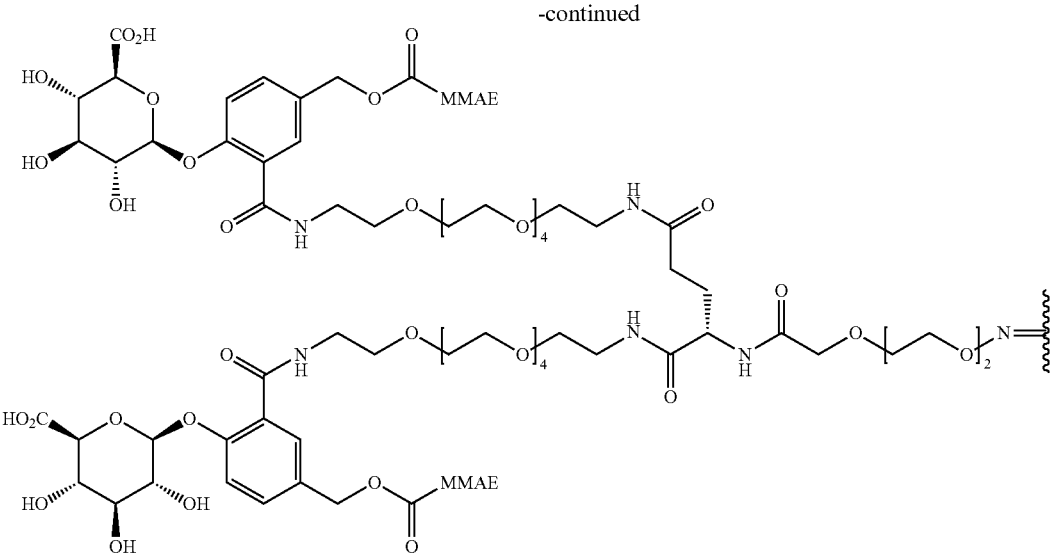
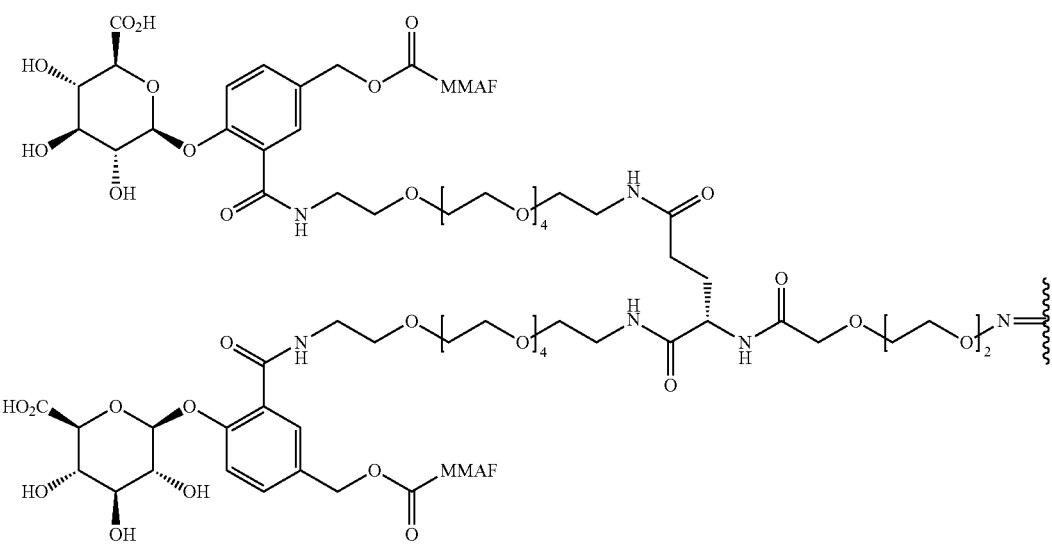
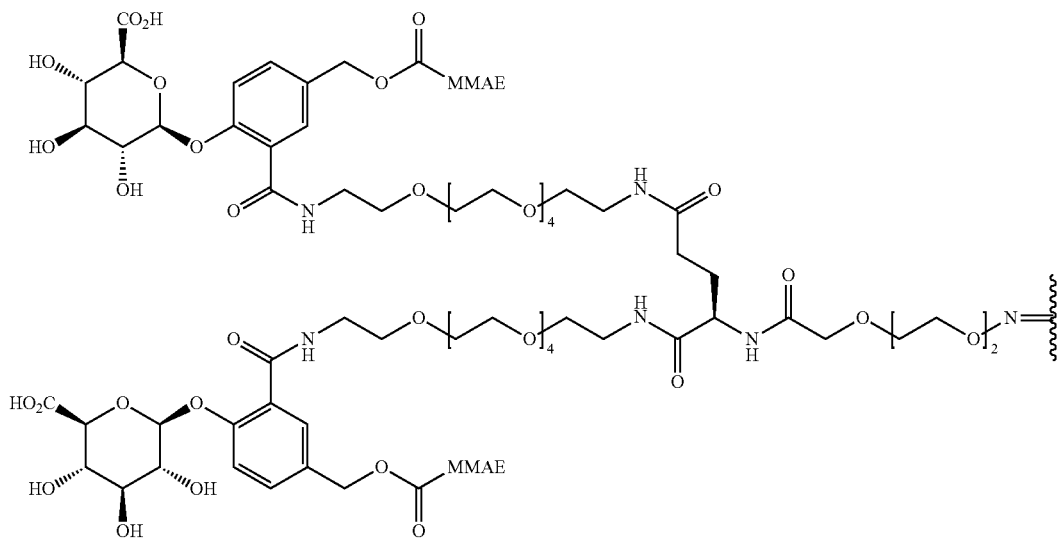

-continued
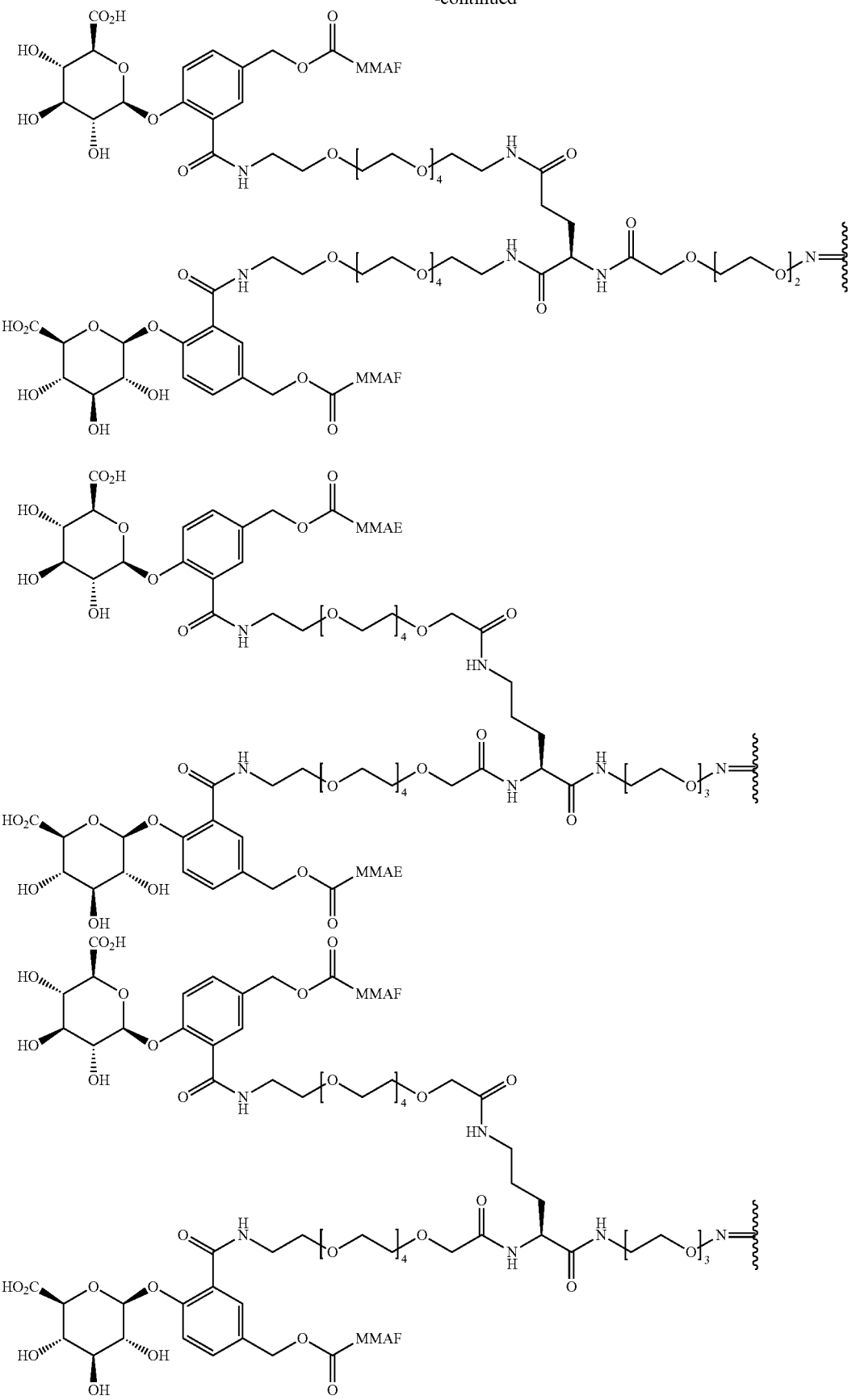

-continued
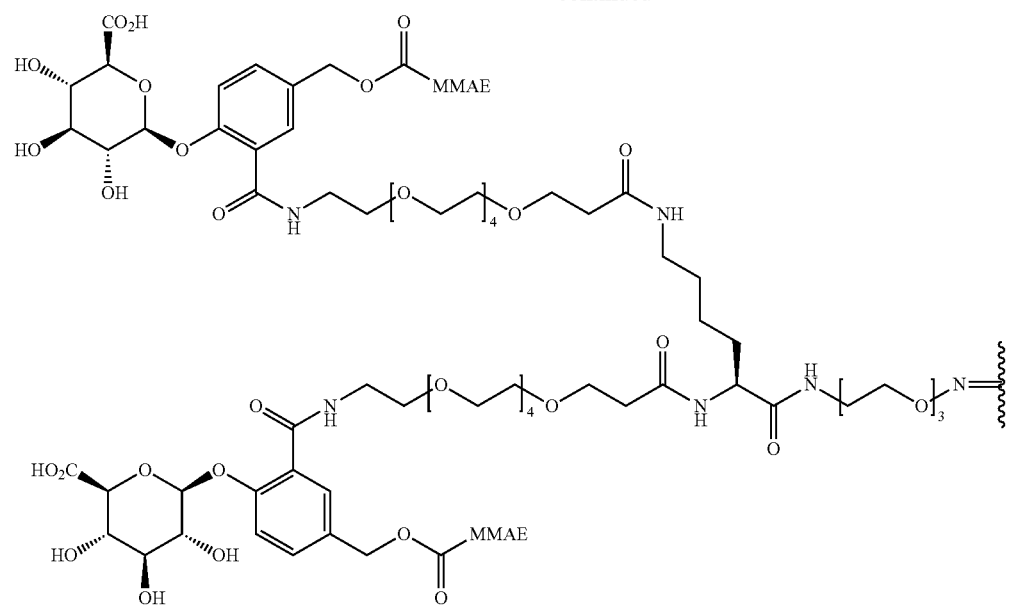
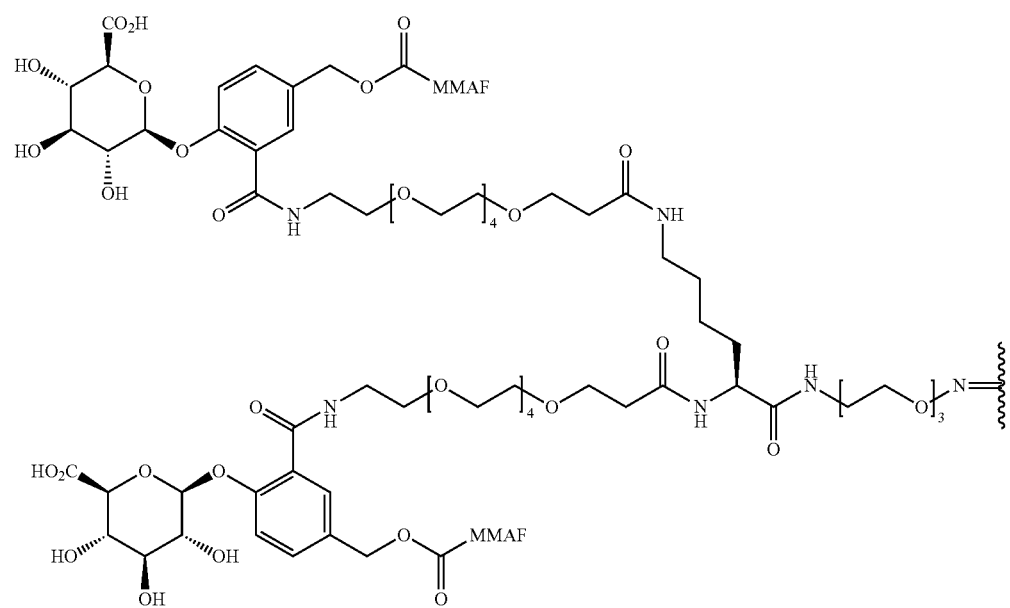

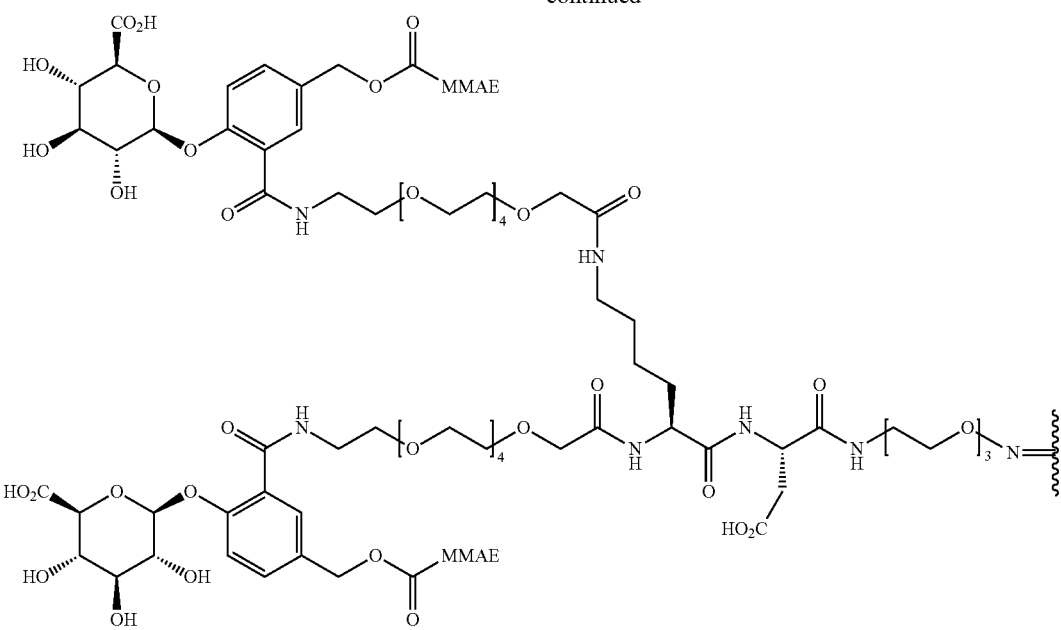
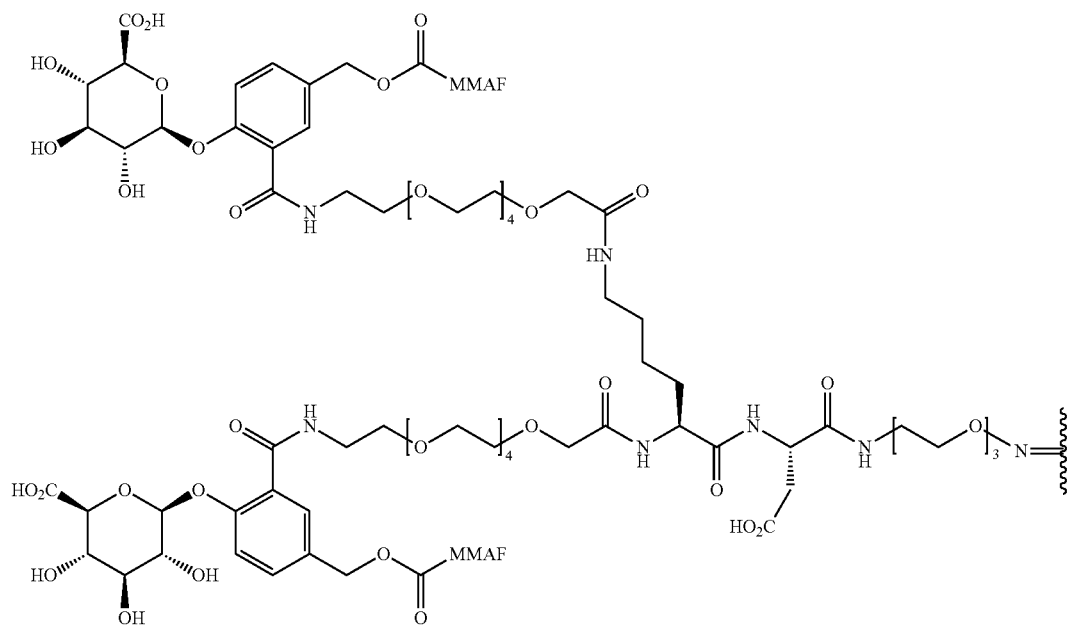

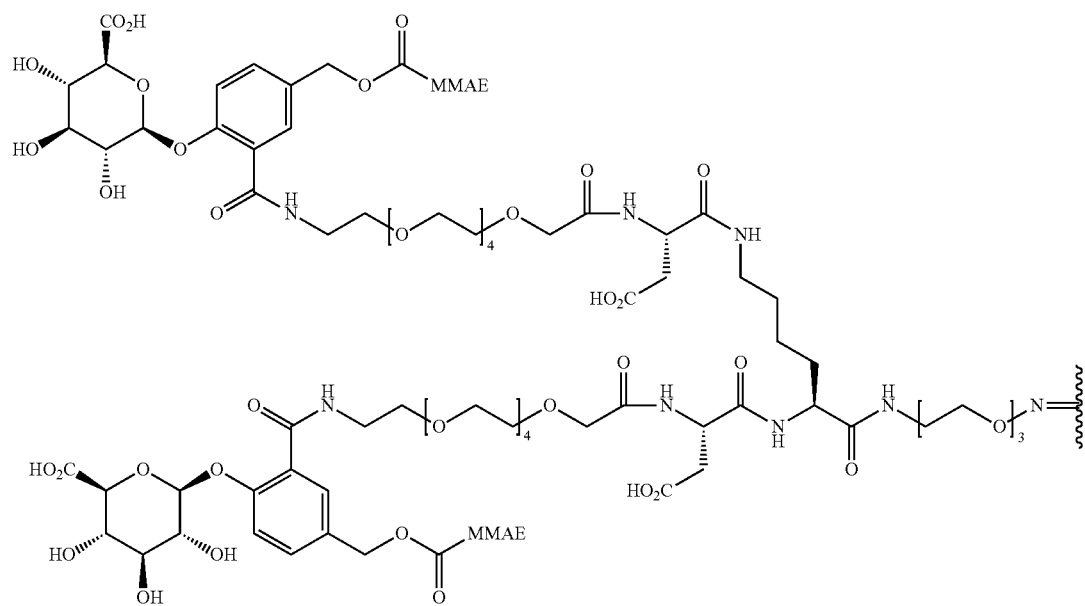
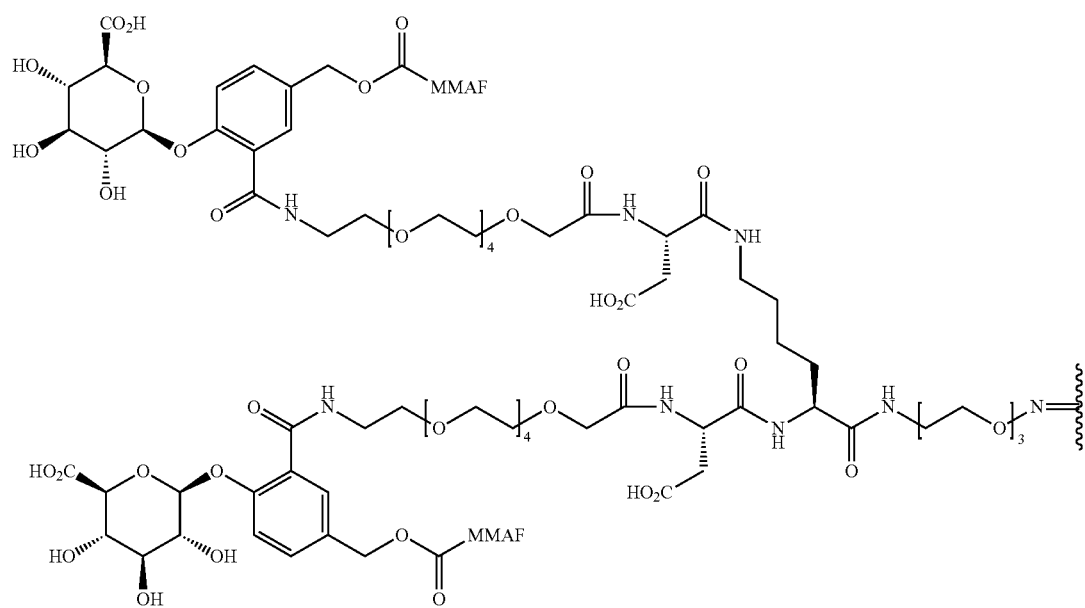

-continued
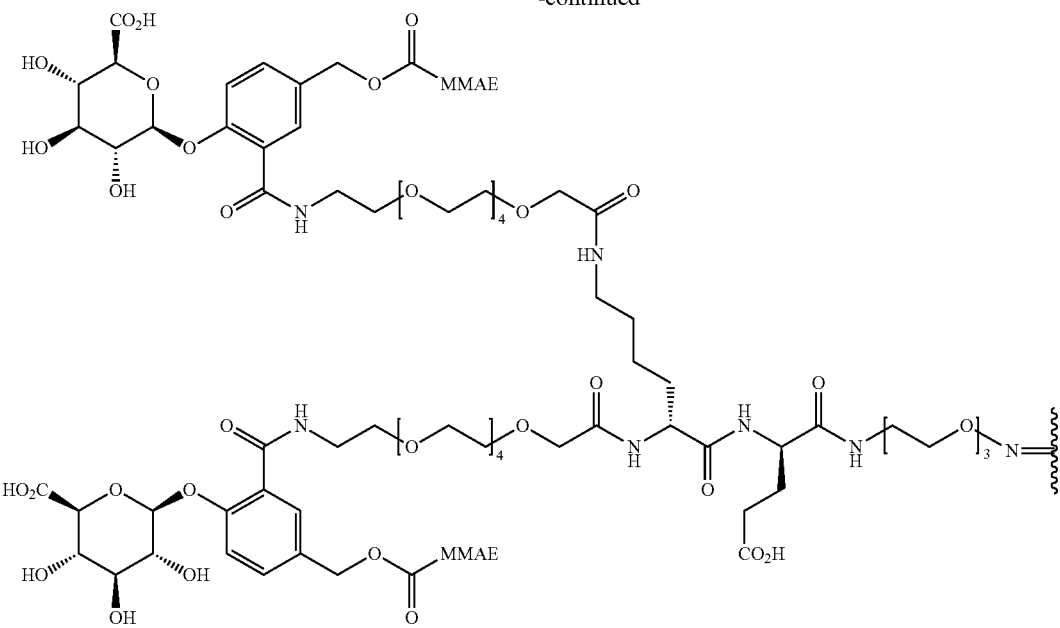
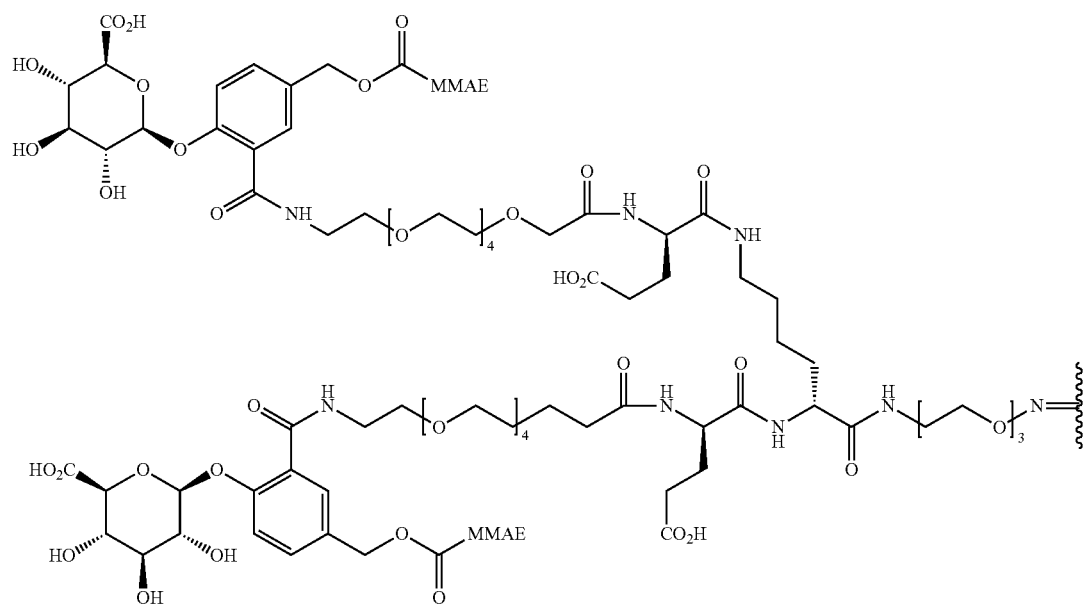

-continued
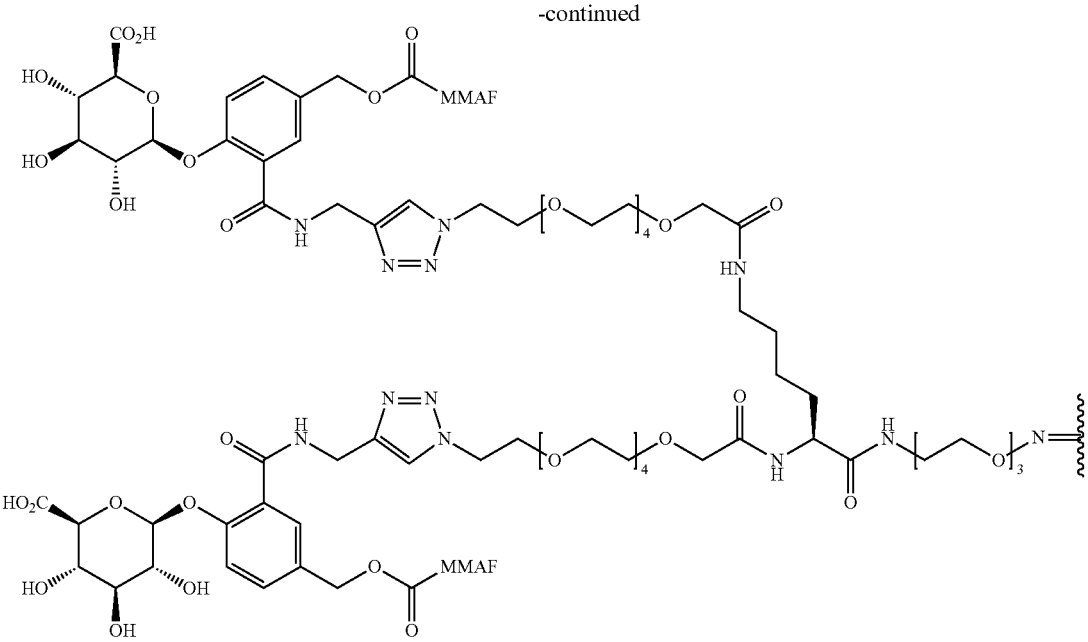

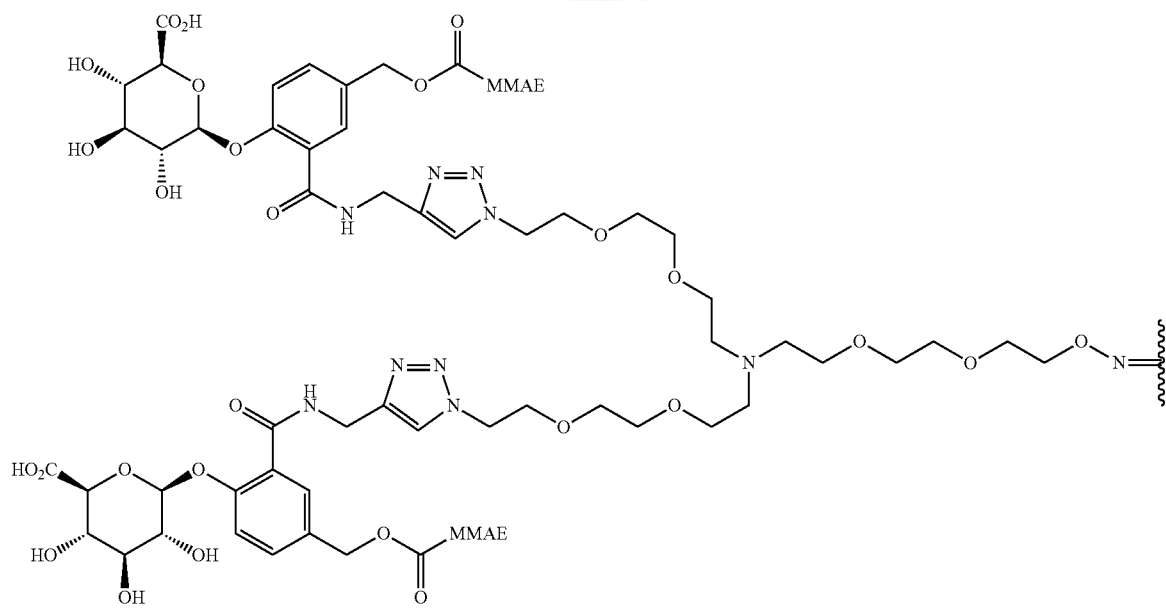
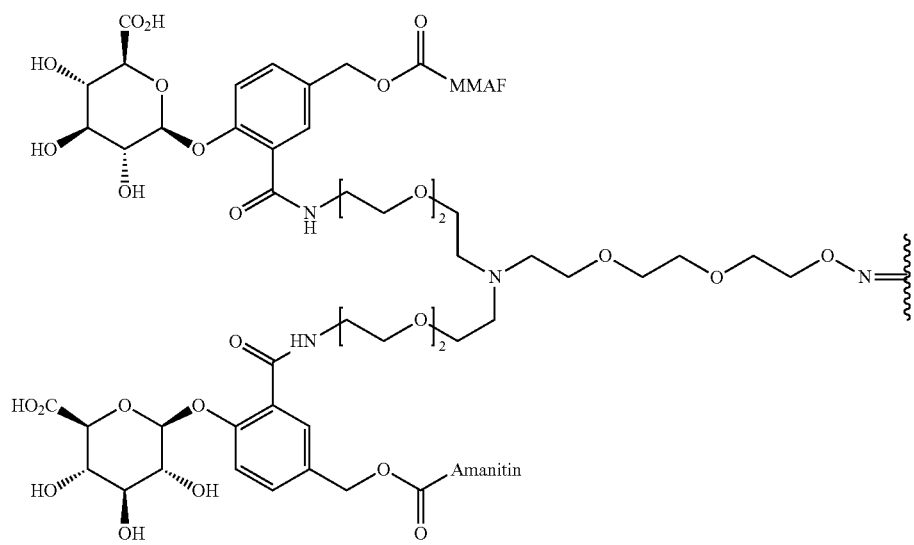

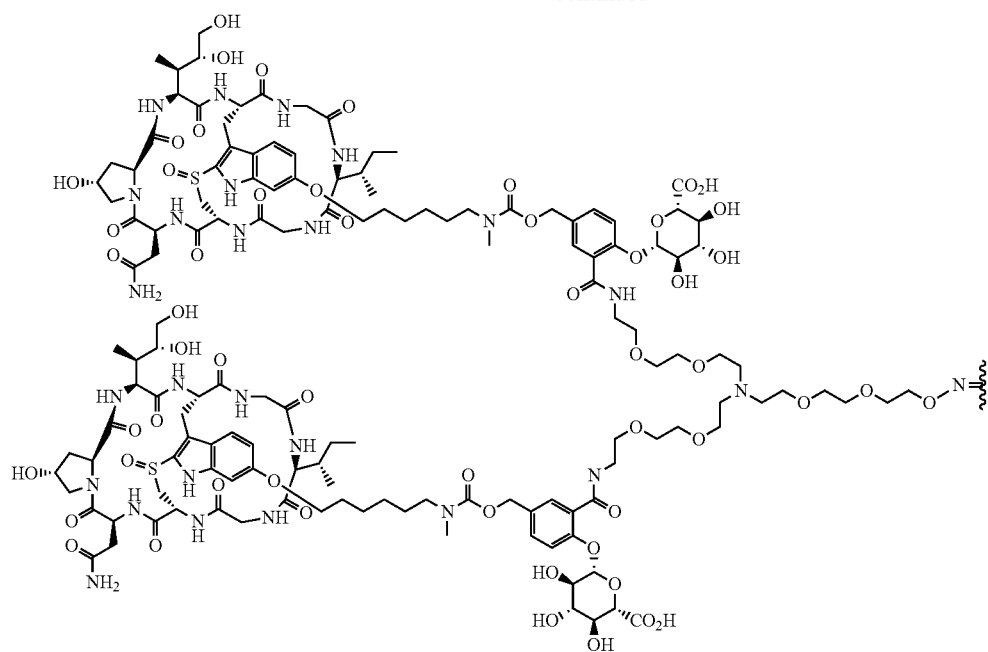
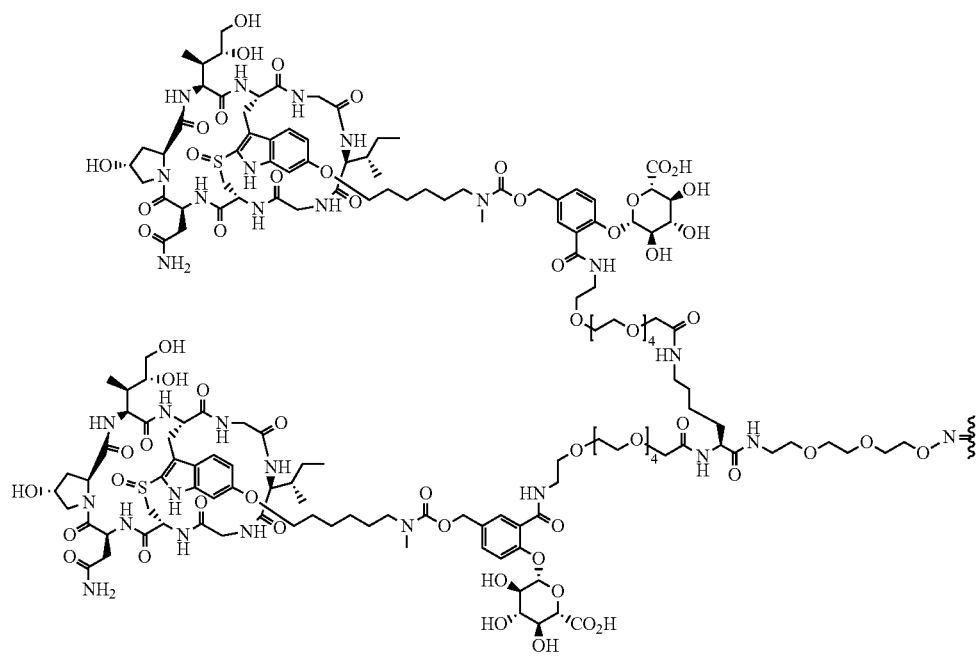

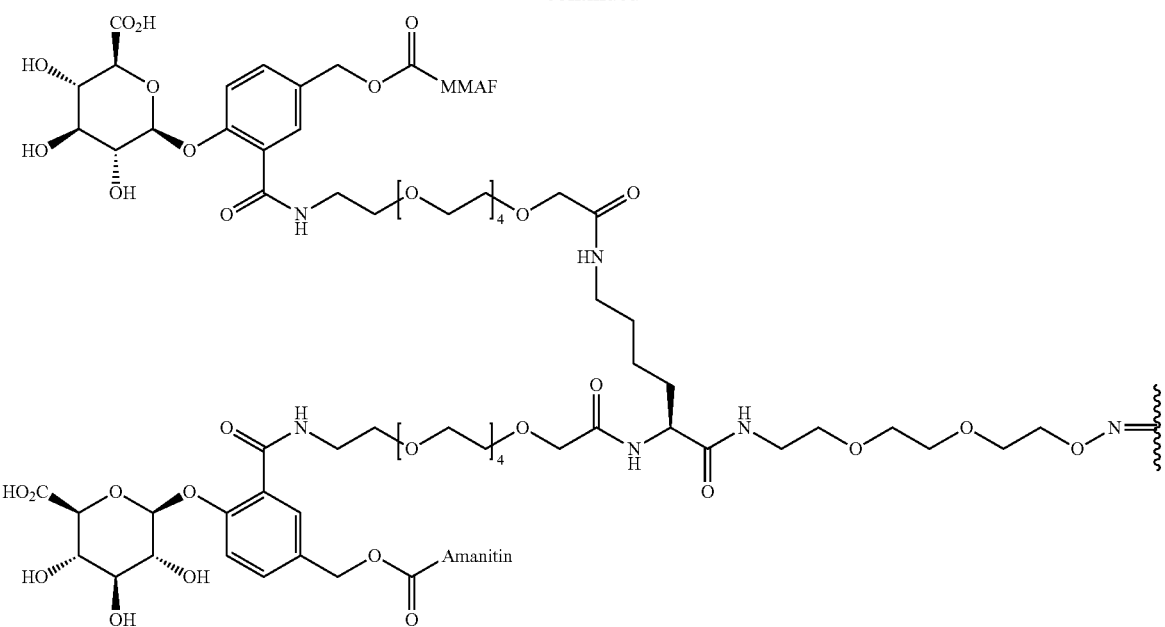
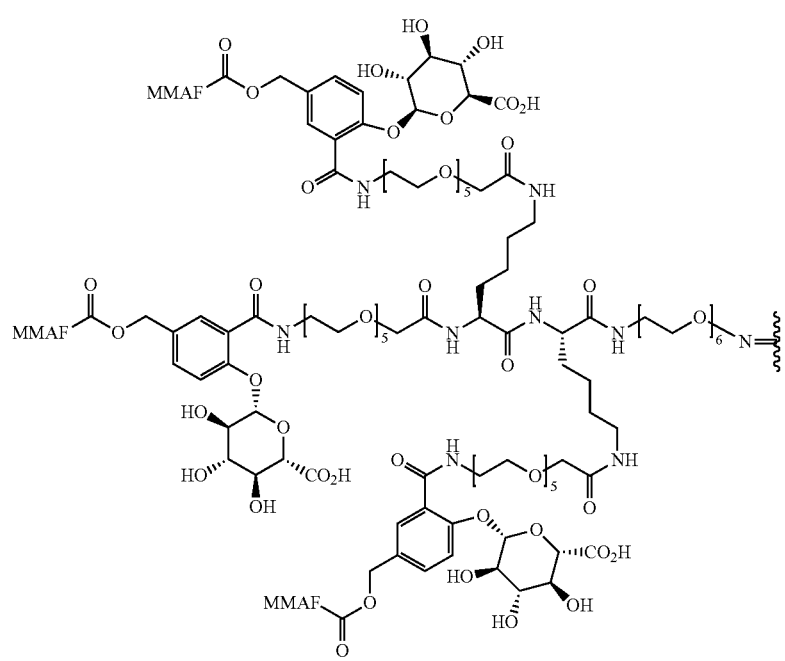

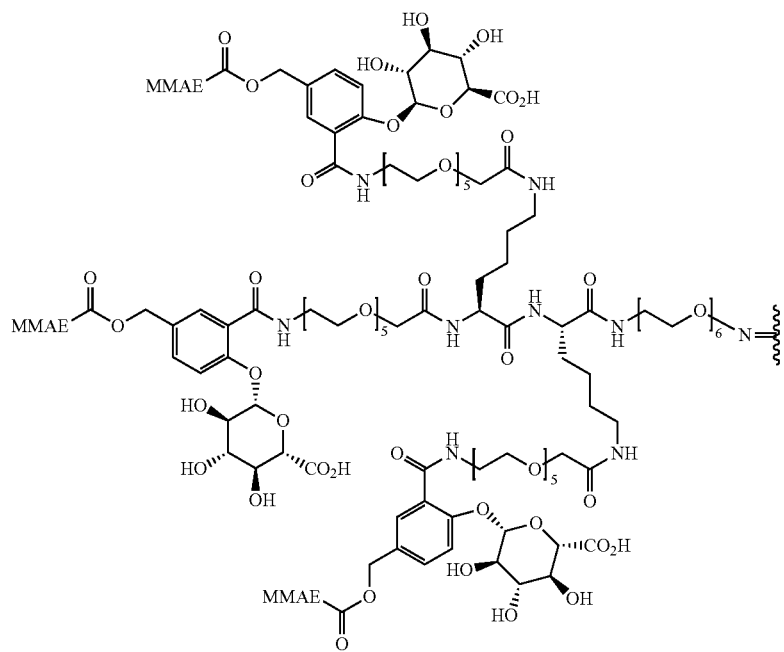
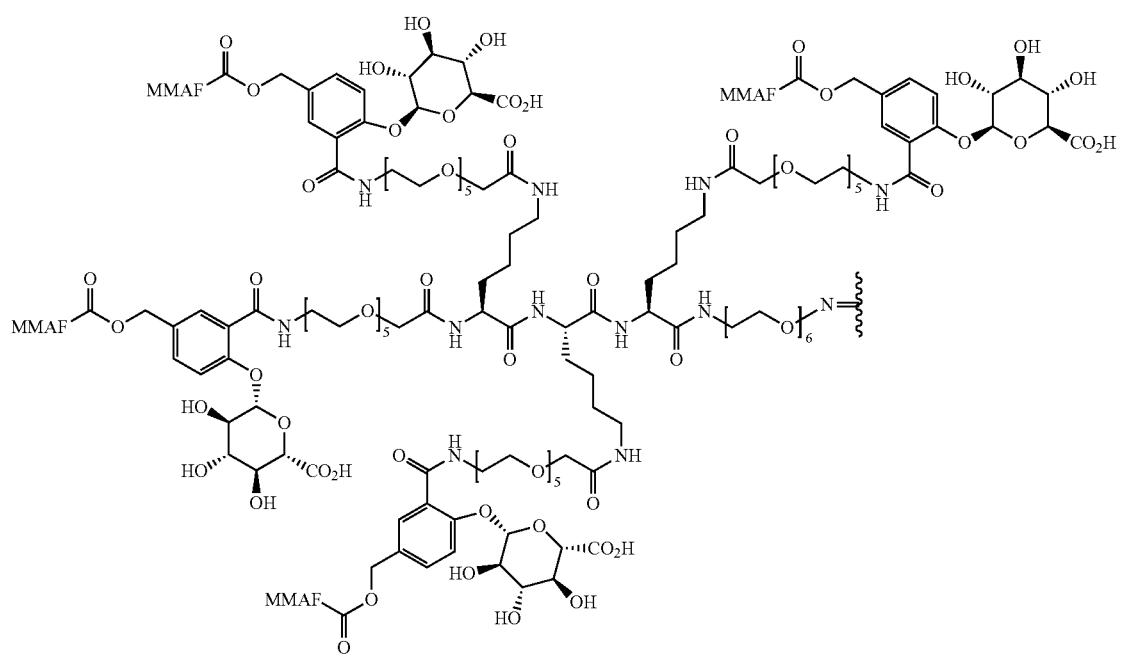

73    74
-continued
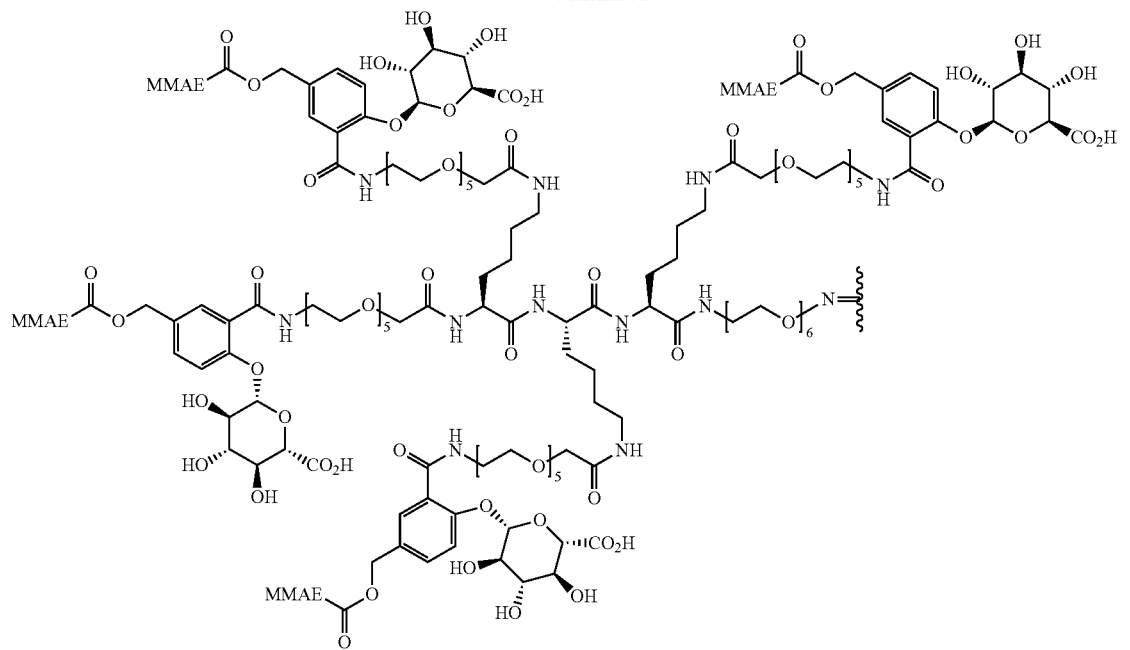
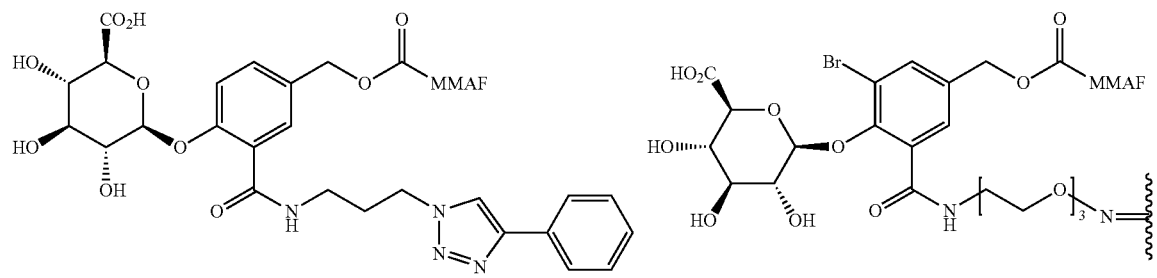
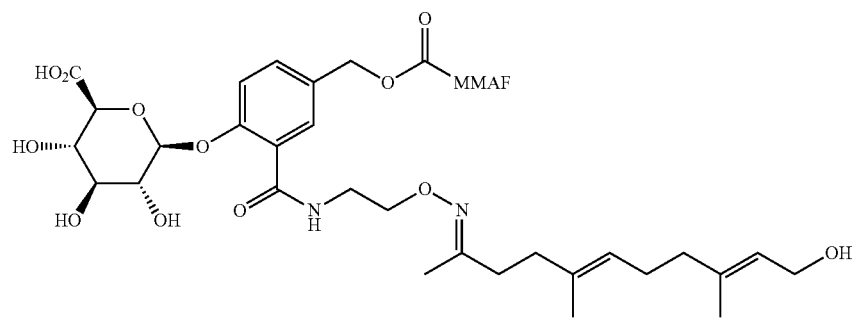
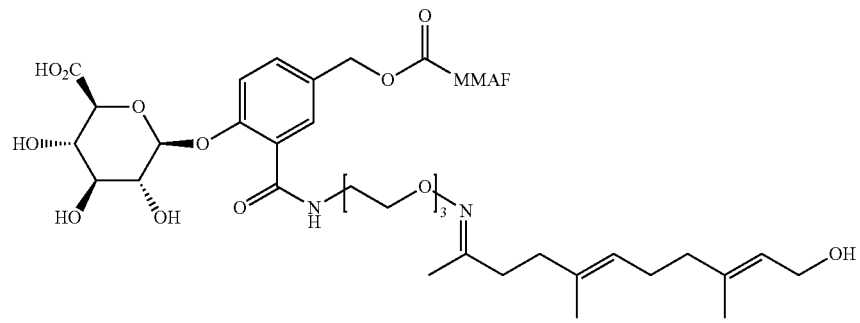

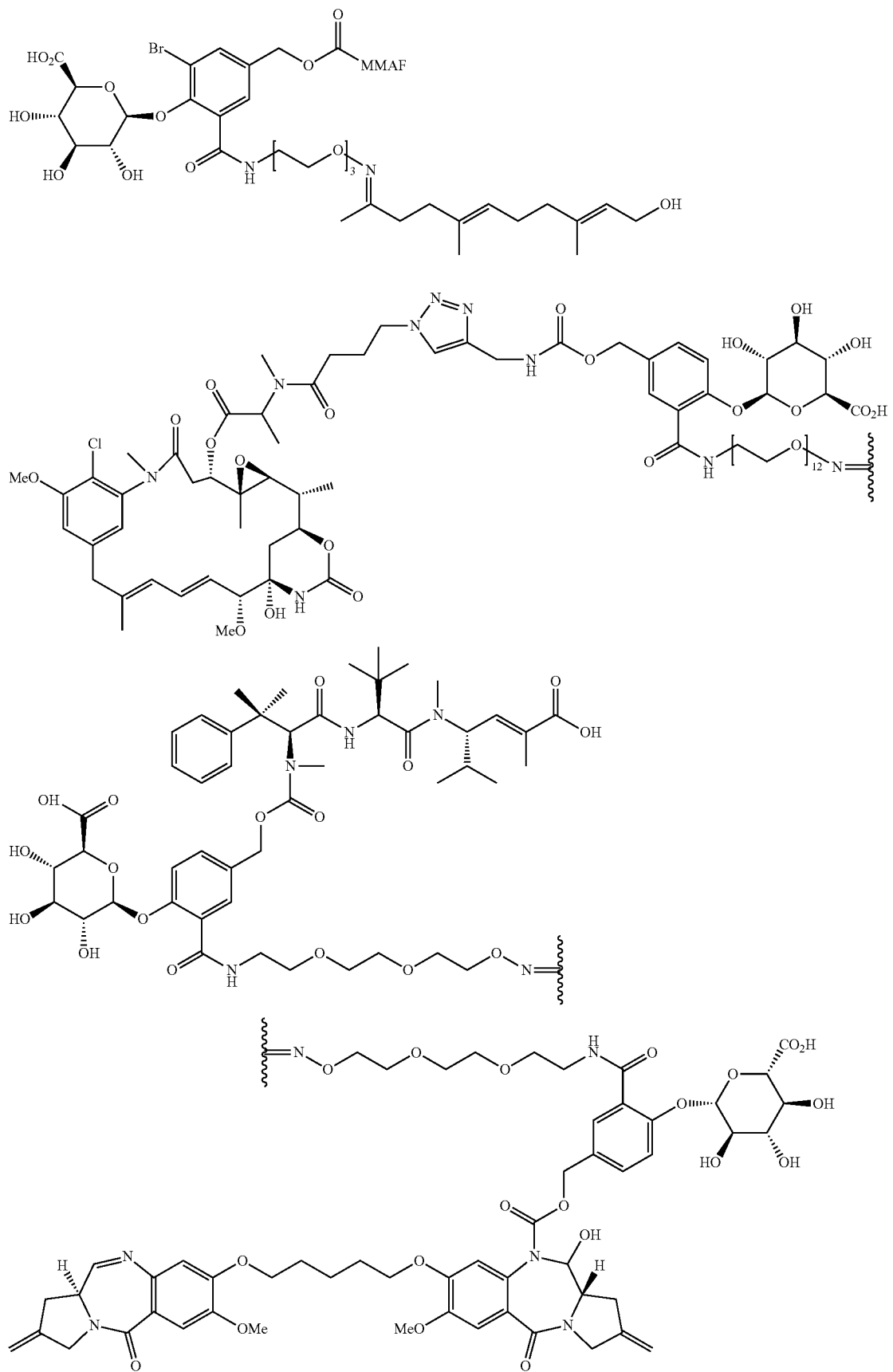

-continued
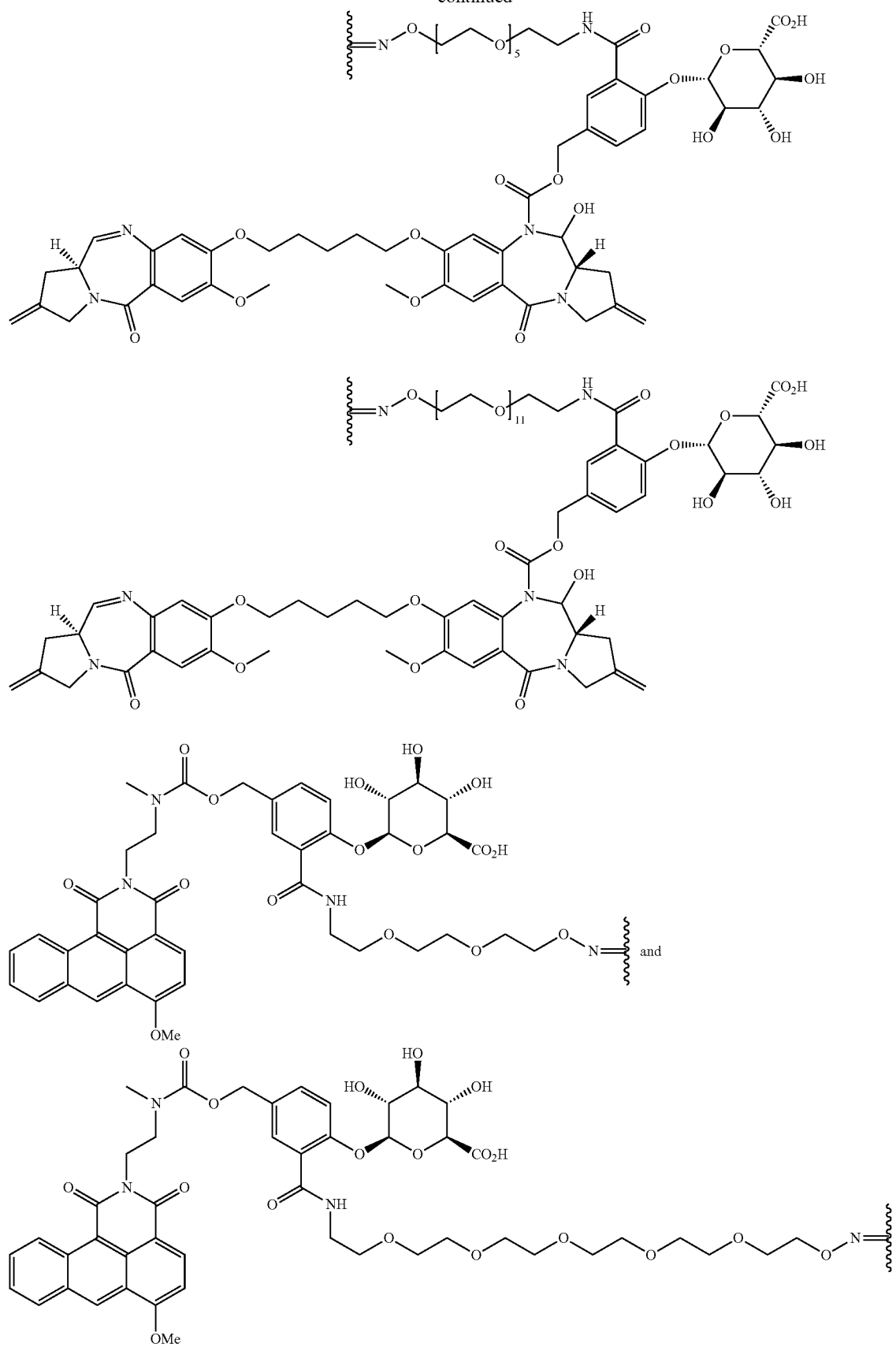

In some embodiments, the active agent is:
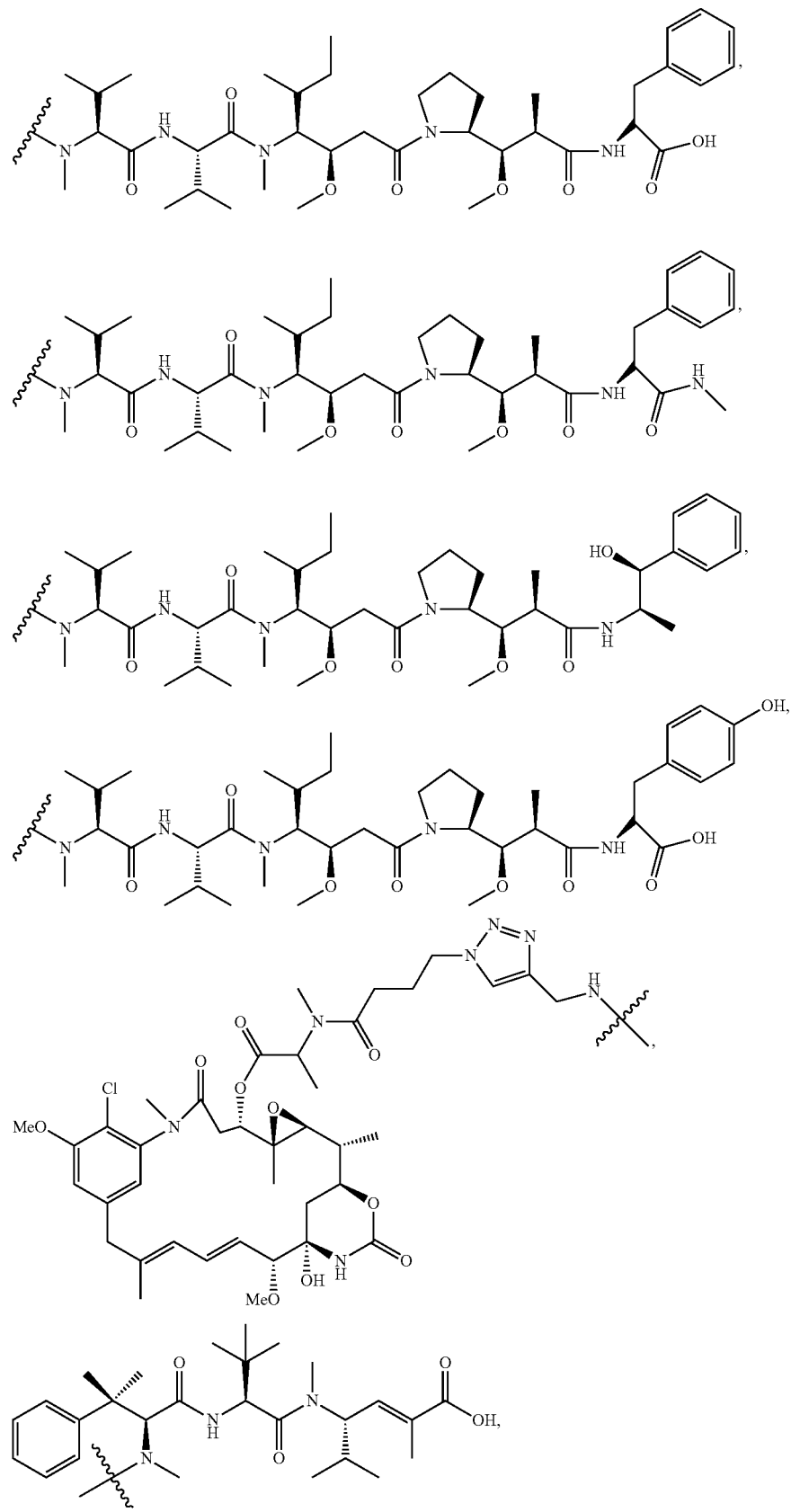

-continued
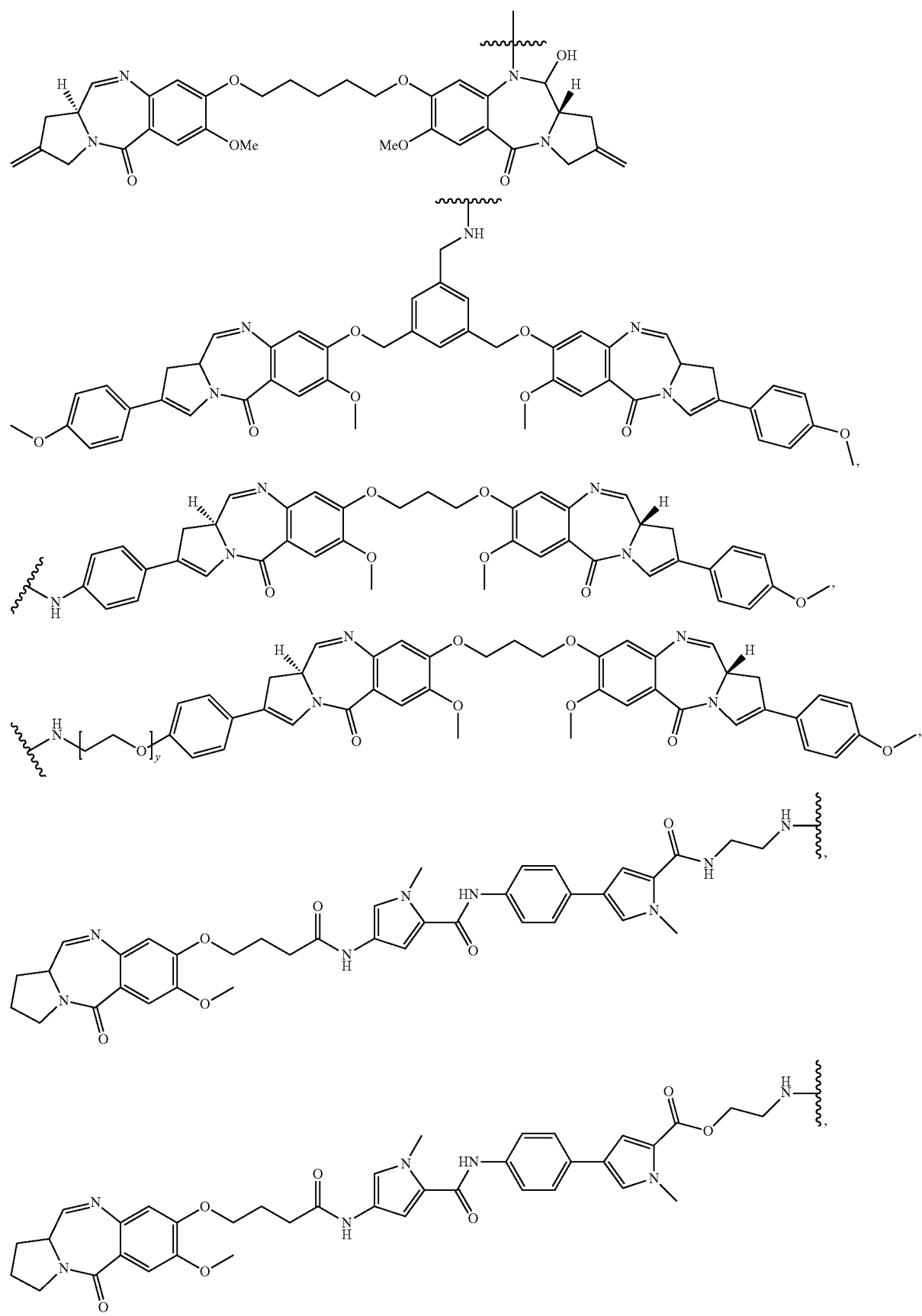

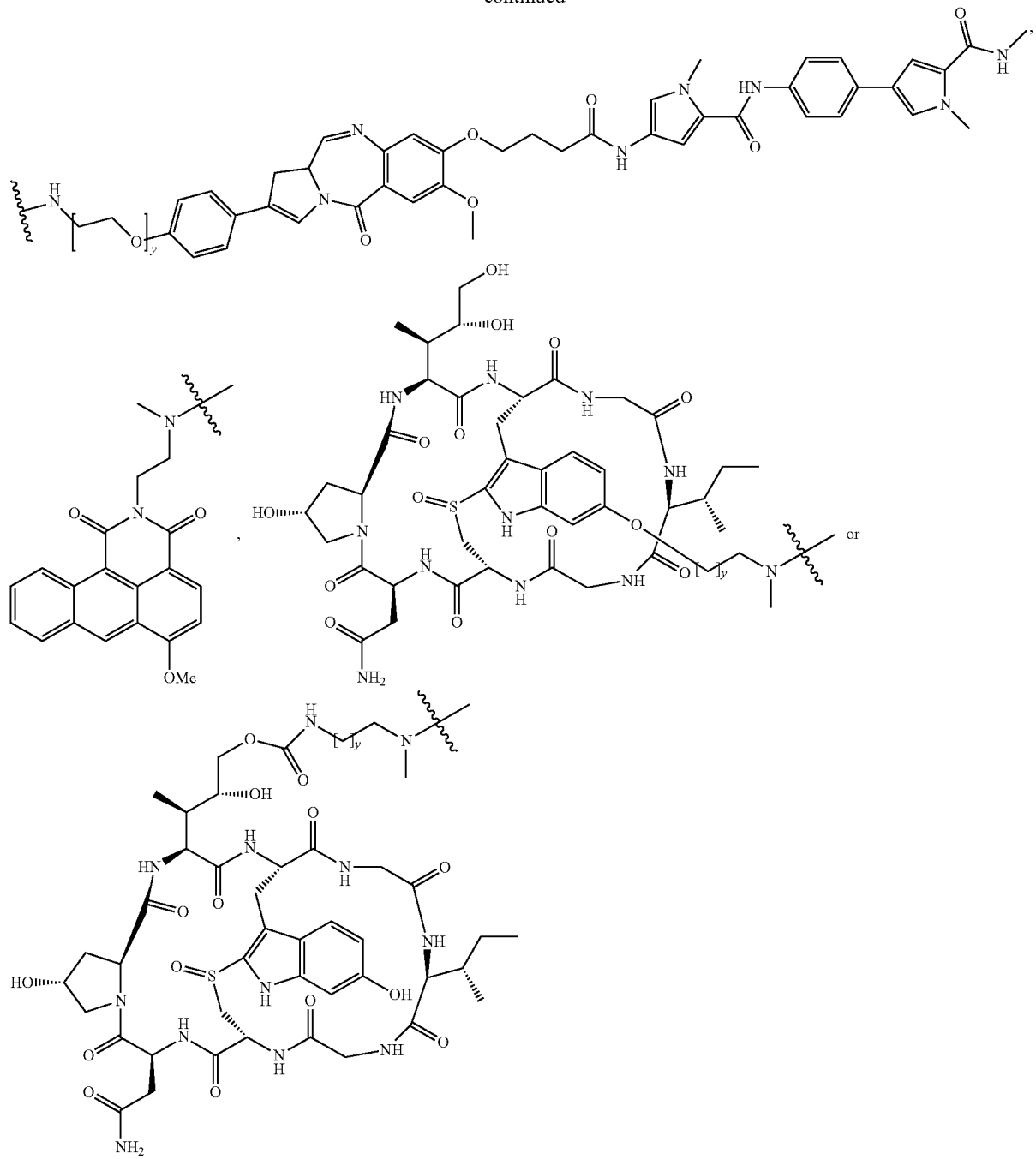

wherein y is an integer of 1 to 10.

In other embodiments, the invention relates to a linker compound, e.g., suitable for coupling to a ligand and one or more active agents to prepare a ligand-drug conjugate as disclosed herein, wherein
  i) the branched linker comprises a branching unit (BR) covalently coupled to the ligand by a primary linker (PL);
  ii) the branching unit is covalently coupled to a first branch (B1), in which a cleavage group (CG) is covalently coupled to a secondary linker (SL); and
  iii) the branching unit is covalently coupled to a second branch (B2), comprising either a) a second cleavage group (CG) covalently coupled to a secondary linker (SL) or b) a polyethylene glycol moiety.

In some embodiments, the invention relates to a linker compound, e.g., suitable for coupling to a ligand and one or more active agents to prepare a linker-active agent conjugate as disclosed herein, wherein
  i) the branched linker comprises a branching unit (BR) covalently coupled to the ligand by a primary linker (PL);
  ii) the branching unit is covalently coupled to a first branch (B1), which has a terminal reactive group, capable of reacting with a cleavage group (CG), covalently coupled to a secondary linker (SL); and iii) the branching unit is covalently coupled to a second branch (B2), comprising either a) a second terminal reactive group, capable of reacting with a cleavage group (CG), covalently coupled to a secondary linker (SL) or b) a polyethylene glycol moiety.

In certain embodiments of such linker compounds, the cleavage group has the formula:

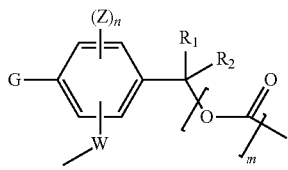

wherein:
G represents a sugar, sugar acid, or modified sugar, preferably a sugar or sugar acid, most preferably glucuronic acid;
W represents —C(O)—, —C(O)NR'—, —C(O)O—, —S(O)$_2$NR'—, —P(O)R"NR'—, —S(O)NR'—, or —PO$_2$NR'—, in each case where the C(O), S, or P is preferably directly bound to the phenyl ring, and R' and R" are each independently hydrogen, (C$_1$-C$_8$)alkyl, mono- or di-carboxyl(C$_1$-C$_8$)alkyl, (C$_3$-C$_5$)cycloalkyl, (C$_1$-C$_8$)alkoxy, (C$_1$-C$_8$)alkylthio, mono- or di-(C$_1$-C$_8$)alkylamino, (C$_3$-C$_{20}$)heteroaryl, or (C$_6$-C$_{20}$)aryl and W is coupled directly or indirectly to the branching unit;
each Z independently represents hydrogen, (C$_1$-C$_8$)alkyl, or an electron-withdrawing group (such as an amide, carboxylic acid, carboxylic acid ester, halogen, cyano, or nitro), preferably a hydrogen, (C$_1$-C$_8$)alkyl, halogen, cyano, or nitro, most preferably hydrogen;
n is an integer from 1 to 3;
m is 0 or 1, preferably 1; and
R$_1$ and R$_2$ are each independently hydrogen, (C$_1$-C$_8$)alkyl, or (C$_3$-C$_8$)cycloalkyl, preferably hydrogen, or R$_1$ and R$_2$ taken together with the carbon atom to which they are attached form a (C$_3$-C$_8$)cycloalkyl ring.

In other embodiments of such linker compounds, the cleavage group has the formula:

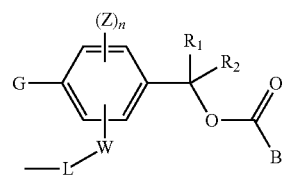

wherein:
G represents a sugar or sugar acid, preferably glucuronic acid;
B represents a leaving group capable of being displaced an active agent, such as a halogen (esp. C$_1$ or Br), or a unit comprising a reactive moiety capable of being coupled to an active agent, such as an isocyanate, an acid chloride, a chloroformate, etc.;
W represents an electron-withdrawing group, preferably —C(O)NR'—, where C(O) is bonded to the phenyl ring and NR' (which may be the amino group of an amino acid, preferably a hydrophilic amino acid) is bonded to L;
each Z independently represents hydrogen, (C$_1$-C$_8$)alkyl, or an electron-withdrawing group (such as an amide, carboxylic acid, carboxylic acid ester, halogen, cyano, or nitro), preferably a hydrogen, (C$_1$-C$_8$)alkyl, halogen, cyano, or nitro, most preferably hydrogen;
n is an integer from 1 to 3;
L represents a linkage to the branching unit;
R$_1$ and R$_2$ are each independently hydrogen, (C$_1$-C$_8$)alkyl, or (C$_3$-C$_8$)cycloalkyl, preferably hydrogen, or R$_1$ and R$_2$ taken together with the carbon atom to which they are attached form a (C$_3$-C$_8$)cycloalkyl ring.

In still other embodiments of such linker compounds, the cleavage group has the formula:

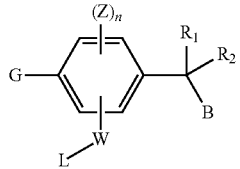

or a pharmaceutically acceptable salt thereof, wherein
G represents a sugar, sugar acid, or modified sugar, preferably a sugar or sugar acid, most preferably glucuronic acid;
B is a unit comprising a reactive moiety capable of being coupled to the active agent,
W represents —C(O)—, —C(O)NR'—, —C(O)O—, —S(O)$_2$NR'—, —P(O)R"NR'—, —S(O)NR'—, or —PO$_2$NR'—, in each case where the C(O), S, or P is directly bound to the phenyl ring, and R' and R" are each independently hydrogen, (C$_1$-C$_8$)alkyl, (C$_3$-C$_8$)cycloalkyl, (C$_1$-C$_8$)alkoxy, (C$_1$-C$_8$)alkylthio, mono- or di-(C$_1$-C$_8$)alkylamino, (C$_3$-C$_{20}$)heteroaryl, or (C$_6$-C$_{20}$)aryl
each Z independently represents hydrogen, (C$_1$-C$_8$)alkyl, or an electron-withdrawing group (such as an amide, carboxylic acid, carboxylic acid ester, halogen, cyano, or nitro), preferably a hydrogen, (C$_1$-C$_8$)alkyl, halogen, cyano, or nitro, most preferably hydrogen;
n is an integer from 1 to 3, preferably 3;
L represents a bond to the branching unit;
R$_1$ and R$_2$ are each independently hydrogen, (C$_1$-C$_8$)alkyl, or (C$_3$-C$_8$)cycloalkyl, preferably hydrogen, or R$_1$ and R$_2$ taken together with the carbon atom to which they are attached form a (C$_3$-C$_8$)cycloalkyl ring.

BRIEF DESCRIPTION OF THE DRAWINGS

FIG. 7 consists of two panels, FIG. 7A and FIG. 7B.

DETAILED DESCRIPTION

Figure 1:
FIG. 1 illustrates an active drug release mechanism from a β-glucuronide based linker.
Figure 1:
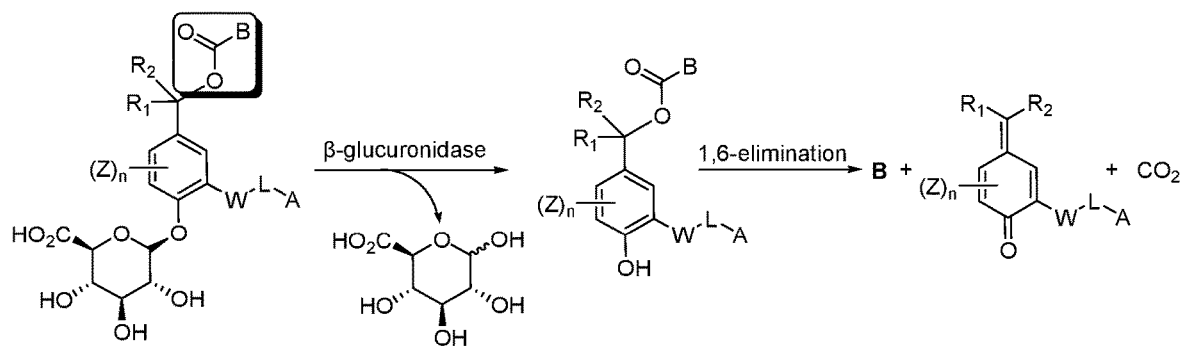
Figure 1:
Figure 1:
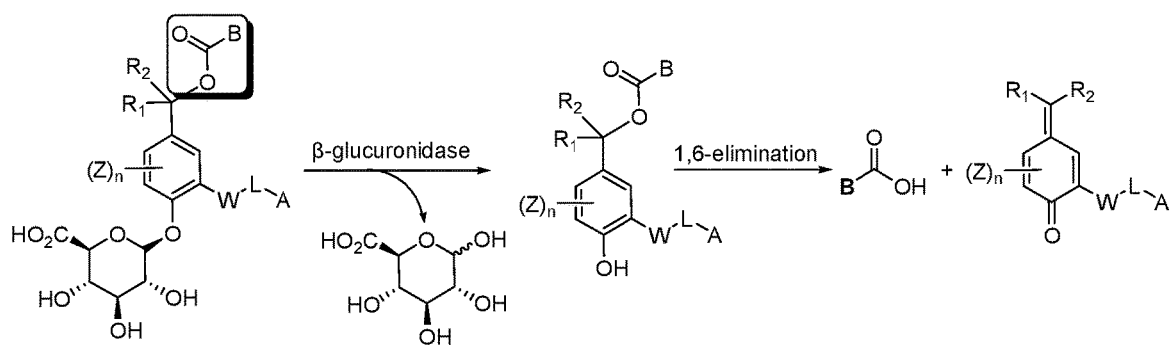

The present invention relates to antibody-drug conjugates (ADCs) wherein a plurality of active agents are conjugated to an antibody through at least one branched linker. However, as one, of skill in the art would recognize, the antibody portion of such conjugates can be replaced by any suitable ligand, and thus the invention relates in equal measure to ligand-drug conjugates. Accordingly, references to and discussions of antibody-drug conjugates herein should be understood, where not contradicted by context, as equally applicable to ligand-drug conjugates and their corresponding intermediates (e.g., ligand-linker conjugates). In all aspects related to the various ligand-drug conjugates disclosed herein, however, the ligand is preferably an antibody.

The branched linker may comprise a branching unit, with two active agents coupled to the branching unit through a secondary linker, while the branching unit is coupled to the antibody by a primary linker. Two or more such branched linkers may be conjugated to an antibody, e.g., 2-4 branched linkers, which may each be coupled to a different C-terminal cysteine of a heavy or light chain of the antibody as described in greater detail herein. The active agents on any branched linker may be the same or different, and active agents may differ from one branched linker to another on the same antibody. One or more of the primary and/or secondary linkers, optionally all of the primary and secondary linkers, may comprise at least one polyethylene glycol unit.

A branched linker may comprise one active agent coupled to the branching unit by a first branch and a second branch that comprises a polyethylene glycol moiety coupled to the branching unit. Two or more such branched linkers may be conjugated to an antibody, e.g., 2-4 branched linkers, which may each be coupled to a different C-terminal cysteine of a heavy or light chain of the antibody.

Branched linkers coupled to different C-terminal cysteines of the heavy or light chain of an antibody may be the same or different. One may be a branched linker of the first type, with an active agent coupled to each branch, while another may be a branched linker of the second type, where one of the branches has a polyethylene glycol moiety but does not have an active agent. The active agents may be the same or different between different branched linkers or even within the same branched linker. For example, one branched linker comprising two active agents coupled to the branching unit may be coupled to the heavy chain of the antibody, and a second branched linker comprising one active agent coupled to the branching unit by a first branch and a second branch comprising a polyethylene glycol moiety may be coupled to the light chain of the antibody. Such combinations allow for 1 to 8 active agents, which may be the same or different, to be coupled to the antibody through a branched linker. This, in turn, allows delivery of a higher number of active agents to the target cells per antibody binding event.

The branching unit of the branched linker may comprise an atom such as nitrogen. The branching unit may comprise any atom or group that permits three linkages, such as an amine, a tertiary amide, or a tertiary or quaternary carbon. In certain preferred embodiments, the branching unit is an amine or an amino acid having a side chain with a group capable of participating in an amide or ester (preferably amide) bond. In some embodiments, the branching unit comprises an amide. When the branching unit comprises an amide, the primary linker may comprise the carbonyl of the amide, or the carbonyl may be included in one of the other branches.

For example, the branched linker may have two active agents, such that when the branching unit is an amide, the secondary linker comprises the carbonyl of the amide. The branching unit may have only one active agent, such that when the branching unit is an amide, either the first branch or the second branch comprises the carbonyl of the amide.

In some embodiments, the branching unit is a lysine unit. The lysine unit may comprise modifications, such as methylation of the ε-amino group, giving methyl-, dimethyl-, and trimethyllysine and even acetylation, sumoylation, and/or ubiquitination. The branching unit may comprise many other amino acids in various embodiments of the invention. For example, an amino acid of the branching unit may be selected from lysine, 5-hydroxylysine, 4-oxalysine, 4-thialysine, 4-selenalysine, 4-thiahomolysine, 5,5-dimethyllysine, 5,5-difluorolysine, trans-4-dehydrolysine, 2,6-diamino-4-hexynoic acid, cis-4-dehydrolysine, 6-N-methyllysine, diaminopimelic acid, ornithine, 3-methylornithine, α-methylornithine, citrulline, and homocitrulline. The branching unit may comprise a L-amino acid or a D-amino acid. The branching unit may comprise an α-amino acid or a β-amino acid. The branching unit may comprise a naturally-occurring amino acid or a non-naturally-occurring amino acid. The branching unit of the antibody-drug conjugate may comprise other amino acids instead of or in addition to lysine.

Active agents may be coupled to a linker by cleavable or non-cleavable bonds, hydrolysable or non-hydrolyzable bonds. In certain preferred embodiments, the active agents are coupled to the branched linker by cleavable bonds. For example, an antibody-drug conjugate may comprise a self-immolative group, preferably a self-immolative group for each active agent, e.g., to release an active agent from the ADC, such a cleavage group having the formula:

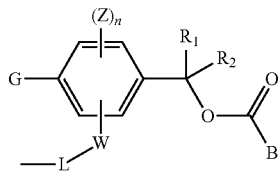

wherein
G is a sugar or sugar acid, preferably glucuronic acid or a derivative thereof;
B represents the active agent, such as a drug;
W represents an electron-withdrawing group, preferably —C(O)NR'—, where C(O) is bonded to the phenyl ring and NR' is bonded to L;
each Z independently represents $(C_1-C_8)$alkyl, halogen, cyano, or nitro, preferably hydrogen;
n is an integer from 1 to 3, preferably 3;
L comprises a chain of 20 to 100 atoms that covalently links the antibody to W; and
$R_1$ and $R_2$ are each independently hydrogen, $(C_1-C_8)$alkyl, or $(C_3-C_8)$cycloalkyl, preferably hydrogen, or $R_1$ and $R_2$ taken together with the carbon atom to which they are attached form a $(C_3-C_8)$cycloalkyl ring.

A cleavage group of any other formula disclosed herein can similarly be used in this fashion.

In some embodiments, L and/or the branched linker comprises a hydrophilic amino acid, e.g., to increase the water solubility of the antibody-drug conjugate, linker, and/or precursors of the antibody-drug conjugate. The hydrophilic amino acid may be located proximal to the active agent, proximal to the antibody, or interposed anywhere along the branched linker, e.g., in the primary linker and/or a secondary linker, preferably each secondary linker. For example, a hydrophilic amino acid may covalently link an oxime of L and/or the primary linker to a polyethylene glycol unit of L and/or the primary linker. A peptide may covalently link an oxime of L and/or the primary linker to a polyethylene glycol unit of L and/or the primary linker.

The electron withdrawing group W may be —C(O)—, —C(O)NR'—, —C(O)O—, —SO$_2$NR'—, —P(O)R''NR'—, —SONR'—, or —PO$_2$NR'—, preferably —C(O)NR'—, and R' and R'' may be each independently hydrogen, $(C_1-C_8)$ alkyl, $(C_3-C_5)$cycloalkyl, $(C_1-C_8)$alkoxy, $(C_1-C_8)$alkylthio, mono- or di-$(C_1-C_8)$alkylamino, $(C_3-C_{2M})$heteroaryl, or $(C_6-C_{20})$aryl, preferably hydrogen. In such embodiments, W is preferably oriented such that the carbonyl, phosphoryl, sulphonyl, or sulphinyl group is directly bound to the phenyl ring. Where Z represents an electron-withdrawing group, Z may represent any of the moieties described in this paragraph for W.

W may represent —C(O)NR'—, and the nitrogen of W may be a nitrogen atom of a hydrophilic amino acid. The hydrophilic amino acid may be a naturally-occurring amino acid or a non-naturally-occurring amino acid. The hydrophilic amino acid may be an α-amino acid or a β-amino acid. The hydrophilic amino acid may be arginine, aspartate, asparagine, glutamate, glutamine, histidine, lysine, ornithine, proline, serine, or threonine, and may be a β-amino acid or an L-amino acid. In certain preferred embodiments, the hydrophilic amino acid is aspartate or glutamate, such as L-aspartate or L-glutamate. In other preferred embodiments, the hydrophilic amino acid is lysine or ornithine, such as L-lysine or L-ornithine. In certain embodiments, the hydrophilic amino acid is arginine, such as L-arginine. In certain embodiments, the hydrophilic amino acid comprises a side chain having a moiety that bears a charge at neutral pH in aqueous solution (e.g., an amine, guanidine, or carboxyl moiety).

The sugar or sugar acid of the cleavage group (i.e., G in the previous figure) is linked to the phenyl ring, e.g., by a bond susceptible to enzymatic cleavage, such as a glycosidic bond to an oxygen substituent on the phenyl ring. The sugar or sugar acid is preferably a monosaccharide, such as glucuronic acid or a derivative thereof, which is capable of being cleaved from the ADC by an enzyme, such as a β-glucuronidase, e.g., an enzyme present in cells to be targeted by the conjugate. Glucuronic acid and derivatives thereof may be represented by the formula:

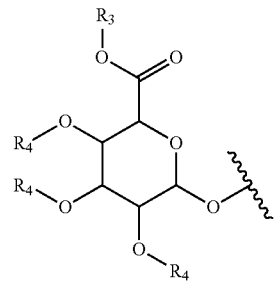

wherein $R_3$ is hydrogen or a carboxyl protecting group, preferably hydrogen, and each $R_4$ is independently hydrogen or a hydroxyl protecting group, preferably hydrogen.

A carboxyl protecting group may be any suitable protecting group for masking a carboxylic acid, e.g., in organic synthesis, such as methyl, methoxymethyl, methylthiomethyl, tetrahydropyranyl, benzyloxymethyl, phenacyl, N-phthalimidomethyl, 2,2,2-trichloroethyl, 2-haloethyl, 2-(p-toluenesulfonyl)ethyl, t-butyl, cinnamyl, benzyl, triphenylmethyl, bis(o-nitrophenyl)methyl, 9-anthrylmethyl, 2-(9,10-dioxo)anthrylmethyl, piperonyl, 2-trimethylsilylethyl, trimethylsilyl, or t-butyldimethylsilyl. In some embodiments, the entire moiety $R_3$—OC(=O)— is replaced by a carboxyl-masking moiety such as 2-alkyl-1,3-oxazolinyl.

A hydroxyl protecting group may be any suitable protecting group suitable for masking a hydroxyl group, e.g., in organic synthesis, such as acetyl, methyl, ethoxyethyl, benzoyl, benzyl, 4-methoxybenzyl, 3,4-dimethoxybenzyl, tetrahydropyranyl (THP), tetrahydrofuranyl (THF), tert-butyldimethylsilyl (TBDMS), trimethylsilyl (TMS), triethylsilyl (TES), triisopropylsilyl (TIPS), tert-butyldiphenylsilyl (TBDPS), tri-isopropylsilyloxymethyl (TOM), β-methoxyethoxymethyl (MEM), methoxymethyl (MOM), allyl, or trityl.

L and/or the branched linker may comprise a substituted or unsubstituted alkylene having 1 to 100 carbon atoms, preferably 20 to 80 carbon atoms, and satisfy at least one, preferably at least two, of the following (i) to (iv):

(i) the alkylene includes at least one unsaturated bond, preferably 3 or 4 double bonds and no triple bonds,
(ii) the alkylene includes at least one heteroarylene,
(iii) at least one carbon atom of the alkylene is replaced by one or more heteroatoms selected from nitrogen (N), oxygen (O), and sulfur (S), preferably at least one nitrogen and at least one oxygen (e.g., as in an oxime), and
(iv) the alkylene is substituted with one or more alkyls having 1 to 20 carbon atoms, preferably 2 or 3 methyls.

In preferred embodiments, a cysteine of the antibody, preferably at a C-terminus of a heavy or light chain of the antibody, forms a thioether bond with a carbon atom of an isoprenyl unit, thereby covalently linking the antibody to the branched linker, e.g., the primary linker. Thus, in some embodiments, L and/or the branched linker (e.g., the primary linker) may comprise at least one isoprenyl unit, preferably two isoprenyl units, each represented by the following formula, which is preferably recognizable by an isoprenoid transferase, e.g., as part of a product or substrate of the isoprenoid transferase.

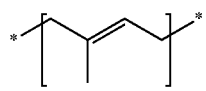

In certain such preferred embodiments, the antibody comprises an amino acid motif capable of being recognized by an isoprenoid transferase. For example, at least one C-terminus of the antibody may comprise an amino acid motif capable of being recognized by an isoprenoid transferase (e.g., as a substrate, for example, prior to forming the antibody-drug conjugate, or as a product of an isoprenoid transferase, for example, after forming the antibody-drug conjugate). The antibody may further comprise a spacer, such as an amino acid or a stretch of amino acids that links a peptide chain of the antibody to the amino acid motif. The spacer may consist of 1 to 20 consecutive amino acids, preferably 7 or more amino acids. Glycine and proline are preferred amino acids for the spacer, and may be used in any combination, such as a series of about 7 glycines. In some embodiments, the C-terminus of the antibody comprises the amino acid sequence GGGGGGGCVIM. The antibody may comprise an addition or deletion at a carboxy terminus, e.g., relative to a form of the antibody not included in an ADC.

Examples of isoprenoid transferases include farnesyl protein transferase (FTase) and geranylgeranyl transferase (GGTase), which can catalyze the transfer of a farnesyl or geranyl-geranyl group to at least one C-terminal cysteine of a target protein. A GGTase may be classified as either GGTase I or GGTase II. FTase and GGTase I may recognize a CAAX motif, and GGTase II may recognize a XXCC, XCXC, or CXX motif, wherein C represents cysteine, A represents an aliphatic amino acid (e.g., isoleucine, valine, methionine, leucine), and each X independently represents, for example, glutamine, glutamate, serine, cysteine, methionine, alanine, or leucine (see Nature Rev. Cancer, 5(5):405-12 (2005); Nature Chemical Biology 17:498-506 (2010); Lane K T, Bees L S, J. Lipid Research, 47:681-699 (2006); Kasey P J, Seabra M C, J. Biological Chemistry, 271(10): 5289-5292 (1996), each of which is hereby incorporated by reference in its entirety).

The antibody-drug conjugates according to the present invention may comprise an amino acid motif, such as CYYX, XXCC, XCXC, or CXX, preferably CYYX (wherein, C represents cysteine, Y represents an aliphatic amino acid, such as leucine, isoleucine, valine, and/or methionine, and X represents an amino acid that determines a substrate specificity of the isoprenoid transferase, such as glutamine, glutamate, serine, cysteine, methionine, alanine, and/or leucine).

Isoprenoid transferases from various sources may be used. For example, the isoprenoid transferase may be obtained from a human, animal, plant, bacteria, virus, or other source. In some embodiments, a naturally occurring isoprenoid transferase is used. In some embodiments, a naturally-modified or artificially-modified isoprenoid transferase may be used. For example, the isoprenoid transferase may comprise one or more amino acid substitutions, additions, and/or deletions, and/or the isoprenoid transferase may be modified by the addition of at least one of Histidine-tag, GST, GFP, MBP, CBP, Isopeptag, BCCP, Myc-tag, Calmodulin-tag, FLAG-tag, HA-tag, Maltose binding protein-tag, Nus-tag, Glutathione-S-transferase-tag, Green fluorescent protein-tag, Thioredoxin-tag, S-tag, Softag 1, Softag 3, Strep-tag, SBP-tag, Ty-tag, and the like.

Isoprenoid transferases recognize an isosubstrate and/or a substrate. The term isosubstrate refers to a substrate analog comprising a chemical modification. Isoprenoid transferases can alkylate a specific amino acid motif (for example, a CAAX motif) at the C-terminus of an antibody (see, e.g., Duckworth, B P et al., ChemBioChem, 8:98 (2007); Uyen T T et al., ChemBioChem, 8:408 (2007); Labadie, G R et al., J. Org. Chem., 72(24):9291 (2007); Wollack, J W et al., ChemBioChem, 10:2934 (2009), each of which is hereby incorporated by reference). A functionalized antibody may be produced using an isoprenoid transferase and an isosubstrate, which may alkylate a C-terminal cysteine.

The isosubstrate may be, for example, the compound having the formula:

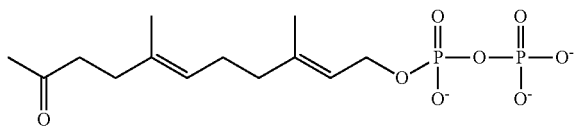 [SMILES: CC(=O)CC/C(C)=C/CC/C(C)=C/COP(=O)([O-])OP(=O)([O-])[O-]]

The cysteine of a C-terminal CAAX motif may be bound to an isosubstrate using an isoprenoid transferase. In some embodiments, part of the motif, e.g., AAX, may subsequently be removed by a protease, e.g., leaving only the cysteine to which the isoprenoid is bound. The cysteine may optionally be methylated at the carboxyl terminus, e.g., by an enzyme (see, e.g., Bell, I M, J. Med. Chem., 47(8):1869 (2004), which is hereby incorporated by reference).

L and/or the branched linker, e.g., the primary linker, may comprise a binding unit formed by a 1,3-dipolar cycloaddition reaction, hetero-Diels-Alder reaction, nucleophilic substitution reaction, non-aldol type carbonyl reaction, addition to a carbon-carbon multiple bond, oxidation reaction, or click reaction. A binding unit may be formed by a reaction between an acetylene and azide, or a non-aldol type carbonyl reaction, such as a reaction between an aldehyde or ketone group and hydrazine or alkoxyamine; such binding units may be represented by Formula (A), (B), (C), or (D).

(A)

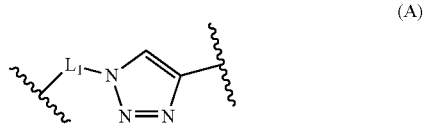

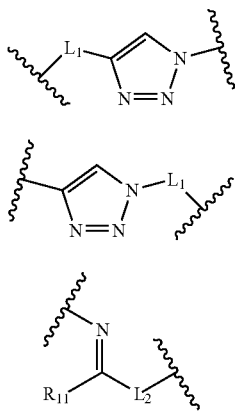

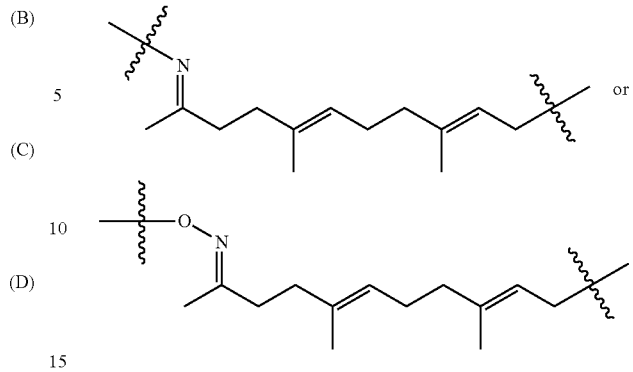

$L_1$ is a single bond or alkylene having 1 to 30 carbon atoms, preferably 12 carbon atoms;
$R_{11}$ is hydrogen or an alkyl having 1 to 10 carbon atoms, preferably methyl; and
$L_2$ is an alkylene having 1 to 30 carbon atoms, e.g., 10 or 11, preferably 11 carbon atoms.

In some embodiments, $L_1$ and/or $L_2$ may comprise at least one isoprenyl unit, preferably two isoprenyl units. $L_2$ may consist of at least one isoprenyl unit, preferably two isoprenyl units. In preferred embodiments, a carbon atom of an isoprenyl unit forms a thioether bond with the sulfur atom of a cysteine of the antibody, most preferably at a C-terminus of a heavy or light chain, thereby covalently linking the antibody and the branched linker, e.g., the primary linker.

An antibody-drug conjugate may comprise the binding unit represented by Formula (D) supra, wherein $L_2$ consists of at least one isoprenyl unit, preferably two isoprenyl units. The binding unit may be an O-substituted oxime, i.e., the nitrogen of the binding unit may be covalently bound to a substituted oxygen. A carbon atom of an isoprenyl unit may form a thioether bond with the sulfur atom of a cysteine of the antibody, most preferably at a C-terminus of a heavy or light chain, thereby covalently linking the binding unit and the antibody.

L and/or the branched linker, e.g., the primary linker, may comprise an isoprenyl group represented by

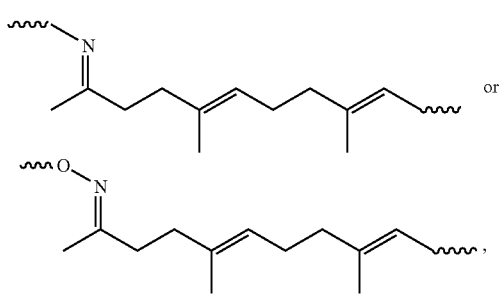

e.g., wherein a carbon atom of the isoprenyl group forms a thioether bond with a sulfur atom of a cysteine of the antibody, thereby covalently linking the isoprenyl group and the antibody. The nitrogen of the isoprenyl group may covalently link the isoprenyl group to a polyethylene glycol unit of L and/or the branched linker, e.g., the primary linker.

L and/or the branched linker, e.g., the primary linker, may comprise an isoprenyl group represented by e.g., wherein a carbon atom of the isoprenyl group forms a thioether bond with a sulfur atom of a cysteine of the antibody, thereby covalently linking the isoprenyl group and the antibody. The nitrogen of the isoprenyl group may covalently link the isoprenyl group to a polyethylene glycol unit of L and/or the branched linker, e.g., the primary linker.

Click chemistry reactions may be carried out under mild conditions, which can be performed in the presence of an antibody without denaturing the antibody. A click chemistry reaction shows high reaction specificity. Therefore, even though antibodies have various functional groups (for example, amines, carboxyls, carboxamides, and guanidiniums), a click chemistry reaction may be performed, for example, without affecting the amino acid side chains of the antibody. A click chemistry reaction between an azide group and an acetylene group, for example, may occur in the presence of an antibody without modifying the amino acid side chain functional groups of the antibody. Further, a click chemistry reaction may precisely target a specific functional group, such as functional groups rarely found in nature, regardless of the nature of the reactants. In some cases, the reactants are selected to improve overall reaction efficiency. For example, an azide-acetylene click chemistry reaction may produce triazole with a high yield (see, e.g., Hia, R K et al., Chem. Rev., 109:5620 (2009); Meldal, M & Tornoe, C W, Chem Rev., 108:2952 (2008); Kolb, H C et al., Angew. Chemie Int. Ed. Engl., 40:2004 (2001), each of which is hereby incorporated by reference).

Azide and acetylene functional groups do not exist in natural proteins. Thus, none of the amino acid side chains, N-terminal amines, or C-terminal carboxyls should be affected by a click chemistry reaction that utilizes these functional groups.

The connection unit may be represented by —$(CH_2)_r$(V$(CH_2)_p)_q$— or —$(CH_2CH_2X)_w$—, wherein
V is a single bond, —O—, —S—, —$NR_{21}$—, —C(O)$NR_{22}$—, —$NR_{23}$C(O)—, —$NR_{24}SO_2$—, or —$SO_2NR_{25}$—, preferably —O—;
X is —O—, ($C_1$-$C_8$)alkylene, or —$NR_{21}$—, preferably —O—;
$R_{21}$ to $R_{25}$ are each independently hydrogen, ($C_1$-$C_6$)alkyl, ($C_1$-$C_6$)alkyl($C_6$-$C_{20}$)aryl, or ($C_1$-$C_6$)alkyl($C_3$-$C_{20}$)heteroaryl, preferably hydrogen;
r is an integer from 1 to 10, preferably 2 or 3;
p is an integer from 0 to 12, preferably 1 or 2;
q is an integer from 1 to 20; and
w is an integer from 1 to 20, preferably 4 to 20.

In some preferred embodiments, q is an integer from 2 to 12. In other preferred embodiments, q is an integer from 4 to 20.

L and/or the branched linker, e.g., the primary linker, may comprise the binding unit represented by Formula (A), (B), (C), or (D) and the connection unit represented by —(CH$_2$)$_r$(V(CH$_2$)$_p$)$_q$— or —(CH$_2$CH$_2$X)$_w$—.

In preferred embodiments, L and/or the branched linker, e.g., the primary linker or the secondary linker, or a combination of both, comprise at least one polyethylene glycol unit represented by either

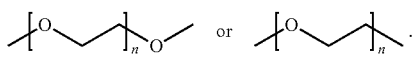

In certain embodiments, the antibody-drug conjugate may comprise from 1 to 20 —OCH$_2$CH$_2$— units, e.g., from 1 to 19 —OCH$_2$CH$_2$— units, such as 1 to 12 —OCH$_2$CH$_2$— units, 5 to 12 —OCH$_2$CH$_2$— units, 6 to 12 —OCH$_2$CH$_2$— units, 5 to 20 —OCH$_2$CH$_2$— units, 6 to 20 —OCH$_2$CH$_2$— units, or 4 to 20 —OCH$_2$CH$_2$-units. Such units may vary in number in the primary and secondary linkers. In embodiments wherein the primary linker comprises an oxime, a polyethylene glycol unit preferentially covalently links the oxime to the peptide, e.g., the N-terminus of the peptide, the C-terminus of the peptide, or a side chain of the peptide.

L and/or the branched linker, e.g., the primary linker, preferably comprises a polyethylene glycol group represented by —(CH$_2$CH$_2$O)$_n$—, wherein n is 1 to 20, such as 1 to 12, 5 to 12, 6 to 12, 5 to 20, or 6 to 20. The secondary linker preferably comprises a polyethylene glycol group represented by —(CH$_2$CH$_2$O)$_n$—, wherein n is 1 to 20, such as 1 to 12, 5 to 12, 6 to 12, 5 to 20, or 6 to 20. In embodiments wherein the primary linker comprises an oxime, a polyethylene glycol group preferentially covalently links the oxime to the peptide. In embodiments wherein the primary linker comprises an oxime, a polyethylene glycol group preferentially covalently links the oxime to W, e.g., wherein W is represented by represent —C(O)NR'—. A carbon of a polyethylene glycol group may form a covalent bond with an atom of W (e.g., the nitrogen of —C(O)NR'—) and/or an oxygen of a polyethylene glycol group may be the oxygen of an oxime.

In some embodiments, the primary linker is preferably represented by one of the following two structures, and thus, the linker may comprise one of the following two structures:

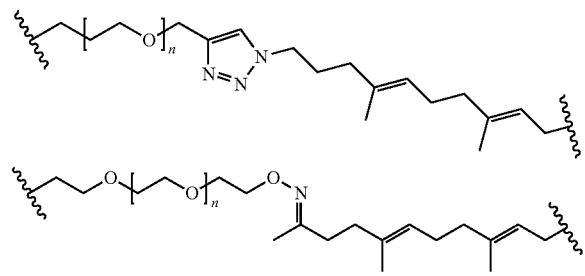

wherein n is an integer from 1 to 20, such as 4 to 20.

L and/or the linker may comprise

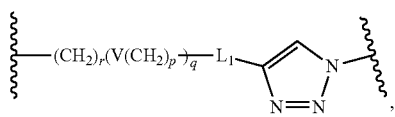

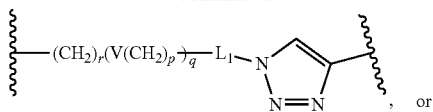

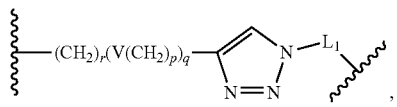

wherein

V represents a single bond, —O—, —S—, —NR$_{21}$—, —C(O)NR$_{22}$—, —NR$_{23}$C(O)—, —NR$_{24}$SO$_2$—, or —SO$_2$NR$_{25}$—, preferably —O—;

R$_{21}$ to R$_{25}$ represents each independently hydrogen, (C$_1$-C$_6$) alkyl, (C$_1$-C$_6$)alkyl(C$_6$-C$_{20}$)aryl, or (C$_1$-C$_6$)alkyl(C$_3$-C$_{20}$) heteroaryl;

r is an integer from 1 to 10, preferably 2 or 3;

p is an integer from 0 to 10, preferably 1 or 2;

q is an integer from 1 to 20, preferably 1 to 6; and

L$_1$ is a single bond.

In some embodiments, the antibody-drug conjugate comprises the structure:

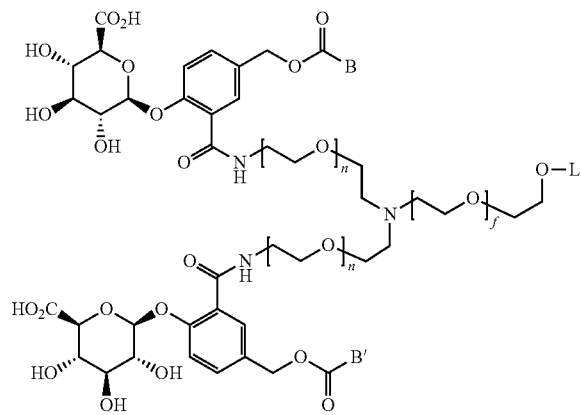

wherein:

B and B' represent active agents, which may be the same or different;

n, independently for each occurrence, represents an integer from 0 to 30;

f, independently for each occurrence, represents an integer from 0 to 30; and

L represents a linkage to the antibody.

In certain preferred embodiments, each n is an integer from 1-20, preferably from 1-10. In certain preferred embodiments, f is an integer from 1-20, preferably from 1-10. Most preferably, each n and f is selected such that f+n is less than 20, e.g., less than 15.

In some embodiments, the antibody-drug conjugate comprises the structure:

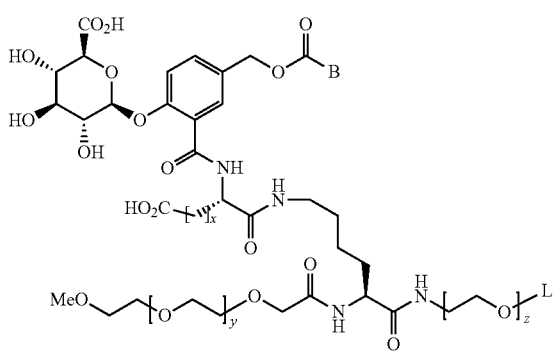

wherein:
B represents an active agent,
x represents an integer from 1 to 3;
y represents an integer from 0 to 20;
z represents an integer from 1 to 20; and
L represents a linkage to the antibody.

In some embodiments, y and z independently represent an integer from 2 and 20. In preferred embodiments, y and z independently represent an integer from 1 to 19, preferably from 4 to 20. In certain preferred embodiments, y and z independently represent an integer less than or equal to 20.

The antibody-drug conjugates of the invention may be prepared using any method known in the art, including molecular biology and cell biology methods. For example, transient or stable transfection methods may be used. Genetic sequences encoding a specific amino acid motif capable of being recognized by an isoprenoid transferase may be inserted into a known plasmid vector using standard PCR and/or ligation technologies so as to express an antibody having the specific amino acid motif at a C-terminus thereof. An antibody having at least one amino acid motif capable of being recognized by the isoprenoid transferase may thus be expressed in a suitable host, e.g., a CHO cell or in E coli.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. Co alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

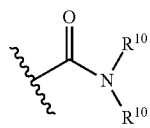

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

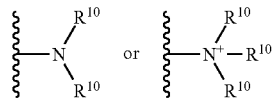

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "carboxy", as used herein, refers to a group represented by the formula —$CO_2H$.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "hydroxyalkyl", as used herein, refers to an alkyl group substituted with a hydroxy group.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkdxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "thioalkyl", as used herein, refers to an alkyl group substituted with a thiol group.

The term "thioester", as used herein, refers to a group —$C(O)SR^{10}$ or —$SC(O)R^{10}$ wherein $R^{10}$ represents a hydrocarbyl.

The term "thioether", as used herein, is equivalent to an ether, wherein the oxygen is replaced with a sulfur.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyiprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

"Covalently coupled" includes both direct bonding and indirect bonding (e.g., through an intervening series of atoms) of two chemical species. For example, an amino acid may be covalently coupled to polyethylene glycol directly, e.g., by forming an ester between the carboxyl of the amino acid and a hydroxyl of the polyethylene glycol, or indirectly, e.g., by reacting the polyethylene glycol with epichlorohydrin to form an epoxypropyl ether and reacting the resulting epoxide with the amino group of the amino acid, thereby covalently linking the amino acid and the polyethylene glycol through a 2-hydroxypropyl linker. Various moieties and reactions for coupling diverse moieties directly or indirectly are well known in the art. In certain preferred embodiments, unless otherwise indicated by the context, an indirect bonding involves only 1-10 intervening atoms (e.g., a methylene, a dibutyl ether, a tripeptide, etc.), most preferably 1-6 intervening atoms.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs.

The term "antibody" refers to an immunoglobulin molecule that recognizes and specifically binds to a different molecule through at least one antigen recognition site within a variable region of the immunoglobulin molecule. As used herein, the term "antibody" includes intact polyclonal antibodies, intact monoclonal antibodies, antibody fragments (for example, Fab, Fab', F(ab')$_2$, Fd, and Fv fragments), single chain Fv (scFv) mutants, multispecific antibodies such as bispecific antibodies generated from two or more intact antibodies, chimeric antibodies, humanized antibodies, human antibodies, fusion proteins including an antigen determination portion of an antibody, and any other modified immunoglobulin molecule including an antigen recognition site. The antibody may be any of the five major classes of immunoglobulins: IgA, IgD, IgE, IgG, and IgM, or subclasses (isotypes) thereof (for example, IgG1, IgG2, IgG3, IgG4, IgA1, and IgA2), based on the identity of its heavy chain constant domains, referred to as alpha, delta, epsilon, gamma, and mu, respectively. The different classes of immunoglobulins have different and well-known subunit structures and three-dimensional configurations. The term "antibody" does not refer to molecules that do not share homology with an immunoglobulin sequence. For example, the term "antibody" as used herein does not include "repebodies".

The term "antibody fragment" refers to a portion of an intact antibody and refers to antigenic determining variable regions of an intact antibody. Examples of antibody fragments include Fab, Fab', F(ab')$_2$, Fd, and Fv fragments, linear antibodies, single chain antibodies, and multispecific antibodies formed from antibody fragments.

The term "monoclonal antibody" refers to a homogeneous antibody population involved in the highly specific recognition and binding of a single antigenic determinant or epitope. This contrasts with polyclonal antibodies that typically include different antibodies directed against a variety of different antigenic determinants. The term "monoclonal antibody" includes antibody fragments (such as Fab, Fab', F(ab')$_2$, Fd, Fv), single chain (scFv) mutants, fusion proteins including an antibody portion, and any other modified immunoglobulin molecule including an antigen recognition site as well as both intact and full-length monoclonal antibodies, but are not limited thereto. Additionally, "monoclonal antibody" refers to such antibodies made in any number of methods, including but not limited to hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. In general, humanized antibodies are human immunoglobulins in which residues from complementary determining region (CDR) are replaced by residues from CDR of a non-human species (e.g., mouse, rat, rabbit, and hamster) having the desired specificity, affinity, and capability (see, e.g., Jones et al., Nature, 321:522-525 (1986); Riechmann et al., Nature, 332:323-327 (1988); Verhoeyen et al., Science, 239:1534-1536 (1988)). In some instances, Fv framework region (FR) residues of a human immunoglobulin are replaced with the corresponding residues in an antibody from a non-human species having a desired specificity, affinity, and/or binding capability. The humanized antibody may be further modified by the substitution of additional residues either in the Fv framework region and/or within the replaced non-human residues to refine and optimize antibody specificity, affinity, and/or binding capability. In general, a humanized antibody includes substantially all of at least one, and typically two or three, variable domains containing all or substantially all of the CDRs that correspond to the non-human immunoglobulin whereas all or substantially all of the framework regions (FRs) have those of a human immunoglobulin consensus sequence. The humanized antibody may also include at least a portion of an immunoglobulin constant region or domain (Fc), typically that of a human immunoglobulin. Examples of methods used to generate humanized antibodies are described in U.S. Pat. No. 5,225,539, hereby incorporated by reference.

The term "human antibody" as used herein refers to an antibody encoded by a human nucleotide sequence or an antibody having an amino acid sequence corresponding to an antibody produced by a human using any technique known in the art. This definition of the human antibody includes intact full-length antibodies and/or fragments thereof.

The term "chimeric antibody" refers to an antibody wherein an amino acid sequence of an immunoglobulin molecule is derived from two or more species, one of which is preferably human. In general, variable regions of both light and heavy chains correspond to variable regions of antibodies derived from one species of mammals (e.g., mouse, rat, rabbit, etc) with the desired specificity, affinity, and capability, while constant regions are homologous to the sequences in antibodies derived from another species (usually human), e.g., to avoid eliciting an immune response in that species.

The terms "epitope" and "antigenic determinant" are used interchangeably herein and refer to that portion of an antigen capable of being recognized and specifically bound by a particular antibody. When the antigen is or comprises a polypeptide or protein, epitopes may be formed from contiguous and/or non-contiguous amino acids, e.g., juxtaposed by secondary, tertiary, and/or quaternary folding of a protein. Epitopes formed from contiguous amino acids are typically retained upon protein denaturing, whereas epitopes formed by tertiary folding may be lost upon protein denaturing. An epitope typically includes 3 or more, 5 or more, or 8 to 10 or more amino acids in a unique spatial conformation.

An antibody "specifically binds" to an epitope or antigenic molecule, which means that the antibody interacts or associates more frequently, more rapidly, with greater duration, with greater affinity, or with some combination of the foregoing to an epitope or antigenic molecule than alternative substances, including unrelated proteins. In specific embodiments, "specifically binds" means, for instance, that an antibody binds to a protein with a $K_D$ of about 0.1 mM or less, but more usually, less than about 1 μM. In specific embodiments, "specifically binds" means that an antibody binds to a protein at times with a $K_D$ of about 0.1 M or less, and at other times, with a $K_D$ of about 0.01 μM or less. Because of the sequence identity between homologous proteins in different species, specific binding may include an antibody recognizing a particular protein in more than one species. It is understood that an antibody or binding residue that specifically binds to a first target may or may not specifically bind to a second target. As described above, "specific binding" does not necessarily require (although it may include) exclusive binding, that is, binding to a single target. Generally, but not necessarily, the term binding used herein means specific binding.

The antibodies, including fragments/derivatives thereof and monoclonal antibodies, may be obtained using methods known in the art (see, e.g., McCafferty et al., Nature 348: 552-554 (1990); Clackson et al., Nature 352:624-628; Marks et al., J. Mol. Biol. 222:581-597 (1991); Marks et al., Bio/Technology 10:779-783 (1992); Waterhouse et al., Nucleic Acids Res. 21:2265-2266 (1993); Morimoto et al., J Biochemical & Biophysical Methods 24:107-117 (1992); Brennan et al., Science 229:81(1985); Carter et al., Bio/Technology 10:163-167 (1992); Kohler et al., Nature 256: 495 (1975); Kilpatrick et al., Hybridoma 16(4):381-389 (1997); Wring et al., J. Pharm. Biomed. Anal. 19(5):695-707 (1999); Bynum et al., Hybridoma 18(5):407-411 (1999); Jakobovits et al., Proc. Natl. Acad. Sci. USA, 90:2551 (1993); Jakobovits et al., Nature, 362:255-258 (1993); Bruggemann et al., Year Immuno. 7:33 (1993); Barbas et al., Proc. Nat. Acad. Sci. USA 91:3809-3813 (1994); Schier et al., Gene 169:147-155 (1995); Yelton et al., J. Immunol. 155:1994-2004 (1995); Jackson et. al., J. Immunol. 154(7): 3310-9 (1995); Hawkins et al., J. Mol. Biol. 226:889-896 (1992), U.S. Pat. Nos. 4,816,567, 5,514,548, 5,545,806, 5,569,825, 5,591,669, 5,545,807; PCT Patent Application Publication No. WO 97/17852, each of which is hereby incorporated by reference in its entirety).

The antibody may be muromonab-CD3 abciximab, rituximab, daclizumab, palivizumab, infliximab, trastuzumab, etanercept, basiliximab, gemtuzumab, alemtuzumab, ibritumomab, adalimumab, alefacept, omalizumab, efalizumab, tositumomab, cetuximab, ABT-806, bevacizumab, natalizumab, ranibizumab, panitumumab, eculizumab, rilonacept, certolizumab, romiplostim, AMG-531, golimumab, ustekinumab, ABT-874, belatacept, belimumab, atacicept, an anti-CD20 antibody, canakinumab, tocilizumab, atlizumab, mepolizumab, pertuzumab, HuMax CD20, tremelimumab, ticilimumab, ipilimumab, IDEC-114, inotuzumab, HuMax EGFR, aflibercept, HuMax-CD4, teplizumab, otelixizumab, catumaxomab, the anti-EpCAM antibody IGN101, adecatumomab, oregovomab, dinutuximab, girentuximab, denosumab, bapineuzumab, motavizumab, efumgumab, raxibacumab, LY2469298, and veltuzumab.

When the antibody comprises at least one light chain and at least one heavy chain, at least one light chain of the antibody, or at least one heavy chain of the antibody, or both may comprise an amino acid region having an amino acid motif capable of being recognized by an isoprenoid transferase. As an antibody may comprise four polypeptide chains (e.g., two heavy chains and two light chains), an antibody may comprise four isoprenylation sequences, each of which can be used to conjugate an active agent to the antibody via a linker. Thus, an antibody-drug conjugate may comprise 4 linkers, each conjugated to an active agent. Accordingly, an antibody-drug conjugate may comprise at least one linker and at least one active agent. An antibody-drug conjugate may comprise at least two linkers, and an antibody-drug conjugate may comprise at least two active agents. An antibody-drug conjugate may comprise 1, 2, 3, or 4 linkers. An antibody-drug conjugate may comprise 1, 2, 3, or 4 active agents.

The active agent may be a drug, toxin, affinity ligand, detection probe, or combination of any of the foregoing.

The active agent may be selected from erlotinib; bortezomib; fulvestrant; sutent; letrozole; imatinib mesylate; PTK787/ZK 222584; oxaliplatin; 5-fluorouracil; leucovorin; rapamycin (Sirolimus); lapatinib; lonafarnib; sorafenib; gefitinib; AG1478; AG1571; alkylating agents (for example, thiotepa or cyclophosphamide); alkyl sulfonate (for example, busulfan, improsulfan, or piposulfan); aziridine (for example, benzodopa, carboquone, meturedopa, or uredopa); ethyleneimine, methylmelamine, altretamine, triethylenemelamine, triethylenephosphoramide, triethylenethiophosphoramide, trimethylolmelamine; acetogenins (for example, bullatacin or bullatacinone); camptothecin and camptothecin derivatives and metabolites (SN-38); topotecan; bryostatin; callystatin; CC-1065 (including its adozelesin, carzelesin, or bizelesin synthetic analogs); cryptophycins (for example, cryptophycin 1 or cryptophycin 8); dolastatin; duocarmycin (including synthetic analogs, e.g., KW-2189 and CB1-TM1); eleutherobin; pancratistatin; sarcodictyin; spongistatin; nitrogen mustard (for example, chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, or uracil mustard); nitrosurea (for example, carmustine, chlorozotocin, fotemustine, lomustine, nimustine, or ranimnustine); antibiotics (for example, enediyne antibiotics such as calicheamicin selected from calicheamicin gamma 1I and calicheamicin omega 1I, or dynemicin including dynemicin A); bisphosphonate (for example, clodronate; esperamicin, neocarzinostatin chromophore, or related chromoprotein enediyne antibiotic chromophores, aclacinomysins, actinomycin, anthramycin, azaserine, bleomycins, cactinomycin, carabicin, carninomycin, carzinophilin, chromomycins, dactinomycin, daunorubicin, detorubucin, 6-diazo-5-oxo-L-norleucine, doxorubicin (for example, morpholino-doxorubicin, cyanomorpholino-doxorubicin, 2-pyrrolino-doxorubicin, liposomal doxorubicin, or deoxydoxorubicin), epirubicin, esorubicin, marcellomycin, mitomycins (for example, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, or zorubicin); anti-metabolites (for example, 5-fluorouracil); folic acid analogs (for example, denopterin, methotrexate, pteropterin, or trimetrexate); purine analogs (for example, fludarabine, 6-mercaptopurine, thiamiprine, or thiguanine); pyrimidine analogs (for example, ancitabine, azacitidine, 6-azauridine, carmofur, cytarabine, dideoxyuridine, doxifluridine, enocitabine, or floxuridine); androgens (for example, calusterone, dromostanolone propionate, epitiostanol, mepitiostane), or testolactone); anti-adrenals (for example, aminoglutethimide, mitotane, or trilostane); folic acid replenisher (for example, folinic acid); aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilone; etoglucid; gallium nitrate; hydroxyurea; lentinan; lonidainine; maytansinoids (for example, maytansine or ansamitocins); trichothecenes (particularly T-2 toxin, verracurin A, roridin A, or anguidine); mitoguazone; mitoxantrone; mopidanmol; nitraerine; pentostatin; phenamet; pirarubicin; losoxantrone; 2-ethylhydrazide; procarbazine; polysaccharide K complex; razoxane; rhizoxin; sizofiran; spirogermanium; tenuazonic acid; triaziquone; 2,2',2"-trichlorotriethylanine; trichothecenes (particularly, T-2 toxin, verracurin A, roridin A, and anguidine); urethane; vindesine; dacarbazine; mannomustine; mitobronitol; mitolactol; pipobroman; gacytosine; arabinoside; cyclophosphamide; thiotepa; taxoids (for example, paclitaxel), ABRAXANE™ cremophor-free, albumin-engineered nanoparticle formulation of paclitaxel, doxetaxel; chlorambucil; gemcitabine; 6-thioguanine; mercaptopurine; platinum analog (for example, cisplatin or carboplatin); vinblastine; platinum; etoposide, ifosfamide; mitoxantrone; vincristine; vinorelbine; novantrone; teniposide; edatrexate; daunomycin; aminopterin; xeloda; ibandronate; CPT-11; topoisomerase inhibitor (RFS 2000); difluoromethylornithine; retinoid (for example, retinoic acid); capecitabine, and pharmaceutically acceptable salts, solvates, acids, or derivatives thereof, but is not necessarily limited thereto.

The active agent may be selected from (i) anti-hormonal agents that act to regulate or inhibit hormone action on tumors such as anti-estrogens and selective estrogen receptor modulators, including, for example, tamoxifen, raloxifene, droloxifene, 4-hydroxytamoxifen, trioxifene, keoxifene, LY117018, onapristone, and toremifene; (ii) aromatase inhibitors that inhibit aromatase enzyme, which regulates estrogen production in the adrenal glands, for example, 4(5)-imidazoles, aminoglutethimide, megestrol acetate, exemestane, letrozole, and anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those that inhibit expression of genes in signaling pathways implicated in adherent cells, for example, PKC-alpha, Raf, H-Ras; (viii) ribozyme, for example, VEGF inhibitor such as ribozyme and HER2 expression inhibitors; (ix) vaccines such as a gene therapy vaccine; ALLOVECTIN® vaccine, LEUVECTIN vaccine, VAXID vaccine; PROLEUKIN®rIL-2; LURTOTECAN® topoisomerase 1 inhibitor; ABARELIX® rmRH; (x) an anti-angiogenic agent such as Bevacizumab; and (xi) pharmaceutically acceptable salts, solvates, acids, or derivatives thereof.

In addition, cytokines may be used as the active agent. Cytokines are small cell-signaling protein molecules that are secreted by numerous cells and are a category of signaling molecules used extensively in intercellular communication. The cytokines include monokines, lymphokines, traditional polypeptide hormones, and the like. Examples of the cytokines include growth hormone (for example, human growth hormone, N-methionyl human growth hormone, or bovine growth hormone); parathyroid hormone; thyroxine; insulin; proinsulin; relaxin; prorelaxin; glycoprotein hormone (for example, follicle stimulating hormone (FSH), thyroid stimulating hormone (TSH), or luteinizing hormone (LH)); hepatic growth factor; fibroblast growth factor; prolactin; placental lactogen; tumor necrosis factor-$\alpha$, tumor necrosis factor-$\beta$; mullerian-inhibiting substance; mouse gonadotropin-associated peptide; inhibin; activin; vascular endothelial growth factor; integrin, thrombopoietin (TPO); nerve growth factor (for example, NGF-$\beta$); platelet-growth factor; transforming growth factor (TGF) (for example, TGF-$\alpha$ or TGF-$\beta$); insulin-like growth factor-I, insulin-like growth factor-II; erythropoietin (EPO); osteoinductive factor; interferon (for example, interferon-$\alpha$, interferon-$\beta$, or interferon-$\gamma$); colony stimulating factor (CSF) (for example, macrophage-CSF (M-CSF), granulocyte-macrophage-CSF (GM-CSF), or granulocyte-CSF (G-CSF)); interleukin (IL) (for example, IL-1, IL-1$\alpha$, IL-2, IL-3, IL-4, IL-5, IL-6, IL-7, IL-8, IL-9, IL-10, IL-11, or IL-12); tumor necrosis factor (TNF) (for example, TNF-$\alpha$ or TNF-$\beta$); and polypeptide factor (for example, LIF or kit ligand), but are not limited thereto. Further, the term "cytokine" also includes cytokines from natural sources or recombinant cell cultures and biologically active equivalents of the native sequence cytokines.

The term "toxin" refers substances that are poisonous to living cells or organisms. Toxins may be small molecules, peptides or proteins capable of causing cell dysfunction or cell death after contact with or absorption by body tissue, e.g., through an interaction with one or more biological macromolecules such as enzymes or cell receptors. Toxins include plant toxins and animal toxins. Examples of animal toxins include diphtheria toxin, botulinum toxin, tetanus toxin, dysentery toxin, cholera toxin, tetrodotoxin, brevetoxin, and ciguatoxin, but are not limited thereto. Examples of plant toxins include ricin and AM-toxin, but are not limited thereto.

Examples of small molecule toxins include auristatin, tubulysin, geldanamycin (Kerr et al., 1997, Bioconjugate Chem. 8(6):781-784), maytansinoid (EP 1391213, ACR 2008, 41, 98-107), calicheamicin (U.S. Patent Publication No. 2009/0105461, Cancer Res. 1993, 53, 3336-3342), daunomycin, doxorubicin, methotrexate, vindesine, SG2285 (Cancer Res. 2010, 70(17), 6849-6858), dolastatin, dolastatin analogs auristatin (U.S. Pat. No. 5,635,483), cryptophycin, camptothecin, rhizoxin derivative, CC 1065 analog or derivative, duocarmycin, enediyne antibiotic, esperamicin, epothilone, pyrrolobenzodiazepine (PBD) derivatives, α-amanitin, and toxoid, but are not limited thereto. Toxins may exhibit cytotoxicity and cell growth-inhibiting activity by tubulin binding, DNA binding, topoisomerase suppression, and the like.

The term "ligand" refers to a molecule capable of forming a complex with a target biomolecule. An example of the ligand is a molecule bound to a predetermined position of a target protein to transmit a signal. The ligand may be a substrate, an inhibitor, a stimulating agent, a neurotransmitter, or a radioisotope.

"Detectable moiety" or a "label" refers to a composition detectable by spectroscopic, photochemical, biochemical, immunochemical, radioactive, or chemical means. For example, useful labels include 32P, 35S, fluorescent dyes, electron-dense reagents, enzymes (for example, enzymes commonly used in an ELISA), biotin-streptavidin, dioxigenin, haptens, and proteins for which antisera or monoclonal antibodies are available, or nucleic acid molecules with a sequence complementary to a target. The detectable moiety often generates a measurable signal, such as a radioactive, chromogenic, or fluorescent signal, that may be used to quantify the amount of bound detectable moiety in a sample. Quantitation of the signal may be achieved, for example, by scintillation counting, densitometry, flow cytometry, ELISA, or direct analysis by mass spectrometry of intact or subsequently digested peptides (one or more peptide may be assessed).

The term "probe" as used herein refers to a material that may (i) provide a detectable signal, (ii) interact a first probe or a second probe to modify a detectable signal provided by the first or second probe, such as fluorescence resonance energy transfer (FRET), (iii) stabilize an interaction with an antigen or a ligand or increase binding affinity; (iv) affect electrophoresis mobility or cell-intruding activity by a physical parameter such as charge, hydrophobicity, etc., or (v) control ligand affinity, antigen-antibody binding, or ionic complex formation.

The active agent may be an immunomodulatory compound, an anticancer agent, an antiviral agent, an antibacterial agent, an antifungal agent, an antiparasitic agent, or a combination thereof.

An immunomodulatory compound may be selected from aminocaproic acid, azathioprine, bromocriptine, chorambucil, chloroquine, cyclophosphamide, cyclosporine, cyclosporine A, danazol, dehydroepiandrosterone, dexamethasone, etanercept, hydrocortisone, hydroxychloroquine, infliximab, meloxicam, methotrexate, mycophenylate mofetil, prednisone, sirolimus, and tacrolimus. An anticancer agent may be selected from 1-methyl-4-phenylpyridinium ion, 5-ethynyl-1-beta-D-ribofuranosylimidazole-4-carboxamide (EICAR), 5-fluorouracil, 9-aminocamptothecin, actinomycin D, asparaginase, bicalutamide, bis-chloroethylnitrosourea (BCNU), bleomycin, bleomycin A2, bleomycin B2, busulfan, camptothecin, carboplatin, carmustine, CB1093, chlorambucil, cisplatin, crisnatol, cyclophosphamide, cytarabine, cytosine arabinoside, cytoxan, dacarbazine, dactinomycin, daunorubicin, decarbazine, deferoxamine, demethoxy-hypocrellin A, docetaxel, doxifluridine, doxorubicin, EB1089, epirubicin, etoposide, floxuridine, fludarabine, flutamide, gemcitabine, goserelin, hydroxyurea, idarubicin, ifosfamide, interferon-α, interferon-γ, irinotecan, KH1060, leuprolide acetate, lomustine, lovastatin, megestrol, melphalan, mercaptopurine, methotrexate, mitomycin, mitomycin C, mitoxantrone, mycophenolic acid, nitrogen mustard, nitrosourea, paclitaxel, peplomycin, photosensitizer Pe4, phthalocyanine, pirarubicin, plicamycin, procarbazine, raloxifene, raltitrexed, revlimid, ribavirin, staurosporine, tamoxifen, teniposide, thalomid, thapsigargin, thioguanine, tiazofurin, topotecan, treosulfan, trimetrexate, tumor necrosis factor, velcade, verapamil, verteporfin, vinblastine, vincristine, vinorelbine, and zorubicin. An antiviral agent may be selected from pencicyclovir, valacyclovir, gancicyclovir, foscarnet, ribavirin, idoxuridine, vidarabine, trifluridine, acyclovir, famciclovir, amantadine, rimantadine, cidofovir, antisense oligonucleotide, immunoglobulin, and interferon. An antibacterial agent may be selected from chloramphenicol, vancomycin, metronidazole, trimethoprin, sulfamethazole, quinupristin, dalfopristin, rifampin, spectinomycin, and nitrofurantoin. The antifungal agent may be selected from amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, balsam of peru, ciclopirox plamine, piroctone olamine, zinc pyrithione, and selenium sulfide. An antiparasitic agent may be selected from mebendazole, pyrantel pamoate, thiabendazole, diethylcarbamazine, ivermectin, niclosamide, praziquantel, albendazole, rifampin, amphotericin B, melarsoprol, eflornithine, metronidazole, tinidazole, and miltefosine.

The antibody may comprise an amino acid motif selected from Ab-HC-(G)$_z$CVIM, Ab-HC-(G)$_z$CVLL, Ab-LC-(G)$_z$CVIM, and Ab-LC-(G)$_z$CVLL, wherein Ab represents an antibody, —HC— represents a heavy chain, -LC- represents a light chain, G represents a glycine, C represents cysteine, V represents valine, I represents isoleucine, M represents methionine, L represents leucine, and z is an integer from 0 to 20.

The active agent of the antibody-drug conjugate may be selected from any one of the following structures:

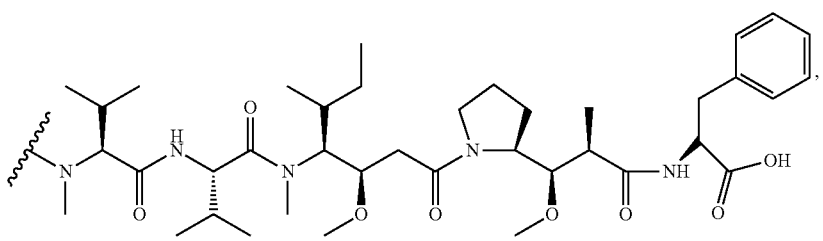

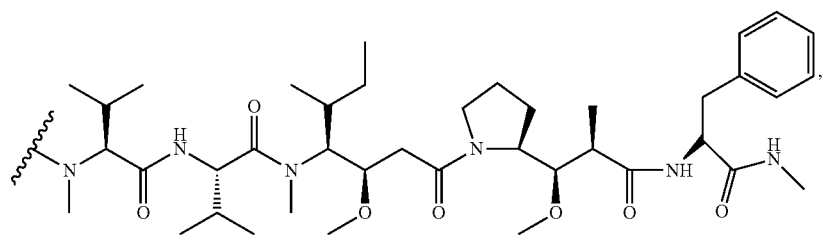
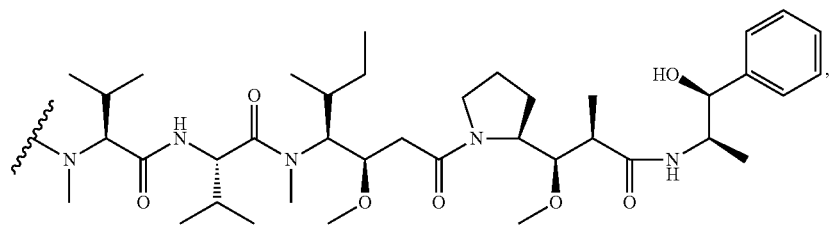
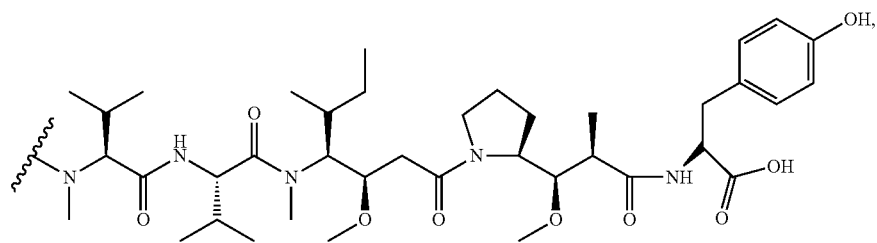
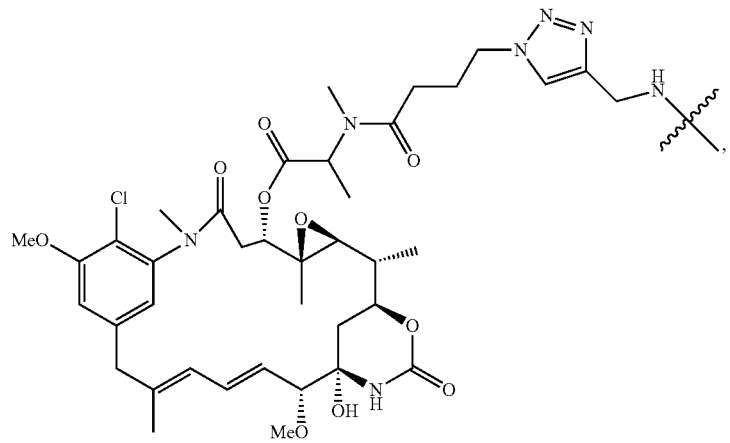
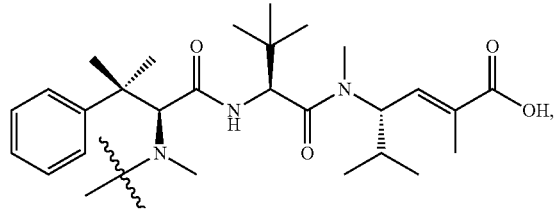
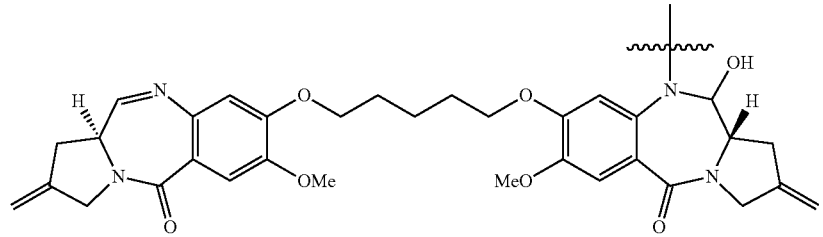

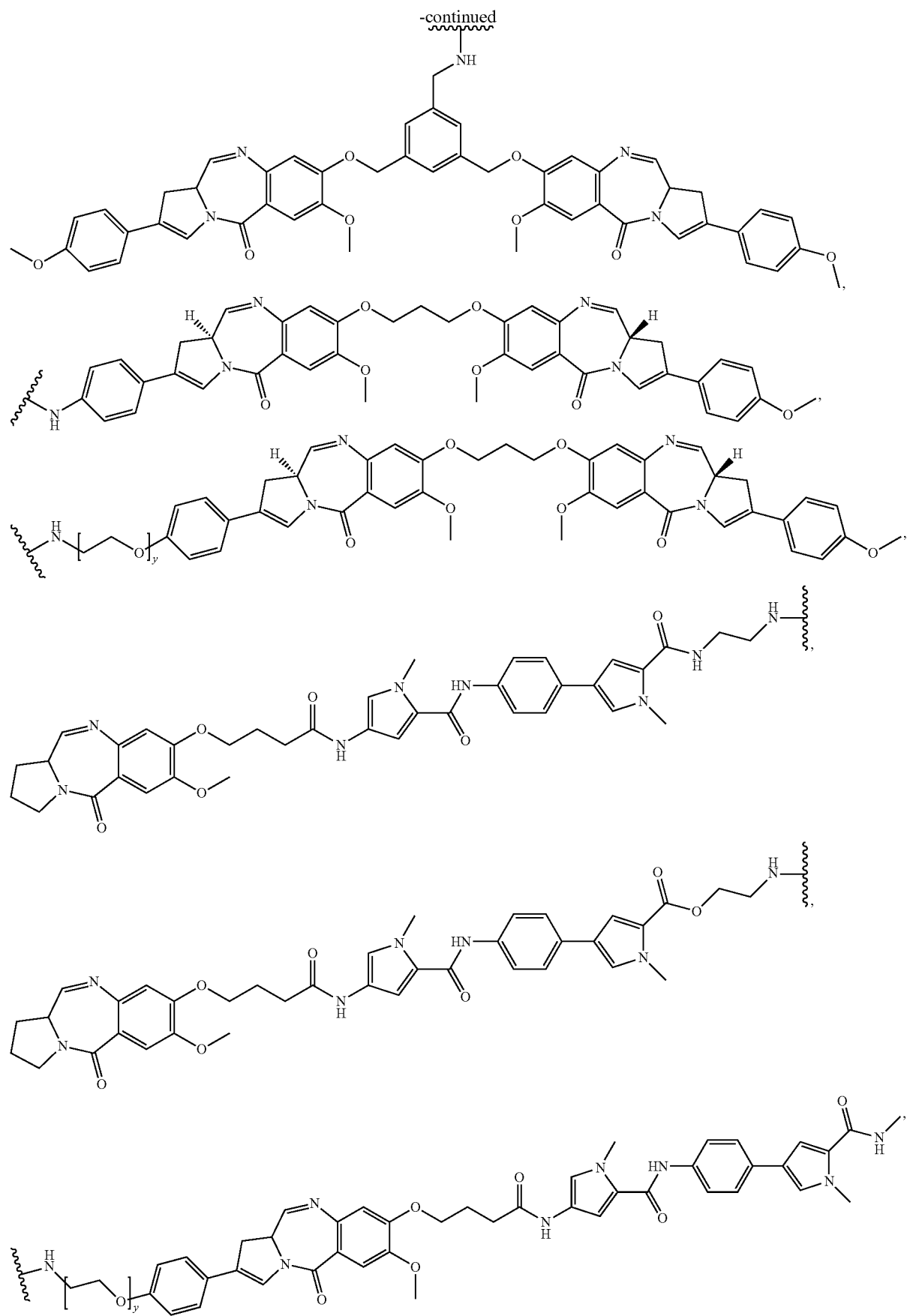

-continued

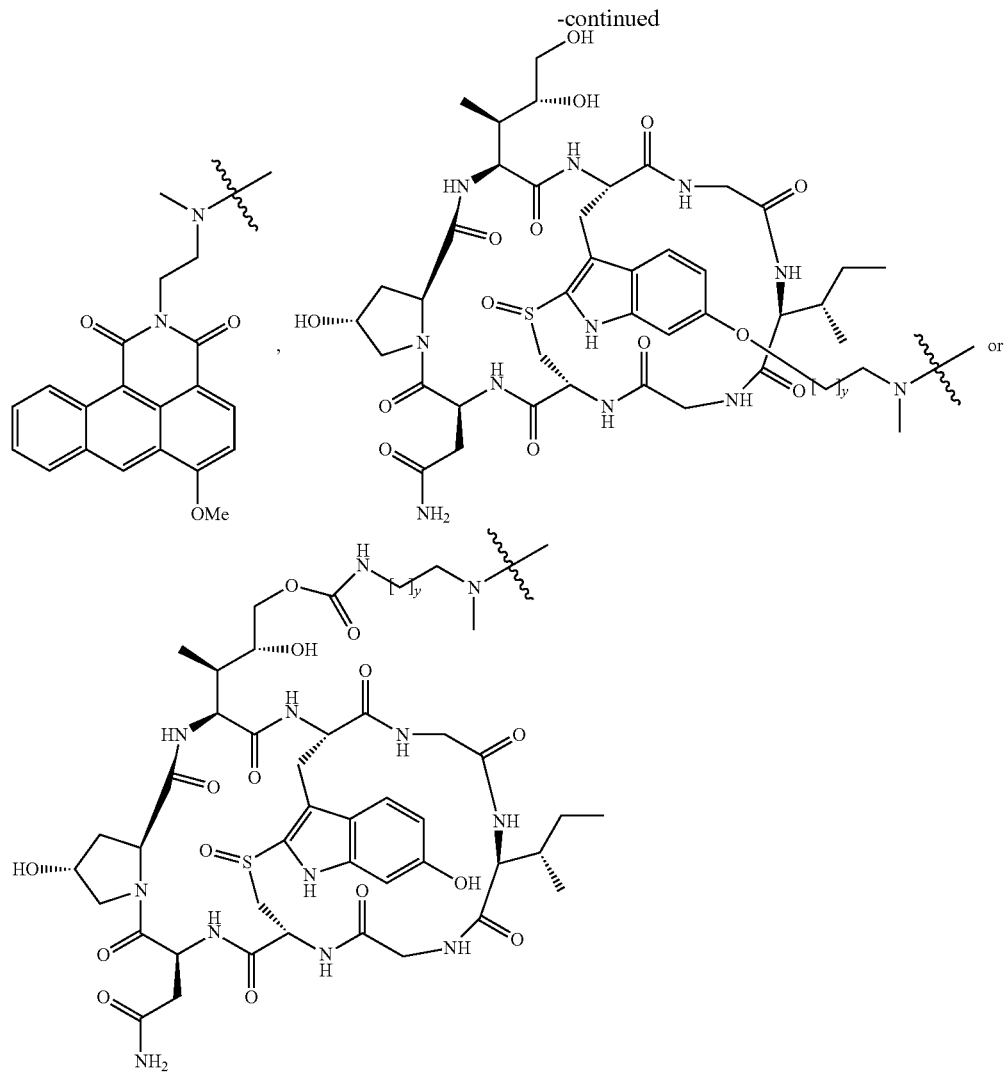

wherein y is an integer from 1 to 10.

The antibody-drug conjugate may be used to transfer the active agent to a target cell of a subject to treat the subject using a method of preparing a composition known to those skilled in the art. In some aspects, the invention relates to a composition (e.g., a pharmaceutical composition) comprising an antibody-drug conjugate as described herein.

Compositions may be prepared in an injectable form, either as a liquid solution or as a suspension. Solid forms suitable for injection may also be prepared, e.g., as emulsions, or with the antibody-drug conjugate encapsulated in liposomes. Antibody-drug conjugates may be combined with a pharmaceutically acceptable carrier, which includes any carrier that does not induce the production of antibodies harmful to the subject receiving the carrier. Suitable carriers typically comprise large macromolecules that are slowly metabolized, for example, proteins, polysaccharides, polylactic acids, polyglycolic acids, polymeric amino acids, amino acid copolymers, lipid aggregates, and the like.

The compositions may also contain diluents, for example, water, saline, glycerol, and ethanol. Auxiliary substances, for example, wetting or emulsifying agents, pH buffering substances, and the like may also be present therein. The compositions may be parenterally administered by injection, wherein such injection may be either subcutaneous or intramuscular injection. In some embodiments, a composition may be administered into a tumor. The composition may be inserted (e.g., injected) into a tumor. Additional formulations are suitable for other forms of administration, such as suppository or oral administration. Oral compositions may be administered as a solution, suspension, tablet, pill, capsule, or sustained release formulation.

The compositions may be administered in a manner compatible with a dose and a formulation. The composition preferably comprises a therapeutically effective amount of the antibody-drug conjugate. The term "therapeutically effective amount" means a single dose or a composition administered in a multiple dose schedule that is effective for the treatment or prevention of a disease or disorder. A dose may vary, depending on the subject to be treated, the subject's health and physical conditions, a degree of protection to be desired, and other relevant factors. The exact amount of an active ingredient (e.g., the antibody-drug conjugate) may depend on the judgment of a doctor. For example, a therapeutically effective amount of the antibody-drug conjugate or composition containing the same may be administered to a patient suffering from a cancer or tumor to treat the cancer or tumor.

The antibody-drug conjugate according to the present invention or the composition containing the same may be administered in the form of a pharmaceutically acceptable salt or solvate thereof. In some embodiments, the antibody-drug conjugate according to the present invention or the composition containing the same may be administered with a pharmaceutically acceptable carrier, a pharmaceutically acceptable excipient, and/or a pharmaceutically acceptable additive. The effective amount and the type of the pharmaceutically acceptable salt or solvate, excipient and additive may be measured using standard methods (see, e.g., Remington's Pharmaceutical Sciences, Mack Publishing Co., Easton, Pa., 18th Edition, 1990).

The term "therapeutically effective amount" with regard to cancer or tumor means an amount that may decrease the number of cancer cells; decrease a size of cancer cells; inhibit cancer cells from intruding into peripheral systems or decrease the intrusion; inhibit cancer cells from spreading to other systems or decrease the spreading; inhibit cancer cells from growing; and/or ameliorate at least one symptom related to the cancer. In the treatment of cancer, the effectiveness of a drug may be assessed by time to tumor progression (TTP) and/or response rate (RR).

The term "pharmaceutically acceptable salts" used herein includes organic salts and inorganic salts. Examples thereof include hydrochloride, hydrobromide, hydroiodide, sulfate, citrate, acetate, oxalate, chloride, bromide, iodide, nitrate, bisulfate, phosphate, acidic phosphate, isonicotinate, lactate, salicylate, acidic citrate, tartrate, oleate, tannate, pantonate, bitartrate, ascorbate, succinate, maleate, gentisinate, fumarate, gluconate, glucoronate, saccharate, formate, benzoate, glutamate, methane sulfonate, ethane sulfonate, benzene sulfonate, p-toluene sulfonate, and pamoate (that is, 1,1'-methylenebis-(2-hydroxy-3-naphthoate)). The pharmaceutically acceptable salt may include another molecule (for example, acetate ions, succinate ions, and/or other counter ions).

Exemplary solvates that may be used for pharmaceutically acceptable solvates of the antibody-drug conjugates described herein include water, isopropanol, ethanol, methanol, dimethyl sulfoxide, ethyl acetate, acetic acid, and ethanol amine.

In some embodiments, the invention relates to a method of treating cancer in a subject, comprising administering a pharmaceutical composition comprising an antibody-drug conjugate as described herein to the subject. A pharmaceutical composition may further comprise a therapeutically effective amount of chemotherapeutic agent. In preferred embodiments, the subject is a mammal. For example, the subject may be selected from rodents, lagomorphs, felines, canines, porcines, ovines, bovines, equines, and primates. In certain preferred embodiments, the subject is a human.

EXEMPLIFICATION

The table below lists the abbreviations used throughout the following Examples:

| Abbreviation | Reference |
| --- | --- |
| Ac | Acetyl |
| AcOH | acetic acid |
| aq. | Aqueous |
| Bn | Benzyl |
| brine | saturated aqueous sodium chloride solution |
| Boc | t-butoxycarbonyl |

-continued

| Abbreviation | Reference |
| --- | --- |
| Cbz | Benzyloxycarbonyl |
| DBU | 1,8-diazabicyclo[5.4.0]undec-7-ene |
| DCM | Dichloromethane |
| DIC | N,N'-diisopropylcarbodiimide |
| DIPEA | N,N-diisopropylethylamine |
| DMAP | 4-(dimethylamino)pyridine |
| DMF | N,N-dimethylformamide |
| DMSO | dimethyl sulfoxide |
| EDC | N-(3-dimethylaminopropyl)-N'-ethylcarbodiimide |
| Et | Ethyl |
| Et2O | diethyl ether |
| EtOAc | ethyl acetate |
| EtOH | Ethanol |
| HBTU | O-(benzotriazol-1-yl)-N,N,N',N'-tetramethyluronium hexafluorophosphate |
| Hex | n-hexane |
| HOBt | 1-hydroxybenzotriazole |
| HPLC | high performance liquid chromatography |
| Me | Methyl |
| MeCN | Acetonitrile |
| MeOH | Methanol |
| MMAE | monomethyl auristatin E |
| MMAF | monomethyl auristatin F |
| MMAF-OMe | monomethyl auristatin F methyl ester |
| i-PrOH | Isopropanol |
| PyBOP | (benzotriazol-1-yloxy)tripyrrolidinophosphonium hexafluorophosphate |
| TBAF | tetrabutylammonium fluoride |
| TBS | t-butyldimethylsilyl |
| THF | Tetrahydrofuran |
| TFA | trifluoroacetic acid |
| Ts | p-toluenesulfonyl |
| wt | Weight |

Example 1. Preparation of Compound 1i

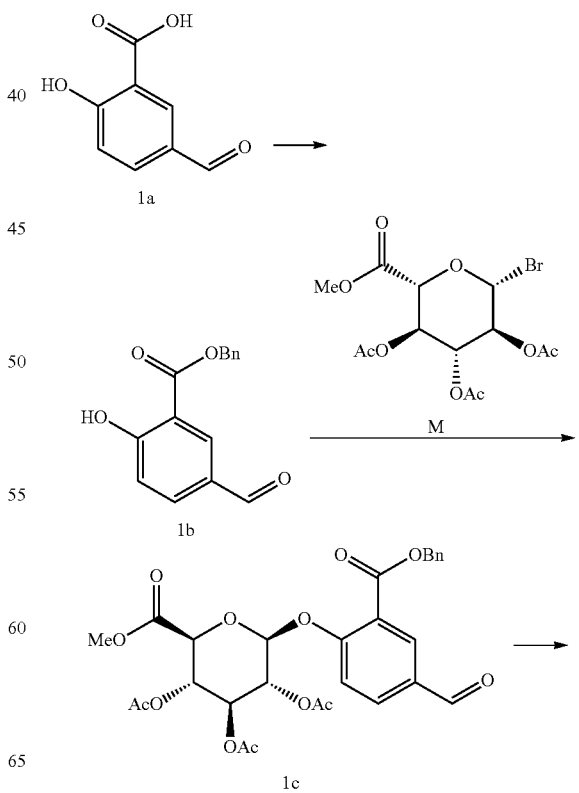

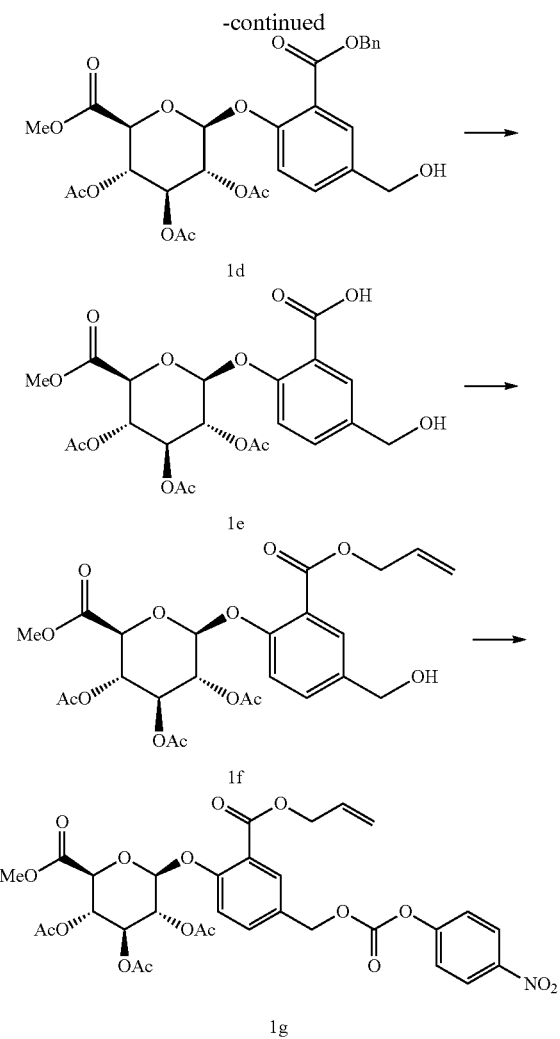

Preparation of Compound 1b

To a suspension of 5-formylsalicylic acid 1a (10.0 g, 60.1 mmol) in THF (30 mL) was added DIPEA (29.8 mL, 180 mmol) and benzyl bromide (7.15 mL, 60.1 mmol) at room temperature. Then the reaction mixture was heated under reflux. After 18 hours under reflux, the reaction mixture diluted with 2 N aq. HCl (100 mL). The resulting mixture was extracted with EtOAc (2×100 mL). The combined organic layers were dried over anhydrous MgSO$_4$, filtered and concentrated. The residue was purified by column chromatography to produce the compound 1b (12.9 g, 83%). $^1$H-NMR (400 MHz, CDCl$_3$) δ 11.38 (s, 1H), 9.86 (s, 1H), 8.40 (s, 1H), 8.01 (d, J=8.8 Hz, 1H), 7.44 (m, 5H), 7.12 (d, J=8.0 Hz, 1H), 5.42 (s, 2H).

Preparation of Compound 1c

To a solution of compound 1b (5.0 g, 19.5 mmol) and compound M (8.5 g, 21.4 mmol, see Example 66) in MeCN (100 mL) were added 4 Å molecular sieve (10 g) and Ag$_2$O (18.0 g, 78.0 mmol). After stirring at room temperature for 12 hours under N$_2$, the reaction mixture was concentrated. Then the concentrated reaction mixture was diluted with H$_2$O (100 mL) and extracted with EtOAc (2×200 mL). The combined organic layers were dried over anhydrous MgSO$_4$, filtered and concentrated. The residue was purified by column chromatography to produce the compound 1c (8.63 g, 77%). $^1$H-NMR (400 MHz, CDCl$_3$) δ 9.94 (s, 1H), 8.28 (s, 1H), 8.02 (d, J=8.8 Hz, 1H), 7.46-7.28 (m, 6H), 5.41-5.32 (m, 6H), 4.27 (d, J=9.2 Hz, 1H), 3.71 (s, 3H), 2.05 (m, 9H).

Preparation of Compound 1d

To a solution of compound 1c (3.10 g, 5.41 mmol) in i-PrOH/CHCl$_3$ (9 mL/45 mL) was added silica gel (3 g) and NaBH$_4$ (0.41 g, 10.82 mmol) at 0° C. After stirring at 0° C. for 2 hours under N$_2$, the reaction mixture was quenched with H$_2$O (100 mL) and extracted with EtOAc (200 mL). The organic layer was dried over anhydrous MgSO$_4$, filtered and concentrated. The crude product was purified by column chromatography to produce the compound 1d (2.73 g, 87%) as white solid. $^1$H-NMR (400 MHz, CDCl$_3$) δ 7.74 (s, 1H), 7.48-7.34 (m, 6H), 7.16 (d, J=8.8 Hz, 1H), 5.35-5.26 (m, 5H), 5.15 (m, 1H), 4.17 (m, 1H), 3.73 (s, 3H), 2.04 (s, 9H), 1.73 (t, 1H).

Preparation of Compound 1e

To a solution of compound 1d (2.40 g, 4.17 mmol) in EtOH (150 mL) Pd/C (10 wt. %, 240 mg) was added. The reaction mixture was stirred at room temperature for 10 minutes, under hydrogen. Then the reaction mixture was filtered through a celite pad and washed with EtOH (100 mL). The filtrate was concentrated to provide the crude product 1e as white solid (2.10 g), which was used without further purification. $^1$H-NMR (400 MHz, CDCl$_3$) δ 8.06 (s, 1H) 7.61 (dd, J=8.8 Hz, 1H), 7.23 (d, J=8.0 Hz 1H), 5.43-5.29 (m, 5H), 4.17 (s, 2H), 4.32 (d, J=8.4 Hz, 1H) 3.69 (s, 3H), 2.11-2.08 (t, 9H), 1.24 (t, 1H).

Preparation of Compound 1f

To a solution of the crude compound 1e (2.10 g, 4.33 mmol) in DMF (50 mL) were added K$_2$CO$_3$ (1.79 g, 13.01 mmol) and allyl bromide (0.41 mL, 4.76 mmol) at room temperature. After stirring at room temperature for 3 hours, the reaction mixture was diluted with 2 N aq. HCl (100 mL). The resulting mixture was extracted with EtOAc (200 mL). The organic layer was dried over anhydrous MgSO$_4$, filtered and concentrated. The residue was purified by column chromatography to produce the compound 1f (1.55 g, 70% for 2 steps). $^1$H-NMR (400 MHz, CDCl$_3$) δ 7.74 (s, 1H), 7.45 (dd, J=8.0 Hz, 2.0 Hz, 1H), 7.16 (d, J=8.8 Hz, 1H), 6.02 (m, 1H), 5.40-5.26 (m, 5H), 5.16 (m, 1H), 4.76 (m, 2H), 4.66 (s, 2H), 4.19 (m, 1H), 3.73 (s, 3H), 2.07-2.05 (m, 9H), 1.68 (t, 1H).

Preparation of Compound 1g

To a solution of compound 1f (2.50 g, 4.77 mmol) in DMF (20 mL) were added bis(4-nitrophenyl)carbonate (1.30 g, 4.29 mmol) and DIPEA (0.80 mL 4.77 mmol) at 0° C. under N$_2$. The reaction mixture was stirred at 0° C. for 30 min and allowed to warm to room temperature for 1 hour. The reaction mixture was diluted with H$_2$O (100 mL) and extracted with EtOAc (200 mL). The organic layer was washed with brine (100 mL) and dried over anhydrous MgSO$_4$. After filtration and concentration under reduced pressure, the resulting crude product was purified by column chromatography to produce the compound 1g (2.80 g, 85%). $^1$H-NMR (400 MHz, CDCl$_3$) δ 8.28 (d, J=15.2 Hz, 2H), 7.85 (d, J=2.4 Hz, 1H), 7.55 (dd, J=3.2 Hz, 2.4 Hz, 1H), 7.38 (d, J=15.2 Hz, 2H), 7.20 (d, J=8.8 Hz, 1H) 6.03 (m, 1H), 5.42-5.19 (m, 8H), 4.78 (d, J=5.2 Hz, 2H), 4.12 (d, J=7.2 Hz, 1H), 3.74 (s, 3H).

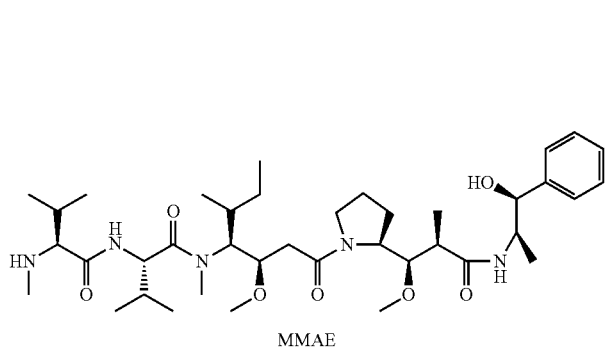 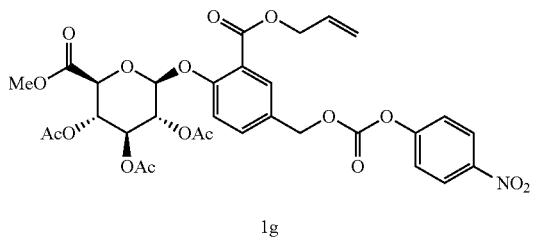

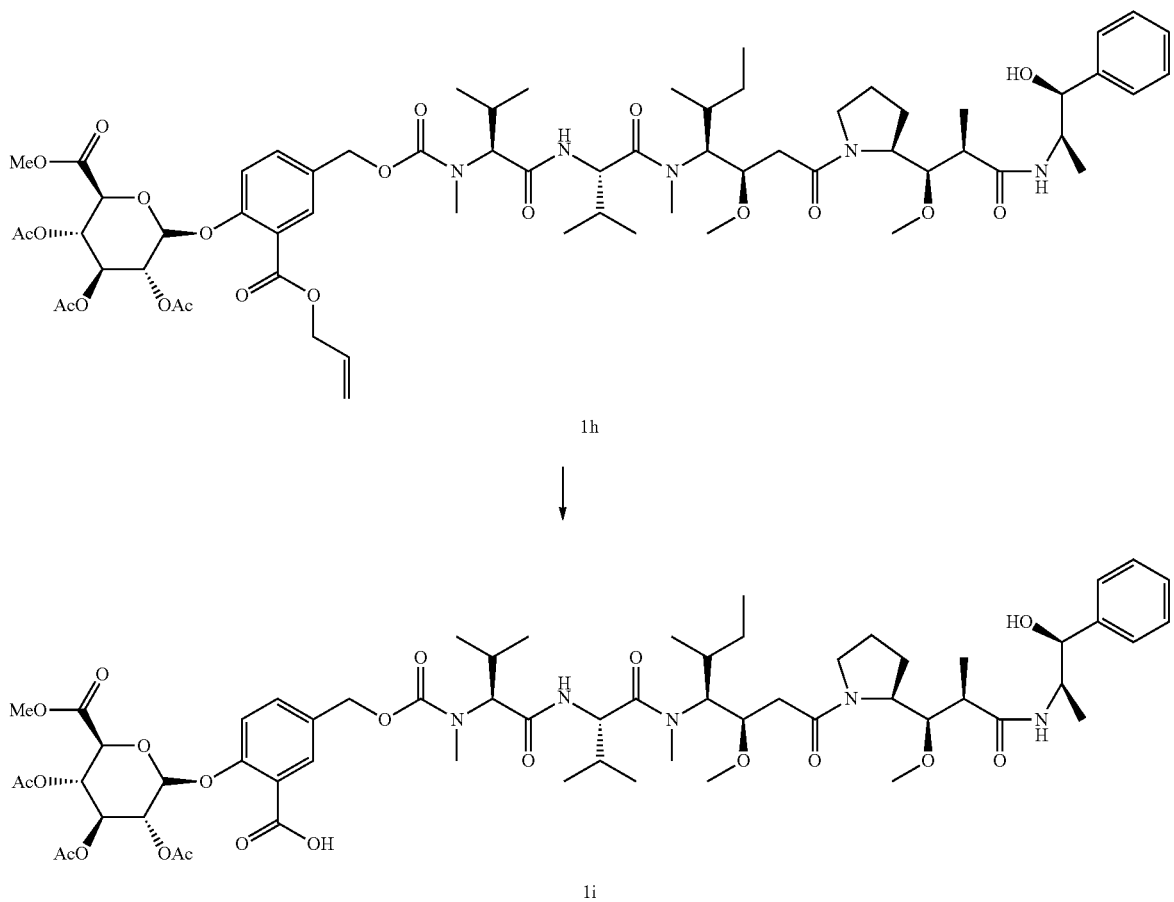

Preparation of Compound 1h

Compound 1g (528 mg, 0.77 mmol), MMAE (500 mg, 0.7 mmol) and anhydrous HOBt (19 mg, 0.14 mmol) were dissolved in DMF (3 mL) at 0° C. Then pyridine (0.7 mL) and DIPEA (0.24 mL, 1.39 mmol) were added. After stirring at room temperature for 24 hours under $N_2$, the reaction mixture was diluted with $H_2O$/saturated aqueous $NH_4Cl$ solution (100 mL/50 mL) and extracted with EtOAc (2×100 mL). The combined organic layers were dried over anhydrous $MgSO_4$, filtered, and concentrated. The residue was purified by column chromatography to produce the compound 1h (600 mg, 67%). EI-MS m/z: $[M+H]^+$ 1269.5, $[M+Na]^+$ 1291.5.

Preparation of Compound 1i

To a solution of compound 1h (600 mg, 0.47 mmol) and triphenylphosphine (31 mg, 0.12 mmol) in DCM (10 mL) were added pyrrolidine (0.047 mL, 0.57 mmol) and $Pd(PPh_3)_4$ (27 mg, 0.02 mmol) at room temperature. After stirring for 2 hours, the reaction mixture was diluted with $H_2O$/1 N aq. HCl (50 mL/50 mL) and extracted with EtOAc (3×50 mL). The combined organic layers were dried over anhydrous $MgSO_4$, filtered, and concentrated. The residue was purified by column chromatography (Hex/EtOAc 1/1 to EtOAc) to produce the compound 1i (480 mg, 82%) as a white solid. EI-MS m/z: $[M+H]^+$ 1228.4, $[M+Na]^+$ 1250.4.

Example 2. Preparation of Compound 1j

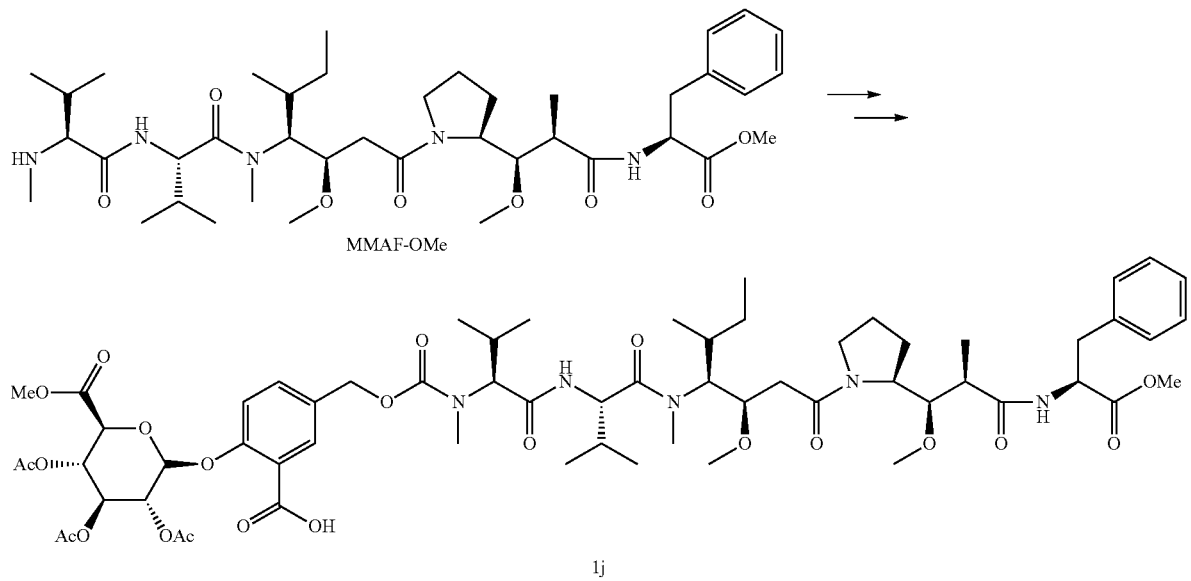

Compound 1j was prepared from MMAF-OMe by a similar method of preparing compound 1i in Example 1.

Example 3. Preparation of Compound 2g

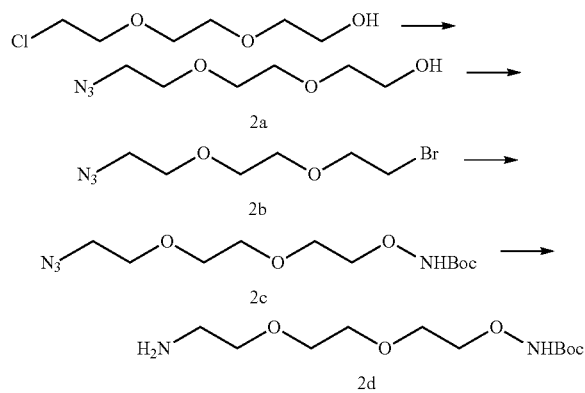

Preparation of Compound 2a 2-(2-(2-Chloroethoxy)ethoxy)ethanol (10 g, 59.3 mmol) was dissolved in DMF (90 mL) at room temperature under nitrogen, and then $NaN_3$ (5.78 g, 88.9 mmol) was added thereto. After stirring at 100° C. for 13 hours, chloroform (200 mL) and distilled water (300 mL) were added thereto to extract an organic layer, and the extracted organic layer was dried over anhydrous $Na_2SO_4$ and concentrated under reduced pressure. The residue was subjected to column chromatography, which produced the compound 2a (10.3 g, 99%). $^1$H-NMR (600 MHz, $CDCl_3$) δ 3.75-3.73 (m, 2H), 3.70-3.68 (m, 6H), 3.63-3.61 (m, 2H), 3.40 (t, J=5.4 Hz, 2H), 2.20 (t, J=6.0 Hz, 1H).

Preparation of Compound 2b $CBr_4$ (21.4 g, 64.6 mmol) was dissolved in DCM (100 mL) at 0° C. under nitrogen, and then triphenylphosphine (16.9 g, 64.6 mmol) in DCM (100 mL) and compound 2a (10.3 g, 58.7 mmol) were added thereto, and the mixture was stirred at room temperature for 13 hours. After the reaction was completed, DCM (300 mL) and distilled water (300 mL) were added thereto to extract an organic layer, and the extracted organic layer was dried over anhydrous $Na_2SO_4$ and concentrated under reduced pressure. The residue was subjected to column chromatography, which produced the compound 2b (12 g, 85%). $^1$H-NMR (400 MHz, $CDCl_3$) δ 3.83 (t, J=6.4 Hz, 2H), 3.72-3.67 (m, 6H), 3.48 (t, J=6.0 Hz, 2H), 3.40 (t, J=4.8 Hz, 2H)

Preparation of Compound 2c

Compound 2b (1 g, 4.20 mmol) was dissolved in MeCN at room temperature under nitrogen, and then N-Boc-hydroxylamine (643 mg, 4.82 mmol) and DBU (0.66 mL, 4.41 mmol) were-added thereto. After stirring at 60° C. for 13 hours, DCM (300 mL) and distilled water (300 mL) were added thereto to extract an organic layer, and the extracted organic layer was dried over anhydrous $Na_2SO_4$ and concentrated under reduced pressure. The residue was subjected to column chromatography, which produced the compound 2c (748 mg, 70%). $^1$H-NMR (400 MHz, $CDCl_3$) δ 7.55 (s, 1H), 4.05-4.03 (m, 2H), 3.76-3.74 (m, 2H), 3.74-3.69 (m, 6H), 3.42 (t, J=4.8 Hz, 2H), 1.49 (s, 9H).

Preparation of Compound 2d

Compound 2c (200 mg, 0.688 mmol) was dissolved in MeOH (5 mL), and then Pd/C (10% wt., 70 mg) was added thereto and stirred under hydrogen for 3 hours. After the reaction was completed, the reaction mixture was celite-filtered and concentrated under reduced pressure, which produced the compound 2d (180 mg, 98%). $^1$H-NMR (400 MHz, $CDCl_3$) δ 4.04-4.01 (m, 2H), 3.74-3.62 (m, 7H), 3.55 (t, J=5.2 Hz, 1H), 2.88 (t, J=5.2 Hz, 1H), 2.81 (t, J=5.2 Hz, 1H), 1.64 (s, 2H), 1.48 (s, 9H).

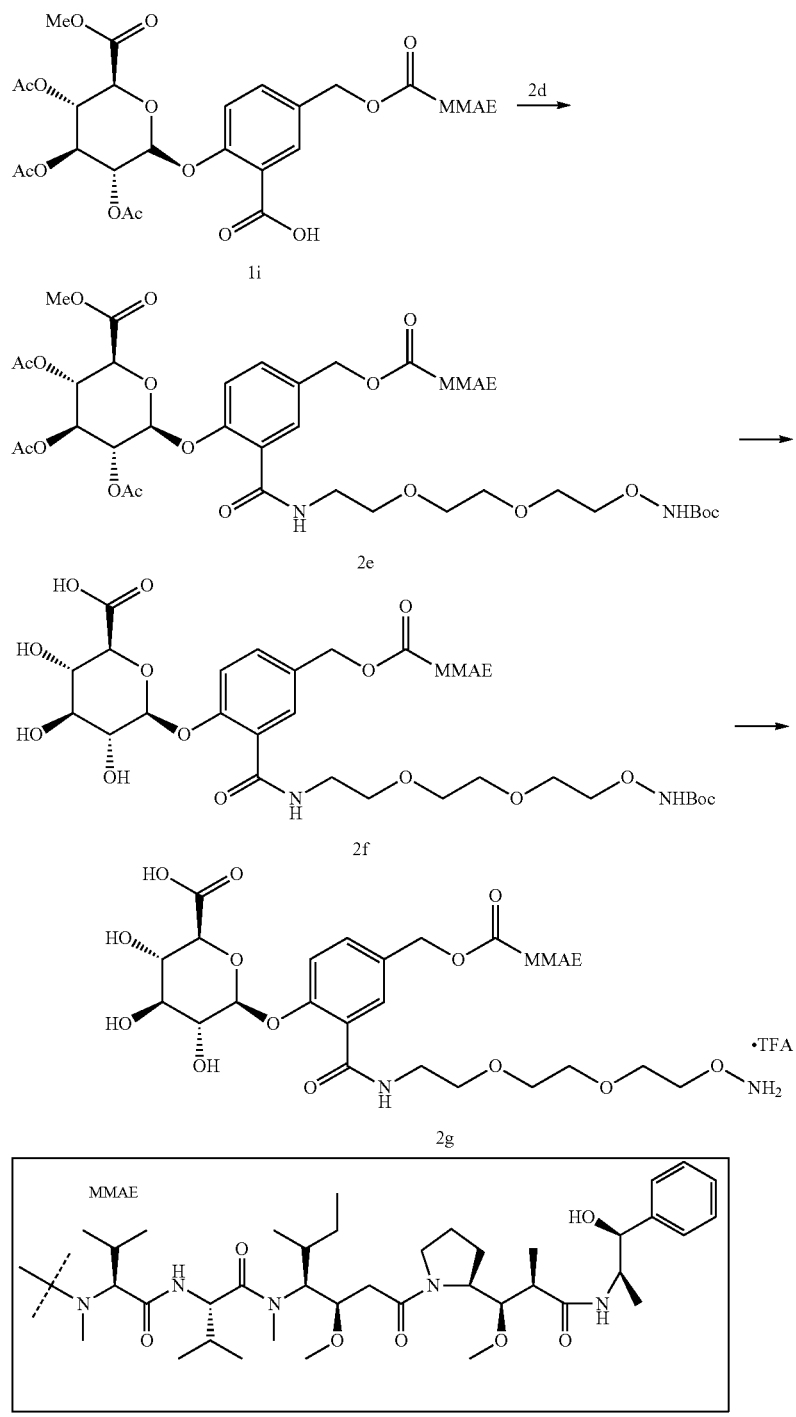

Preparation of Compound 2e

DIPEA (0.042 mL, 0.32 mmol) and PyBOP (126 mg, 0.24 mmol) were added to a stirred mixture of compound 1i (200 mg, 0.16 mmol) and compound 2d (51 mg, 0.19 mmol) in DMF (4 mL). After stirring at room temperature for 4 hours under $N_2$, the reaction mixture was diluted with $H_2O$ (100 mL) and extracted with EtOAc (2×100 mL). The combined organic layers were dried over anhydrous $Na_2SO_4$, filtered and concentrated. The resulting residue was purified by column chromatography to yield the compound 2e (142 mg, 60%). EI-MS m/z: [M+H]$^+$ 1474.7.

Preparation of Compound 2f

To a solution of compound 2e (142 mg, 0.096 mmol) in MeOH (2 mL) was added LiOH monohydrate (36 mg, 0.86 mmol) in $H_2O$ (2 mL) at −20° C. After stirred at 0° C. for 1 hour, the reaction mixture was diluted with $H_2O$/2 N aq. HCl solution (50 mL/2 mL) and extracted with $CHCl_3$ (2×100 mL). The combined organic layers were dried over anhydrous $Na_2SO_4$, filtered and concentrated to yield the crude compound 2f (128 mg), which was used without further purification. EI-MS m/z: [M+H]$^+$ 1334.5.

125

Preparation of Compound 2g

To a solution of crude compound 2f (105 mg, 0.08 mmol) in DCM (3 mL) HCl (4 M in 1,4-dioxane, 1 mL) was added at 0° C. After 1 hour, the solvent and excess HCl were removed by N2 flow and then the residue was purified by HPLC, which produced the compound 2g (47 mg, 46%) as white solid. EI-MS m/z: [M+H]+ 1234.4.

Example 4. Preparation of Compound 2h

126 dropwise. The mixture was then gradually warmed up to 0° C. and kept for 15 minutes at this temperature. Then the reaction mixture was dried over anhydrous MgSO4, filtered and concentrated to produce the syrupy residue. Then, the syrupy residue was purified by column chromatography (EtOAc to EtOAc/MeOH 10/1). The pure fractions were evaporated in vacuo to yield the compound 3a (1.18 g, 77%). 1H-NMR (400 MHz, CDCl3) δ 7.80 (d, J=8.4 Hz, 2H), 7.34

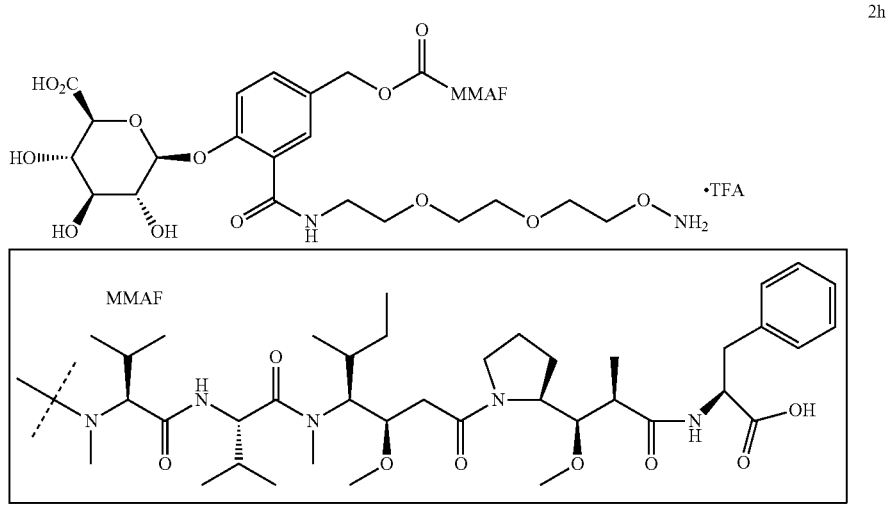

2h

Compound 2h was prepared from compound 1j and compound 2d by a similar method of preparing compound 2g in Example 3. EI-MS m/z: [M+H]+ 1248.9.

Example 5. Preparation of Compound 3f (d, J=8.4 Hz, 2H), 4.16 (m, 2H), 3.72-3.58 (m, 22H), 2.97 (br, 1H), 2.45 (s, 3H).

Preparation of Compound 3b

Compound 3a (1.18 g, 2.71 mmol) and NaN3 (264 mg, 4.07 mmol) were dissolved in DMF (3 mL). And then the

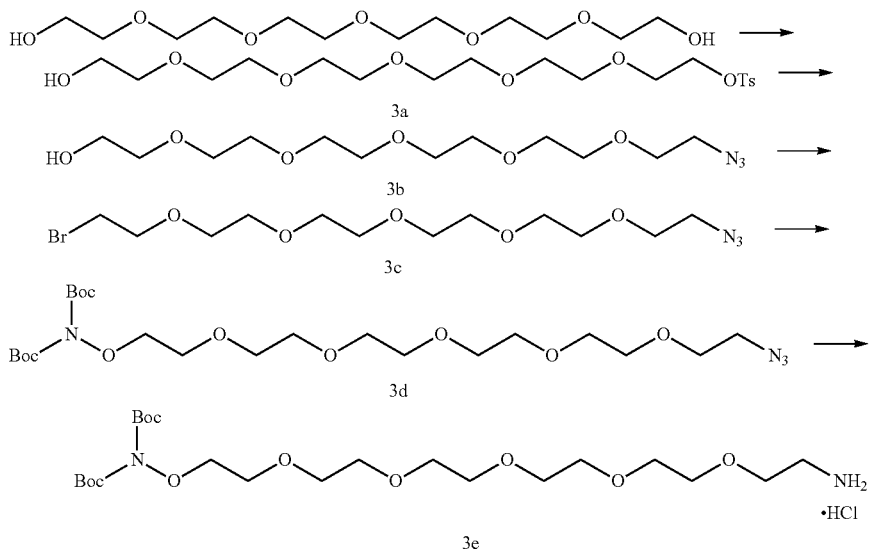

Preparation of Compound 3a

A mixture of hexaethylene glycol (1.0 g, 3.54 mmol), Ag2O (1.23 g, 5.31 mmol) and KI (117 mg, 0.71 mmol) in DCM (10 mL) was sonicated for 15 min. The suspension was cooled to −30° C. and a solution of p-toluenesulfonyl chloride (688 mg, 3.61 mmol) in DCM (13 mL) was added reaction mixture was heated at 100° C. After 15 hours at 100° C., the reaction mixture was filtered and concentrated. The residue was purified by column chromatography (EtOAc to EtOAc/MeOH 10/1) to yield the compound 3b (728 mg, 87%). 1H-NMR (400 MHz, CDCl3) δ 3.75-3.70

(m, 2H), 3.69-3.63 (m, 18H), 3.62-3.60 (m, 2H), 3.39 (d, J=5.2 Hz, 2H), 3.07 (br, 1H).

Preparation of Compound 3c

To a stirred solution of compound 3b (728 mg, 2.36 mmol) in THF (10 mL) at 0° C. were added triethylamine (0.73 mL, 5.21 mmol) and methanesulfonic anhydride (619 mg, 3.55 mmol). After 2 hours, LiBr (1.03 g, 11.8 mmol) was added to a stirred solution and the resulting reaction mixture was refluxed for 5 hours. After cooling to room temperature, the reaction mixture was concentrated under reduced pressure. The residue was purified by column chromatography (EtOAc to EtOAc/MeOH 10/1) to yield the compound 3c (810 mg, 92%). $^1$H-NMR (400 MHz, CDCl$_3$) δ 3.81 (t, J=6.4 Hz, 2H), 3.69-3.65 (m, 18H), 3.47 (t, J=6.4 Hz, 2H), 3.39 (t, J=5.2 Hz, 2H).

Preparation of Compound 3d

NaH (60% in oil, 564 mg, 12.9 mmol) was added to a stirred mixture of compound 3c (3.42 g, 9.24 mmol) and N,N-diBoc-hydroxylamine (2.80 g, 12.0 mmol, synthesized by the procedures in PCT publication No. WO2004/018466A2, hereby incorporated by reference) in DMF (20 mL) at 0° C. The reaction mixture was warmed to room temperature and kept for 2 hours at this temperature. The solvent was evaporated under reduced pressure and the residue was purified by column chromatography (EtOAc/Hex 1/20 to 1/5), which produced the compound 3d (3.51 g, 73%). $^1$H-NMR (400 MHz, CDCl$_3$) δ 4.08 (t, J=4.8 Hz, 2H), 3.73 (t, J=4.8 Hz, 2H), 3.69-3.62 (m, 18H), 3.39 (t, J=5.6 Hz, 2H), 1.53 (s, 18H).

Preparation of Compound 3e

To a stirred mixture of compound 3d (123 mg, 0.23 mmol), and Pd/C (10 wt. %, 25 mg) in MeOH (5 mL) at 0° C. was added HCl (4 N in 1,4-dioxane, 0.05 mL, 0.21 mmol). After stirring at room temperature for 5 hours under hydrogen, the reaction mixture was filtered through a celite pad and washed with MeOH (100 mL). The filtrate was concentrated to produce the compound 3e (118 mg, 95%) as colorless oil, which was used without further purification. $^1$H-NMR (400 MHz, DMSO-d$_6$) δ 3.98 (t, J=4.4 Hz, 2H), 3.61-3.51 (m, 22H), 2.95 (br, 3H), 1.46 (s, 18H). EI-MS m/z: [M+H]$^+$ 497.6.

Preparation of Compound 3f

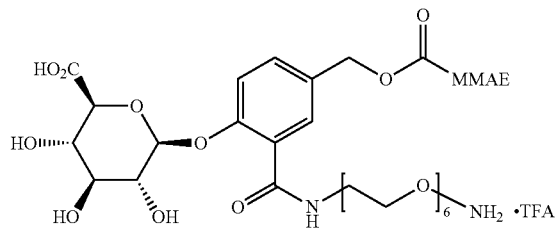

3f

Compound 3f was prepared from compound 1i and compound 3e by a similar method of preparing compound 2g in Example 3. EI-MS m/z: [M+H]$^+$ 1366.6, [M+Na]$^+$ 1389.6.

Example 6. Preparation of Compound 3g

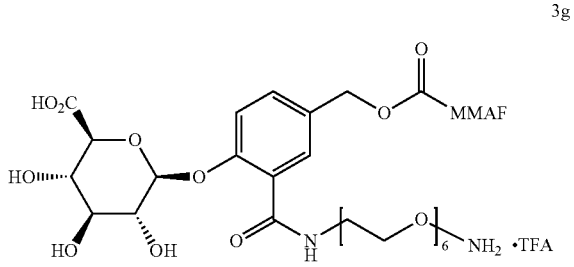

3g

Compound 3g was prepared from compound 1j and compound 3e by a similar method of preparing compound 2g in Example 3. EI-MS m/z: [M+H]$^+$ 1380.6, [M+Na]$^+$ 1403.6.

Example 7. Preparation of Compound 4f

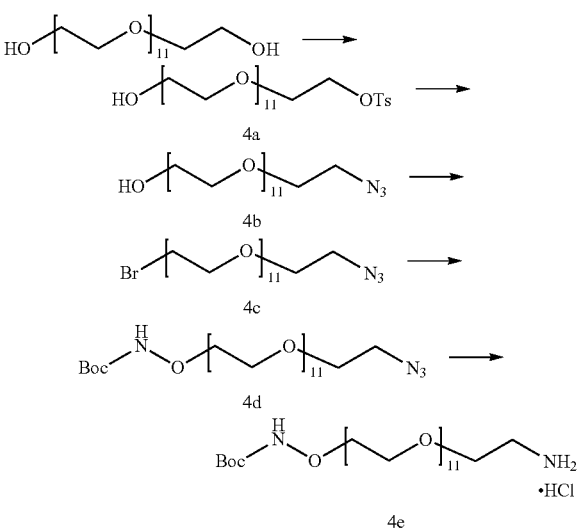

Preparation of Compound 4a

To a stirred solution of dodecaethylene glycol (1.8 g, 3.2 mmol) in DCM (18 mL) was added p-toluenesulfonyl chloride (656 mg, 3.4 mmol), Ag$_2$O (1.13 g, 4.9 mmol) and KI (108 mg, 0.65 mmol). After stirring at room temperature for 30 minutes, the reaction mixture was filtered through a celite pad and washed with DCM (50 mL). The filtrate was concentrated. The resulting residue was purified by column chromatography to produce the compound 4a (490 mg, 21%) as light yellowish oil. $^1$H-NMR (400 MHz, CDCl$_3$) δ 7.81 (d, 2H), 7.35 (d, 2H), 4.16 (t, 2H), 3.72-3.58 (m, 46H), 2.82 (br s, 1H), 2.45 (s, 3H).

Preparation of Compound 4b

Compound 4a (490 mg, 0.69 mmol) and NaN$_3$ (68 mg, 1.04 mmol) were dissolved in DMF (16 mL) and the reaction mixture was heated at 100° C. for 3 hours. The reaction mixture was filtered and concentrated. The crude product was purified by column chromatography to yield the compound 4b (267 mg, 67%). $^1$H-NMR (400 MHz, CDCl$_3$) δ 3.72-3.60 (m, 46H), 3.39 (t, 2H), 2.84 (t, 1H), 3.40 (m, 2H).

Preparation of Compound 4c

To a stirred solution of compound 4b (265 mg, 0.46 mmol) in THF (10 mL) at 0° C. were added 4-methylmorpholine (0.066 mL, 0.60 mmol) and methanesulfonic anhydride (121 mg, 0.69 mmol). After 2 hours, LiBr (120 mg, 1.38 mmol) was added to a stirred solution and the resulting reaction mixture was refluxed for 6 hours. After cooling to room temperature, the reaction mixture was concentrated under reduced pressure. The residue was purified by column chromatography (EtOAc to EtOAc/MeOH 10/1) to yield the compound 4c (178 mg, 60%). $^1$H-NMR (400 MHz, CDCl$_3$) δ 3.81 (t, 2H), 3.65 (m, 42H), 3.47 (t, 2H), 3.39 (t, 2H).

Preparation of Compound 4d

NaH (60% in oil, 14 mg, 0.33 mmol) was added to a stirred mixture of compound 4c (175 mg, 0.27 mmol), and N-Boc-hydroxylamine (47 mg, 0.35 mmol) in DMF (5 mL) at 0° C. The reaction mixture was warmed up to room temperature and kept for 12 hours at this temperature. The solvent was evaporated under reduced pressure and the residue was purified by column chromatography (MeOH/CHCl$_3$ 1/20 to 1.5/20), which produced the compound 4d (148 mg, 78%). $^1$H-NMR (400 MHz, CDCl$_3$) δ 4.00 (t, 2H), 3.66 (m, 44H), 3.39 (t, 2H), 1.47 (d, 9H).

Preparation of Compound 4e

To a stirred mixture of compound 4d (148 mg, 0.21 mmol), and Pd/C (10 wt. %, 28 mg) in MeOH (5 mL) at 0° C. was added HCl (4 N in 1,4-dioxane, 0.053 mL, 0.21 mmol). After stirring at room temperature for 30 minutes under hydrogen, the reaction mixture was filtered through a celite pad and washed with MeOH (30 mL). The filtrate was concentrated to produce the compound 4e (142 mg, 96%) as colorless oil, which was used without further purification. $^1$H-NMR (400 MHz, DMSO-d$_6$) δ 4.00 (t, 2H), 3.92 (t, 2H), 3.76-3.64 (m, 42H), 3.18 (t, 2H) 1.47 (s, 9H).

Preparation of Compound 4f

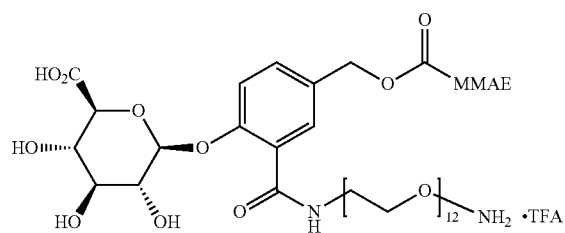

Compound 4f was prepared from compound 1i and compound 4e by a similar method of preparing compound 2g in Example 3. EI-MS m/z: [M+H]$^+$ 1631.9.

Example 8. Preparation of Compound 4g

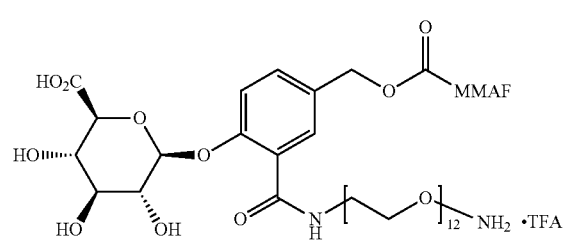

Compound 4g was prepared from compound 1j and compound 4e by a similar method of preparing compound 2g in Example 3. EI-MS m/z: EI-MS m/z [M+H]$^+$ 1645.3.

Example 9. Preparation of Compound 5e

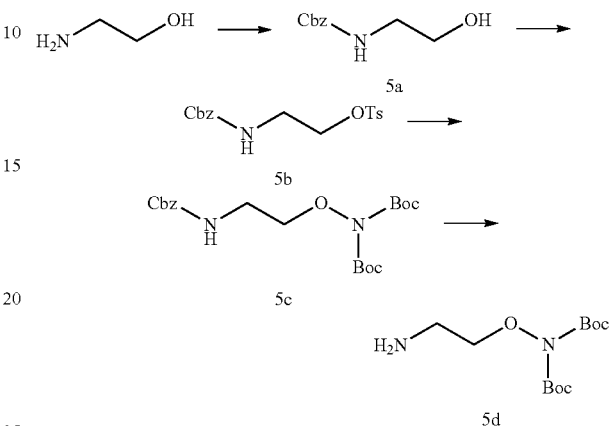

Preparation of Compound 5a

To a solution of 2-aminoethanol (10 g, 164 mmol) in DCM (70 mL) were added triethylamine (3.9 mL, 28.1 mmol) and benzyl chloroformate (30 mL, 213 mmol) in DCM (30 mL) at 0° C. under N$_2$. After 24 hours, the reaction mixture was concentrated. The resulting residue was diluted with H$_2$O (50 mL) and extracted with EtOAc (3×100 mL). The organic layers were combined, dried over anhydrous MgSO$_4$, filtered and concentrated. The crude product was purified by column chromatography to produce the compound 5a (17 g, 53%). $^1$H-NMR (400 MHz, CDCl$_3$) δ 7.40-7.27 (m, 5H), 5.11 (s, 2H), 3.72 (s, 2H), 3.56 (s, 2H), 2.13 (br s, 1H).

Preparation of Compound 5b

To a solution of compound 5a (5.0 g, 25.6 mmol) in DCM (70 mL) triethylamine (3.9 mL, 28.1 mmol) were added DMAP (100 mg, 5.12 mmol) and p-toluenesulfonyl chloride (5.4 g, 28.1 mmol) in DCM (30 mL) at 0° C. under N$_2$. After 15 hours at 0° C., the reaction mixture was diluted with saturated aq. NH$_4$Cl (100 mL) and extracted with DCM (2×100 mL). The organic layers were combined, dried over anhydrous MgSO$_4$, filtered and concentrated. The crude product was purified by column chromatography to produce the compound 5b (8.29 g, 92%). $^1$H-NMR (400 MHz, CDCl$_3$) δ 7.77 (d, J=7.6 Hz, 2H), 7.40-7.28 (m, 7H), 5.07 (s, 3H), 4.09 (s, 2H), 3.45 (s, 2H), 2.43 (s, 3H).

Preparation of Compound 5c

To a solution of compound 5b (2.0 g, 7.23 mmol) in THF (20 mL) was added N,N-diBoc-hydroxylamine (1.7 g, 7.44 mmol) and NaH (300 mg, 6.86 mmol) at 0° C. under N2. After stirring at room temperature for 17 hours, the reaction mixture was diluted with saturated aqueous NH$_4$Cl (50 mL) and extracted with EtOAc (3×50 mL). The organic layers were combined, dried over anhydrous MgSO$_4$, filtered and concentrated. The crude product was purified by column chromatography to produce the compound 5c (375 mg, 16%). $^1$H-NMR (400 MHz, CDCl$_3$) δ 7.45-7.27 (m, 5H), 5.11 (s, 2H), 4.01 (br s, 2H), 3.44 (d, J=4.8 Hz, 2H), 1.52 (s, 18H). EI-MS m/z: [M+H]$^+$ 410.7.

Preparation of Compound 5d

To a solution of compound 5c (187 mg, 0.45 mmol) in MeOH (20 mL) Pd/C (10% wt. %, 20 mg) was added and then the reaction mixture was stirred at room temperature for 4 hours under hydrogen. The reaction mixture was filtered through a celite pad and washed with MeOH (20 mL). The filtrate was concentrated to produce the compound 5d (120 mg) as colorless oil, which was used without further purification.

Preparation of Compound 5e

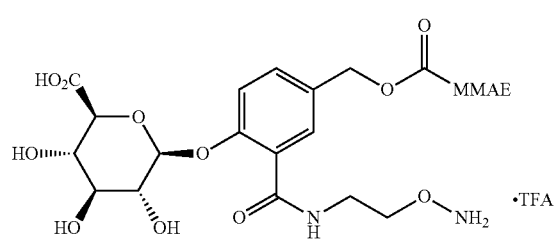

5e

Compound 5e was prepared from compound 1i and compound 5d by a similar method of preparing compound 2g in Example 3. EI-MS m/z: [M+H]$^+$ 1146.4.

Example 10. Preparation of Compound 5f

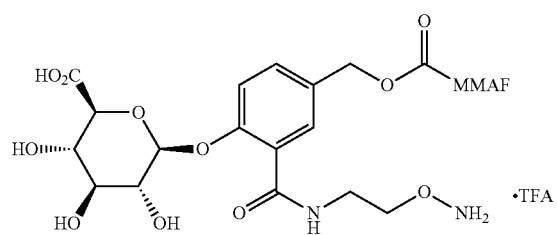

5f

Compound 5f was prepared from compound 1j and compound 5d by a similar method of preparing compound 2g in Example 3. EI-MS m/z: [M+H]$^+$ 1160.3.

Example 11. Preparation of Compound 6e

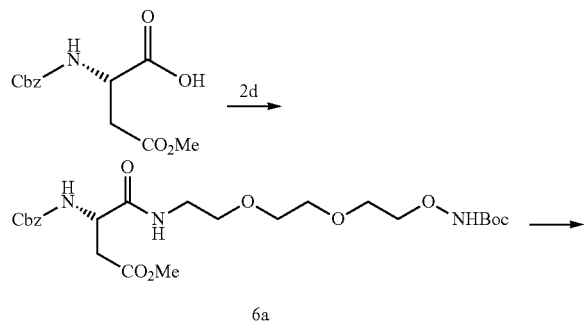

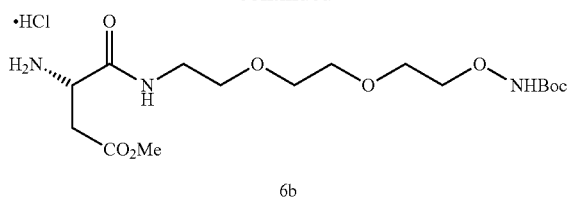

6b

Preparation of Compound 6a

DIPEA (1.2 mL, 9.96 mmol) and HBTU (1.69 g, 6.22 mmol) were added to a stirred mixture of Z-Asp(OMe)-OH (500 mg, 1.78 mmol) and compound 2d (642 mg, 2.98 mmol) in DMF (5 mL). The reaction mixture was stirred at room temperature for 22 hours under N$_2$. The reaction mixture was diluted with H$_2$O (100 mL) and extracted with EtOAc (2×100 mL). The combined organic layers were dried over anhydrous Na$_2$SO$_4$, filtered and concentrated. The resulting residue was purified by column chromatography to yield the compound 6a (368 mg, 40%). $^1$H-NMR (400 MHz, CDCl$_3$) δ 7.85-7.70 (m, 1H), 7.45-7.28 (m, 5H), 7.04 (s, 1H), 6.02 (d, J=8.4 Hz, 1H), 5.11 (s, 2H), 4.65-4.50 (m, 1H), 4.00 (d, J=3.6 Hz, 2H), 3.72-3.30 (m, 10H), 2.80 (dd, J=5.6 Hz, 2H), 1.46 (s, 9H).

Preparation of Compound 6b

To a stirred mixture of compound 6a (150 mg, 0.28 mmol) and Pd/C (10 wt. %, 20 mg) in MeOH (5 mL) at 0° C. was added HCl (4 N in 1,4-dioxane, 0.07 mL, 0.28 mmol). After stirring at room temperature for 2 hours under hydrogen, the reaction mixture was filtered through a celite pad and washed with MeOH (20 mL). The filtrate was concentrated to produce the compound 6b (169 mg) as colorless oil, which was used without further purification. EI-MS m/z: [M+1]$^+$ 393.7.

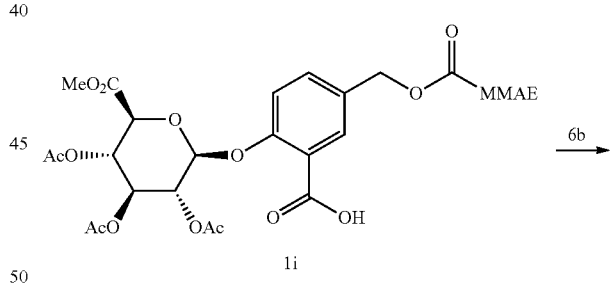

1i

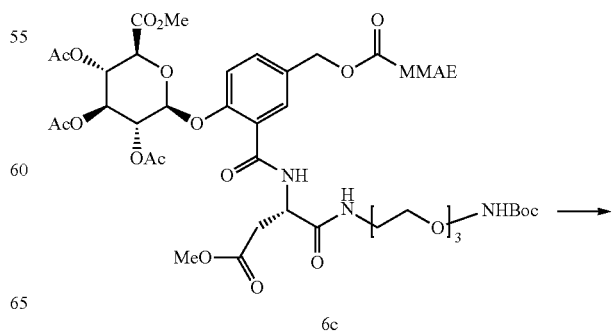

6c

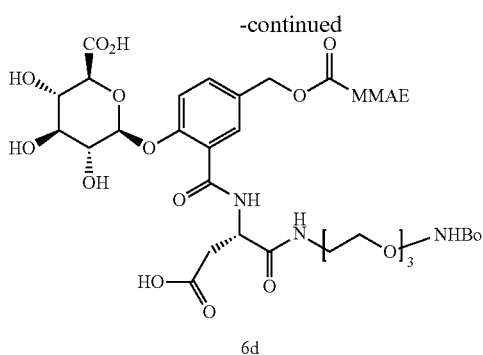

6d

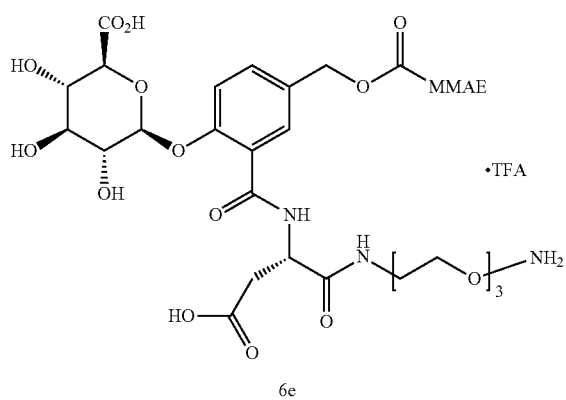

6e

Preparation of Compound 6c

DIPEA (0.022 mL, 0.12 mmol) and HBTU (20 mg, 0.05 mmol) were added to a stirred mixture of compound 1i (50 mg, 0.04 mmol) and compound 6b (22 mg, 0.05 mmol) in DMF (1 mL). The reaction mixture was stirred at room temperature for 14 hours under $N_2$. Then, the reaction mixture was diluted with $H_2O$ (10 mL) and extracted with EtOAc (2×20 mL). The combined organic layers were dried over anhydrous $Na_2SO_4$, filtered and concentrated. The resulting residue was purified by column chromatography to yield the compound 6c (38 mg, 60%). EI-MS m/z: [M+H]$^+$ 1604.5.

Preparation of Compound 6d

To a solution of compound 6c (38 mg, 0.023 mmol) in MeOH (1 mL) was added LiOH monohydrate (5 mg, 0.118 mmol) in $H_2O$ (1 mL) at 0° C. After 2 hours at 0° C., the pH of the solution was adjusted with AcOH to 4-5 and concentrated under reduced pressure. The residue was dissolved in DMSO (1.5 mL) and purified by HPLC to produce the compound 6d (26 mg, 78%).

EI-MS m/z: [M+H]$^+$ 1450.5.

Preparation of Compound 6e

TFA (0.3 mL) was added to a stirred solution of compound 6d (26 mg, 0.018 mmol) in DCM (1.5 mL). After stirring at 0° C. for 2 hours, the solvent and excess TFA were removed by $N_2$ flow. Then the residue was dissolved in DMSO (1 mL) and purified by HPLC. Pure fractions with the same retention time were combined and lyophilized to produce the compound 6e (19.5 mg, 80%) as white solid. EI-MS m/z: [M+H]$^+$ 1350.6.

Example 12. Preparation of Compound 7e

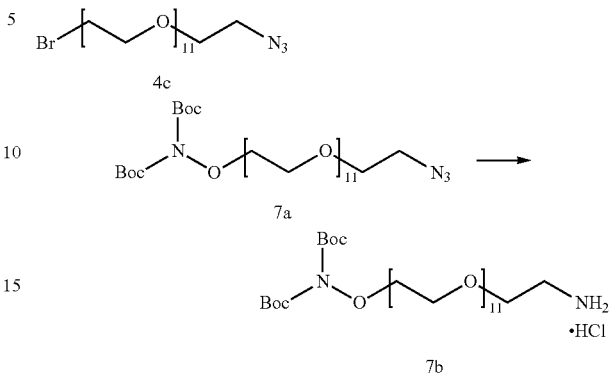

Preparation of Compound 7a

NaH (60 wt. %, 500 mg, 12.49 mmol) was added to a stirred mixture of compound 4c (6.10 g, 9.61 mmol) and N,N-diBoc-hydroxylamine (2.69 g, 11.53 mmol) in DMF (90 mL) at 0° C. The reaction mixture was heated up to room temperature and kept for 12 hours at this temperature. The reaction mixture was evaporated under reduced pressure and the resulting residue was purified by column chromatography. Pure fractions were evaporated in vacuo to yield the compound 7a (5.70 g, 75%). $^1$H-NMR (400 MHz, CDCl$_3$) δ 4.05 (t, 2H), 3.71 (t, 2H), 3.64 (m, 42H), 3.37 (t, 2H), 1.51 (d, 18H).

Preparation of Compound 7b

To a stirred mixture of compound 7a (5.70 g, 7.21 mmol), and Pd/C (10 wt. %, 570 mg) in MeOH (100 mL) at 0° C. was added HCl (4 N in 1,4-dioxane, 1.9 mL, 7.2 mmol). After stirring at room temperature for 30 minutes under hydrogen, the reaction mixture was filtered through a celite pad and washed with MeOH (30 mL). The filtrate was concentrated to produce the compound 7b (5.10 g, 87%) as colorless oil, which was used without further purification. $^1$H-NMR (400 MHz, DMSO-d$_6$) δ 4.21 (t, 2H), 4.07 (s, 2H), 3.95-3.78 (m, 42H), 3.32 (s, 2H) 1.63 (s, 18H).

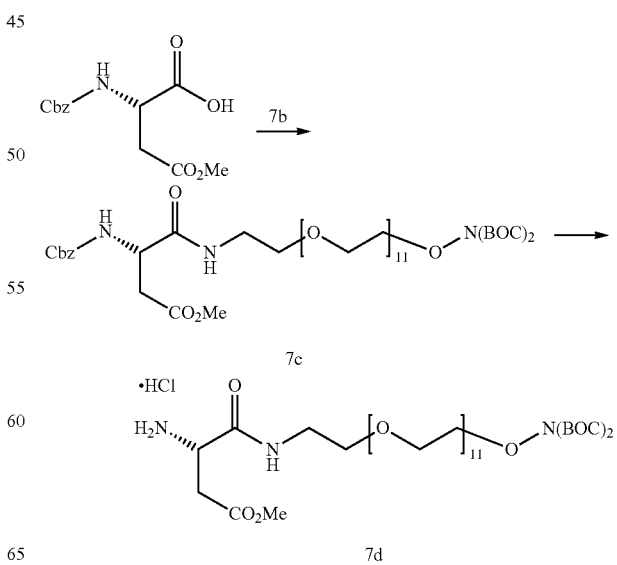

Preparation of Compound 7c

DIPEA (0.25 mL, 1.42 mmol) and HBTU (337 g, 0.89 mmol) were added to a stirred mixture of Z-Asp(OMe)-OH (100 mg, 0.36 mmol) and compound 7b (340 mg, 0.43 mmol) in DMF (10 mL). The reaction mixture was stirred at room temperature for 20 hours under $N_2$. Then, the reaction mixture was diluted with $H_2O$ (100 mL) and extracted with EtOAc (2×100 mL). The combined organic layers were dried over anhydrous $Na_2SO_4$, filtered and concentrated. The resulting residue was purified by column chromatography to yield the compound 7c (123 mg, 58%). EI-MS m/z: $[M+H]^+$ 1024.2.

Preparation of Compound 7d

To a stirred mixture of compound 7c (120 mg, 0.12 mmol) and Pd/C (10 wt. %, 20 mg) in MeOH (5 mL) at 0° C. was added HCl (4 N in 1,4-dioxane, 0.03 mL, 0.12 mmol). After stirring at room temperature for 2 hours under hydrogen, the reaction mixture was filtered through a celite pad and washed with MeOH (20 mL). The filtrate was concentrated to produce the compound 7d (120 mg) as colorless oil, which was used without further purification.

Preparation of Compound 7e

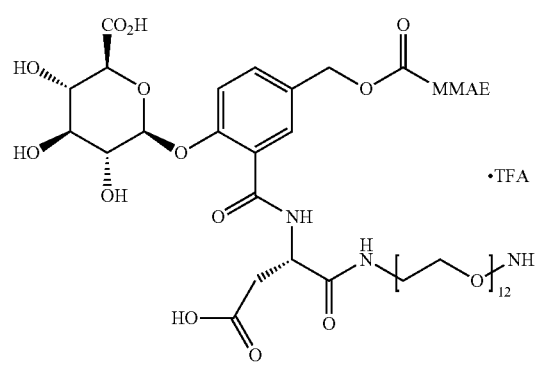

Compound 7e was prepared from compound 1i and compound 7d by a similar method of preparing compound 6e in Example 11. EI-MS m/z: $[M+H]^+$ 1747.1.

Example 13. Preparation of Compound 8f

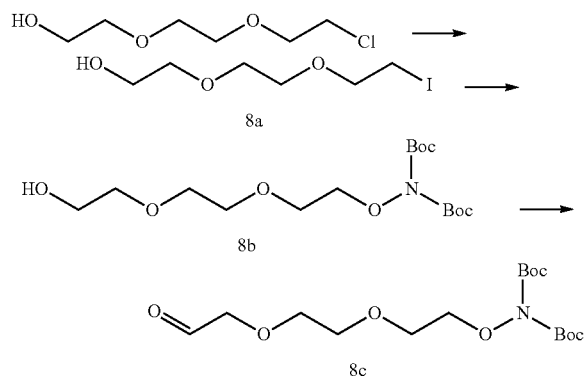

Preparation of Compound 8a

To a solution of 2-(2-(2-chloroethoxy)ethoxy)ethanol (5.0 g, 29.6 mmol) in acetone (30 mL) was added NaI (13.3 g, 88.9 mmol). The reaction mixture was refluxed for 12 hours. After the reaction was completed, the reaction mixture was filtered and concentrated. The crude product was purified by column chromatography to produce the compound 8a (7.0 g, 91%). $^1$H-NMR (400 MHz, $CDCl_3$) δ 3.80-3.73 (m, 4H), 3.72-3.65 (m, 4H), 3.63-3.61 (m, 2H), 3.27 (t, J=6.4 Hz, 2H).

Preparation of Compound 8b

NaH (500 mg, 12.49 mmol) was added to a stirred mixture of compound 8a (2.0 g, 7.69 mmol), and N,N-diBoc-hydroxylamine (2.33 g, 10.00 mmol) in DMF (20 mL) at 0° C. under $N_2$. After stirring at room temperature for 17 hours, the reaction mixture was diluted with saturated aq. $NH_4Cl$ (50 mL) and extracted with EtOAc (3×50 mL). The organic layers were combined, dried over anhydrous $MgSO_4$, filtered and concentrated. The crude product was purified by column chromatography to produce the compound 8b (1.54 g, 54%). $^1$H-NMR (400 MHz, $CDCl_3$) δ 7.45-7.27 (m, 5H), 5.11 (s, 2H), 4.01 (br s, 2H), 3.44 (d, J=4.8 Hz, 2H), 1.52 (s, 18H). EI-MS m/z: $[M+H]^+$ 410.7.

Preparation of Compound 8c

To a stirred solution of the compound 8b (123 mg, 0.242 mmol) in DMSO (2 mL) and DCM (2 mL) were added $SO_3$.pyridine complex (116 mg, 0.726 mmol) and triethylamine (0.17 mL, 1.21 mmol) at 0° C. under $N_2$. After 1 hour, the reaction mixture was diluted with saturated aq. $NH_4Cl$ (10 mL) and extracted with DCM (2×10 mL). The organic layers were combined, dried over anhydrous $MgSO_4$, and filtered. Concentration under reduced pressure provided the compound 8c (88 mg), which was used without further purification. $^1$H-NMR (400 MHz, $CDCl_3$) δ 9.74 (s, 1H), 4.19 (s, 2H), 3.77-3.69 (m, 6H), 3.42 (m, 2H).

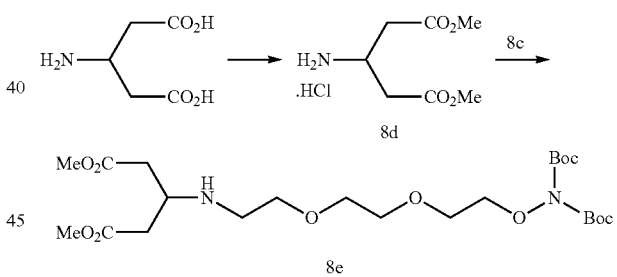

Preparation of Compound 8d

To a solution of glutamic acid (500 mg, 0.339 mmol) in MeOH (10 mL) was added thionyl chloride (0.148 mL, 2.04 mmol) at 0° C. under $N_2$. After 24 hours, the reaction mixture was concentrated to produce the compound 8d (697 mg), which was used without further purification. $^1$H-NMR (400 MHz, $CDCl_3$) δ 7.40-7.27 (m, 5H), 5.11 (s, 2H), 3.72 (s, 2H), 3.56 (s, 2H), 2.13 (br s, 1H).

Preparation of Compound 8e

To a solution of compound 8d (34 mg, 0.16 mmol) and compound 8c (88 mg, 0.24 mmol) in MeOH (5 mL) was added $NaCNBH_3$ (10 mg, 0.16 mmol) at room temperature under $N_2$. After 3 hours, the reaction mixture was filtered and concentrated. The crude product was purified by column chromatography to produce the compound 8e (53 mg, 63%). $^1$H-NMR (400 MHz, $CDCl_3$) δ 7.45-7.25 (m, 10H), 5.60 (br s, 2H), 5.03 (s, 4H), 3.80-3.25 (m, 20H), 2.81 (s, 4H).

Preparation of Compound 8f

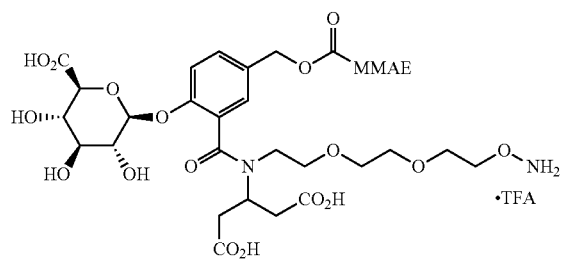

Compound 8f was prepared from compound 1i and compound 8e by a similar method of preparing compound 6e in Example 11. EI-MS m/z: [M+H]$^+$ 1365.0.

Example 14. Preparation of Compound 9j

Preparation of Compound 9a

To a solution of hexaethylene glycol (10.48 g, 37.12 mmol) in DCM (400 mL) was added imidazole (3.20 g, 44.54 mmol) at 0° C. under $N_2$. After 5 minutes, the reaction mixture was added dropwise to the solution of TBSCl (5.60 g, 37.12 mmol) in DCM (50 mL) at the same temperature under $N_2$ atmosphere. The reaction mixture was stirred at 0° C. and warmed to room temperature for 21 hours under $N_2$. After the reaction was completed, the reaction mixture was diluted with water (200 mL) and extracted with DCM (2×100 mL). The organic layers were dried over anhydrous $Na_2SO_4$ and concentrated under reduced pressure. The resulting residue was purified by column chromatography. The pure fractions were evaporated in vacuo to yield the compound 9a (6.70 g, 46%). $^1$H-NMR (400 MHz, CDCl$_3$) δ 3.77-3.71 (m, 4H), 3.66-3.60 (m, 18H), 3.56-3.54 (t, 2H), 0.89 (s, 9H), 0.06 (s, 6H).

Preparation of Compound 9b

To a solution of compound 9a (3.32 g, 8.37 mmol) in dry THF (40 mL) was added NaH (55% in oil, 438 mg, 10.05

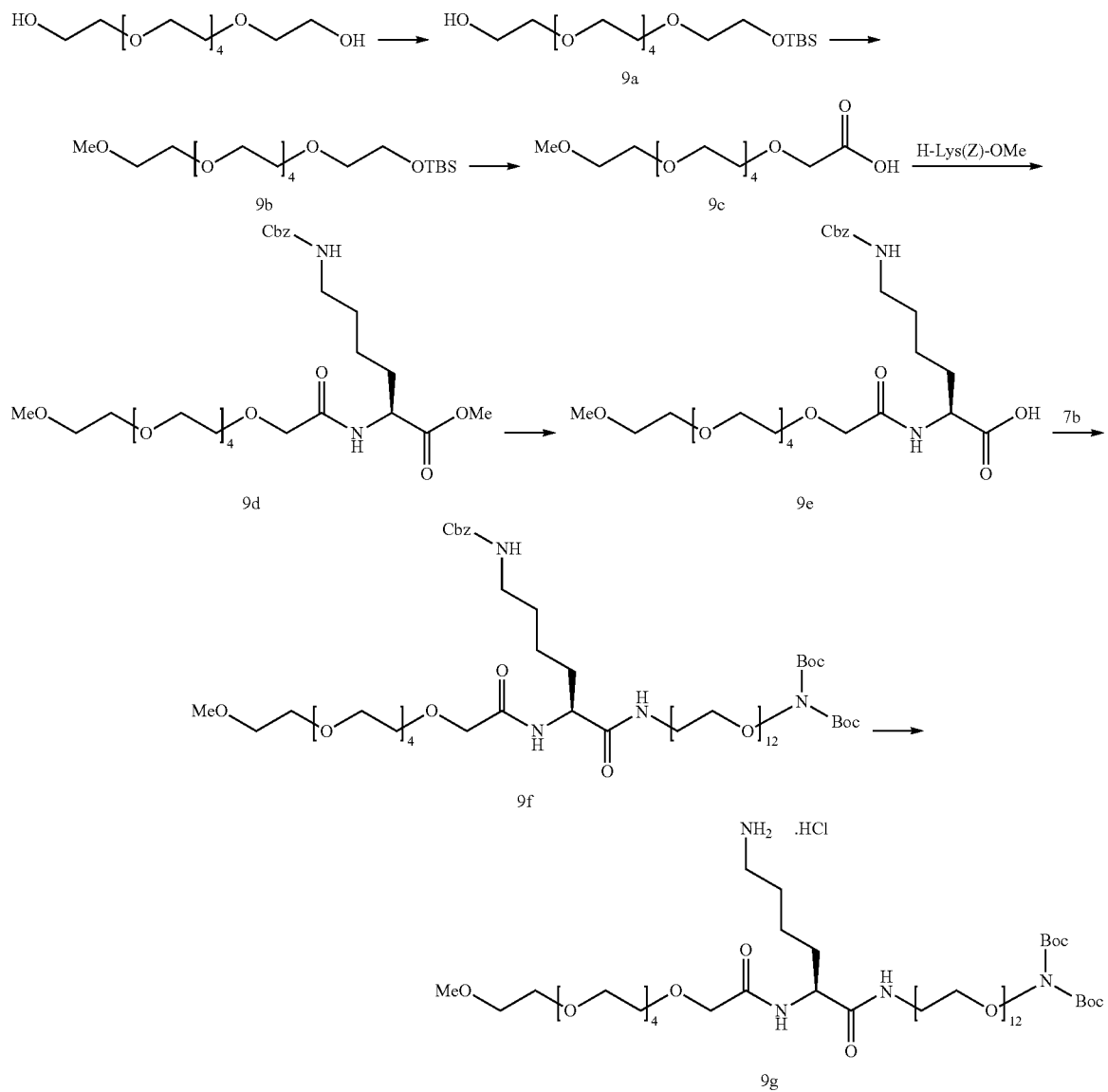

mmol) at 0° C. under N$_2$. After 30 minutes, MeI (0.78 mL, 12.56 mmol) was added to the reaction mixture at the same temperature under N$_2$. The reaction mixture was stirred and warmed to room temperature for 18 hours under N$_2$. After the reaction was completed, quenched with H$_2$O (10 mL) and extracted with EA (3×10 mL). The organic layers were combined, washed with saturated aq. NH$_4$Cl (5 mL) and brine (10 mL), dried over anhydrous Na$_2$SO$_4$ and evaporated under reduced pressure. The resulting residue was purified by column chromatography. Pure fractions were evaporated in vacuo to yield the compound 9b (3.16 g, 92%). $^1$H-NMR (400 MHz, CDCl$_3$) δ 3.78-3.75 (t, 2H), 3.65 (s, 20H), 3.57-3.54 (t, 4H), 3.38 (s, 3H), 0.89 (s, 9H), 0.06 (s, 6H).

Preparation of Compound 9c

To a solution of compound 9b (3.16 g, 7.69 mmol) in acetone (100 mL) was added Jones reagent (10 mL) at 0° C. under N$_2$. The reaction mixture was stirred and warmed to room temperature for 17 hours under N$_2$. After the reaction was completed, the reaction mixture was filtered and evaporated under reduced pressure. The residue was diluted with H$_2$O (100 mL) and extracted with CHCl$_3$ (3×50 mL). The organic layers were combined, dried over anhydrous Na$_2$SO$_4$ and evaporated under reduced pressure. The resulting crude compound 9c (2.28 g, 95%) was used without further purification. $^1$H-NMR (400 MHz, CDCl$_3$) δ 4.16 (s, 2H), 3.76-3.75 (t, 2H), 3.69-3.67 (m, 16H), 3.57-3.55 (t, 2H), 3.38 (s, 3H).

Preparation of Compound 9d

DIPEA (3.8 mL, 22.03 mmol), HOBt (1.29 g, 9.55 mmol) and EDC·HCl (1.83 g, 9.55 mmol) were added to a stirred mixture of compound 9c (2.28 g, 7.34 mmol) and H-Lys(Z)—OMe hydrochloride (2.91 g, 8.81 mmol) in DMF (30 mL). After stirring at room temperature for 14 hours under N$_2$, the reaction mixture was concentrated. Purification by column chromatography gave the compound 9d (1.23 g, 72%). $^1$H-NMR (400 MHz, CDCl$_3$) δ 7.38-7.31 (m, 5H), 5.10 (s, 2H), 5.00 (s, 1H) 4.68-4.62 (m, 1H), 4.03 (s, 2H), 3.75 (s, 3H), 3.68-3.64 (m, 16H), 3.56 (t, 2H), 3.39 (s, 3H), 3.20 (m, 2H), 1.89 (m, 1H), 1.74 (m, 1H), 1.55 (m, 1H), 1.40 (m, 1H). EI-MS m/z: [M+H]$^+$ 586.8, [M+Na]$^+$ 608.9.

Preparation of Compound 9e

To a solution of compound 9d (2.16 g, 3.68 mmol) in THF/MeOH/H$_2$O (18 mL/6 mL/6 mL) was added LiOH monohydrate (307 mg, 7.31 mmol) at 0° C. under N$_2$. The reaction mixture was stirred for 1 hour at room temperature. Then the pH of the solution was adjusted to 2-3 with 1 N aq. HCl. The reaction mixture was poured into H$_2$O (20 mL) and extracted with DCM (3×50 mL). The organic layers were combined, dried over Na$_2$SO$_4$. Filtration and concentration produced the compound 9e (2.28 g, 99%), which was used without further purification. $^1$H-NMR (400 MHz, CDCl$_3$) δ 7.34-7.30 (m, 5H), 5.08 (s, 2H), 4.66-4.60 (q, 1H), 4.01 (s, 2H), 3.67-3.55 (m, 18H), 3.37 (s, 3H), 3.20 (m, 2H), 1.87 (m, 1H), 1.72 (m, 1H), 1.53 (m, 1H), 1.38 (m, 1H).

Preparation of Compound 9f

DIPEA (0.45 mL, 2.63 mmol), HOBt (154 mg, 0.11 mmol) and EDC·HCl (218 mg, 0.11 mmol) were added to a stirred mixture of compound 9e (502 mg, 0.88 mmol) and compound 7b (700 mg, 0.88 mmol) in DMF (8 mL). After stirring at room temperature for 14 hours under N$_2$, the reaction mixture was poured into H$_2$O (20 mL) and extracted with EtOAc (3×20 mL). The combined organic layers were washed with aq. NaHCO$_3$ (20 mL) and brine (20 mL) and dried over anhydrous Na$_2$SO$_4$. After filtration and concentration under reduced pressure, the resulting residue was purified by column chromatography to yield the compound 9f (499 mg, 43%). $^1$H-NMR (400 MHz, CDCl$_3$) δ 7.35-7.30 (m, 5H), 6.83 (s, 1H), 5.15 (s, 1H), 5.08 (s, 2H), 4.43 (q, 1H) 4.07 (t, 1H), 3.65-3.60 (m, 54H), 3.55-3.53 (m, 4H), 3.37 (s, 3H), 3.16 (m, 2H), 1.85 (m, 1H), 1.53-1.52 (d, 19H), 1.38 (m, 2H). EI-MS m/z: [M+H]$^+$ 1337.5.

Preparation of Compound 9g

To a stirred mixture of compound 9f (499 mg, 0.37 mmol) and Pd/C (10 wt. %, 50 mg) in MeOH (20 mL) at 0° C. was added HCl (4 N in 1,4-dioxane, 0.1 mL, 0.37 mmol). After stirring at room temperature for 90 minutes under hydrogen, the reaction mixture was filtered through a celite pad and washed with MeOH (10 mL). The filtrate was concentrated to produce the compound 9g (458 mg, 98%) as colorless oil, which was used without further purification. EI-MS m/z: [M+H]$^+$ 1218.6.

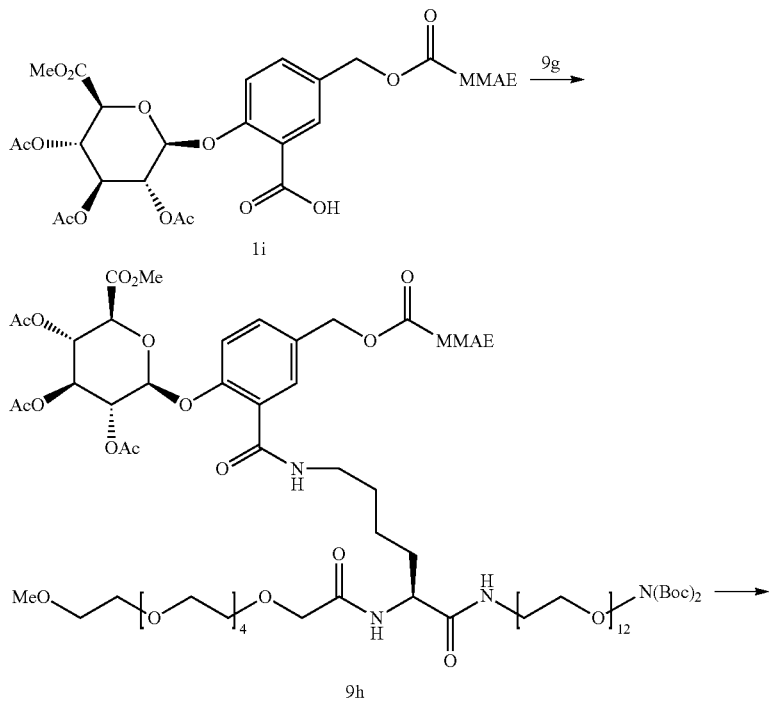

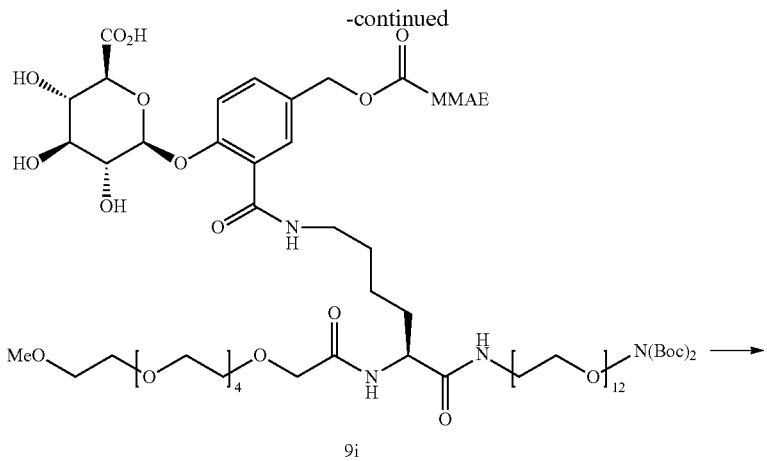

9i

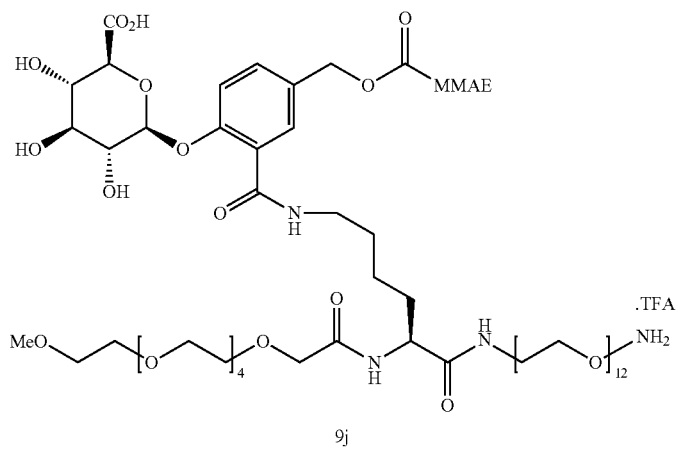

9j

Preparation of Compound 9h

DIPEA (0.019 mL, 0.11 mmol) and HBTU (18 mg, 0.05 mmol) were added to a stirred mixture of compound 1i (45 mg, 0.04 mmol) and compound 9g (57 mg, 0.05 mmol) in DMF (0.5 mL). The reaction mixture was stirred at room temperature for 14 hours under $N_2$. The reaction mixture was diluted with $H_2O$/DMSO (1.5 mL/1.5 mL) and purified by HPLC, which produced compound 9h (65 mg, 57%). EI-MS m/z: 1/2[M+H]$^+$ 1181.7.

Preparation of Compound 9i

To a solution of compound 9h (65 mg, 0.03 mmol) in MeOH (1.5 mL) was added LiOH monohydrate (10 mg, 0.24 mmol) in $H_2O$ (1.5 mL) at 0° C. After 1 hour at 0° C., the pH of the solution was adjusted with AcOH to 4-5 and concentrated under reduced pressure. Then the reaction mixture was dissolved in $H_2O$/DMSO (1.5 mL/1.5 mL) and purified by HPLC, which produced compound 9i (45 mg, 55%). EI-MS m/z: 1/2[M+Na]$^+$1098.7.

Preparation of Compound 9j

TFA (0.2 mL) was added to a stirred solution of compound 9i (45 mg, 0.02 mmol) in DCM (1 mL). After stirring at 0° C. for 30 minutes, the solvent and excess TFA were removed by $N_2$ flow. Then the residue was dissolved in $H_2O$/DMSO (1 mL/1 mL) and purified by HPLC. Pure fractions with the same retention time were combined and lyophilized to produce the compound 9j (14 mg, 32%) as white solid. EI-MS m/z: 1/2[M+H]$^+$ 1026.3.

Example 15. Preparation of Compound 10c

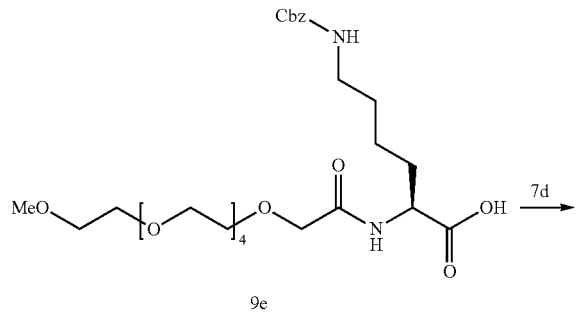

9e

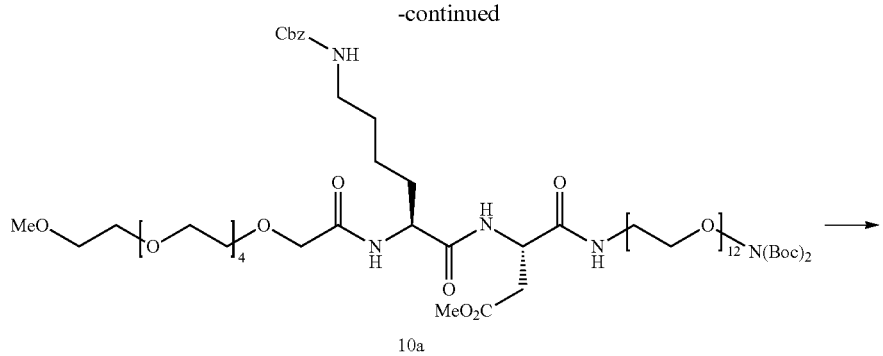

10a

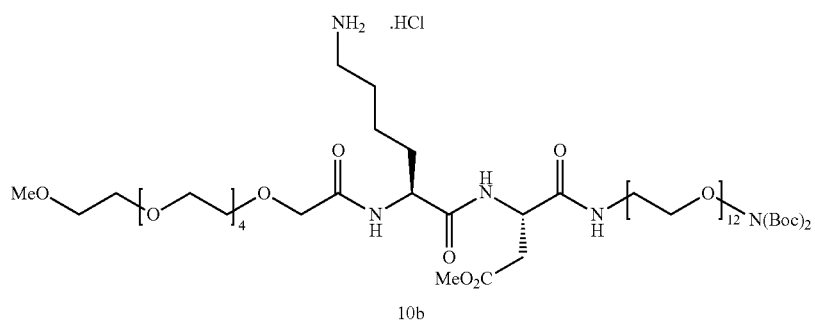

10b

Preparation of Compound 10a

DIPEA (0.03 mL, 0.17 mmol), HOBt (10 mg, 0.075 mmol) and EDC-HCl (14 mg, 0.075 mmol) were added to a stirred mixture of compound 9e (33 mg, 0.058 mmol) and compound 7d (54 mg, 0.058 mmol) in DMF (3 mL). After stirring at room temperature for 14 hours under $N_2$, the reaction mixture was poured into $H_2O$ (10 mL) and extracted with EtOAc (3×10 mL). The combined organic layers were washed with 1 N aq. HCl (8 mL), saturated aq. $NaHCO_3$ (8 mL) and brine (8 mL), and dried over anhydrous $Na_2SO_4$. After filtration and concentration, the residue was purified by column chromatography, which produced the compound 10a (61 mg, 73%). EI-MS m/z: $[M+H]^+$ 1445.0, $[M+H-Boc]^+$1344.9.

Preparation of Compound 10b

To a stirred mixture of compound 10a (60 mg, 0.04 mmol), and Pd/C (10 wt. %, 30 mg) in MeOH (10 mL) at 0° C. was added HCl (4 N in 1,4-dioxane, 0.01 mL, 0.01 mmol). After stirring at room temperature for 3 hours under hydrogen, the reaction mixture was filtered through a celite pad and washed with MeOH (40 mL). The filtrate was concentrated to produce the compound 10b (56 mg, 100%) as colorless oil, which was used without further purification. EI-MS m/z: $[M+H]^+$ 1311.0, $[M+Na+]^+$1332.9.

Preparation of Compound 10c

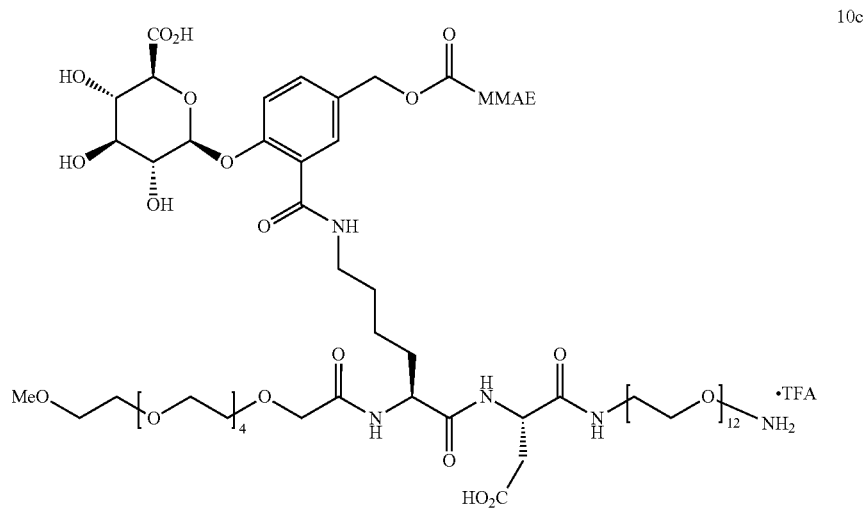

10c

Compound 10c was prepared from compound 1i and compound 10b by a similar method of preparing compound 9j in Example 14. EI-MS m/z: ½[M+H]$^+$ 1083.8.
Example 16. Preparation of Compound 10d
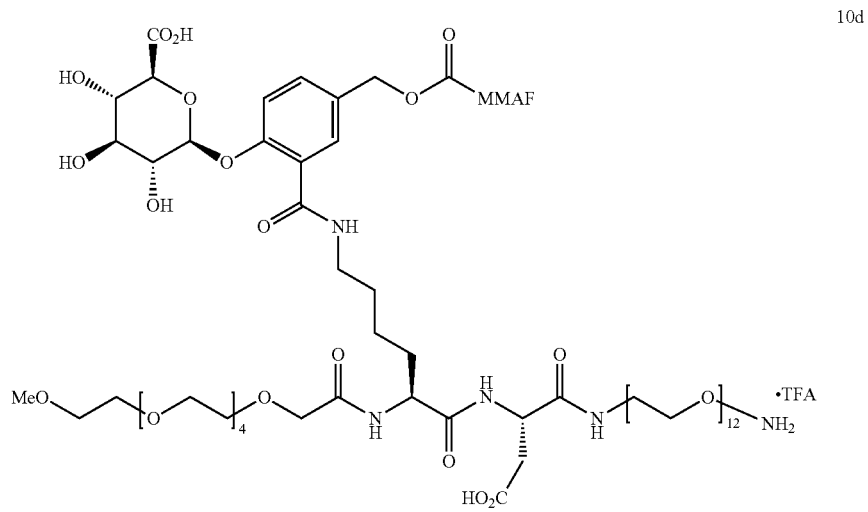
Compound 10d was prepared from compound 1j and compound 10b by a similar method of preparing compound 9j in Example 14. EI-MS m/z: [M+H]$^+$ 2181.3, ½[M+H]$^+$ 1091.3.
Example 17. Preparation of Compound 11i
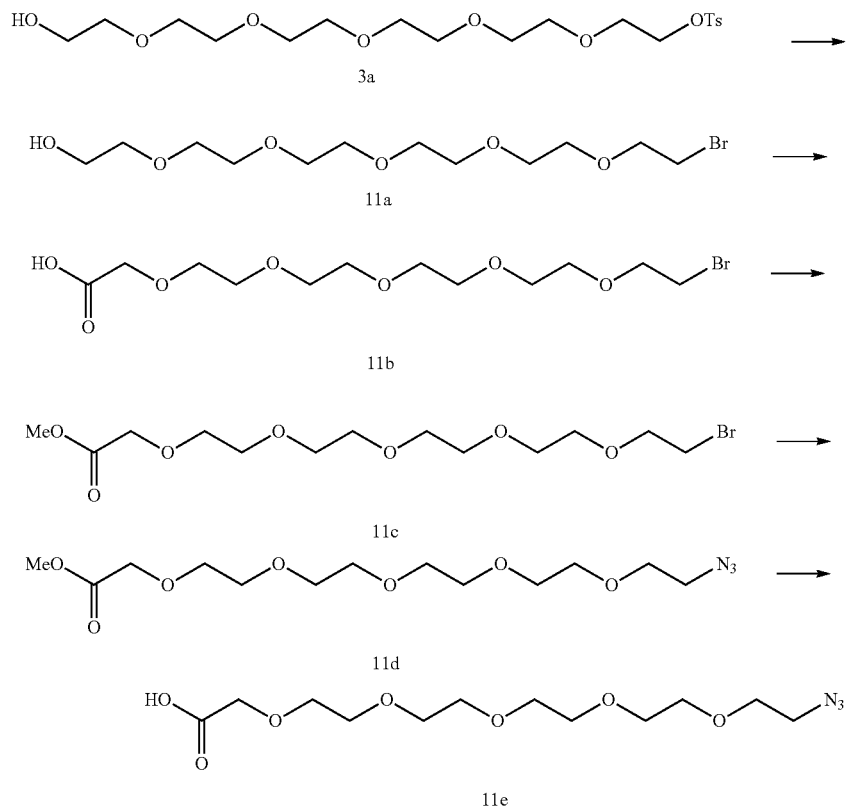

Preparation of Compound 11a

To a solution of compound 3a (8.0 g, 18.3 mmol) in THF (50 mL) was added LiBr (7.9 g, 91.6 mmol) at room temperature. After stirring for 17 hours under reflux, the reaction mixture was filtered and concentrated. The crude product was purified by column chromatography to produce the compound 11a (3.2 g, 50%). $^1$H-NMR (400 MHz, CDCl$_3$) δ 3.95-3.50 (m, 24H).

Preparation of Compound 11b

To a solution of compound 11a (3.2 g, 12.3 mmol) in acetone (20 mL) at 0° C. was added Jones reagent (20 mL). After 15 hours at 0° C., the reaction mixture was filtered and concentrated. The residue was diluted with H$_2$O (50 mL) and extracted with EtOAc (2×100 mL). The organic layers were combined, dried over anhydrous MgSO$_4$, filtered and concentrated. The crude product was purified by column chromatography to produce the compound 11b (3.2 g, 72%). $^1$H-NMR (400 MHz, CDCl$_3$) δ 4.16 (s, 2H), 3.95-3.30 (m, 20H).

Preparation of Compound 11c

To a solution of compound 11b (3.2 g, 8.90 mmol) in MeOH (30 mL) was added oxalyl chloride (1.15 mL, 13.3 mmol) at 0° C. under N$_2$. After 16 hours, the reaction mixture was concentrated and purified by column chromatography, which produced the compound 11c (2.7 g, 81%). $^1$H-NMR (400 MHz, CDCl$_3$) δ 4.17 (s, 2H), 3.80-3.60 (m, 21H), 3.47 (t, J=6.4 Hz, 2H).

Preparation of Compound 11d

Compound 11c (1.0 g, 2.67 mmol) and NaN$_3$ (261 mg, 4.01 mmol) were dissolved in DMF (3 mL). The reaction mixture was heated at 100° C. for 5 hours. After the reaction was completed, the reaction mixture was filtered and concentrated. The residue was purified by column chromatography (EtOAc to EtOAc/MeOH 10/1), which produced the compound 11d (854 mg, 95%). $^1$H-NMR (400 MHz, CDCl$_3$) δ 4.17 (s, 2H), 3.76-3.64 (m, 21H), 3.39 (t, J=5.2 Hz, 2H).

Preparation of Compound 11e

To a stirred solution of compound 11d (854 mg, 2.54 mmol) in MeOH (25 mL) at 0° C. was added 2 M aq. NaOH (6.3 mL, 12.64 mmol). The reaction mixture was stirred at room temperature for 3 hours. The solution was then concentrated under reduced pressure. The resulting suspension was acidified with aqueous 2 N HCl while cooling at 0° C. The residue was extracted by CHCl$_3$ (8×50 mL). The organic layers were combined, dried over Na$_2$SO$_4$ and concentrated to produce the compound 11e (783 mg, 96%). $^1$H-NMR (400 MHz, CDCl$_3$) δ 4.16 (s, 2H), 3.76-3.65 (m, 18H), 3.40 (t, J=5.2 Hz, 2H).

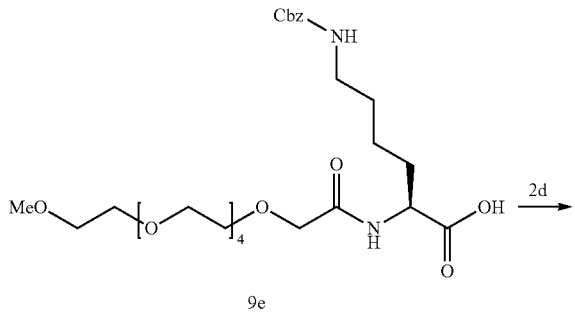

9e

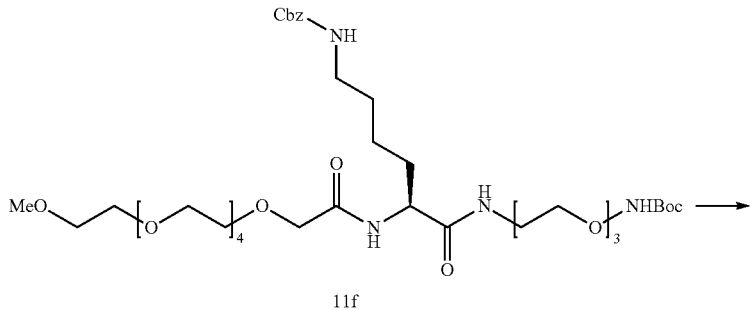

11f

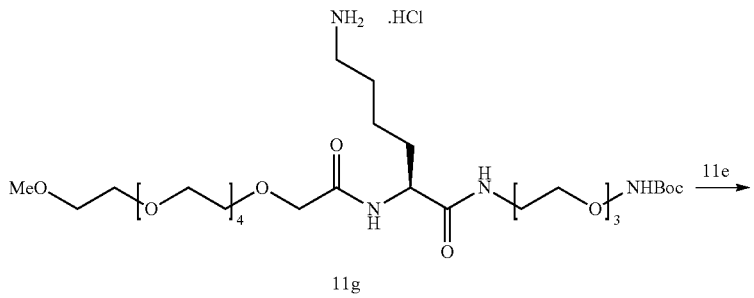

11g

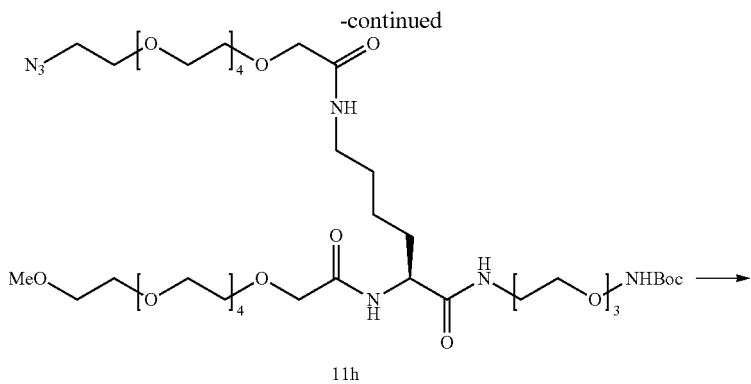

11h

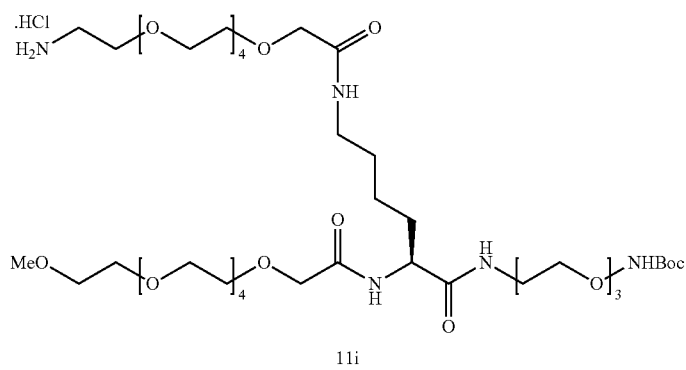

11i

Preparation of Compound 11f

DIPEA (0.47 mL, 2.72 mmol), HOBt (160 mg, 1.18 mmol) and EDC.HCl (226 mg, 1.18 mmol) were added to a stirred mixture of compound 9e (520 mg, 0.91 mmol) and compound 2d (270 mg, 0.91 mmol) in DMF (5 mL). After stirring at room temperature for 14 hours under $N_2$, the reaction mixture was poured into $H_2O$ (20 mL) and extracted with EtOAc (3×30 mL). The combined organic layers were washed with 1 N aq. HCl (15 mL), saturated aq. $NaHCO_3$ (15 mL) and brine (15 mL), and dried over anhydrous $Na_2SO_4$. After filtration and concentration, the residue was purified by column chromatography, which produced the compound 11f (631 mg, 85%).

EI-MS m/z: $[M+H]^+$819.1, $[M+H-Boc]^+$719.1 $[M+Na+]^+$ 841.1.

Preparation of Compound 11g

To a stirred mixture of compound 11f (300 mg, 0.36 mmol), and Pd/C (10 wt. %, 70 mg) in MeOH (20 mL) at 0° C. was added HCl (4 N in 1,4-dioxane, 0.08 mL, 0.08 mmol). After stirring at room temperature for 3 hours under hydrogen, the reaction mixture was filtered through a celite pad and washed with MeOH (40 mL). The filtrate Was concentrated to produce the compound 11g (200 mg, 99%) as colorless oil, which was used without further purification. EI-MS m/z: $[M+H]^+$ 685.1, $[M+Na]^+$707.1.

Preparation of Compound 11h

DIPEA (0.024 mL, 0.41 mmol), HOBt (24 mg, 0.18 mmol) and EDC.HCl (34 mg, 0.18 mmol) were added to a stirred mixture of compound 11g (100 mg, 0.14 mmol) and compound 11e (44 mg, 0.14 mmol) in DMF (5 mL). After stirring at room temperature for 14 hours under $N_2$, the reaction mixture was poured into $H_2O$ (10 mL) and extracted with DCM (3×10 mL). The combined organic layers were dried over anhydrous $Na_2SO_4$. After filtration and concentration, the residue was purified by column chromatography, which produced the compound 11h (73 mg, 53%). EI-MS m/z: $[M+H]^+$ 988.4, $[M+Na-Boc]^+$888.2, $[M+Na]+$1010.4.

Preparation of Compound 11i

To a stirred mixture of compound 11h (73 mg, 0.07 mmol), and Pd/C (10 wt. %, 10 mg) in MeOH (7 mL) at 0° C. was added HCl (4 N in 1,4-dioxane, 0.018 mL, 0.018 mmol). After stirring at room temperature for 2 hours under hydrogen, the reaction mixture was filtered through a celite pad and washed with MeOH (30 mL). The filtrate was concentrated to produce the compound 11i (72 mg, 99%) as colorless oil, which was used without further purification. EI-MS m/z: $[M+H]^+$ 962.4, $[M+Na]^+$984.4.

Preparation of Compound 11i
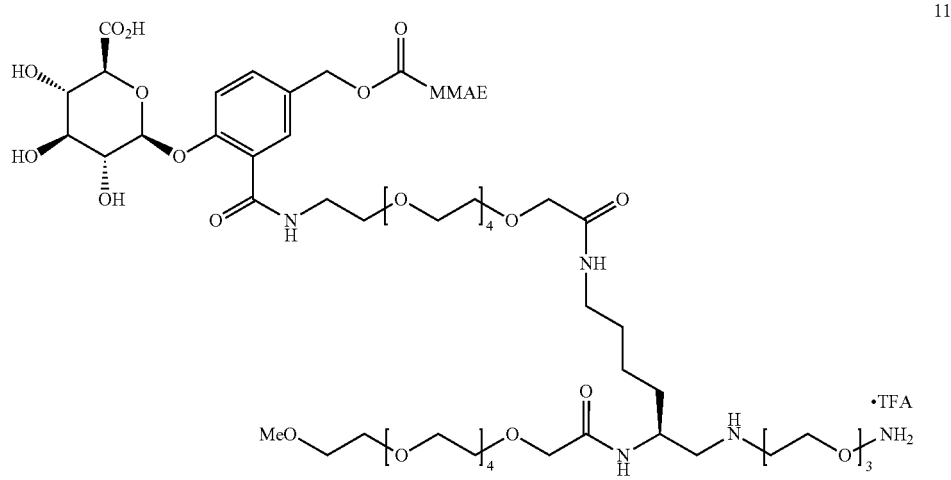
Compound 11j was prepared from compound 1i and compound 11i by a similar method of preparing compound 9j in Example 14. EI-MS m/z: [M+H]$^+$ 1932.5.
Example 18. Preparation of Compound 11k
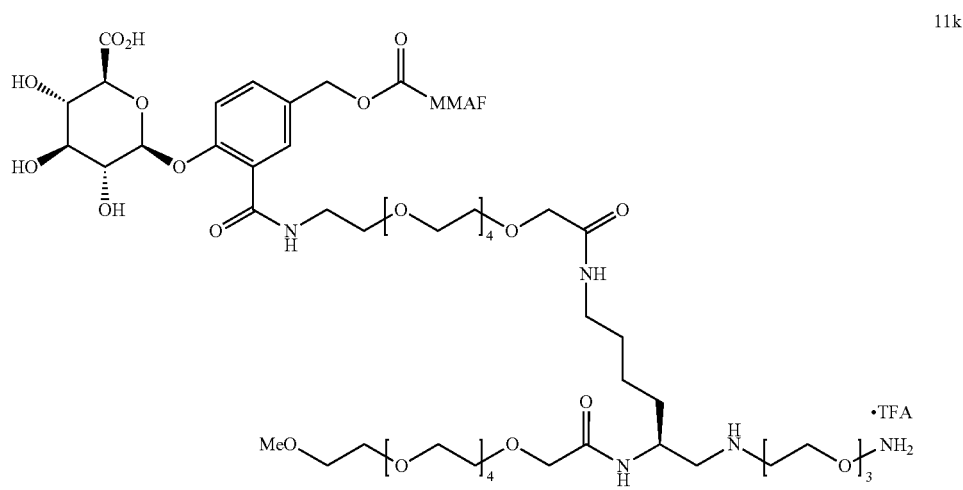
Compound 11k was prepared from compound 1j and compound 11i by a similar method of preparing compound 9j in Example 14. EI-MS m/z: [M+H]$^+$ 1947.1.

Example 19. Preparation of Compound 12c

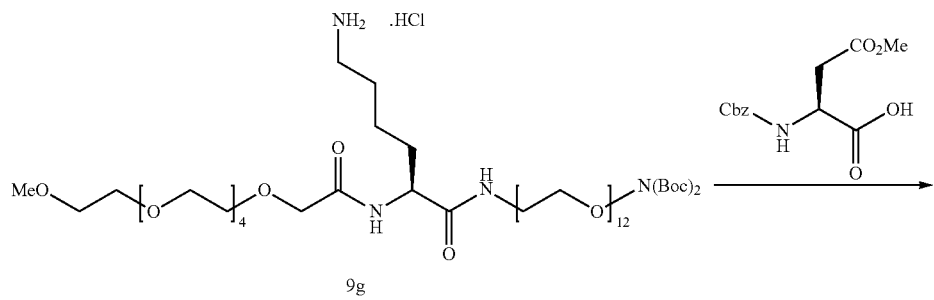

9g

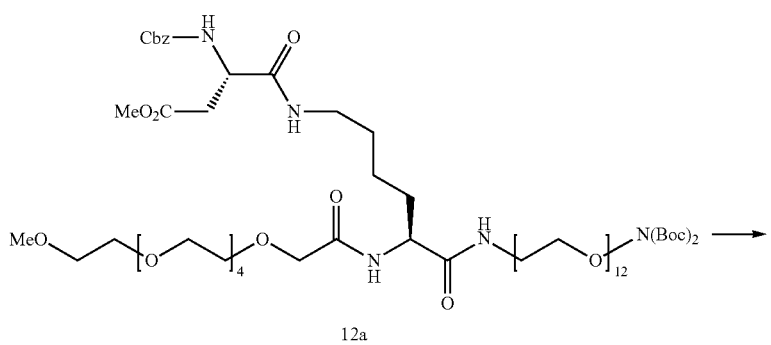

12a

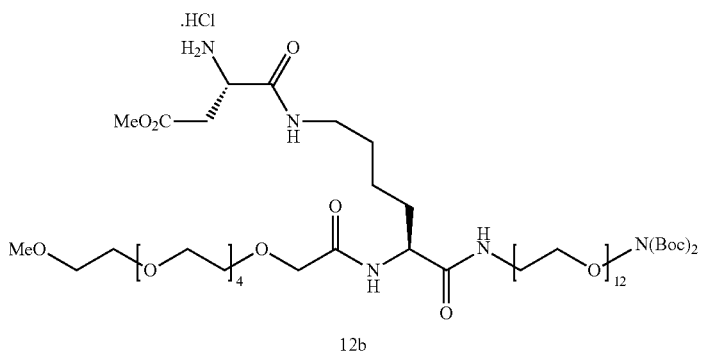

12b

Preparation of Compound 12a

DIPEA (0.13 mL, 0.77 mmol) and HBTU (110 mg, 0.35 mmol) were added to a stirred mixture of compound 9g (235 mg, 0.1929 mmol) and Z-Asp(OMe)-OH (54 mg, 0.212 mmol) in DMF (5 mL). After stirring at room temperature for 14 hours under $N_2$, the reaction mixture was poured into $H_2O$ (20 mL) and extracted with EtOAc (3×20 mL). The combined organic layers were washed with 1 N aq. HCl (7 mL), saturated aq. $NaHCO_3$ (7 mL) and brine (7 mL), and dried over anhydrous $Na_2SO_4$. After filtration and concentration, the residue was purified by column chromatography, which produced the compound 12a (260 mg, 93%). $^1$H-NMR (400 MHz, $CDCl_3$) δ 8.07 (t, 1H), 7.62 (t, 1H), 7.54-7.52 (m, 1H), 5.73 (s, 2H), 4.27-4.25 (q, 1H), 3.96 (t, 2H), 3.88 (s, 2H), 3.82 (s, 2H), 3.58-3.48 (m, 52H), 3.19- 3.18 (m, 3H), 3.04-3.03 (m, 3H), 1.44 (s, 18H), 1.39-1.37 (m, 3H), 1.21-1.19 (m, 3H). EI-MS m/z: $[M+H-2Boc]^+$ 1031.6.

Preparation of Compound 12b

To a stirred mixture of compound 12a (260 mg, 0.179 mmol), and Pd/C (10 wt. %, 72 mg) in MeCOH (20 mL) at 0° C. was added HCl (4 N in 1,4-dioxane, 0.040 mL, 0.179 mmol). After stirring at room temperature for 3 hours under hydrogen, the reaction mixture was filtered through a celite pad and washed with MeOH (40 mL). The filtrate was concentrated to produce the compound 12b (242 mg, 100%) as colorless oil, which was used without further purification. EI-MS m/z: $[M+H]^+$ 625.0, $[M+H-Boc]^+$525.0, $[M+H-2Boc]^+$424.9.

Preparation of Compound 12c
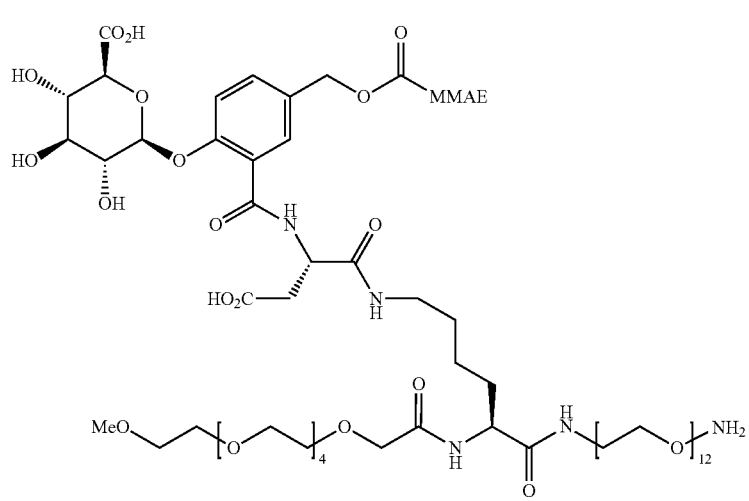
12c
Compound 12c was prepared from compound 1i and compound 12b by a similar method of preparing compound 9j in Example 14. EI-MS m/z: ½[M+H]$^+$ 1083.5.
Example 20. Preparation of Compound 12d
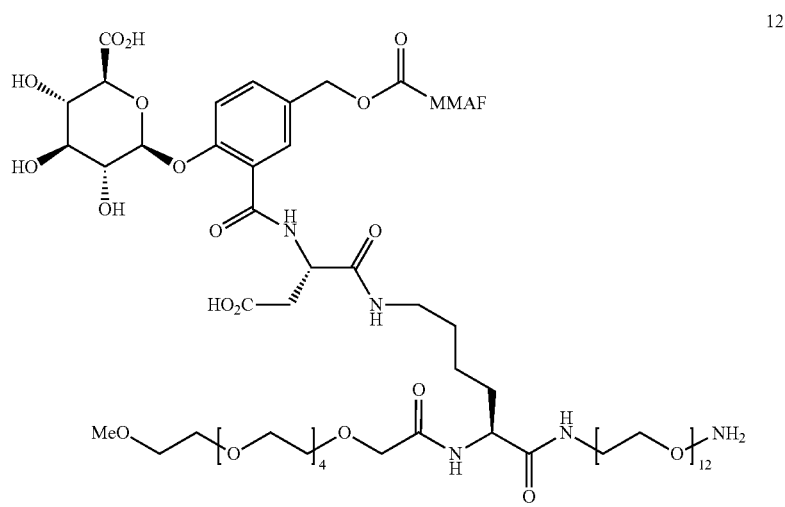
12d
Compound 12d was prepared from compound 1j and compound 12b by a similar method of preparing compound 9j in Example 14. EI-MS m/z: ½[M+H]$^+$ 1090.5.

Example 21. Preparation of Compound 13e

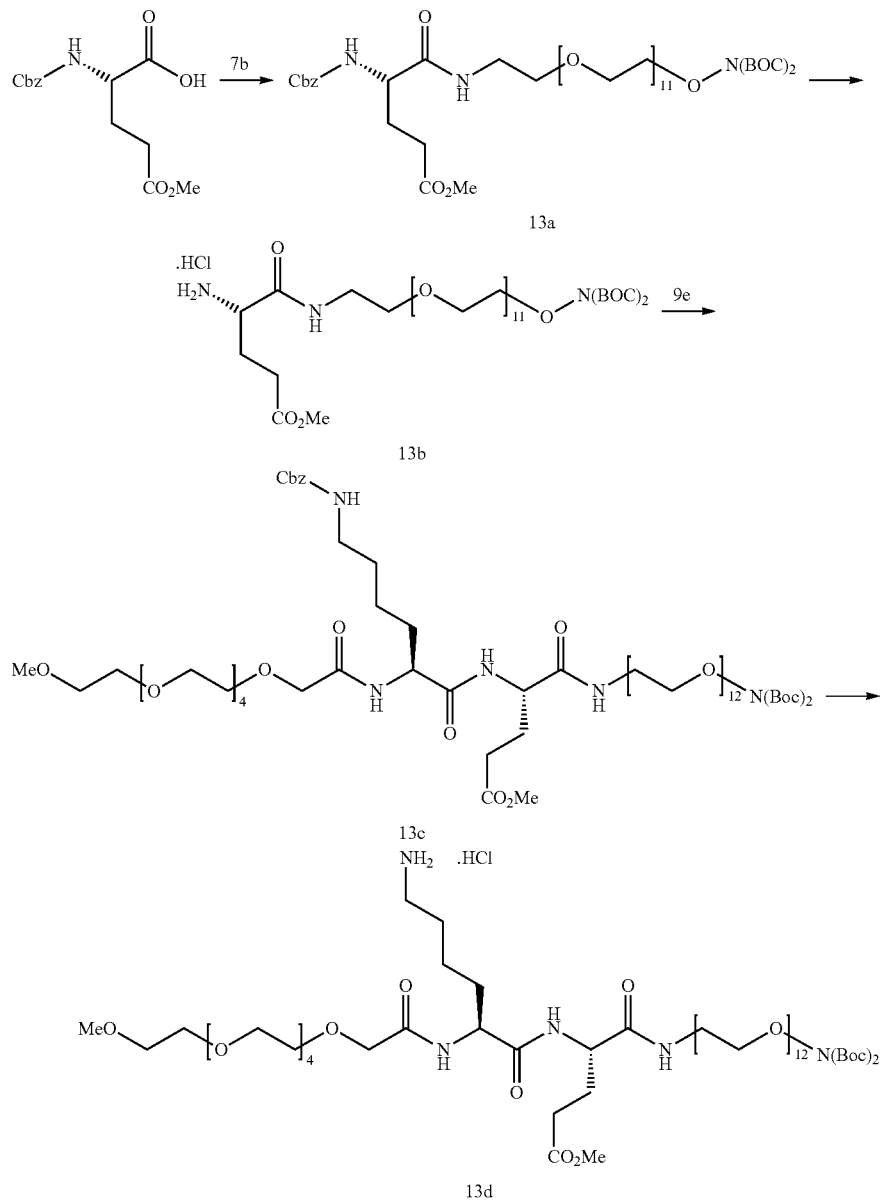

Preparation of Compound 13a

DIPEA (0.22 mL, 1.25 mmol) and HBTU (356 mg, 0.94 mmol) were added to a stirred mixture of Z-Glu(OMe)-OH (222 mg, 0.75 mmol) and compound 7b (500 mg, 0.62 mmol) in DMF (5.0 mL). The reaction mixture was stirred at room temperature for 14 hours under $N_2$. The reaction mixture was diluted with water (200 mL) and extracted with EA (3×100 mL). The organic layers were dried over anhydrous $MgSO_4$, filtered and concentrated under reduced pressure. The resulting residue was purified by column chromatography to yield the compound 13a (370 mg, 57%). $^1$H-NMR (400 MHz, $CDCl_3$) δ 7.34 (br, 5H), 6.73 (br, 1H), 5.72 (d, J=7.6 Hz, 1H), 5.06 (br, 2H), 4.28-4.18 (m, 1H), 4.07 (t, J=4.4 Hz, 2H), 3.76-3.71 (m, 2H), 3.70-3.50 (m, 45H), 3.48-3.42 (m, 2H), 2.53-2.36 (m, 2H), 2.20-2.08 (m, 1H), 2.00-1.88 (m, 1H), 1.53 (s, 18H). EI-MS m/z: [M+Na]$^+$ 1061.2.

Preparation of Compound 13b

4N HCl in 1,4-dioxane (0.08 mL, 0.32 mmol) was added to a stirred mixture of the compound 13a (370 mg, 0.35 mmol), and Pd/C (38 mg) in MeOH (8 mL) at 0° C. After stirring at room temperature for 20 hours under hydrogen, the reaction mixture was filtered through a celite pad and washed with MeOH (400 mL). The filtrate was concentrated, producing compound 13b (301 mg, 90%) as yellow liquid, which was used without further purification. $^1$H-NMR (400 MHz, $CDCl_3$) δ 8.41 (br, 1H), 8.09 (br, 3H), 4.13 (br, 1H), 3.85-3.56 (m, 51H), 2.55 (br, 2H), 2.38-2.18 (m, 2H), 1.53 (s, 18H). EI-MS m/z: [M+H]$^+$ 905.0.

Preparation of Compound 13c

DIPEA (0.165 mL, 0.96 mmol) and HBTU (279 mg, 0.74 mmol) were added to a stirred mixture compound 13b (300 mg, 0.32 mmol) and compound 9e (366 mg, 0.64 mmol) in DMF (5.0 mL). The reaction mixture was stirred at room temperature for 14 hours under $N_2$. The reaction mixture was diluted with water (200 mL) and extracted with EtOAc (3×100 mL). The organic layers were dried over anhydrous $MgSO_4$, filtered and concentrated under reduced pressure. The resulting residue was purified by column chromatography to yield the compound 13c (290 mg, 62%). 1H-NMR (400 MHz, $CDCl_3$) δ 7.40-7.32 (m, 7H), 7.00 (br, 1H), 6.73 (br, 1H), 5.07 (br, 2H), 4.44-4.36 (m, 2H), 4.07 (t, J=4.8 Hz, 2H), 4.02 (br, 2H), 3.73 (t, J=5.2 Hz, 2H), 3.71-3.52 (m, 68H), 3.24-3.14 (m, 2H), 2.52-2.34 (m, 3H), 2.18-2.06 (m, 2H), 1.98-1.82 (m, 4H), 1.76-1.64 (m, 3H), 1.53 (s, 18H). EI-MS m/z: $[M+H]^+$ 1459.7.

Preparation of Compound 13d

Pd/C (21 mg) was added to a stirred mixture of compound 13c (290 mg, 0.19 mmol) in MeOH (5 mL) at 0° C. After stirring at room temperature for 20 hours under hydrogen, the reaction mixture was filtered through a celite pad and washed with MeOH (400 mL). The filtrate was concentrated, producing compound 13c (247 mg, 94%) as yellow liquid, which was used without further purification. $^1$H-NMR (400 MHz, $CDCl_3$) δ 8.20 (d, J=8.4 Hz, 1H), 7.74 (br, 1H), 7.30 (br, 1H), 4.66-4.48 (m, 2H), 4.07 (t, J=5.2 Hz, 2H), 4.01 (br, 2H), 3.74-3.62 (m, 70H), 3.57-3.53 (m, 2H), 3.04-2.98 (m, 2H), 2.24-2.15 (m, 2H), 2.14-2.06 (m, 2H), 1.99-1.86 (m, 4H), 1.84-1.74 (m, 2H), 1.53 (s, 18H). EI-MS m/z: $[M+H]^+$ 1325.5.

Preparation of Compound 13e

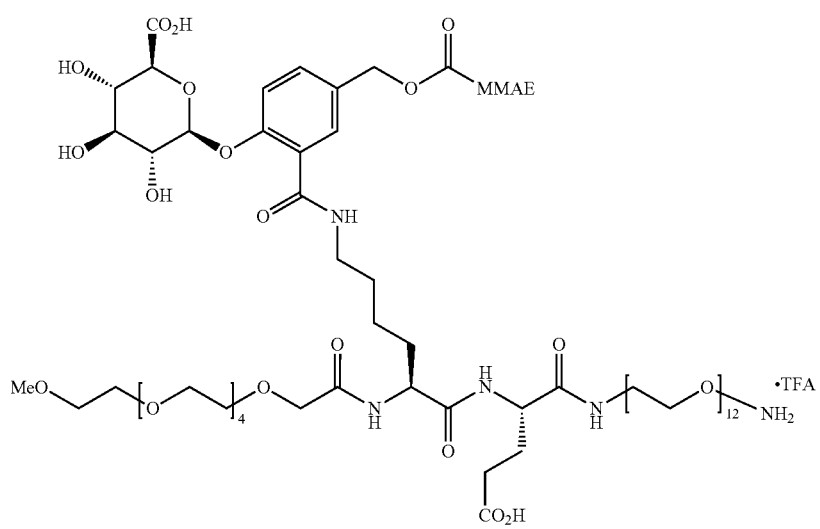

13e

Compound 13e was prepared from compound 1i and compound 13d by a similar method of preparing compound 9j in Example 14. EI-MS m/z: $[M+H]^+$ 2181.5.

Example 22. Preparation of Compound 13f

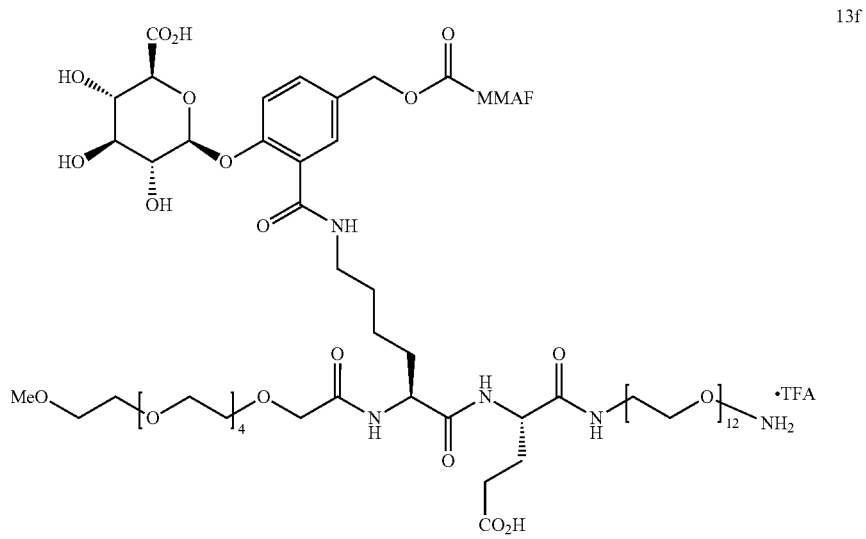

13f

Compound 13f was prepared from compound 1j and compound 13d by a similar method of preparing compound 9j in Example 14. EI-MS m/z: [M+H]+ 2195.5.

Example 23. Preparation of Compound 14m

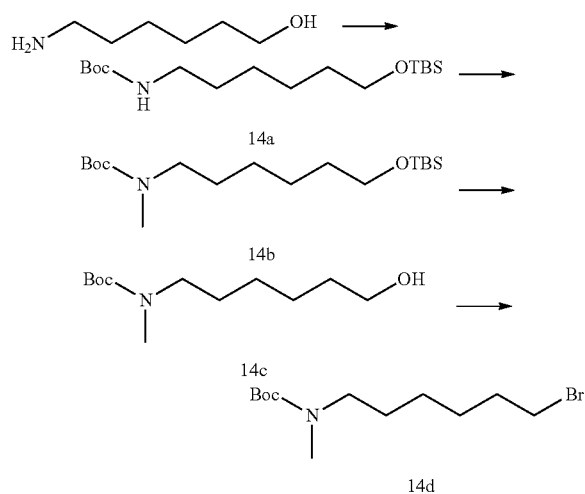

Preparation of Compound 14a

To a solution of 6-amino-1-hexanol (5.0 g, 42.6 mmol) in DCM (30 mL) was added di-tert-butyl dicarbonate (9.3 g, 42.6 mmol) at room temperature. After stirring for 18 hours, triethylamine (8.7 mL, 63.9 mmol) and t-butyldimethylsilyl chloride (7.7 g, 51.2 mmol) were added to the reaction mixture at 0° C. After 24 hours at room temperature, the reaction mixture diluted with saturated aq. NH$_4$Cl (200 mL). The resulting mixture was extracted with EtOAc (100 mL). The organic layer was washed with brine (100 mL) and dried over anhydrous MgSO$_4$, filtered and concentrated. The residue was purified by column chromatography to produce the compound 14a (12 g, 84%). $^1$H-NMR (400 MHz, CDCl$_3$) δ 4.50 (br s, 1H), 3.58 (t, J=6.8 Hz, 2H), 3.10 (d, J=6.4 Hz, 2H), 1.72-1.20 (m, 17H), 0.88 (s, 9H), 0.04 (s, 6H).

Preparation of Compound 14b

To a solution of compound 14a (6.0 g, 18.1 mmol) in THF (30 mL) were added NaH (60% in oil, 2.4 g, 54.2 mmol) and methyl iodide (3.4 mL, 54.2 mmol) at 0° C. under N$_2$. After 14 hours, the reaction mixture was diluted with H$_2$O (50 mL) and extracted with EtOAc (2×100 mL). The organic layers were combined, dried over anhydrous MgSO$_4$, filtered and concentrated. The crude product was purified by column chromatography to produce the compound 14b (4.3 g, 69%). $^1$H-NMR (400 MHz, CDCl$_3$) δ 3.59 (t, J=6.4 Hz, 2H), 3.17 (br s, 2H), 2.82 (s, 3H), 1.62-1.21 (m, 17H), 0.88 (s, 9H), 0.04 (s, 6H).

Preparation of Compound 14c

To a solution of compound 14b (4.3 g, 12.4 mmol) in THF (15 mL) was added TBAF (1 M in THF, 15 mL, 14.9 mmol) at 0° C. under N$_2$. After 5 hours, the reaction mixture was diluted With H$_2$O (50 mL) and extracted with diethyl ether (2×100 mL). The organic layers were combined, dried over anhydrous MgSO$_4$, filtered and concentrated. The crude product was purified by column chromatography to produce the compound 14c (3.0 g, 98%). $^1$H-NMR (400 MHz, CDCl$_3$) δ 3.63 (br s, 2H), 3.20 (br s, 2H), 2.82 (s, 3H), 1.65-1.23 (m, 17H).

Preparation of Compound 14d

To a solution of compound 14c (3.0 g, 12.9 mmol) in THF (30 mL) was added carbon tetrabromide (6.4 g, 19.4 mmol) and triphenylphosphine (5.1 g, 19.4 mmol) at 0° C. under N$_2$. After 2 hours., the reaction mixture was filtered through silica gel and washed diethyl ether (100 mL). The filtrate was concentrated and purified by column chromatography to produce the compound 14d (3.3 g, 86%). $^1$H-NMR (400 MHz, CDCl$_3$) δ 3.40 (t, J=6.8 Hz, 2H), 3.19 (br s, 2H), 2.83 (s, 3H), 1.90-1.70 (m, 2H), 1.65-1.40 (m, 13H), 1.38-1.25 (m, 2H).

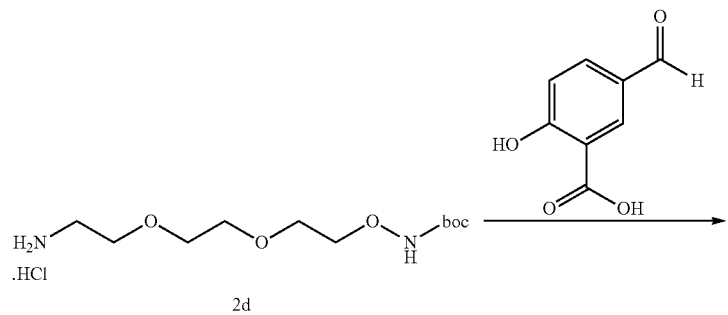

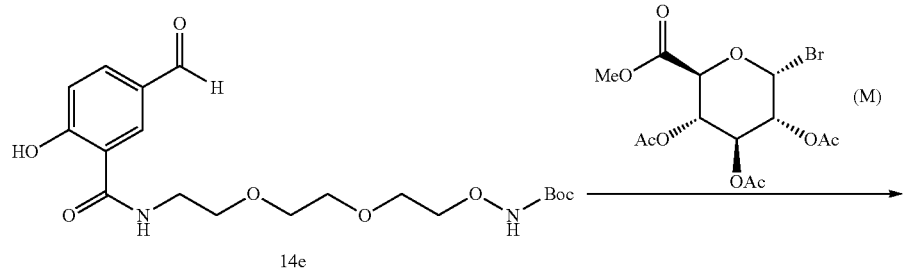

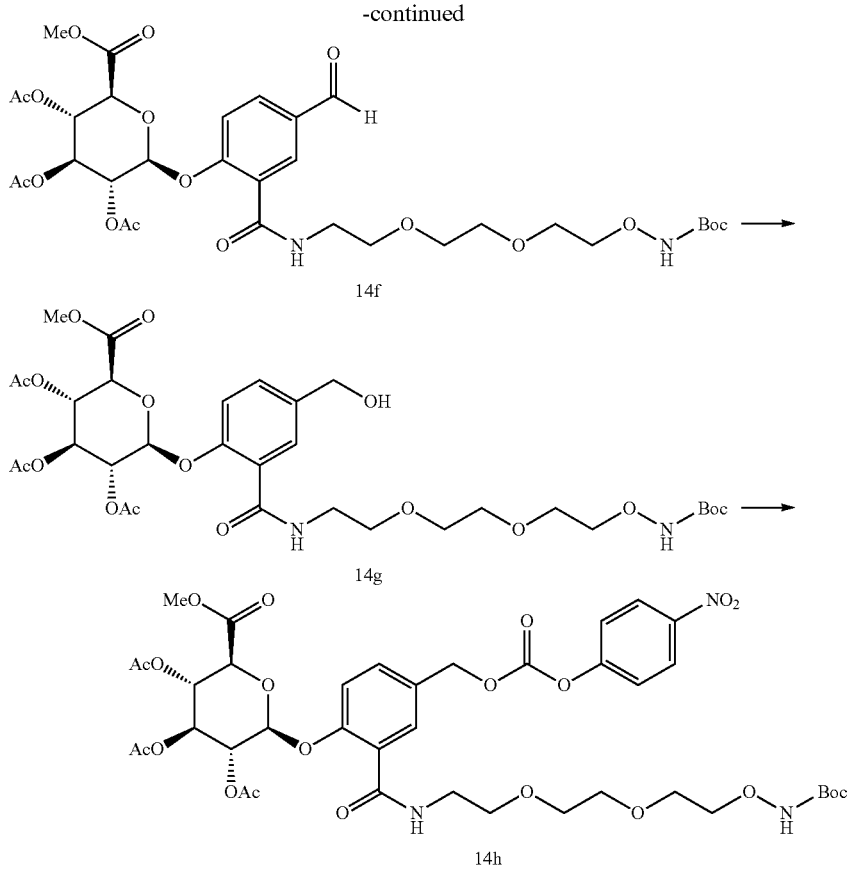

Preparation of Compound 14e

DIPEA (53.0 mL, 302.5 mmol) and EDC.HCl (35.7 g, 186.2 mmol) were added to a stirred mixture of compound 2d (35.0 g, 116.4 mmol) and 5-formylsalicylic acid (21.3 g, 128.0 mmol) in DCM (1.6 L) at 0° C. The reaction mixture was stirred at room temperature for 20 hours under $N_2$. The reaction mixture was diluted with saturated aq. $NH_4Cl$ solution (1.5 L) and extracted DCM (2×1.5 L). The combined organic layers washed with brine (1.5 L) and dried anhydrous $MgSO_4$, filtered and concentrated. The crude product was purified by column chromatography to produce the compound 14e (28.2 g, 59%). $^1$H-NMR (400 MHz, $CDCl_3$) δ 13.37 (br s, 1H), 9.86 (s, 1H), 8.20 (s, 1H), 8.07 (br s, 2H), 7.90 (d, J=8.4 Hz, 1H), 7.07 (d, J=8.4 Hz, 1H), 4.06-4.01 (m, 2H), 3.79-3.66 (m, 10H), 1.47 (s, 9H).

Preparation of Compound 14f

To a solution of compound 14e (28.0 g, 67.9 mmol) in MeCN (500 mL) were added compound M (29.7 g, 74.7 mmol), 4 Å molecular sieve (30 g) and $Ag_2O$ (62.9 g, 272 mmol). After stirring at room temperature for 12 hours under $N_2$, the reaction mixture was concentrated, diluted with $H_2O$ (800 mL) and extracted with EtOAc (1 L). The combined organic layers were dried over anhydrous $MgSO_4$, filtered and concentrated. The residue was purified by column chromatography to produce the compound 14f (30.1 g, 61%). $^1$H-NMR (400 MHz, $CDCl_3$) δ 9.99 (s, 1H), 8.54 (s, 1H), 7.99 (d, J=8.8 Hz, 1H), 7.68 (s, 1H), 7.44 (br s, 1H), 7.18 (d, J=8.8 Hz, 1H), 5.45-5.30 (m, 4H), 4.26 (d, J=9.2 Hz, 1H), 4.02-3.97 (m, 2H), 3.80-3.55 (m, 13H), 2.06 (s, 9H), 1.46 (s, 9H):

Preparation of Compound 14g

To a solution of compound 14f (29.0 g, 39.8 mmol) in i-PrOH/$CHCl_3$ (90 mL/450 mL) was added silica gel (16.7 g) and $NaBH_4$ (3.70 g, 99.5 mmol) at 0° C. After stirring at 0° C. for 2 hours under $N_2$, the reaction mixture was quenched with $H_2O$ (500 mL) and extracted with EtOAc (1 L). The organic layer was dried over anhydrous $MgSO_4$, filtered and concentrated. The crude product was purified by column chromatography to produce the compound 14g (24.1 g, 83%). $^1$H-NMR (400 MHz, $CDCl_3$) δ 7.98 (s, 1H), 7.72 (s, 1H), 7.46 (d, J=8.8 Hz, 1H), 7.41 (br, 1H), 7.04 (d, J=8.8 Hz, 1H), 5.41-5.24 (m, 4H), 4.67 (d, J=6.6 Hz, 2H), 4.19 (d, J=8.8 Hz, 1H), 3.99-3.93 (m, 2H), 3.79-3.65 (m, 12H), 3.59-3.50 (m, 1H), 2.08-2.00 (m, 10H), 1.46 (s, 9H).

Preparation of Compound 14h

To a solution of compound 14g (23.7 g, 31.5 mmol) in DMF (50 mL) were added bis(4-nitrophenyl)carbonate (8.9 g, 29.3 mmol) and DIPEA (5.65 mL, 31.5 mmol) at 0° C. under $N_2$. The reaction mixture was stirred at 0° C. for 30 minutes and allowed to warm to room temperature for 1 hour. The reaction mixture was diluted with $H_2O$ (500 mL) and extracted with EtOAc (500 mL). The organic layer was washed with brine (2×200 mL), dried over anhydrous $MgSO_4$, filtered, and concentrated. The crude product was purified by column chromatography to produce the compound 14h (22.4 g, 77%) as white foam. $^1$H-NMR (400 MHz, $CDCl_3$) δ 8.28 (d, J=7.2 Hz, 2H), 8.13 (s, 1H), 7.68 (br s, 1H), 7.52 (d, J=8.8 Hz, 1H), 7.47 (br, 1H), 7.38 (d, J=7.2 Hz, 2H), 7.08 (d, J=8.8 Hz, 1H), 5.44-5.24 (m, 6H), 4.21 (d, J=9.6 Hz, 1H), 4.00 (br s, 2H), 3.80-3.64 (m, 12H), 3.64-3.54 (m, 1H), 2.06 (s, 9H), 1.47 (s, 9H).

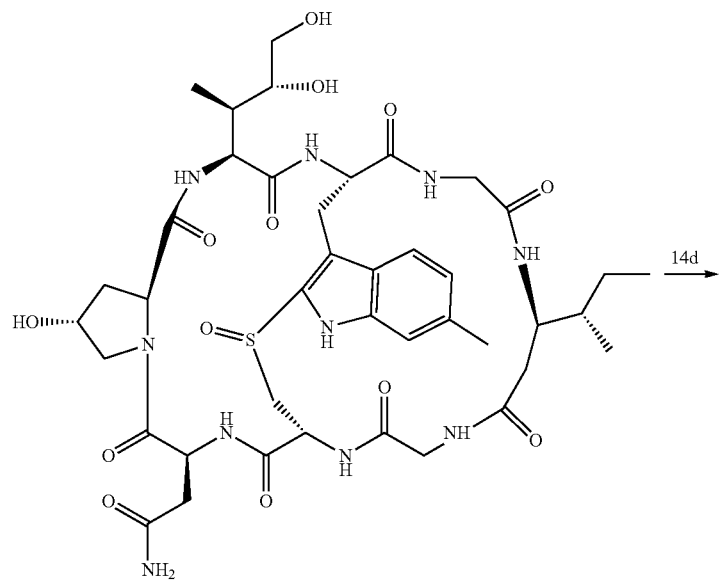
α-amanitin
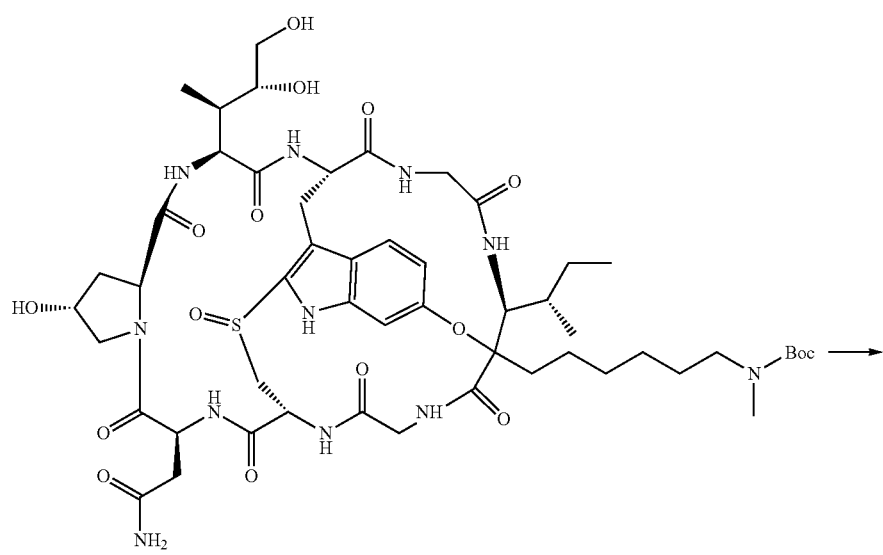
14i

-continued
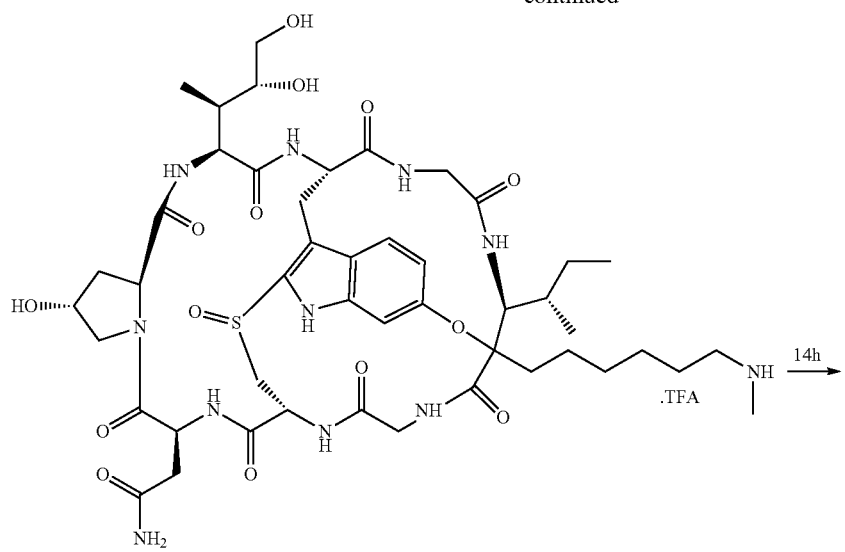
14j
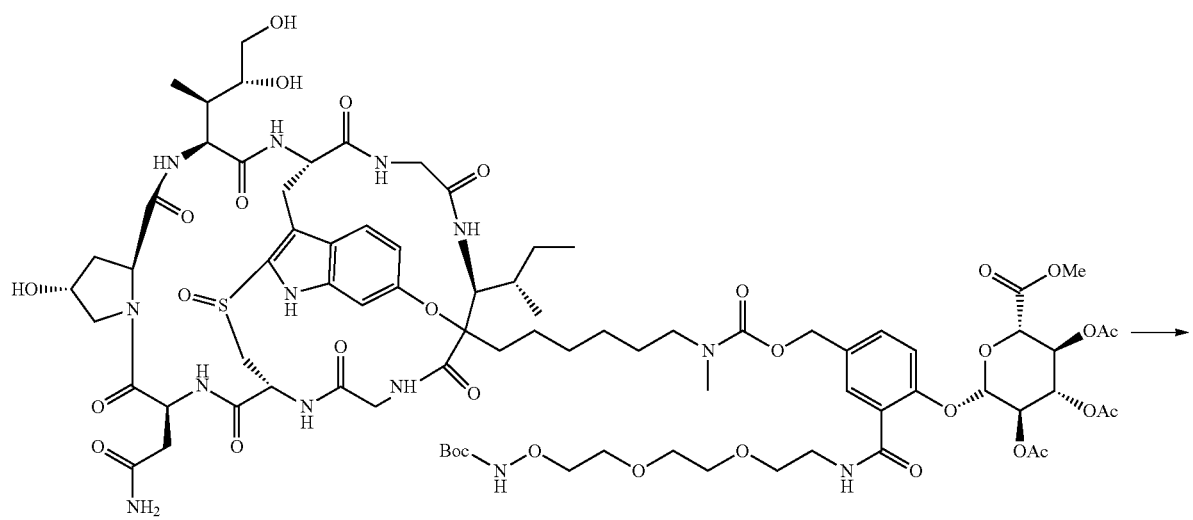
14k
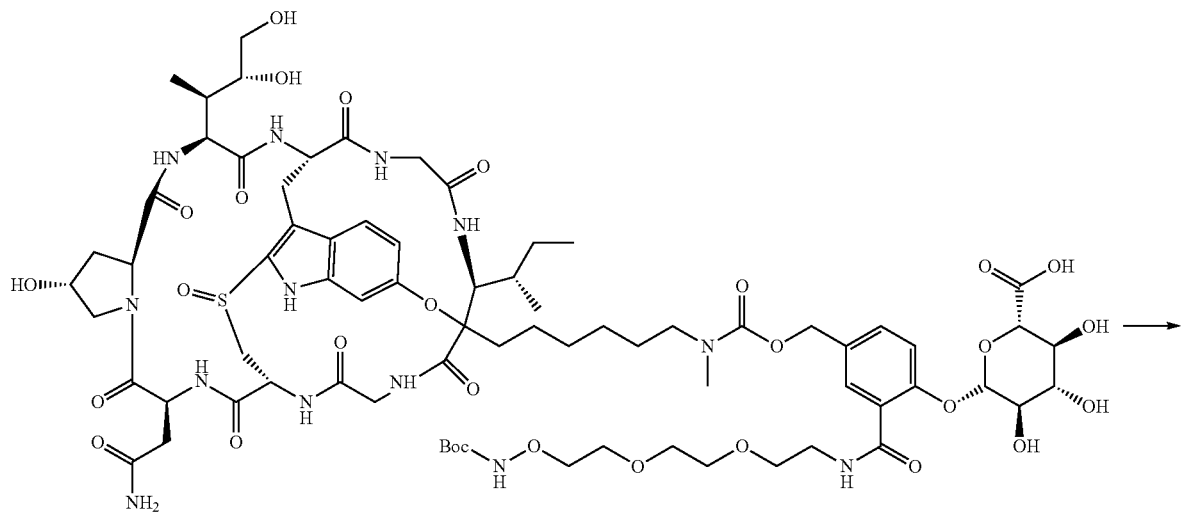
14l

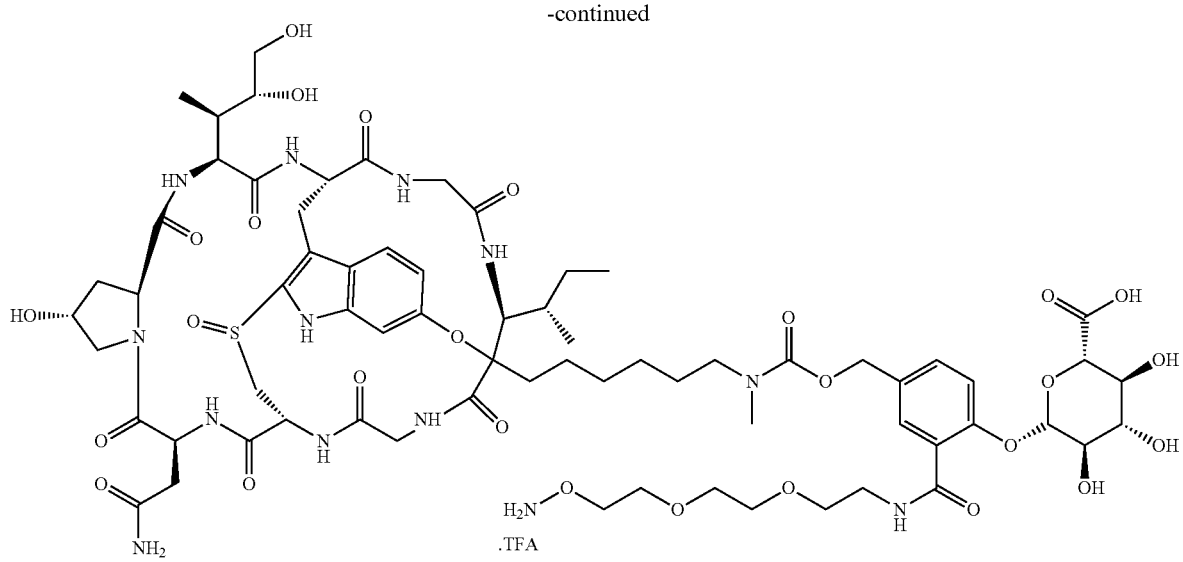

14m

Preparation of Compound 14i

α-Amanitin (60.0 mg, 0.065 mmol) was dissolved in DMSO (2 mL) and compound 14d (114 mg, 0.39 mmol) and potassium tert-butoxide (0.065 mL, 0.065 mmol) were added at 0° C. under $N_2$. After 4 hours at 0° C., the pH of the solution was adjusted to 4~5 with acetic acid. The residue was dissolved in DMSO (1 mL) and purified by HPLC, which produced the compound 14i (29 mg, 39%) as white solid. EI-MS m/z: [M-Boc]$^+$1032.4.

Preparation of Compound 14j

To a solution of compound 14i (29 mg, 0.026 mmol) in DCM (3 mL) was added TEA (0.5 mL) at 0° C. After 2 hours at 0° C., the solvent and excess TFA were removed by $N_2$ flow and the resulting residue was purified by HPLC, which produced the compound 14j (26 mg, 99%) as white solid. EI-MS m/z: [M+H]$^+$ 1032.3, [M+Na]$^+$1054.3.

Preparation of Compound 14k

Compound 14j (13 mg, 0.011 mmol), compound 14h (10 mg, 0.011 mmol) and anhydrous HOBt (0.3 mg, 0.002 mmol) were dissolved in DMF (0.5 mL) at 0° C. Then pyridine (0.2 mL) and DIPEA (0.004 mL, 0.023 mmol) were added. After stirring at room temperature for 24 hours under $N_2$, the reaction mixture was dissolved in DMSO (1 mL) and purified by HPLC, which produced the compound 14k (11 mg, 54%). EI-MS m/z: [M+H]$^+$ 1788.1.

Preparation of Compound 14l To a solution of compound 14k (11 mg, 0.006 mmol) in MeOH (0.2 mL) was added LiOH monohydrate (1.3 mg, 0.03 mmol) in $H_2O$ (0.2 mL) at −20° C. After 1 hour at 0° C., the pH of the solution was adjusted to 4-5 with acetic acid. The resulting solution was dissolved in DMSO (1 mL) and purified by HPLC, which produced the compound 14l (7.5 mg, 75%) as white solid. EI-MS m/z: [M+H]$^+$ 1648.6.

Preparation of Compound 14m

To a solution of compound 14l (7.5 mg, 0.0045 mmol) in DCM (3 mL) was added TFA (0.5 mL) at 0° C. After 2 hours at 0° C., the solvent and excess TFA were removed by $N_2$ flow. Then the residue was purified by HPLC, which produced the compound 14m (6.2 mg, 85%) as white solid. EI-MS m/z: [M+H]$^+$: 1548.5.

Example 24. Preparation of Compound 15b

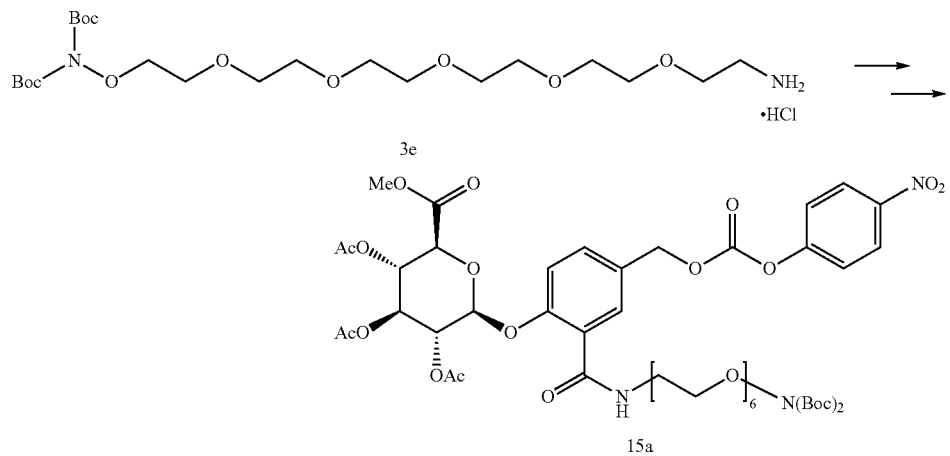

Preparation of Compound 15a

Compound 15a was prepared from compound 3e by a method similar to method of preparing compound 14h of Example 23. EI-MS m/z: [M+H]$^+$ 1128.3, [M+H-Boc]$^+$ 1028.3, [M+H-2Boc]$^+$ 928.2.

stirred at −78° C. for 30 minutes. To this solution was added compound 2a (3.8 g, 21.7 mmol) at −78° C. and stirred for 1 hour. Triethylamine (15.1 mL, 108 mmol) in DCM (20 mL) was added and then the reaction mixture was allowed to warm to room temperature, diluted with H$_2$O (100 mL)

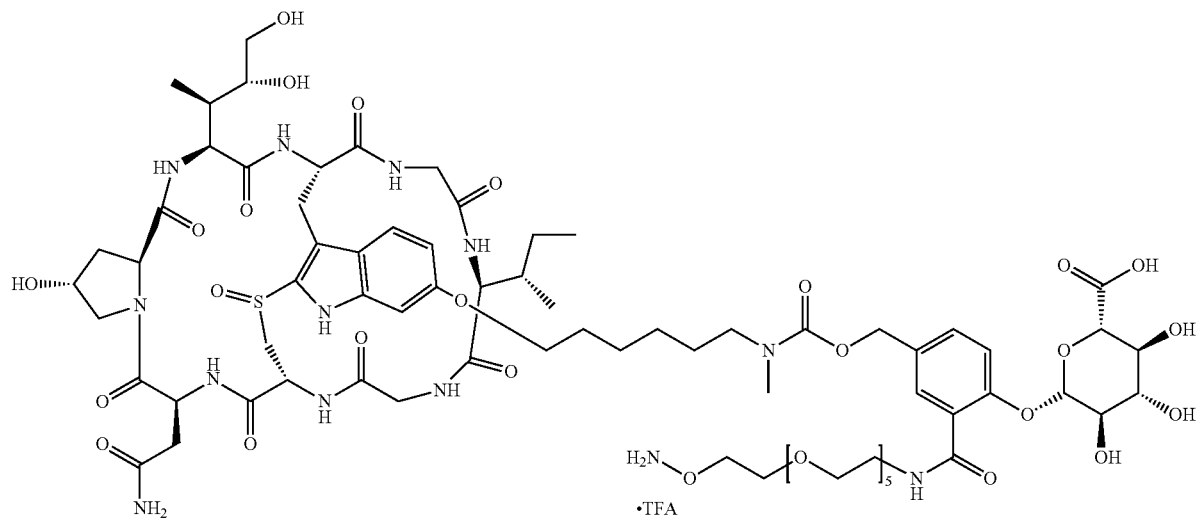

Preparation of Compound 15b

Compound 15b was prepared from compound 14j and compound 15a by a method similar to method of preparing compound 14m of Example 23. EI-MS m/z: [M+H]$^+$ 1681.6.

Example 25. Preparation of Compound 16f and extracted with DCM (2×100 mL). The organic layers were combined, dried over anhydrous MgSO$_4$, filtered and concentrated. The residue was purified by column chromatography to produce the compound 16a (1.8 g, 48%). $^1$H-NMR (400 MHz, CDCl$_3$) δ 9.74 (s, 1H), 4.19 (s, 2H), 3.77-3.69 (m, 6H), 3.42 (m, 2H).

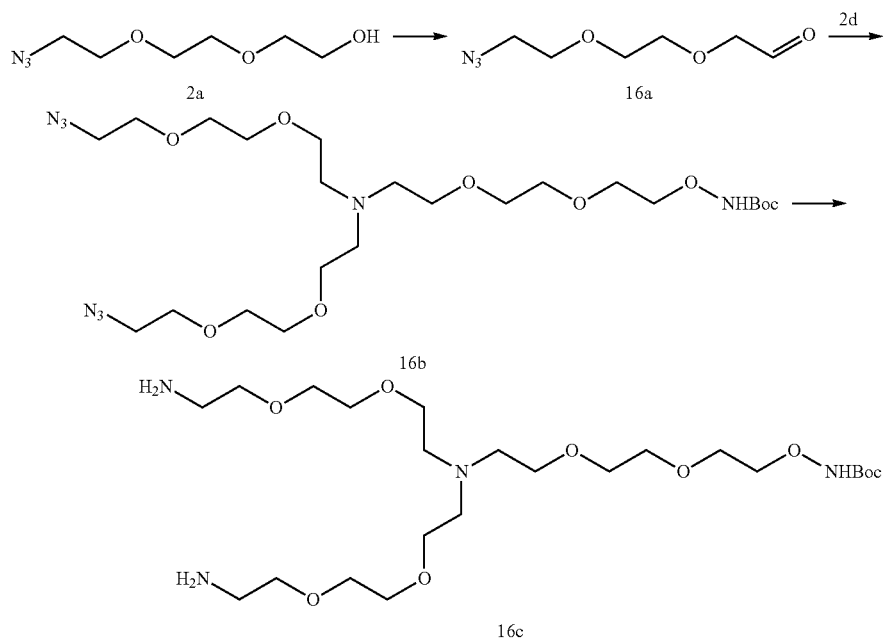

Preparation of Compound 16a

To a stirred solution of oxalyl chloride (2.8 mL, 32.5 mmol) in DCM (5 mL) DMSO (3.08 mL, 43.4 mmol) was added in DCM (15 mL) and then the reaction mixture was Preparation of Compound 16b To a solution of compound 16a (1.0 g, 3.32 mmol) and compound 2d (1.72 g, 9.96 mmol) in MeOK (15 mL) AcOH (0.19 mL, 3.32 mmol) was added at 0° C. After stirring for 30 minutes at 0° C., NaCNBH$_3$ (658 mg, 9.96 mmol) was added and allowed to warm to room temperature over 2 hours. After the reaction was completed, the reaction mixture was diluted with H$_2$O (50 mL) and then extracted with DCM (3×100 mL). The organic layers were combined, dried over anhydrous MgSO$_4$, filtered and concentrated. The residue was purified by column chromatography to produce the compound 16b (800 mg, 41%) as light yellowish oil. $^1$H-NMR (400 MHz, CDCl$_3$) δ 7.78 (brs, 1H), 4.01 (m, 2H), 3.69-3.65 (m, 24H), 3.39 (m, 4H), 3.04 (m, 6H), 1.47 (s, 9H).

Preparation of Compound 16c

To a solution of compound 16b (350 mg, 0.60 mmol) in MeOH (10 mL) Pd/C (10 wt. %, 300 mg) was added. After stirring at room temperature for 8 hours under hydrogen, the reaction mixture was filtered through a celite pad and washed with MeOH (100 mL). Concentration provided compound 16c as colorless oil (300 mg, 94%), which was used without further purification. $^1$H-NMR (400 MHz, CDCl$_3$) δ 4.02 (m, 2H), 3.71 (m, 2H), 3.65-3.55 (m, 22H), 2.92 (m, 4H), 2.76 (t, J=5.2 Hz, 6H), 1.47 (s, 9H). EI-MS m/z: [M+H]$^+$. 527.6.

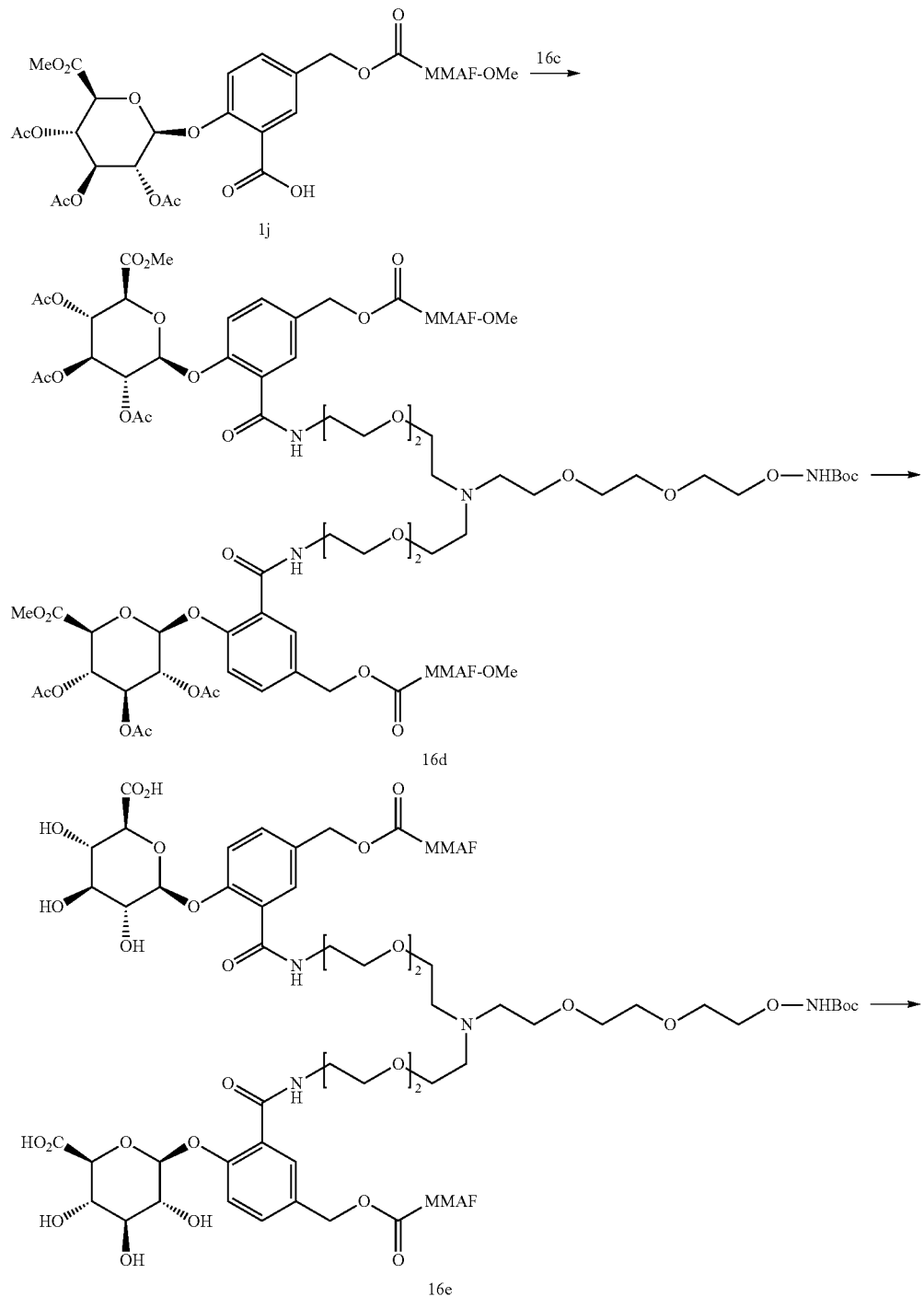

-continued

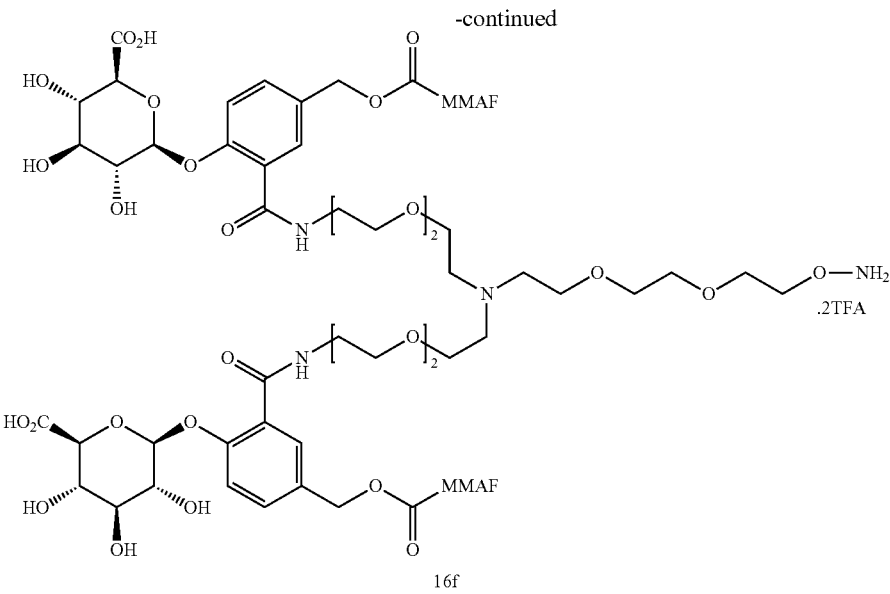

16f

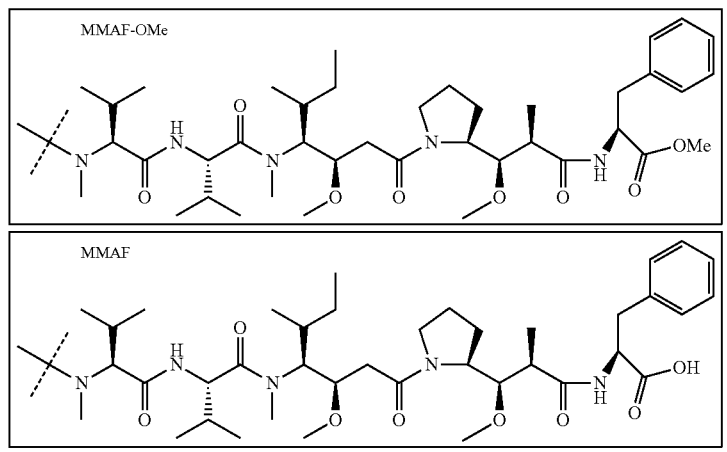

Preparation of Compound 16d

DIPEA (0.40 mL, 2.24 mmol) and PyBOP (711 mg, 1.34 mmol) were added to a stirred mixture of compound 1j (1.57 g, 1.23 mmol) and compound 16c (300 mg, 0.56 mmol) in DMF (15 mL). After stirring at room temperature for 4 hours under $N_2$, the reaction mixture was diluted $H_2O$ (200 mL) and extracted with EtOAc (3×100 mL). The combined organic layers were dried over anhydrous $Na_2SO_4$, filtered and concentrated under reduced pressure. The residue was dissolved in $H_2O$/DMSO (5 mL/5 mL) and purified by HPLC produced the compound 16d (1.57 g, 91.8%). EI-MS m/z: ½[M+H]$^+$ 1502.7.

Preparation of Compound 16f

To a solution of compound 16d (1.10 g, 0.36 mmol) in MeOH/THF (5 mL/10 mL) NaOH (175 mg, 4.32 mmol) was added dropwise in $H_2O$ (3 mL) at 0° C. After 3 hours at 0° C., the pH of the solution was adjusted to pH 4 using 2 N aq. HCl and concentrated. The residue was diluted with DCM (12 mL) and TFA (3 mL) at 0° C. After 2 hours at 0° C., the solvent and excess TFA were removed by $N_2$ flow. The residue was dissolved in $H_2O$/MeCN (7.5 mL/7.5 mL) and purified by HPLC produced the compound 16f (432 mg, 46%) as white solid. EI-MS m/z: ½[M+H]$^+$ 1298.5.

Example 26. Preparation of Compound 16g
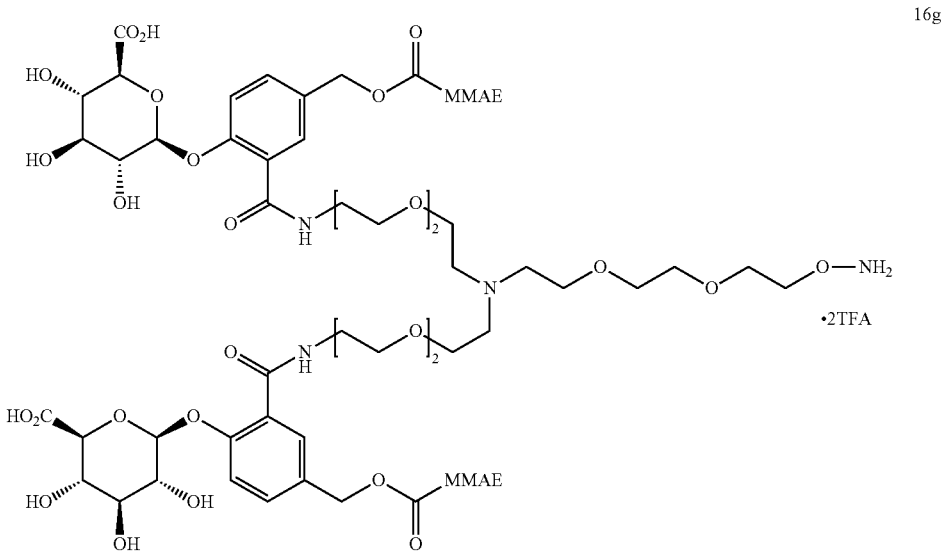
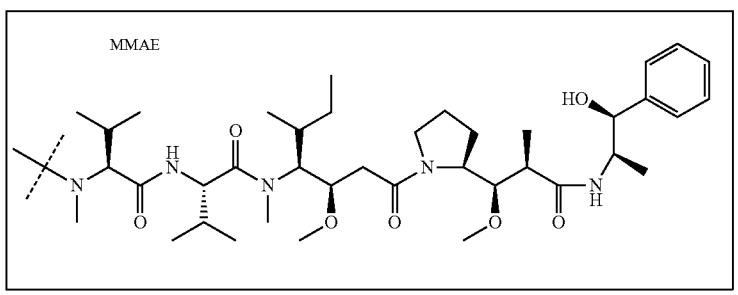
Compound 16g was prepared from compound 1i and compound 16c by a similar method of preparing compound 16f in Example 25. EI-MS m/z: ½[M+H]$^+$ 1284.5.
Example 27. Preparation of Compound 17d
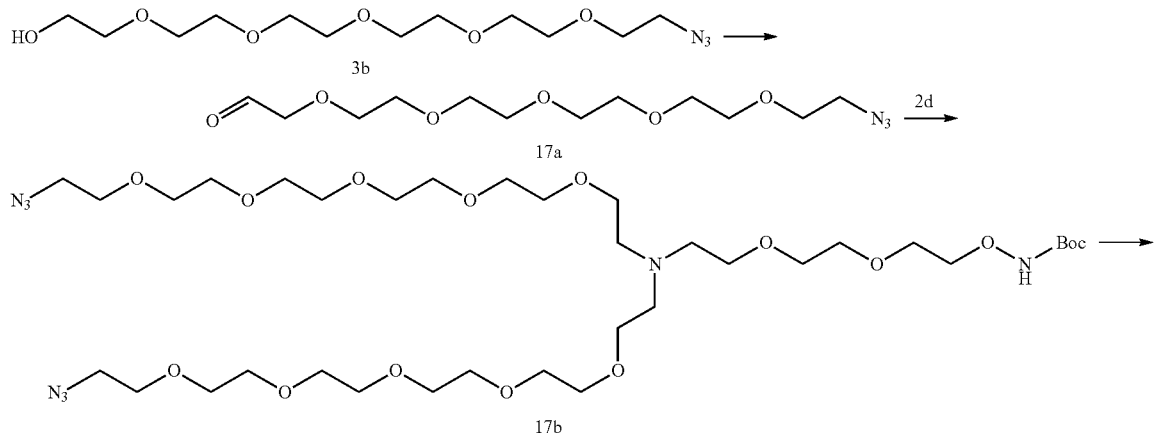

-continued

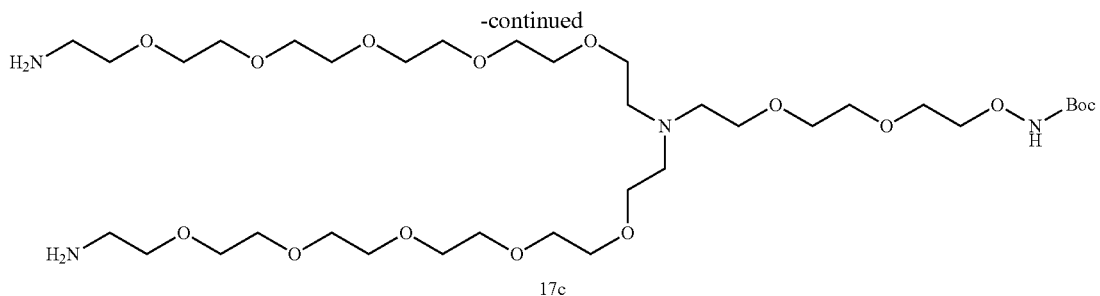

17c

Preparation of Compound 17a

To a stirred solution of oxalyl chloride (0.62 mL, 7.3 mmol) in DCM (4 ML) DMSO (1.04 mL, 14.6 mmol) was added in DCM (10 mL) and then the reaction mixture was stirred at −78° C. for 30 minutes. To this solution was added compound 3b (1.5 g, 4.88 mmol) at −78° C. and stirred for 1 hour. Triethylamine (2.72 mL, 19.50 mmol) in DCM (7 mL) was added and then the reaction mixture was allowed to warm to room temperature. After concentration under reduced pressure, the residue was purified by column chromatography (EtOAc to EtOAc/MeOH 10/1), which produced the compound 17a (1.23 g, 82%). $^1$H-NMR (400 MHz, CDCl$_3$) δ 9.73 (s, 1H), 4.16 (s, 2H), 3.75-3.61 (m, 18H), 3.39 (t, J=5.2 Hz, 2H).

Preparation of Compound 17b

NaCNBH$_3$ (257 mg, 4.09 mmol) was added to a stirred mixture of compound 17a (1.30 g, 4.25 mmol) and compound 2d (492 mg, 1.63 mmol) in MeOH (5 mL) at 0° C. The reaction mixture was then gradually heated up to room temperature over 2 hours. After the reaction was completed, the reaction mixture was concentrated under reduced pressure. The residue was purified by column chromatography (EtOAc to EtOAc/MeOH 10/1), which produced the compound 17b (620 mg, 45%).

$^1$H-NMR (400 MHz, DMSO-d$_6$) δ 9.96 (br, 1H), 3.79 (t, J=4.8 Hz, 2H) 3.59 (t, J=4.8 Hz, 4H), 3.56-3.46 (m, 38H), 3.44-3.37 (m, 10H), 2.66-2.56 (m, 6H), 1.39 (s, 9H).

Preparation of Compound 17c

To a solution of compound 17b (300 mg, 0.35 mmol) in MeOH (7 mL) was added Pd/C (10 wt. %, 38 mg). After stirring at room temperature for 4 hours under hydrogen, the reaction mixture was filtered through a celite pad and washed with MeOH (400 mL). Concentration provided compound 17c as colorless oil (253 mg, 90%), which was used without further purification. $^1$H-NMR (400 MHz, DMSO-d$_6$) δ 3.79 (t, J=4.4 Hz, 2H), 3.55-3.45 (m, 38H), 3.42 (t, J=6.0 Hz, 10H), 2.66-2.56 (m, 10H), 1.39 (s, 9H). EI-MS m/z: [M+H]$^+$ 791.0.

Preparation of Compound 17d

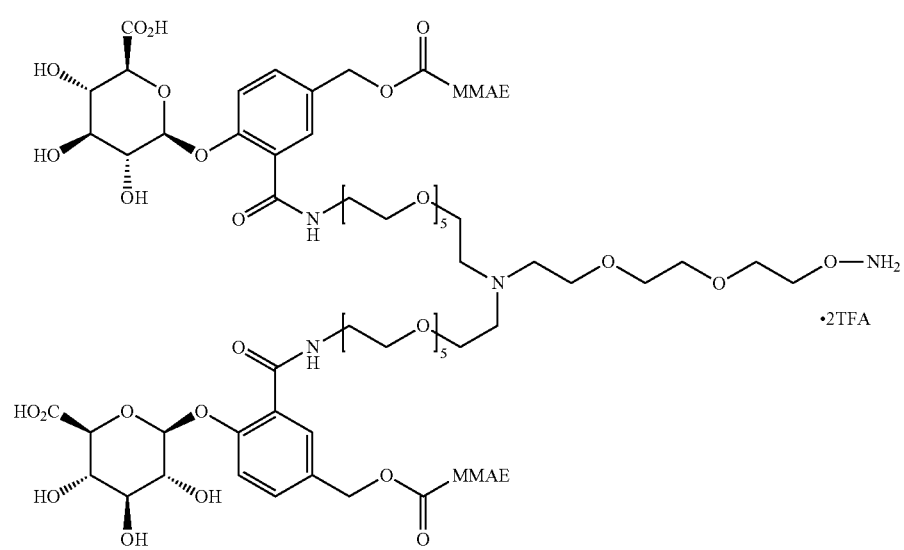

17d

Compound 17d was prepared from compound 1i and compound 17c by a similar method of preparing compound 16f in Example 25. EI-MS m/z: ½[M+H]⁺ 1415.6.

Example 28. Preparation of Compound 18c

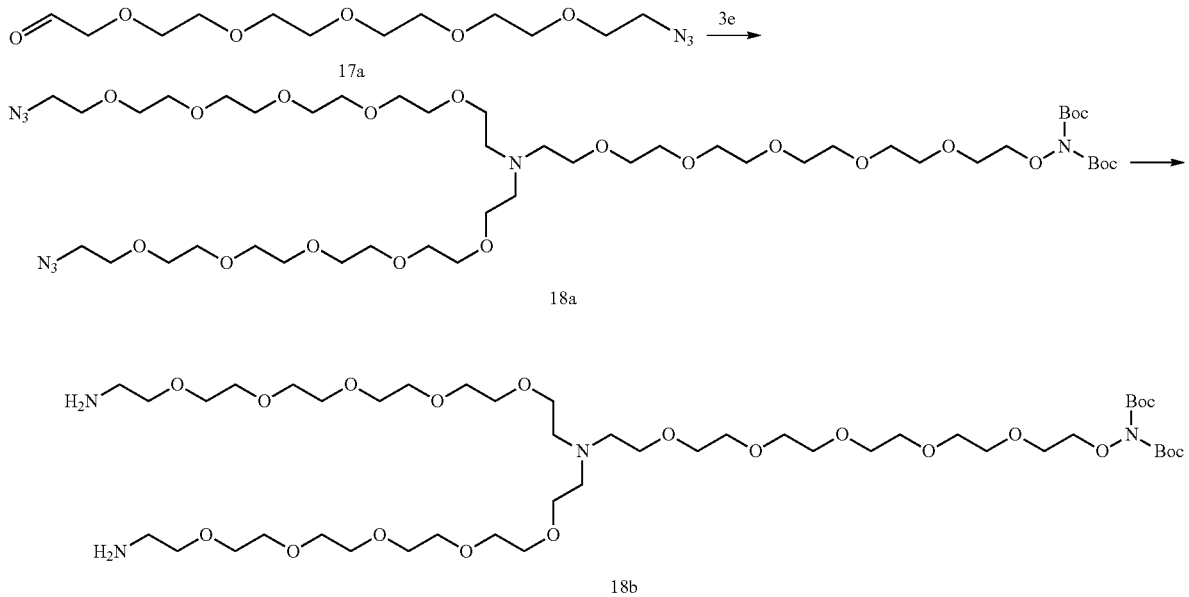

Preparation of Compound 18a

NaCNBH₃ (197 mg, 3.14 mmol) was added to a stirred mixture of compound 17a (998 mg, 3.26 mmol) and compound 3e (670 mg, 1.25 mmol) in MeOH (4 mL) at 0° C. The reaction mixture was then gradually heated up to room temperature over 2 hours. After the reaction was completed, the reaction mixture was concentrated under reduced pressure. The residue was purified by column chromatography (EtOAc to EtOAc/MeOH 10/1), which produced the compound 18a (668 mg, 49%). ¹H-NMR (400 MHz, DMSO-d₆) δ 3.97 (m, 2H) 3.63-3.57 (m, 6H), 3.56-3.44 (m, 46H), 3.44-3.36 (m, 12H), 2.66-2.61 (m, 6H), 1.45 (s, 18H).

Preparation of Compound 18b

To a solution of compound 18a (60 mg, 0.055 mmol) in MeOH (1.2 mL) Pd/C (10 wt. %, 6 mg) was added. After stirring at room temperature for 4 hours under hydrogen, the reaction mixture was filtered through a celite pad and washed with MeOH (400 mL). Concentration provided compound 18b (55 mg, 96%) as colorless oil, which was used without further purification. ¹H-NMR (400 MHz, DMSO-d₆) δ 3.97 (m, 2H), 3.62-3.57 (m, 4H), 3.54-3.45 (m, 50H), 3.45-3.39 (m, 10H), 2.66-2.61 (m, 10H), 1.46 (s, 18H). EI-MS m/z: ½[M+H]⁺ 1023.3.

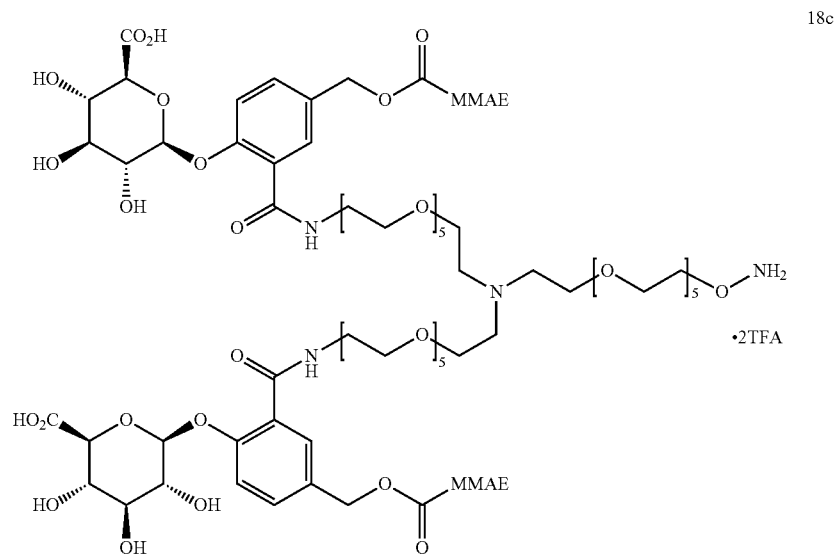

Compound 18c was prepared from compound 1i and compound 18b by a similar method of preparing compound 16f in Example 25. EI-MS m/z: ½[M+H]$^+$ 1481.7.

Example 29. Preparation of Compound 19c

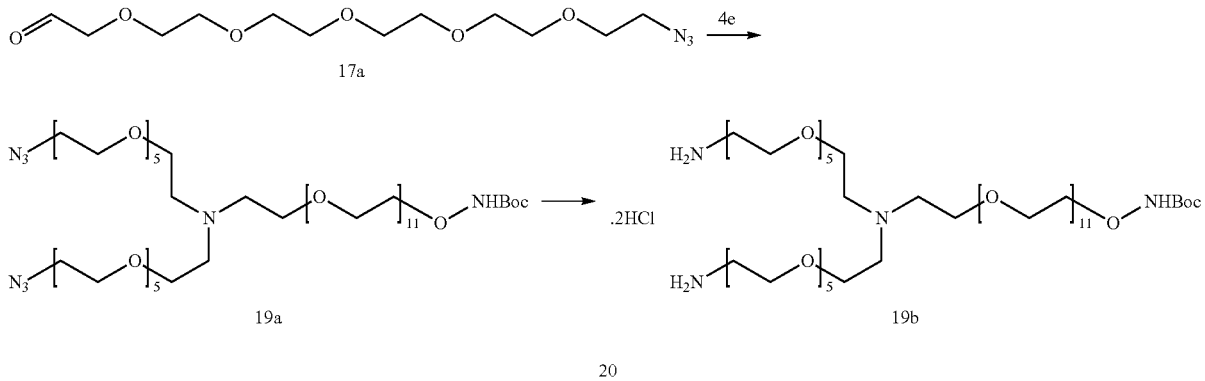

Preparation of Compound 19a

NaCNBH$_3$ (197 mg, 3.14 mmol) was added to a stirred mixture of compound 17a (118 mg, 0.16 mmol) and compound 4e (232 mg, 0.76 mmol) in MeOH (1 mL) at 0° C. The reaction mixture was then gradually heated up to room temperature over 2 hours. After the reaction was completed, the reaction mixture was evaporated under reduced pressure. The residue was purified by column chromatography (EtOAc to EtOAc/MeOH 10/1), which produced the compound 19a (135 mg, 68%). $^1$H-NMR (400 MHz, DMSO-d$_6$) δ 7.72 (br s, 1H) 4.02 (t, 2H), 3.72-3.53 (m, 86H), 3.39 (t, 4H), 2.77 (bs, 4H), 1.47 (s, 9H). EI-MS m/z: [M+H]$^+$ 1239.6.

Preparation of Compound 19b

To a solution of compound 19a (133 mg, 0.107 mmol) in MeOH (2 mL) Pd/C (10 wt. %, 26 mg) was added and HCl (4 N in 1,4-dioxane, 0.054 mL, 0.21 mmol) at 0° C. After stirring at room temperature for 40 minutes under hydrogen, the reaction mixture was filtered through a celite pad and washed with MeOH (40 mL). Concentration provided compound 19b (132 mg, 97%) as colorless oil, which was used without further purification. $^1$H-NMR (400 MHz, DMSO-d$_6$) δ 7.79 (s, 1H), 4.06-4.02 (m, 8H), 3.88 (m, 2H), 3.73-3.64 (m, 80H), 3.22 (s, 4H), 1.47 (s, 9H). EI-MS m/z: [M+H]$^+$: 1187.5.

Preparation of Compound 19c

Compound 19c was prepared from compound 1i and compound 19b by a similar method of preparing compound 16f in Example 25. EI-MS m/z: ½[M+H]$^+$ 1614.5.

Example 30. Preparation of Compound 20q

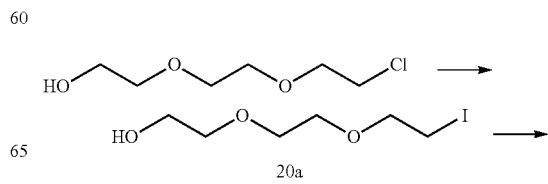

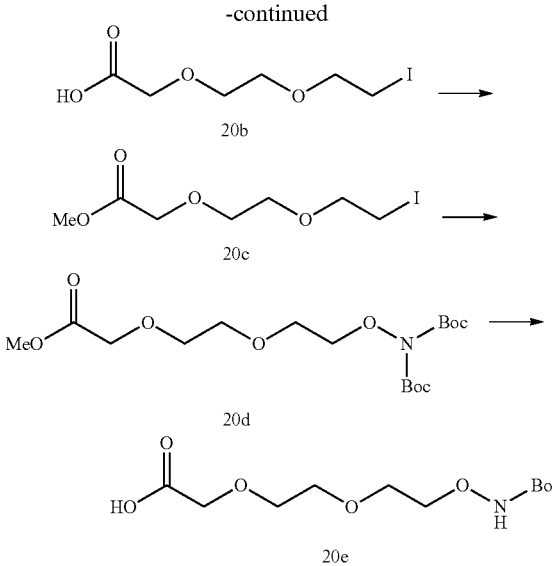

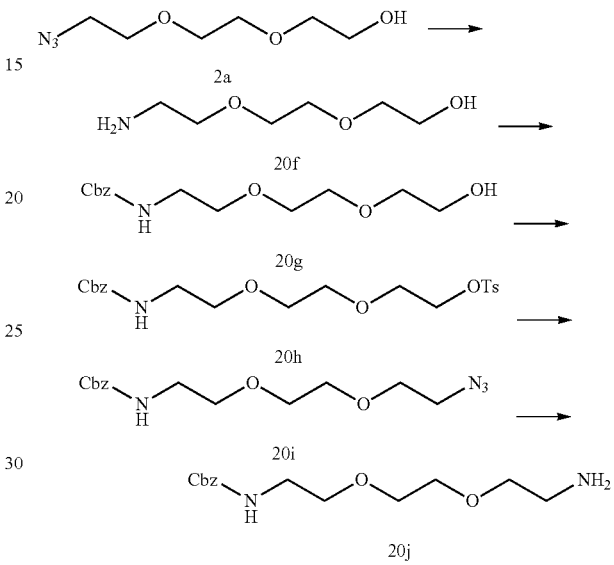

Preparation of Compound 20a

To a solution of 2-(2-(2-chloroethoxy)ethoxy)ethanol (5.0 g, 29.6 mmol) in acetone (30 mL) was added NaI (13.3 g, 88.9 mmol). The reaction mixture was refluxed for 12 hours. After the reaction was completed, the reaction mixture was filtered and concentrated. The crude product was purified by column chromatography to produce the compound 20a (7.0 g, 91%). $^1$H-NMR (400 MHz, CDCl$_3$) δ 3.80-3.73 (m, 4H), 3.72-3.65 (m, 4H), 3.63-3.61 (m, 2H), 3.27 (t, J=6.4 Hz, 2H).

Preparation of Compound 20b

To a solution of compound 20a (7.0 g, 26.9 mmol) in acetone (200 mL) at 0° C. Jones reagent (20 mL) was added. After 15 hours at 0° C., the reaction mixture was filtered and concentrated. The residue was diluted with H$_2$O (150 mL) and extracted with EtOAc (2×100 mL). The organic layers were combined, dried over anhydrous MgSO$_4$, filtered and concentrated. The crude product was purified by column chromatography to produce the compound 20b (7.0 g, 94%). $^1$H-NMR (400 MHz, CDCl$_3$) δ 4.22 (s, 2H), 3.85-3.70 (m, 6H), 3.35-3.25 (m, 2H).

Preparation of Compound 20c

To a solution of compound 20b (7.0 g, 25.5 mmol) in MeOH (70 mL) oxalyl chloride (3.2 mL, 38.3 mmol) was added at 0° C. under N$_2$. After 16 hours, the reaction mixture was concentrated and purified by column chromatography, which produced the compound 20c (5.7 g, 77%). $^1$H-NMR (400 MHz, CDCl$_3$) δ 4.19 (s, 2H), 3.80-3.67 (m, 9H), 3.27 (t, J=6.8 Hz, 2H).

Preparation of Compound 20d

To a solution of compound 20c (2.5 g, 8.67 mmol) and N,N-diBoc-hydroxylamine (2.6 g, 11.2 mmol) in DMF (30 mL) was added NaH (60% in oil, 454 mg, 10.4 mmol) at 0° C. under N$_2$. After 15 hours, the reaction mixture was diluted with H$_2$O (50 mL) and extracted with EtOAc (3×100 mL). The organic layers were combined, dried over anhydrous MgSO$_4$, filtered and concentrated. The crude product was purified by column chromatography to produce the compound 20d (1.87 g, 73%). $^1$H-NMR (400 MHz, CDCl$_3$) δ 4.17 (s, 2H), 4.08 (m, 2H), 3.78-3.65 (m, 9H), 1.53 (s, 18H).

Preparation of Compound 20e

To a solution of compound 20d (1.87 g, 6.38 mmol) in THF/MeOH/H$_2$O (45 mL/15 mL/15 mL) NaOH (600 mg, 15.9 mmol) was added at 0° C. under N$_2$. The reaction mixture was stirred for 3 hours at room temperature. Then the pH of the solution was adjusted to 4-5 with 1 N aqueous HCL. The reaction mixture was poured into H$_2$O (100 mL) and extracted with EtOAc (2×100 mL). The organic layers were combined, dried over MgSO$_4$, filtered and concentrated. The compound 20e (1.6 g, 90%) was produced as colorless oil, and it was used without further purification. $^1$H-NMR (400 MHz, CDCl$_3$) δ 4.17 (s, 2H), 4.08-4.02 (m, 2H), 3.80-3.67 (m, 6H), 1.48 (s, 9H).

Preparation of Compound 20f

Pd/C (10 wt. %, 1.0 g) was added to a solution of compound 2a (6.7 g, 38.2 mmol) in MeOH (38 mL). After stirring at room temperature for 8 hours under hydrogen, the reaction mixture was filtered through a celite pad and washed with MeOH (100 mL). Concentration provided compound 20f (5.6 g, 99%) as colorless oil, which was used without further purification. $^1$H-NMR (400 MHz, CDCl$_3$) δ 3.95-3.25 (m, 12H), 2.90 (s, 2H).

Preparation of Compound 20g

Benzyl chloroformate (6 mL, 42.2 mmol) were slowly added to a solution of compound 20f (5.6 g, 38.2 mmol) and triethylamine (8 mL, 57.6 mmol) in THF (200 mL) at 0° C. for 30 minutes under N$_2$. After stirring for 1 hour at 0° C., the reaction mixture was concentrated and the crude product was purified by column chromatography, which produced the compound 20g (5.7 g, 53%). $^1$H-NMR (400 MHz, CDCl$_3$) δ 7.45-7.20 (m, 5H), 5.61 (br s, 1H), 5.07 (s, 2H), 3.85-3.20 (m, 12H).

Preparation of Compound 20h

To a solution of compound 20g (2.7 g, 9.53 mM) in DCM (30 ML) were added triethylamine (1.9 mL, 12.3 mmol) and p-toluenesulfonyl chloride (2.3 g, 10.4 mmol) at room temperature under N$_2$. After 8 hours, the reaction mixture was diluted with H$_2$O (50 mL) and extracted with DCM (3×100 mL). The organic layers were combined, dried over anhydrous MgSO$_4$, filtered and concentrated. The crude product was purified by column chromatography to produce the compound 20h (3.51 g, 84%). $^1$H-NMR (400 MHz, CDCl$_3$) δ 7.78 (d, J=7.2 Hz, 2H), 7.45-7.25 (m, 7H), 5.20 (br s, 1H), 5.09 (s, 2H), 4.20-4.05 (m, 2H), 3.75-3.25 (m, 10H), 2.43 (s, 3H).

Preparation of Compound 20i

A solution of compound 20h (3.51 g, 8.02 mmol) and NaN$_3$ (3.8 g, 57.6 mmol) in DMF (27 mL) was heated at 100° C. for 15 hours. After the reaction was completed, the reaction mixture was filtered and concentrated. The residue was diluted with H$_2$O (50 mL) and extracted with EtOAc (2×100 mL). The organic layers were combined, dried over anhydrous MgSO$_4$, filtered and concentrated. The crude product was purified by column chromatography to produce the compound 20i (2.05 g, 83%). $^1$H-NMR (400 MHz, CDCl$_3$) δ 7.45-7.25 (m, 5H), 5.20 (br s, 1H), 5.10 (s, 2H), 3.80-3.25 (m, 12H).

Preparation of Compound 20j

Triphenylphosphine (2.09 g, 7.97 mmol) was added to a solution of compound 20i (2.05 g, 6.64 mmol) in THF (27 mL) at room temperature. After stirring for 2 hours under N$_2$, H$_2$O (0.6 mL, 33.2 mmol) was added and the reaction mixture was refluxed for 3 hours. Then the reaction mixture was concentrated and purified by column chromatography, which produced the compound 20j (1.78 g, 95%). $^1$H-NMR (400 MHz, CDCl$_3$) δ 7.45-7.25 (m, 5H), 5.63 (br s, 1H), 5.10 (s, 2H), 3.80-3.25 (m, 10H), 2.88 (s, 2H).

Preparation of Compound 20k

To a stirred solution of oxalyl chloride (1.4 mL, 15.9 mmol) in DCM (14 mL) was added DMSO (2.3 mL, 31.9 mmol) in DCM (28 mL) and then the reaction mixture was stirred at −78° C. for 30 minutes. To this solution was added compound 20g (3.01 g, 10.6 mmol) at −78° C. After stirring for 1 hour at −78 at 0° C., triethylamine (7.4 mL, 53.1 mmol) was added and the reaction was allowed to warm to room temperature. The reaction mixture was poured into H$_2$O (100 mL) and extracted with EtOAc (2×100 mL). The organic layers were combined, dried over MgSO$_4$. Filtration and concentration produced the compound 20k (2.6 g), which was used without further purification. $^1$H-NMR (400 MHz, CDCl$_3$) δ 9.70 (s, 1H), 7.45-7.25 (m, 5H), 5.25 (br s, 1H), 5.10 (s, 2H), 3.80-3.25 (m, 10H).

Preparation of Compound 20l

To a solution of compound 20j (1.78 g, 6.30 mmol) and compound 20k (2.13 g, 7.56 mmol) in MeOH (63 mL) was added NaCNBH$_3$ (674 mg, 10.7 mmol) at room temperature under N$_2$. After 3 hours, the reaction mixture was filtered and concentrated. The crude product was purified by column chromatography to produce the compound 20l (2.01 g, 58%). $^1$H-NMR (400 MHz, CDCl$_3$) δ 7.45-7.25 (m, 10H), 5.60 (br s, 2H), 5.03 (s, 4H), 3.80-3.25 (m, 20H), 2.81 (s, 4H).

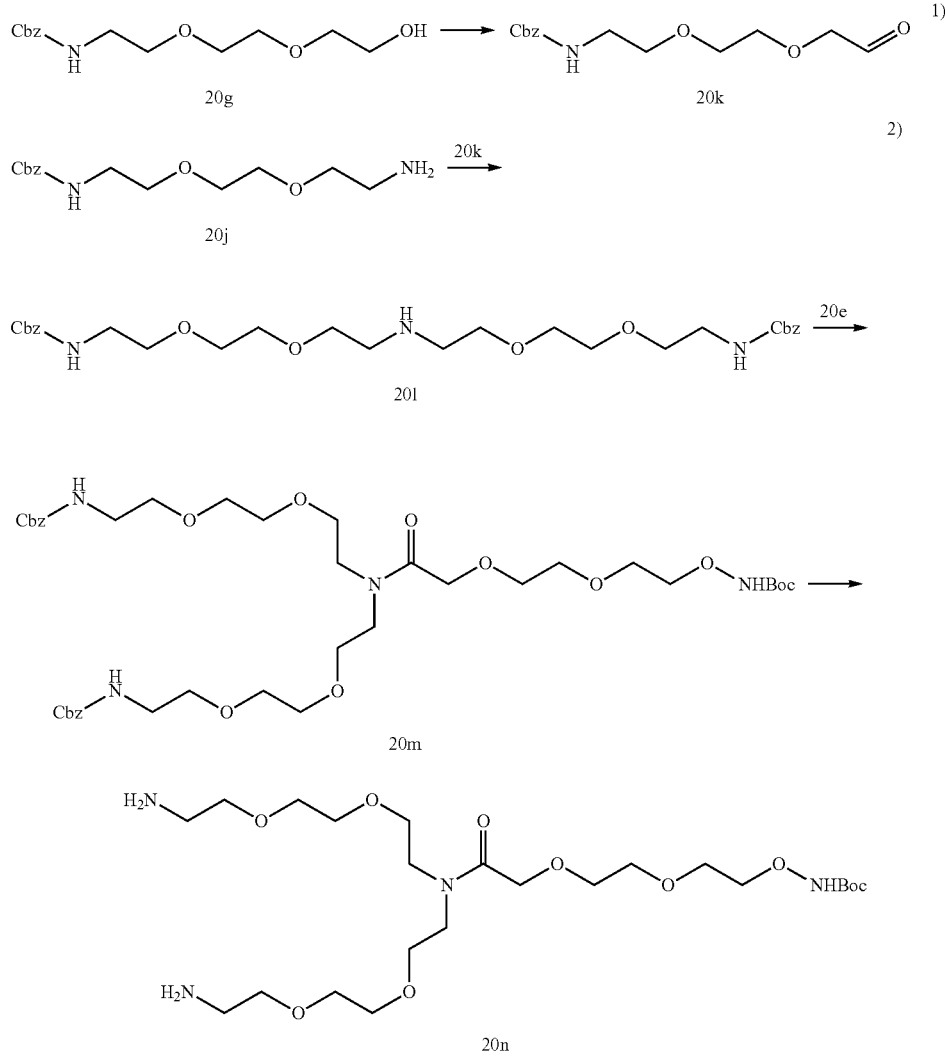

Preparation of Compound 20m

DIPEA (0.4 mL, 2.28 mmol) and PyBOP (713 mg, 1.36 mmol) were added to a stirred solution of compound 20l (500 mg, 0.91 mmol) and compound 20e (306 mg, 1.09 mmol) in DMF (10 mL). After stirring at room temperature for 6 hours under $N_2$, the reaction mixture was diluted water (100 mL) and extracted with EtOAc (3×100 mL). The combined organic layers were dried over anhydrous $Na_2SO_4$, filtered and concentrated under reduced pressure. The crude product was purified by column chromatography to produce the compound 20m (318 mg, 43%). $^1$H-NMR (400 MHz, $CDCl_3$) δ 7.45-7.25 (m, 10H), 5.47 (br s, 1H), 5.37 (br s, 1H), 5.09 (s, 4H), 3.80-3.25 (m, 34H), 1.46 (s, 9H). EI-MS m/z: $[M+H]^+$ 808.9.

Preparation of Compound 20n

To a solution of compound 20m (318 mg, 0.39 mmol) in MeOH (30 mL) was added Pd/C (10 wt. %, 1.0 g). After stirring at room temperature for 3 hours under hydrogen, the reaction mixture was filtered through a celite pad and washed with MeOH (100 mL). Concentration provided compound 20n (180 mg) as colorless oil, which was used without further purification. EI-MS m/z: $[M+H]^+$ 541.2.

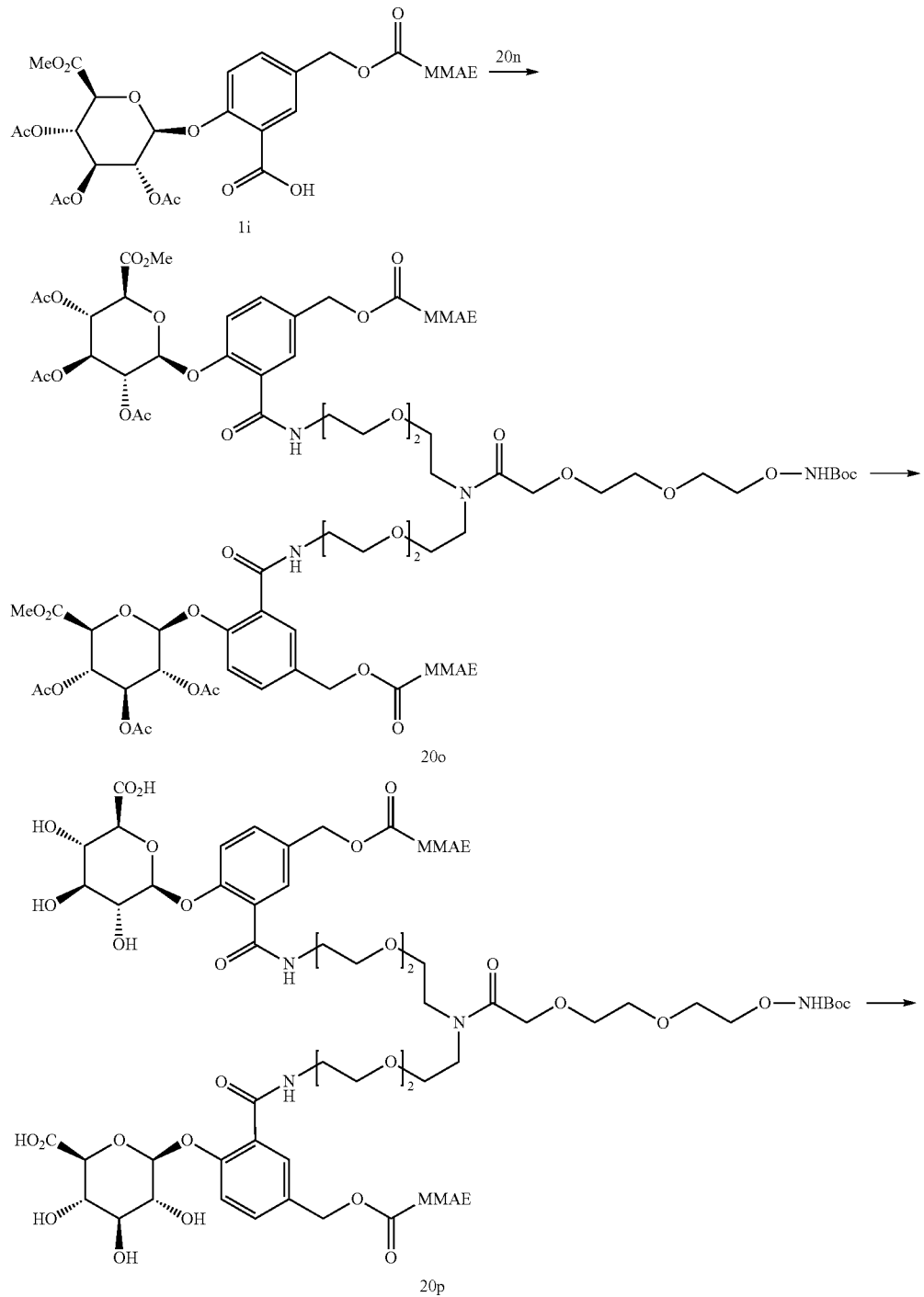

-continued

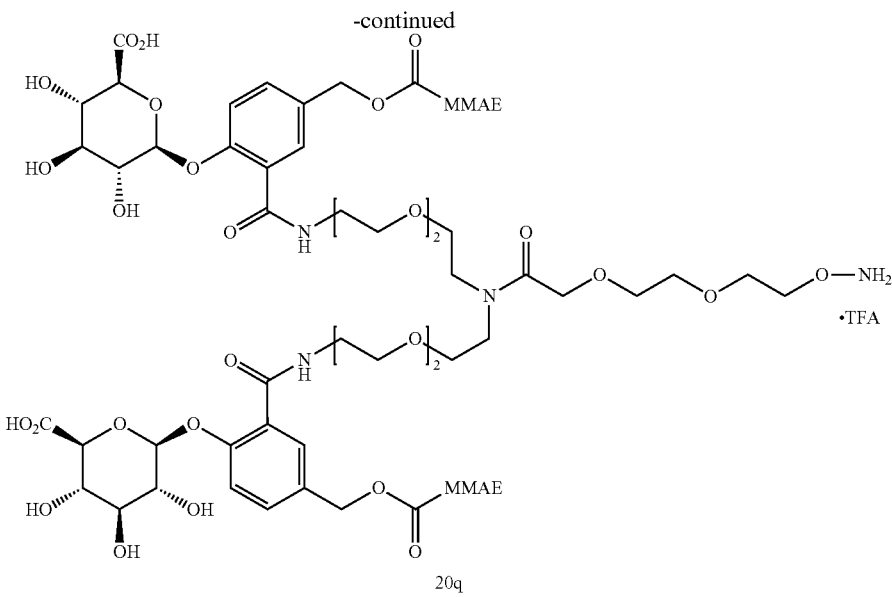

20q

Preparation of Compound 20o

DIPEA (0.034 mL, 0.19 mmol) and PyBOP (63 mg, 0.12 mmol) were added to a stirred solution of compound 1i (130 mg, 0.10 mmol) and compound 20n (26 mg, 0.04 mmol) in DMF (3 mL) at 0° C. After stirring at 0° C. for 30 minutes, the reaction was allowed to warm to room temperature over 20 hours under $N_2$. The reaction mixture was poured into $H_2O$ (50 mL) and extracted with EtOAc (3×50 mL). The organic layers were combined, filtered and concentrated under reduced pressure. The residue was dissolved in DMSO (1 mL) and purified by HPLC, which produced the compound 20o (28 mg, 10%) as white solid. EI-MS m/z: ½[M+H]⁺ 1481.5, ½[M+Na]⁺1503.8.

Preparation of Compound 20p

To a solution of compound 20o (28 mg, 0.009 mmol) in MeOH (1 mL) was added LiOH monohydrate (2 mg, 0.047 mmol) in $H_2O$ (1 mL) at −5° C. The reaction mixture was stirred at −5° C. for 1 hour. After the reaction was completed, the pH of the solution was adjusted to 4-5 with acetic acid. The residue was dissolved in DMSO (1 mL) and purified by HPLC, which produced the compound 20p (16 mg, 67%) as white solid. EI-MS m/z: ½[M+H]⁺: 1341.4.

Preparation of Compound 20a

To a solution of compound 20p (16 mg, 0.0059 mmol) in DCM (2 mL) was added TFA (0.2 mL) at 0° C. After 2 hours at 0° C., the solvent and excess TFA were removed by $N_2$ flow. The residue was dissolved in DMSO (1 mL) and purified by HPLC, which produced the compound 20q (8.5 mg, 56%) as white solid. EI-MS m/z: ½[M+H]⁺: 1291.3.

Example 31. Preparation of Compound 21i

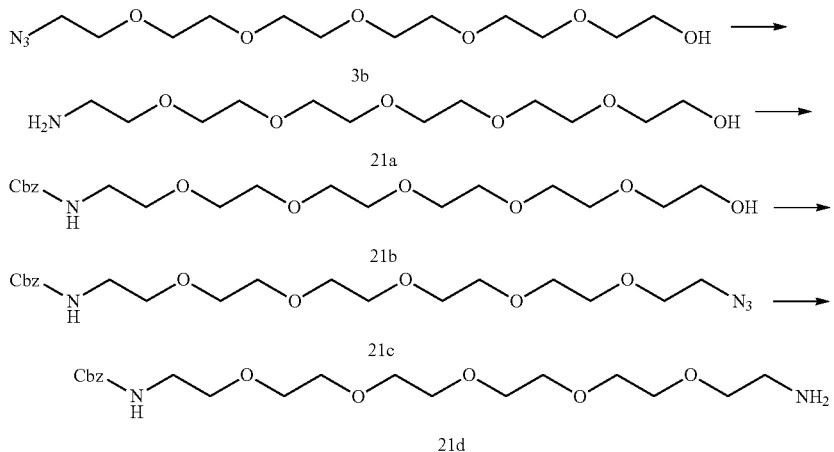

Preparation of Compound 21a

To a solution of compound 3b (9.0 g, 29.2 mmol) in MecOH (146 mL) was added Pd/C (10 wt. %, 3.0 g) and the reaction mixture was stirred at room temperature for 5 hours under hydrogen. Then the reaction mixture was filtered through a celite pad and washed with MeOH (100 mL). Concentration provided compound 21a (8.2 g, 100%) as colorless oil, which was used without further purification. ¹H-NMR (400 MHz, CDCl₃) δ 3.80-3.60 (m, 24H), 3.01 (t, J=4.8 Hz, 2H).

Preparation of Compound 21b

To a solution of compound 21a (8.24 g, 29.2 mmol) in THF (190 mL) was added triethylamine (6.1 mL, 43.9 mmol) and benzyl chloroformate (4.6 mL 32.2 mmol) at 0° C. under $N_2$. The reaction mixture was concentrated and the crude product was purified by column chromatography to produce the compound 21b (5.59 g, 46%). $^1$H-NMR (400 MHz, $CDCl_3$) δ 7.45-7.20 (m, 5H), 5.61 (br s, 1H), 5.09 (s, 2H), 3.85-3.50 (m, 22H), 3.39 (m, 2H).

Preparation of Compound 21c

To a solution of compound 21b (3.09 g, 7.43 mmol) in THF (75 mL) were added 4-methylmorpholine (1.1 mL, 9.66 mmol) and methanesulfonic anhydride (1.43 g, 8.18 mmol) at 0° C. under $N_2$. After 5 hours at 0° C., $NaN_3$ (969 mg, 14.9 mmol) and DMF (20 mL) were added. After 16 hours under reflux, the reaction mixture was filtered and concentrated. The residue was diluted with $H_2O$ (50 mL) and extracted with EtOAc (2×100 mL). The organic layers were combined, dried over anhydrous $MgSO_4$, filtered and concentrated. The crude product was purified by column chromatography to produce the compound 21c (2.62 g, 80%). $^1$H-NMR (400 MHz, $CDCl_3$) δ 7.45-7.20 (m, 5H), 5.45 (br s, 1H), 5.09 (s, 2H), 3.85-3.25 (m, 24H).

Preparation of Compound 21d

Triphenylphosphine (1.87 g, 7.13 mmol) was added to a solution of compound 21c (2.62 g, 5.94 mmol) in THF (30 mL) at room temperature. After stirring for 2 hours under $N_2$, $H_2O$ (0.54 mL, 29.7 mmol) was added and the reaction mixture was refluxed for 3 hours. The reaction mixture was concentrated and purified by column chromatography, which produced the compound 21d (2.47 g, 95%). $^1$H-NMR (400 MHz, $CDCl_3$) δ 7.45-7.25 (m, 5H), 5.63 (br s, 1H), 5.09 (s, 2H), 3.80-3.25 (m, 22H), 3.00-2.80 (m, 2H).

Preparation of Compound 21e

To a stirred solution of oxalyl chloride (0.78 mL, 9.02 mmol) in DCM (14 mL) was added DMSO (1.3 mL, 18.1 mmol) in DCM (6 mL) and then the reaction mixture was stirred at −78° C. for 30 minutes. To this solution was added compound 21b (2.5 g, 6.01 mmol) at −78° C. After stirred for 1 hour at −78° C., triethylamine (4.2 mL, 30.1 mmol) was added and the reaction was allowed to warm to room temperature. The reaction mixture was poured into $H_2O$ (100 mL) and extracted with EtOAc (2×100 mL). The organic layers were combined, dried over $MgSO_4$. Filtration and concentration produced the compound 21e (2.29 g), which was used without further purification. $^1$H-NMR (400 MHz, $CDCl_3$) δ 9.70 (s, 1H), 7.45-7.25 (m, 5H), 5.25 (br s, 1H), 5.10 (s, 2H), 3.80-3.25 (m, 24H).

Preparation of Compound 21f

To a solution of compound 21d (2.47 g, 5.95 mmol) and compound 21e (2.29 g, 5.52 mmol) in MeOH (50 mL) was added $NaCNBH_3$ (530 mg, 8.44 mmol) at room temperature under $N_2$. After 3 hours, the reaction mixture was filtered and concentrated. The crude product was purified by column chromatography to produce the compound 21f (2.05 g, 51%). $^1$H-NMR (400 MHz, $CDCl_3$) δ 7.45-7.25 (m, 10H), 5.47 (br s, 1H), 5.37 (br s, 1H), 5.09 (s, 4H), 3.80-3.25 (m, 48H).

Preparation of Compound 21g

DIPEA (0.27 mL, 1.53 mmol) and HBTU (350 mg, 0.92 mmol) were added to a stirred solution of compound 21f (380 mg, 0.61 mmol) and compound 20e (206 mg, 0.73 mmol) in DMF (6 mL). After stirring at room temperature

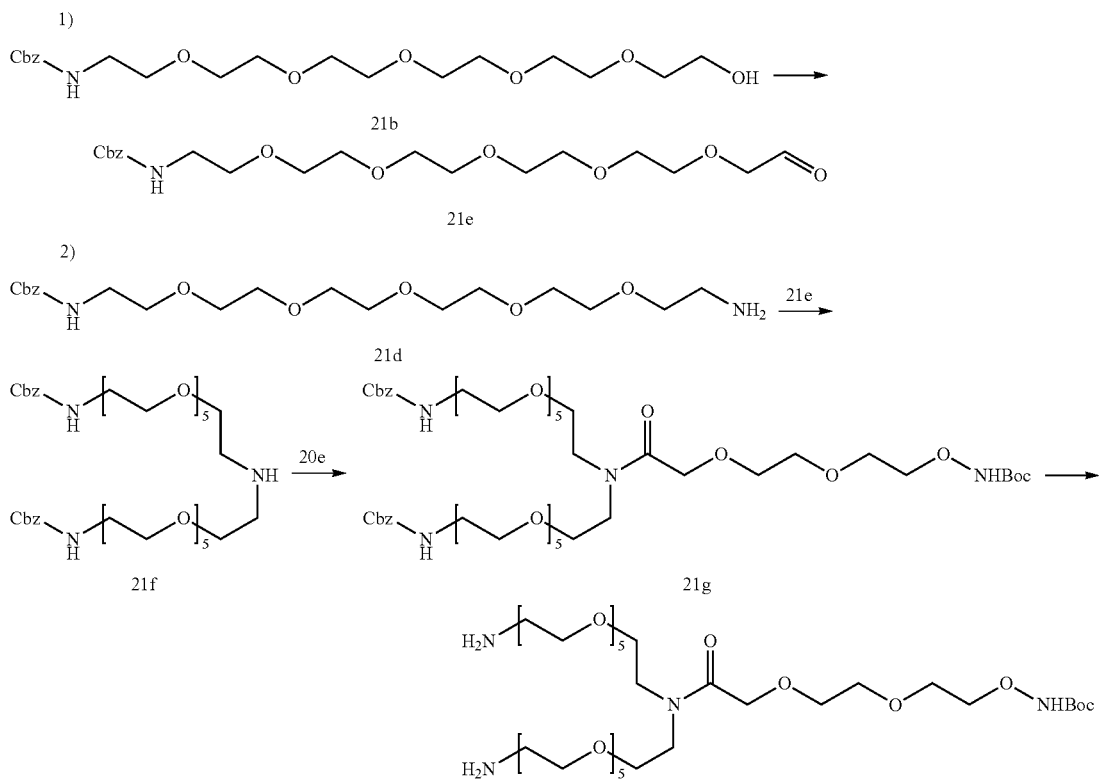

for 6 hours under $N_2$, the reaction mixture was diluted water (100 mL) and extracted with EtOAc (3×100 mL). The combined organic layers were dried over anhydrous $Na_2SO_4$, filtered and concentrated under reduced pressure. The crude product was purified by column chromatography to produce the compound 21g (210 mg, 42%). $^1$H-NMR (400 MHz, $CDCl_3$) δ 7.45-7.25 (m, 10H), 5.47 (br s, 1H), 5.37 (br s, 1H), 5.09 (s, 4H), 3.80-3.25 (m, 34H), 1.46 (s, 9H).

Preparation of Compound 21h

To a solution of compound 21g (210 mg, 0.19 mmol) in MeOH (30 mL) was added Pd/C (10 wt. %, 1.0 g) and then the reaction mixture was stirred at room temperature for 4 hours under hydrogen. The reaction mixture was filtered through a celite pad and washed with MeOH (50 mL). Concentration provided compound 21h (30 mg) as colorless oil, which was used without further purification. EI-MS m/z: $[M+H]^+$ 805.2, $[M+Na]^+$ 827.2.

Preparation of Compound 21i

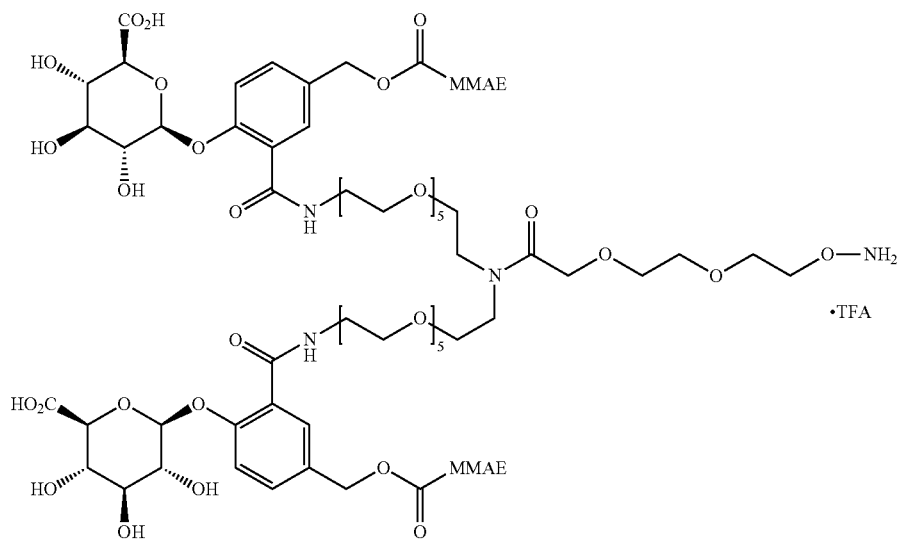

Compound 21i was prepared from compound 1i and compound 21h by a similar method of preparing compound 20q in Example 30. EI-MS m/z: ½$[M+H]^+$ 1423.7, ½$[M+Na]^+$ 1445.2.

Example 32. Preparation of Compound 22h

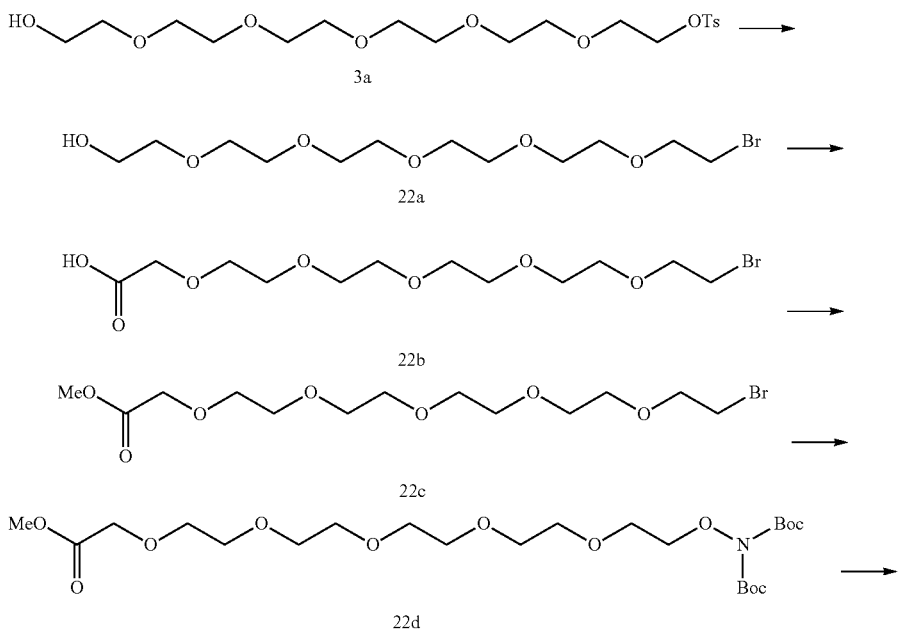

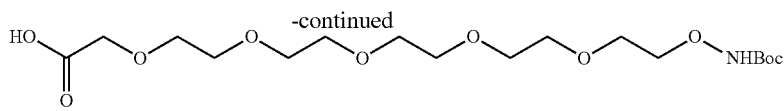

22e

Preparation of Compound 22a

To a solution of compound 3a (8.0 g, 18.3 mmol) in THF (50 mL) was added LiBr (7.9 g, 91.6 mmol) at room temperature. After stirring for 17 hours under reflux, the reaction mixture was filtered and concentrated. The crude product was purified by column chromatography to produce the compound 22a (3.2 g, 50%). $^1$H-NMR (400 MHz, CDCl$_3$) δ 3.95-3.50 (m, 24H).

Preparation of Compound 22b

To a solution of compound 22a (3.2 g, 12.3 mmol) in acetone (20 mL) at 0° C. was added Jones reagent (20 mL). After 15 hours at 0° C., the reaction mixture was filtered and concentrated. The residue was diluted with H$_2$O (50 mL) and extracted with EtOAc (2×100 mL). The organic layers were combined, dried over anhydrous MgSO$_4$, filtered and concentrated. The crude product was purified by column chromatography to produce the compound 22b (3.2 g, 72%). $^1$H-NMR (400 MHz, CDCl$_3$) δ 4.16 (s, 2H), 3.95-3.30 (m, 20H).

Preparation of Compound 22c

To a solution of compound 22b (3.2 g, 8.90 mmol) in MeOH (30 mL) was added oxalyl chloride (1.15 mL, 13.3 mmol) at 0° C. under N$_2$. After 16 hours, the reaction mixture was concentrated and purified by column chromatography, which produced the compound 22c (2.7 g, 81%). $^1$H-NMR (400 MHz, CDCl$_3$) δ 4.17 (s, 2H), 3.80-3.60 (m, 21H), 3.47 (t, J=6.4 Hz, 2H).

Preparation of Compound 22d

NaH (60% in oil, 378 mg, 8.63 mmol) was added to a solution of compound 22c (2.7 g, 7.23 mmol) and N,N-diBoc-hydroxylamine (2.2 g, 9.4 mmol) in DMF (30 mL) at 0° C. under N$_2$. After 17 hours, the reaction mixture was concentrated. The residue was diluted with H$_2$O (50 mL) and extracted with EtOAc (3×100 mL). The organic layers were combined, dried over anhydrous MgSO$_4$, filtered and concentrated. The crude product was purified by column chromatography to produce the compound 22d (2.1 g, 55%). $^1$H-NMR (400 MHz, CDCl$_3$) δ 4.17 (s, 2H), 4.08 (t, J=5.2 Hz, 2H), 3.78-3.60 (m, 21H), 1.53 (s, 18H).

Preparation of Compound 22e

To a solution of compound 22d (2.1 g, 3.99 mmol) in THF/MeOH/H$_2$O (30 mL/10 mL/10 mL) was added NaOH (400 mg, 9.98 mmol) at 0° C. under N$_2$. The reaction mixture was stirred for 3 hours at room temperature. Then the pH of the solution was adjusted to 4-5 with 1 N aqueous HCl. The reaction mixture was poured into H$_2$O (50 mL) and extracted with EtOAc (2×100 mL). The organic layers were combined, dried over MgSO$_4$. Filtration and concentration produced the compound 22e (1.6 g) as colorless oil, which was used without further purification. $^1$H-NMR (400 MHz, CDCl$_3$) δ 7.90 (s, 1H), 4.15 (s, 2H), 4.03 (br s, 2H), 3.80-3.60 (m, 18H), 1.47 (s, 9H).

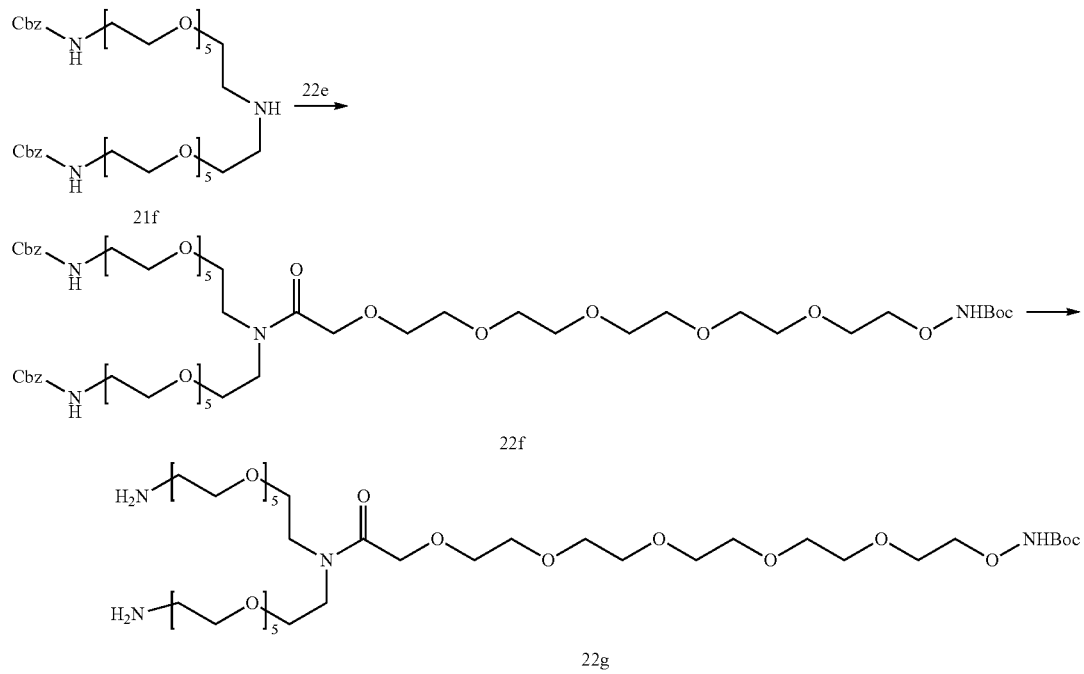

Preparation of Compound 22f

DIPEA (0.13 mL, 0.73 mmol) and HBTU (187 mg, 0.49 mmol) were added to a stirred solution of compound 21f (200 mg, 0.24 mmol) and compound 22e (152 mg, 0.36 mmol) in DMF (5 mL). The reaction mixture was stirred at room temperature for 6 hours under N$_2$. The reaction mixture was diluted H$_2$O (100 mL) and extracted with EtOAc (3×100 mL). The combined organic layers were dried over anhydrous Na₂SO₄, filtered and concentrated under reduced pressure. The crude product was purified by column chromatography to produce the compound 22f (100 mg, 34%). EI-MS m/z: ½[M+H]⁺ 1205.6.

Preparation of Compound 22g

To a solution of compound 22f (100 mg, 0.08 mmol) in MeOH (20 mL) was added Pd/C (10 wt. %, 20 mg) and then the reaction mixture was stirred at room temperature for 4 hours under hydrogen. The reaction mixture was filtered through a celite pad and washed with MeOH (20 mL). Concentration provided compound 22g as colorless oil (70 mg), which was used without further purification. EI-MS m/z: [M+H]⁺ 937.4, [M+Na]⁺959.3.

Preparation of Compound 22h

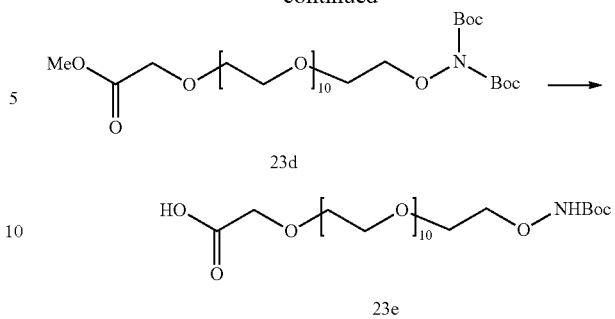

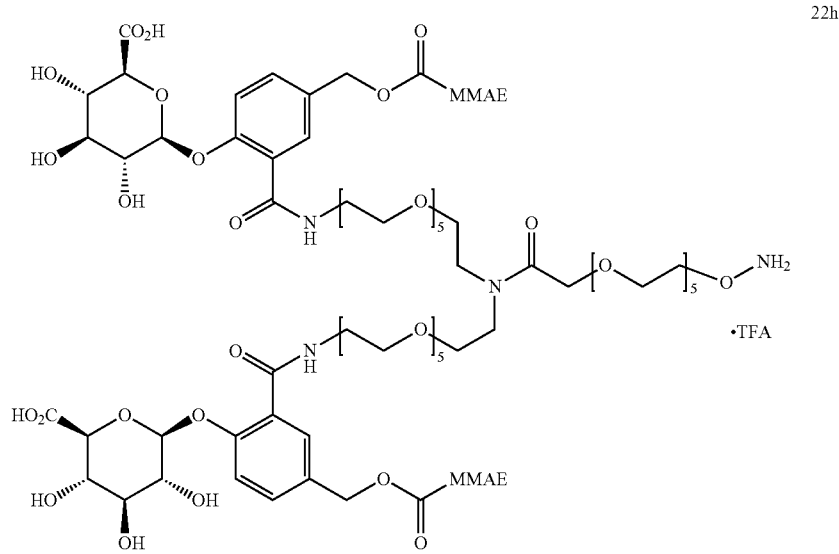

Compound 22h was prepared from compound 1i and compound 22g by a similar method of preparing compound 20q in Example 30. EI-MS m/z: ½[M+H]⁺ 1489.4.

Example 33. Preparation of Compound 23h

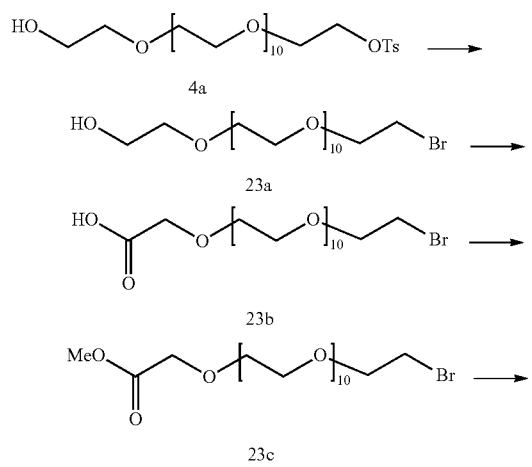

Preparation of Compound 23a

To a solution of compound 4a (483 mg, 0.69 mmol) in THF (10 mL) was added LiBr (180 mg, 2.06 mmol). The reaction mixture refluxed for 12 hours under N₂. Then the reaction mixture was concentrated under reduced pressure. The residue was purified by column chromatography to produce the compound 23a (330 mg, 78%). ¹H-NMR (400 MHz, CDCl₃) δ 3.81 (t, J=6.4 Hz, 2H), 3.72-3.59 (m, 44H), 3.47 (t, J=6.4 Hz, 2H).

Preparation of Compound 23b

To a solution of compound 23a (330 mg, 0.54 mmol) in acetone (2 mL) at 0° C. was added Jones reagent (2 mL). After 15 hours at 0° C., the reaction mixture was filtered and concentrated. The residue was diluted with H₂O (15 mL) and extracted with EtOAc (2×20 mL). The organic layers were combined, dried over anhydrous MgSO₄, filtered and concentrated. The resulting crude compound 23b was used without further purification.

Preparation of Compound 23c

To a solution of crude compound 23b (266 mg, 0.43 mmol) in MeOH (5 mL) was added oxalyl chloride (0.054 mL, 0.64 mmol) at 0° C. under N₂. After 16 hours, the reaction mixture was concentrated and purified by column chromatography, which produced the compound 23c (200 mg, 58% for 2 steps). ¹H-NMR (400 MHz, CDCl₃) δ 4.17 (s, 2H), 3.81 (t, J=6.4 Hz, 2H), 3.79-3.64 (m, 43H), 3.48 (t, J=6.4 Hz, 2H).

Preparation of Compound 23d

To a solution of compound 23c (200 mg, 0.31 mmol) in DMF (3 mL) were added N,N-diBoc-hydroxylamine (95 mg, 0.40 mmol) and NaH (60% in oil, 16 mg, 0.37 mmol) at 0° C. under $N_2$. After 17 hours, the reaction mixture was concentrated. The residue was diluted with $H_2O$ (5 mL) and extracted with EtOAc (3×10 mL). The organic layers were combined, dried over anhydrous $MgSO_4$, filtered and concentrated. The crude product was purified by column chromatography to produce the compound 23d (120 mg, 49%). $^1$H-NMR (400 MHz, $CDCl_3$) δ 4.17 (s, 2H), 4.13 (t, J=8.0 Hz, 2H), 3.75-3.64 (m, 45H), 1.53 (s, 18H).

Preparation of Compound 23e

To a solution of compound 23d (120 mg, 0.15 mmol) in THF/MeOH/$H_2O$ (3 mL/1 mL/1 mL) was added NaOH (15 mg, 0.38 mmol) at 0° C. under $N_2$. The reaction mixture was stirred for 1 hour at room temperature. Then the pH of the solution was adjusted to 4-5 with 1 N aqueous HCl. The reaction mixture was poured into $H_2O$ (10 mL) and extracted with $CHCl_3$ (2×20 mL). The organic layers were combined, dried over anhydrous $Na_2SO_4$. Filtration and concentration produced the compound 23e (100 mg), which was used without further purification. $^1$H-NMR (400 MHz, $CDCl_3$) δ 4.23 (t, J=8.0 Hz, 2H), 4.15 (s, 2H), 4.08 (t, J=4.0 Hz, 1H), 4.01 (t, J=4.0 Hz, 1H), 3.74-3.64 (m, 40H), 1.53 (s, 9H).

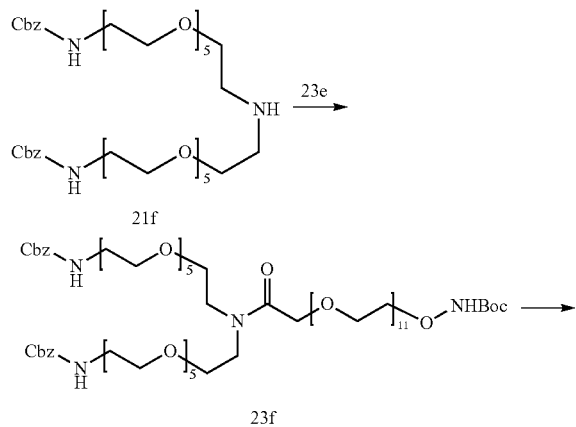

Preparation of Compound 23f

DIPEA (0.052 mL, 0.29 mmol) and HBTU (75 mg, 0.20 mmol) were added to a stirred solution of compound 21f (80 mg, 0.09 mmol) and compound 23e (100 mg, 0.15 mmol) in DMF (3 mL). After stirring at room temperature for 6 hours under $N_2$, the reaction mixture was diluted with $H_2O$ (50 mL) and extracted with EtOAc (3×50 mL). The combined organic layers were dried over anhydrous $Na_2SO_4$, filtered and concentrated under reduced pressure. The crude product was purified by column chromatography to produce the compound 23f (140 mg, 97%). $^1$H-NMR (400 MHz, $CDCl_3$) δ 7.38-7.31 (m, 10H), 5.44 (br, 2H), 5.09 (s, 4H), 4.34 (s, 2H), 4.26-4.17 (m, 4H), 4.09-4.08 (m, 1H), 4.07 (br, 1H), 3.73-3.47 (m, 76H), 3.39-3.38 (m, 4H), 1.53 (s, 9H). EI-MS m/z: [M+Na]$^+$1491.6, [M+H-Boc]$^+$: 1369.6.

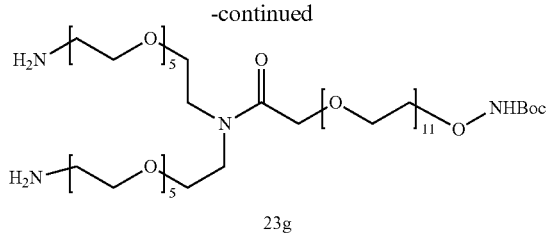

Preparation of Compound 23g

To a solution of compound 23f (140 mg, 0.09 mmol) in MeOH (20 mL) was added Pd/C (10 wt. %, 20 mg) and then the reaction mixture was stirred at room temperature for 4 hours under hydrogen. The reaction mixture was filtered through a celite pad and washed with MeOH (20 mL). Concentration provided compound 23g as colorless oil (120 mg), which was used without further purification. EI-MS m/z: [M+H]$^+$ 1201.7, [M+Na]$^+$1223.7.

Preparation of Compound 23h

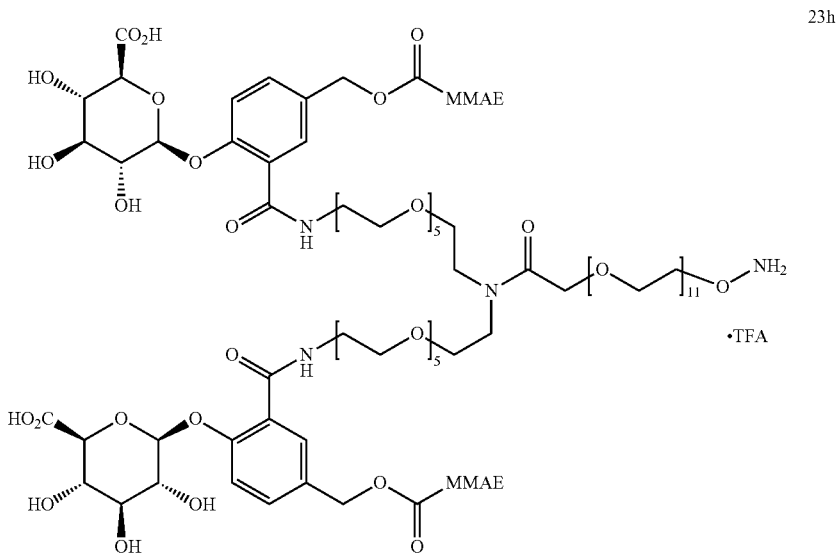

Compound 23h was prepared from compound 1i and compound 23g by a similar method of preparing compound 20q in Example 30. EI-MS m/z: ½[M+H]⁺ 1620.3, ½[M+Na]⁺1632.1.

Example 34. Preparation of Compound 241

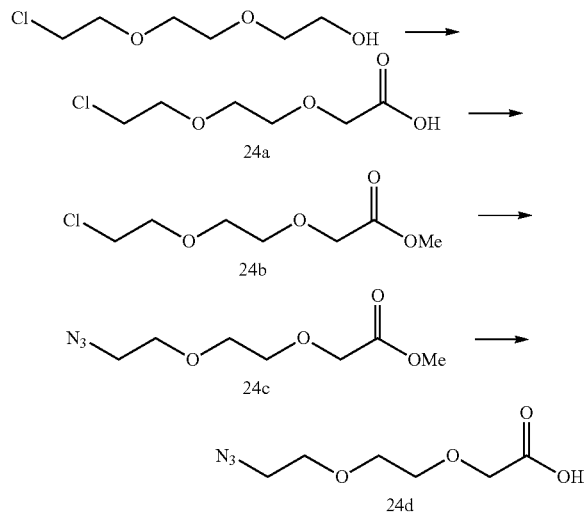

Preparation of Compound 24a

Jones reagent (90 mL) was slowly added to a solution of compound 2-[2-(2-chloroethoxy)ethoxy]ethanol (15.0 g, 88.9 mmol) in acetone (600 mL) at 0° C. After 15 hours at 0° C., the reaction mixture was filtered and concentrated. The residue was diluted with H$_2$O (200 mL) and extracted with CHCl$_3$ (5×300 mL). The organic layers were combined, dried over anhydrous MgSO$_4$. Concentration provided compound 24a (20.0 g), which was used without further purification. ¹H-NMR (400 MHz, CDCl$_3$) δ 4.18 (s, 2H), 3.81-3.64 (m, 8H).

Preparation of Compound 24b

To a solution of compound 24a (20.0 g, 88.9 mmol) in MeOH (500 mL) was added oxalyl chloride (11.5 mL, 133.4 mmol) at 0° C. for 30 minutes under N$_2$. After 16 hours, the reaction mixture was concentrated and purified by column chromatography, which produced the compound 24b (13.0 g, 75%). ¹H-NMR (400 MHz, CDCl$_3$) δ 4.18 (s, 2H), 3.78-3.67 (m, 9H), 3.65 (t, J=5.6 Hz, 2H).

Preparation of Compound 24c

Compound 24b (13.0 g, 66.1 mmol) and NaN$_3$ (6.4 g, 99.2 mmol) were dissolved in DMF (130 mL). After stirring at 100° C. for 2 hours, the reaction mixture was diluted with brine (200 mL) and extracted with CHCl$_3$ (2×100 mL). The organic layers were combined, dried over anhydrous MgSO$_4$. Concentration provided compound 24c (11.7 g, 87%), which was used without further purification. ¹H-NMR (400 MHz, CDCl$_3$) δ 4.18 (s, 2H), 3.76-3.67 (m, 9H), 3.41 (t, J=5.6 Hz, 2H).

Preparation of Compound 24d

To a solution of compound 24c (11.5 g, 56.6 mmol) in THF/MeOH/H$_2$O (300 mL/100 mL/100 mL) was added NaOH (4.53 g, 113.2 mmol) at 0° C. After 2 hours at 0° C. under N$_2$, the pH of the solution was adjusted to 2 with 4 M aqueous HCl. The reaction mixture was poured into H$_2$O (100 mL) and extracted with CHCl$_3$ (3×500 mL). The organic layers were combined, dried over MgSO$_4$. Filtration and concentration produced the compound 24d (10.7 g, 99%) as colorless oil, which was used without further purification. ¹H-NMR (400 MHz, CDCl$_3$) δ 4.19 (s, 2H), 3.79-3.77 (m, 2H), 3.72-3.70 (m, 4H), 3.44 (t, J=5.2 Hz, 2H).

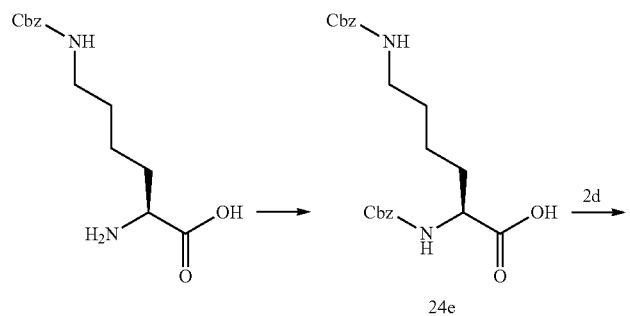

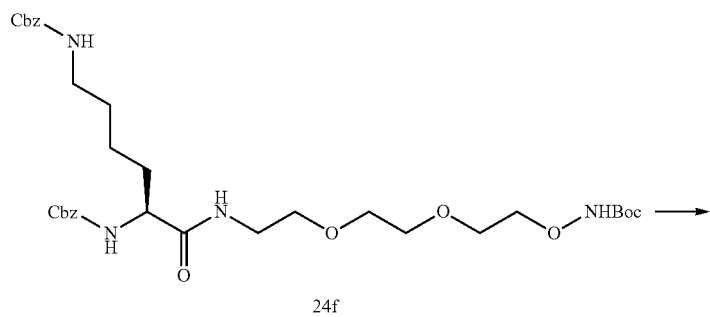

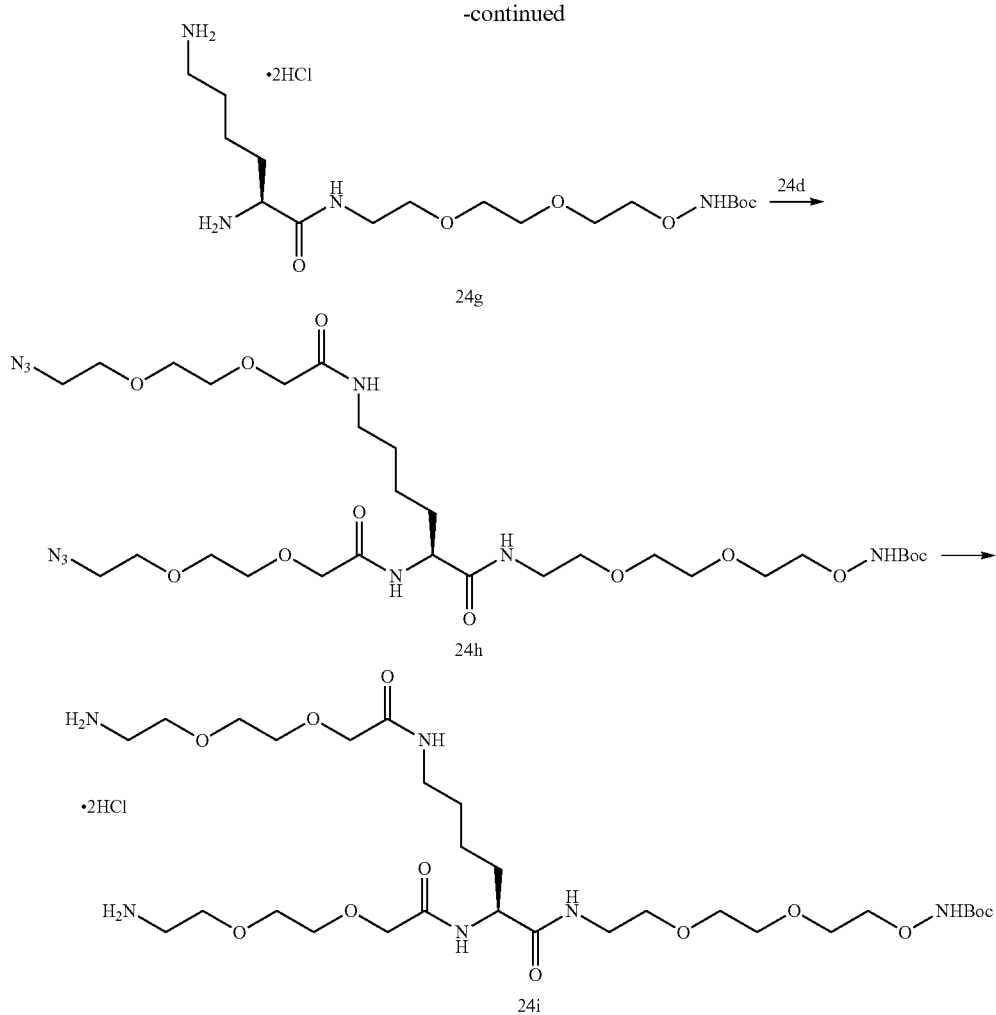

Preparation of Compound 24e

A three-necked flask was loaded consecutively with H₂O (40 mL), 1,4-dioxane (70 mL) and H-Lys(Z)—OH (10 g, 35.7 mmol). The mixture was stirred until complete dissolution. The pH was adjusted to about 10.5 by adding of 2 M aqueous Na₂CO₃. Benzyl chloroformate (6.69 g, 39.2 mmol) was added while maintaining the pH at about 10-11 by adding at the same time 2 M aqueous Na₂CO₃. After completing addition, the reaction mixture was stirred at 20° C. for 1 hour. Then EtOAc (50 mL) was added and pH of the resulting mixture was adjusted to 2-3 with c-HCl. The organic layer was separated and the aqueous layer was extracted with EtOAc (50 mL). The combined organic layers were washed with brine (50 mL), and dried over Na₂SO₄. Filtration and concentration under reduced pressure yielded the compound 24e as yellowish oil (14.7 g, 99%). ¹H-NMR (400 MHz, CDCl₃) δ 7.33-7.27 (m, 10H), 5.07-5.04 (d, 4H), 4.08 (m, 1H), 3.09 (t, 2H), 1.51 (br s, 1H), 1.49 (bs, 1H), 1.47-1.40 (m, 4H).

Preparation of Compound 24f

DIPEA (0.40 mL, 2.37 mmol), HOBt (143 mg, 1.06 mmol) and EDC.HCl (240 mg, 1.25 mmol) were added to a stirred mixture of compound 24e (400 mg, 0.96 mmol) and compound 2d (261 mg, 0.86 mmol) in DMF (3 mL). After stirring at room temperature for 14 hours under N₂, the reaction mixture was poured into H₂O (50 mL), extracted with EtOAc (3×50 mL), washed with aq NaHCO₃ (50 mL) and brine (50 mL) and dried over anhydrous Na₂SO₄. After filtration and concentration under reduced pressure, the resulting residue was purified by column chromatography to yield the compound 24f (380 mg, 59%). ¹H NMR (400 MHz, CDCl₃) δ 8.16 (s, 1H), 7.34-7.28 (m, 10H), 7.49 (s, 1H) 5.08-5.07 (m, 5H), 4.17 (m, 1H), 3.99 (t, 2H), 3.68-3.16 (m, 10H), 3.17 (d, 2H), 1.66 (m, 1H), 1.51-1.27 (m, 14H). EI-MS m/z: [M+H]⁺ 661.0.

Preparation of Compound 24g

To a stirred mixture of compound 24f (370 mg, 0.55 mmol) and Pd/C (10 wt. %, 74 mg) in MeOH (10 mL) at 0° C. was added HCl (4 N in 1,4-dioxane, 0.27 mL, 1.1 mmol). After stirring at room temperature for 2 h under hydrogen, the reaction mixture was filtered through a celite pad and washed with MeOH (40 mL). The filtrate was concentrated to produce the compound 24g (223 mg, 87%) as colorless oil, which was used without further purification. ¹H-NMR (400 MHz, DMSO-d₆) δ 10.02 (s, 1H), 8.62 (s, 1H), 8.22 (br, 2H), 7.90 (br, 2H), 3.81 (t, 2H), 3.56 (m, 4H), 3.46 (t, 2H), 3.39-3.27 (m, 26H), 2.75 (m, 2H), 1.73 (q, 2H), 1.55 (p, 2H), 1.40-1.33 (m, 14H).

Preparation of Compound 24h

DIPEA (1.6 mL, 9.45 mmol), HOBt (746 mg, 5.52 mmol) and EDC.HCl (1.19 g, 6.42 mmol) were added to a stirred mixture of compound 24g (1.0 g, 5.29 mmol) and compound 24d (1.1 g, 2.35 mmol) in DMF (15 mL). After stirring at room temperature for 14 hours under N$_2$, the reaction mixture was poured into H$_2$O (20 mL), extracted with DCM (3×50 mL) and dried over anhydrous Na$_2$SO$_4$. After filtration and concentration under reduced pressure, the resulting residue was purified by column chromatography to yield the compound 24h (1.25 g, 70%). $^1$H-NMR (400 MHz, CDCl$_3$) δ 8.36 (s, 1H), 7.30 (d, 1H), 7.08 (s, 1H), 7.68 (t, 1H), 4.46 (q, 1H), 4.07-3.98-4.01 (m, 4H), 3.98 (s, 2H), 3.75-3.663 (m, H) 3.57 (t, 2H), 3.44 (m, 6H), 3.28 (m, 2H), 1.87 (m, 1H), 1.66 (m, 1H), 1.59-1.52 (p, 2H), 1.48 (s, 9H), 1.41-1.33 (r. 2H). EI-MS m/z: [M+H]$^+$ 735.0.

Preparation of Compound 24i

To a stirred mixture of compound 24h (1.2 g, 0.163 mmol), and Pd/C (10 wt. %, 250 mg) in MeOH (30 mL) at 0° C., 4 N HCl (1,4-dioxane, 0.81 mL, 3.26 mmol) was added. After stirring at room temperature for 1.5 hours under hydrogen, the reaction mixture was filtered through a celite pad and washed with MeOH (100 mL). The filtrate was concentrated to produce the compound 24i (1.39 g, 99%) as colorless oil, which was used without further purification. $^1$H-NMR (400 MHz, DMSO-d$_6$) δ 9.99 (s, 1H), 8.22 (t 1H) 7.74 (t, 1H), 7.61 (d, 1H), 4.31, (q, 1H), 3.93 (s, 2H), 3.86 (s, 2H), 3.79 (t, 2H), 3.60-3.50 (m, 18H), 3.06 (q, 2H), 2.97 (p, 4H), 1.60-1.49 (m, 2H), 1.39 (m, 11H), 1.20 (m, 2H). EI-MS m/z: [M+H]$^+$ 683.

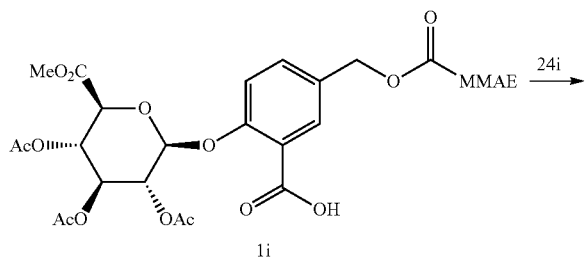

1i

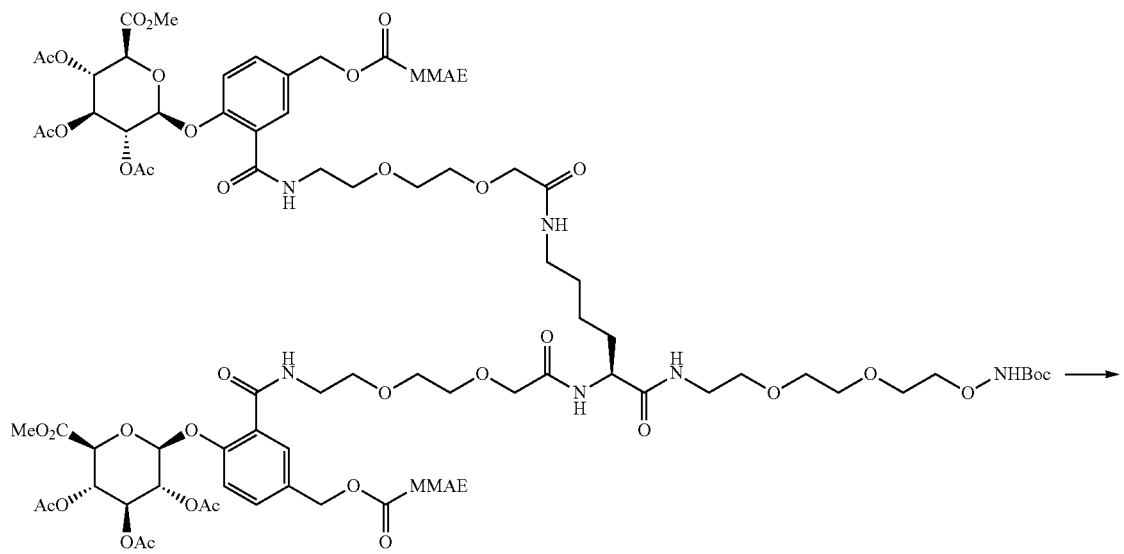

24j

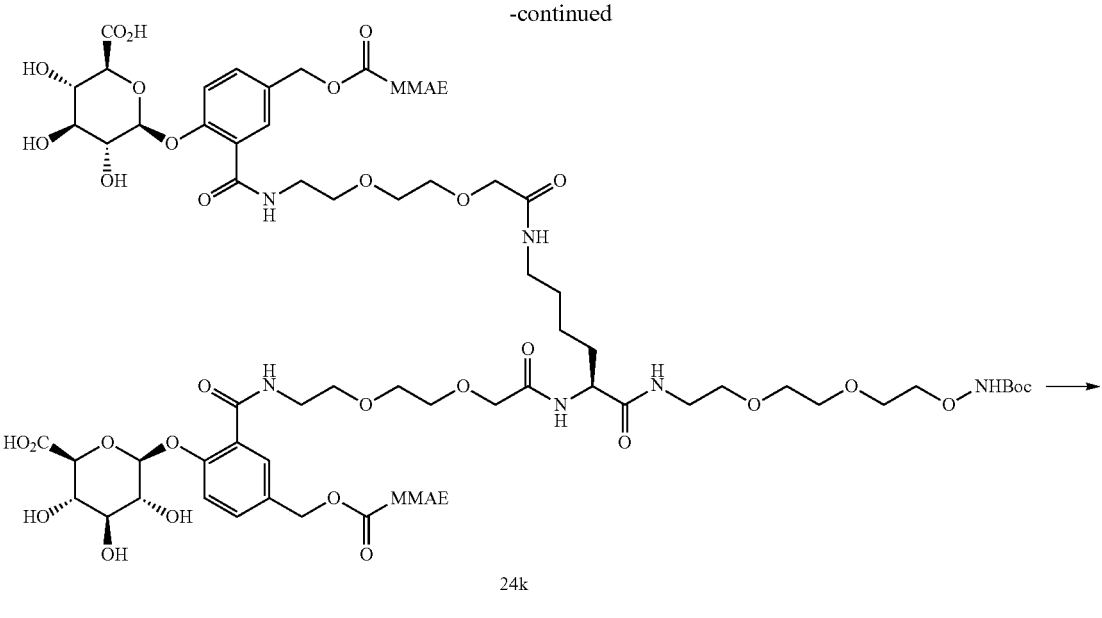

24k

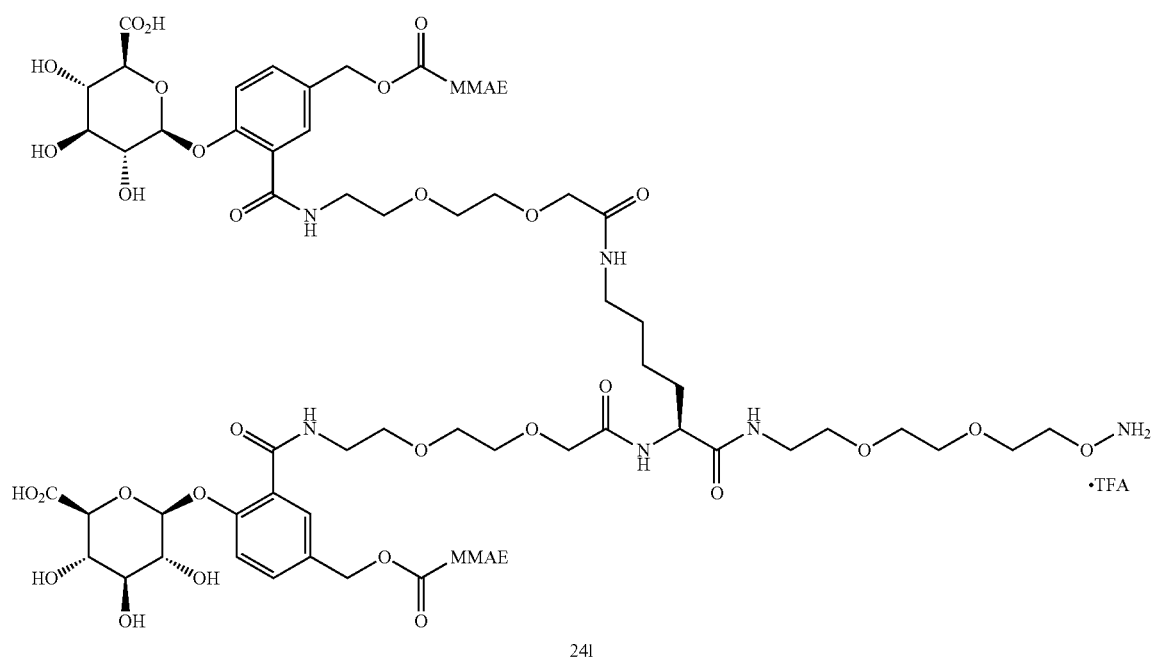

24l

Preparation of Compound 24i

DIPEA (0.021 mL, 0.125 mmol) and HBTU (29 mg, 0.078 mmol) were added to a stirred mixture of compound 1i (85 mg, 0.069 mmol) and compound 24i (23 mg, 0.031 mmol) in DMF (0.7 mL). After stirring at room temperature for 14 hours under $N_2$, the reaction mixture was dissolved in $H_2O$/DMSO (1.5 mL/1.5 mL) and purified by HPLC. Pure fractions with the same retention time were combined and concentrated to produce the compound 24j (67 mg, 68%). EI-MS m/z: ½[M+H]⁺ 1552.5.

Preparation of Compound 24k

To a solution of compound 24j (67 mg, 0.021 mmol) in MeOH (1.7 mL) was added LiOH monohydrate (16 mg, 0.388 mmol) in $H_2O$ (1.7 mL) at 0° C. After stirring for 2 hours at 0° C., the reaction mixture was neutralized using acetic acid (0.018 mL) and concentrated under reduced pressure. The reaction mixture was dissolved in $H_2O$/DMSO (1.5 mL/1.5 mL) and purified by HPLC. Pure fractions with the same retention time were combined and concentrated to produce the compound 24k (37 mg, 62%). EI-MS m/z: ½[M+H]⁺ 1412.3.

Preparation of Compound 24l

TFA (0.4 mL) was added to a stirred solution of compound 24k (37 mg, 0.013 mmol) in DCM (2.0 mL). After stirring at 0° C. for 2 hours, the solvent and excess TFA were blown off with $N_2$. The residue was dissolved in $H_2O$/acetonitrile (1 mL/1 mL) and purified by HPLC. Pure fractions with the same retention time were combined and lyophilized to produce the compound 24l (19.8 mg, 53%) as white solid. EI-MS m/z: ½[M+H]⁺ 1362.3.

Example 35. Preparation of Compound 25e

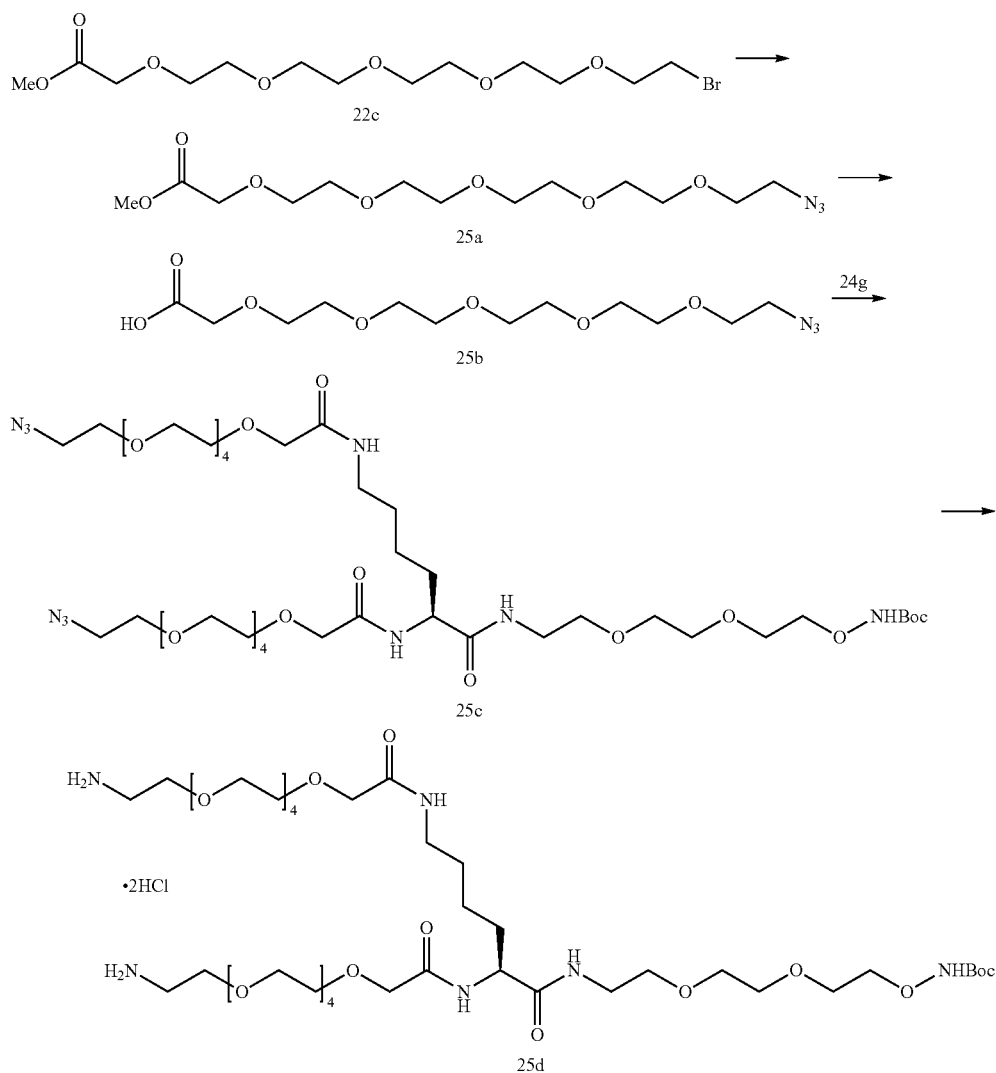

Preparation of Compound 25a

Compound 22c (1.0 g, 2.67 mmol) and NaN$_3$ (261 mg, 4.01 mmol) were dissolved in DMF (3 mL). The reaction mixture was heated at 100° C. for 5 hours. After the reaction was completed, the reaction mixture was filtered and concentrated. The residue was purified by column chromatography (EtOAc to EtOAc/MeOH 10/1), which produced the compound 25a (854 mg, 95%).

$^1$H-NMR (400 MHz, CDCl$_3$) δ 4.17 (s, 2H), 3.76-3.64 (m, 21H), 3.39 (t, J=5.2 Hz, 2H).

Preparation of Compound 25b

To a stirred solution of compound 25a (854 mg, 2.54 mmol) in MeCOH (25 mL) at 0° C., 2 M aq. NaOH (6.3 mL, 12.64 mmol) was added. The reaction mixture was stirred at room temperature for 3 hours. The solution was then concentrated under reduced pressure. The resulting suspension was acidified with aqueous 2 N HCl while cooling at 0° C. The residue was extracted by CHCl$_3$ (8×500 mL). The organic layers were combined, dried over Na$_2$SO$_4$ and concentrated to produce the compound 25b (783 mg, 96%). $^1$H-NMR (400 MHz, CDCl$_3$) δ 4.16 (s, 2H), 3.76-3.65 (m, 18H), 3.40 (t, J=5.2 Hz, 2H).

Preparation of Compound 25c

DIPEA (0.30 mL, 1.70 mmol) and HBTU (483 mg, 1.27 mmol) were added to a stirred mixture of compound 25b (337 mg, 1.05 mmol) and compound 24g (198 mg, 0.42 mmol) in DMF (3 mL). After stirring at room temperature for 14 hours under N$_2$, the reaction mixture was concentrated and purified by column chromatography (EtOAc to EtOAc/MeOH 10/1), which produced the compound 25c (358 mg, 84%). $^1$H-NMR (400 MHz, DMSO-d$_6$) δ 9.98 (s, 1H), 8.09 (t, J=5.2 Hz, 1H), 7.63 (t, J=5.2 Hz, 1H), 7.55 (d, J=8.4 Hz, 1H), 4.31-4.25 (m, 1H), 3.90 (s, 2H), 3.84 (s, 2H), 3.80 (m, 2H), 3.62-3.46 (m, 34H), 3.42-3.36 (m, 6H), 3.25-3.17 (m, 2H), 3.08-3.03 (m, 2H), 1.61-1.51 (m, 2H), 1.39 (s, 9H), 1.26-1.10 (m, 7H). EI-MS m/z: [M+H]$^+$ 999.1.

Preparation of Compound 25d

To a solution of compound 25c (358 mg, 0.35 mmol) in MeOH (7 mL) was added Pd/C (10 wt. %, 38 mg) and HCl (4 N in 1,4-dioxane, 0.18 mL, 0.72 mmol). After stirring at room temperature for 5 hours under hydrogen, the reaction mixture was filtered through a celite pad and washed with MeOH (400 mL). The filtrate was concentrated to produce the compound 25d (314 mg, 93%) as colorless oil, which was used without further purification. $^1$H-NMR (400 MHz, DMSO-$d_6$) δ 9.98 (s, 1H), 8.10 (m, 1H), 7.68 (m, 1H), 7.57 (m, 1H), 4.31-4.25 (m, 1H), 3.90 (s, 2H), 3.84 (s, 2H), 3.80 (m, 2H), 3.62-3.46 (m, 30H), 3.42-3.36 (m, 10H), 3.45-3.16 (m, 4H), 3.08-3.03 (m, 3H), 2.72-2.66 (m, 3H), 1.61-1.51 (m, 2H), 1.39 (s, 9H), 1.26-1.10 (m, 6H). EI-MS m/z: [M+H]$^+$ 947.1.
Preparation of Compound 25e
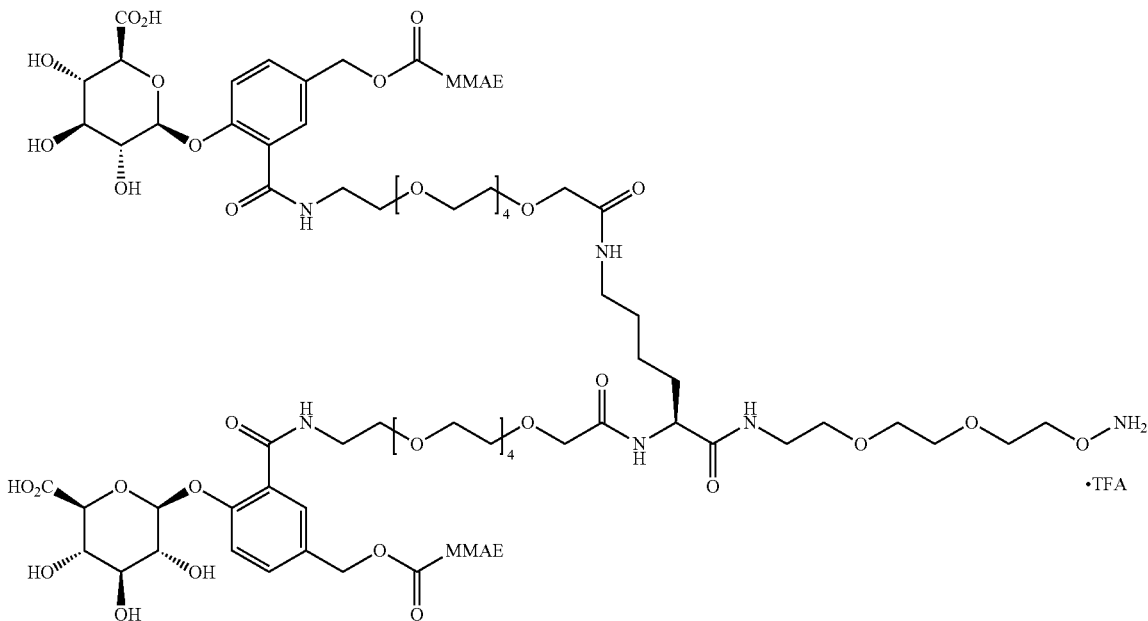
Compound 25e was prepared from compound 1i and compound 25d by a similar method of preparing compound 241 in Example 34. EI-MS m/z: ½[M+H]$^+$ 1493.7.
Example 36. Preparation of Compound 25f
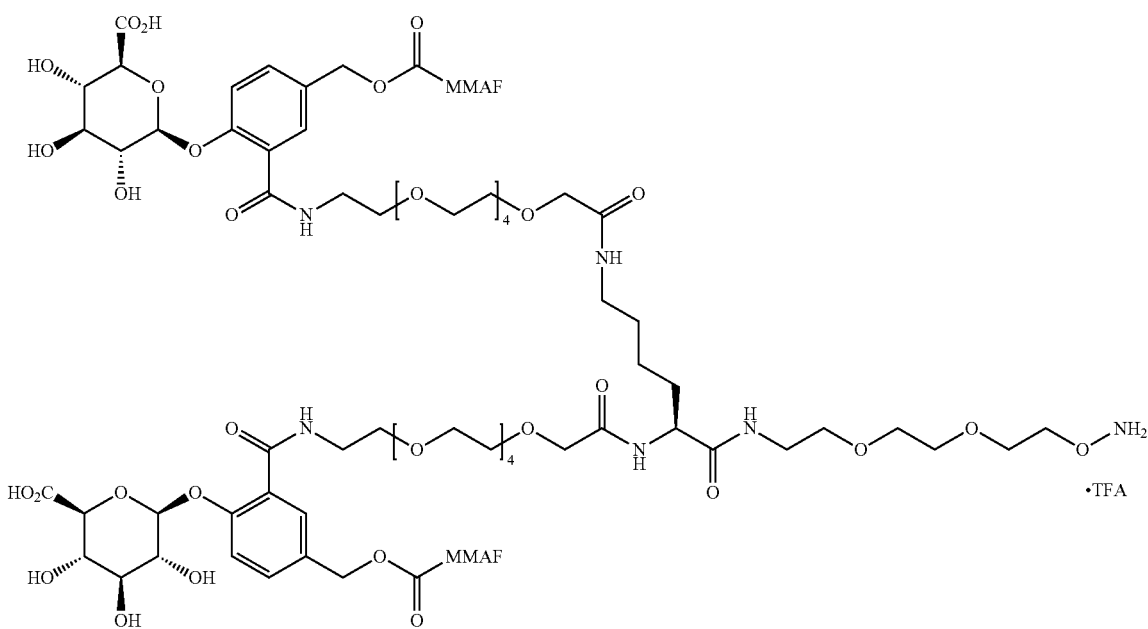

Compound 25f was prepared from compound 1j and compound 25d by a similar method of preparing compound 241 in Example 34. EI-MS m/z: ½[M+H]⁺ 1508.2.

Example 37. Preparation of Compound 26e

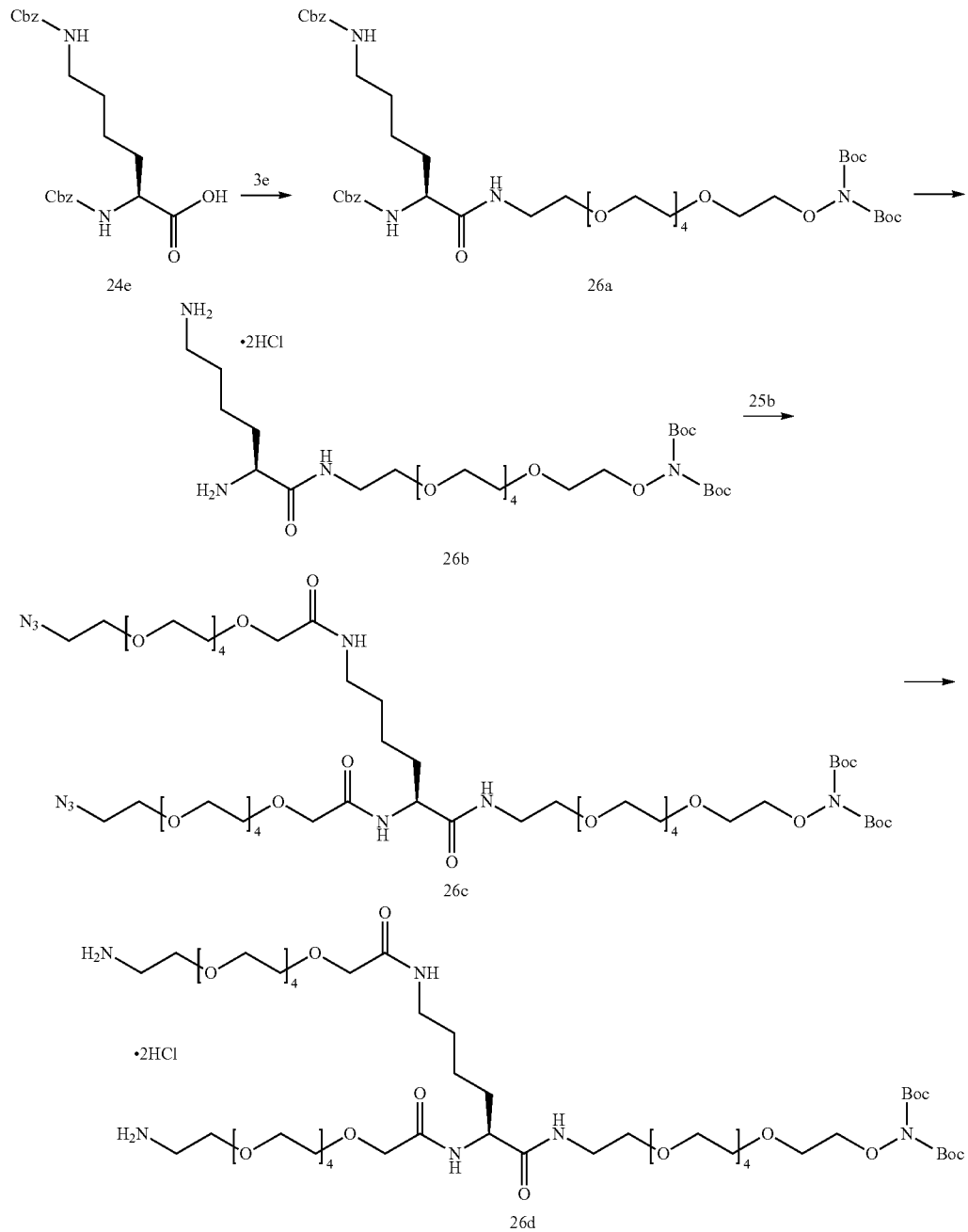

Preparation of Compound 26a

DIPEA (0.65 mL, 0.004 mmol), HOBt (218 mg, 1.61 mmol) and EDC.HCl (364 mg, 1.9 mmol) were added to a stirred mixture of compound 24e (1.0 g, 2.43 mmol) and compound 3e (810 mg, 1.52 mmol) in DMF (10 mL). After stirring at room temperature for 14 hours under N₂, the reaction mixture was poured into H₂O (50 mL) and extracted with EtOAc (3×50 mL). The combined organic layers were washed with 1 N aq. HCl (30 mL), saturated aq. NaHCO₃(30 mL), and brine (30 mL), and dried over anhydrous Na₂SO₄. After filtration and concentration, the residue was purified by column chromatography, which produced the compound 26a (988 mg, 73%).

¹H-NMR (400 MHz, CDCl₃) δ 7.33-7.26 (m, 8H), 6.85 (s, 1H), 5.63 (s, 1H), 5.08-5.02 (s, 4H), 4.16-4.11 (m, 1H), 4.09-4.05 (m, 2H), 3.72-3.70 (m, 2H), 3.62-3.59 (m, 14H), 3.53 (s, 2H), 3.44-3.43 (m, 2H), 3.18-3.16 (m, 2H), 1.82 (m, 1H), 1.72 (s, 7H), 1.66 (m, 1H), 1.52 (s, 18H), 1.38-1.36 (m, 2H), 1.24-1.27 (s, 1H). EI-MS m/z: [M+H-2Boc]⁺693.1.

Preparation of Compound 26b

To a stirred mixture of compound 26a (988 mg, 1.1 mmol) and Pd/C (10 wt. %, 196 mg) in MeOH (6 mL) at 0° C. was added HCl (4 N in 1,4-dioxane, 0.55 mL, 2.2 mmol). After stirring at room temperature for 1.5 hours under hydrogen, the reaction mixture was filtered through a celite pad and washed with MeOH (40 mL). The filtrate was concentrated to produce the compound 26b (767 mg, 99%) as a yellow form, which was used without further purification. EI-MS m/z: [M+H]$^+$ 625.0, [M+H-Boc]$^+$525.0, [M+H-2Boc]$^+$ 424.9.

Preparation of Compound 26c

DIPEA (0.2 mL, 1.14 mmol), HOBt (89 mg, 0.66 mmol) and EDC-HCl (142 mg, 0.74 mmol) were added to a stirred mixture of compound 26b (200 mg, 0.29 mmol) and compound 25b (202 mg, 0.63 mmol) in DMF (5 mL). After stirring at room temperature for 14 hours under $N_2$, the reaction mixture was poured into $H_2O$ (10 mL) and extracted with DCM (3×10 mL). The combined organic layers were dried over anhydrous $Na_2SO_4$. After filtration and concentration, the residue was purified by column chromatography, which produced the compound 26c (270 mg, 77%). $^1$H-NMR (400 MHz, CDCl$_3$) δ 8.07 (t, 1H), 7.62 (t, 1H), 7.54-7.52 (m, 1H), 5.73 (s, 2H), 4.27-4.25 (q, 1H), 3.96 (t, 2H), 3.88 (s, 2H), 3.82 (s, 2H), 3.58-3.48 (m, 52H), 3.19-3.18 (m, 3H), 3.04-3.03 (m, 3H), 1.44 (s, 18H), 1.39-1.37 (m, 3H), 1.21-1.19 (m, 3H). EI-MS m/z: [M+H-2Boc]$^+$ 1031.6.

Preparation of Compound 26d

To a stirred mixture of compound 26c (160 mg, 0.13 mmol) and Pd/C (10 wt. %, 28 mg) in MeOH (20 mL) at 0° C. was added HCl (4 N in 1,4-dioxane, 0.07 mL, 0.28 mmol). After stirring at room temperature for 30 minutes under hydrogen, the reaction mixture was filtered through a celite pad and washed with MeOH (30 mL). The filtrate was concentrated to produce the compound 26d (140 mg, 91%) as colorless oil, which was used without further purification. EI-MS m/z: [M+H]$^+$ 1179.7.

Preparation of Compound 26e

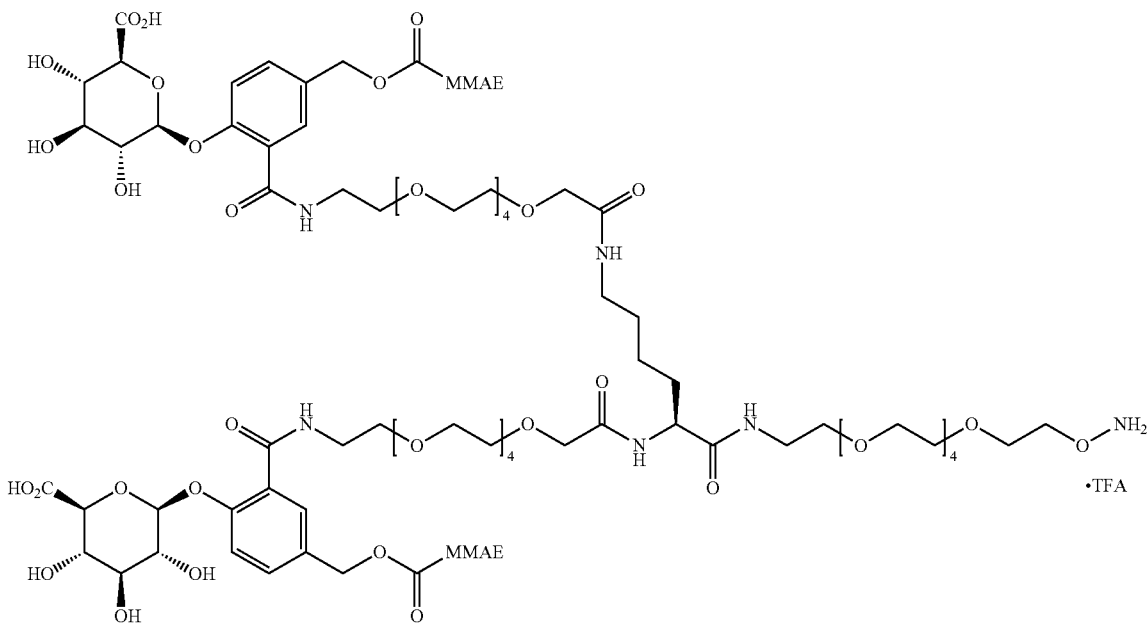

Compound 26e was prepared from compound 1i and compound 26d by a similar method of preparing compound 241 in Example 34. EI-MS m/z: ½[M+H]$^+$ 1560.6, ⅓[M+H]$^+$ 1040.7.

Example 38. Preparation of Compound 27e

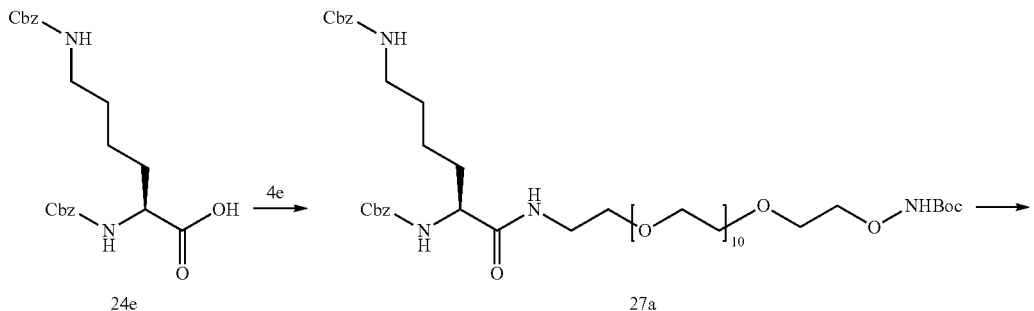

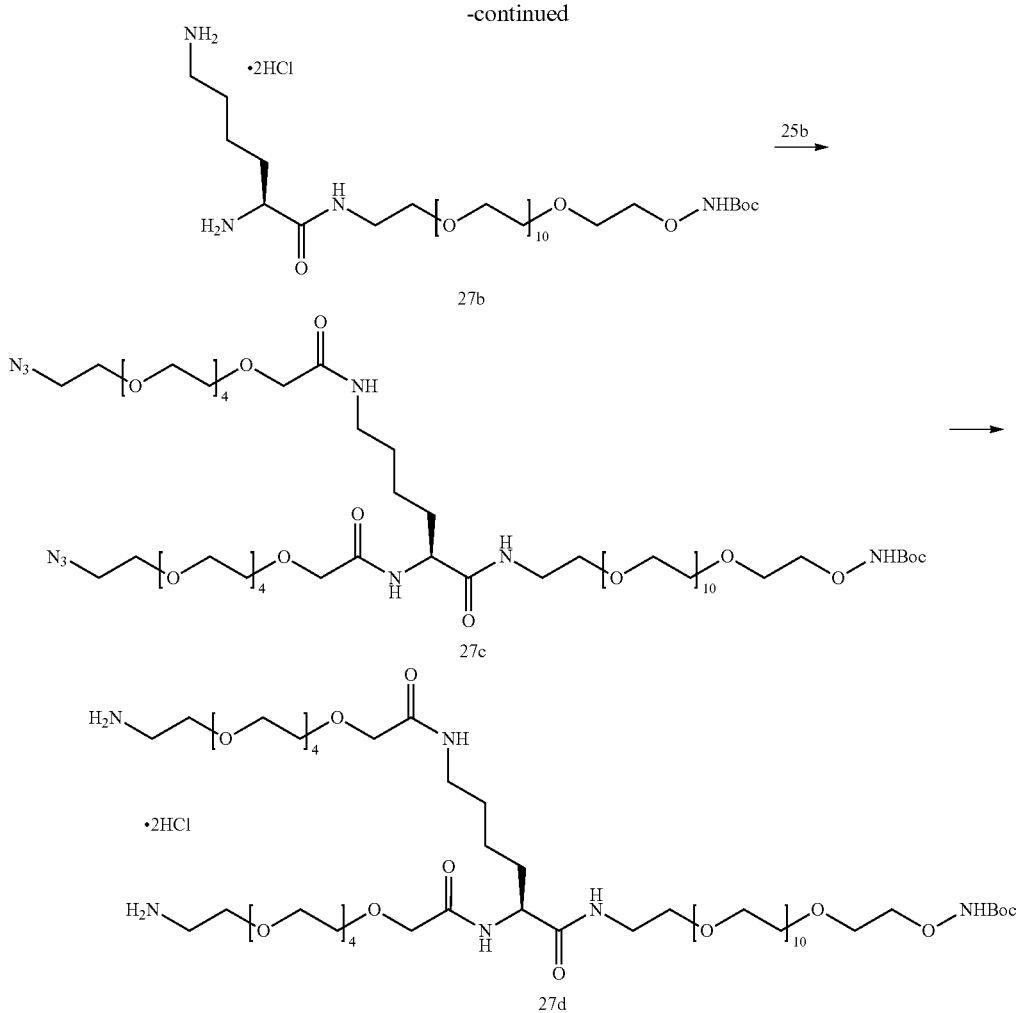

Preparation of Compound 27a

DIPEA (0.19 ml, 1.1 mmol), HOBt (64 mg, 0.47 mmol), and EDC-HCl (91 mg, 0.47 mmol) were added to a stirred mixture of compound 24e (228 mg, 0.55 mmol) and compound 4e (256 mg, 0.36 mmol) in DMF (4 mL). After stirring at room temperature for 4 hours under $N_2$, the reaction mixture was poured into $H_2O$ (10 mL) and extracted with EtOAc (3×15 mL). The combined organic layers were washed with 1 N aq. HCl (20 mL), saturated aq. $NaHCO_3$(10 mL), and brine (10 mL), and dried over anhydrous $Na_2SO_4$. After filtration and concentration, the residue was purified by column chromatography, which produced the compound 27a (327 mg, 85%).

$^1$H-NMR (400 MHz, $CDCl_3$) δ 7.73 (s, 1H), 7.33-7.26 (m, 11H), 6.91 (s, 1H), 5.67 (br, 1H) 5.08-5.07 (m, 5H), 4.15 (m, 1H), 4.02 (t, 2H), 3.72-3.44 (m, 46H), 3.16 (d, 2H), 1.82 (m, 1H), 1.63 (m, 1H), 1.55-1.36 (m, 13H).

Preparation of Compound 27b

To a stirred mixture of compound 27a (327 mg, 0.309 mmol) and Pd/C (10 wt. %, 65 mg) in MeOH (6 mL) at 0° C. was added HCl (4 N in 1,4-dioxane, 0.15 mL, 0.618 mmol). After stirring at room temperature for 1.5 hours under hydrogen, the reaction mixture was filtered through a celite pad and washed with MeOH (40 mL). The filtrate was concentrated to produce the compound 27b (244 mg, 91%) as colorless oil, which was used without further purification. EI-MS m/z: $[M+H]^+$ 789.2.

Preparation of Compound 27c

DIPEA (0.19 ml, 1.13 mmol), HOBt (95 mg, 0.707 mmol), and EDC-HCl (135 mg, 0.707 mmol) were added to a stirred mixture of compound 25b (227 mg, 0.707 mmol) and compound 27b (244 mg, 0.283 mmol) in DMF (6 mL). After stirring at room temperature for 3 hours under $N_2$, the reaction mixture was poured into $H_2O$ (5 mL) and extracted with DCM (3×10 mL). The combined organic layers were dried over anhydrous $Na_2SO_4$. After filtration and concentration, the residue was purified by column chromatography, which produced the compound 27c (339 mg, 85%). $^1$H NMR (400 MHz, $CDCl_3$) δ 7.69 (s, 1H), 7.29 (d, 1H), 6.99 (s, 1H), 6.82 (s, 1H), 4.39 (q, 1H), 3.99-3.94 (m, 6H), 3.69-3.58 (m, 80H), 3.51 (t, 2H), 3.44-3.34 (m, 8H), 3.25 (m, 2H), 1.68-1.64 (m, 1H). 1.53-1.48 (m, 2H), 1.44 (s, 9H), 1.33 (m, 2H). EI-MS m/z: $[M+H]^+$ 1395.6.

Preparation of Compound 27d

To a stirred mixture of compound 27c (339 mg, 0.242 mmol), and Pd/C (10 wt. %, 67 mg) in MeOH (6 mL) at 0° C. was added HCl (4 N in 1,4-dioxane, 0.12 mL, 0.484 mmol). After stirring at room temperature for 30 minutes under hydrogen, the reaction mixture was filtered through a celite pad and washed with MeOH (30 mL). The filtrate was concentrated to produce the compound 27d (300 mg, 87%) as colorless oil, which was used without further purification. EI-MS m/z: $[M+H]^+$ 1343.5.

Preparation of Compound 27e
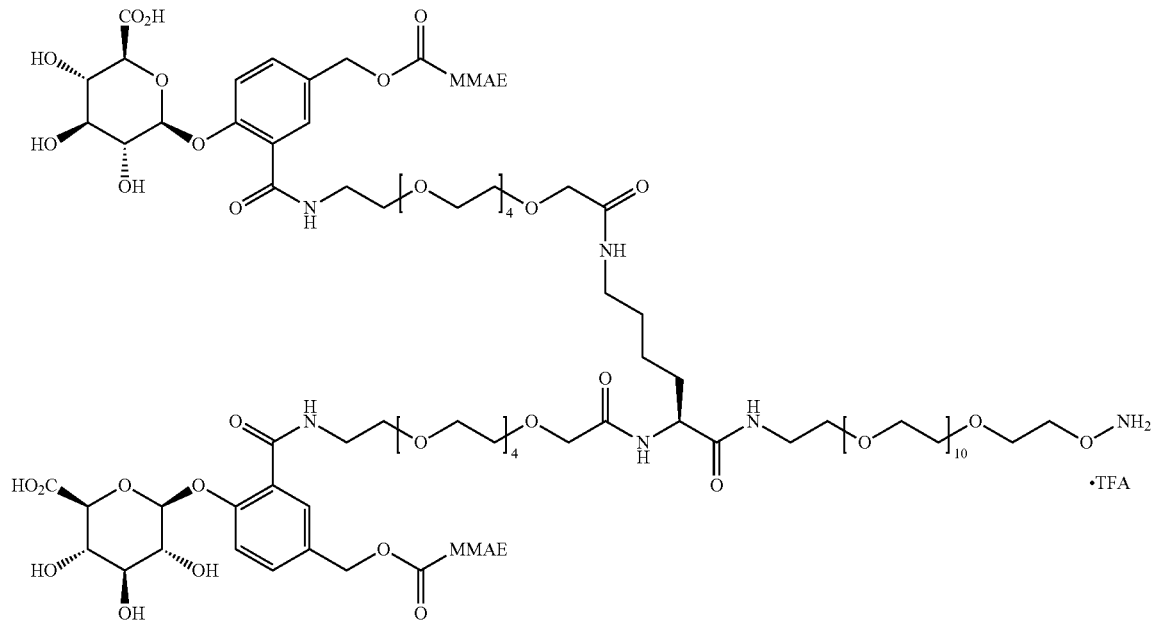
Compound 27e was prepared from compound 1i and compound 27d by a similar method of preparing compound 241 in Example 34. EI-MS m/z: ½[M+H]$^+$ 1692.5.
Example 39. Preparation of Compound 28d
Preparation of Compound 28c
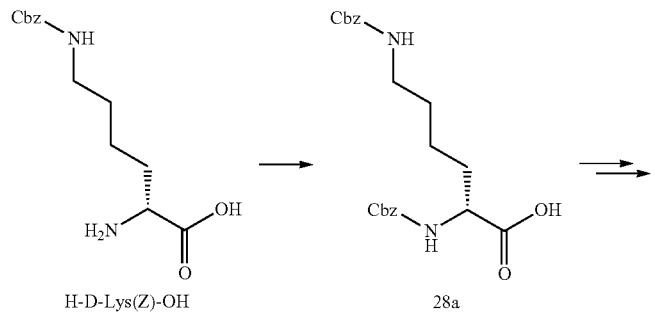
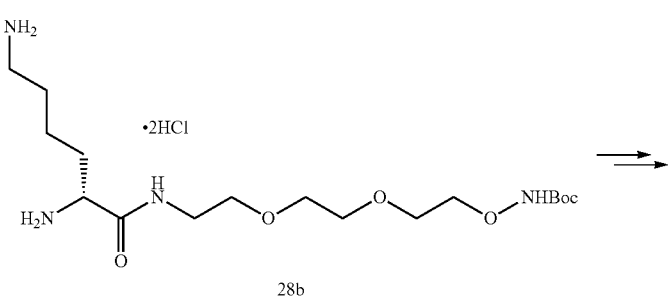

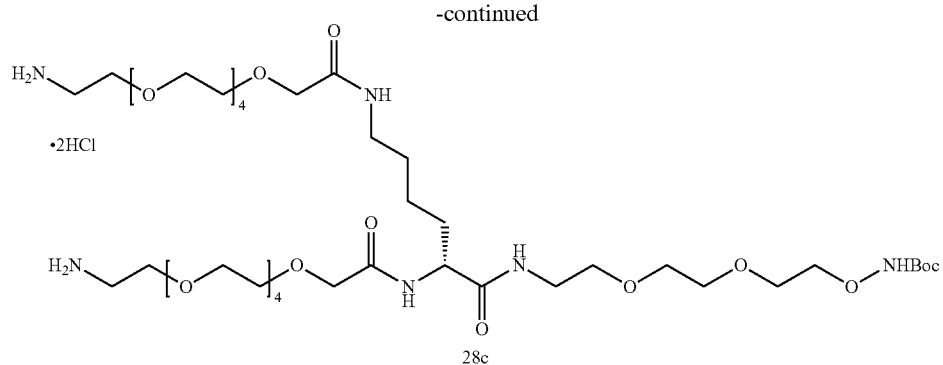
Compound 28c was prepared from H-D-Lys(Z)—OH by a similar method of preparing compound 25d in Example 35.
Preparation of Compound 28d
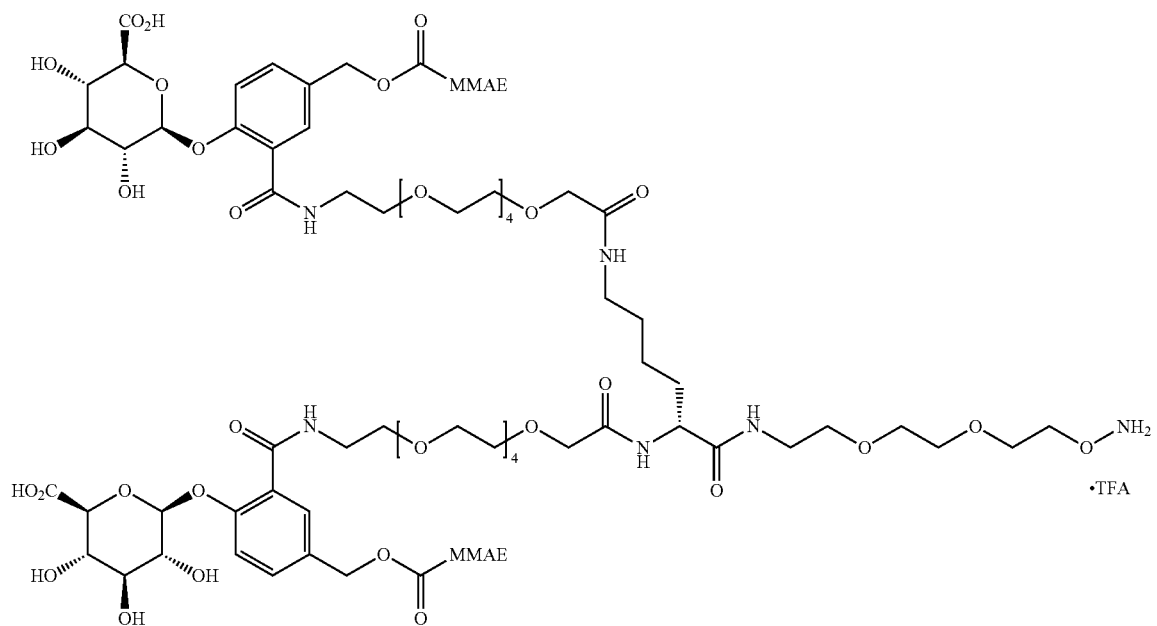
Compound 28d was prepared from compound 1i and compound 28c by a similar method of preparing compound 25e in Example 35. EI-MS m/z: ½[M+H]$^+$ 1494.9.

Example 40. Preparation of Compound 28e

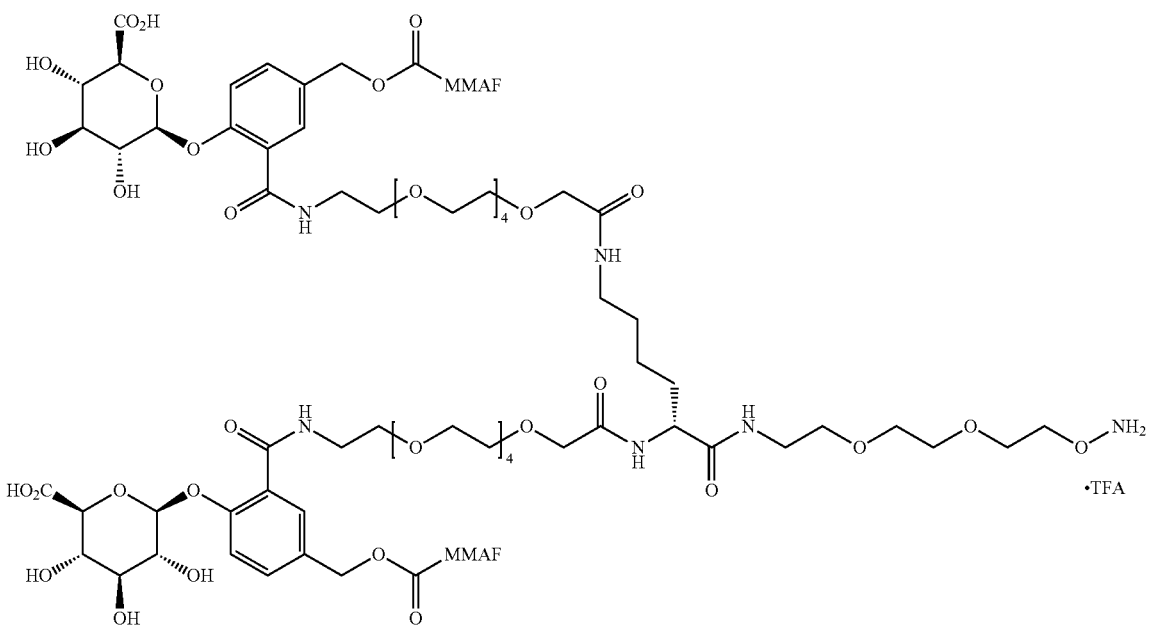

Compound 28e was prepared from compound 1j and compound 28c by a similar method of preparing compound 25e in Example 35. EI-MS m/z: ½[M+H]$^+$ 1509.2.

Example 41. Preparation of Compound 29j

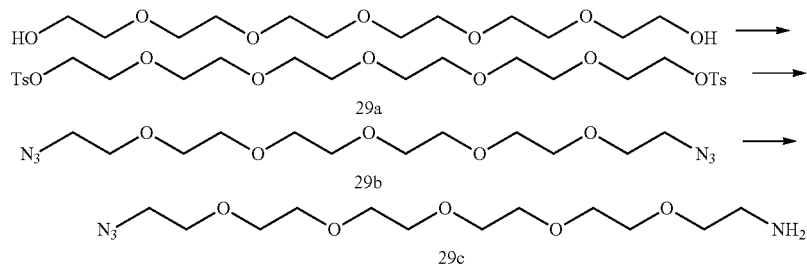

Preparation of Compound 29a

To a solution of hexaethylene glycol (25.0 g, 88.5 mmol) in DCM (100 mL) were added triethylamine (61.7 mL, 443 mmol) and p-toluenesulfonyl chloride (50.6 g, 266 mmol) at 0° C. under $N_2$. After 5 hours at 0° C., the reaction mixture was poured into 1 N aq. HCl (200 mL) and extracted with DCM (2×200 mL). The combined organic layers were washed with saturated aq. NaHCO$_3$ (100 mL) and brine (100 mL), and dried over anhydrous Na$_2$SO$_4$. After filtration and concentration, the residue was purified by column chromatography, which produced the compound 29a (45.0 g, 87%) as brown oil. $^1$H-NMR (400 MHz, CDCl$_3$) δ 7.79 (d, J=7.6 Hz, 4H), 7.34 (d, J=7.6 Hz, 4H), 4.16-4.14 (m, 4H), 3.69-3.67 (m, 4H), 3.64-3.56 (m, 16H), 2.44 (s, 6H).

Preparation of Compound 29b

To a solution of compound 29a (17.6 g, 29.7 mmol) in DMF (100 mL) were added NaN$_3$ (9.65 g, 148 mmol) and tetrabutylammonium iodide (550 mg, 1.49 mmol). The reaction mixture was heated up to 80° C. After stirring for 16 hours at 80° C., the reaction mixture was allowed to cool to room temperature. The reaction mixture was filtered through a celite pad and washed with DCM (100 mL). After concentration, the residue was purified by column chromatography, which produced the compound 29b (9.4 g, 94%). $^1$H-NMR (400 MHz, CDCl$_3$) δ 3.68 (m, 20H), 3.39 (t, 4H).

Preparation of Compound 29c

To a solution of 29b (8.4 g, 24.9 mmol) in DCM (24 mL) and toluene (24 mL) were added 1 N aq. HCl (40.3 mL) and triphenylphosphine (6.9 g, 23.6 mmol). The reaction mixture was stirred at room temperature under $N_2$ for 16 hours. After removal of the solvent under reduced pressure, $H_2O$ (20 mL) was added into the reaction mixture, and the aqueous layer was extracted with EtOAc (20 mL). Then the pH of the aqueous phase was adjusted to 13. The resulting aqueous phase was extracted with DCM (3×30 mL). The combined organic layers were dried over anhydrous Na$_2$SO$_4$, filtered, and concentrated under reduced pressure to produce the compound 29c (6.6 g, 84%) as colorless oil. $^1$H-NMR (400 MHz, CDCl$_3$) δ 3.67 (m, 20H), 3.52 (t, 2H), 3.39 (t, 2H), 2.86 (t, 2H). EI-MS m/z: [M+H]$^+$ 306.9.

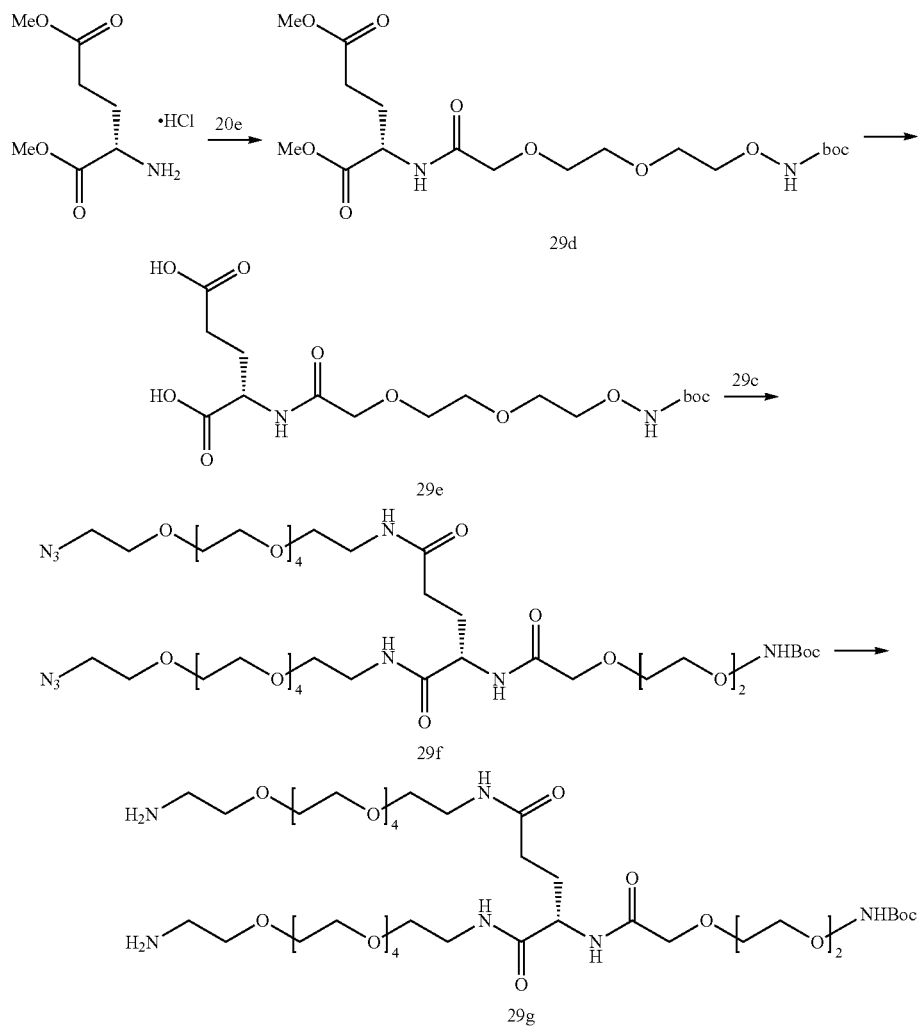

Preparation of Compound 29d

DIPEA (2.67 mL, 15.4 mmol) and HBTU (3.49 g, 9.21 mmol) were added to a stirred mixture of L-glutamic acid dimethyl ester hydrochloride (1.3 g, 6.14 mmol) and compound 20e (1.72 g, 6.14 mmol) in DMF (15 mL) at 0° C. The reaction mixture was stirred at 0° C. for 30 minutes and allowed to warm to room temperature over 16 hours under $N_2$. The reaction mixture was poured into water (50 mL) and extracted with DCM (3×50 mL). The combined organic layers were washed with 0.5 N HCl (50 mL), saturated aq. $NaHCO_3$ (50 mL) and brine (50 mL) sequentially, and dried over anhydrous $Na_2SO_4$. After filtration and concentration under reduced pressure, the resulting crude product was purified by column chromatography to produce the compound 29d (2.18 g, 81%). $^1$H-NMR (400 MHz, DMSO-$d_6$) δ 10.00 (s, 1H), 8.04 (d, 1H), 4.34 (m, 1H), 3.93 (s, 1H), 3.77 (s, 1H), 3.63 (s, 3H), 3.58 (s, 9H), 3.38-3.34 (t, 2H), 2.14 (m, H), 1.90 (m, 1H), 1.39 (s, 9H). EI-MS m/z: [M+H]$^+$ 437.35.

Preparation of Compound 29e

To a solution of compound 29d (2.18 g, 4.99 mmol) in THF:MeOH:$H_2O$ (12 mL:4 mL:4 mL) was added NaOH (499 mg, 12.5 mmol) at room temperature under $N_2$. After 3 hours, the pH of the reaction mixture was adjusted to 4 and concentrated. Then the residue was extracted with DCM/MeOH (80 mL/20 mL). Concentration provided compound 29e (1.0 g, 49%) as yellow oil, which was used without further purification. EI-MS m/z: [M+H-Boc]+309.20.

Preparation of Compound 29f

DIPEA (1.7 mL, 9.79 mmol) and HBTU (2.79 g, 7.35 mmol) were added to a stirred mixture of compound 29e (1.0 g, 2.45 mmol) and compound 29c (2.25 g, 7.35 mmol) in DMF (10 mL) at 0° C. The reaction mixture was stirred at 0° C. for 30 minutes and allowed to warm to room temperature over 16 hours under $N_2$. The reaction mixture was poured into water (50 mL) and extracted with DCM (3×50 mL). The combined organic layers were washed with 0.5 N aq. HCl (50 mL), saturated aq. $NaHCO_3$(50 mL) and brine (50 mL) sequentially, and dried over anhydrous $Na_2SO_4$. After filtration and concentration under reduced pressure, the resulting crude product was purified by column chromatography to produce the compound 29f (611 mg, 25%). $^1$H-NMR (400 MHz, DMSO-$d_6$) δ 9.97 (s, 1H), 8.08 (t, 1H), 7.85 (t, 1H), 7.64 (d, 1H), 4.27 (m, 1H), 3.83 (s, 2H), 3.82-3.61 (m, 2H), 3.61-3.50 (m, 42H), 3.42-3.37 (m, 8H), 3.28-3.15 (m, 4H), 2.90 (s, H), 2.08-2.04 (m, 2H), 1.88 (m, 1H), 1.75 (m, 1H), 1.39 (s, 9H). EI-MS m/z: [M+H]$^+$ 986.73.

Preparation of Compound 29g

To a stirred mixture of compound 29f (611 mg, 0.62 mmol) in MeOH (50 mL) was added Pd/C (10 wt. %, 132 mg 0.62 mmol). After stirring at room temperature for 2 hours under hydrogen, the reaction mixture was filtered through a celite pad and washed with MeOH (40 mL). The filtrate was concentrated to produce the compound 29g as colorless oil (518 mg, crude), which was used without further purification. EI-MS m/z: [M+H]$^+$ 933.85.
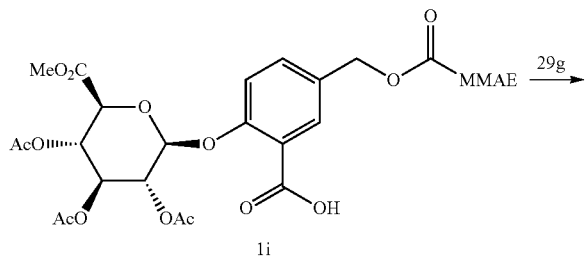
1i
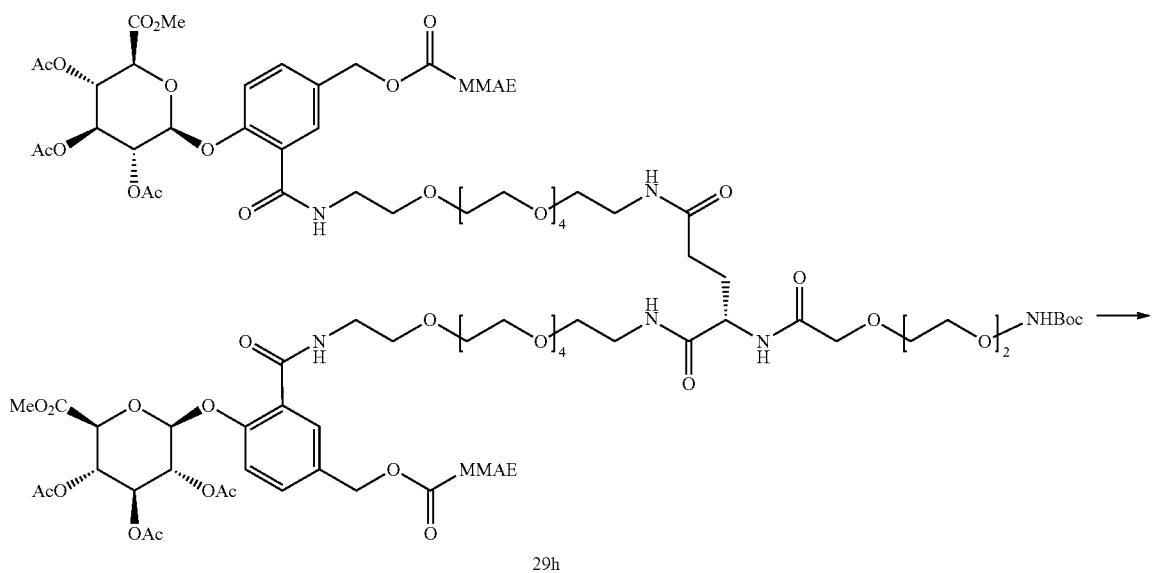
29h
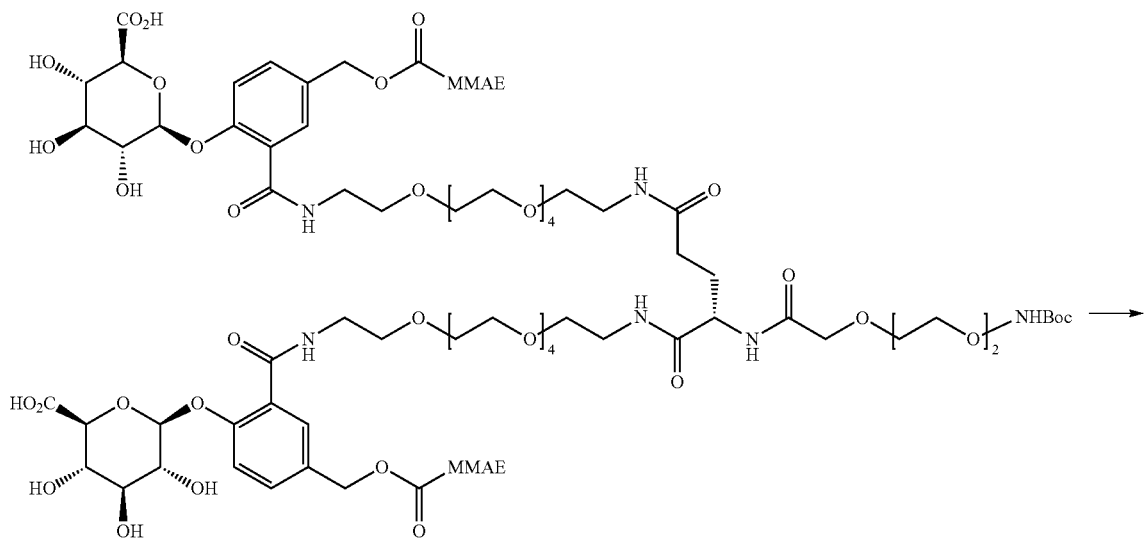
29i

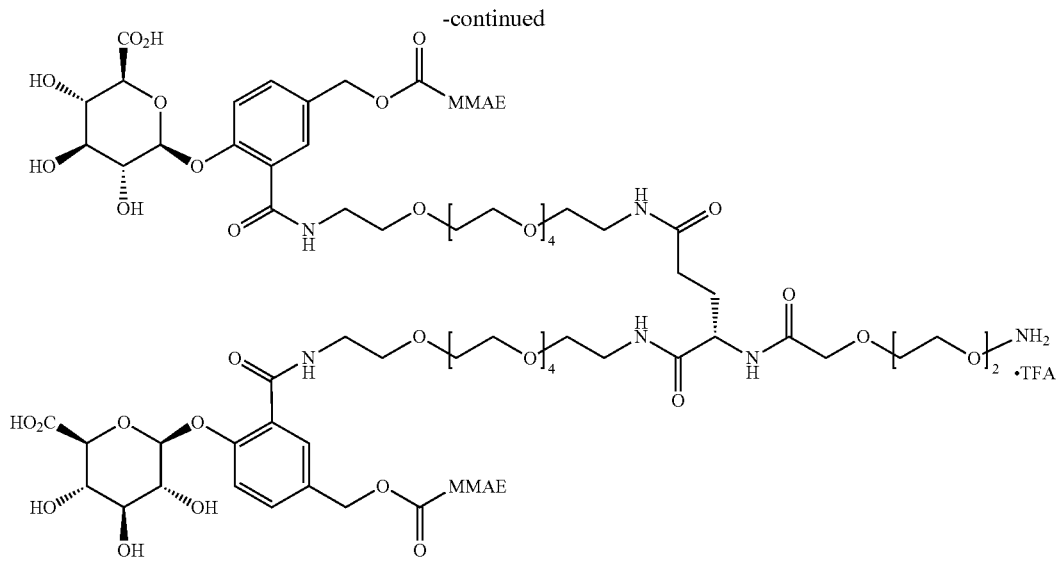

29j

Preparation of Compound 29h

DIPEA (0.026 mL, 0.150 mmol) and HBTU (40 mg, 0.105 mmol) were added to a stirred mixture of compound 29g (35 mg, 0.037 mmol) and compound 1i (106 mg, 0.086 mmol) in DMF (3 mL). After stirring at room temperature for 16 hours under $N_2$, the reaction mixture was diluted water (20 mL) and extracted with EtOAc (3×10 mL). The combined organic layers were washed with 0.5 N HCl (20 mL), saturated aq. $NaHCO_3$ (20 mL) and brine (20 mL) sequentially, and dried over anhydrous $Na_2SO_4$. After filtration and concentration under reduced pressure, the resulting crude product was purified by column chromatography to produce the compound 29h (81.4 mg, 65%). EI-MS m/z: ½[M+H]⁺ 1677.94, ⅓[M+H]⁺ 1119.03.

Preparation of Compound 29i

To a solution of compound 29h (81 mg, 0.024 mmol) in MeOH (1 mL) was added LiOH monohydrate (8.1 mg, 0.19 mmol) in $H_2O$ (1 mL) at −10° C. After stirring for 2 hours at −10° C., the reaction mixture was neutralized using acetic acid and concentrated under reduced pressure. Then the reaction mixture was dissolved in $H_2O$/DMSO (1.5 mL/1.5 mL) and purified by HPLC, which produced the compound 29i (53 mg, 72%) as white solid. EI-MS m/z: ½[M+H]⁺ 1537.86, ⅓[M+H]⁺ 1025.66.

Preparation of Compound 29i

TFA (0.3 mL) was added to a stirred solution of compound 29i (53 mg, 0.017 mmol) in DCM (1.0 mL) at 0° C. After stirring for 1 hour, the solvent and excess TFA were removed by $N_2$ flow. Then the residue was dissolved in $H_2O$/MeCN (1 mL/1 mL) and purified by HPLC. Pure fractions with the same retention time were combined and lyophilized to produce the compound 29j (23.1 mg, 43%) as white solid. EI-MS m/z: ½[M+H]⁺ 1487.99, ⅓[M+H]⁺ 992.40.

Example 42. Preparation of Compound 29k

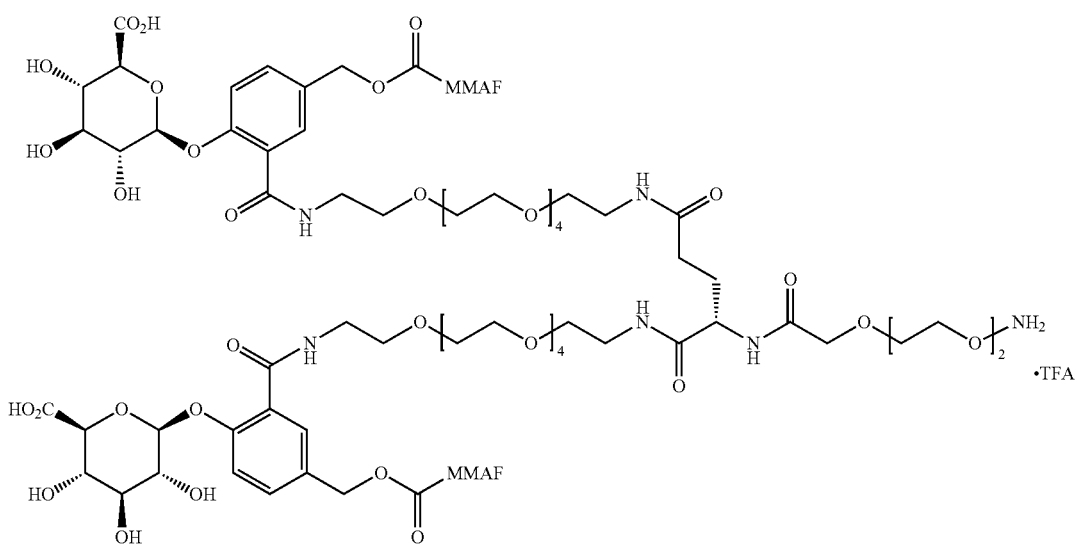

29k

Compound 29k was prepared from compound 1j and compound 29g by a similar method of preparing compound 29j in Example 41. EI-MS m/z: ½[M+H]⁺ 1501.93, ⅓[M+H]⁺ 1001.69.

Example 43. Preparation of Compound 30b

Preparation of Compound 30a

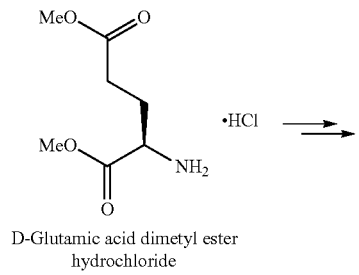

D-Glutamic acid dimetyl ester hydrochloride

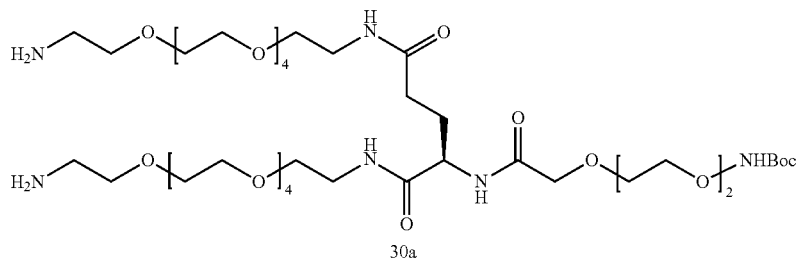

30a

Compound 30a was prepared from D-glutamic acid dimethyl ester hydrochloride by a similar method of preparing compound 29g in Example 41. EI-MS m/z: [M+H]⁺ 933.89.

Preparation of Compound 30b

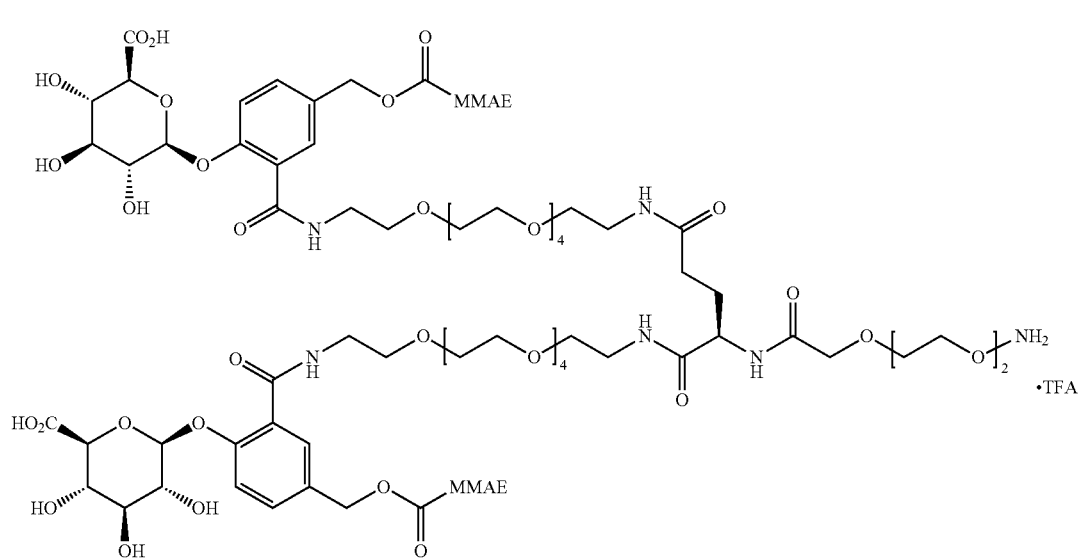

30b

Compound 30b was prepared from compound 1i and compound 30a by a similar method of preparing compound 29j in Example 41. EI-MS m/z: ½[M+H]⁺ 1488.07, ⅓[M+H]⁺ 992.40.

Example 44. Preparation of Compound 30c

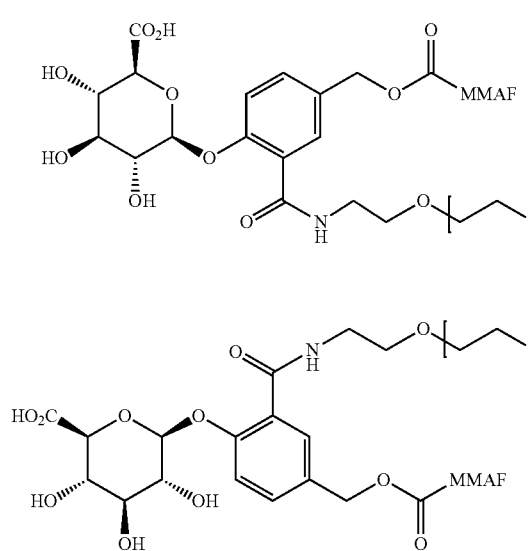

30c

Compound 30c was prepared from compound 1j and compound 30a by a similar method of preparing compound 29j in Example 41. EI-MS m/z: ½[M+H]$^+$ 1501.93, ⅓[M+H]$^+$ 1001.69.

Example 45. Preparation of Compound 31f

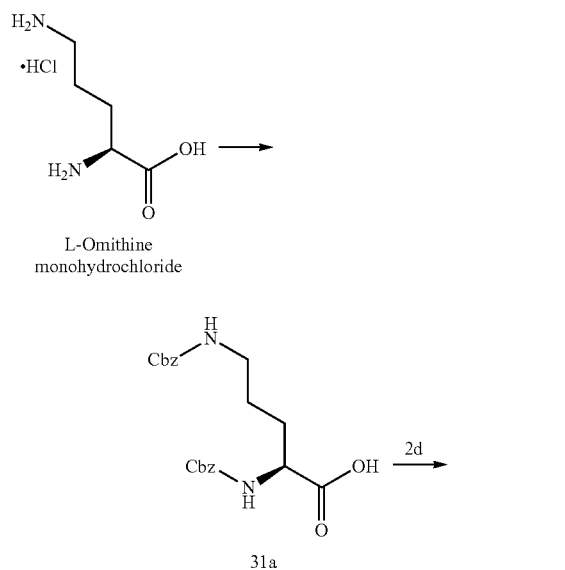

L-Ornithine monohydrochloride

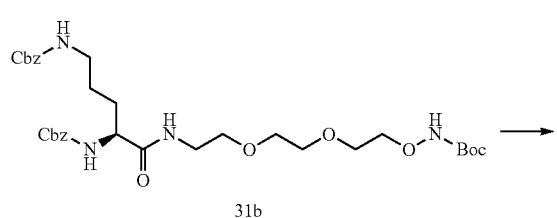

31a

31b

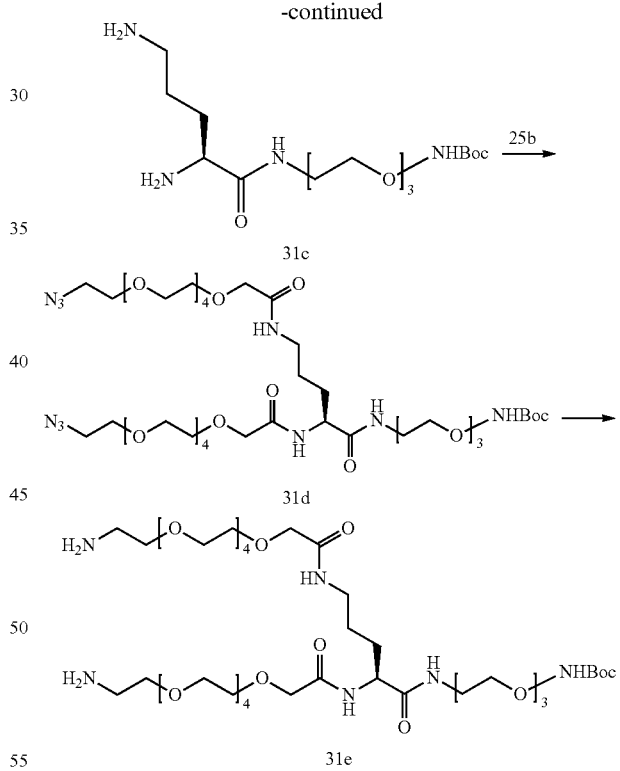

-continued

31c

31d

31e

Preparation of Compound 31a

A three-necked flask was loaded consecutively with H$_2$O (18 mL), 1,4-dioxane (30 mL) and L-ornithine monohydrochloride (3.0 g, 17.8 mmol). The mixture was stirred until complete dissolution. The pH was adjusted to about 10.5 by addition of 2 M aq. Na$_2$CO$_3$. Benzyl chlorofosmate (6.37 g, 37.4 mmol) was added while maintaining the pH at about 10-11 by adding at the same time 2 M aq. Na$_2$CO$_3$. After the end of the addition, the reaction mixture was stirred at 20° C. for 1 hour. Then EtOAc (50 mL) was added and pH of the resulting mixture was adjusted to 2-3 with c-HCl. The organic layer was separated and the aqueous layer was extracted with EtOAc (50 mL). The combined organic layers were washed with brine (50 mL), and dried over $Na_2SO_4$. Filtration and concentration under reduced pressure provided compound 31a (7.1 g). $^1$H-NMR (400 MHz, DMSO-$d_6$) δ 12.54 (s, 1H), 7.54 (s, 1H), 7.44-7.29 (m, 10H), 7.24-7.22 (m, 1H), 5.16-5.00 (d, 4H), 3.95-3.89 (m, 1H), 3.00-2.96 (m, 2H), 1.98-1.57 (m, 1H), 1.56-1.46 (m, 3H).

Preparation of Compound 31b

DIPEA (1.41 mL, 8.12 mmol) and HBTU (1.85 g, 4.87 mmol) were added to a stirred mixture of compound 31a (1.30 g, 3.25 mmol) and compound 2d (891 mg, 3.57 mmol) in DMF (10 mL) at 0° C. The reaction mixture was stirred at 0° C. for 30 minutes and allowed to warm to room temperature over 16 hours under $N_2$. The reaction mixture was poured into water (50 mL) aid extracted with DCM (3×50 mL). The combined organic layers were washed with 0.5 N aq. HCl (50 mL), saturated aq. $NaHCO_3$ (50 mL) and brine (50 mL) sequentially, and dried over anhydrous $Na_2SO_4$. After filtration and concentration under reduced pressure, the resulting crude product was purified by column chromatography to produce the compound 31b (1.2 g, 57%). EI-MS m/z: $[M+H]^+$ 647.54, $[M+H-Boc]^+$ 547.47

Preparation of Compound 31c

To a stirred mixture of compound 31b (1.2 g, 1.86 mmol) in MeOH (50 mL) was added Pd/C (10 wt. %, 59 mg 5.57 mmol). After stirring at room temperature for 2 hours under hydrogen, the reaction mixture was filtered through a celite pad and washed with MeOH (40 mL). The filtrate was concentrated to produce the compound 31c (717 mg), which was used without further purification. $^1$H-NMR (400 MHz, DMSO-$d_6$) δ 7.93 (s, 1H), 3.81 (t, 2H), 3.55 (t, 2H), 3.51 (s, 5H), 3.42-3.22 (m, 13H), 1.37 (s, 9H).

Preparation of Compound 31d

DIPEA (0.55 mL, 3.17 mmol) and HBTU (902 mg, 2.38 mmol) were added to a stirred mixture of compound 31c (300 mg, 0.79 mmol) and compound 25b (637 mg, 1.98 mmol) in DMF (5 mL) at 0° C. The reaction mixture was stirred at 0° C. for 30 minutes and allowed to warm to room temperature over 16 hours under $N_2$. The reaction mixture was poured into water (30 mL) and extracted with DCM (3×30 mL). The combined organic layers were washed with 0.5 N aq. HCl (30 mL), saturated aq. $NaHCO_3$ (30 mL) and brine (30 mL) sequentially, and dried over anhydrous $Na_2SO_4$. After filtration and concentration under reduced pressure, the resulting crude product was purified by column chromatography to produce the compound 31d (551 mg, 71%). EI-MS m/z: $[M+H]^+$ 985.87.

Preparation of Compound 31e

To a stirred mixture of compound 31d (491 mg, 0.50 mmol) in MeOH (30 mL) was added Pd/C (10 wt. %, 106 mg 1.00 mmol). After stirring at room temperature for 2 hours under hydrogen, the reaction mixture was filtered through a celite pad and washed with MeOH (40 mL). The filtrate was concentrated to produce the compound 31e (452 mg), which was used without further purification. EI-MS m/z: $[M+H]^+$ 933.94.

Preparation of Compound 31f

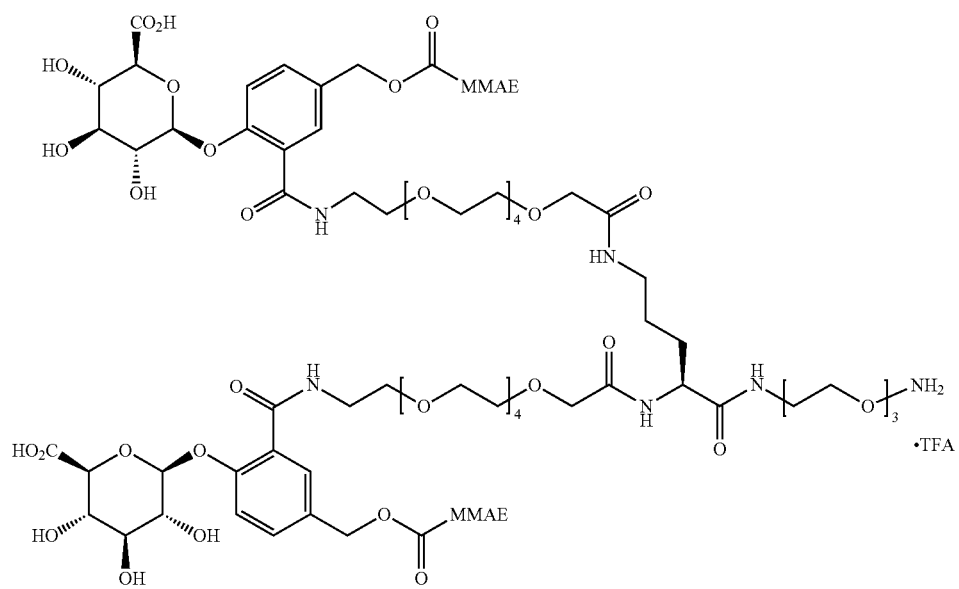

31f

Compound 31f was prepared from compound 1i and compound 31e by a similar method of preparing compound 25e in Example 35. EI-MS m/z: ½$[M+H]^+$ 1488.20, ⅓$[M+H]^+$ 992.54.

Example 46. Preparation of Compound 31g
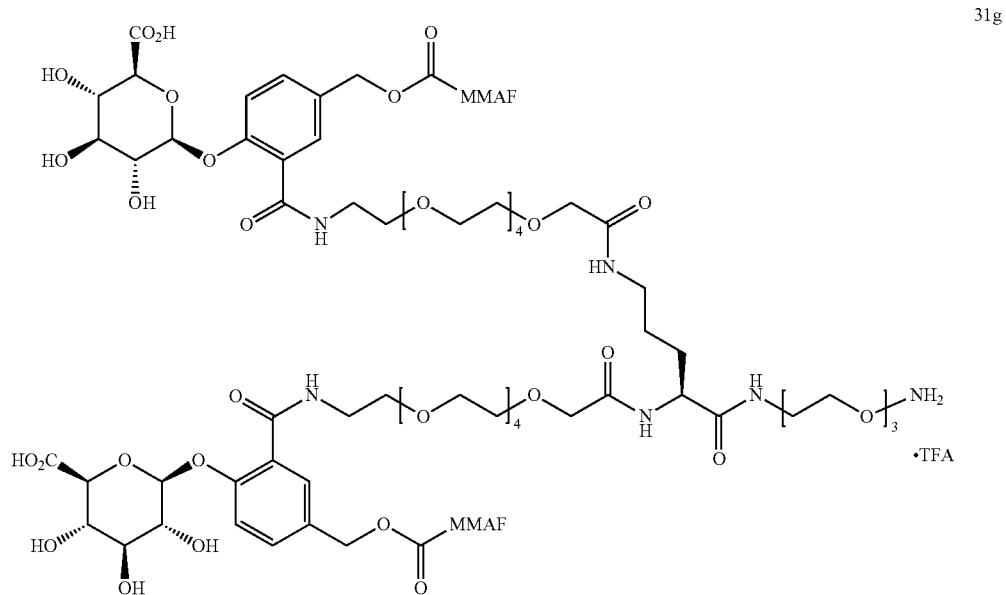
Compound 31g was prepared from compound 1j and compound 31e by a similar method of preparing compound 25e in Example 35. EI-MS m/z: ½[M+H]$^+$ 1502.23, ⅓ [M+H]$^+$ 1001.86.
Example 47. Preparation of Compound 32c
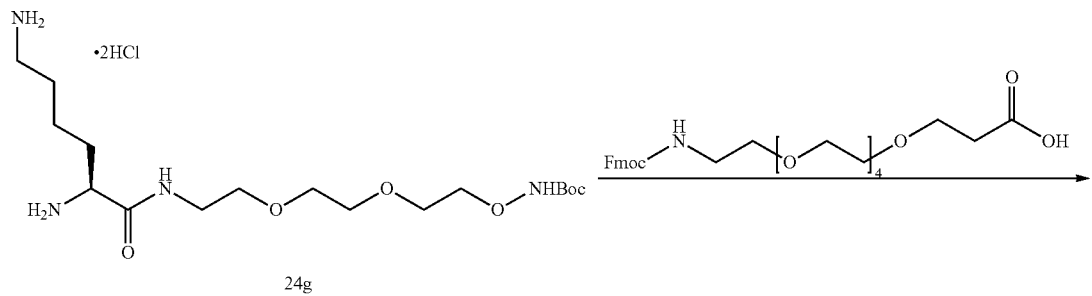
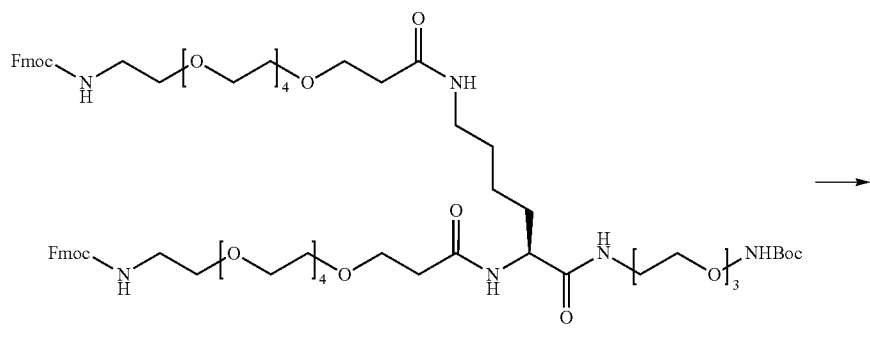

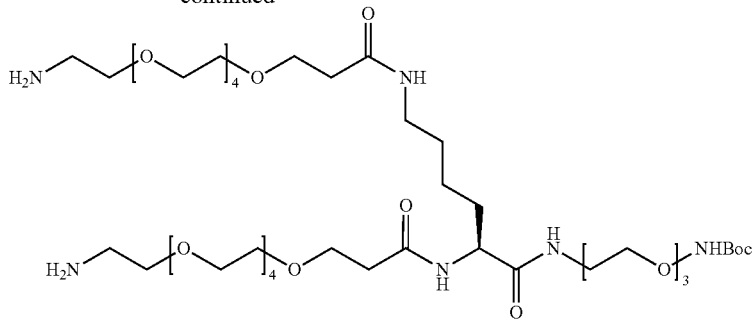

32b

Preparation of Compound 32a

DIPEA (0.6 mL, 7.07 mmol) and HBTU (972 mg, 5.30 mmol) were added to a stirring mixture of compound 24g (483 mg, 0.855 mmol) and Fmoc-NH-PEG5-CH$_2$CH$_2$COOH (1.0 g, 3.89 mmol) in DMF (10 mL). After stirring at room temperature for 14 hours under N$_2$, the reaction mixture was poured into H$_2$O (30 mL) and extracted with EtOAc (3×30 mL). The combined organic layers were washed with 1 N aq. HCl (10 mL), saturated aq. NaHCO$_3$ (10 mL) and brine (10 mL) sequentially, and dried over anhydrous Na$_2$SO$_4$. After filtration and concentration, the resulting residue was purified by column chromatography, which produced the compound 32a (1.16 g, 90%). $^1$H-NMR (400 MHz, CDCl$_3$) δ 7.77 (d, 4H), 7.60 (d, 4H), 7.39 (t, 4H), 7.31 (t, 4H), 4.39 (d, 4H), 4.33 (m, 1H), 4.22 (m, 2H), 4.09 (m, 2H), 3.71-3.39 (m, 52H), 3.19 (m, 2H), 2.51 (m, 4H), 1.50 (m, 1H), 1.46 (m, 1H), 1.43 (s, 9H), 1.25 (m, 2H). EI-MS m/z: [M+H]$^+$ 1520.0.

Preparation of Compound 32b

To a solution of compound 32a (500 mg, 0.328 mmol) in THF (8 mL) was added piperidine (2 mL) at room temperature. After stirring for 20 minutes, the reaction mixture was concentrated under reduced pressure. The resulting residue was purified by column chromatography to produce the compound 32b (175 mg, 50%). $^1$H-NMR (400 MHz, CDCl$_3$) δ 4.41 (m, 1H), 4.01 (m, 2H), 3.75-3.56 (m, 43H), 3.54 (m, 2H), 3.24 (m, 2H), 2.89 (m, 3H), 2.52 (m, 4H), 1.83 (m, 1H), 1.80 (m, 1H), 1.53 (s, 9H), 1.39 (m, 2H). EI-MS m/z: [M+H]$^+$ 975.5.

Preparation of Compound 32c

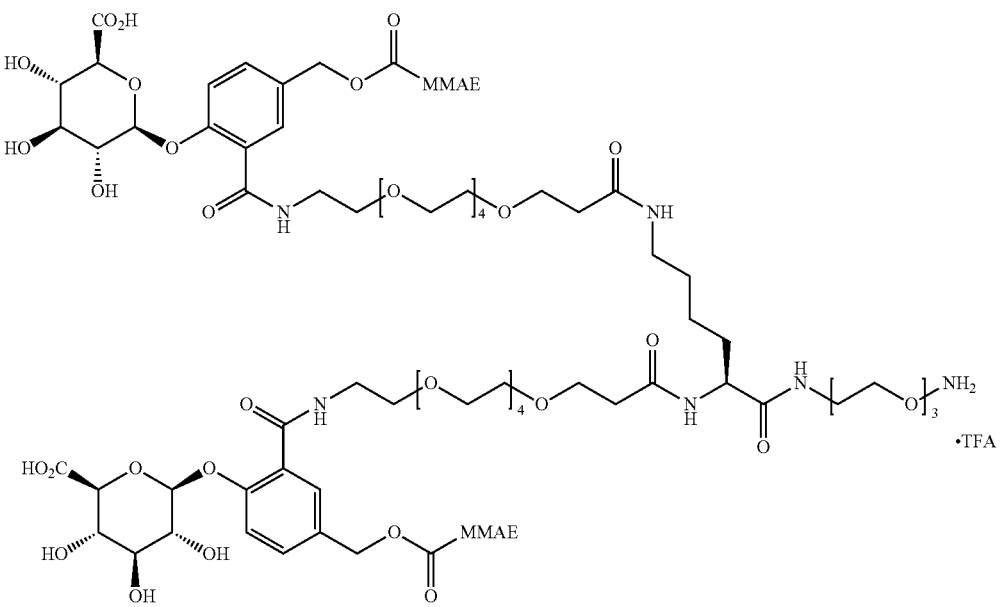

32c

Compound 32c was prepared from compound 1i and compound 32b by a similar method of preparing compound 25e in Example 35. EI-MS m/z: ½[M+H]$^+$ 1508.8.

Example 48. Preparation of Compound 32d
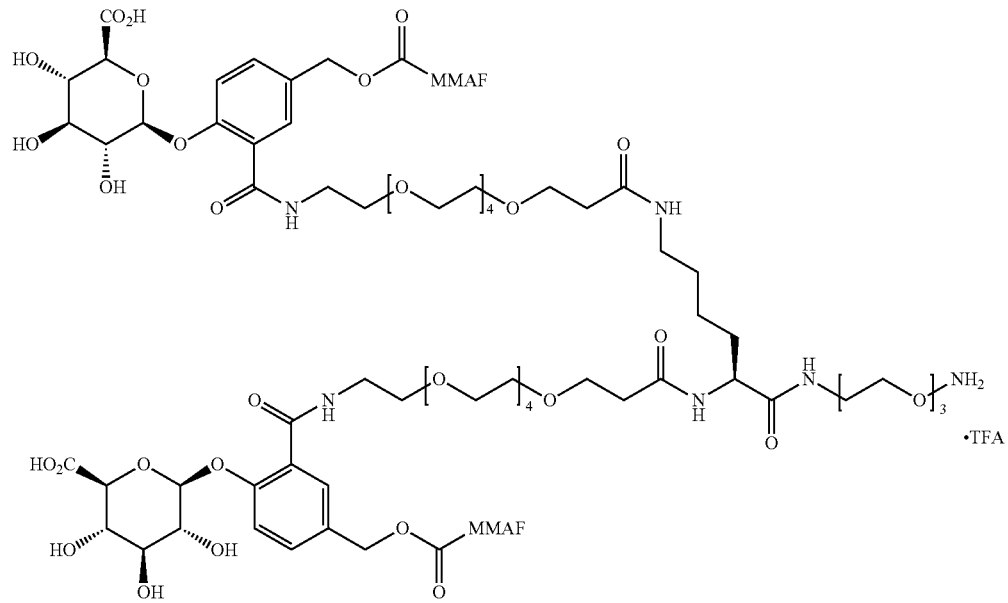
Compound 32d was prepared from compound 1j and compound 32b by a similar method of preparing compound 25e in Example 35. EI-MS m/z: ½[M+H]$^+$ 1522.8.
Example 49. Preparation of Compound 33e
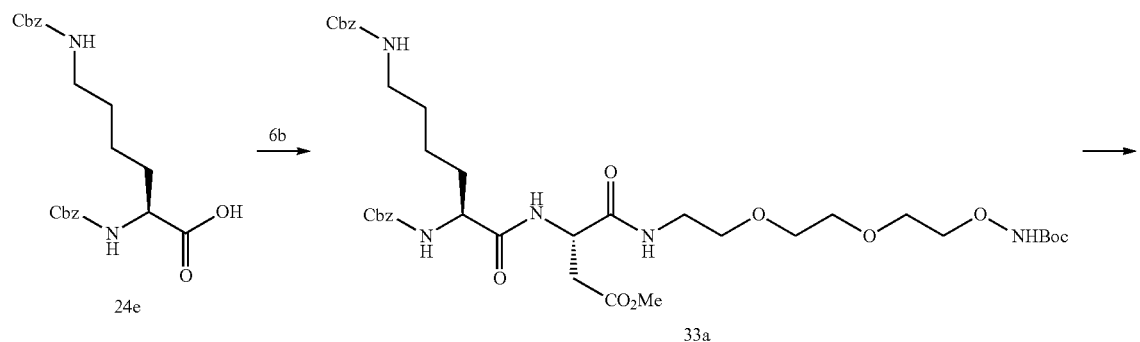
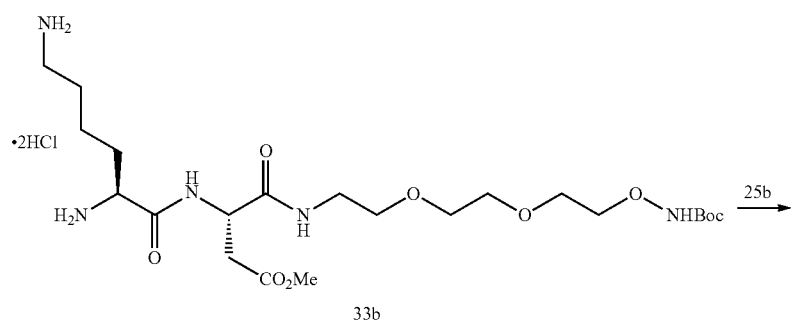

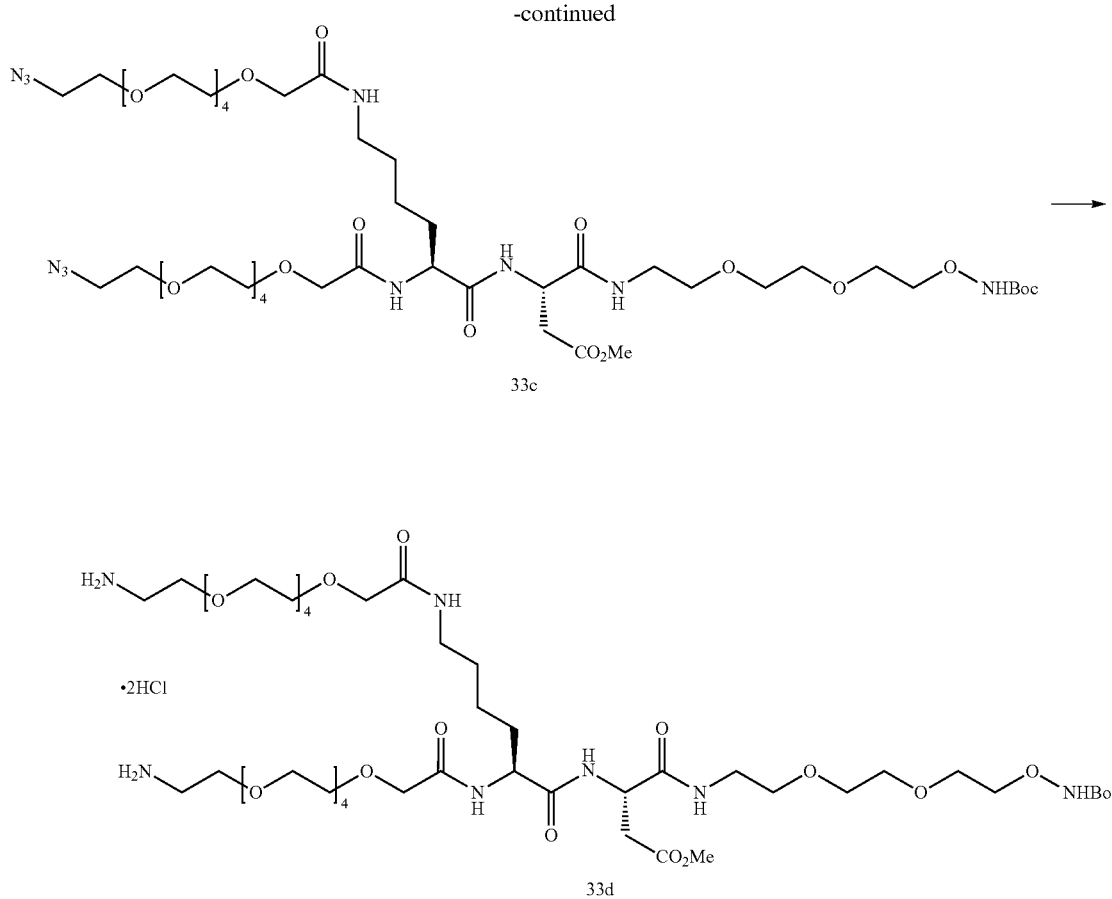

Preparation of Compound 33a

DIPEA (1.98 mL, 11.37 mmol) and HBTU (2.15 g, 5.68 mmol) were added to a stirred mixture of compound 24e (1.57 g, 3.79 mmol) and compound 6b (1.30 g, 3.15 mmol) in DMF (37 mL). After stirring at room temperature for 14 hours under $N_2$, the reaction mixture was poured into $H_2O$ (40 mL) and extracted with EtOAc (3×40 mL). The combined organic layers were washed with 1 N aq. HCl (40 mL), saturated aq. $NaHCO_3$ (40 mL) and brine (40 mL) sequentially, and dried over anhydrous $Na_2SO_4$. After filtration and concentration, the residue was purified by column chromatography, which produced the compound 33a (2.2 g, 88%). $^1$H-NMR (400 MHz, DMSO-$d_6$) δ 9.99 (s, 1H), 8.19 (d, 1H), 7.79 (t, 1H), 7.47 (d, 1H), 7.34-7.31 (m, 5H), 7.24 (t, 1H), 5.01 (d, 4H), 4.55 (q, 1H), 3.91 (q, 1H), 3.79 (t, 2H), 3.55-3.48 (m, 9H), 3.24-3.11 (m, 2H), 2.75-2.54 (m, 2H), 1.57-1.49 (m, 2H), 1.38 (s, 9H), 1.25 (m, 2H). EI-MS m/z: $[M+H]^+$ 790.47, $[M+Na]^+$812.4.

Preparation of Compound 33b

To a stirred mixture of compound 33a (2.2 g, 2.78 mmol) and Pd/C (10 wt. %, 400 mg) in MeCOH (60 mL) at 0° C. was added HCl (4 N in 1,4-dioxane, 1.39 mL, 5.56 mmol). After stirring at room temperature for 3 hours under hydrogen, the reaction mixture was filtered through a celite pad and washed with MeOH (40 mL). The filtrate was concentrated to produce the compound 33b (1.67 g, 99%), which was used without further purification. $^1$H-NMR (400 MHz, DMSO-$d_6$) δ 9.98 (s, 1H), 8.87 (d, 1H), 8.28 (bs, 3H), 8.12 (1H), 7.96 (bs, 3H), 4.51 (q, 1H), 3.77 (t, 2H), 3.72 (bs, 1H), 3.57 (s, 3H), 3.52-3.47 (m, 7H), 3.12 (s, 3H), 2.76-2.61 (m, 4H) 1.71 (q, 2H), 1.55 (q, 2H) 1.36 (s, 9H). EI-MS m/z: $[M+H]^+$ 522.4, $[M+Na]^+$544.3.

Preparation of Compound 33c

DIPEA (1.95 mL, 11.23 mmol) and HBTU (3.19 g, 8.42 mmol) were added to a stirred mixture of compound 25b (1.98 g, 6.17 mmol) and compound 33b (1.67 g, 2.80 mmol) in DMF (20 mL). After stirring at room temperature for 14 hours under $N_2$, the reaction mixture was concentrated and purified by column chromatography, which produced the compound 33c (2 g, 63%). $^1$H-NMR (400 MHz, DMSO-$d_6$) δ 9.97 (s, 1H), 8.28 (d, 1H), 7.82 (t, 1H), 7.65 (s, 1H), 7.64 (s, 1H), 4.54 (q, 1H), 4.25 (q, 1H), 3.91 (s, 2H), 3.84 (s, 2H), 3.80 (t, 2H), 3.60-3.49 (m, 48H), 3.26-3.12 (m, 3H), 3.07 (q, 2H), 2.75-2.54 (m, 2H), 1.65-1.55 (m, 2H), 1.39 (s, 10H), 1.21 (m, 3H). EI-MS m/z: $[M+H]^+$ 1128.8, $[M+Na]^+$1150.7.

Preparation of Compound 33d

To a stirred mixture of compound 33c (1 g, 0.88 mmol) and Pd/C (10 wt. %, 200 mg) in MeOH (20 mL) at 0° C. was added HCl (4 N in 1,4-dioxane, 0.44 mL, 0.88 mmol). After stirring at room temperature for 3 hours under hydrogen, the reaction mixture was filtered through a celite pad and washed with MeOH (20 mL). The filtrate was concentrated to produce the compound 33d (936 mg, 92%), which was used without further purification. $^1$H-NMR (400 MHz, DMSO-$d_6$) δ 9.98 (s 1H), 8.30 (d, 1H), 7.70 (t, 2H), 4.54 (q, 1H), 4.26 (q, 1H), 3.93 (s, 2H), 3.85 (s, 2H), 3.80 (t, 2H), 3.61-3.49 (m, 46H), 3.22-3.12 (m, 4H), 3.06 (q, 2H), 2.97 (q, 4H), 2.76-2.54 (m, 2H), 1.64-1.55 (m, 2H), 1.39 (s, 10H), 1.26 (m, 3H). EI-MS m/z: $[M+H]^+$ 1076.8.

Preparation of Compound 33e
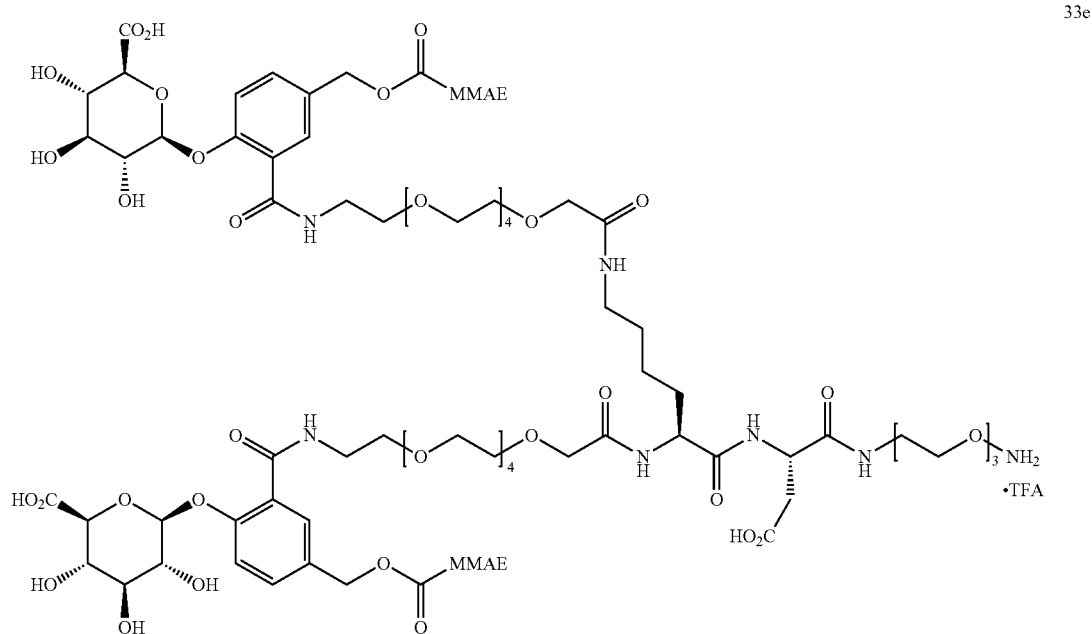
Compound 33e was prepared from compound 1i and compound 33d by a similar method of preparing compound 25e in Example 35. EI-MS m/z: ½[M+H]⁺ 1552.2.
Example 50. Preparation of Compound 33f
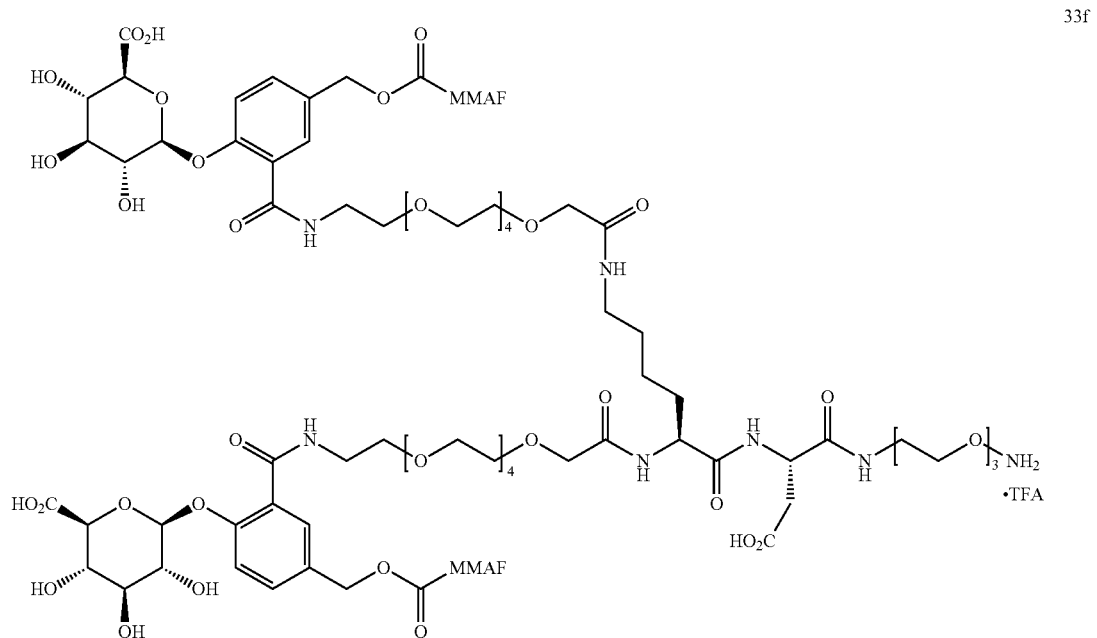
Compound 33f was prepared from compound 1j and compound 33d by a similar method of preparing compound 25e in Example 35. EI-MS m/z: ½[M+H]⁺ 1566.4.

Example 51. Preparation of Compound 34e

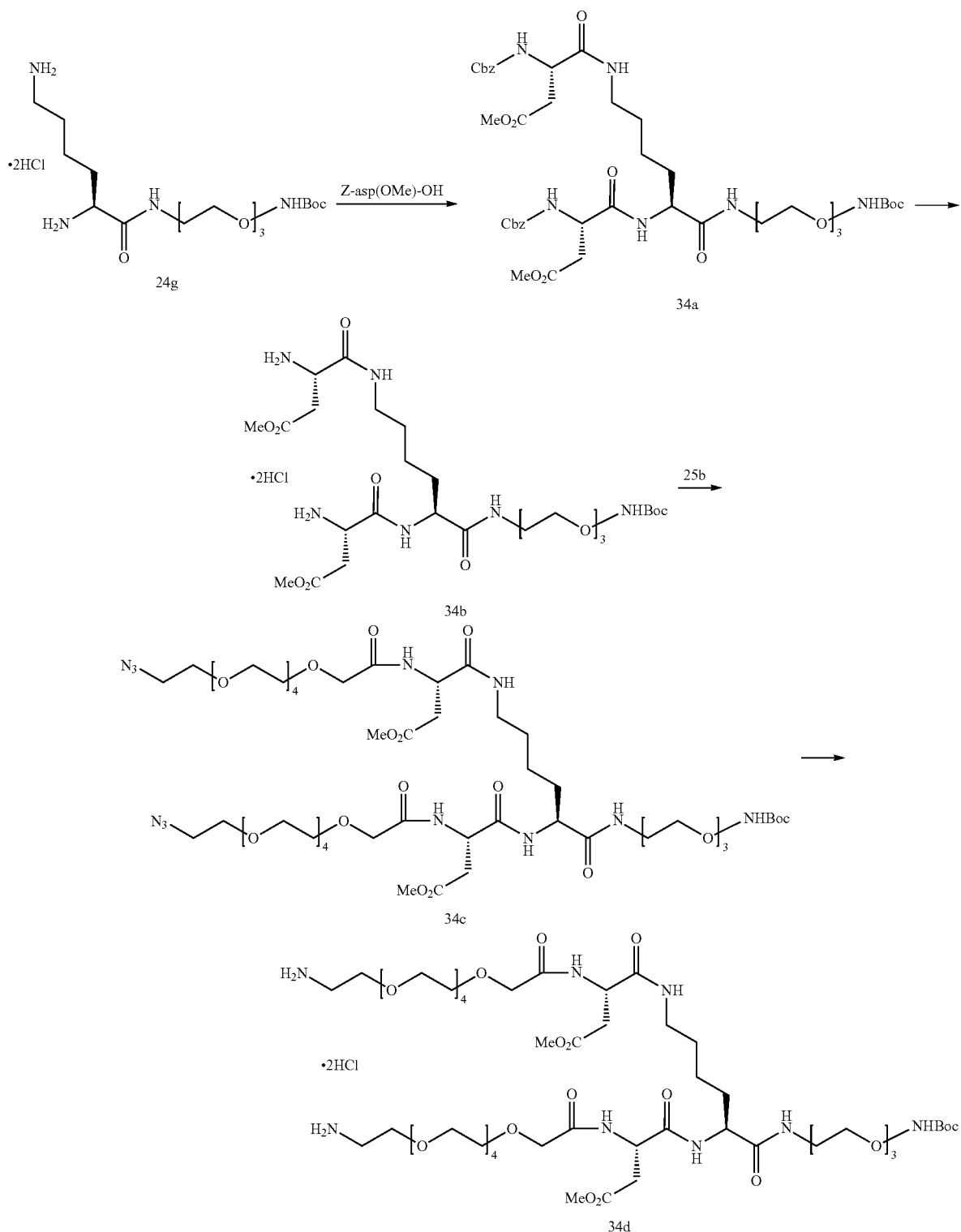

Preparation of Compound 34a

DIPEA (0.8 mL, 4.56 mmol) and HBTU (1.3 g, 3.42 mmol) were added to a stirred mixture of compound 24g (530 mg, 1.14 mmol) and Z-Asp(OMe)-OH (704 mg, 2.5 mmol) in DMF (5 mL). After stirring at room temperature for 14 hours under $N_2$, the reaction mixture was poured into $H_2O$ (50 mL) and extracted with EtOAc (3×30 mL). The combined organic layers were washed with 1 N aq. HCl (40 mL), saturated aq. $NaHCO_3$ (40 mL) and brine (40 mL) sequentially, and dried over anhydrous $Na_2SO_4$. After filtration and concentration, the residue was purified by column chromatography, which produced the compound 34a. (713 mg, 68%). $^1$H-NMR (400 MHz, DMSO-$d_6$): δ 9.97 (s, 1H), 7.88 (m, 3H), 7.64 (d, 2H), 7.51 (d, 2H), 7.35 (m, 10H), 5.02 (m, 4H), 4.43-4.31 (m, 2H), 4.17 (m, 1H), 3.80 (t, 2H), 3.58-3.50 (m, 12H), 3.41-3.16 (m, 6H), 2.98 (m, 2H), 2.79-2.67 (m, 3H), 2.57 (m, 2H), 1.60-1.34 (m, 13H).

Preparation of Compound 34b

To a solution of compound 34a (530 mg, 0.58 mmol) in MeOH (5 mL) was added Pd/C (20 wt. %, 106 mg) and HCl (4 N in 1,4-dioxane, 0.29 mL, 1.16 mmol). After stirring at room temperature for 3 hours under hydrogen, the reaction mixture was filtered through a celite pad and washed with MeOH (30 mL). The filtrate was concentrated to produce the compound 34b (420 mg, 100%), which was used without further purification. $^1$H-NMR (400 MHz, DMSO-$d_6$) δ 9.97 (s, 1H), 8.62 (d, 1H), 8.54 (s, 1H), 8.27 (m, 4H), 7.02 (s, 1H), 4.17 (m, 2H), 4.02 (m, 1H), 3.76 (t, 2H), 3.61 (m, 4H), 3.51-3.11 (m, 12H), 3.09-2.77 (m, 8H), 1.60-1.24 (m, 13H). EI-MS m/z: [M+H]$^+$ 651.5.

Preparation of Compound 34c

DIPEA (0.4 mL, 2.32 mmol) and HBTU (660 mg, 1.74 mmol) were added to a stirred mixture of compound 34b (420 mg, 0.58 mmol) and compound 25b (299 mg, 0.93 mmol) in DMF (5 mL). After stirring at room temperature for 14 hours under N$_2$, the reaction mixture was poured into H$_2$O (30 mL) and extracted with EtOAc (3×30 mL). The combined organic layers were washed with 1 N aq. HCl (20 mL), saturated aq. NaHCO$_3$ (20 mL) and brine (20 mL) sequentially, and dried over anhydrous Na$_2$SO$_4$. After filtration and concentration, the residue was purified by column chromatography, which produced the compound 34c (466 mg, 70.8%). $^1$H-NMR (400 MHz, CDCl$_3$): δ 8.28 (s, 1H), 7.78 (q, 1H), 7.31 (d, 1H), 7.71 (s, 1H), 6.94 (s, 1H), 4.85 (m, 2H), 4.35 (m, 1H), 4.07-4.03 (m, 6H), 3.75-3.41 (m, 56H), 3.23 (q, 2H), 2.92-2.84 (m, 4H), 1.91-1.32 (m, 15H). EI-MS m/z: [M+2H]$^+$1158.1.

Preparation of Compound 34d

To a stirred mixture of compound 34c (260 mg, 0.21 mmol) and Pd/C (10 wt. %, 52 mg) in MeOH (20 ml) at 0° C. was added HCl (4 N in 1,4-dioxane, 0.10 mL, 0.41 mmol). After stirring at room temperature for 2 hours under hydrogen, the reaction mixture was filtered through a celite pad and washed with MeOH (50 mL). The filtrate was concentrated to produce the compound 34d (249 mg, 100%), which was used without further purification. EI-MS m/z: [M+2H]$^+$1206.1.

Preparation of Compound 34e

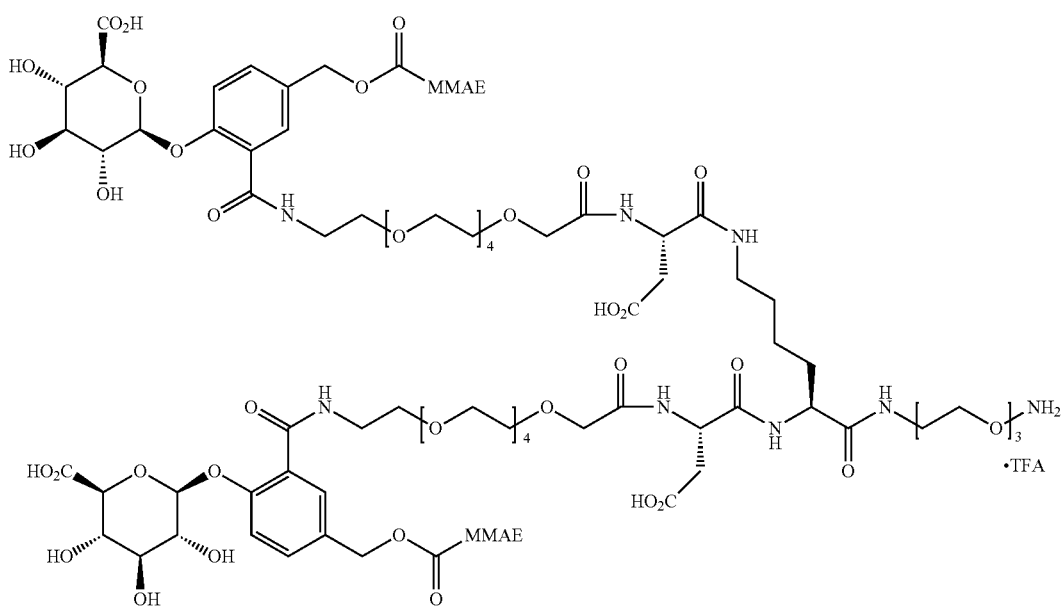

34e

Compound 34e was prepared from compound 1i and compound 34d by a similar method of preparing compound 25e in Example 35. EI-MS m/z: ½[M+H]$^+$ 1610.4.

Example 52. Preparation of Compound 34f
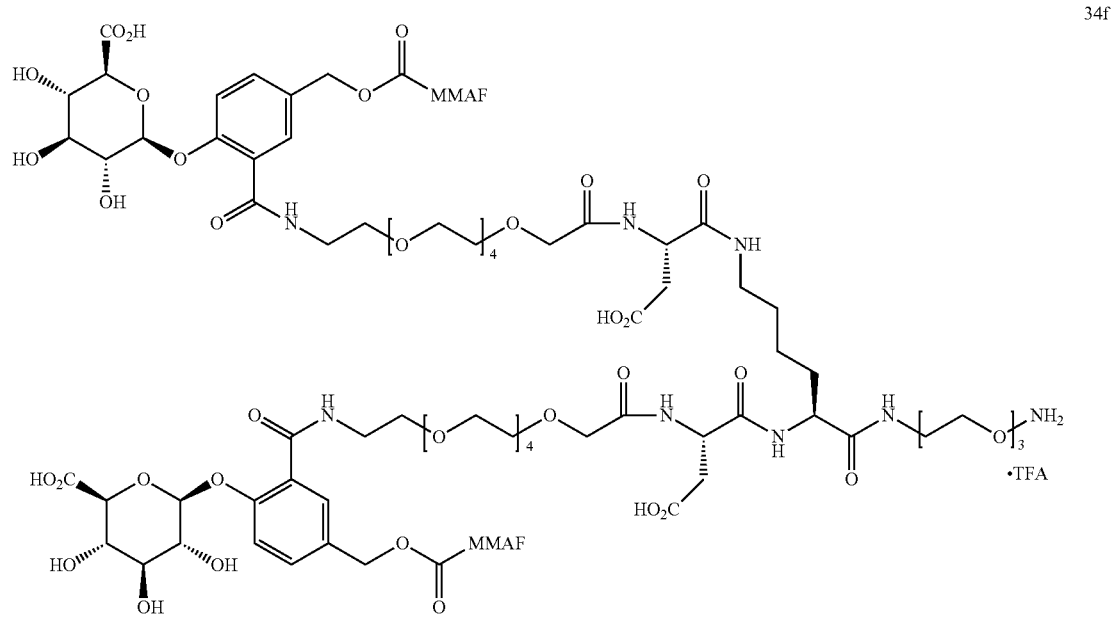
Compound 34f was prepared from compound 1j and compound 34d by a similar method of preparing compound 25e in Example 35. EI-MS m/z: ½[M+H]$^+$ 1624.3.
Example 53. Preparation of Compound 35g
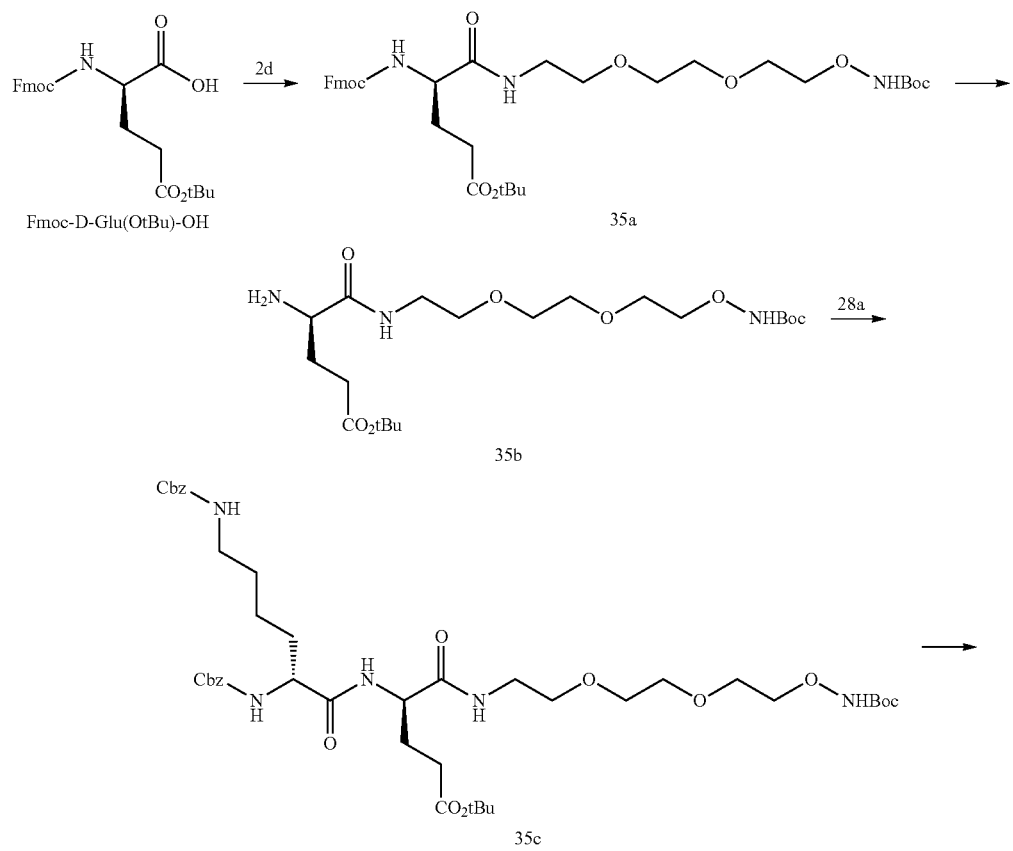

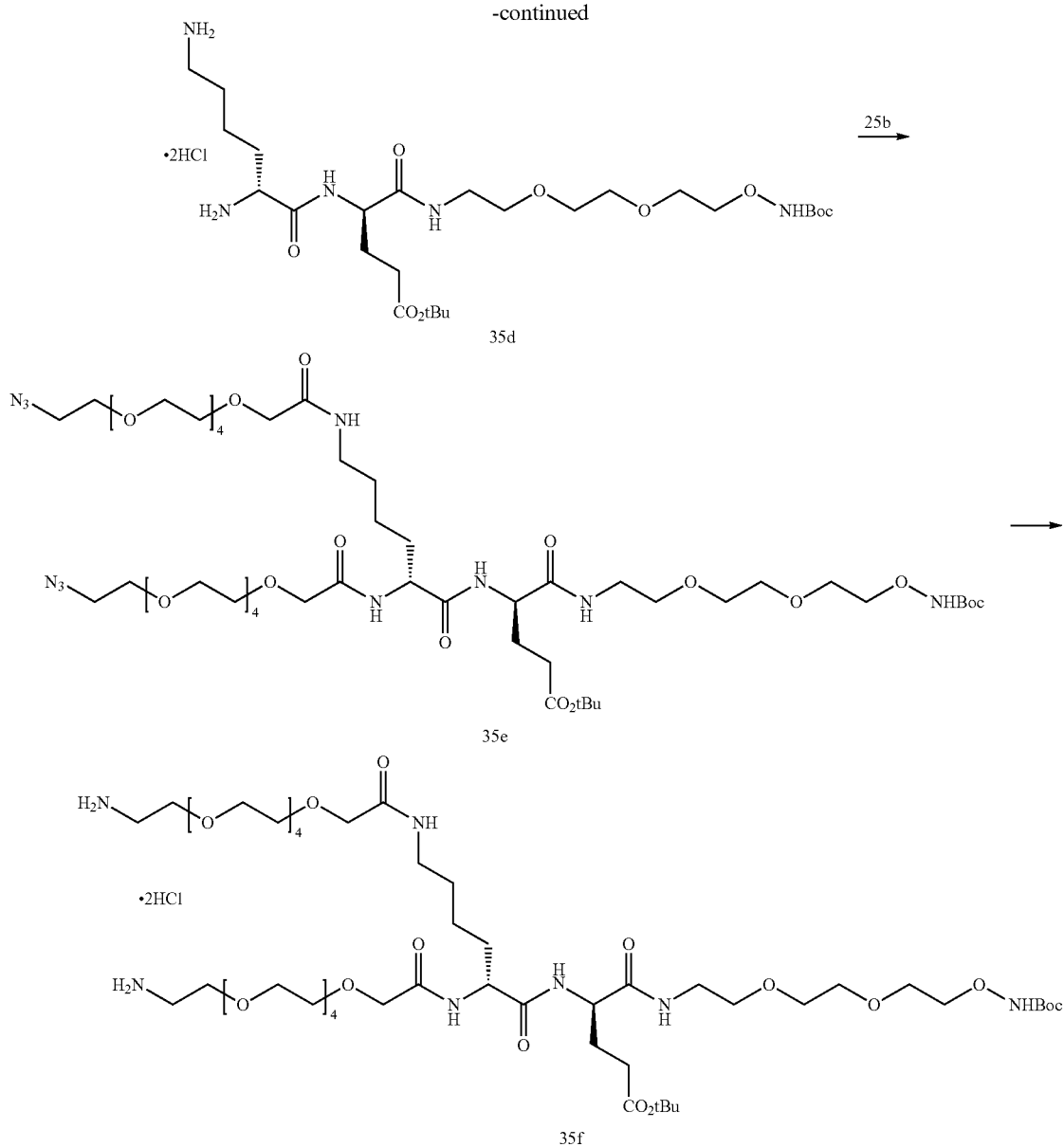

Preparation of Compound 35a

DIPEA (0.61 mL, 3.52 mmol) and HBTU (665 mg, 1.175 mmol) were added to a stirring mixture of Fmoc-D-Glu(OtBu)-OH (500 mg, 1.17 mmol) and compound 2d (424 mg, 1.404 mmol) in DMF (10 mL). After stirring at room temperature for 14 hours under $N_2$, the reaction mixture was poured into $H_2O$ (30 mL) and extracted with EtOAc (3×30 mL). The combined organic layers were washed with 1 N aq. HCl (20 mL), saturated aq. $NaHCO_3$ (20 mL) and brine (20 mL) sequentially, and dried over anhydrous $Na_2SO_4$. After filtration and concentration, the resulting residue was purified by column chromatography, which produced the compound 35a (708 mg, 89%). EI-MS m/z: $[M+H]^+$ 672.7.

Preparation of Compound 35b

To a solution of compound 35a (708 mg, 1.04 mmol) in THF (8 mL) was added piperidine (2 mL) at room temperature. After stirring for 20 minutes, the reaction mixture was concentrated under reduced pressure. The resulting residue was purified by column chromatography, which produced the compound 35b (400 mg, 85%). EI-MS m/z: $[M+H]^+$ 450.1.

Preparation of Compound 35c

DIPEA (0.19 mL, 1.1 mmol) and HBTU (253 mg, 0.66 mmol) were added to a stirring mixture of compound 28a (203 mg, 0.484 mmol) and compound 35b (200 mg, 0.44 mmol) in DMF (10 mL). After stirring at room temperature for 14 hours under $N_2$, the reaction mixture was poured into $H_2O$ (30 mL) and extracted with EtOAc (3×30 mL). The combined organic layers were washed with 1 N aq. HCl (10 mL), saturated aq. $NaHCO_3$ (10 mL) and brine (10 mL) sequentially, and dried over anhydrous $Na_2SO_4$. After filtration and concentration, the residue was purified by column chromatography, which produced the compound 35c (235 mg, 63%). EI-MS m/z: $[M+H]^+$ 847.0.

Preparation of Compound 35d

To a solution of compound 35c (235 mg, 0.277 mmol) in MeOH (15 mL) was added Pd/C (10 wt. %, 30 mg). After stirring at room temperature for 2 hours under hydrogen, the reaction mixture was filtered through a celite pad and washed with MeOH (50 mL). The filtrate was concentrated to produce the compound 35d (160 mg, 100%), which was used without further purification. EI-MS m/z: [M+H]+ 578.7.

Preparation of Compound 35e

DIPEA (0.145 mL, 1.758 mmol) and HBTU (262 mg, 1.465 mmol) were added to a stirring mixture of compound 35d (160 mg, 0.276 mmol) and compound 25b (187 mg, 0.581 mmol) in DMF (3 mL). After stirring at room temperature for 14 hours under $N_2$, the reaction mixture was poured into $H_2O$ (30 mL) and extracted with EtOAc (3×30 mL). The combined organic layers were washed with 1 N aq. HCl (10 mL), saturated aq. $NaHCO_3$ (10 mL) and brine (10 mL) sequentially, and dried over anhydrous $Na_2SO_4$. After filtration and concentration, the residue was purified by column chromatography, which produced the compound 35e (260 mg, 79%). EI-MS m/z: [M+H]+ 1185.4.

Preparation of Compound 35f

To a solution of compound 35e (70 mg, 0.059 mmol) in MeOH (5 mL) was added Pd/C (10 wt. %, 15 mg). After stirring at room temperature for 90 minutes under hydrogen, the reaction mixture was filtered through a celite pad and washed with MeOH (30 mL). The filtrate was concentrated to produce the compound 35f (67 mg, 100%), which was used without further purification. EI-MS m/z: [M+H]+: 1133.3.

Preparation of Compound 35g

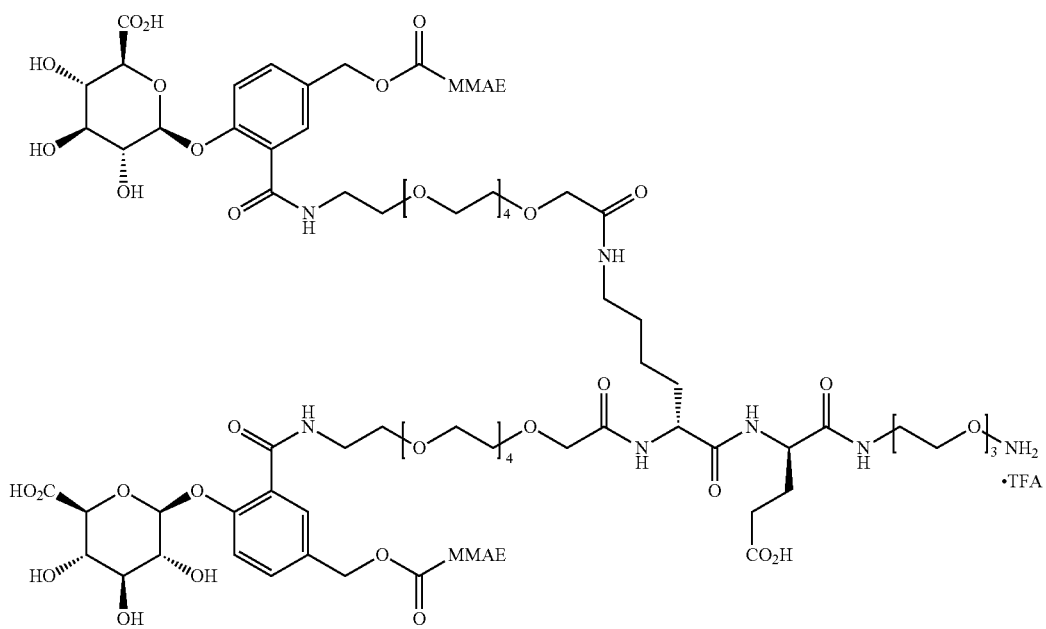

35g

Compound 35g was prepared from compound 1i and compound 35f by a similar method of preparing compound 25e in Example 35. EI-MS m/z: ½[M+H]+ 1559.9.

Example 54. Preparation of Compound 36e

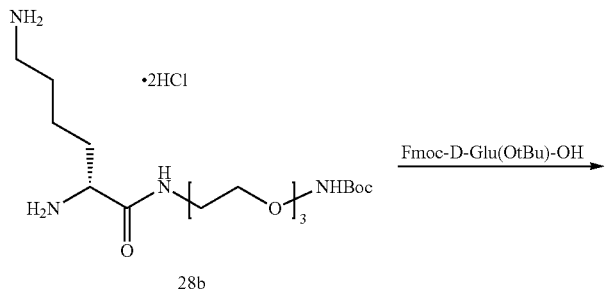

28b

-continued
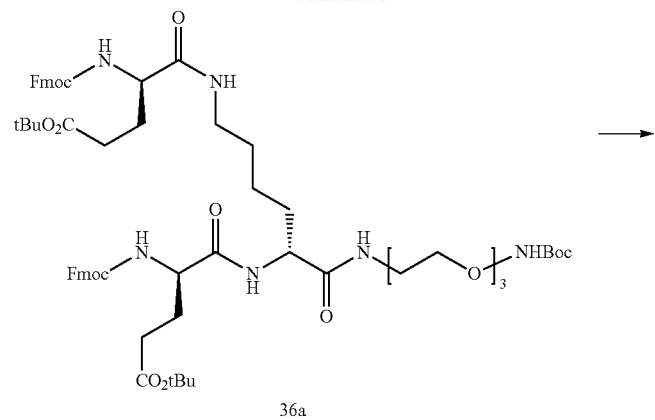
36a
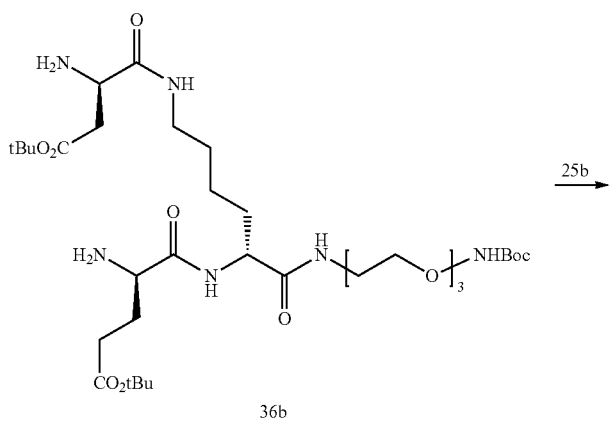
36b
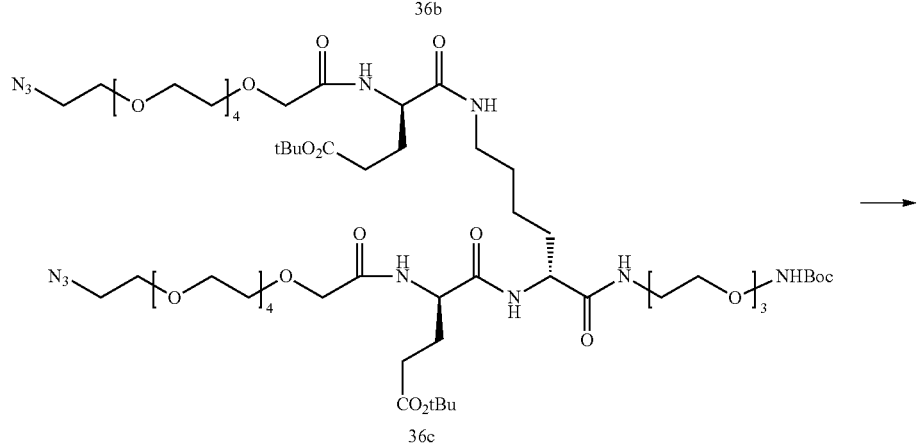
36c
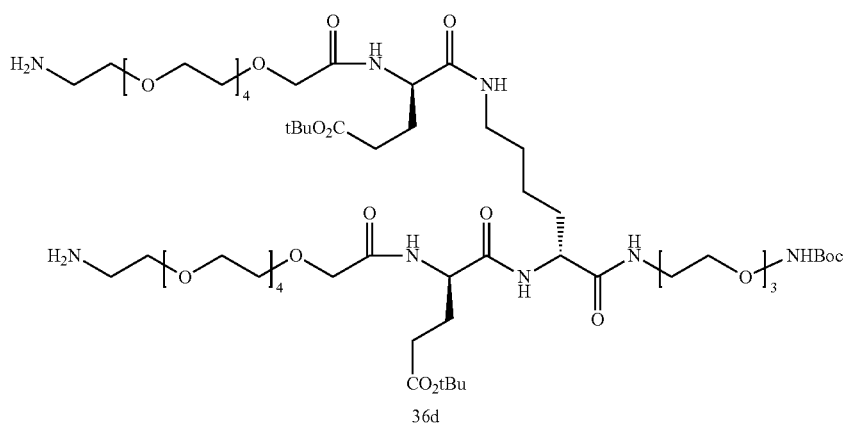
36d

Preparation of Compound 36a

DIPEA (0.3 mL, 3.10 mmol) and HBTU (474 mg, 2.275 mmol) were added to a stirring mixture of the Fmoc-D-Glu (OtBu)-OH (484 mg, 1.138 mmol) and compound 28b (223 mg, 0.569 mmol) in DMF (7 mL). After stirring at room temperature for 14 hours under $N_2$, the reaction mixture was poured into $H_2O$ (30 mL) and extracted with EtOAc (3×30 mL). The combined organic layers were washed with 1 N aq. HCl (20 mL), saturated aq. $NaHCO_3$ (20 mL) and brine (20 mL), and dried over anhydrous $Na_2SO_4$. After filtration and concentration, the residue was purified by column chromatography, which produced the compound 36a (593 mg, 86%). EI-MS m/z: $[M+H]^+$ 1208.3.

Preparation of Compound 36b

To a solution of compound 36a (593 mg, 0.49 mmol) in THF (8 mL) was added piperidine (1 mL) at room temperature. After stirring for 20 minutes, the reaction mixture was concentrated under reduced pressure. The resulting residue was purified by column chromatography, which produced the compound 36b (166 mg, 44%). EI-MS m/z: $[M+H]^+$ 763.9.

Preparation of Compound 36c

DIPEA (0.15 mL, 0.84 mmol) and HBTU (247 mg, 0.63 mmol) were added to a stirred mixture of compound 36b (166 mg, 0.21 mmol) and compound 25b (147 mg, 0.441 mmol) in DMF (3 mL). After stirring at room temperature for 14 hours under $N_2$, the reaction mixture was poured into $H_2O$ (30 mL) and extracted with EtOAc (3×30 mL). The combined organic layers were washed with 1 N aq. HCl (10 mL), saturated aq. $NaHCO_3$ (10 mL) and brine (10 mL) sequentially, and dried over anhydrous $Na_2SO_4$. After filtration and concentration, the residue was purified by column chromatography, which produced the compound 36c (195 mg, 68%). EI-MS m/z: $[M+H]^+$ 1370.6.

Preparation of Compound 36d

To a solution of compound 36c (195 mg, 0.14 mmol) in MeOH (10 mL) was added Pd/C (10 wt. %, 30 mg). Then the reaction mixture was stirring at room temperature for 90 minutes under hydrogen. The reaction mixture was filtered through a celite pad and washed with MeOH (30 mL). The filtrate was concentrated to produce the compound 36d (187 mg, 100%), which was used without further purification. EI-MS m/z: $[M+H]^+$ 1318.6.

Preparation of Compound 36e

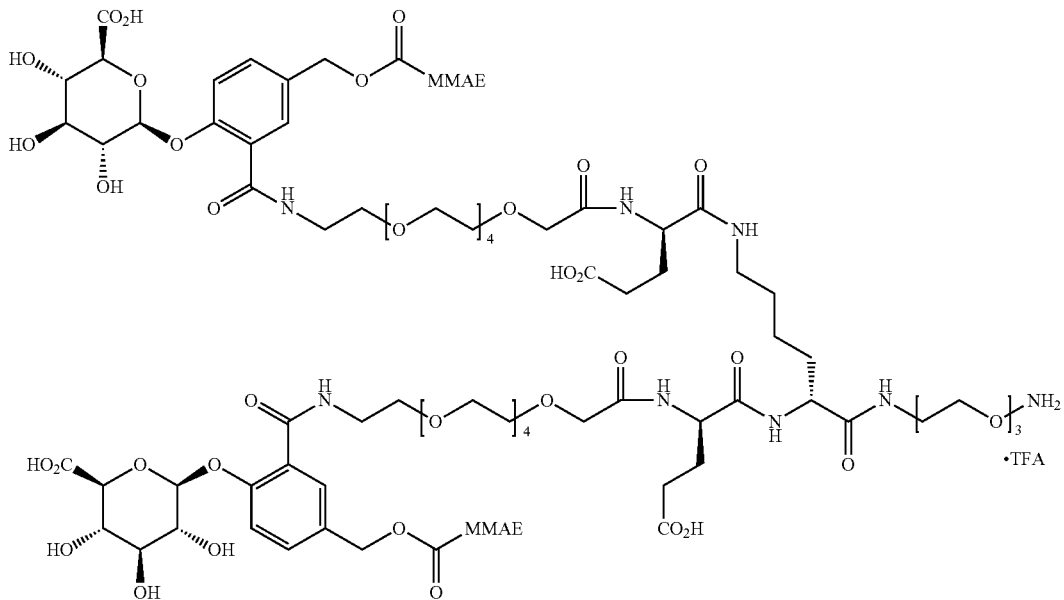

36e

Compound 36e was prepared from compound 1i and compound 36d by a similar method of preparing compound 25e in Example 35. EI-MS m/z: $½[M+H]^+$ 1624.4.

Example 55. Preparation of Compound 37d

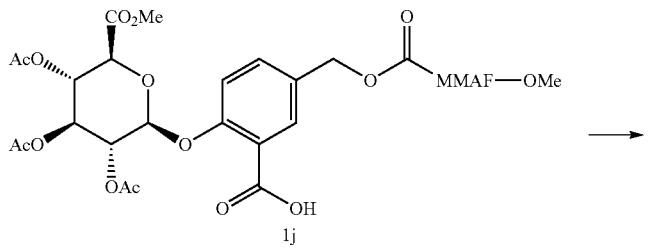

1j

-continued
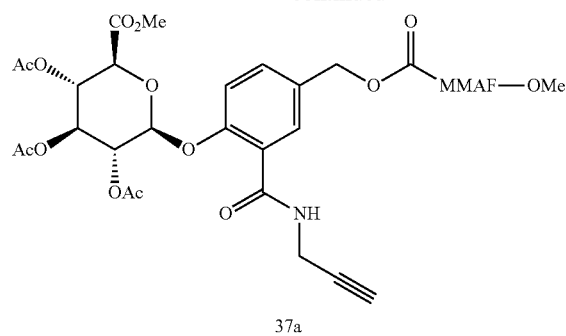
37a
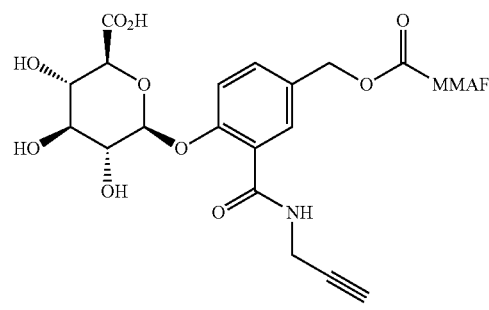
37b
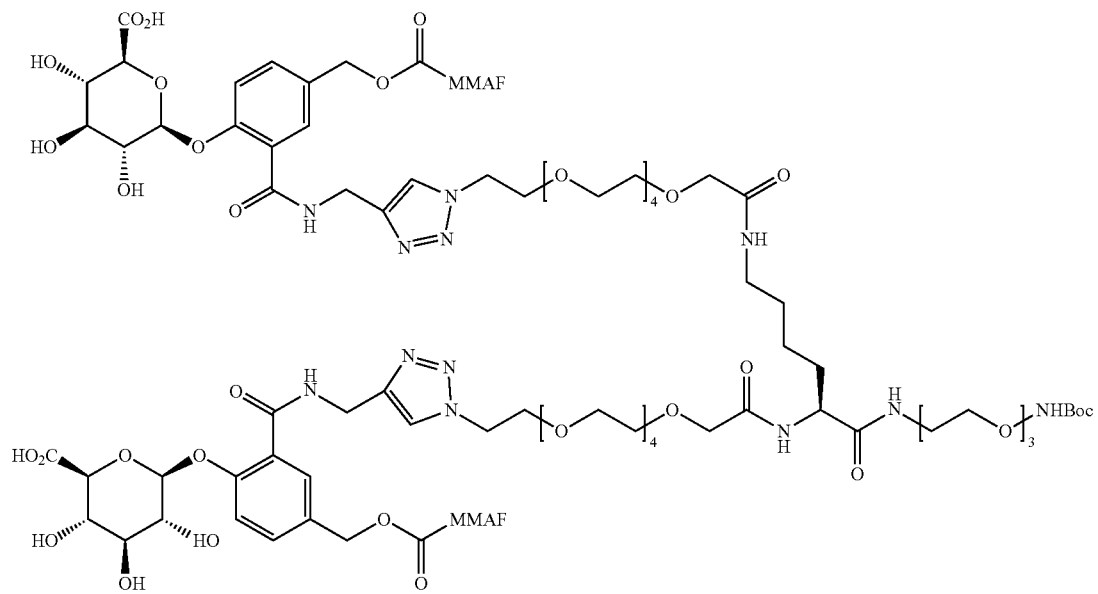
37c

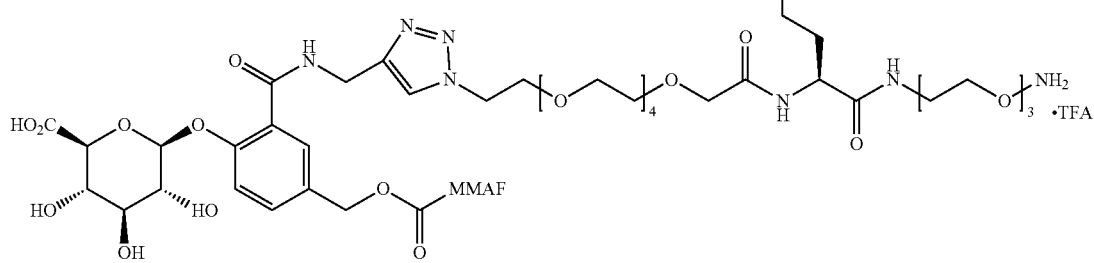

37d

Preparation of Compound 37a

DIPEA (0.083 mL, 0.71 mmol) and HBTU (136 mg, 0.36 mmol) were added to a stirred mixture of propargyl amine (0.018 mL, 0.285 mmol) and compound 1j (300 mg, 0.238 mmol) in DMF (3 mL). After stirring at room temperature for 14 hours under $N_2$, the reaction mixture was poured into $H_2O$ (10 mL) and extracted with EtOAc (3×10 mL). The combined organic layers were washed with 1 N aq. HCl (10 mL), saturated aq. $NaHCO_3$ (10 mL) and brine (10 mL) sequentially, and dried over anhydrous $Na_2SO_4$. After filtration and concentration, the resulting residue was purified by column chromatography, which produced the compound 37a (300 mg, 97%). EI-MS m/z: $[M+H]^+$ 1294.0.

Preparation of Compound 37b

To a solution of compound 37a (300 mg, 0.24 mmol) in THF (2 mL) and MeOH (2 mL) was added LiOH monohydrate (50 mg, 1.20 mmol) in $H_2O$ (2 mL) at 0° C. After stirring for 2 hours at 0° C., the reaction mixture was neutralized using acetic acid and was concentrated under reduced pressure. Then the residue was dissolved in $H_2O$/DMSO (1.5 mL/1.5 mL) and purified by HPLC. Pure fractions with the same retention time were combined and concentrated to produce the compound 37b (165 mg, 60%). EI-MS m/z: $[M+H]^+$ 1140.8.

Preparation of Compound 37c $CuSO_4·5H_2O$ (1 mg) and sodium ascorbate (2 mg) were added to a stirred mixture of compound 37b (50 mg, 0.042 mmol) and compound 25c (23 mg, 0.02 mmol) in THF (2 mL) and $H_2O$ (2 mL). The pH was adjusted to about 7 by addition of 1 M aq. $Na_2CO_3$. After stirring at 20° C. for 1 hour, the reaction mixture was dissolved in $H_2O$/DMSO (1.5 mL/1.5 mL) and purified by HPLC. Pure fractions with the same retention time were combined and concentrated to produce the compound 37c (32.4 mg, 48%). EI-MS m/z: $½[M+H]^+$ 1638.2.

Preparation of Compound 37d

TFA (0.4 mL) was added to a solution of compound 37c (32.4 mg, 0.01 mmol) in DCM (2 mL). After stirring at 0° C. for 2 hours, the solvent and excess TFA were removed by $N_2$ flow. Then the residue was dissolved in $H_2O$/MeCN (1 mL/1 mL) and purified by HPLC. Pure fractions with the same retention time were combined and lyophilized to produce the compound 37d (19.6 mg, 62%) as white solid. EI-MS m/z: $½[M+H]^+$ 1590.2.

Example 56. Preparation of Compound 38b

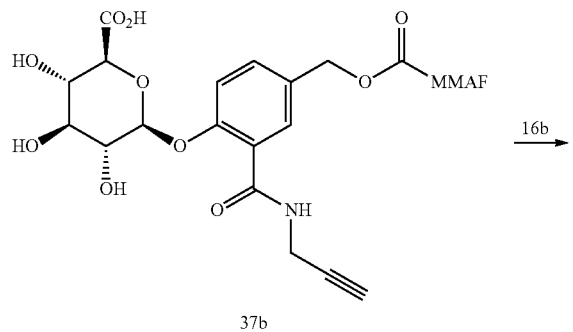

37b

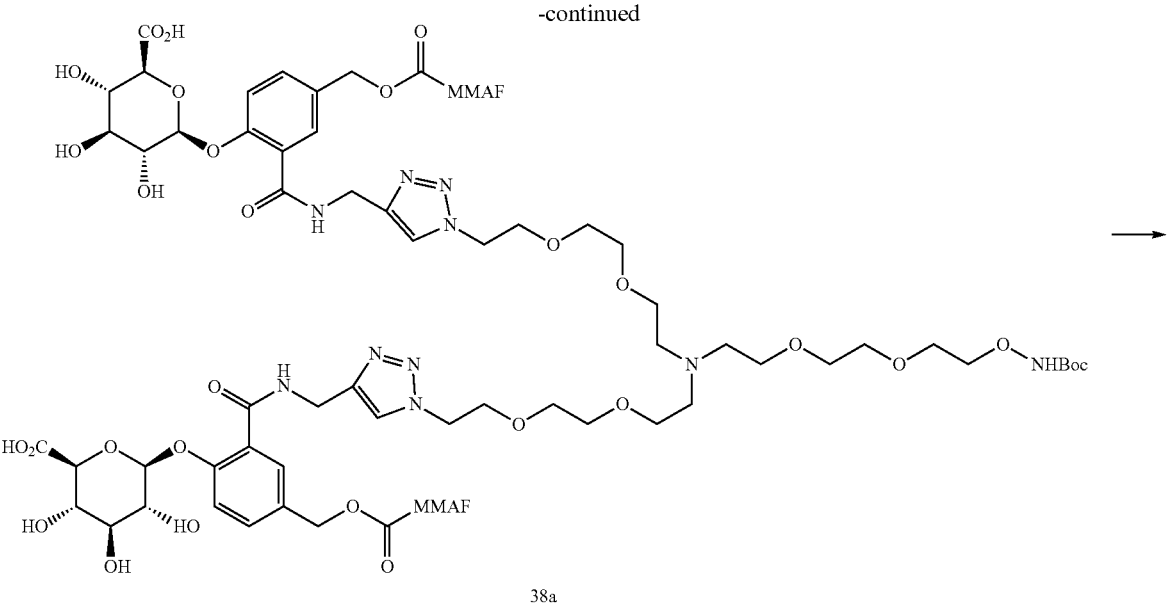
38a
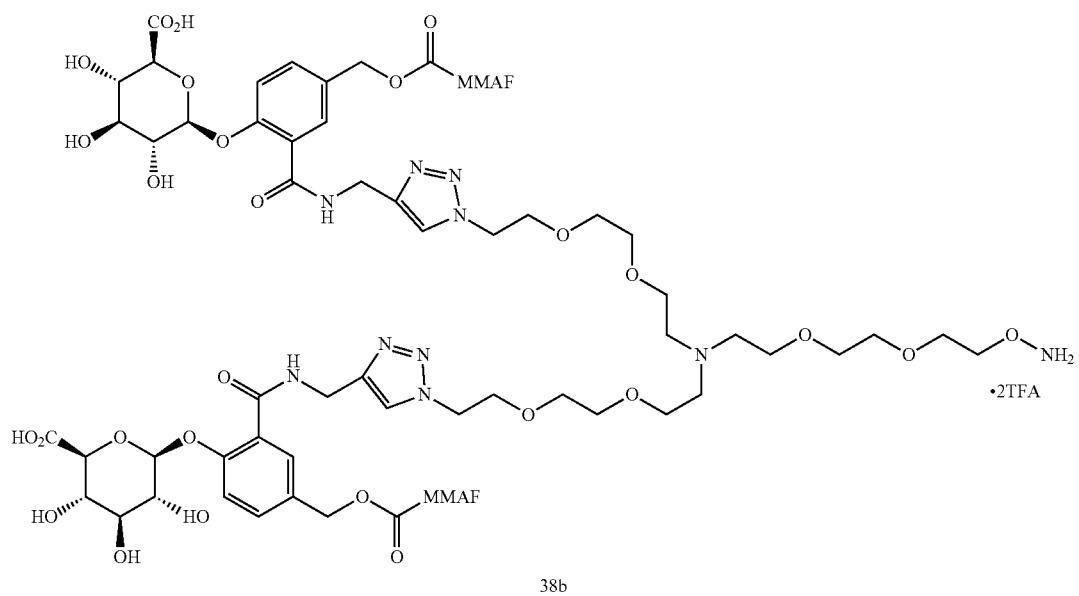
38b
Preparation of Compound 38a
CuSO₄.5H₂O (1 mg) and sodium ascorbate (2 mg) were added to a stirred mixture of compound 37b (60 mg, 0.052 mmol) and compound 16b (14 mg, 0.025 mmol) in THF (2 mL) and H₂O (2 mL). The pH was adjusted to about 7 by addition of 1 M aq. Na₂CO₃. After stirring at 20° C. for 1 hour, the reaction mixture was dissolved in H₂O/DMSO (1.5 mL/1.5 mL) and purified by HPLC. Pure fractions with the same retention time were combined and concentrated to produce the compound 38a (61 mg, 82%). EI-MS m/z: ½[M+H]$^+$ 1430.2.

Preparation of Compound 38b

TFA (0.4 mL) was added to a solution of compound 38a (59.8 mg, 0.02 mmol) in DCM (2.0 mL). After stirring at 0° C. for 2 hours, the solvent and excess TFA were removed by N$_2$ flow. Then the residue was dissolved in H$_2$O/AN (1 mL/1 mL) and purified by HPLC. Pure fractions with the same retention time were combined and lyophilized to produce the compound 38b (14.6 mg, 24%) as white solid. EI-MS m/z: ½[M+H]$^+$ 1380.1.

Example 57. Preparation of Compound 38e

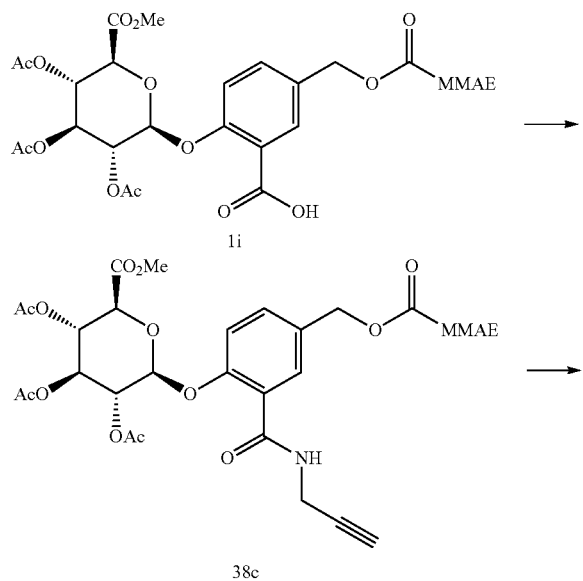

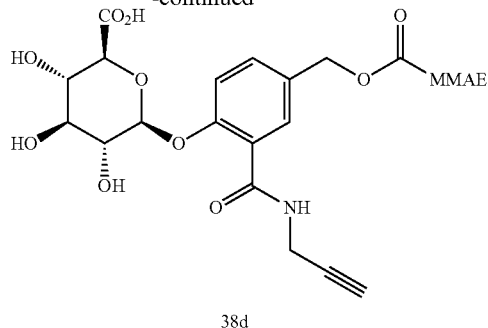

Preparation of Compound 38c

DIPEA (0.075 mL, 0.428 mmol) and HBTU (122 mg, 0.321 mmol) were added to a stirred mixture of propargyl amine (0.016 mL, 0.256 mmol) and compound 1i (264 mg, 0.214 mmol) in DMF (3 mL). After stirring at room temperature for 14 hours under N$_2$, the reaction mixture was poured into H$_2$O (10 mL) and extracted with EtOAc (3×10 mL). The combined organic layers were washed with 1 N aq. HCl (10 mL), saturated aq. NaHCO$_3$ (10 mL) and brine (10 mL) sequentially, and dried over anhydrous Na$_2$SO$_4$. After filtration and concentration, the residue was purified by column chromatography, which produced the compound 38c (270 mg, 100%). EI-MS m/z: [M+H]$^+$ 1266.2.

Preparation of Compound 38d

To a solution of compound 38c (270 mg, 0.213 mmol) in THF (2 mL) and MeOH (2 mL) was added LiOH monohydrate (36 mg, 0.853 mmol) in H$_2$O (2 mL) at 0° C. After stirring for 2 hours at 0° C., the reaction mixture was neutralized using acetic acid and was concentrated under reduced pressure. Then the residue was dissolved in H$_2$O/DMSO (1.5 mL/1.5 mL) and purified by HPLC. Pure fractions with the same retention time were combined and concentrated to produce the compound 38d (168 mg, 70%). EI-MS m/z: [M+H]$^+$ 1126.1.

Preparation of Compound 38e

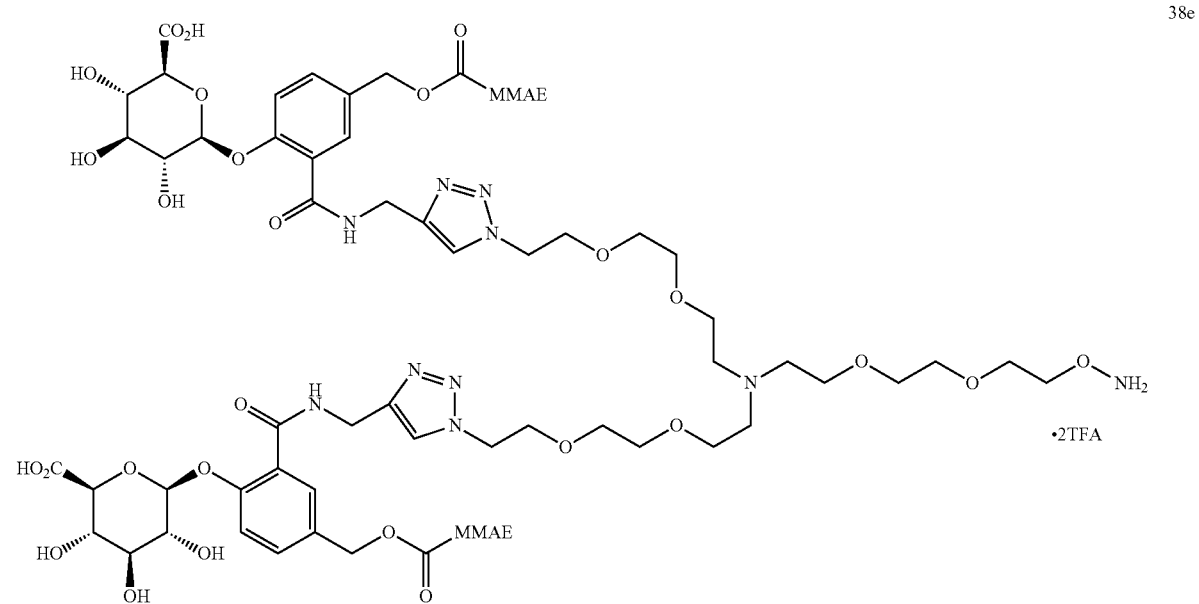

Compound 38e was prepared from compound 38d and compound 16b by a similar method of preparing compound 38b in Example 56. EI-MS m/z: ½[M+H]⁺ 1366.2.
Example 58. Preparation of Compound 39e
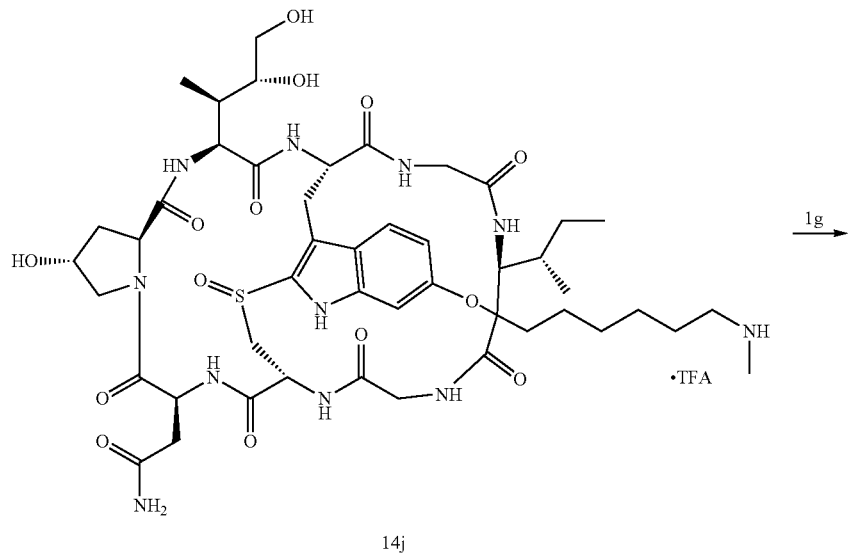
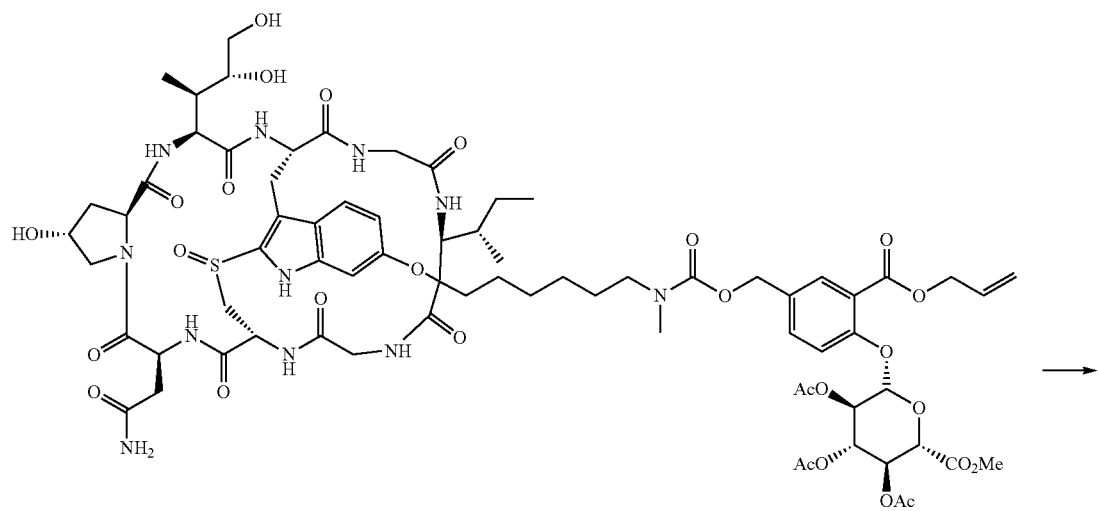

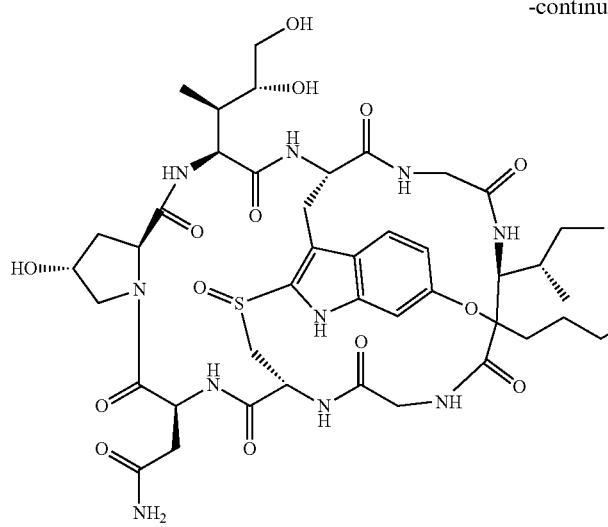

39b

Preparation of compound 39a

Compound 1g (27 mg, 0.039 mmol), compound 14j (45 mg, 0.039 mmol) and anhydrous HOBt (1 mg, 0.0078 mmol) were dissolved in DMF (2 mL) at 0° C. Then pyridine (0.2 mL) and DIPEA (0.014 mL, 0.078 mmol) were added. After stirring at 0° C. to room temperature for 24 hours under $N_2$, the reaction mixture was dissolved in DMSO (1 mL) and purified by HPLC, which produced the compound 39a (36 mg, 58%) as white solid. EI-MS m/z: [M+H]$^+$ 1582.9, [M+Na]$^+$1604.5.

Preparation of compound 39b

Compound 39a (35 mg, 0.022 mmol) and triphenylphosphine (1.5 mg, 0.005 mmol) were dissolved in DCM (2 mL). Pyrrolidine (0.0025 mL, 0.026 mmol) and Pd(PPh$_3$)$_4$ (1.3 mg, 0.001 mmol) were added to the reaction mixture at room temperature and then allowed to stir for 2 hours. The reaction mixture was diluted with H$_2$O (50 mL) and extracted with n-butanol (2×50 mL). The combined organic layers were dried over anhydrous MgSO$_4$, evaporated under reduced pressure. The resulting residue was dissolved in DMSO (1 mL) and purified by HPLC, which produced the compound 39b (34 mg, crude) as white solid. EI-MS m/z: [M+H]$^+$: 1542.7.

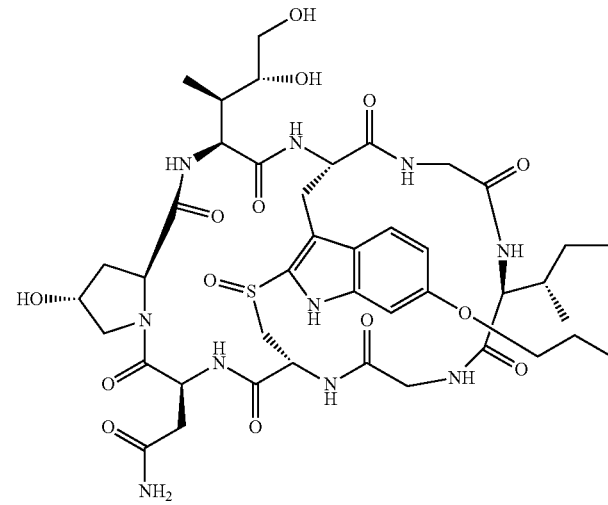

39b

275
-continued
276
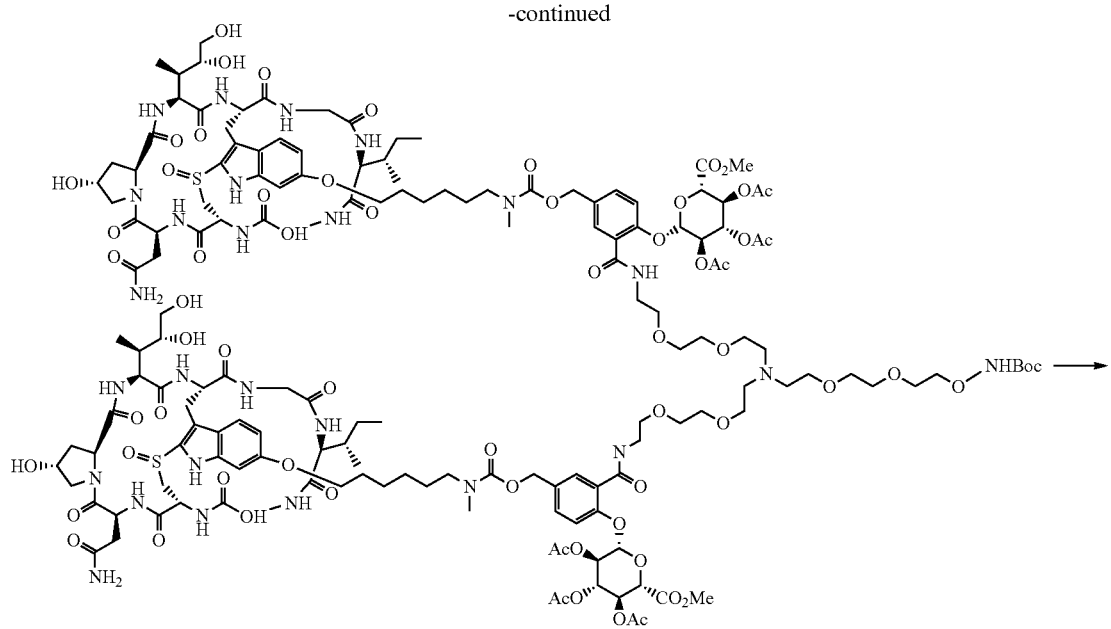
39c
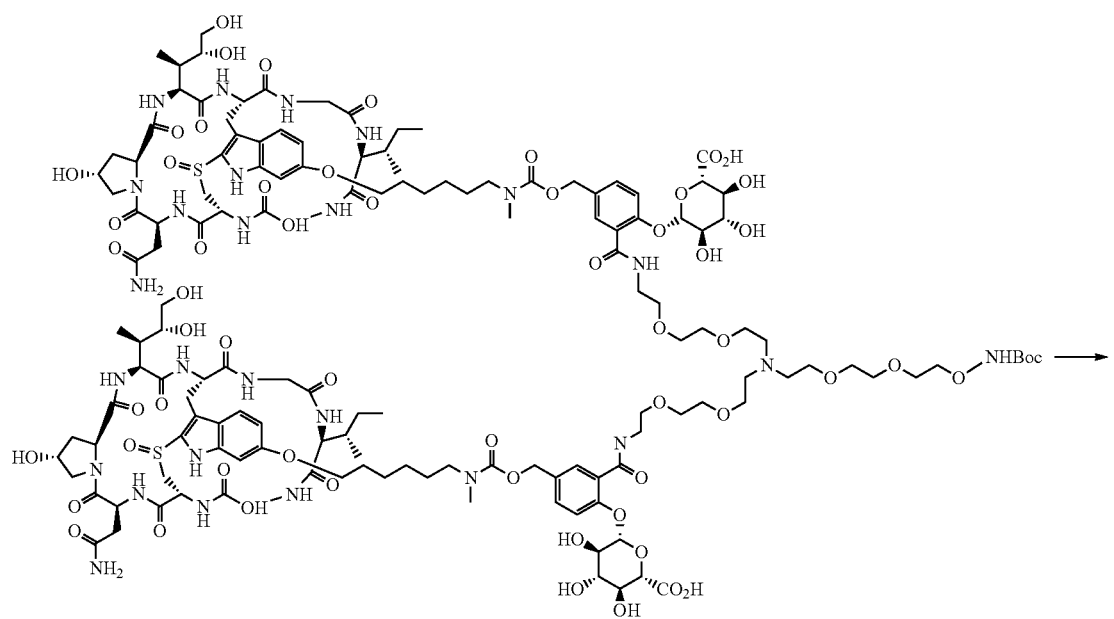
39d

-continued

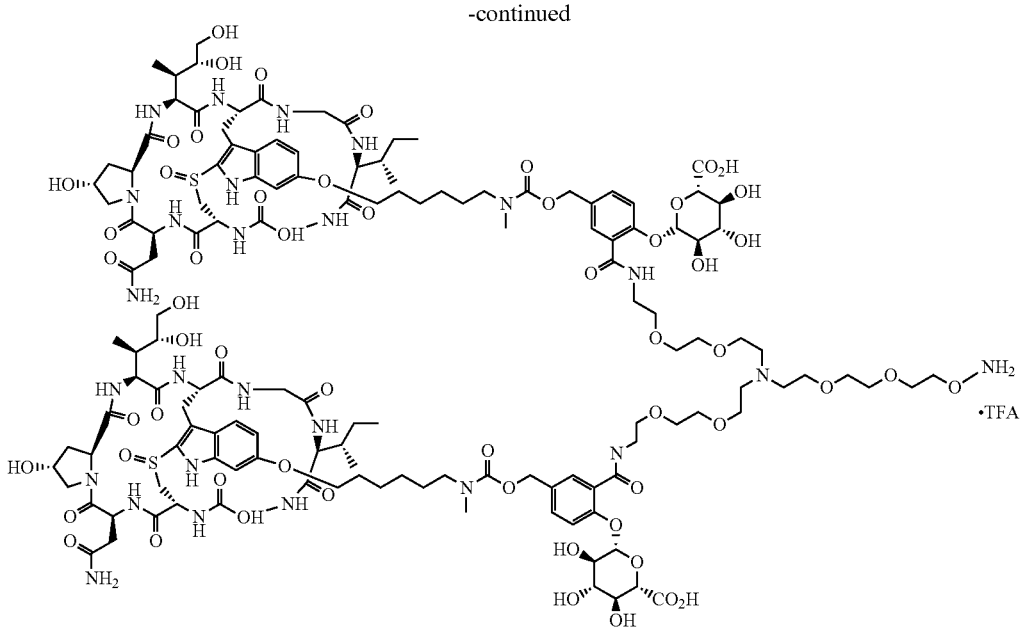

39e

Preparation of Compound 39c

DIPEA (0.0026 mL, 0.039 mmol) and PyBOP (4.7 mg, 0.023 mmol) were added to a stirred mixture of compound 39b (15 mg, 0.009 mmol) and compound 16c (2.0 mg, 0.0038 mmol) in DMF (0.3 mL). After stirring at room temperature for 13 hours under $N_2$, the reaction mixture was dissolved in DMSO (1.5 mL) and purified by HPLC, which produced the compound 39c (12 mg, 35%) as white solid. EI-MS m/z: ½[M+H]$^+$ 1788.5.

Preparation of Compound 39d

To a solution of compound 39c (12 mg, 0.0033 mmol) in MeOH (1 mL) was added LiOH monohydrate (1.4 mg, 0.033 mmol) in $H_2O$ (1 mL) at 0° C. After 2 hours at 0° C., the pH of the solution was adjusted with acetic acid to 4-5, and the reaction mixture was concentrated under reduced pressure. The resulting residue was dissolved in DMSO (1.5 mL) and purified by HPLC, which produced the compound 39d (11 mg, 98%). EI-MS m/z: ½[M+H]$^+$ 1648.6.

Preparation of Compound 39e

TFA (0.5 mL) was added to a stirred solution of compound 39d (11 mg, 0.003 mmol) in DCM (3.0 mL) at 0° C. After 2 hours at 0° C., the solvent and excess TFA were removed by $N_2$ flow. Then the residue was dissolved in DMSO (1 mL) and purified by HPLC, which produced the compound 39e (1.2 mg, 11%) as white solid. EI-MS m/z: ½[M+H]$^+$ 1598.3.

Example 59. Preparation of Compound 40c

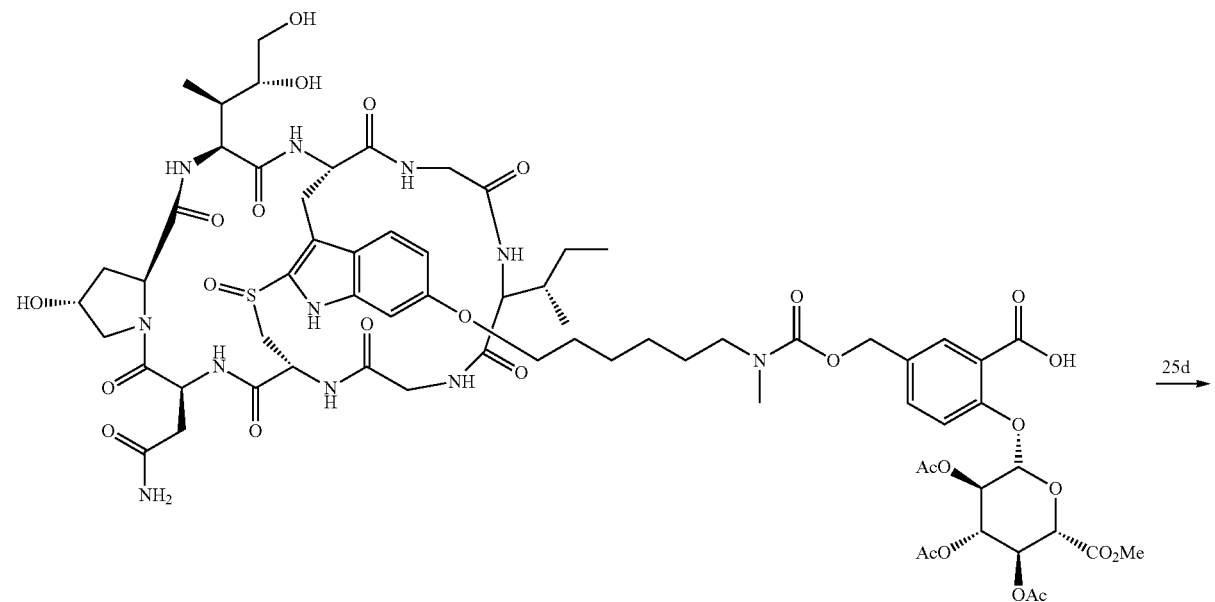

39b

-continued
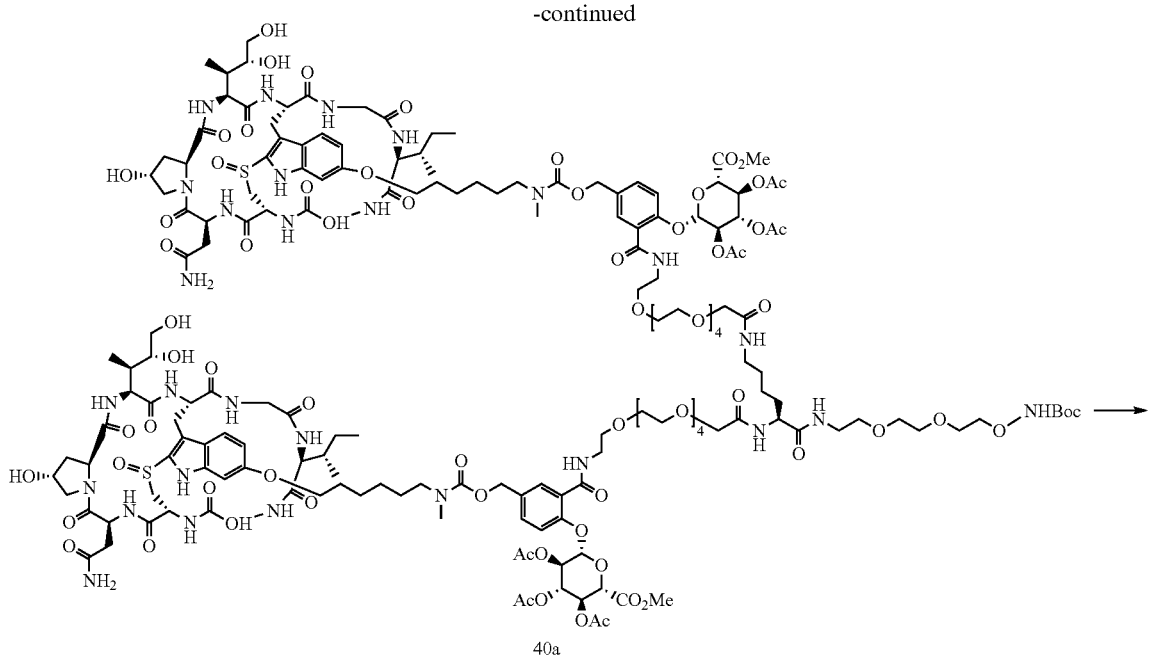
40a
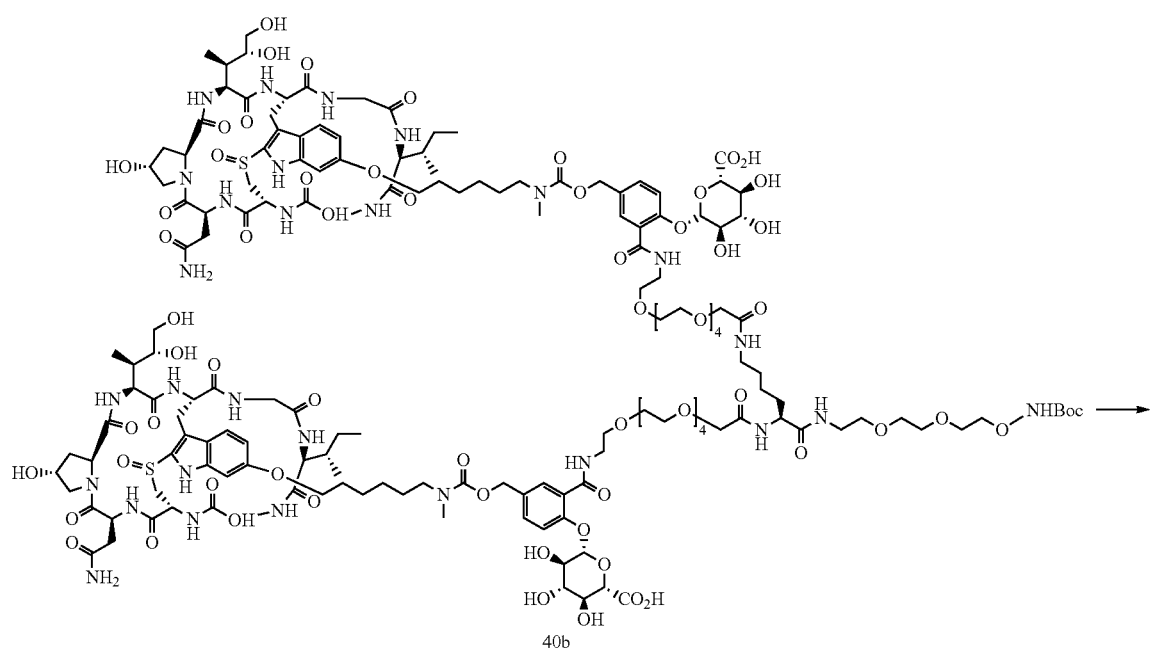
40b

-continued

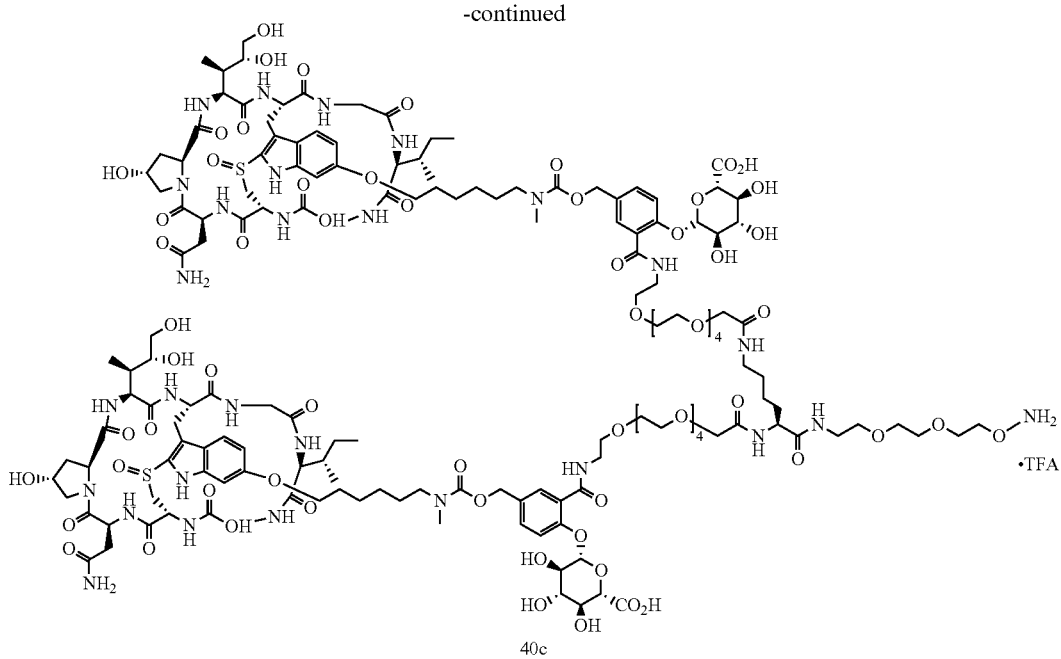

40c

Preparation of Compound 40a

DIPEA (0.004 mL, 0.021 mmol) and HBTU (5.0 mg, 0.013 mmol) were added to a stirred mixture of compound 39b (20 mg, 0.012 mmol) and compound 25d (5.0 mg, 0.005 mmol) in DMF (0.1.5 mL). After stirring at room temperature for 14 hours under $N_2$, the reaction mixture was dissolved in DMSO (1.0 mL) and purified by HPLC, which produced the compound 40a (14.5 mg, 30%). EI-MS m/z: ½[M+H]$^+$ 1998.8.

Preparation of Compound 40b

To a solution of compound 40a (10 mg, 0.0025 mmol) in MeOH (1 mL) was added LiOH monohydrate (1.0 mg, 0.025 mmol) in $H_2O$ (1 mL) at 0° C. After 2 hours at 0° C., the reaction mixture was neutralized using acetic acid and concentrated under reduced pressure. Then the residue was dissolved in DMSO (1.5 mL) and purified by HPLC, which produced the compound 40b (6.9 mg, 74%). EI-MS m/z: ½[M+H]$^+$ 1858.3.

Preparation of Compound 40c

TFA (0.2 mL) was added to a stirred solution of compound 40b (6.9 mg, 0.0018 mmol) in DCM (2.0 mL). After stirring at 0° C. for 2 hours, the solvent and excess TFA were removed by $N_2$ flow. Then the residue was dissolved in DMSO (1 mL) and purified by HPLC. Pure fractions with the same retention time were combined and lyophilized to produce the compound 40c (1.5 mg, 23%) as white solid. EI-MS m/z: ½[M+H]$^+$ 1808.6.

Example 60. Preparation of Compound 41c

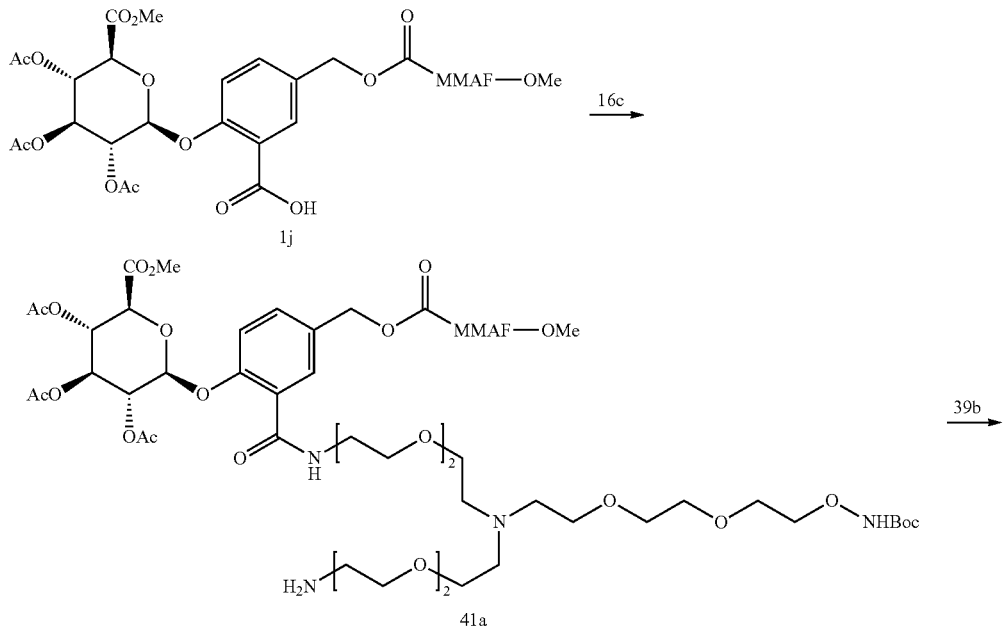

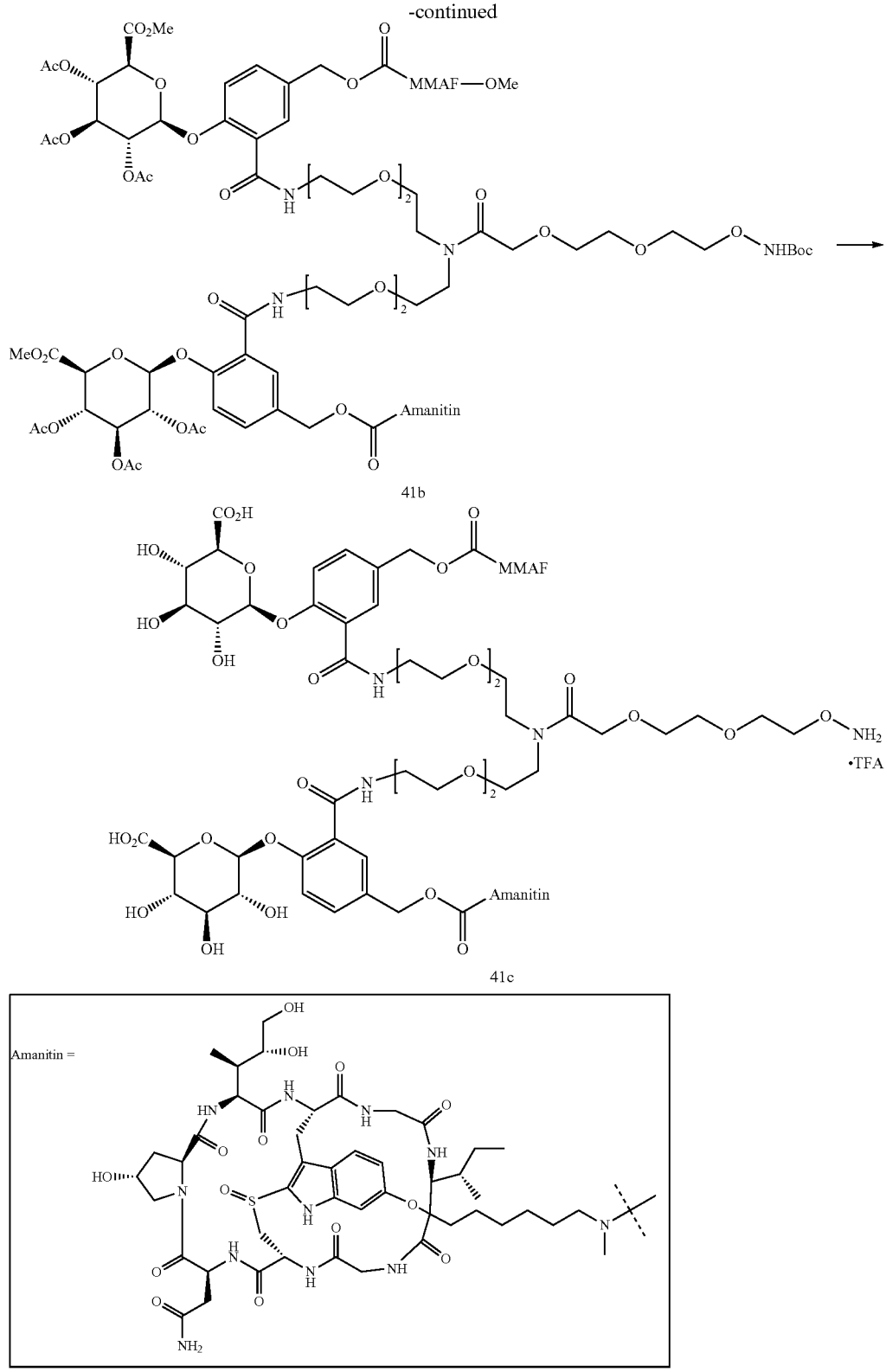

Preparation of Compound 41a

DIPEA (0.116 mL, 0.66 mmol) and PyBOP (127 mg, 0.24 mmol) were added to a stirred mixture of compound 16c (280 mg, 0.22 mmol) and compound 1j (587 mg, 1.10 mmol) in DMF (10 mL). After stirring at room temperature for 2 hours under $N_2$, the reaction mixture was diluted with $H_2O$ (200 mL) and extracted with EtOAc (2×100 mL). The combined organic layers were dried over anhydrous $MgSO_4$, filtered and concentrated. The crude product was purified by column chromatography to produce the compound 41a (250 mg, 64%). EI-MS m/z: ½[M+H]+ 883.2, [M+H]+ 1766.
Preparation of Compound 41b DIPEA (0.0017 mL, 0.0096 mmol) and PyBOP (2.0 mg, 0.0038 mmol) were added to a stirred mixture of compound 41a (5.7 mg, 0.0032 mmol) and compound 39b (5.0 mg, 0.0032 mmol) in DMF (0.5 mL). After stirring at room temperature for 3 hours under $N_2$, the reaction mixture was dissolved in MeCN (1 mL) and purified by HPLC, which produced the compound 41b (8.0 mg, 75%). EI-MS m/z: ½[M+H]+ 1645.
Preparation of Compound 41c To a solution of compound 41b (8.0 mg, 0.0024 mmol) in MeOH (0.5 mL) was added LiOH monohydrate (1.2 mg, 0.028 mmol) in $H_2O$ (0.1 mL) at 0° C. After 2 hours at 0° C., the reaction mixture was neutralized using 2 N aq. HCl solution and concentrated under reduced pressure. The resulting residue was diluted with DCM (2 mL) and $H_2O$ (3 drops). Then TFA (0.1 mL) was added at 0° C. After 2 hours at 0° C., the solvent and excess TFA were removed by $N_2$ flow. Then the residue was dissolved in DMSO (1 mL) and purified by HPLC. Pure fractions with the same retention time were combined and lyophilized to produce the compound 41c (3.1 mg, 44%) as white solid. EI-MS m/z: ½[M+H]+ 1448, ½[M+Na]+ 1459.

Example 61. Preparation of Compound 42d

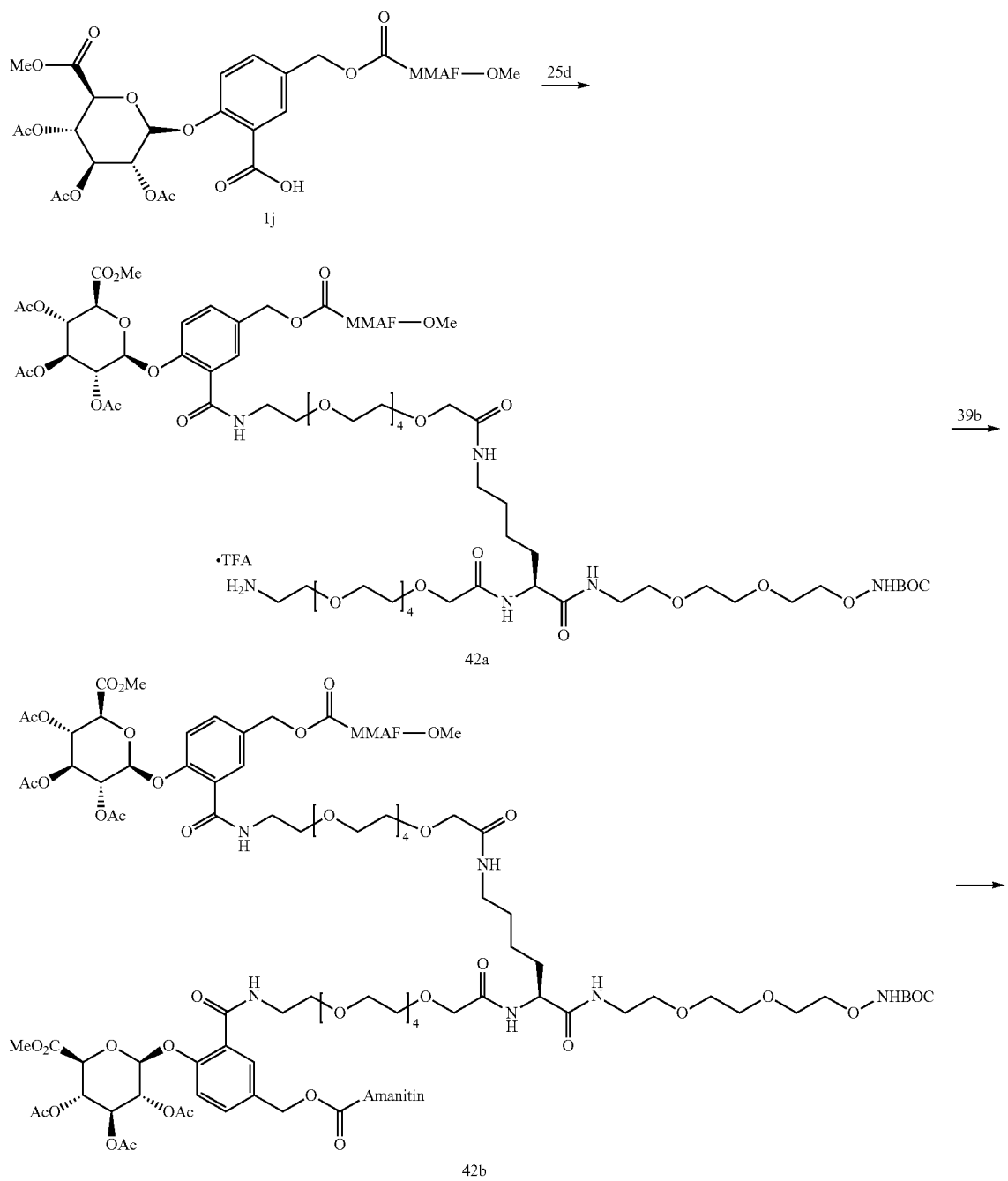

-continued
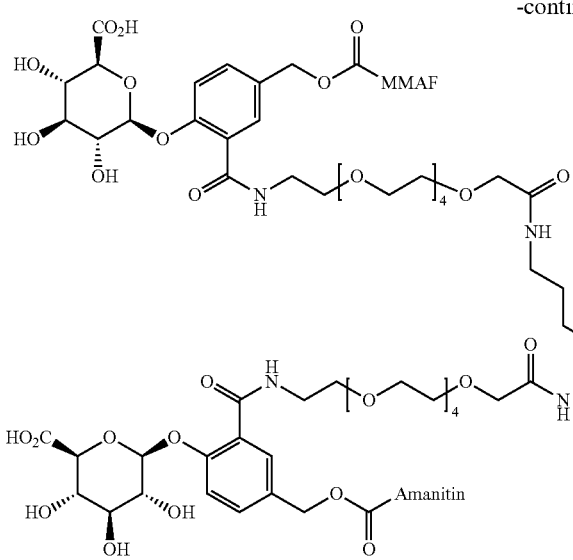
42c
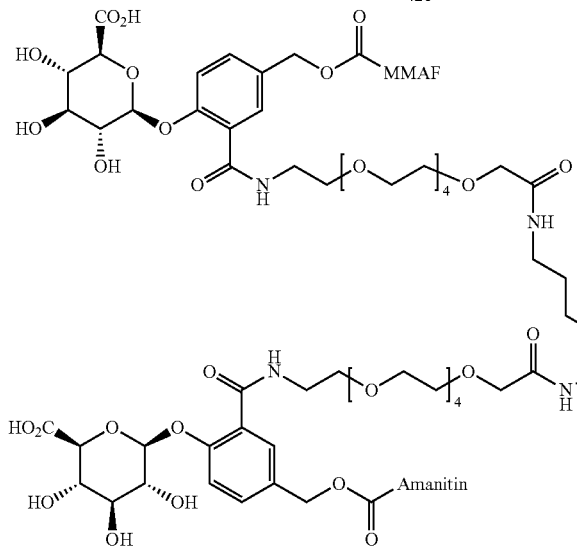
42d
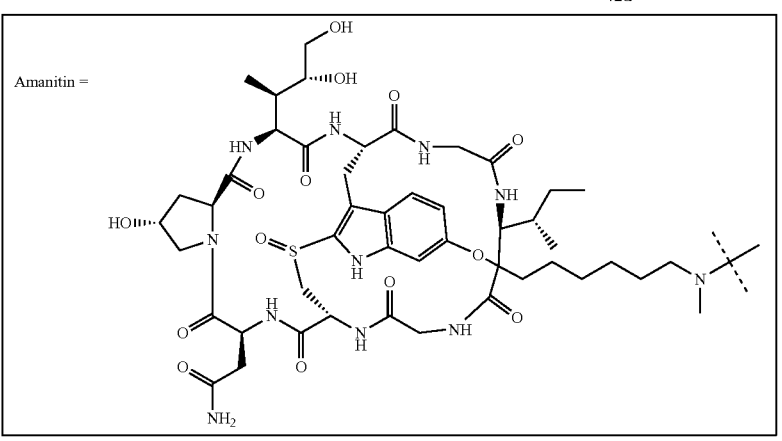
Preparation of Compound 42a
DIPEA (0.026 mL, 0.23 mmol) and HBTU (22 mg, 0.06 mmol) were added to a stirred mixture of compound 1j (60 mg, 0.048 mmol) and compound 25d (214 mg, 0.19 mmol) in DMF (3 mL). After stirring at room temperature for 14 hours under $N_2$, the reaction mixture was dissolved in DMSO (1.0 mL) and purified by HPLC, which produced the compound 42a (64 mg, 58%). EI-MS m/z: [M+H]$^+$ 2286.8.

Preparation of Compound 42b

DIPEA (0.011 mL, 0.06 mmol) and HBTU (14 mg, 0.036 mmol) were added to a stirred mixture of compound 42a (68 mg, 0.03 mmol) and compound 39b (46 mg, 0.03 mmol) in DMF (3 mL). After stirring at room temperature for 14 hours under $N_2$, the reaction mixture was dissolved in DMSO (1.0 mL) and purified by HPLC, which produced the compound 42b (60 mg, 52%). EI-MS m/z: ½[M+H]$^+$ 1906.3.

Preparation of Compound 42c

To a solution of compound 42b (60 mg, 0.016 mmol) in MeOH (2 mL) was added LiOH monohydrate (5 mg, 0.126 mmol) in $H_2O$ (2 mL) at 0° C. After 2 hours at 0° C., the reaction mixture was neutralized using acetic acid and concentrated under reduced pressure. Then the residue was dissolved in DMSO (1 mL) and purified by prep. HPLC, which produced the compound 42c (37 mg, 65%). EI-MS m/z: ½[M+H]$^+$ 1759.3.

Preparation of Compound 42d

TFA (0.3 mL) was added to a stirred solution of compound 42c (37 mg, 0.01 mmol) in DCM (3 mL). After stirring at 0° C. for 2 hours, the solvent and excess TFA were removed by $N_2$ flow. Then the residue was dissolved in DMSO (1 mL) and purified by HPLC. Pure fractions with the same retention time were combined and lyophilized to produce the compound 42d (15 mg, 45%) as white solid. EI-MS m/z: ½[M+H]$^+$ 1659.6.

Example 62. Preparation of Compound 43i

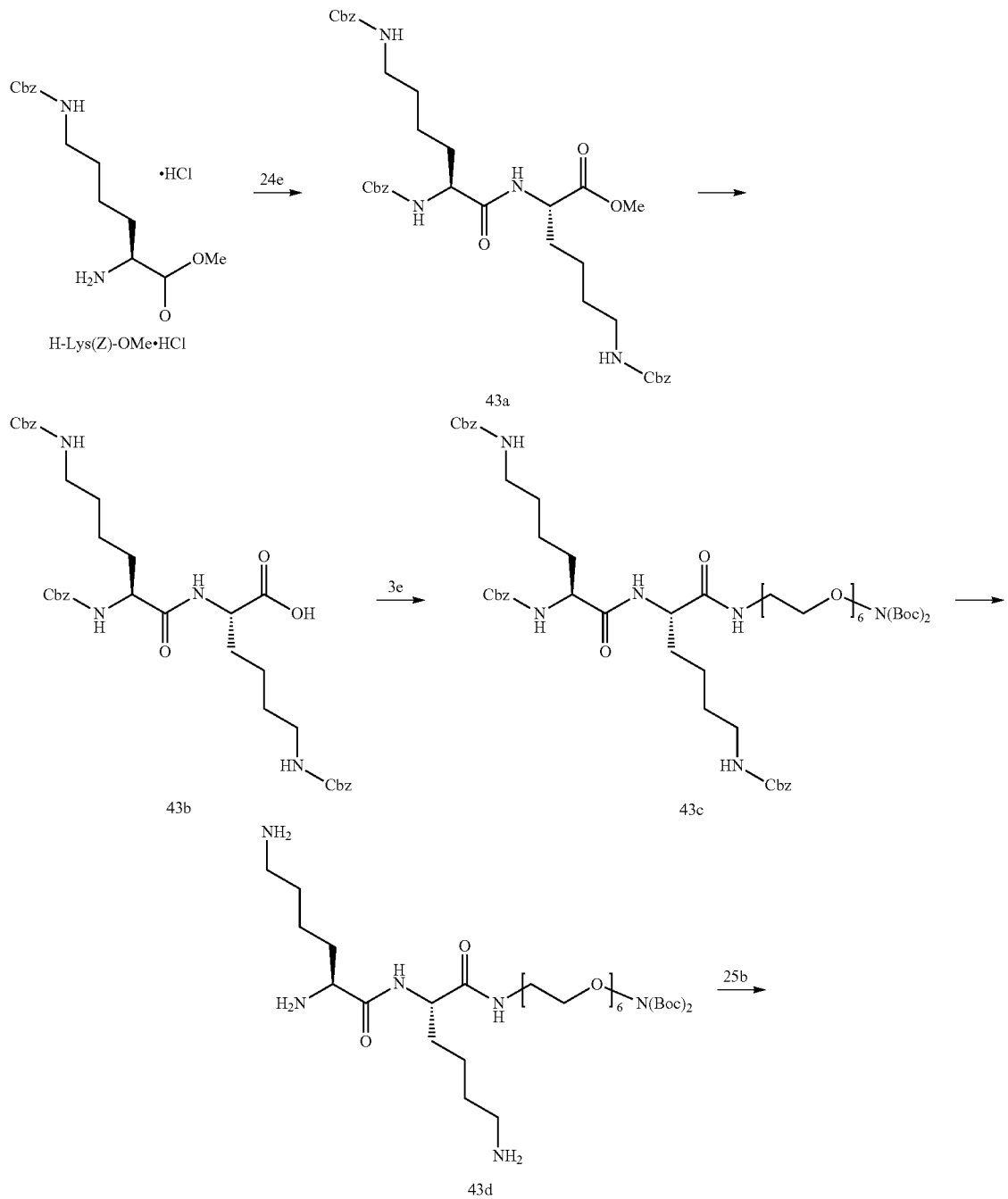

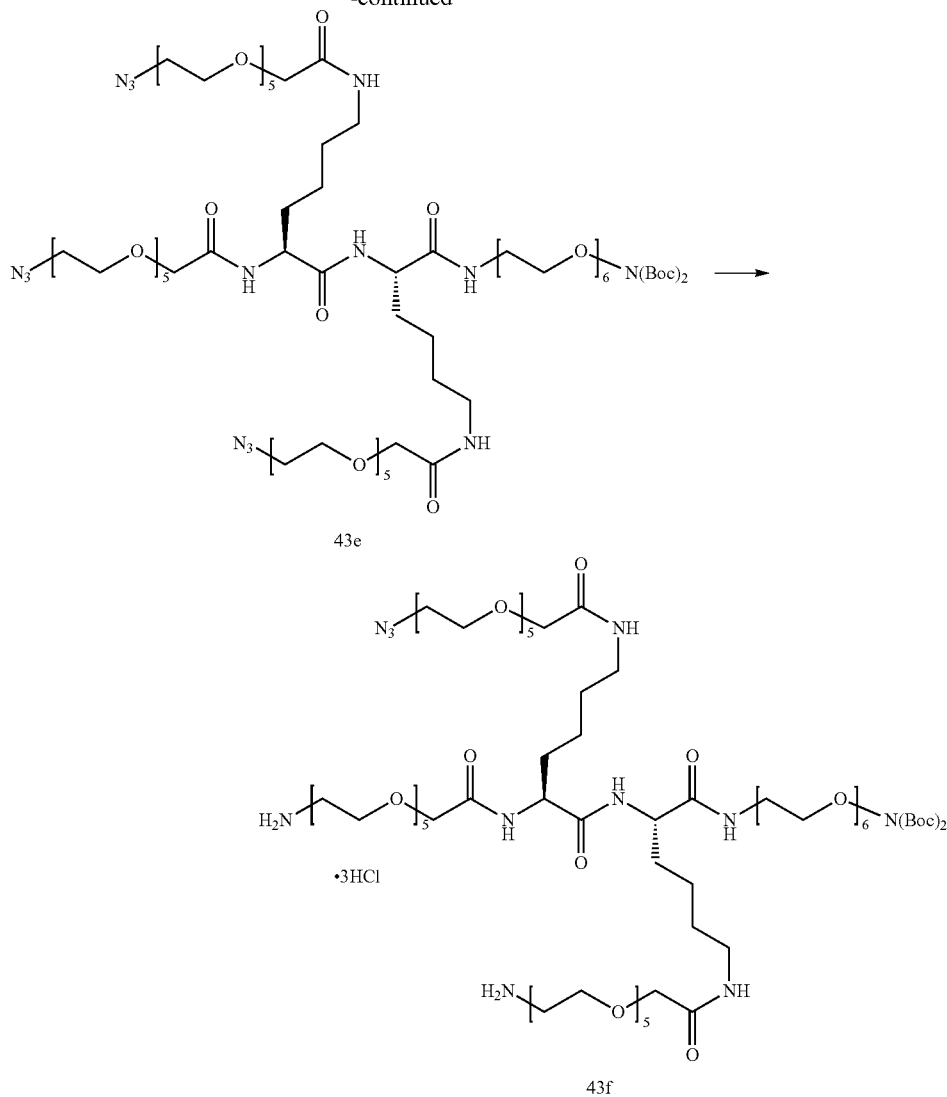

Preparation of Compound 43a

DIPEA (10.4 mL, 23.8 mmol) and HBTU (13.5 g, 35.7 mmol) were added to a stirred mixture of H-Lys(z)-OMe hydrochloride (7.0 g, 23.8 mmol) and compound 24e (9.86 mg, 23.8 mmol) in DMF (50 mL). After stirring at room temperature for 8 hours under $N_2$, the reaction mixture was diluted water (100 mL) and extracted with EtOAc (3×50 mL). The combined organic layers were washed with 0.5 N aq. HCl (50 mL), saturated aq. $NaHCO_3$ (50 mL) and brine (50 mL) sequentially, and dried over anhydrous $Na_2SO_4$. After filtration and concentration under reduced pressure, the resulting crude product was purified by column chromatography to produce the compound 43a (9.3 g, 57%). $^1$H-NMR (400 MHz, DMSO-$d_6$) δ 8.22 (d, 1H), 7.37-7.29 (m, 15H), 7.22 (m, 2H), 5.00 (s, 6H), 4.18 (m, 1H), 4.00 (m, 1H), 3.59 (s, 3H), 2.96 (m, 4H), 1.67-1.50 (m, 4H), 1.38-1.29 (m, 4H), 1.19-1.18 (m, 4H). EI-MS m/z: [M+Na]$^+$ 712.96.

Preparation of Compound 43b

To a solution of compound 43a (9.3 g, 13.5 mmol) in THF:MeOH:$H_2O$ (60 mL:30 mL:30 mL) was added LiOH monohydrate (1.13 g, 26.9 mmol) at 0° C. under $N_2$. After 2 hours, the reaction mixture was acidified with 1 N aq. HCl until pH 4, and extracted with EtOAc (3×100 mL). The combined organic layers were dried over anhydrous $Na_2SO_4$. Filtration and concentration under reduced pressure provided compound 43b (9.1 g, crude), which was used without further purification. EI-MS m/z: [M+H]$^+$ 677.48, 2[M+H]$^+$ 1353.82.

Preparation of Compound 43c

DIPEA (1.47 mL, 8.44 mmol), HOBt (484 mg, 3.58 mmol) and EDC·HCl (809 mg, 4.22 mmol) were added to a stirred mixture of compound 43b (2.5 g, 3.71 mmol) and compound 3e (1.8 g, 3.38 mmol) in DMF (20 mL). After stirring at room temperature for 14 hours under $N_2$, the reaction mixture was poured into water (50 mL) and extracted with EtOAc (3×50 mL). The combined organic layers were washed with 0.5 N aq. HCl (50 mL), saturated aq. $NaHCO_3$(50 mL) and brine (50 mL) sequentially, and dried over anhydrous $Na_2SO_4$. After filtration and concentration under reduced pressure, the resulting residue was purified by column chromatography to produce the compound 43c (2.3 g, 59%). EI-MS m/z: [M+H]$^+$ 1155.92, [M+H-Boc]$^+$1055.83.

Preparation of Compound 43d

To a stirred mixture of compound 43c (2.3 g, 1.99 mmol) and Pd/C (10 wt. %, 424 mg 3.98 mmol) in MeOH (200 mL) was added HCl (4 N in 1,4-dioxane, 0.99 mL, 3.98 mmol). After stirring at room temperature for 2 hours under hydrogen, the reaction mixture was filtered through a celite pad and washed with MeOH (100 mL). The filtrate was concentrated to produce the compound 43d (1.5 g, crude), which was used without further purification. EI-MS m/z: $[M+H]^+$ 753.29.

Preparation of Compound 43e

DIPEA (0.14 mL, 0.80 mmol), HOBt (59 mg, 0.43 mmol) and EDC HCl (102 mg, 0.53 mmol) were added to a stirred mixture of compound 43d (2.5 g, 3.71 mmol) and compound 25b (150 g, 0.46 mmol) in DMF (5 mL). After stirring at room temperature for 14 hours under $N_2$, the reaction mixture was poured into water (50 mL) and extracted with EtOAc (3×50 mL). The combined organic layers were washed with 1 N aq. HCl (30 mL), saturated aq. $NaHCO_3$ (30 mL) and brine (30 mL) sequentially, and dried over anhydrous $Na_2SO_4$. After filtration and concentration under reduced pressure, the resulting crude product was purified by column chromatography to produce the compound 43e (100 mg, 45%) as colorless oil. EI-MS m/z: $[M+Na]^+$ 1685.11, $½[M+H-Boc]^+$ 731.82.

Preparation of Compound 43f

To a stirred mixture of compound 43e (100 mg, 0.06 mmol) and Pd/C (10 wt. %, 20 mg 0.192 mmol) in MeOH (20 mL) was added HCl (4 N in 1,4-dioxane, 0.045 mL, 0.18 mmol). After stirring at room temperature for 2 hours under hydrogen, the reaction mixture was filtered through a celite pad and washed with MeOH (30 mL). The filtrate was concentrated to produce the compound 43f (95 mg) as brown foam, which was used without further purification. EI-MS m/z: $[M+H]^+$ 1586.30, $½[M+H]^+$ 793.02.

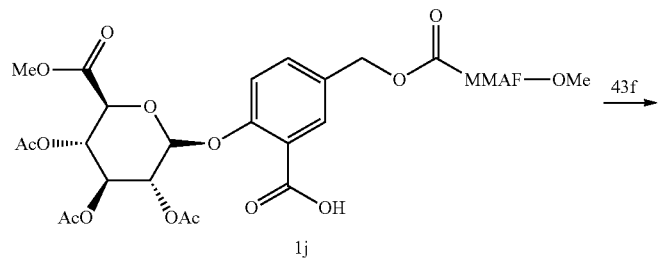

1j

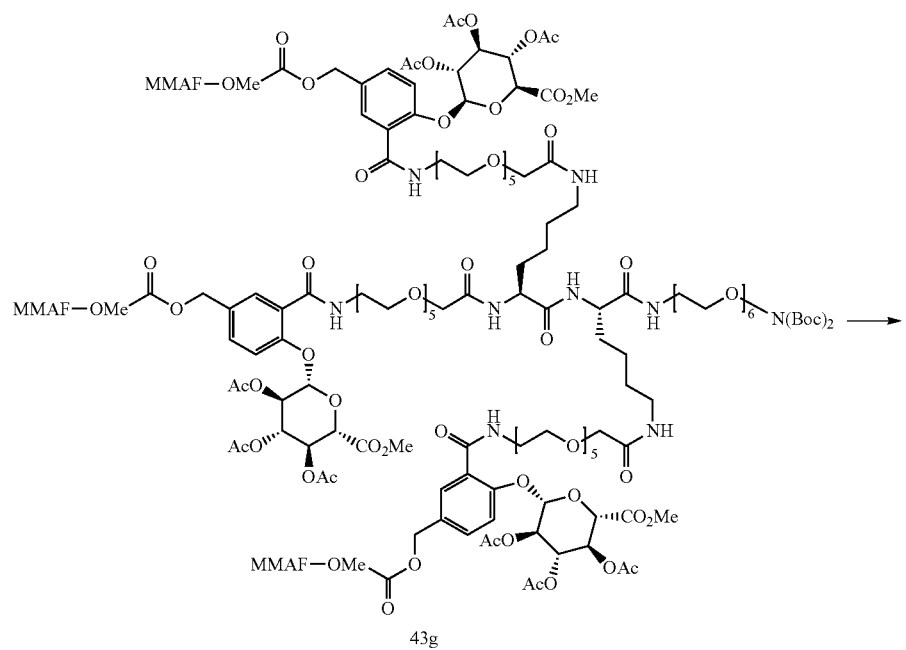

43g

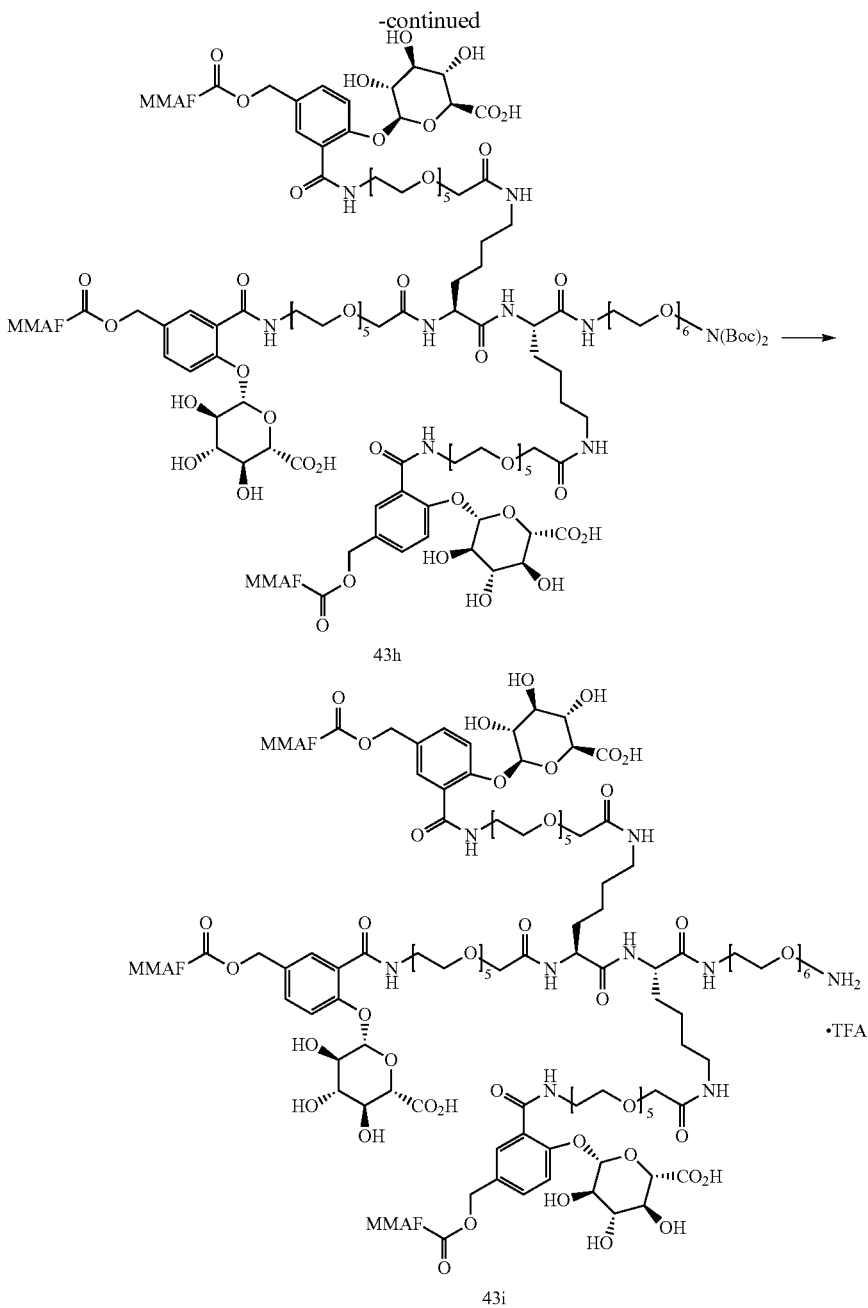

43h

43i

Preparation of Compound 43g

DIPEA (0.030 mL, 0.170 mmol) and HBTU (36 mg, 0.094 mmol) were added to a stirred mixture of compound 43f (45 mg, 0.028 mmol) and compound 1j (114 mg, 0.091 mmol) in DMF (3 mL). After stirring at room temperature for 16 hours under $N_2$, the reaction mixture was dissolved in $H_2O$/DMSO (1.5 mL/1.5 mL) and purified by HPLC. Pure fractions with the same retention time were combined and concentrated to produce the compound 43g (31 mg, 21%). EI-MS m/z: ⅓[M+H-Boc]$^+$1705.74, ¼[M+H-2Boc]$^+$ 1254.79.

Preparation of Compound 43h

To a solution of compound 43g (31 mg, 0.006 mmol) in MeOH (1 mL) was added LiOH monohydrate (3.7 mg, 0.088 mmol) in $H_2O$ (1 mL) at −20° C. After stirring for 2 hours at −20° C., the reaction mixture was neutralized using acetic acid and concentrated under reduced pressure. Then the reaction mixture was dissolved in $H_2O$/DMSO (1.5 mL/1.5 mL) and purified by HPLC, which produced the compound 43h (18 mg, 64%) as white solid. EI-MS m/z: ⅓[M+H-Boc]$^+$1735.19, ¼[M+H]$^+$ 1301.95, ⅕[M+H-Boc]$^+$ 1021.71.

Preparation of Compound 43i

TFA (0.3 mL) was added to a stirred solution of compound 43h (18 mg, 0.004 mmol) in DCM (1.0 mL) at 0° C. After stirring for 1 hour, the solvent and excess TFA were removed by $N_2$ flow. Then the residue was dissolved in $H_2O$/MeCN (1 mL/1 mL) and purified by HPLC. Pure fractions with the same retention time were combined and lyophilized to produce the compound 43i (6 mg, 33%) as white solid. EI-MS m/z: ⅓[M+H]⁺ 1547.75, ¼[M+H]⁺ 1161.14.
Example 63. Preparation of Compound 43j
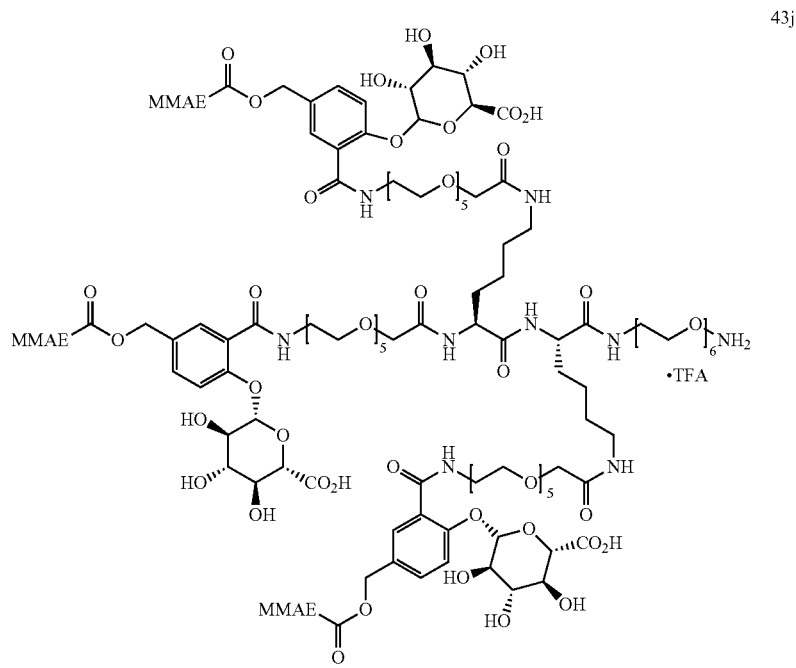
Compound 43j was prepared from compound 1i and compound 43f by a similar method of preparing compound 43i in Example 62. EI-MS m/z: ⅓[M+H]⁺ 1532.37, ¼[M+H]⁺ 1149.69.
Example 64. Preparation of Compound 44i
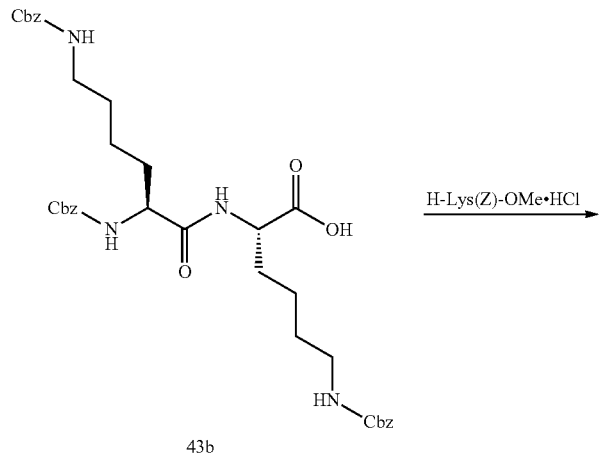

299                                    300
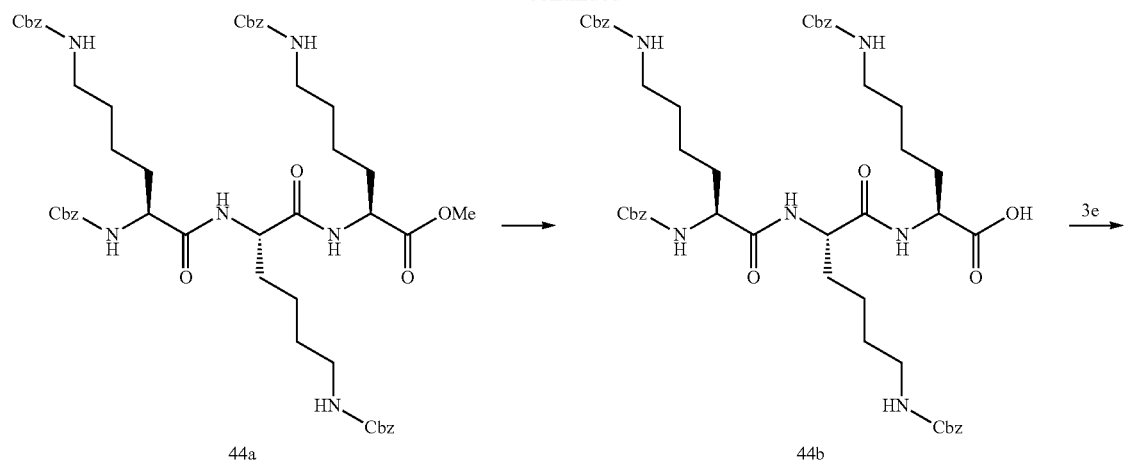
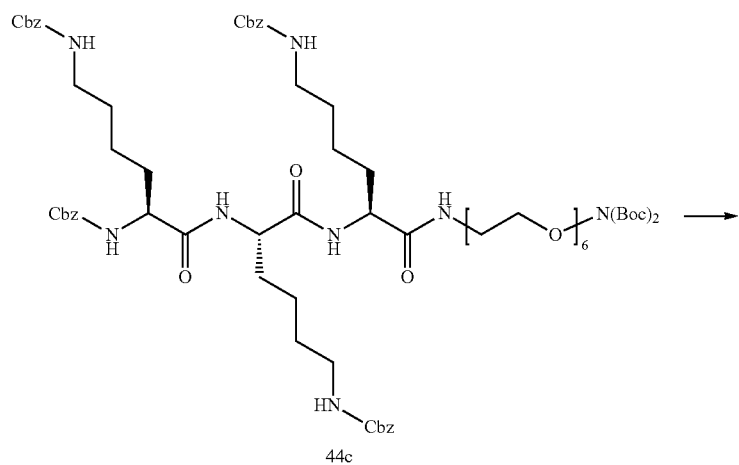
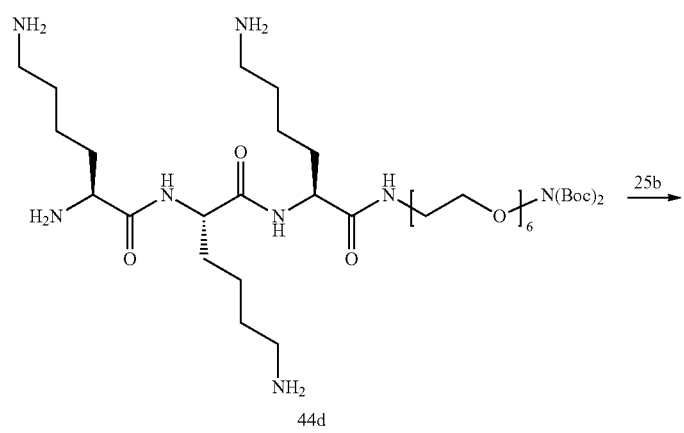

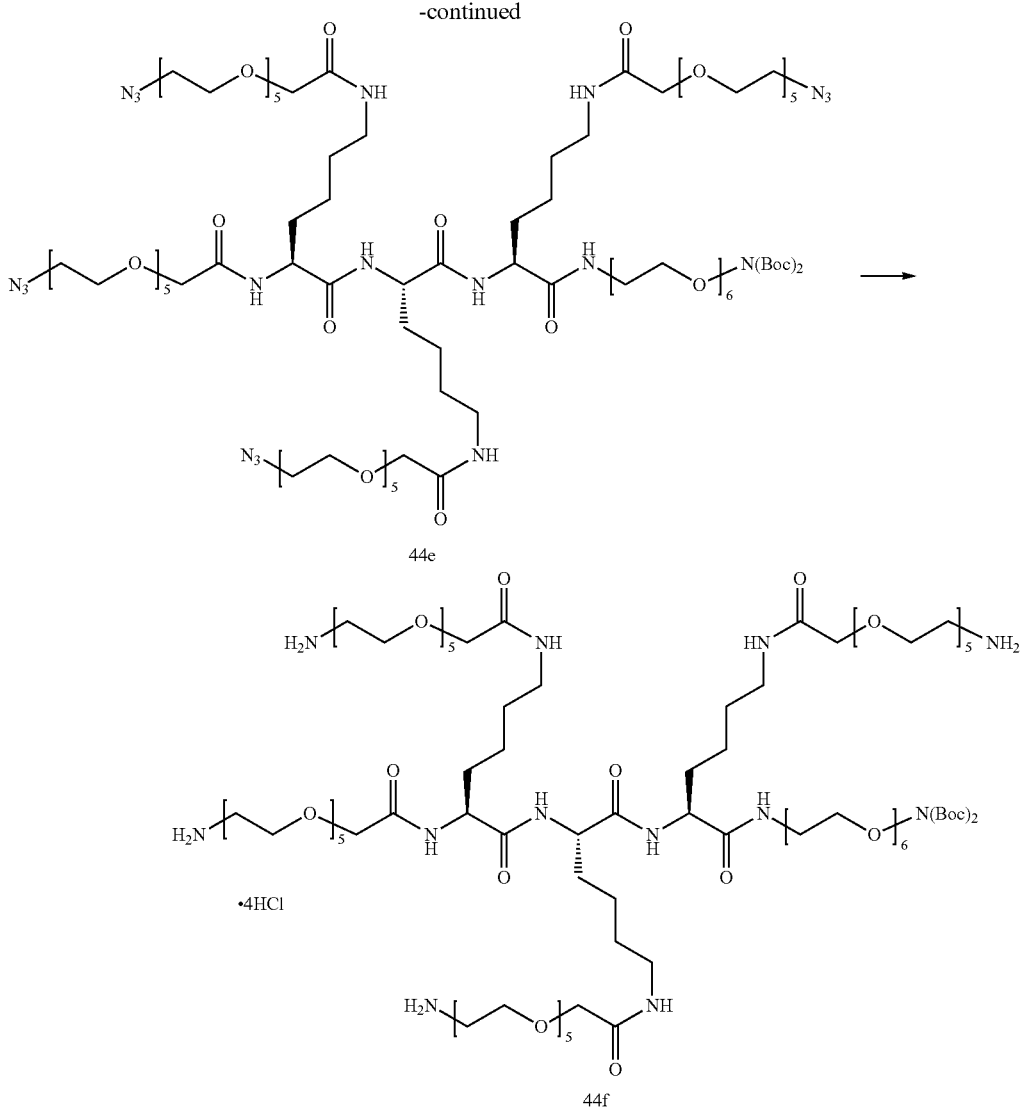

Preparation of Compound 44a

DIPEA (1.9 mL, 11.0 mmol) and HBTU (2.5 g, 6.64 mmol) were added to a stirred mixture of compound H-Lys(z)-OMe hydrochloride (1.3 g, 4.43 mmol) and compound 43b (3.0 g, 4.43 mmol) in DMF (30 mL). After stirring at room temperature for 14 hours under $N_2$, the reaction mixture was diluted water (100 mL) and extracted with EtOAc (3×50 mL). The combined organic layers were washed with 0.5 N aq. HCl (50 mL), saturated aq. $NaHCO_3$ (50 mL) and brine (50 mL), and dried over anhydrous $Na_2SO_4$. After filtration and concentration under reduced pressure, the resulting residue was purified by column chromatography to produce the compound 44a (3.9 g, 93%). EI-MS m/z: [M+H]$^+$ 953.42.

Preparation of Compound 44b

To a solution of compound 44a (2.1 g, 2.20 mmol) in THF:MeOH:$H_2O$ (24 mL:8 mL:8 mL) was added LiOH monohydrate (185 mg, 4.40 mmol) at room temperature under $N_2$. After 2 hours, the reaction mixture was acidified with 1 N aq. HCl until pH 4, and extracted with EtOAc (3×50 mL). The combined organic layers were dried over anhydrous $Na_2SO_4$. Filtration and concentration under reduced pressure provided compound 44b (2.0 g), which was used without further purification. EI-MS m/z: [M+H]$^+$ 939.35, [M+Na]$^+$961.37.

Preparation of Compound 44c

DIPEA (0.93 mL, 5.33 mmol) and HBTU (1.21 g, 3.20 mmol) were added to a stirred mixture of compound 44b (2.0 g, 2.13 mmol) and compound 3e (1.14 g, 2.13 mmol) in DMF (20 mL). After stirring at room temperature for 14 hours under $N_2$, the reaction mixture was poured into water (50 mL) and extracted with EtOAc (3×50 mL). The combined organic layers were washed with 0.5 N aq. HCl (50 mL), saturated aq. $NaHCO_3$ (50 mL) and brine (50 mL) sequentially, and dried over anhydrous $Na_2SO_4$. After filtration and concentration under reduced pressure, the resulting residue was purified by column chromatography to produce the compound 44c (2.60 g, 86%). EI-MS m/z: [M+H]$^+$ 1418.44, [M+Na]$^+$1440.39, [M+H-Boc]$^+$1318.47.

Preparation of Compound 44d

To a stirred mixture of compound 44c (2.60 g, 1.83 mmol) and Pd/C (10 wt. %, 781 mg 7.34 mmol) in MeOH (50 mL) was added HCl (4 N in 1,4-dioxane, 0.9 mL, 3.67 mmol). And then the reaction was stirred at room temperature for 2 hours under hydrogen. The reaction mixture was filtered through a celite pad and washed with MeOH (50 mL). The filtrate was concentrated to produce the compound 44d (1.73 g) as yellow form, which was used without further purification. EI-MS m/z: [M+H]+ 881.90.

Preparation of Compound 44e

DIPEA (1.58 mL, 9.08 mmol) and HBTU (2.58 g, 6.81 mmol) were added to a stirred mixture of compound 44d (1.0 g, 1.13 mmol) and compound 25b (1.82 g, 5.67 mmol) in DMF (20 mL). After stirring at room temperature for 14 hours under N$_2$, the reaction mixture was diluted water (100 mL) and extracted with EtOAc (3×50 mL). The combined organic layers were washed with 0.5 N HCl (50 mL), saturated aq. NaHCO$_3$ (50 ML) and brine (50 mL) sequentially, and dried over anhydrous Na$_2$SO$_4$. After filtration and concentration under reduced pressure, the resulting residue was purified by column chromatography to produce the compound 44e (848 mg, 36%). EI-MS m/z: ½[M+H-2Boc]+ 947.63.

Preparation of Compound 44f

To a stirred mixture of compound 44e (848 mg; 0.40 mmol) and Pd/C (10 wt. %, 172 mg 1.62 mmol) in MeOH (50 mL) was added HCl (4 N in 1,4-dioxane, 0.4 mL, 1.62 mmol). After stirring at room temperature for 2 hours under hydrogen, the reaction mixture was filtered through a celite pad and washed with MeOH (50 mL). The filtrate was concentrated to produce the compound 44f (625 mg, crude), which was used without further purification. EI-MS m/z: ½[M+H]+ 996.40, ⅓ [M+H]+ 664.59

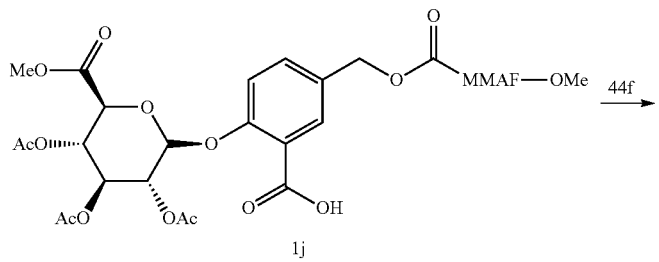

1j

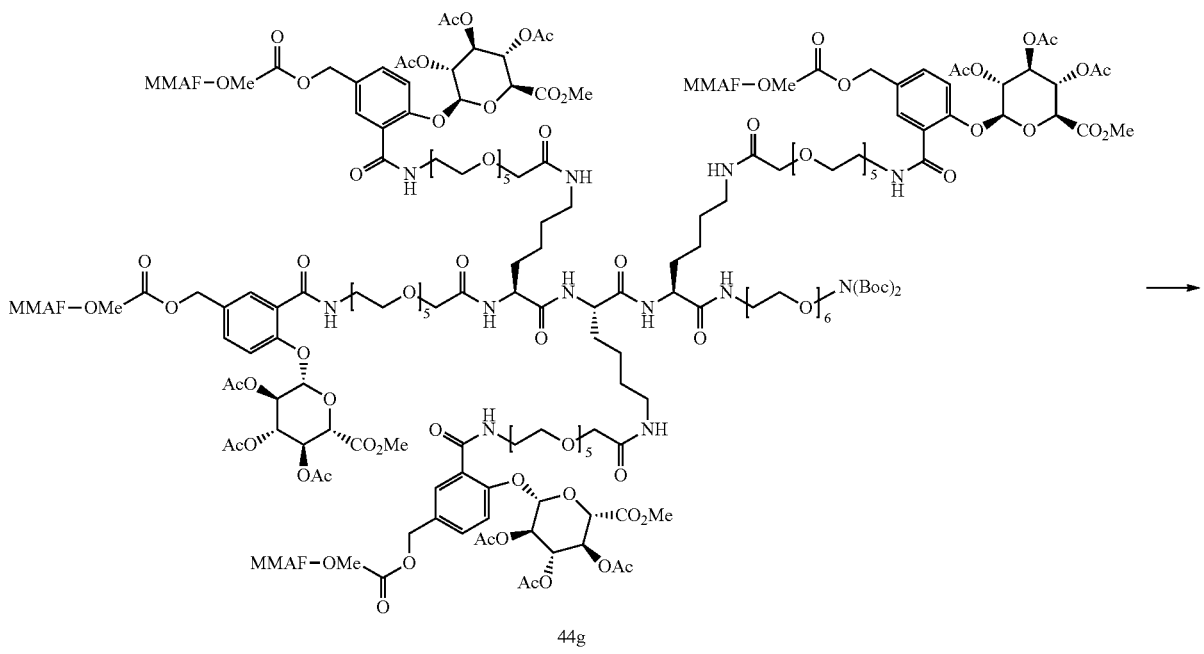

44g

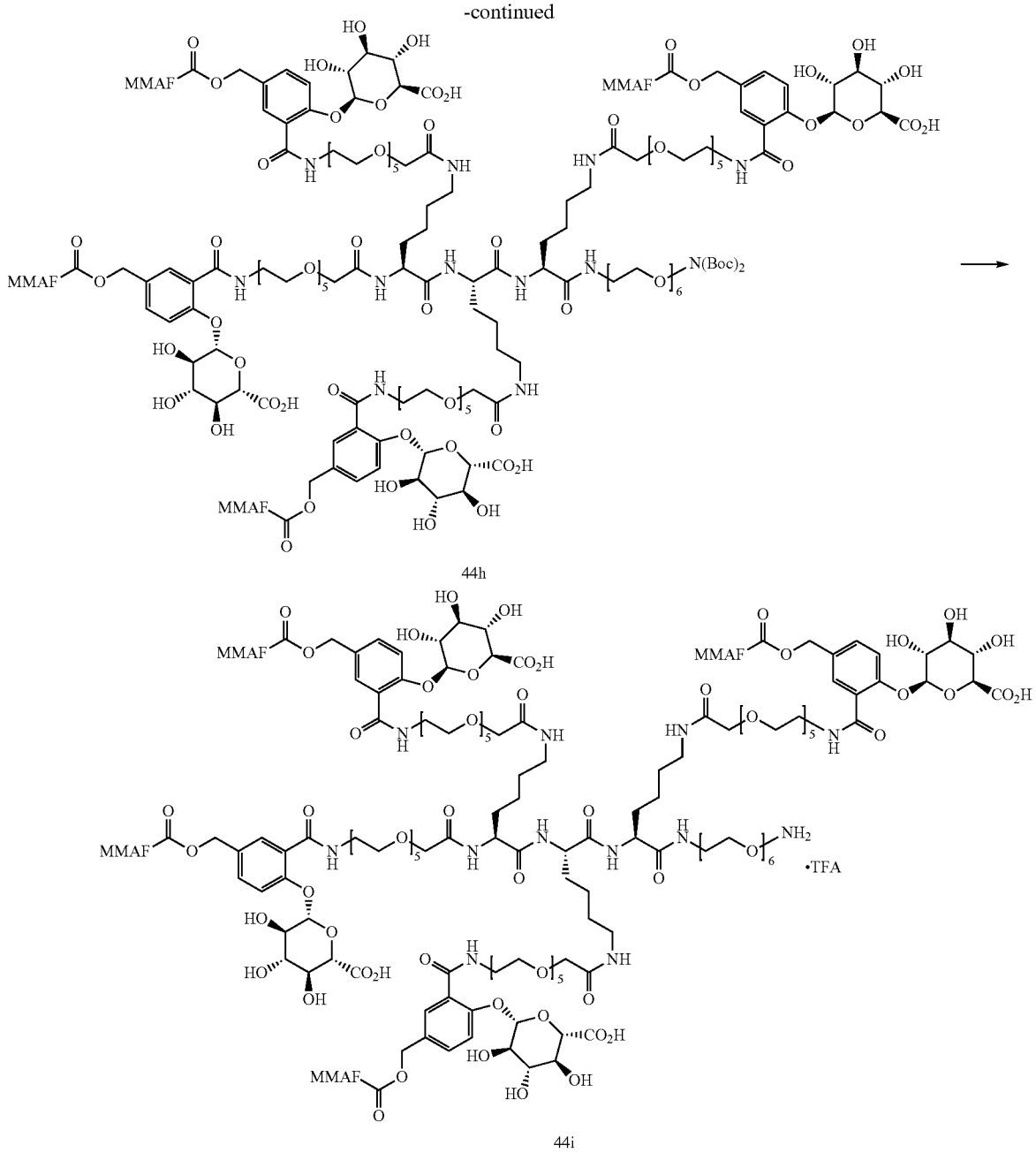

Preparation of Compound 44g

DIPEA (0.067 mL, 0.386 mmol) and HBTU (110 mg, 0.289 mmol) were added to a stirred mixture of compound 44f (96 mg, 0.048 mmol) and compound 1j (303 mg, 0.24 mmol) in DMF (3 mL). After stirring at room temperature for 16 hours under $N_2$, the reaction mixture was dissolved in $H_2O$/DMSO (1.5 mL/1.5 mL) and purified by HPLC. Pure fractions with the same retention time were combined and concentrated to produce the compound 44g (67 mg, 20%). EI-MS m/z: ⅓[M+H]$^+$ 2315.93, ¼[M+H]$^+$ 1737.60, ⅕[M+H]$^+$ 1390.37.

Preparation of Compound 44h

To a solution of the compound 44g (67 mg, 0.009 mmol) in MeOH (1 mL) was added LiOH monohydrate (8.1 mg, 0.192 mmol) in $H_2O$ (1 mL) at −20° C. After stirring for 2 hours at −20° C., the reaction mixture was neutralized using acetic acid and concentrated under reduced pressure. Then the reaction mixture was dissolved in $H_2O$/DMSO (1.5 mL/1.5 mL) and purified by HPLC, which produced the compound 44h (27.9 mg, 45%) as white solid. EI-MS m/z: ⅓[M+H]$^+$ 2110.24, ¼[M+H]$^+$ 1582.97, ¼[M+H-Boc]$^+$ 1557.91.

Preparation of Compound 44i

TFA (0.3 mL) was added to a stirred solution of compound 44h (27.9 mg, 0.004 mmol) in DCM (1.0 mL) at 0° C. After stirring for 1 hour, the solvent and excess TFA were removed by $N_2$ flow. Then the residue was dissolved in $H_2O$/MeCN (1 mL/1 mL) and purified by HPLC. Pure fractions with the same retention time were combined and lyophilized to produce the compound 44i (13.6 mg, 50%) as white solid. EI-MS m/z: ⅓[M+H]⁺ 2043.49, ¼[M+H]⁺ 1532.96, ⅕[M+H]⁺ 1226.62.

Example 65. Preparation of Compound 44j

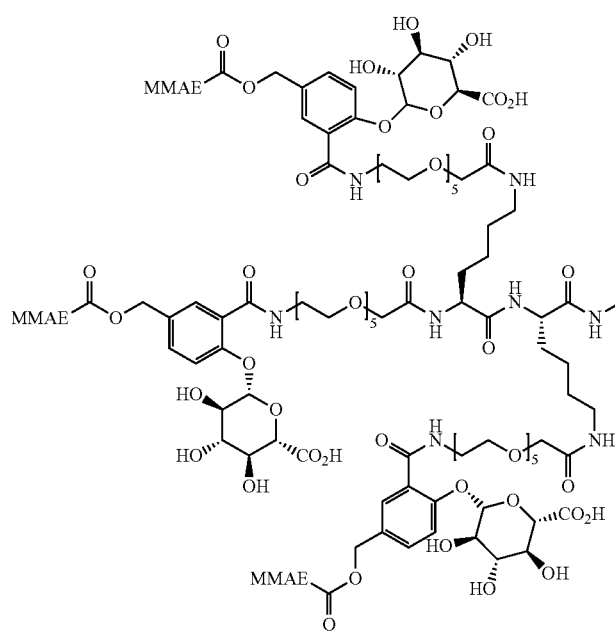
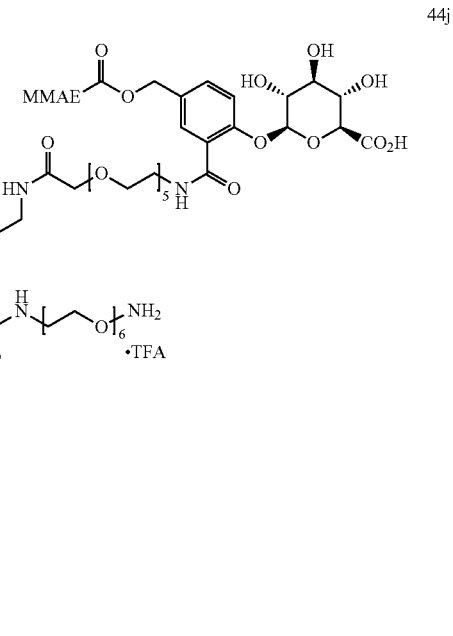

Compound 44j was prepared from compound 1i and compound 44f by a similar method of preparing compound 44i in Example 64. EI-MS m/z: ⅓[M+H]⁺ 2025.37, ¼[M+H]⁺ 1519.10, ⅕[M+H]⁺ 1215.60.

Example 66. Preparation of Compound 45k

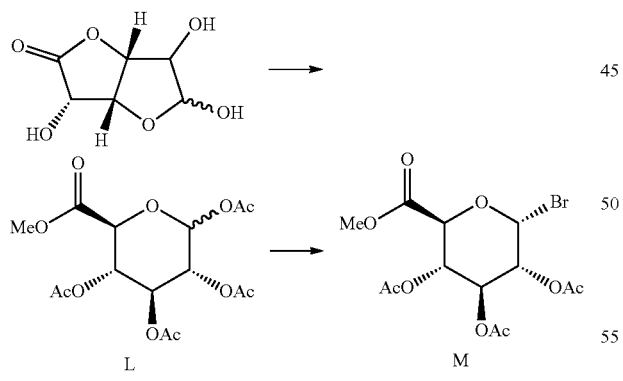

Preparation of Compound L

D-Glucurono-6,3-lactone (25.0 g, 141.9 mmol) was dissolved in MeOH (250 mL) at room temperature under nitrogen, and a solution of NaOH (141 mg) in MeOH (100 mL) was slowly added thereto. After stirring for 24 hours, the reaction mixture was concentrated under reduced pressure, and then pyridine (66 mL) and acetic anhydride (71 mL) were added below 10° C. After stirring at room temperature for 4 hours, the reaction mixture was concentrated under reduced pressure and was subjected to column chromatography, which produced the compound L (41.6 g, 77%). $^1$H-NMR (600 MHz, CDCl$_3$) δ 5.77 (d, J=7.8 Hz, 1H), 5.31 (t, J=9.6 Hz, 1H), 5.24 (t, J=9.6 Hz, 1H), 5.14 (m, 1H), 4.17 (d, J=9 Hz, 1H), 3.74 (s, 3H), 2.12 (s, 3H), 2.04 (m, 9H).

Preparation of Compound M

Compound L (10.0 g, 26.6 mmol) was dissolved in HBr (33% in AcOH, 20 mL) at 0° C. under nitrogen. The reaction mixture was warmed to room temperature. After stirring for 2 hours, toluene (50 mL) was added thereto, and the mixture was concentrated under reduced pressure. The resulting residue was purified by column chromatography to produce the compound M (10.9 g, 99%). $^1$H-NMR (600 MHz, CDCl$_3$) δ 6.64 (d, J=3.6 Hz, 1H), 5.61 (t, J=3.6 Hz; 1H), 5.24 (t, J=3.6 Hz, 1H), 4.85 (m, 1H), 4.58 (d, d, J=10.2 Hz, 1H), 3.76 (s, 3H), 2.10 (s, 3H), 2.06 (s, 3H), 2.05 (s, 3H).

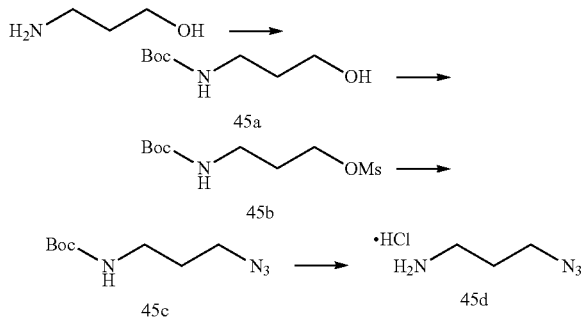

Preparation of Compound 45a

3-Amino-1-propanol (3.0 g, 66.57 mmol) was dissolved in DCM (150 mL) at 0° C. under nitrogen, and di-tert-butyl dicarbonate (16 g, 73.23 mmol) was added thereto. The obtained mixture was stirred at room temperature for 12 hours. After the reaction was completed, the solvent was concentrated under reduced pressure. The residue was subjected to column chromatography, which produced the compound 45a (6.4 g, 92%). ¹H-NMR (400 MHz, CDCl₃) δ 4.78 (s, 1H), 3.65 (m, 2H), 3.30 (m, 2H), 2.90 (s, 1H), 1.68 (m, 2H), 1.48 (s, 9H).

Preparation of Compound 45b

Compound 45a (6.04 g, 34.47 mmol) and triethylamine (14.4 mL, 103.4 mmol) were dissolved in THF at 0° C. under nitrogen and then, slowly treated with methanesulfonic anhydride (7.21 g, 41.36 mmol). The obtained mixture was stirred at room temperature under nitrogen for 12 hours. After the reaction was completed, the solvent was concentrated under reduced pressure. The residue was subjected to column chromatography, which produced the compound 45b (9.01 g, 98%). ¹H-NMR (400 MHz, CDCl₃) δ 4.73 (s, 1H), 4.30 (t, J=5.9 Hz, 2H), 3.31-3.24 (m, 2H), 3.04 (s, 3H), 1.94 (t, J=6.1 Hz, 2H), 1.44 (s, 9H).

Preparation of Compound 45c

Compound 45b (3.0 g, 11.84 mmol) was dissolved in DMF (40 mL) at room temperature under nitrogen, and then treated with NaN₃ (924 mg, 14.21 mmol), and the obtained mixture was stirred at 60° C. for 12 hours. After the reaction was completed, EtOAc (50 mL), distilled water (50 mL), and 1 N aq. HCl (5 mL) were added thereto. The organic layer was dried over anhydrous Na₂SO₄, filtered and concentrated under reduced pressure. The residue was subjected to column chromatography, which produced the compound 45c (2.3 g, 99%). ¹H-NMR (600 MHz, CDCl₃) δ 4.63 (s, 1H), 3.36 (t, J=6.6 Hz, 2H), 3.24-3.18 (m, 2H), 1.80-1.75 (m, 2H), 1.45 (s, 9H).

Preparation of Compound 45d

Compound 45c (3.8 g, 18.98 mmol) was dissolved in DCM (10 mL) at 0° C. under nitrogen, and then 4 M-HCl in dioxane (10 mL) was slowly added thereto. After stirring for 12 hours, the reaction mixture was concentrated under reduced pressure, which produced the compound 45d (2.5 g, 99%). ¹H-NMR (600 MHz, DMSO-d₆) δ 8.06 (s, 3H), 3.47 (t, J=6.6 Hz, 2H), 2.82 (t, J=7.2 Hz, 2H), 1.84-1.79 (m, 2H).

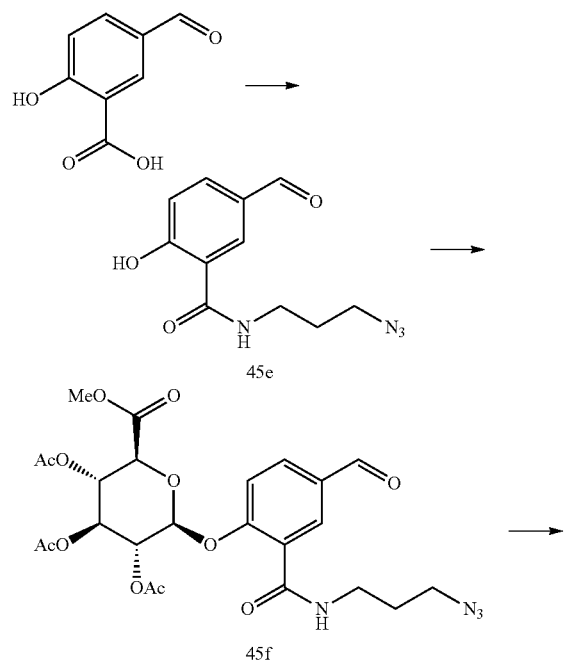

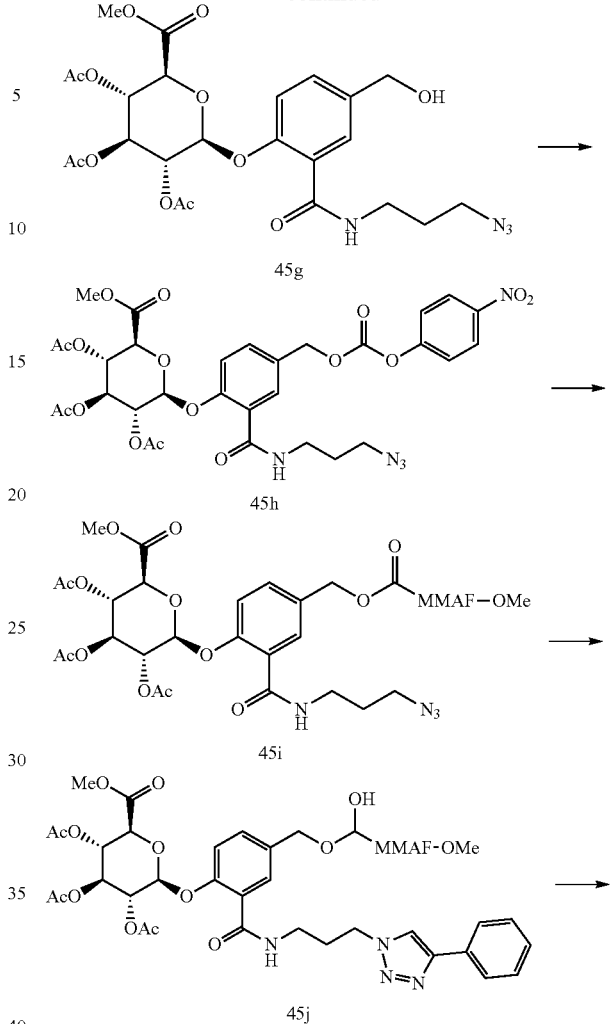

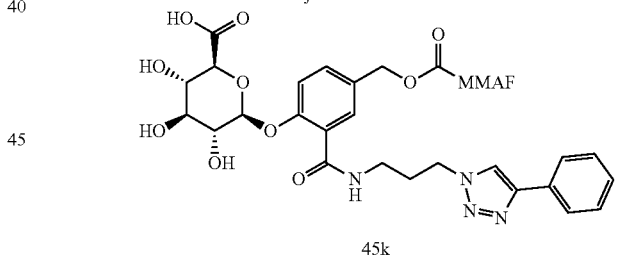

Preparation of Compound 45e

Compound 45d (58 mg, 0.42 mmol) and 5-formylsalicylic acid (100 mg, 0.60 mmol) were dissolved in DMF (2 mL) at 0° C. under nitrogen, and then DIPEA (0.2 mL, 1.20 mmol) and PyBop (375 mg, 0.72 mmol) were added to the reaction mixture. After stirring at room temperature for 3 hours, EtOAc (30 mL) and distilled water (10 mL) were added thereto. The organic layer was dried over anhydrous Na₂SO₄, filtered and concentrated under reduced pressure. The residue was subjected to column chromatography, which afforded compound 45e (82 mg, 79%). ¹H-NMR (400 MHz, CDCl₃) δ 13.39 (s, 1H), 9.87 (s, 1H), 8.29 (s, 1H), 7.89 (dd, J=1.6, 7.2 Hz. 1H), 7.60 (s, 1H), 7.10 (d, J=8.8 Hz, 1H), 3.63-3.57 (m, 2H), 3.48 (t, J=6.4 Hz, 2H), 1.99-1.92 (m, 2H).

Preparation of Compound 45f

Compound 45e (78 mg, 0.31 mmol) and compound M (125 mg, 0.31 mmol) were dissolved in MeCN (3 mL) at room temperature under nitrogen, and then silver oxide (291 mg, 1.26 mmol) and 4 Å molecular sieve (125 mg) were added thereto. After stirring at room temperature for 3 hours, the mixture was celite-filtered, and the filtrate was concentrated under reduced pressure. The residue was subjected to column chromatography, which produced the compound 45f (160 mg, 90%). $^1$H-NMR (400 MHz, CDCl$_3$) δ 10.00 (s, 1H), 8.66 (d, J=2.4 Hz, 1H), 8.02 (dd, J=2.0, 6.4 Hz, 1H), 7.46 (t, J=6.4 Hz, 1H), 7.14 (d, J=8.4 Hz, 1H), 5.48-5.33 (m, 4H), 4.28 (d, J=8.8 Hz, 1H), 3.74 (s, 3H), 3.73-3.64 (m, 1H), 3.50-3.42 (m, 3H), 2.09-2.07 (m, 9H), 2.00-1.92 (m, 2H).

Preparation of Compound 45g

Compound 45f (160 mg, 1.51 mmol) was dissolved in 2-propanol (0.4 mL) and chloroform (2 mL) at 0° C. under nitrogen, and then silica gel (2 g) and sodium borohydride (27 mg, 0.71 mmol) were added thereto. After stirring at 0° C. for 2 hours, the reactant was celite-filtered, and the filtrate was concentrated under reduced pressure. The residue was subjected to column chromatography, which produced the compound 45g (115 mg, 71%). $^1$H-NMR (600 MHz, CDCl$_3$) δ 8.06 (d, J=2.4 Hz, 1H), 7.50-7.44 (m, 2H), 7.01 (d, J=9.0 Hz, 1H), 5.45-5.31 (m, 4H), 4.38 (s, 2H), 4.22 (d, J=9.0 Hz, 1H), 3.74 (s, 3H), 3.67-3.61 (m, 1H), 3.46-3.41 (m, 3H), 2.07-2.04 (m, 9H), 1.97-1.91 (m, 2H).

Preparation of Compound 45h

Compound 45g (100 mg, 0.18 mmol) was dissolved in DMF (1 mL) at 0° C. under nitrogen, and then bis(4-nitrophenyl)carbonate (110 mg, 0.35 mmol) and DIPEA (0.050 mL, 0.27 mmol) were added thereto. After stirring at room temperature for 2 hours, EtOAc (30 mL) and distilled water (10 mL) were added thereto. The organic layer was dried over anhydrous Na$_2$SO$_4$ and concentrated under reduced pressure. The residue was subjected to column chromatography to produce the compound 45h (75 mg, 58%). $^1$H-NMR (600 MHz, CDCl$_3$) δ 8.29-8.27 (m, 2H), 8.23 (d, J=2.4 Hz, 1H), 7.54 (dd, J=2.4, 6.6 Hz, 1H), 7.49 (t, J=6.4 Hz, 1H), 7.39-7.37 (m, 2H), 7.04 (d, J=8.4 Hz, 1H), 5.45-5.29 (m, 4H), 5.28 (s, 2H), 4.23 (d, J=9.0 Hz, 1H), 3.75 (s, 3H), 3.68-3.64 (m, 1H), 3.46-3.42 (m, 3H), 2.08-2.05 (m, 9H), 1.98-1.93 (m, 2H).

Preparation of Compound 45i

Compound 45h (50 mg, 0.068 mmol) was dissolved in DMF (0.8 mL) at room temperature under nitrogen, and then MMAF-OMe (51 mg, 0.068 mmol) was added thereto. The resulting mixture was treated with HOBT (2 mg, 0.013 mmol), pyridine (0.24 mL), and DIPEA (0.012 mL, 0.068 mmol). After stirring at room temperature for 18 hours, EtOAc (20 mL) and distilled water (10 mL) were added thereto. The organic layer was dried over anhydrous Na$_2$SO$_4$ and concentrated under reduced pressure. The residue was subjected to column chromatography to produce the compound 45i (71 mg, 78%). EI-MS m/z: [M+H]$^+$ 1339.

Preparation of Compound 45i

Compound 45i (30 mg, 0.022 mmol) and phenylacetylene (3.7 μL, 0.033 mmol) were dissolved in EtOH (0.2 mL) and water (30 L) at room temperature under nitrogen, and then 0.1 M CuSO$_4$ aq. solution (30 μL) and 1.0 M sodium ascorbate aq. solution (30 L) were added thereto. The resulting mixture was treated with HOBT (2 mg, 0.013 mmol), pyridine (0.24 mL), and DIPEA (12 μL, 0.068 mmol). After stirring at room temperature for 5 hours, EtOAc (20 mL) and distilled water (5 mL) were added thereto. The organic layer was dried over anhydrous Na$_2$SO$_4$ and concentrated under reduced pressure. The residue was subjected to column chromatography to produce the compound 45j (26 mg, 81%). EI-MS m/z: [M+H]$^+$ 1441.

Preparation of Compound 45k

Compound 45j (20 mg, 0.013 mmol) was dissolved in MeOH (0.2 mL) at 0° C. under nitrogen, and then LiOH—H$_2$O (6 mg, 0.14 mmol) in water (0.2 mL) was added thereto. After stirring at room temperature for 1 hour, chloroform (10 mL), MeOH (1 mL), distilled water (10 mL), and 0.5 N aq. HCl (1 mL) were added thereto. The organic layer was dried over anhydrous Na$_2$SO$_4$ and concentrated under reduced pressure. The residue was subjected to column chromatography to produce the compound 45k (17 mg, 87%). EI-MS m/z: [M+H]$^+$ 1286.

Example 67. Preparation of Compound 46b

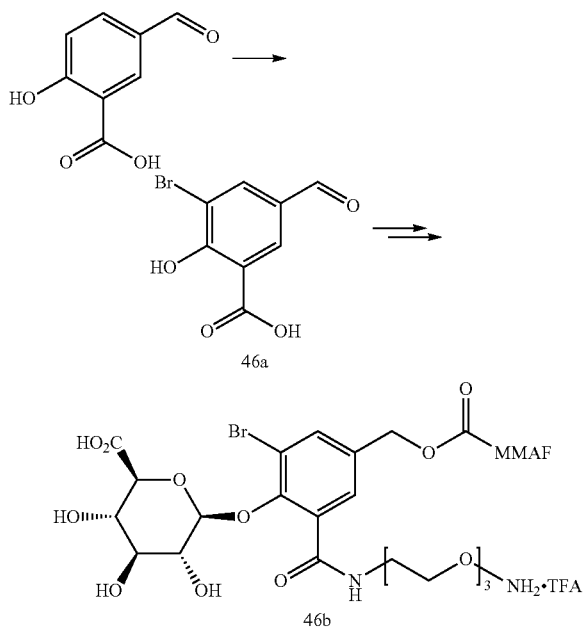

Preparation of Compound 46a

5-Formylsalicylic acid (1.0 g, 6.02 mmol) was dissolved in DMF (20 mL) at 0° C. under nitrogen, and then N-bromosuccinimide (1.07 g, 6.11 mmol) was added thereto and the mixture was stirred at 70° C. for 3 hours. After the reaction was completed, EtOAc (100 mL), 2 N aq. HCl solution (2 μL), and distilled water (100 mL) were added thereto. The organic layer was dried over anhydrous Na$_2$SO$_4$ and concentrated under reduced pressure. The residue was subjected to column chromatography to produce the compound 46a (1.2 g, 84%). $^1$H-NMR (400 MHz, DMSO-d$_6$) δ 9.64 (s, 1H), 8.19 (d, J=2.4 Hz, 1H), 8.00 (d, J=2.0 Hz, 1H), 3.16 (s, 1H).

Preparation of Compound 46b

Compound 46b was prepared from compound 46a by a similar method of preparing compound 2h in Example 4. EI-MS m/z: [M+H]$^+$ 1328.

Examples 68 to 70. Preparation of Compound 47a, Compound 48a, and Compound 49a

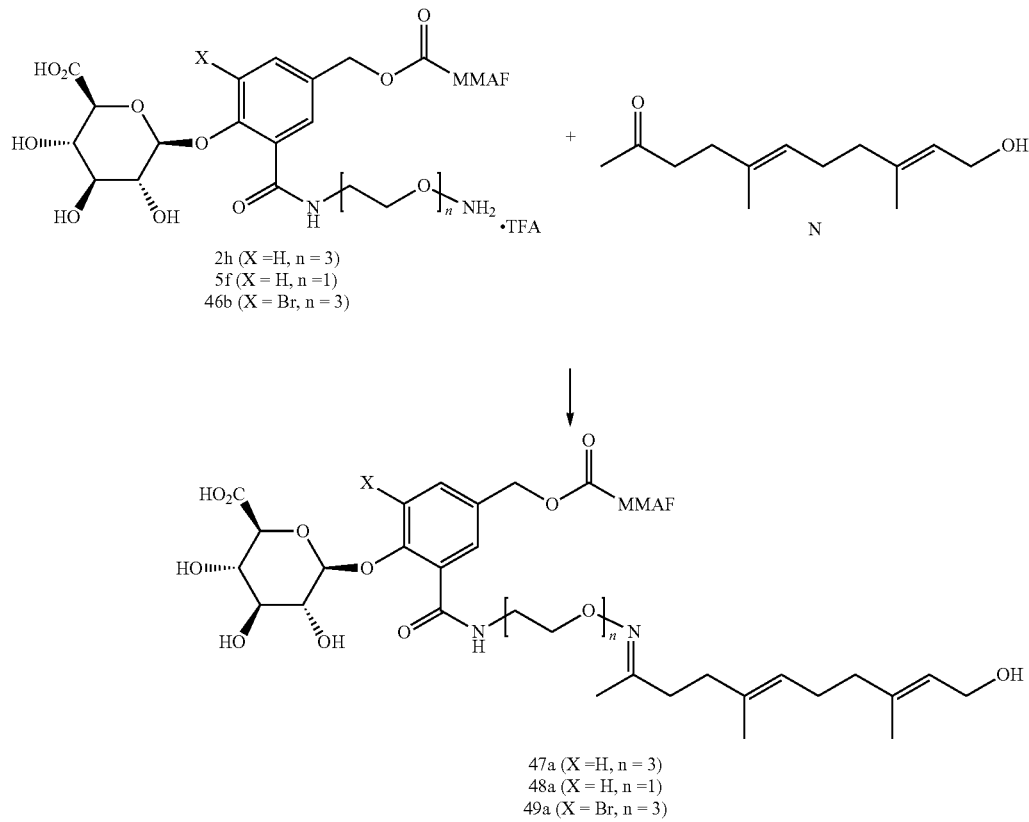

2h (X =H, n = 3)
5f (X = H, n =1)
46b (X = Br, n = 3)

47a (X =H, n = 3)
48a (X = H, n =1)
49a (X = Br, n = 3)

Compound N was prepared by a method disclosed in Korean Patent Laid-Open Publication No. 10-2014-0035393.

Examples 68. Preparation of Compound 47a

Compound 2h (20 mg, 0.014 mmol) was dissolved in EtOH (0.7 mL) at room temperature under nitrogen, and then compound N (3.7 mg, 0.017 mmol) was added thereto, and the mixture was stirred at 45° C. for 2 hours. After the reaction was completed, compound 47a (10.2 mg, 49%) was obtained using HPLC. EI-MS m/z: [M+H]$^+$ 1441.

Examples 69 and 70. Preparation of Compound 48a and 49a

Compound 48a (Example 69) and compound 49a (Example 70) were prepared by a similar method of preparing compound 47a in Example 68. EI-MS of compound 48a m/z: [M+H]$^+$ 1353. EI-MS of compound 49a m/z: [M+H]$^+$ 1520.

Comparative Example 66. Preparation of Compound 50k

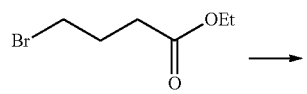

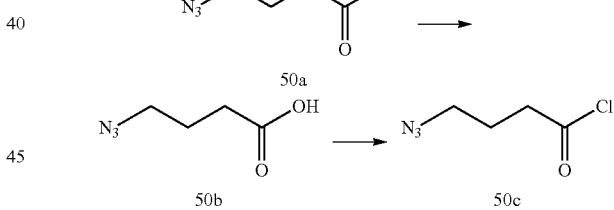

Preparation of Compound 50a

Ethyl 4-bromobutanoate (5.0 mL, 34.6 mmol) was dissolved in MeOH (75 mL) at room temperature under nitrogen, and then NaN$_3$ (4.5 g, 69.2 mmol) in water (25 mL) was added thereto and stirred at 85° C. for 8 hours. After the reaction was completed, the solvent was concentrated under reduced pressure, and chloroform (300 mL) and distilled water (200 mL) were added thereto. The organic layer obtained as described above was dried over anhydrous Na$_2$SO$_4$ and concentrated under reduced pressure. The residue was subjected to column chromatography to produce the compound 50a (5.1 g, 94%). $^1$H-NMR (600 MHz, CDCl$_3$) δ 4.15 (q, J=7.2 Hz, 2H), 3.36 (t, J=7.2 Hz, 2H), 2.41 (t, J=7.2 Hz, 2H), 1.94-1.89 (m, 2H), 1.28 (t, J=8.4 Hz, 3H).

Preparation of Compound 50b

Compound 50a (2.0 g, 12.7 mmol) was dissolved in MeOH (32 mL) at 0° C. under nitrogen, and then KOH (3.56 g, 63.6 mmol) in water (26 mL) was slowly added thereto.

After stirring at room temperature for 6 hours, the solvent was concentrated under reduced pressure, and chloroform (300 mL), 1 N aq. HCl (100 mL), and distilled water (100 mL) were added thereto. The organic layer obtained as described above was dried over anhydrous $Na_2SO_4$ and concentrated under reduced pressure. The resulting residue was subjected to column chromatography to produce the compound 50b (1.28 g, 78%). $^1$H-NMR (600 MHz, $CDCl_3$) δ 3.38 (t, J=7.2 Hz, 2H), 2.48 (t, J=7.2 Hz, 2H), 1.95-1.90 (m, 2H).

Preparation of Compound 50c

Compound 50b (850 mg, 6.58 mmol) was dissolved in MeOH (10 mL) at 0° C. under nitrogen, and then oxalyl chloride (1.1 mL, 13.2 mmol) and DMF (1 drop) were added thereto and stirred at room temperature for 6 hours. After the reaction was completed, the solvent was concentrated under reduced pressure to produce the compound 50c (965 mg), which was used without further purification.

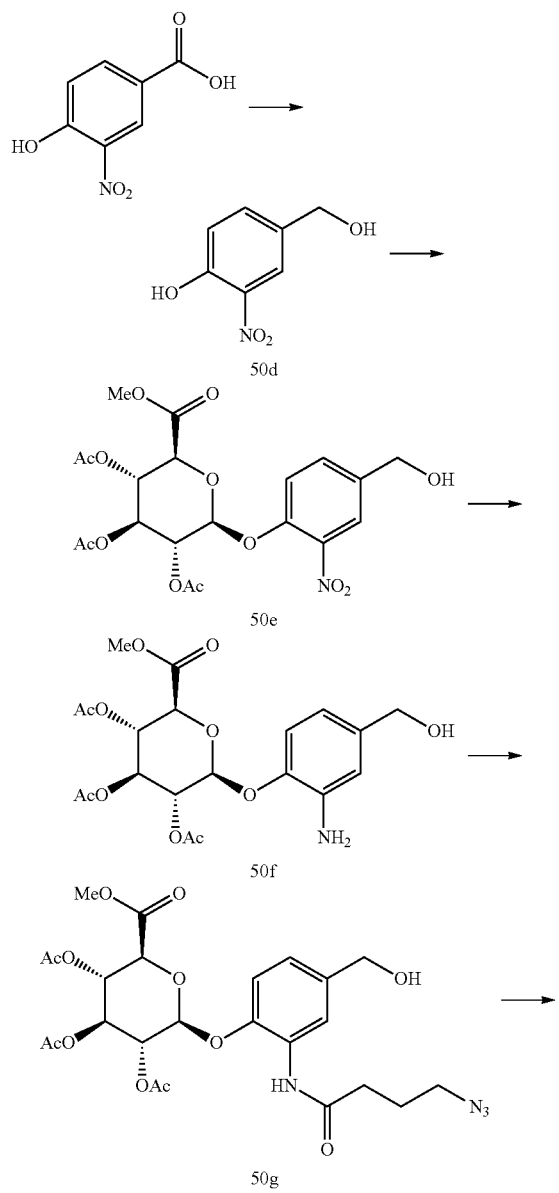

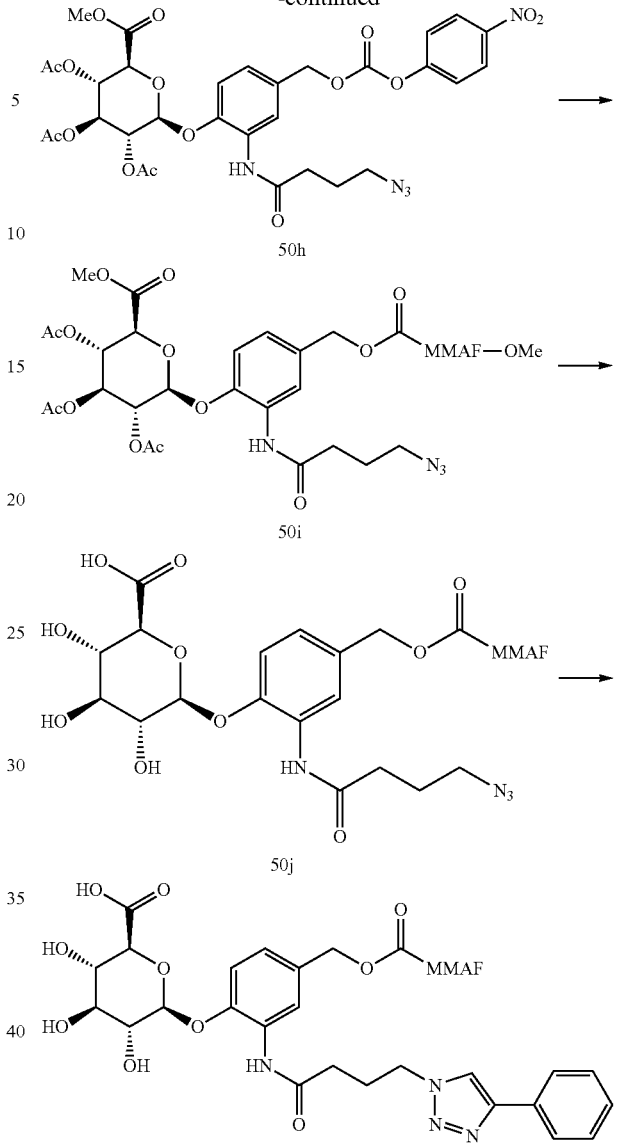

Preparation of Compound 50d

4-Hydroxy-3-nitrobenzoic acid (5.0 g, 27.3 mmol) was dissolved in THF (120 mL) at 0° C. under nitrogen, and then 1 M $BH_3$-THF complex (54.6 mL, 54.6 mmol) was added thereto and stirred at room temperature for 20 hours. After the reaction was completed, EtOAc (200 mL), 0.5 N aq. HCl (20 mL), and distilled water (100 mL) were added thereto. The organic layer obtained as described above was dried over anhydrous $Na_2SO_4$ and concentrated under reduced pressure. The resulting residue was subjected to column chromatography to produce the compound 50d (4.2 g, 91%). $^1$H-NMR (600 MHz, $CD_3OD$) δ 8.06 (d, J=1.2 Hz, 1H), 7.59 (dd, J=1.2, 7.8 Hz, 1H), 7.12 (d, J=8.4 Hz, 1H), 4.83 (s, 2H).

Preparation of Compound 50e

Compound 50d (937 mg, 5.54 mmol) was dissolved in MeCN (15 mL) at room temperature under nitrogen, and compound M (2.0 g, 5.04 mmol), silver oxide (4.66 g, 20.1 mmol), and 4 Å molecular sieve (2.0 g) were added thereto, and stirred at room temperature for 14 hours. After the reaction was completed, the mixture was celite-filtered, and the filtrate was concentrated under reduced pressure. The resulting residue was subjected to column chromatography to produce the compound 50e (1.0 g, 40%). $^1$H-NMR (600 MHz, CDCl$_3$) δ 7.81 (d, J=1.8 Hz, 1H), 7.54 (dd, J=1.8, 6.6 Hz, 1H), 7.37 (d, J=8.4 Hz, 1H), 5.37-5.27 (m, 3H), 5.20 (d, J=6.6 Hz, 1H), 4.72 (d, J=6.0 Hz, 2H), 4.21 (d, J=9.0 Hz, 1H), 3.75 (s, 3H), 2.12 (s, 3H), 2.06 (s, 3H), 2.05 (s, 3H), 2.04-2.02 (m, 1H).

Preparation of Compound 50f

Compound 50e (900 mg, 6.35 mmol) was dissolved in EtOAc (100 mL), and then platinum (IV) oxide (84.2 mg, 0.370 mmol) was added thereto and stirred at room temperature under hydrogen for 3 hours. After the reaction was completed, the mixture was celite-filtered, and the filtrate was concentrated under reduced pressure to produce the compound 50f (700 mg, 83%), which was used without further purification.

Preparation of Compound 502

Compound 50f (350 mg, 0.77 mmol) was dissolved in DCM (10 mL) at 0° C. under nitrogen, and then compound 50c (136 mg, 0.92 mmol) and DIPEA (0.27 mL, 1.54 mmol) were added thereto and stirred at room temperature for 20 minutes. After the reaction was completed, EtOAc (50 mL) and distilled water (50 mL) were added thereto. The organic layer obtained as described above was dried over anhydrous Na$_2$SO$_4$ and concentrated under reduced pressure. The resulting residue was subjected to column chromatography to produce the compound 50g (280 mg, 65%). $^1$H-NMR (600 MHz, CDCl$_3$) δ 8.37 (d, J=1.2 Hz, 1H), 8.00 (s, 1H), 7.07 (dd, J=1.8, 6.6 Hz, 1H), 6.93 (d, J=8.4 Hz, 1H), 5.43-5.28 (m, 3H), 5.06 (d, J=7.8 Hz, 1H), 4.63 (s, 2H), 4.19 (d, J=9.6 Hz, 1H), 3.76 (s, 3H), 3.44-3.41 (m, 2H), 2.56 (t, J=7.8 Hz, 2H), 2.17-2.00 (m, 12H).

Preparation of Compound 50h

Compound 50g (250 mg, 0.44 mmol) was dissolved in DMF (4 mL) at 0° C. under nitrogen, and then bis(4-nitrophenyl)carbonate (270 mg, 0.88 mmol) and DIPEA (0.12 mL, 0.66 mmol) were added thereto, and stirred at room temperature for 1 hour. After the reaction was completed, EtOAc (50 mL) and distilled water (50 mL) were added thereto. The organic layer obtained as described above was dried over anhydrous Na$_2$SO$_4$ and concentrated under reduced pressure. The resulting residue was subjected to column chromatography to produce the compound 50h (290 mg, 90%). $^1$H-NMR (600 MHz, CDCl$_3$) δ 8.54 (d, J=1.8 Hz, 1H), 8.28-8.25 (m, 2H), 8.02 (s, 1H), 7.40-7.36 (m, 2H), 7.11 (dd, J=1.8, 6.6 Hz, 1H), 6.96 (d, J=8.4 Hz, 1H), 5.44-5.29 (m, 3H), 5.23 (s, 2H), 5.10 (d, J=7.8 Hz, 1H), 4.21 (d, J=9.6 Hz, 1H), 3.76 (s, 3H), 3.45-3.42 (m, 2H), 2.58 (t, J=7.2 Hz, 2H), 2.11-2.00 (m, 12H).

Preparation of Compound 50i

Compound 50h (250 mg, 0.34 mmol) was dissolved in DMF (4 mL) at room temperature under nitrogen, and then MMAF-OMe (255 mg, 0.34 mmol) was added thereto. The resulting mixture was treated with HOBT (9 mg, 0.068 mmol), pyridine (1.2 mL), and DIPEA (0.060 mL, 0.34 mmol). After stirring at room temperature for 2 days, EtOAc (50 mL), 2 N aq. HCl (5 mL), and distilled water (50 mL) were added thereto. The organic layer obtained as described above was dried over anhydrous Na$_2$SO$_4$ and concentrated under reduced pressure. The residue was subjected to column chromatography to produce the compound 50i (340 mg, 74%). EI-MS m/z: [M+H]$^+$ 1339.

Preparation of Compound 50j

Compound 50i (210 mg, 0.156 mmol) was dissolved in MeOH (2 mL) at 0° C. under nitrogen, and then LiOH.H$_2$O (66 mg, 1.56 mmol) in water (2 mL) was added thereto. After stirring at room temperature for 1.5 hours, chloroform (50 mL), MeOH (5 mL), distilled water (50 mL), and 0.5 N aq. HCl (5 mL) were added thereto. The organic layer obtained as described above was dried over anhydrous Na$_2$SO$_4$ and concentrated under reduced pressure. The resulting residue was subjected to column chromatography to produce the compound 50j (107 mg, 57%). EI-MS m/z: [M+H]$^+$ 1184.

Preparation of Compound 50k

Compound 50j (10 mg, 0.008 mmol) and phenylacetylene (0.92 μL, 0.008 mmol) were dissolved in EtOH (0.15 mL) and water (10 μL) at room temperature under nitrogen, and then 0.1 M CuSO$_4$ aqueous solution (10 μL) and 1.0 M sodium ascorbate aqueous solution (10 μL) were added thereto. After stirring at room temperature for 5 hours, EtOAc (10 mL) and distilled water (5 mL) were added thereto. The organic layer obtained as described above was dried over anhydrous Na$_2$SO$_4$ and concentrated under reduced pressure. The resulting residue was subjected to column chromatography to produce the compound 50k (5 mg, 46%). EI-MS m/z: [M+H]$^+$ 1286.

Example 71. Preparation of Compound 51h

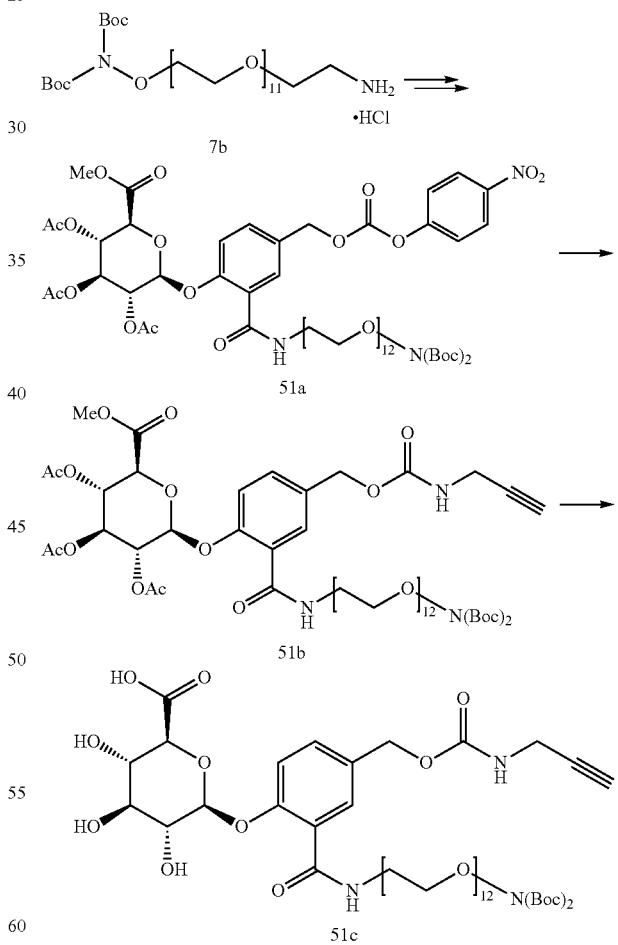

Preparation of Compound 51a

Compound 51a was prepared from compound 7b by a method similar to method of preparing compound 14h of Example 23. EI-MS m/z: [M+H]$^+$ 1392.8, [M+H-Boc]$^+$ 1292.7, [M+Na]$^+$ 1414.8.

Preparation of Compound 51b

Compound 51a (1.8 g, 1.29 mmol), propargylamine (0.1 mL, 1.55 mmol) and anhydrous HOBt (35 mg, 0.25 mmol) were dissolved in DMF (5 mL) at 0° C. Then pyridine (0.2 mL) and DIPEA (0.45 mL, 2.59 mmol) were added. After stirring at room temperature for 24 hours under $N_2$, the reaction mixture was diluted with $H_2O$ (100 mL) and saturated aq. $NH_4Cl$ solution (50 mL). After extraction with EtOAc (2×100 mL), the combined organic layers were dried over anhydrous $MgSO_4$, filtered, and concentrated. The residue was purified by column chromatography to produce the compound 51b (1.15 g, 68%). $^1$H-NMR (400 MHz, $CDCl_3$) δ 8.01 (s, 1H), 7.48-7.31 (m, 2H), 7.02 (d, J=8.4 Hz, 1H), 5.45-5.20 (m, 4H), 5.09 (s, 2H), 4.19 (d, J=9.2 Hz, 1H), 4.10-4.05 (m, 2H), 3.97 (s, 2H), 3.85-3.45 (m, 49H), 2.24 (s, 1H), 2.05 (s, 9H), 1.53 (s, 18H). EI-MS m/z: $[M+Na]^+$ 1330.3.

Preparation of Compound 51c

To a solution of compound 51b (1.15 g, 0.879 mmol) in THF/MeOH (20 mL/20 mL) was added LiOH monohydrate (151 mg, 3.603 mmol) in $H_2O$ (20 mL) at 0° C. After 2 hours at 0° C., the reaction mixture was neutralized using acetic acid and concentrated under reduced pressure. The resulting residue was dissolved in DMSO (5 mL) and purified by prep. HPLC, which produced the compound 51c (600 mg, 60%). EI-MS m/z: $[M+H]^+$ 1169.2.

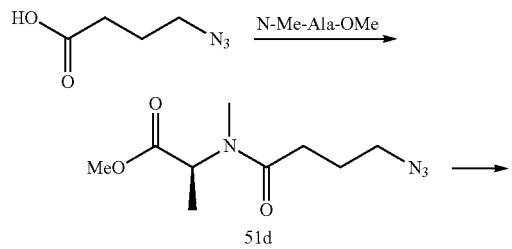

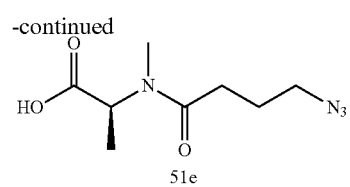

51e

Preparation of Compound 51d

DIPEA (0.92 mL, 5.30 mmol) and HBTU (1.0 g, 2.64 mmol) were added to a stirred mixture of 4-azidobutanoic acid (228 mg, 1.76 mmol) and N-Me-Ala-OMe (298 mg, 1.94 mmol) in DMF (10 mL). After stirring at room temperature for 14 hours under $N_2$, the reaction mixture was diluted with $H_2O$ (50 mL) and extracted with EtOAc (2×50 mL). The combined organic layers were dried over anhydrous $Na_2SO_4$, filtered and concentrated. The resulting residue was purified by column chromatography to yield the compound 51d (310 mg, 77%). $^1$H-NMR (400 MHz, $CDCl_3$) δ 5.22 (q, 1H), 3.71 (s, 3H), 3.39 (t, J=6.6 Hz, 2H), 2.95 (s, 3H), 2.52-2.39 (m, 2H), 1.98-1.92 (m, 2H), 1.41 (d, 3H).

Preparation of Compound 51e

To a solution of compound 51d (310 mg, 1.36 mmol) in MeOH (3 mL) was added LiOH monohydrate (114 mg, 2.72 mmol) in $H_2O$ (3 mL) at −20° C. After stirring at 0° C. for 1 hour, the reaction mixture was diluted with $H_2O$/2 N aq. HCl solution (50 mL/2 mL) and extracted with $Et_2O$ (2×30 mL). The combined organic layers were dried over anhydrous $Na_2SO_4$. Filtration and concentration produced the compound 5e (246 mg), which was used without further purification. $^1$H-NMR (400 MHz, $CDCl_3$) δ 5.15 (q, 1H), 3.39 (t, J=6.6 Hz, 2H), 2.98 (s, 3H), 2.49-2.45 (m, 2H), 1.98-1.92 (m, 2H), 1.41 (d, 3H).

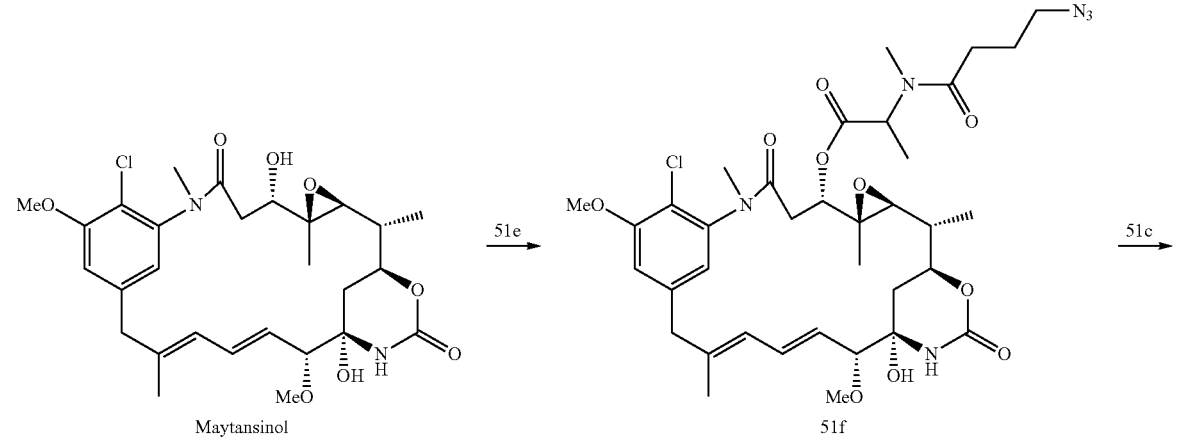

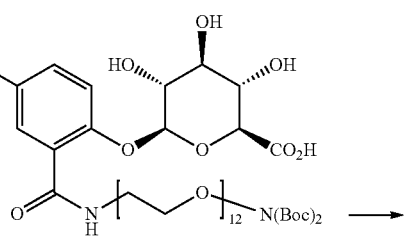

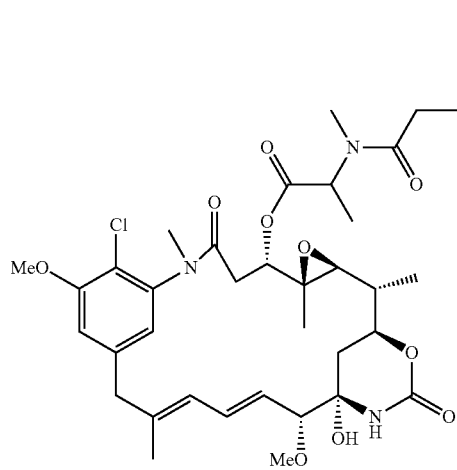

51g

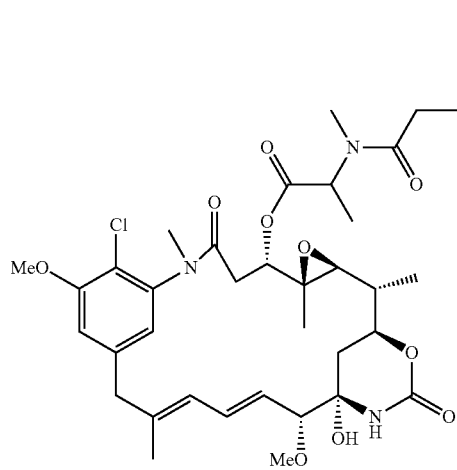

51h

Preparation of Compound 51f

To a solution of maytansinol (50 mg, 0.088 mmol) and compound 51e (113 mg, 0.528 mmol) in DCM (6 mL) under $N_2$ was added a solution of DIC (0.087 mL, 0.557 mmol) in DCM (1.4 mL). After 1 minute, a solution of $ZnCl_2$ (1 M in $Et_2O$, 0.11 mL, 0.11 mmol) was added. After stirring at room temperature for 2 hours, the reaction mixture was diluted with EtOAc (10 mL). The organic layer was washed with saturated aq. $NaHCO_3$ (4 mL) and brine (2 mL), dried over anhydrous $Na_2SO_4$ and evaporated under reduced pressure. The resulting residue was purified by column chromatography to yield a mixture of diastereomeric maytansinoids compound 51f (50 mg, 74%). EI-MS m/z: [M+H]$^+$ 761.7.

Preparation of Compound 51g $CuSO_4.5H_2O$ (2 mg) and sodium ascorbate (10 mg) were added to a stirring mixture of compound 51f (78 mg, 0.102 mmol) and compound 51c (132 mg, 0.112 mmol) in DMSO (4 mL) and $H_2O$ (1 mL). The pH was adjusted to about 7 by addition of 1 M aq. $Na_2CO_3$. After stirring at 20° C. for 1 hour, the reaction mixture was dissolved in $H_2O$/DMSO (1.5 mL/1.5 mL) and purified by HPLC. Pure fractions with the same retention time were combined and concentrated to produce the compound 51g (72.1 mg, 37%). EI-MS m/z: [M+H]$^+$ 1930.9, [M+H-Boc]$^+$1830.9.

Preparation of Compound 51h

TFA (0.2 mL) was added to a stirring solution of compound 51g (72.1 mg, 0.037 mmol) in DCM (1 mL). After stirring at 0° C. for 2 hours, the solvent and excess TFA were removed by $N_2$ flow. Then the residue was dissolved in $H_2O$/MeCN (1 mL/1 mL) and purified by HPLC. Pure fractions with the same retention time were combined and lyophilized to produce the compound 51h (more polar isomer 17 mg and less polar isomer 6.0 mg, 36,%) as white solid. EI-MS m/z: [M+H]$^+$ 1730.8.

Example 72. Preparation of Compound 52c
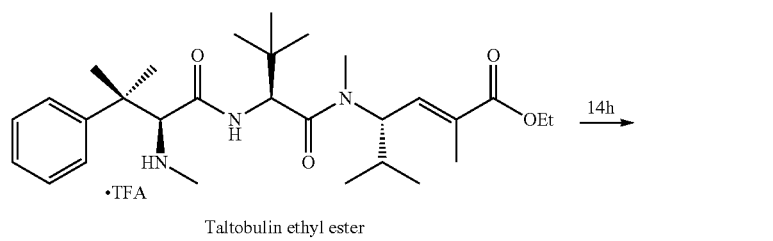
Taltobulin ethyl ester
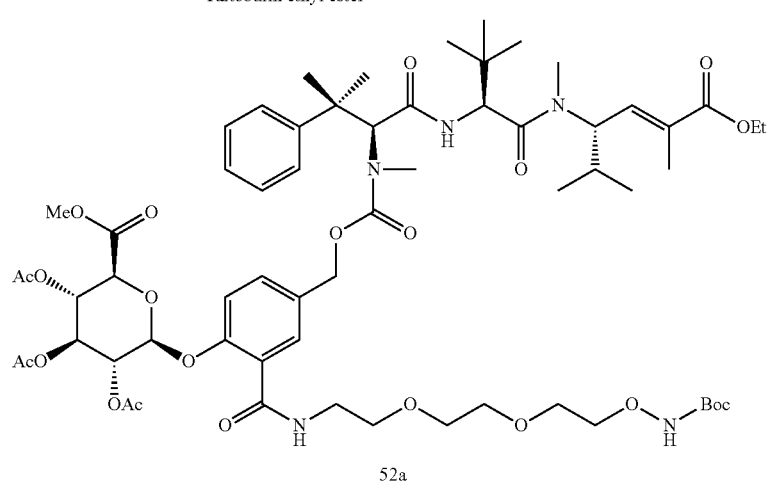
52a
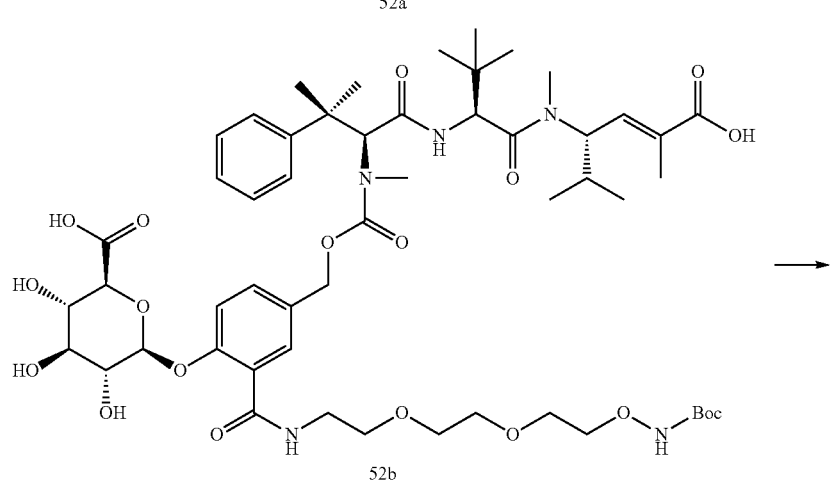
52b
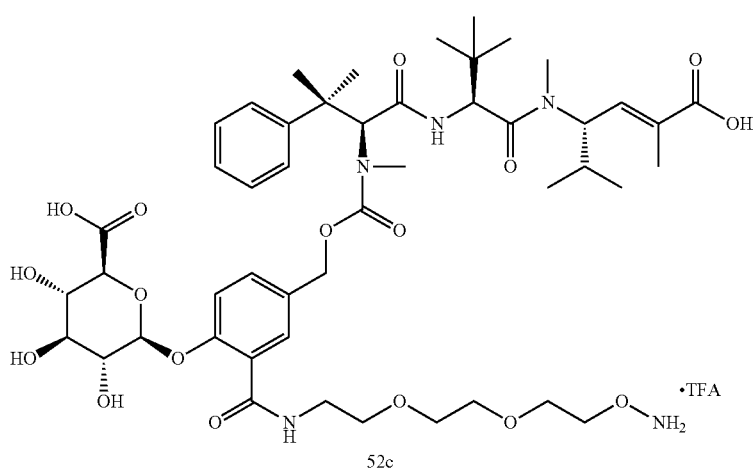
52c Preparation of Compound 52a Taltobulin ethyl ester (TFA salt, 80 mg, 0.029 mmol), compound 14h (128 mg, 0.0142 mmol) and anhydrous HOBt (3.5 mg, 0.026 mmol) were dissolved in DMF (3 mL) at 0° C. Then pyridine (0.5 mL) and DIPEA (0.045 mL, 0.26 mmol) were added. After stirring at room temperature for 24 hours under $N_2$, the reaction mixture was diluted with $H_2O$ (10 mL) and extracted with EtOAc (2×10 mL). The combined organic layers were dried over anhydrous $Na_2SO_4$, filtered and concentrated. The resulting residue was purified by column chromatography to yield the compound 52a (70 mg, 43%). EI-MS m/z: [M+H]$^+$ 1258.6, [M+H-Boc]$^+$ 1158.6.

Preparation of Compound 52b

To a solution of compound 52a (70 mg, 0.055 mmol) in MeOH (1.4 mL) was added LiOH monohydrate (11.7 mg, 0.275 mmol) in $H_2O$ (1.4 mL) at −20° C. After 1 hour at 0° C., the pH of the solution was adjusted to 4-5 with acetic acid. The resulting solution was dissolved in DMSO (1 mL) and purified by HPLC, which produced the compound 52b (4.5 mg, 8%) as white solid. EI-MS m/z: [M+H]$^+$ 1090.4.

Preparation of Compound 52c

To a solution of compound 52b (4.5 mg, 0.0041 mmol) in DCM (1 mL) was added TFA (0.2 mL) at 0° C. After 2 hours at 0° C., the solvent and excess TFA were removed by $N_2$ flow. Then the residue was purified by HPLC, which produced the compound 52c (2.4 mg, 59%) as white solid. EI-MS m/z: [M+H]$^+$ 990.4.

Example 73. Preparation of Compound 53f

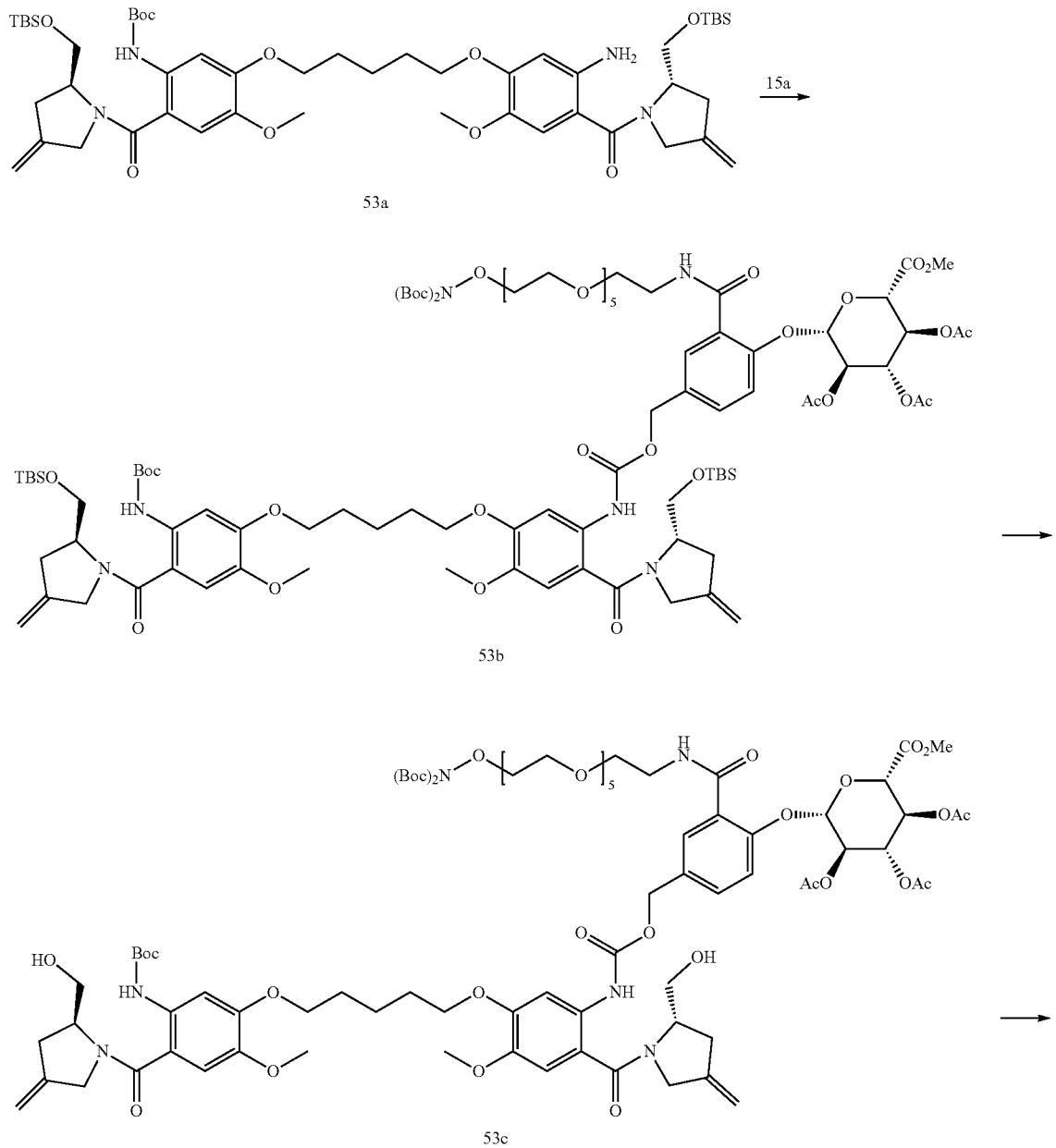

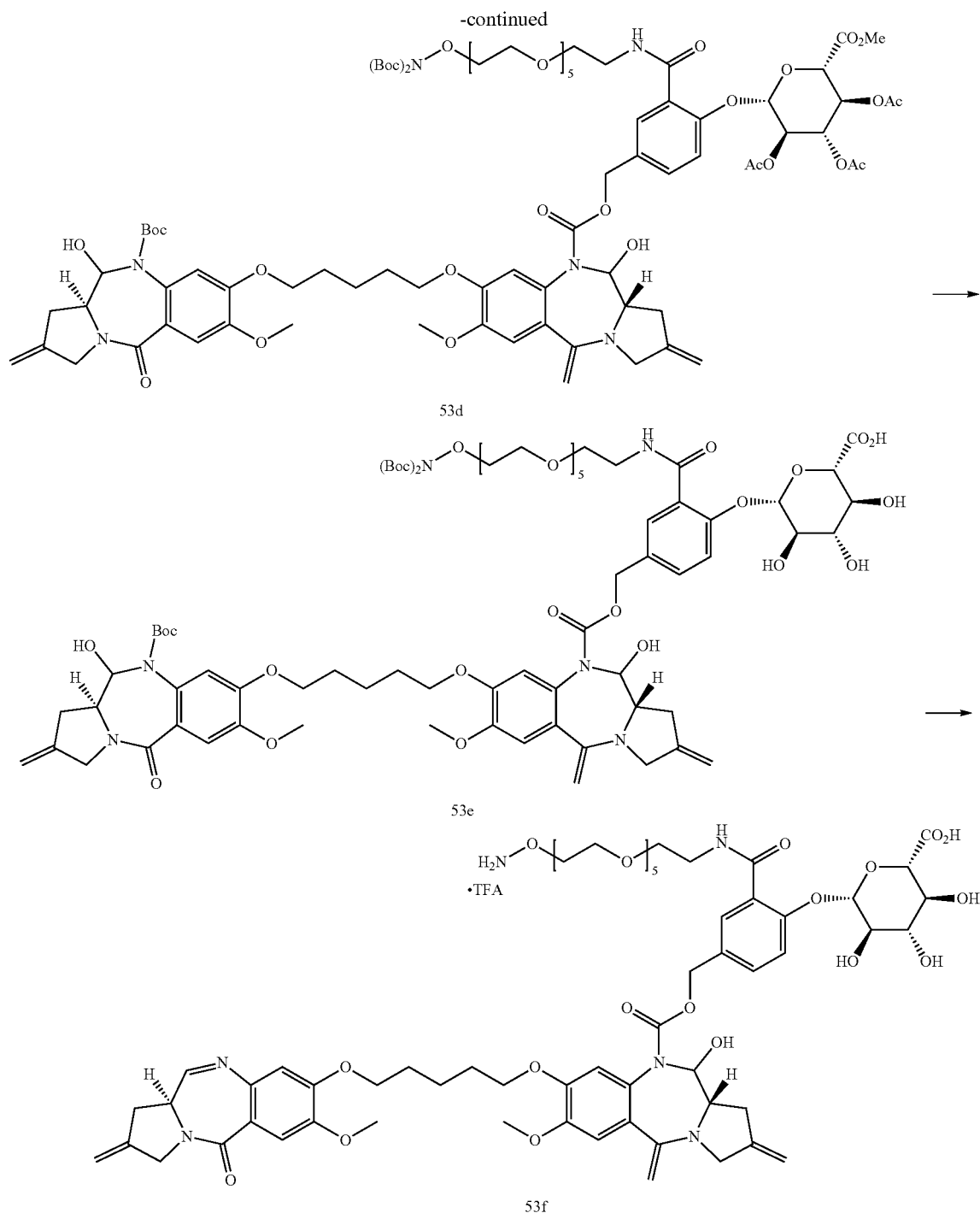

Preparation of Compound 53b

Compound 53a (300 mg, 0.31 mmol, Compound 53a was prepared by a method disclosed in patent WO2013/055987 A1), compound 15a (355 mg, 0.31 mmol) and anhydrous HOBt (10 mg, 0.06 mmol) were dissolved in DMF (0.5 mL) at 0° C. Then pyridine (0.3 mL) and DIPEA (0.14 mL, 0.78 mmol) were added. After stirring at room temperature for 23 hours under $N_2$, the reaction mixture was diluted with $H_2O$/saturated aq. $NH_4Cl$ solution (100 mL/50 mL) and extracted with EtOAc (2×100 mL). The combined organic layers were dried over anhydrous $MgSO_4$, filtered, and concentrated. The residue was purified by column chromatography to produce the compound 53b (250 mg, 41%). EI-MS m/z: [M+H]$^+$ 1943.6, [M+Na]$^+$ 1965.6.

Preparation of Compound 53c

To a solution of compound 53b (300 mg, 0.31 mmol) in THF/$H_2O$ (2 mL/1 mL) was added acetic acid (3 mL) at 0° C. under $N_2$. After 22 hours, the reaction mixture was diluted with $H_2O$ (100 mL) and extracted with EtOAc (2×100 mL). The combined organic layers were dried over anhydrous $Na_2SO_4$, filtered and concentrated. The resulting residue was purified by column chromatography to yield the compound 53c (140 mg, 68%). EI-MS m/z: [M+H]+ 1713.6.

Preparation of Compound 53d

To a solution of compound 53c (120 mg, 0.07 mmol) in DCM (10 mL) were added pyridinium chlorochromate (158 mg, 0.42 mmol) and 4 Å molecular sieve (50 mg) at room temperature under $N_2$. After stirring for 18 hours, the reaction mixture was filtered through a celite pad and concentrated under reduced pressure. The resulting compound 53d (95 mg, 75%) was obtained as colorless oil, which was used without further purification. EI-MS m/z: [M+Na]+1732.8.

Preparation of Compound 53e

To a solution of compound 53d (95 mg, 0.056 mmol) in MeOH (1 mL) was added LiOH monohydrate (12 mg, 0.278 mmol) in $H_2O$ (1 mL) at 0° C. After 2 hours at 0° C., the reaction mixture was neutralized using acetic acid and concentrated under reduced pressure. The resulting residue was dissolved in DMSO (1 mL) and purified by prep. HPLC, which produced the compound 53e (6 mg, 7%). EI-MS m/z: [M+H]+ 1569.7.

Preparation of Compound 53f

TFA (0.2 mL) was added to a stirred solution of compound 53e (6 mg, 0.004 mmol) in DCM (2 mL). After stirring at 0° C. for 2 hours, the solvent and excess TFA were removed by $N_2$ flow. Then the residue was dissolved in DMSO (1 mL) and purified by HPLC. Pure fractions with the same retention time were combined and lyophilized to produce the compound 53f (2.7 mg, 53%) as white solid. EI-MS m/z: [M+H]+ 1251.3.

Example 74. Preparation of Compound 54a

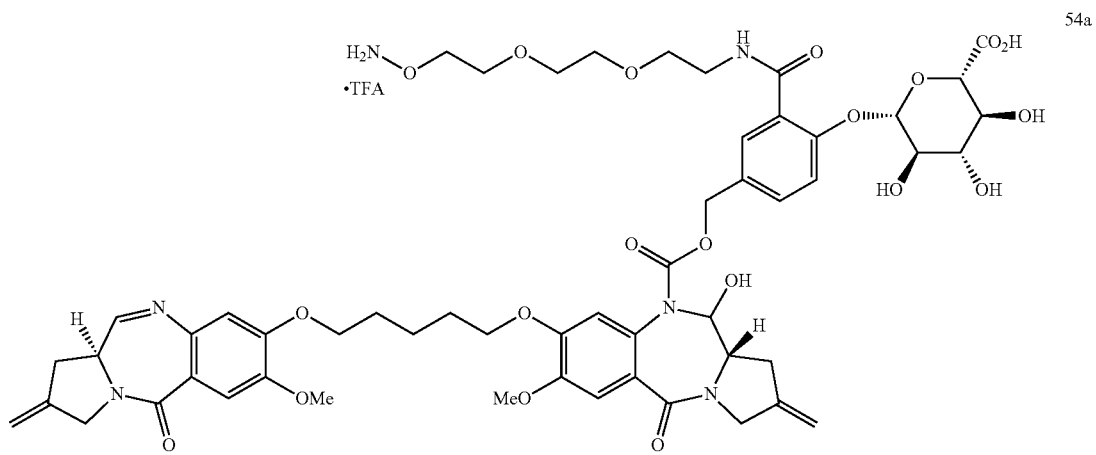 [SMILES: C=C1C[C@H]2C=Nc3cc(OCCCCCOc4cc5c(cc4OC)C(=O)N4CC(=C)C[C@H]4C(O)N5C(=O)OCc4ccc(O[C@@H]5O[C@H](C(=O)O)[C@@H](O)[C@H](O)[C@H]5O)c(C(=O)NCCOCCOCCON)c4)c(OC)cc3C(=O)N2C1]

Compound 54a was prepared from compound 53a and compound 14h by a similar method of preparing compound 53f in Example 73.

Example 75. Preparation of Compound 55a

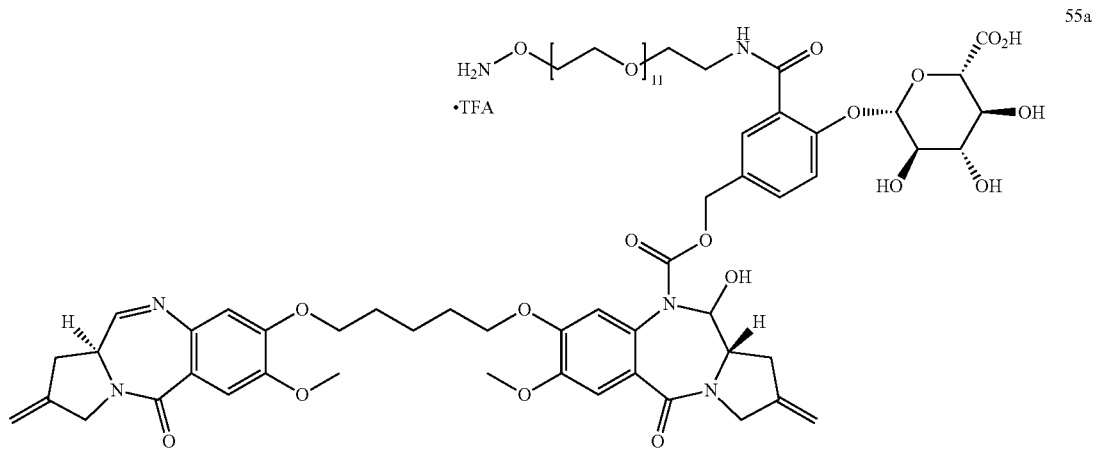

Compound 55a was prepared from compound 53a and compound 51a by a similar method of preparing compound 53f in Example 73. EI-MS m/z: [M+H]$^+$ 1516.7, ½[M+H]$^+$ 758.7.
Example 76. Preparation of Compound 56d
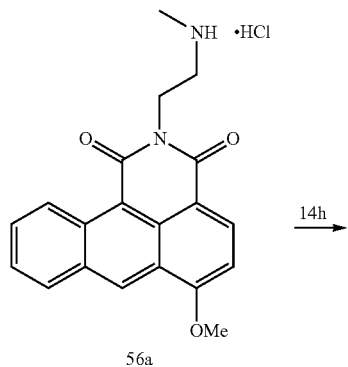
56a
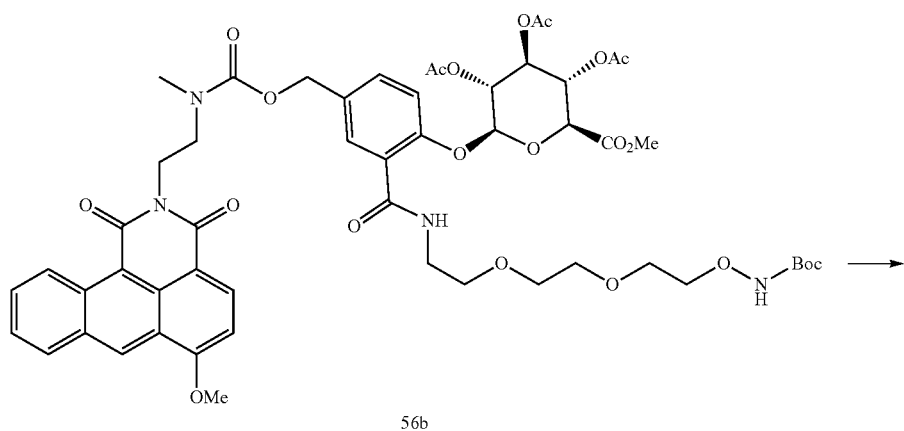
56b
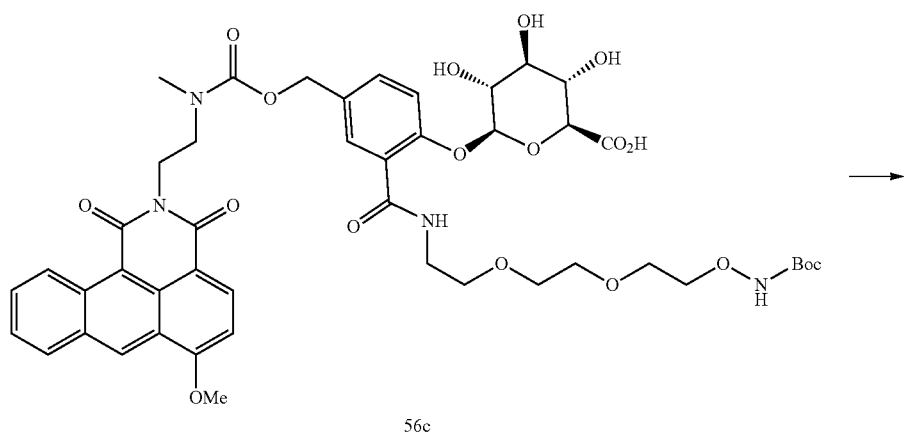
56c

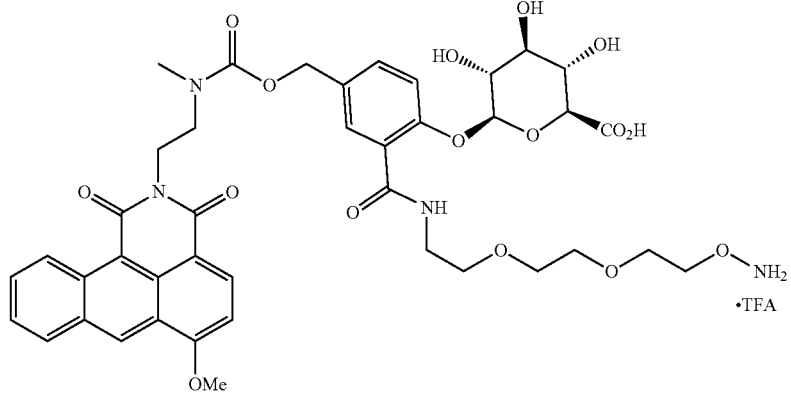

56d

Preparation of Compound 56b

Compound 56a (HCl salt, 100 mg, 0.27 mmol, Compound 56a was prepared by a method disclosed in *Curr. Med. Chem.* 2009, 16, 1192-1213), compound 14h (242 mg, 0.27 mmol), and anhydrous HOBt (7.3 mg, 0.05 mmol) were dissolved in DMF (3 mL) at 0° C. Then pyridine (0.4 mL) and DIPEA (0.09 mL, 0.60 mmol) were added. After stirring at room temperature for 16 hours under $N_2$, the reaction mixture was diluted with saturated aq. $NH_4Cl$ solution (10 mL) and extracted with EtOAc (2×20 mL). The combined organic layers were dried over anhydrous $MgSO_4$, filtered and concentrated. The residue was purified by column chromatography to produce the compound 56b (184 mg, 63%). EI-MS m/z: $[M+H]^+$ 1091.9, $[M+H-Boc]^+$991.7.

Preparation of Compound 56c

To a solution of compound 56b (90 mg, 0.08 mmol) in MeOH (2 mL) was added LiOH monohydrate (17 mg, 0.41 mmol) in $H_2O$ (2 mL) at −20° C. After stirring for 2 hours at −20° C., the reaction mixture was neutralized using acetic acid and concentrated under reduced pressure. Then the reaction mixture was dissolved in $H_2O$/DMSO (1.5 mL/1.5 mL) and purified by HPLC, which produced the compound 56c (35 mg, 45%) as yellow solid. EI-MS m/z: $[M+H]^+$ 951.7, $[M+H-Boc]^+$851.5.

Preparation of Compound 56d

TFA (0.3 mL) was added to a stirred solution of compound 56c (35 mg, 0.04 mmol) in DCM (2.0 mL) at 0° C. After stirring for 1 hour, the solvent and excess TFA were removed by $N_2$ flow. Then the residue was dissolved in $H_2O$/MeCN (1 mL/1 mL) and purified by HPLC. Pure fractions with the same retention time were combined and lyophilized to produce the compound 56d (24.9 mg, 68%) as yellow solid. EI-MS m/z: $[M+H]^+$ 851.6.

Example 77. Preparation of Compound 57a

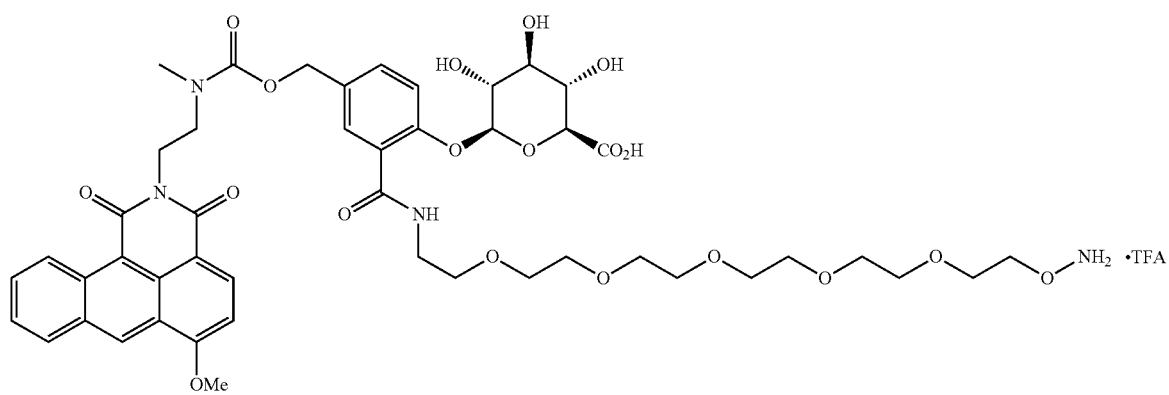

57a

Compound 57a was prepared from compound 56a and compound 15a by a similar method of preparing compound 56d in Example 76. EI-MS m/z: $[M+H]^+$ 983.3.

Experimental Example 1. Responsiveness Comparison Test with Respect to β-Glucuronidase In order to compare responsiveness of Compound 45k of Example 66 and Compound 50k of Comparative Example 66 to §i-glucuronidase with each other, comparison test was performed as follows.

Compound 45k of Example 66 and Compound 50k of Comparative Example 66 were each prepared as 500 μM and 50 μM DMSO stock solutions. Reaction solutions in which 880 μL of phosphate buffer saline (PBS) solution and 100 μL of Compound 45k and Compound 50k stock solutions were mixed with each other, respectively, were prepared (final concentrations thereof were 50 μM and 5 μM, respectively).

After 20 μL of *E. coli* (β-glucuronidase enzyme (1 mg/ml, Sigma: E.C.3.2.1.31 Type IX-A; 1 mg/mL in PBS; 3.6 μg, 13 μmol) was added to the reaction solutions, reactions were initiated in a constant temperature water bath at 37° C. 100 μL of the mixed solutions were dispensed at 0 min, 25 min, 60 min, and 90 min, respectively, and 200 μL. of acetonitrile was added thereto. MMAF released from each of the supernatants obtained by performing centrifugation (4° C., 15 min, 14000 rpm) on the mixture samples was quantitatively analyzed using LC-MS/MS (the experiment was performed by a method similar to a method disclosed in U.S. Pat. No. 8,568,728, hereby incorporated by reference).

Figure 2:
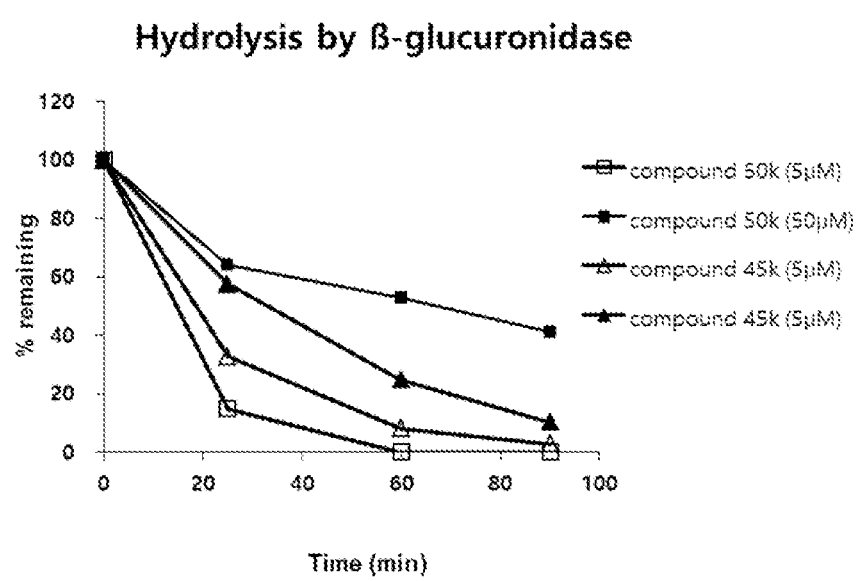
FIG. 2 is a graph depicting the hydrolysis of a linker by β-glucuronidase from Experimental Example 1.

The test results were illustrated in FIG. 2, and it was confirmed from FIG. 2 that MMAF was significantly rapidly released from each Compound 45k of Example 66 and Compound 50k of Comparative Example 66 through a 1,6-elimination reaction after enzyme reactions by β-glucuronidase (U.S. Pat. No. 8,568,728, hereby incorporated by reference).

Experimental Example 2. Plasma Stability Comparison Test Linker Toxin

The plasma stability of Compound 45k of Example 66 and Compound 50k of Comparative Example 66 were compared.

10 μL of Compound 45k or 50 k was dissolved in DMSO at 5 mM, and each composition was mixed with 990 μL of mouse plasma, thereby preparing 50 μM samples, for assessing plasma stability. The plasma/compound solutions were incubated at 37° C. for 7 days. During the 6-day incubation, 100 μL aliquots were taken at 0, 1, 2, and 7 days and mixed with 200 μL of acetonitrile containing an internal standard for monitoring plasma protein precipitation. Supernatants were obtained by centrifuging the acetonitrile/plasma samples (4° C., 15 min, 14000 rpm), and the amount of each compound and product was quantified by performing LC-MS/MS on the supernatants. (The experiment was performed using similar to those disclosed in J. Chromatography B, 780:451-457 (2002)).

Figure 3:
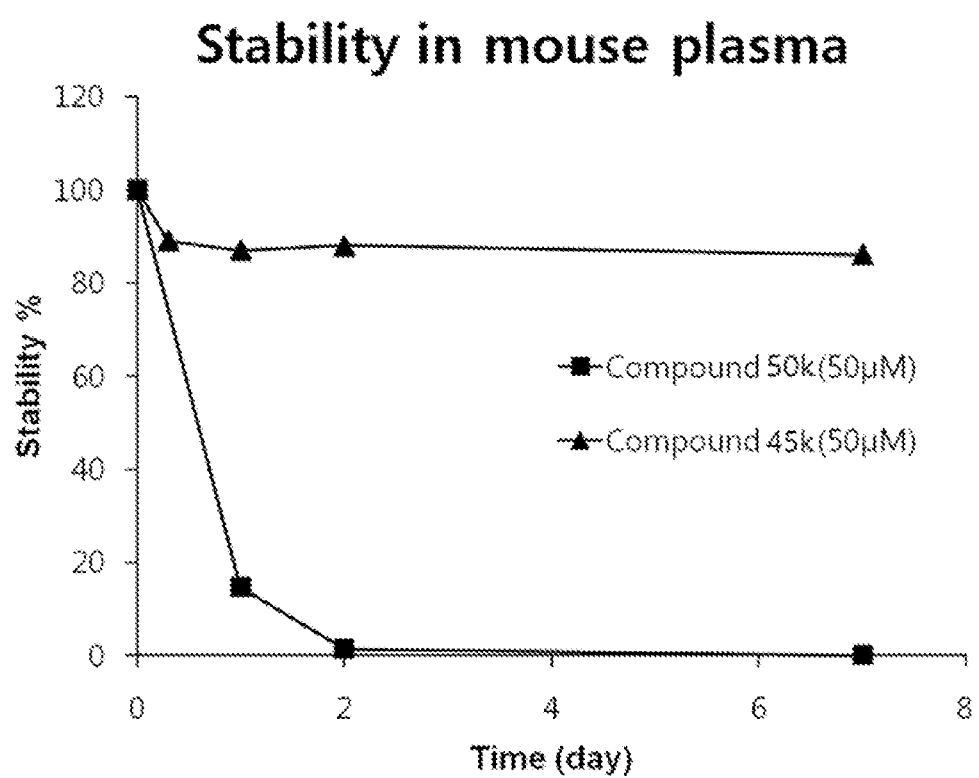
FIG. 3 is a graph depicting the plasma stability of two drug-linker conjugates from Experimental Example 2.

Results obtained for Compound 45k of Example 66 and Compound 50k of Comparative Example 66 using LS-MS/MS are illustrated in FIG. 3 and Table 1. The stability of Compound 50k of Comparative Example 66 and stability of Compound 45k of Example 66 was 14% and 80% at 1 day, respectively. Thus, the stability of Compound 45k of Example 66 in mouse plasma was superior to Compound 50k of Comparative Example 66.

TABLE 1

Stability of Compound 45 k and Compound 50 k in mouse plasma

|  | Compound 45 k of Example 66 | Compound 50 k of Comparative Example 66 |
|---|---|---|
| Linker | Glucuronide | Glucuronide |
| Plasma Stability (mouse plasma) | 80% Stability (@7 days) | 14% Stability (@1 day) |
| Result | Stable | Unstable |

Figure 4:
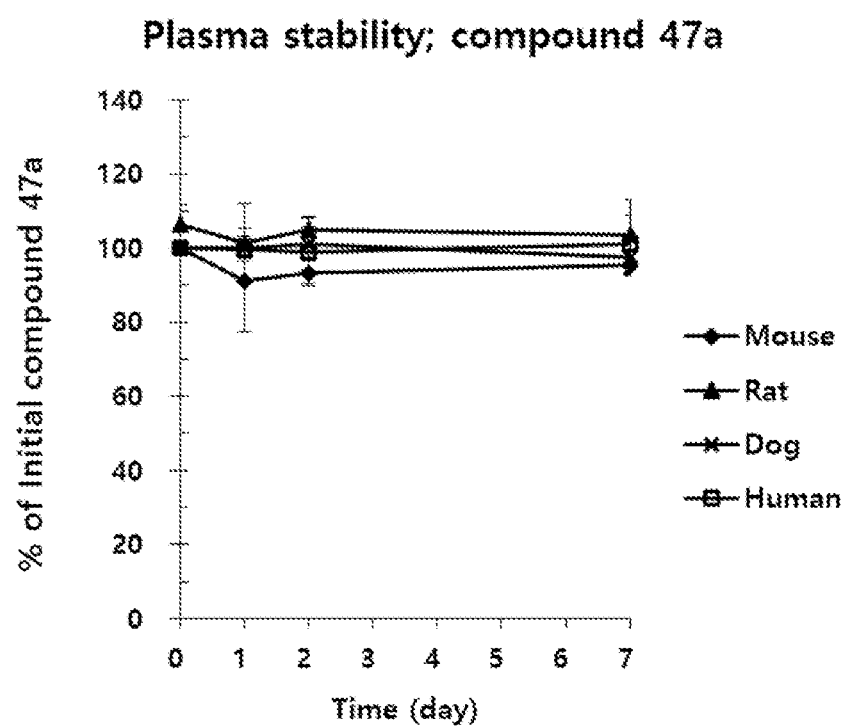
FIG. 4 is a graph depicting the plasma stability of compound 47a, described in Example 68.
Figure 5:
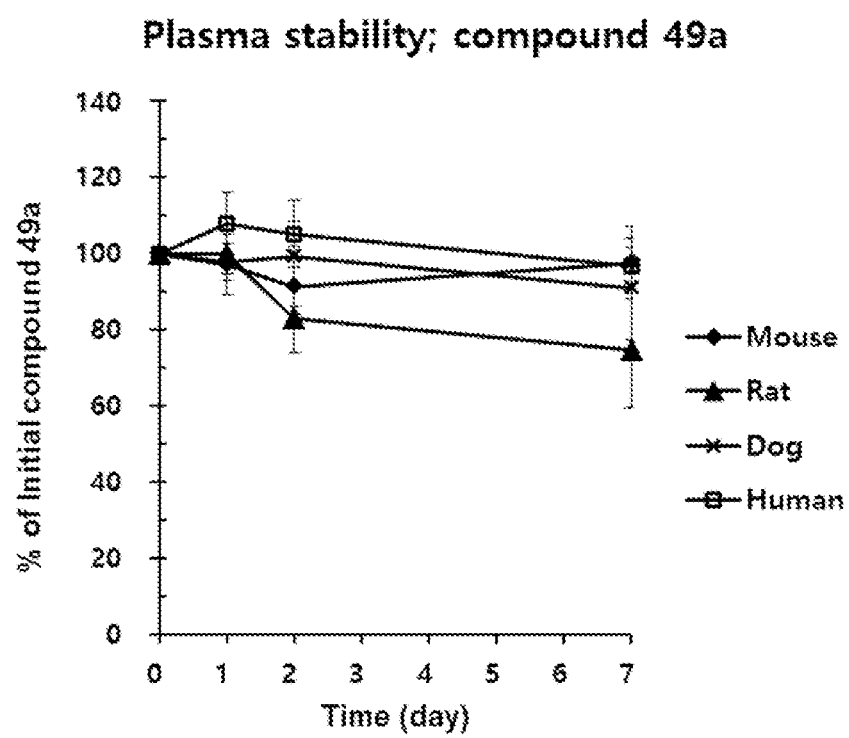
FIG. 5 is a graph depicting the plasma stability of compound 49a, described in Example 70.
Figure 6:
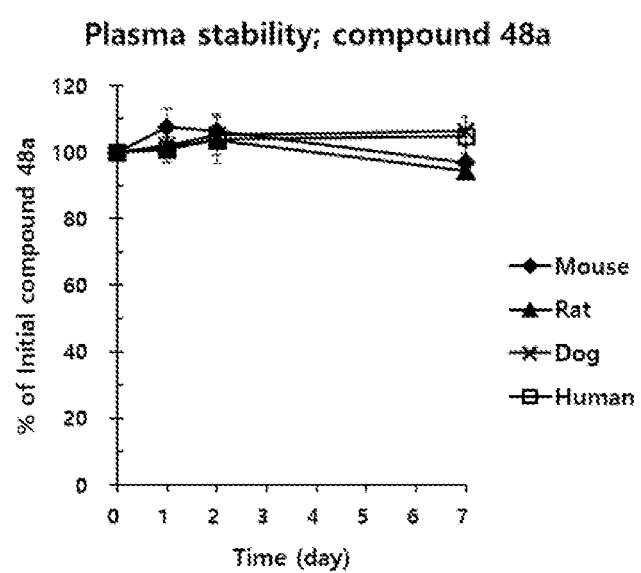
FIG. 6 is a graph depicting the plasma stability of compound 48a, described in Example 69.
Figure 7A:
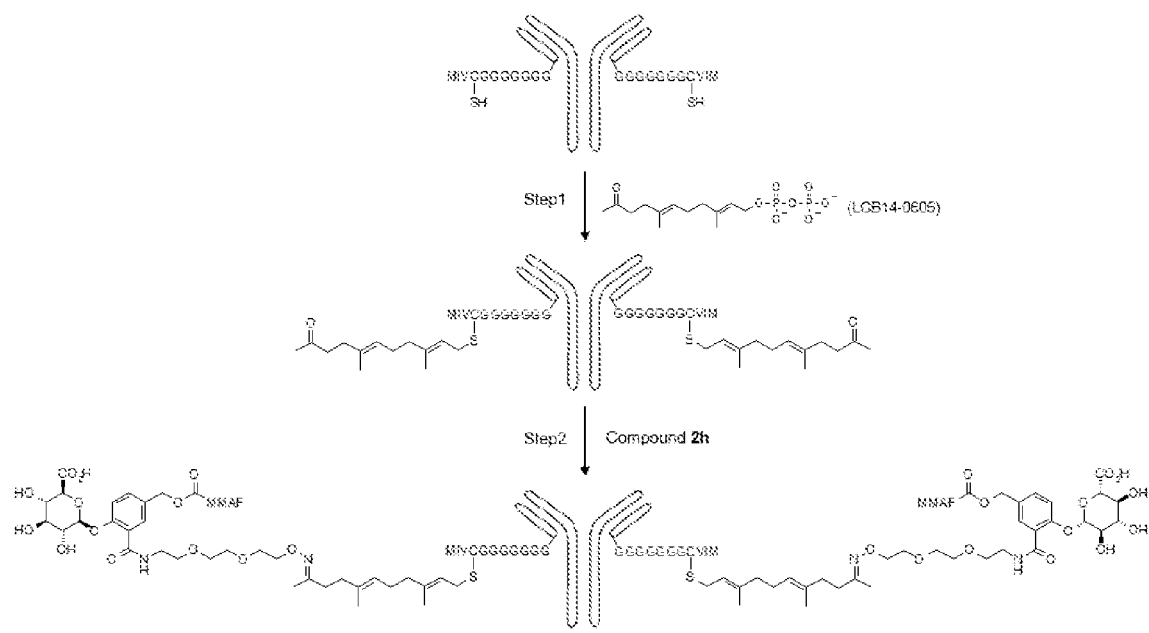
FIG. 7A displays a strategy for conjugating a drug to an antibody (DAR2).
Figure 7B:
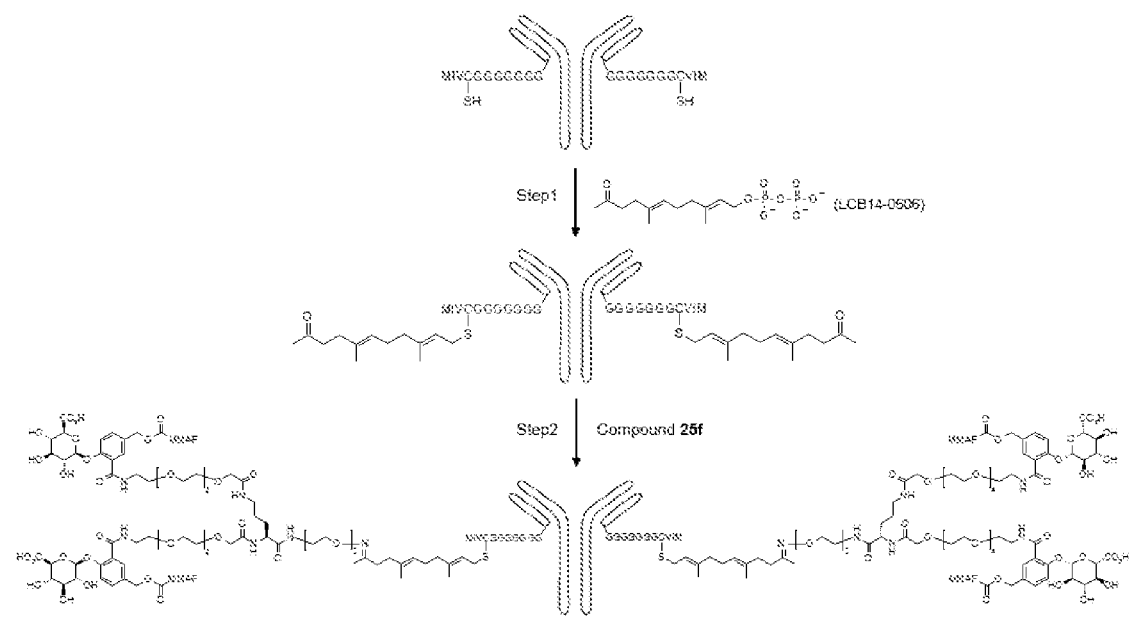
FIG. 7B displays a strategy for conjugating a drug to an antibody (DAR4).
Figure 8:
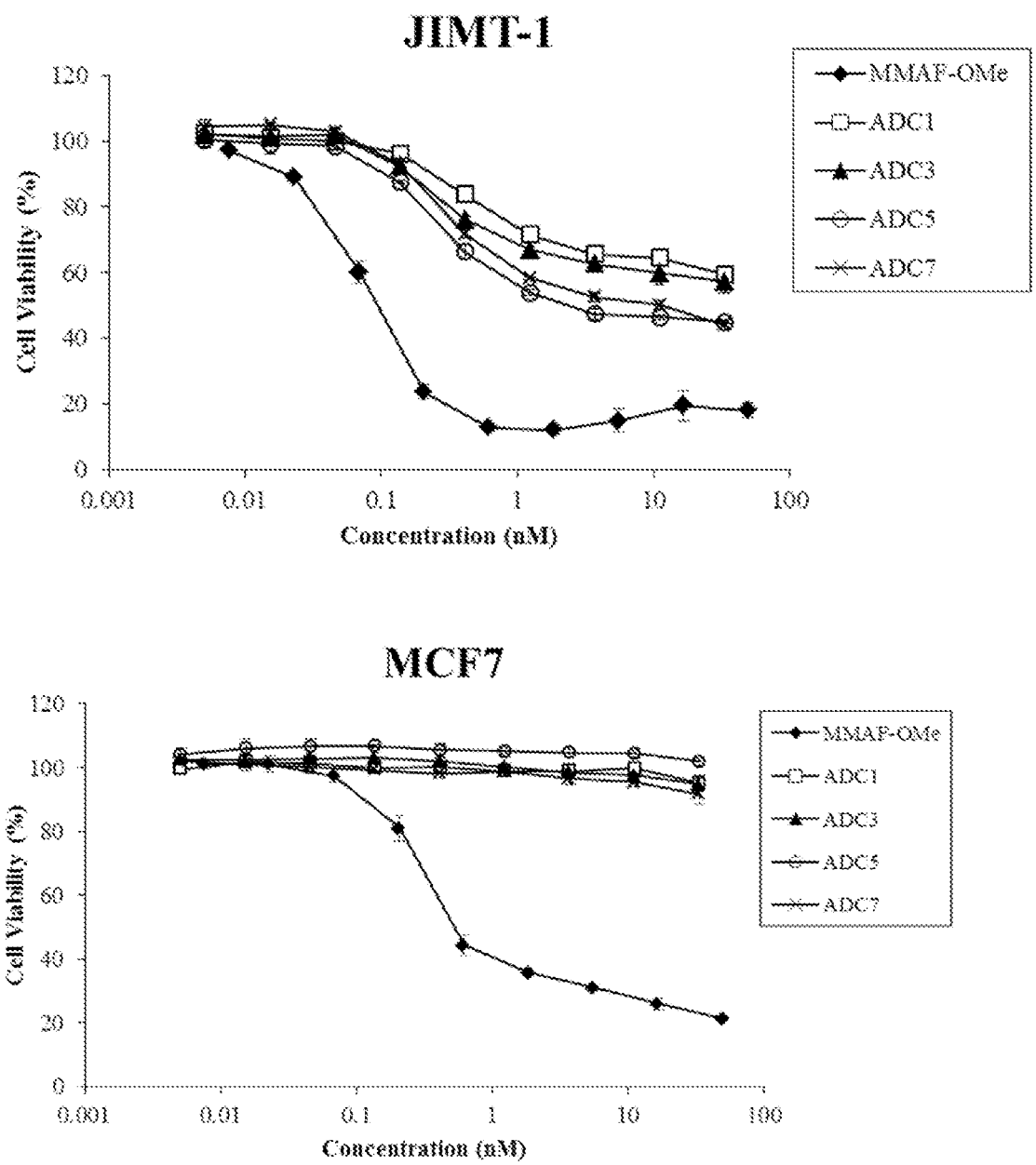
FIG. 8 shows relative in vitro activities of the DAR2 MMAE-conjugates, with varying PEG length in the linker, against JIMT-1 (HER2 positive) and MCF7 cells (HER2 negative).
Figure 9:
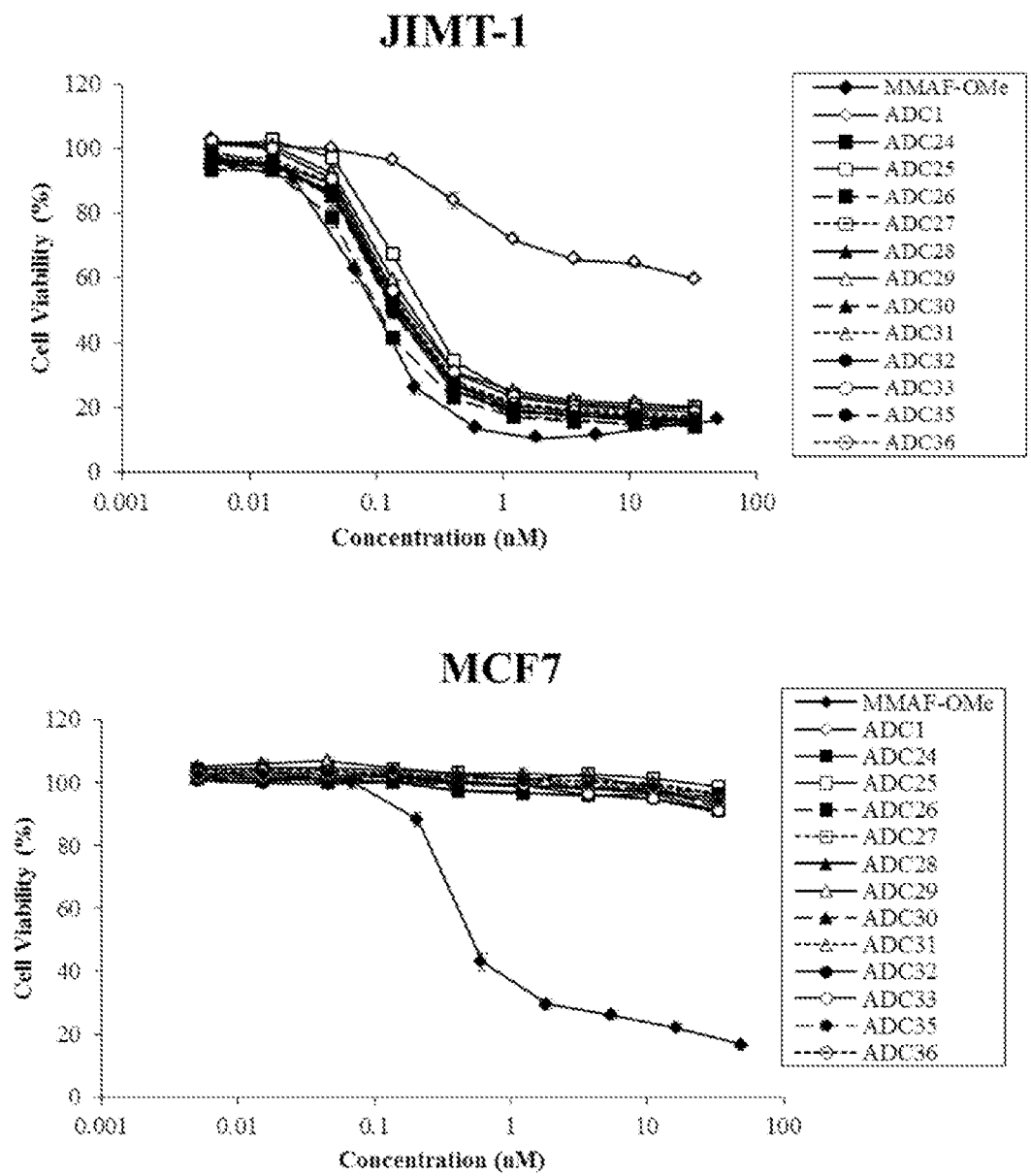
FIG. 9 shows relative in vitro activities of the DAR4 MMAE-conjugates, which have a different PEG length in linker part, against JIMT-1 (HER2 positive) and MCF7 cells (HER2 negative).

The plasma stability of Compound 47a, 48a, and 49a were performed by using the method mentioned above (FIG. 4-6).

Experimental Example 3. Preparation of Antibody-Drug Conjugate

Step 1. Method of Prenylated Antibody (Prepared According to the Method of Korean Patent Laid-Open Publication No. 10-2014-0035393)

A prenylation reaction mixture of an antibody was prepared and reacted at 30° C. for 16 hours. The antibodies comprising the GGGGGGGCVIM sequence ("G7CVIM") added to the c-terminus of each light chain were used. The G7CVIM sequence was added at the C-terminus of heavy chain (ADC86-91) or both heavy and light chain (ADC75-77). The sources of sequences of antibodies used were like following Table 2.

TABLE 2

The used antibody list for ADC preparation

| Target (Antibody) | References |
|---|---|
| HER2 (Herceptin ®) | http://www.drugbank.ca/drugs/DB00002 |
| EGFR (Erbitux ®) | http://www.drugbank.ca/drugs/DB00002 |
| CD19 (DI-B4) | US8691952 B2 |
| CD20 (Rituxan ®) | hllp://www.drugbank.ca/drugs/DB00073 |
| EGFR wt & EGFRvIII (ABT806) | US 2014/02555410 A9 |

The reaction mixture was composed of a buffer solution (50 mM Tris-HCl (pH7.4), 5 mM $MgCl_2$, 10 μM $ZnCl_2$, 0.25 mM DTT) containing 24 μM antibody, 200 nM FTase (Calbiochem #344145), and 144 μM LCB14-0606 (prepared in house according to the method of Korean Patent Laid-Open Publication No. 10-2014-0035393, hereby incorporated by reference). After the reaction was completed, a prenylated antibody was purified by FPLC.

Step 2. Method of Preparing ADC

An oxime bond formation reaction mixture between the prenylated antibody and linker-toxin was prepared by mixing 100 mM Na-acetate buffer (pH 4.5, 10% DMSO), 12 μM prenylated antibody, and 120 μM linker-toxin (in house) and gently stirred at 30° C.

After incubating the reaction for 24 hours, the antibody-drug conjugate was purified by desalting via FPLC and hydrophobic interaction chromatography-HPLC.

TABLE 3

List of anti- HER2 ADCs (DAR2)

| ADC# | Comp'd # |
|---|---|
| ADC1 | 2g |
| ADC2 | 2h |
| ADC3 | 3f |
| ADC4 | 3g |
| ADC5 | 4f |
| ADC6 | 4g |
| ADC7 | 5e |
| ADC8 | 5f |
| ADC9 | 6e |
| ADC10 | 7e |
| ADC11 | 8f |
| ADC12 | 9j |
| ADC13 | 10c |
| ADC14 | 10d |
| ADC15 | 11j |
| ADC16 | 11k |
| ADC17 | 12c |
| ADC18 | 12d |
| ADC19 | 13e |
| ADC20 | 13f |
| ADC86 | 2h |
| ADC87 | 2g |

TABLE 4

List of anti- HER2 ADCs (DAR4)

| ADC# | Comp'd # |
|---|---|
| ADC23 | 16f |
| ADC24 | 16g |
| ADC25 | 17d |
| ADC26 | 18c |
| ADC27 | 19c |
| ADC28 | 20q |
| ADC29 | 21i |
| ADC30 | 22h |
| ADC31 | 23h |
| ADC32 | 24l |
| ADC33 | 25e |
| ADC34 | 25f |
| ADC35 | 26e |
| ADC36 | 27e |
| ADC37 | 28d |
| ADC38 | 28e |
| ADC39 | 29j |
| ADC40 | 29k |
| ADC41 | 30b |
| ADC42 | 30c |
| ADC43 | 31f |
| ADC44 | 31g |
| ADC45 | 32c |
| ADC46 | 32d |
| ADC47 | 33e |
| ADC48 | 33f |
| ADC49 | 34e |
| ADC50 | 34f |
| ADC51 | 35g |
| ADC52 | 36e |
| ADC53 | 37d |
| ADC54 | 38b |
| ADC55 | 38e |
| ADC76 | 2h |
| ADC88 | 16f |
| ADC89 | 16g |
| ADC90 | 25f |
| ADC91 | 25e |

TABLE 5

List of anti- HER2 ADCs (DAR4<)

| | ADC# | Comp'd # |
|---|---|---|
| <DAR6> | ADC60 | 43i |
| | ADC61 | 43j |
| <DAR8> | ADC62 | 44i |
| | ADC63 | 44j |
| | ADC77 | 16f |

TABLE 6

List of anti-HER2 ADCs using amanitin as a payload

| DAR 2 | | DAR4 | |
|---|---|---|---|
| ADC# | Comp'd # | ADC# | Comp'd # |
| ADC21 | 14m | ADC56 | 39e |
| ADC22 | 15b | ADC57 | 40c |
| | | ADC58 | 41c |
| | | ADC59 | 42d |

TABLE 7

List of ADCs using antibodies targeting various proteins

| Target (Antibody) | ADC# | Comp'd # |
|---|---|---|
| EGFR (Erbitux ®) | ADC64 | 2h |
| | ADC65 | 25e |
| | ADC66 | 25f |
| CD19 (DI-B4) | ADC67 | 2h |
| | ADC68 | 25e |
| | ADC69 | 25f |
| CD20 (Rituxan ®) | ADC70 | 2h |
| | ADC71 | 25e |
| | ADC72 | 25f |
| | ADC73 | 4g |
| EGFR wt & EGFRvIII (ABT806) | ADC74 | 25e |
| | ADC75 | 25f |

Experimental Example 4. Cytotoxicity of Anti-HER2 ADCs

Commercially available human breast cancer cell lines MCF-7 (HER2 negative to normal), OE-19 (HER2 positive), NCI-N87 (HER2 positive), SK-OV-3 (HER2 positive), JIMT-1 (HER2 positive), and SK-BR-3 (HER2 positive) were used. The cell lines were cultured according to recommended specifications provided with the commercially available cell lines.

Anti-proliferation activities of the antibodies, drugs, and conjugates with regard to the cancer cell lines were measured. The cells were plated in 96-well, tissue culture plates at $1 \times 10^4$ cells per well. After 24 hour incubation, the antibodies, drugs, and conjugates were added in various concentrations. The number of viable cells after 72 hours were counted using SRB assay. Absorbance was measured at 540 nm using SpectraMax 190 (Molecular Devices, USA).

TABLE 8

$IC_{50}$ value of the different anti-HER2 ADCs (DAR2)

| Payload | ADC | Linker-toxin | SK-BR-3 | JIMT-1 | OE-19 | NCI-N87 | SK-OV-3 | MCF-7 |
|---|---|---|---|---|---|---|---|---|
| MMAF | ADC8 | 5f | 0.10 | 0.34 | — | — | — | >33.33 |
| | ADC2 | 2h | 0.14 | 0.16 | 0.42 | 0.75 | 1.19 | >33.33 |
| | ADC4 | 3g | 0.10 | 0.32 | — | 0.97 | 1.21 | >33.33 |
| | ADC6 | 4g | 0.03 | 0.38 | — | — | — | >33.33 |
| | ADC16 | 11k | 0.06 | 0.26 | — | — | — | >33.33 |
| | ADC14 | 10d | 0.09 | 0.31 | — | — | — | >33.33 |
| | ADC18 | 12d | 0.10 | 0.34 | — | — | — | >33.33 |
| | ADC20 | 13f | 0.08 | 0.29 | — | — | — | >33.33 |
| MMAE | ADC7 | 5e | 0.10 | 13.44 | — | — | — | >33.33 |
| | ADC1 | 2g | 0.47 | 275 | — | 0.69 | 241 | >33.33 |
| | ADC3 | 3f | 0.29 | 1.63 | — | 1.04 | 1.34 | >33.33 |
| | ADC5 | 4f | 0.15 | 0.97 | — | 0.40 | 1.04 | >33.33 |
| | ADC9 | 6e | 0.10 | >33.3 | — | — | — | >33.33 |

TABLE 8-continued

IC$_{50}$ value of the different anti-HER2 ADCs (DAR2)

| Payload | ADC | Linker-toxin | SK-BR-3 | JIMT-1 | OE-19 | NCI-N87 | SK-OV-3 | MCF-7 |
|---|---|---|---|---|---|---|---|---|
| | ADC15 | 11j | 0.17 | >33.3 | — | — | — | >33.33 |
| | ADC10 | 7e | 0.12 | 0.64 | — | — | — | >33.33 |
| | ADC12 | 9j | 0.20 | 2.01 | — | — | — | >33.33 |
| | ADC13 | 10c | 0.19 | 1.09 | — | — | — | >33.33 |
| | ADC17 | 12c | 0.03 | 0.11 | — | — | — | >33.33 |
| | ADC19 | 13e | 0.13 | 0.38 | — | — | — | >33.33 |

TABLE 9

IC$_{50}$ value of the different PEG length-ADCs

| | | Test samples | | | IC$_{50}$ (nM) | |
|---|---|---|---|---|---|---|
| Toxin | DAR | ADC | # of PEG unit | Linker-toxin | JIMT-1 | MCF-7 |
| MMAE | 2 | ADC7 | 1 | 5e | >10.0 | >10.0 |
| | | ADC1 | 3 | 2g | >10.0 | >10.0 |
| | | ADC3 | 6 | 3f | >10.0 | >10.0 |
| | | ADC5 | 12 | 4f | 1.01 | >10.0 |

TABLE 10

IC$_{50}$ value of MMAF ADCs with the different types of linkers

| ADC | Linker-toxin | SK-BR-3 | JIMT-1 | NCI-N87 | SK-OV-3 | MCF-7 |
|---|---|---|---|---|---|---|
| ADC23 | 16f | 0.05 | 0.12 | 0.35 | 0.44 | >33.33 |
| ADC34 | 25f | 0.03 | 0.10 | — | — | >33.33 |
| ADC38 | 28e | 0.03 | 0.05 | — | — | >33.33 |
| ADC40 | 29k | 0.02 | 0.06 | — | — | >33.33 |
| ADC42 | 30c | 0.03 | 0.04 | — | — | >33.33 |
| ADC44 | 31g | 0.03 | 0.05 | — | — | >33.33 |
| ADC46 | 32d | 0.04 | 0.08 | — | — | >33.33 |
| ADC48 | 33f | 0.03 | 0.08 | — | — | >33.33 |
| ADC50 | 34f | 0.03 | 0.05 | — | — | >33.33 |
| ADC53 | 37d | 0.03 | 0.05 | — | — | >33.33 |
| ADC54 | 38b | 0.05 | 0.12 | — | — | >33.33 |

TABLE 11

IC$_{50}$ value of MMAE ADCs with the different types of linkers

| ADC | Linker-toxin | SK-BR-3 | JIMT-1 | NCI-N87 | SK-OV-3 | MCF-7 |
|---|---|---|---|---|---|---|
| ADC24 | 16g | 0.14 | 0.26 | 0.17 | 0.37 | >33.33 |
| ADC25 | 17d | 0.03 | 0.10 | 0.36 | 0.37 | >33.33 |
| ADC26 | 18c | 0.08 | 0.14 | — | — | >33.33 |
| ADC27 | 19c | 0.05 | 0.43 | 0.29 | 0.38 | >33.33 |
| ADC28 | 20q | 0.03 | 0.12 | 0.36 | 0.36 | >33.33 |
| ADC29 | 21i | 0.03 | 0.41 | 0.31 | 0.49 | >33.33 |
| ADC30 | 22h | 0.05 | 0.41 | 0.30 | 0.35 | >33.33 |
| ADC31 | 23h | 0.14 | 0.24 | — | — | >33.33 |
| ADC32 | 24l | 0.03 | 0.40 | 0.32 | 0.35 | >33.33 |
| ADC33 | 25e | 0.04 | 0.23 | 0.27 | 0.33 | >33.33 |
| ADC35 | 26e | 0.13 | 0.19 | — | — | >33.33 |
| ADC36 | 27e | 0.13 | 0.22 | — | — | >33.33 |
| ADC37 | 28d | 0.04 | 0.07 | — | — | >33.33 |
| ADC39 | 29j | 0.03 | 0.11 | — | — | >33.33 |
| ADC41 | 30b | 0.03 | 0.10 | — | — | >33.33 |
| ADC43 | 31f | 0.03 | 0.04 | — | — | >33.33 |
| ADC45 | 32c | 0.03 | 0.08 | — | — | >33.33 |
| ADC47 | 33e | 0.04 | 0.07 | — | — | >33.33 |
| ADC49 | 34e | 0.03 | 0.05 | — | — | >33.33 |
| ADC51 | 35g | 0.04 | 0.24 | 0.34 | — | >33.33 |
| ADC52 | 36e | 0.07 | 0.40 | 0.37 | — | >33.33 |
| ADC55 | 38e | 0.04 | 0.07 | — | — | >33.33 |

TABLE 12

IC$_{50}$ value of the hybrid ADCs

| Test samples | | | | IC$_{50}$ (nM) | | | | |
|---|---|---|---|---|---|---|---|---|
| Toxin | DAR | ADC | Linker-toxin | SK-BR-3 | JIMT-1 | NCI-N87 | SK-OV-3 | MCF-7 |
| MMAF | 2 | ADC2 | 2h | 0.08 | 0.40 | 0.84 | 0.84 | >33.33 |
| | 4 | ADC23 | 16f | 0.05 | 0.10 | 0.25 | 0.36 | >33.33 |
| Amanitin | 2 | ADC21 | 14m | 0.09 | >33.3 | 0.88 | 0.25 | >33.33 |
| MMAF & Amanitin | 4 | ADC58 | 41c | 0.06 | 0.73 | 0.95 | 0.64 | >33.33 |
| | 8 | ADC78 | 41c | 0.03 | 0.03 | 0.33 | 0.76 | >33.33 |
| MMAF-OMe | | | | 0.12 | 0.07 | 0.49 | 0.78 | 0.60 |

The comparison of two different toxin conjugated ADCs and same toxin conjugated ADCs

TABLE 13

$IC_{50}$ value of the various DAR-ADCs

| Test samples | | | | |
|---|---|---|---|---|
| | | Linker- | $IC_{50}$ (nM) | |
| DAR# | ADC code | toxin | JIMT-1 | MCF-7 |
| DAR2 | ADC2 | 2h | 1.37 | >33.33 |
| DAR4 | ADC23 | 16f | 0.21 | >33.33 |
| | ADC34 | 25f | 0.09 | >33.33 |
| | ADC76 | 2h | 0.27 | >33.33 |
| DAR8 | ADC62 | 44i | 0.08 | >33.33 |
| | ADC77 | 16f | 0.02 | >33.33 |

Experimental Example 5. Cytotoxicity of Erbitux (LC)-Glucuronide Linker-MMAF

A431 cells, which express high levels of EGFR, and MCF-7 cells, which express low levels of EGFR, were plated at about 1000 cells per well in a 96-well plate in 100 µL of media. HCC-827 cells, which express an intermediate level of EGFR were plated at about 5000 cells per well in a 96-well plate in 100 µL of media. The cells were incubated at 37° C. in 5% $CO_2$ for 24 hours. Then, serial dilutions of monomethyl auristatin F—OMe (MMAF-OMe), Erbitux (LC)-G7CVIM, and the antibody drug conjugate ADC64 comprising Erbitux (LC)-G7CVIM and MMAF were added to the cells at concentrations of 100 to 0.00128 nM. The cells were incubated for 72 hours and then fixed for 1 hour at 4° C. after adding 100 µL of ice-cold 10% trichloroacetic acid to each well. Viable cells were counted using SRB dye (Sulforhodamine B, Sigma S1402) and a Molecular Devices SpectraMax 190 plate reader running Softmax Pro v5, monitoring absorbance at 540 nm (Table 14)

Erbitux (LC)-G7CVIM had an $IC_{50}$ greater than 100 nM for each cell line (A431, MCF-7, and HCC-827). MMAF-OMe had an $IC_{50}$ of 1.81 nM against MCF-7 cells, 1.99 nM against HCC-827 cells, and 1.11 nM against A431 cells. The antibody-drug conjugate ADC64, 65, and 66 had an $IC_{50}$ of greater than 100 nM against MCF-7 cells, 0.47, 0.17, and 0.11 nM against HCC-827 cells, respectively. ADC64 showed 1.3 nM against A431 cells, thus displaying superior specificity over MMAF-OMe and superior potency over Erbitux (LC)-G7CVIM.

TABLE 14

$IC_{50}$ value of anti-EGFR mAb, Erbitux based ADCs

| | Cell-lines | | |
|---|---|---|---|
| ADC Code | A431 | HCC-827 | MCF-7 |
| ADC64 | 1.30 | 0.47 | >33.33 |
| ADC65 | — | 0.17 | >33.33 |
| ADC66 | — | 0.11 | >33.33 |

Experimental Example 6. Cytotoxicity of ABT-806 (LC)-Glucuronide Linker-MMAF

Cytotoxicity of ABT-806 based ADCs were tested against patient derived cell lines established Samsung Medical Center (Seoul, Republic of Korea). The cells were maintained in Neurobasal®-A Media (Thermo Fisher Scientific) with supplement of L-glutamine (200 nM), bFGF (0 ng/mL), EGF (20 ng/mL), N2 supplement, and B27 supplement. For the viability test, cells were aliquoted to 96-well plate (5000 cells/well) and incubated at 37° C. in 5% $CO_2$ for day before treatment. After ADC treatment, cells were incubated for 72 hr. 100 µL of CellTiter-Glo® Reagent (Promega) was added to each well to analyze the cell viability. Aft r 10 minutes incubation, luminescent signal was analyzed using Luminometer.

DAR4 ADCs (ADC74, ADC75) had better potency than DAR2 ADC (ADC73) as expected. Some patient's cells showed a little different sensitive to payload. 22 & 780 cells were more sensitive to MMAF over MMAE, 464 cells vice versa.

TABLE 15

Cytotoxic activity of ABT-806 based ADCs against patient derived cell lines

| Test samples | | Patient Derived Cell-lines | | | | |
|---|---|---|---|---|---|---|
| | | vIII352T1 | 780 | 437 | 464 | 22 |
| ABT806 | ADC73 | 0.572 | 0.959 | 0.357 | 0.472 | 0.501 |
| | ADC75 | 0.104 | 0.227 | 0.241 | 0.151 | 0.282 |
| | ADC74 | 0.170 | 0.425 | 0.253 | 0.069 | 0.489 |

Experimental Example 7. Cytotoxicity of Anti-CD19 ADCs

Ramos cells, which are human Burkitt's lymphoma cells, were seeded in a 96-well plate at 20,000 cells/well in 100 µL of growth media. The cells were incubated at 37° C. in 5% $CO_2$ for 1 day. Serial dilutions of anti-CD19 antibodies DI-B4-(LC)-G7CVIM and ADCs from 33.33 nM to 5.1 µM in 100 µL media were added to the wells, and the cells were incubated with the antibody & ADCs for 72 hours. Cell viability was assessed using WST-1 (TaKaRa MK400) and a Molecular Devices SpectraMax 190 plate reader running Softmax Pro v5, monitoring absorbance at 450 nm (Table 16).

The experiments in Ramos cells were performed in parallel with experiments on K562 cells, human myelogenous leukemia cells that do not express CD19, as a negative control to assess any non-specific cytotoxicity.

ADC68 and ADC69 displayed an $IC_{50}$ of 0.09 nM against Ramos cells, which was superior to unconjugated DI-B4 (Table 16). No antibody displayed cytotoxicity below 33.33 nM against the K562 control cells.

TABLE 16

Cytotoxic activity of anti-CD19 antibody based ADCs

| | Cell-lines | |
|---|---|---|
| ADC Code | Ramos | K562 |
| ADC67 | >33.33 | >33.33 |
| ADC68 | 0.09 | >33.33 |
| ADC69 | 0.09 | >33.33 |

Experimental Example 8. Cytotoxicity of Rituxan Based ADCs

Ramos cells, which are human Burkitt's lymphoma cells, were seeded in a 96-well plate at 20,000 cells/well in 100 µL of growth media. The cells were incubated at 37° C. in 5% $CO_2$ for 1 day. Serial dilutions of Rituxan (LC)-G7CVIM and ADCs from 33.33 nM to 5.1 µM in 100 µL media were added to the wells, and the cells were incubated with the antibody & ADCs for 72 hours. Cell viability was assessed using WST-1 (TaKaRa MK400) and a Molecular Devices SpectraMax 190 plate reader running Softmax Pro v5, monitoring absorbance at 450 nm (Table 17).

The experiments in Ramos cells were performed in parallel with experiments on K562 cells, human myelogenous leukemia cells that do not express CD20, as a negative control to assess any non-specific cytotoxicity.

ADC70, ADC71, and ADC72 displayed an $IC_{50}$ of 4.56 nM, 1.47 nM, and 1.78 nM against Ramos cells respectively, which was superior to unconjugated anti-CD20 antibody (Table 17). No antibody displayed cytotoxicity below 33.33 nM against the K562 control cells.

TABLE 17

Cytotoxic activity of Rittman-based ADCs

| ADC Code | Cell-lines | |
|---|---|---|
| | Ramos | K562 |
| ADC70 | 4.56 | >33.33 |
| ADC71 | 1.47 | >33.33 |
| ADC72 | 1.78 | >33.33 |

Experimental Example 9. Differences in Beta Glucuronidase Susceptibility

Figure 10:
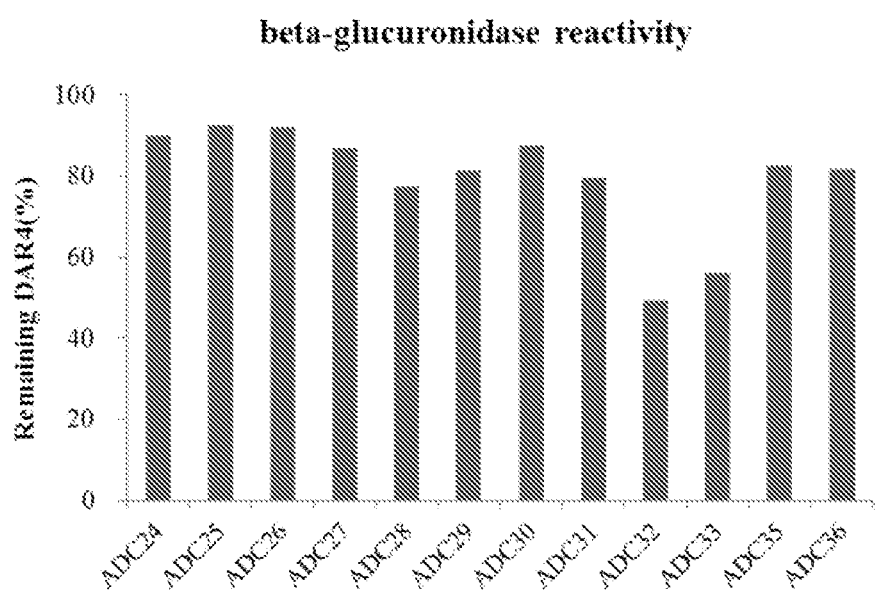
FIG. 10 shows human beta-glucuronidase reactivity in DAR4 ADCs, which have the various linker types. 12 μM of ADCs were incubated with 0.01 μg of human beta-glucuronidase (R&D Systems) for 3 hours at 37° C.

ADCs in 0.06 M Na-acetate buffer (pH5.2) were aliquoted into the 1.5 mL micro tube. The final concentration of ADC in the mixture was adjusted to 12 µM. 0.001 µg of human β-glucuronidase (R&D systems: 6144-GH-020) was added to each tube. Then, the mixtures were incubated at 37° C. water bath for 3 h. The reaction was terminated by the addition of cold PBS buffer (pH7.4) to the 15-fold dilution. The change of ADC-pattern by beta-glucuronidase was analyzed by HIC-HPLC. The efficacy of enzyme activity was visualized by % of remaining (FIG. 10)

The attribute to susceptibility seemed to be the Branch Unit (BR) of linker-toxin part. When Lys was located in BR, the toxin release was occurred very efficiently. Amide and amine showed less susceptibility than Lys.

Experimental Example 10. Plasma Stability of ADCs

To compare plasma stability between ADC2 (Herceptin—LBG-MMAF, DAR2) and Kadcyla, those ADCs were incubated in mouse and human plasma for 5 seconds (0 h) or 96 hours (96 h), followed by SRB in vitro cytotoxicity test using SK-BR3 cells for 72 hr.

Figure 11:
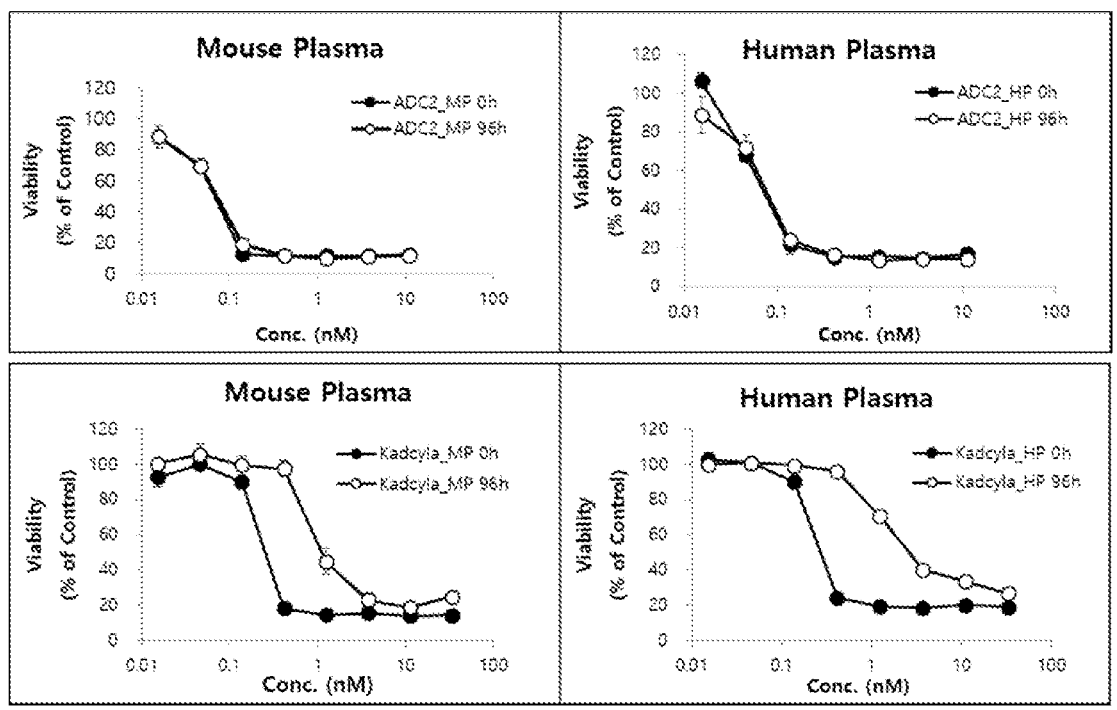
FIG. 11 shows plasma stability of ADC2 and Kadcyla in mouse or human plasma.

Plasma-incubated ADC2 retains potent cytotoxicity (no change in $IC_{50}$; 0.06 (0 h) and 0.07 nM (96 h) for MP, 0.08 (0 h) and 0.08 nM (96 h) for HP) while plasma-incubated Kadcyla displayed decreased cytotoxicity compared to 0 h Kadcyla (increase in $IC_{50}$; 0.26 (0 h) and 1.59 nM (96 h) for MP, 0.29 (0 h) and 4.21 nM (96 h) for HP) (FIG. 11)

Figure 12:
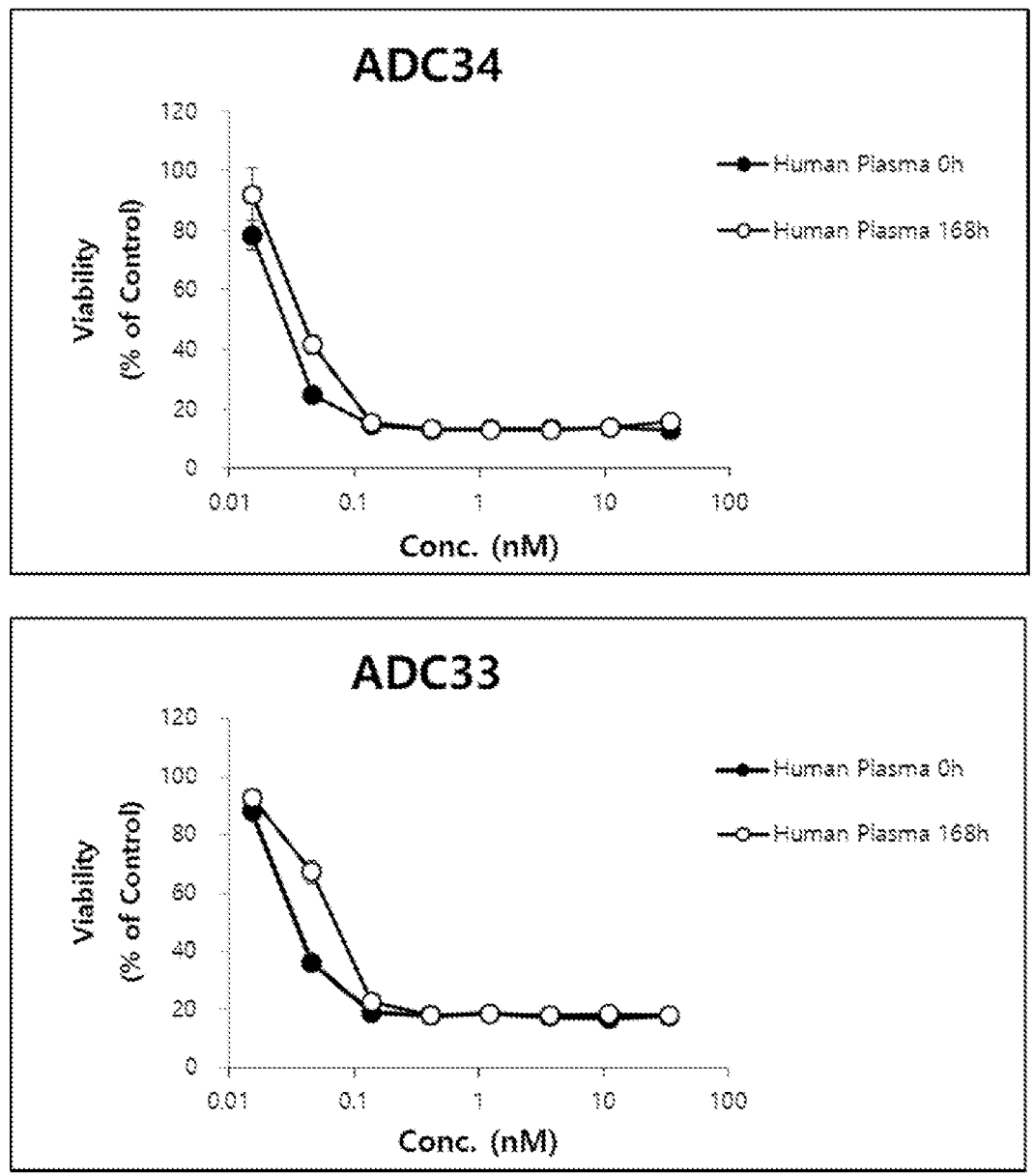
FIG. 12 shows human plasma stability of ADC33 and ADC34 for 7 days.

To characterize the plasma stability of ADCs made of various antibody, ADCs were incubated in human plasma for 5 seconds (0 h) or 168 hours (168 h), followed by SRB in vitro cytotoxicity test using SK-BR3 cells for 72 hr. (Table 18-20, and FIG. 12)

TABLE 18

Plasma stability of Herceptin based ADCs (nM)

| Test samples | | | Plasma incubation time | |
|---|---|---|---|---|
| | | | 0 h | 168 h |
| MMAF-OMe | | | 0.48 | N.D. |
| Herceptin | MMAF | ADC2 | 0.09 | 0.15 |
| | | ADC6 | 0.07 | 0.09 |
| | | ADC8 | 0.11 | 0.18 |
| | | ADC14 | 0.06 | 0.08 |
| | | ADC16 | 0.05 | 0.07 |
| | | ADC23 | 0.04 | 0.05 |
| | | ADC34 | 0.03 | 0.04 |
| | | ADC40 | 0.03 | 0.05 |
| | | ADC46 | 0.03 | 0.03 |
| | | ADC48 | 0.03 | 0.04 |
| | | ADC62 | 0.02 | 0.02 |
| | MMAE | ADC1 | 0.26 | 0.41 |
| | | ADC3 | 0.20 | 0.32 |
| | | ADC5 | 0.19 | 0.31 |
| | | ADC7 | 0.17 | 0.26 |
| | | ADC12 | 0.51 | 0.79 |
| | | ADC13 | 0.63 | 0.87 |
| | | ADC15 | 0.52 | 0.70 |
| | | ADC24 | 0.08 | 0.11 |
| | | ADC25 | 0.07 | 0.12 |
| | | ADC26 | 0.17 | 0.22 |
| | | ADC27 | 0.10 | 0.14 |
| | | ADC28 | 0.07 | 0.08 |
| | | ADC29 | 0.06 | 0.08 |
| | | ADC30 | 0.15 | 0.19 |
| | | ADC31 | 0.08 | 0.12 |
| | | ADC32 | 0.05 | 0.09 |
| | | ADC33 | 0.04 | 0.09 |
| | | ADC35 | 0.11 | 0.21 |
| | | ADC36 | 0.09 | 0.12 |
| | | ADC39 | 0.12 | 0.17 |
| | | ADC45 | 0.04 | 0.05 |
| | | ADC47 | 0.04 | 0.05 |
| | | ADC61 | 0.32 | 0.32 |

TABLE 19

Plasma stability of anti-CD19 antibody based ADCs (nM)

| Test samples | | | Plasma incubation | |
|---|---|---|---|---|
| | | | 0 h | 168 h |
| MMAF-OMe | | | 0.160 | N.D. |
| CD19 | | ADC68 | 0.036 | 0.048 |
| | | ADC69 | 0.047 | 0.135 |

TABLE 20

Plasma stability of anti-CD20 antibody based ADCs (nM)

| Test samples | | Plasma incubation | |
|---|---|---|---|
| | | 0 h | 168 h |
| MMAF-OMe | | 0.160 | N.D. |
| CD20 | ADC71 | 4.001 | 4.134 |
| | ADC72 | 2.026 | 3.851 |

Experimental Example 11. Pharmacokinetics of Herceptin® and ADCs

Male Sprague Dawley rats were dosed intravenously with 3 mg/kg of antibodies or the antibody-drug conjugates. Blood samples were taken at multiple time points after dosing, chilled in ice water, and plasma was isolated. Plasma was frozen at −80° C. until subsequent LC/MS/MS analysis.

20 μL, of each sample was mixed with 340 μL of PBS and 60 μL of protein A magnetic beads and incubated for 2 hours at room temperature with gentle shaking. The beads were washed three times with PBS. Then, 25 μL of an internal standard (isotope-labeled peptides at 10 μg/mL), 75 μL of RapiGest SF (Waters), and 10 μL of dithiothreitol were added to the beads. The mixture was shaken for 1 minute and then incubated for 1 hour at 60° C. 25 μL of iodoacetic acid was added to the mixture, the mixture was shaken for 1 minute, and then incubated for 30 minutes at room temperature. 10 μL of sequencing grade modified trypsin (Promega) was added to the mixture, the mixture was shaken for 1 minute, and the mixture was incubated overnight at 37° C. 15 μL of hydrochloric acid was added to the mixture, the mixture was shaken for 1 minute, and the mixture was incubated for 30 minutes at 37° C. The mixture was centrifuged at 5000×g for 10 minutes at 4° C. and the supernatant was transferred into an HPLC vial.

Figure 13:
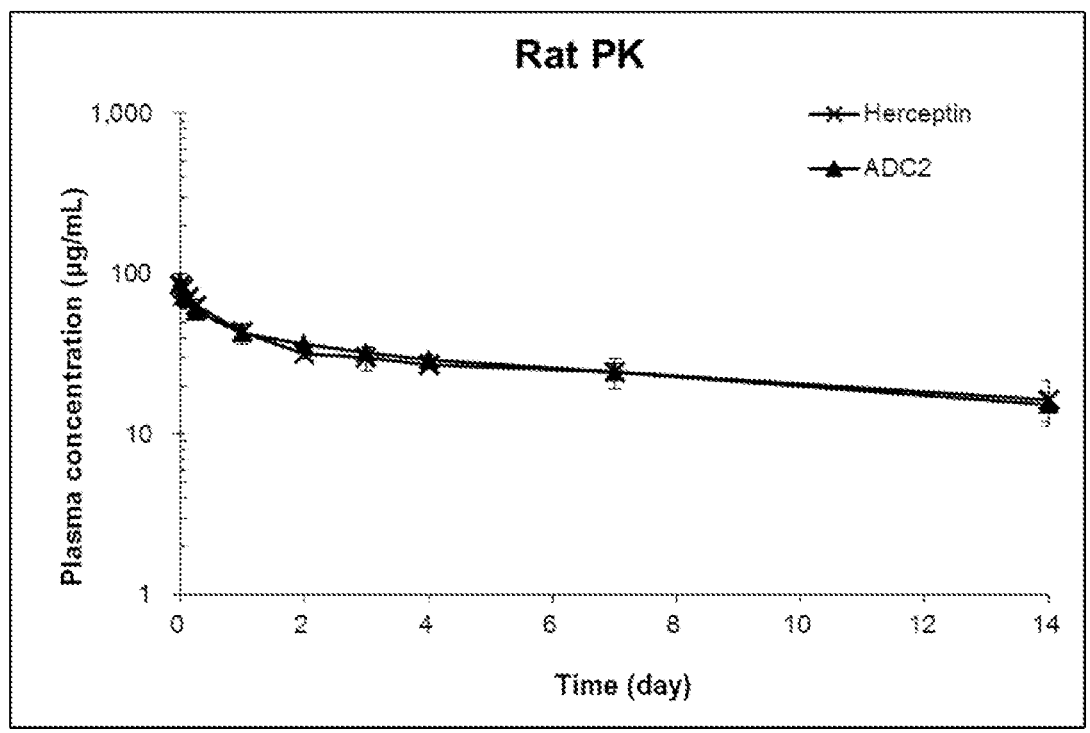
FIG. 13 shows Rat PK profile of Herceptin and ADC2.

The liquid chromatography-mass spectrometry system consisted of two Shimadzu LC-20AD pumps, a Shimadzu CBM-20A HPLC pump controller (Shimadzu Corporation, Columbia, Md., USA), a CTC HTS PAL autosampler (CEAP Technologies, Carrboro, N.C., USA) and a triple time of flight 5600 mass spectrometer (Triple TOF MS) (AB Sciex, Foster City, Calif., USA). The analytical column was a Phenomenex Kinetex XB-C18 column, 2.1×30 (2.6 μm). HPLC was performed with a water/acetonitrile gradient and acidified with 0.1% formic acid. Injection volumes were 10 μL. Triple TOF MS, equipped with a Duospray™ ion source, was used to complete the high resolution experiment. The Triple TOF MS was operated in the positive ion mode. High-purity nitrogen gas was used for the nebulizer/Duospray™ and curtain gases. The source temperature was set at 500° C. with a curtain gas flow of 30 L/min. The ion spray voltage was set at 5500 V, declustering potential was 145 V, and the collision energy was 38 V. The product ion mode was used as scan mode. Analyst® TF Version 1.6 (AB Sciex) operated with Windows® (Microsoft) was used for instrument control and data acquisition. Peak integrations were performed with MultiQuant® Version 2.1.1 (AB Sciex). Calculations were performed with MultiQuant® Version 2.1.1 for peak area ratios, standard curve regressions, sample concentration values, and descriptive statistics. The LC/MS/MS was calibrated using standard solutions at concentrations of 0.1, 0.4, 1, 2, 5, 10, 20, 40, 80, and 100 μg/mL. A representative PK profile was shown in FIG. 13. PK profile of ADC2 (Herceptin (LC)-MMAF, DAR2) was a very similar with that of Herceptin.

Figure 14:
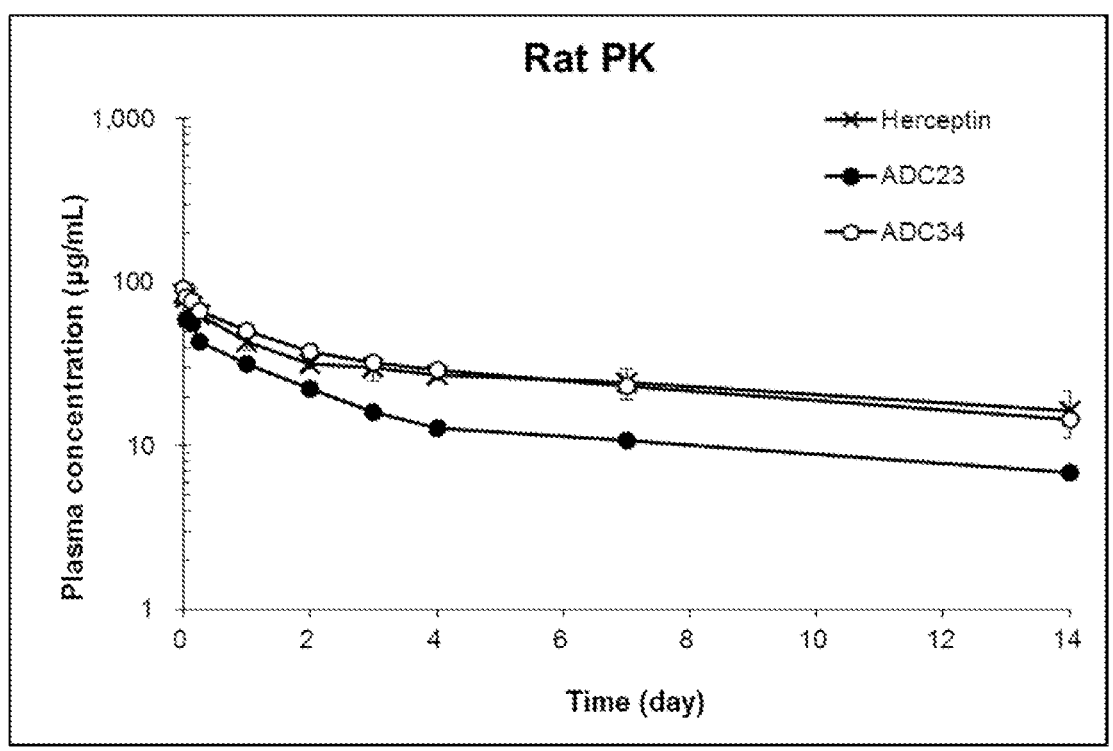
FIG. 14 shows Rat PK profile of ADC23 and ADC34.
Figure 15:
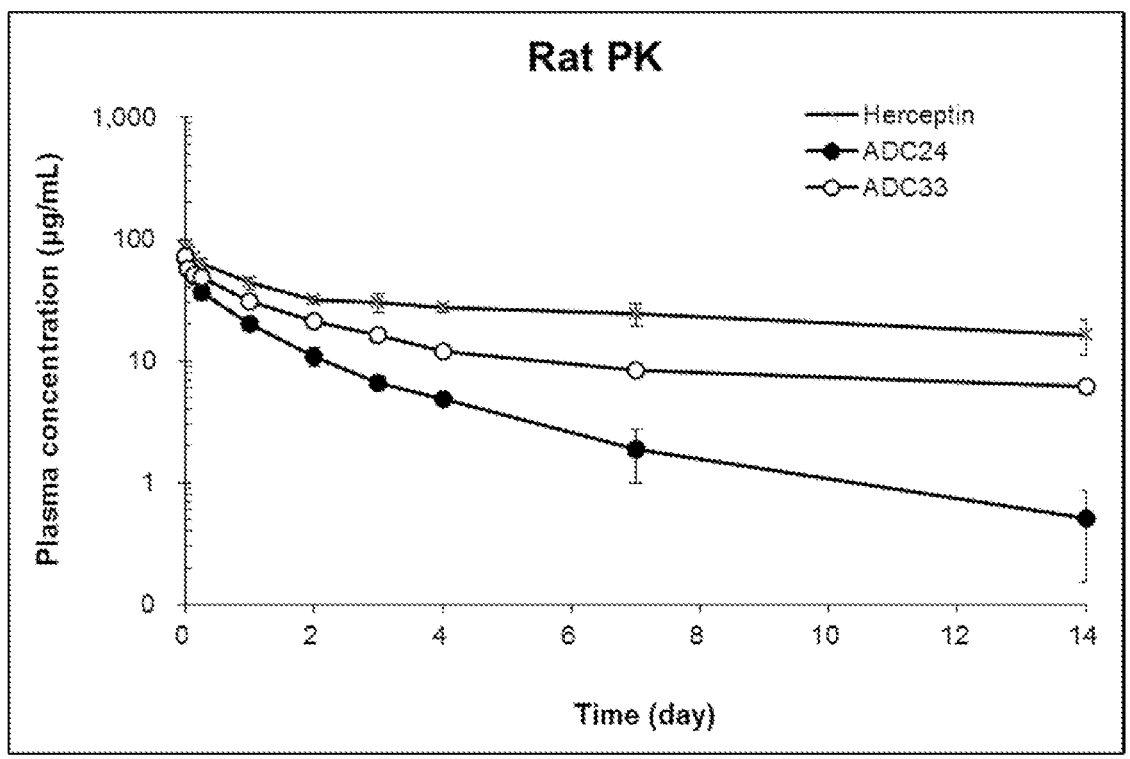
FIG. 15 shows Rat PK profile improvement of MMAE-based ADCs by replacing linker-toxin from 2g to 11j.
Figure 16:
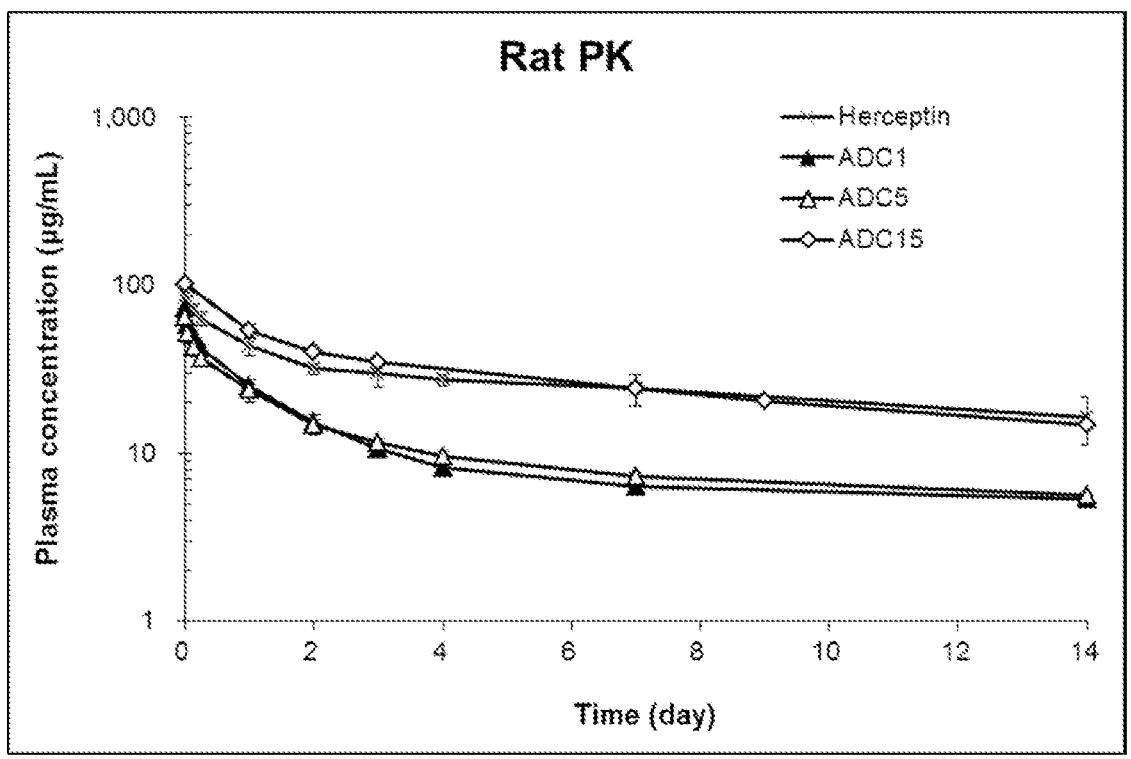
FIG. 16 shows Rat PK profile improvement by branched linker unit.

Experimental Example 12. PEG (Connecting Unit) Combination Effect in Branched Linker-Toxin To identify critical attributes that affect PK profile of ADC, different length and structure of connecting unit (PEG number and arrangement) were tested. Experiment for PK analysis was done as described in experimental example 9. Although ADC23 (a DAR4 ADC) had more potent efficacy in vitro and in vivo than DAR2 ADCs, its PK profile was reduced in half life and AUC (FIG. 14). By replacing linker-toxin from 16f to 25f (attaching additional connecting unit (3 PEGs) to after branch unit (BR), PK profile had been recovered as much as that of Herceptin (FIG. 14). These effects were well reproduced in MMAE based ADCs, ADC24 & ADC33 (FIG. 15). Because MMAE is more hydrophobic than MMAF, ADCs based on MMAE has worsened in PK profile as shown by ADC1 and ADC24. Adding longer PEG unit was traditional application for extending half-life and AUC. However, simple elongation of PEG unit numbers from 3 to 12 didn't show big differences, when comparing ADC1 with ADC5. In the other hand, by replacing linear linker unit (compound 2g or 4f) to branched one (compound 11j, ADC15), the PK profile was significantly improved (FIG. 16), indicating that critical attribute for PK might not be a just simple length, but the structure of connecting unit.

Figure 17:
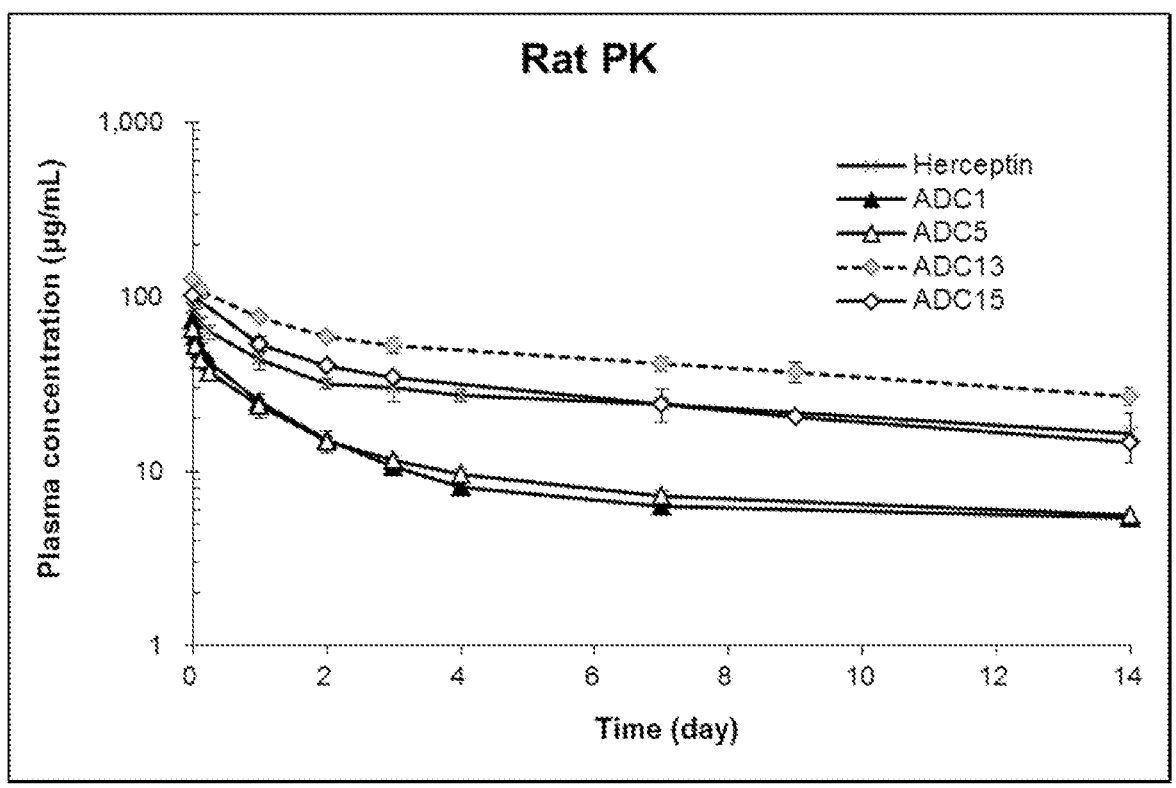
FIG. 17 shows impact of polar amino acid on Rat PK profile in MMAE ADC.
Figure 18:
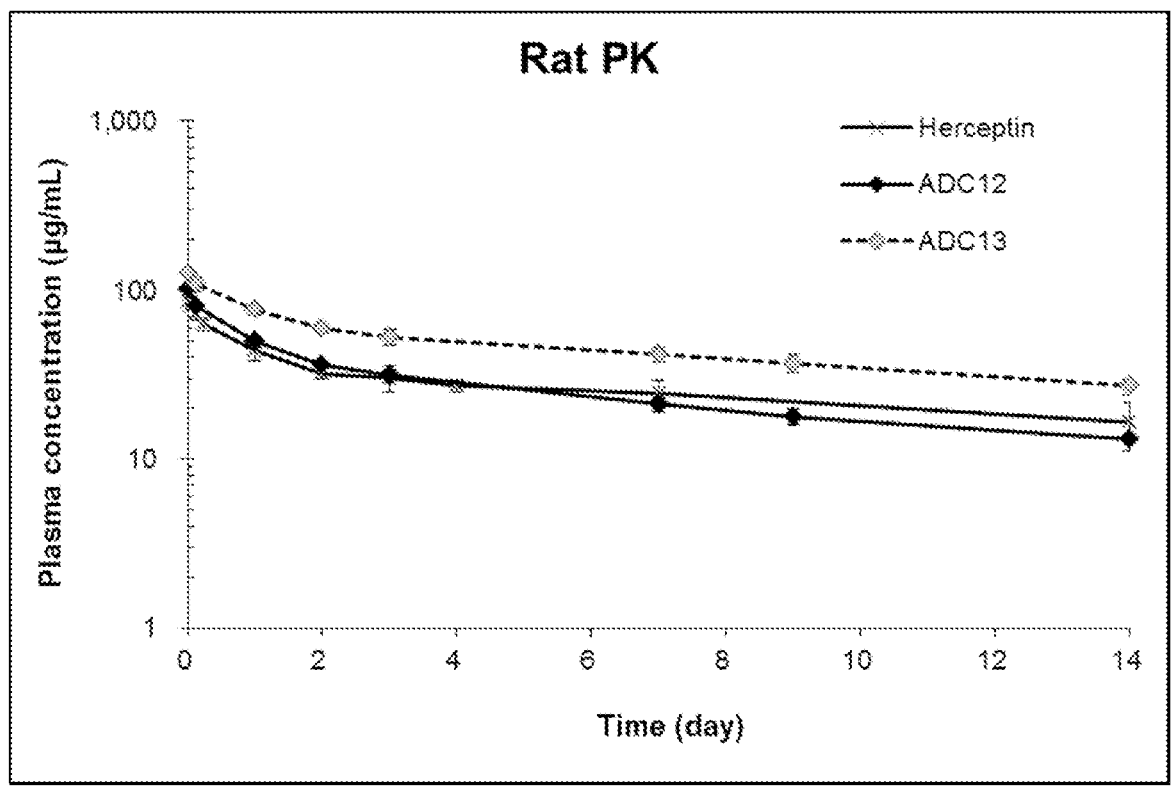
FIG. 18 shows Rat PK profile improvement by branched linker-toxin with or without polar amino acid in ADC with DAR2.
Figure 19:
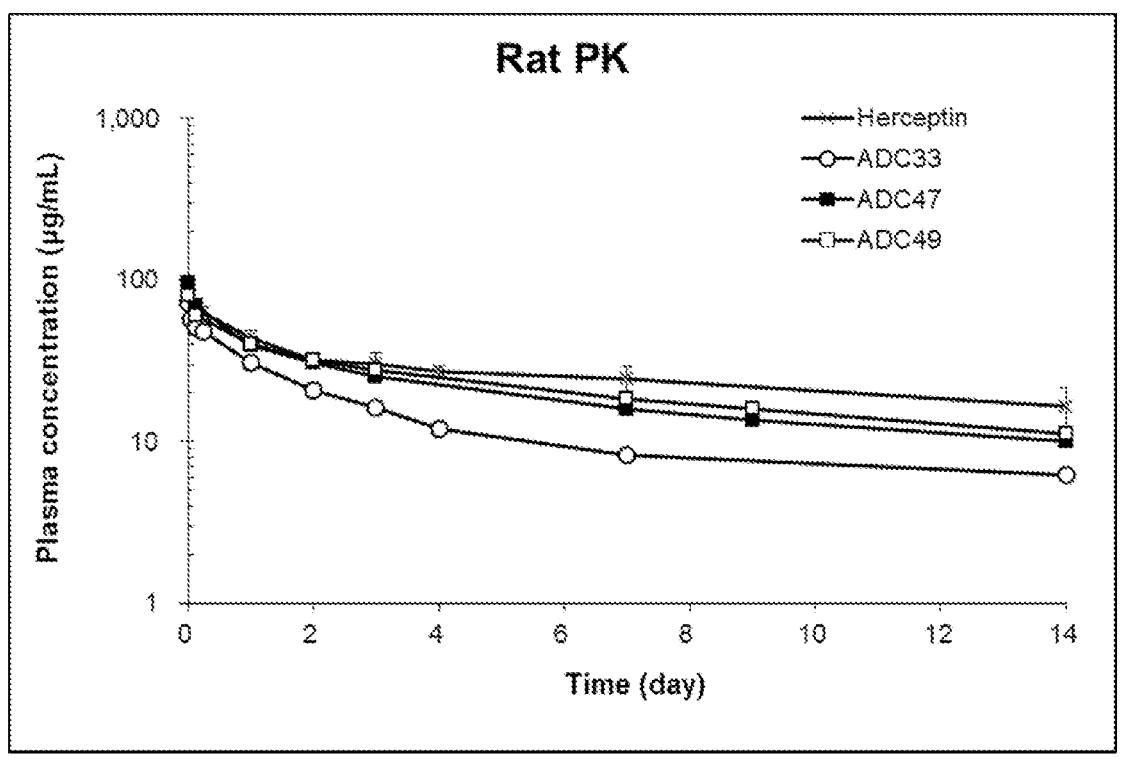
FIG. 19 shows effects of Asp in linker-toxin unit on Rat PK profile of ADC with DAR4.
Figure 20:
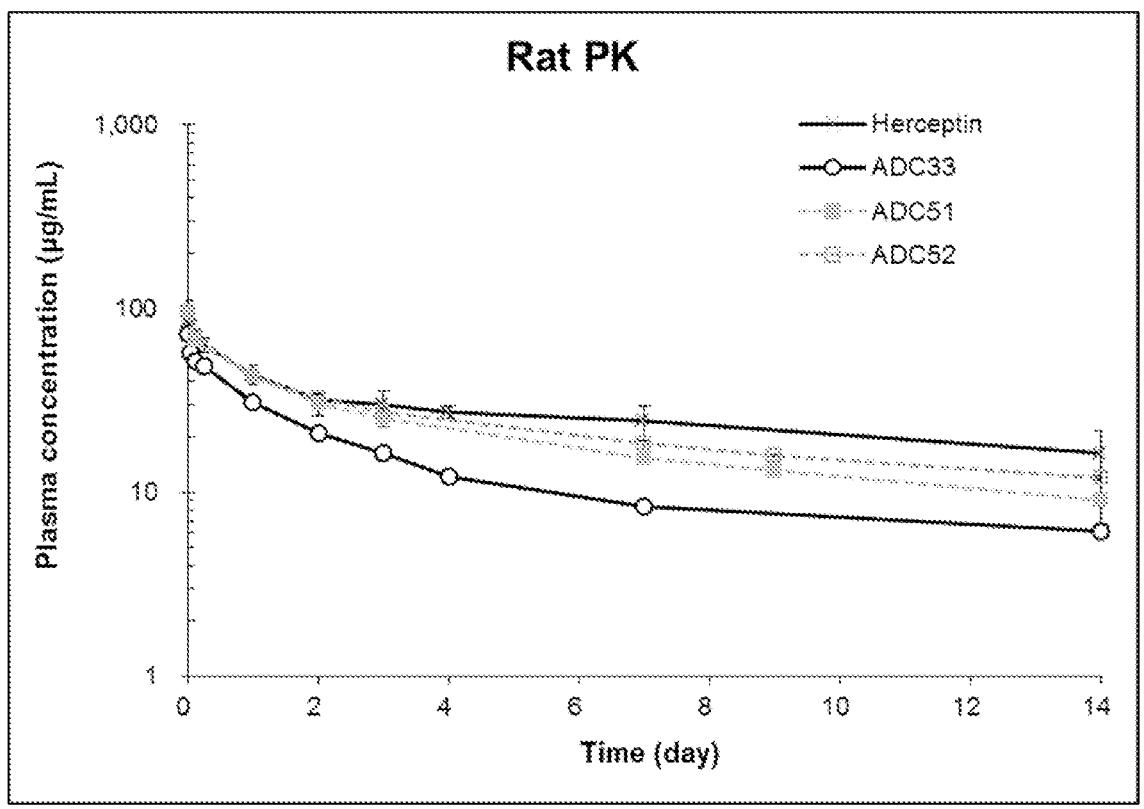
FIG. 20 shows effects of Glu in linker-toxin unit on Rat PK profile of ADC with DAR4.

Experimental Example 13. Effects of Hydrophilic Connecting Unit in PK of ADC Many payloads used for ADC have hydrophobic character, resulted in bad PK property. To compensate the hydrophobicity, hydrophilic compounds were tested as a part of connecting unit. Inserting hydrophilic compounds such as Asp enhanced AUC and half-life of ADCs (FIG. 17, 18, 19). In cases of DAR2, ADC with connecting unit including Asp showed higher AUC than Herceptin (FIG. 17, 18). The compensate effect by polar amino acid, such as Asp or Glu, can be observed in ADCs with DAR4 (FIG. 19, 20). ADC49 (2 Asp) and ADC52 (2 D-Glu) were superior to ADC47 (1 Asp) and ADC51 (1D-Glu) respectively in AUC and half-life.

Experimental Example 14. In Vivo Efficacy

A frozen JIMT-1 cell stock was thawed and cultivated under the 37° C., 5% $CO_2$ condition. JIMT-1 cells of the best condition that the viability was more than 95% were used for implantation. Cells of $5 \times 10^6$ suspended in 50 μL cold-saline were implanted into right hind leg of balb/c-nude mouse. 5 mice per group were used for the experiments. Tumor formation and growth were periodically monitored. Tumor volume was calculated by the formulation; volume=$(a^2b)/2$, "a" means short diameter and "b" means long diameter.

Figure 21:
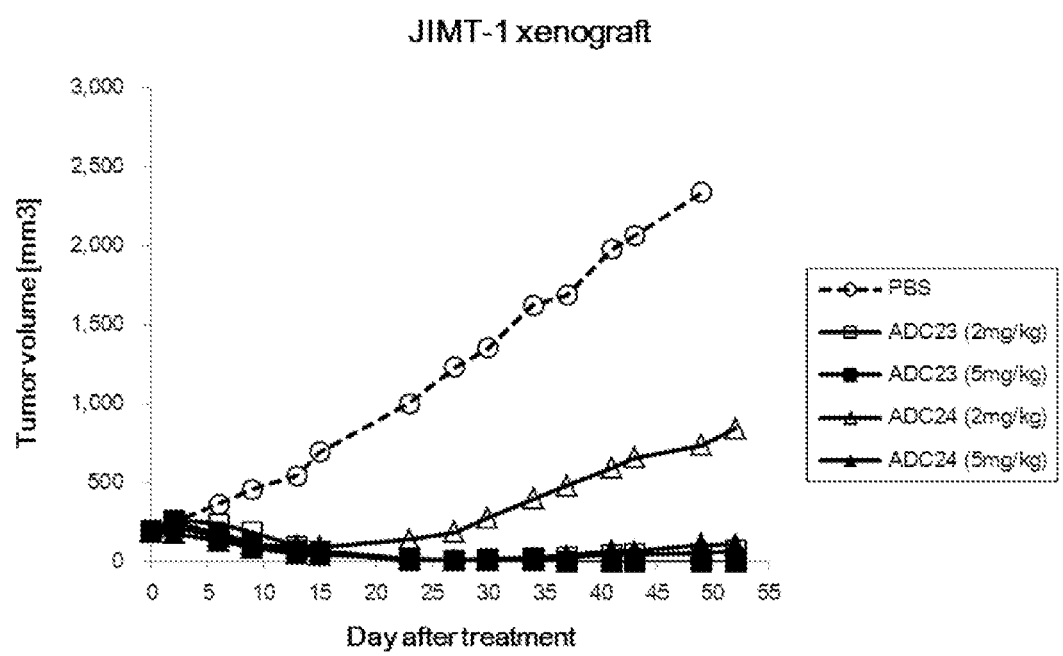
FIG. 21 shows in vivo efficacy of representative amine type DAR4 ADC using MMAF (ADC23) or MMAE (ADC24).
Figure 22:
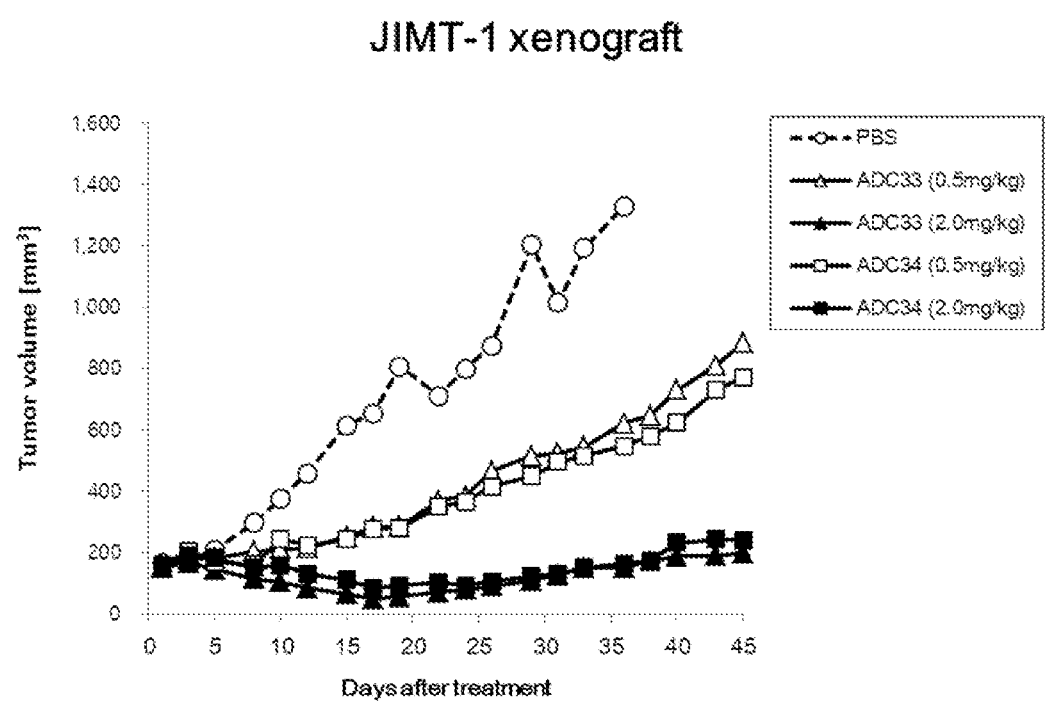
FIG. 22 shows in vivo efficacy of representative amide type DAR4 ADC using MMAF (ADC34) or MMAE (ADC33).
Figure 23:
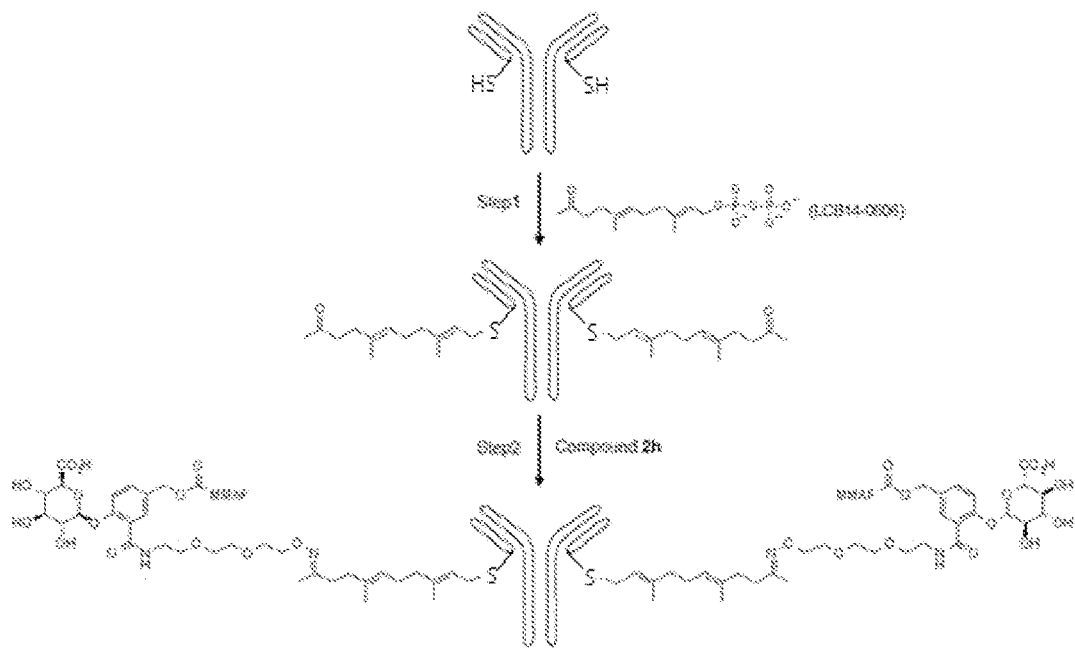
FIG. 23 shows ADC2 Synthesis.
Figure 24:
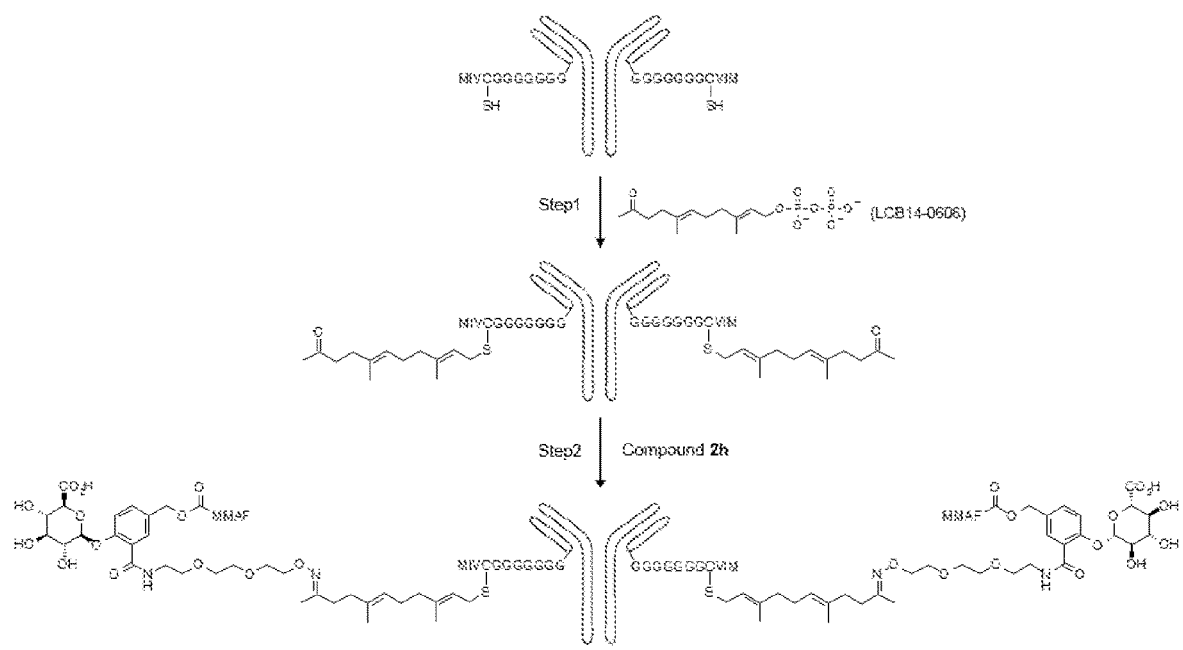
FIG. 24 shows ADC2 Synthesis.
Figure 25:
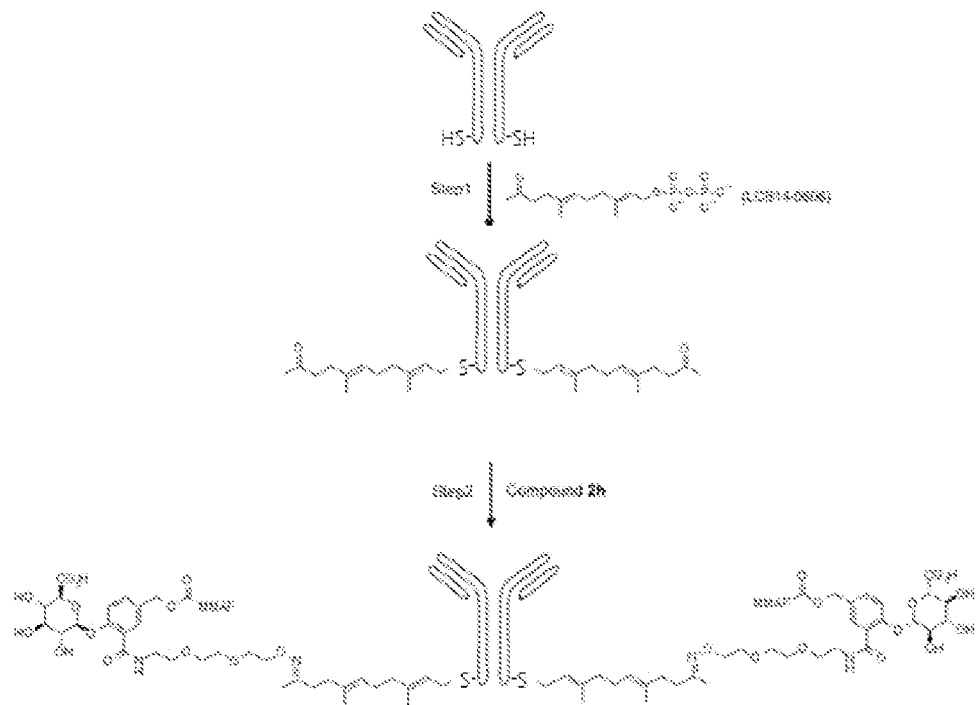
FIG. 25 shows ADC86 Synthesis.
Figure 26:
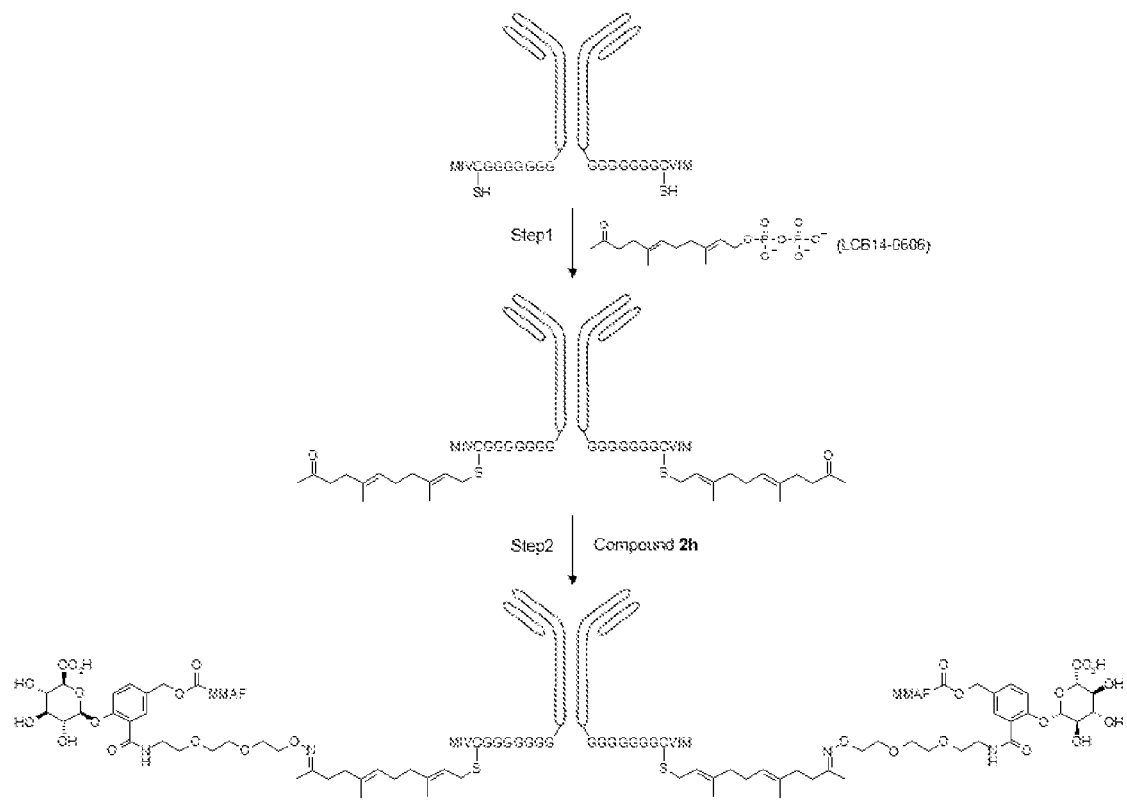
FIG. 26 shows ADC86 Synthesis.
Figure 27:
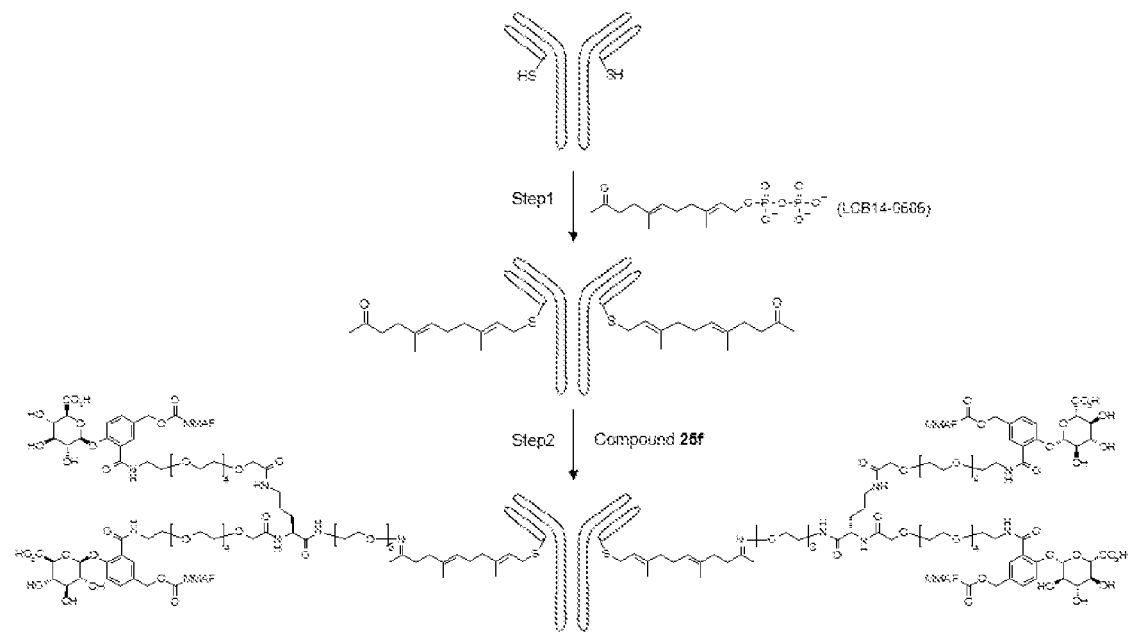
FIG. 27 shows ADC4 Synthesis.
Figure 28:
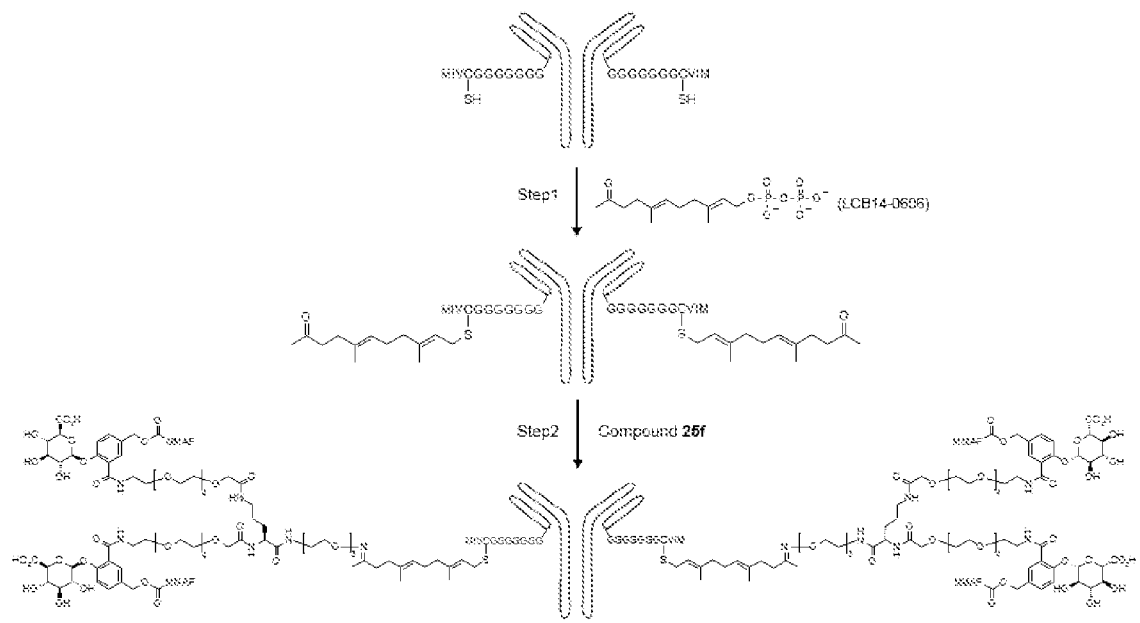
FIG. 28 shows ADC4 Synthesis.
Figure 29:
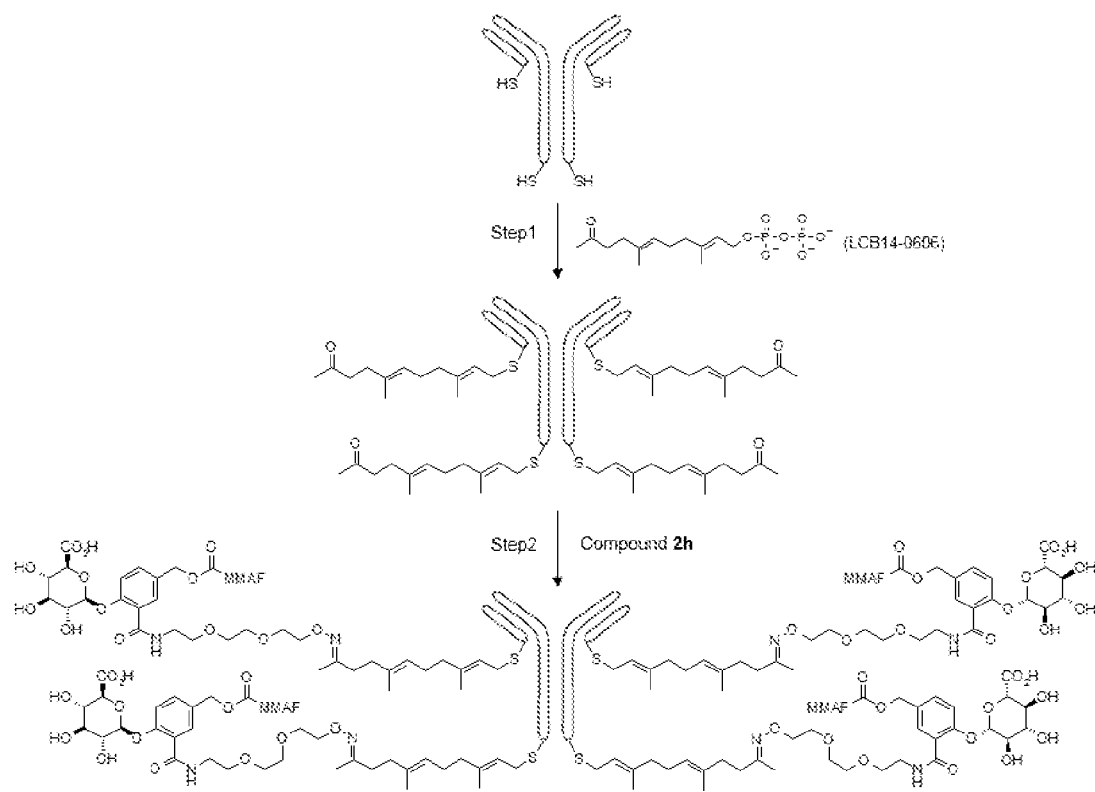
FIG. 29 shows ADC75 Synthesis.
Figure 30:
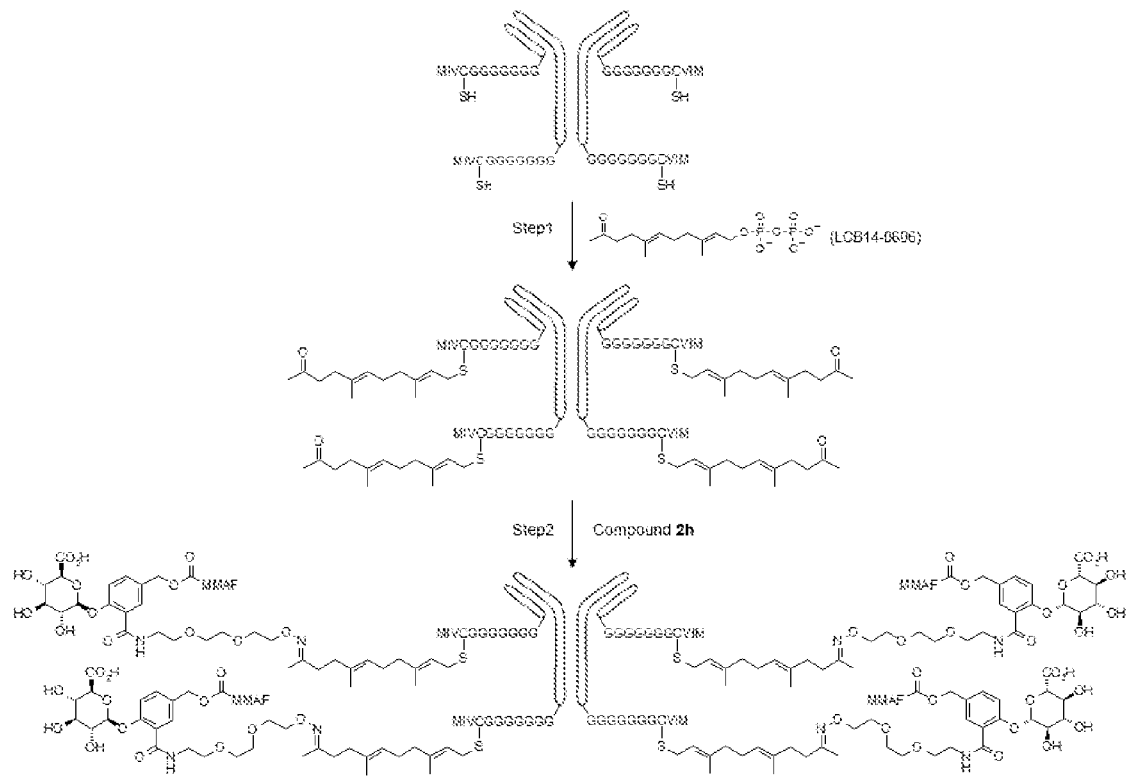
FIG. 30 shows ADC75 Synthesis.

When the tumor volume reaches to about 200 mm³, mice having average value were selected and grouped according to tumor volume. Then, mice were treated with PBS (vehicle control), or ADCs indicated in FIGS. 21 and 22. Tumor size was determined 2 times a week in 3-4 days interval during the experimental period. Tumor volumes measured from the first day of administration to the end date were plotted for tumor growth curve.

Representative ADCs were tested by single injection. In general, the ADCs with branching unit (BR) containing Lys had better efficacy than ADCs with BR containing amide.

INCORPORATION BY REFERENCE

Each of the patents, published patent applications, and non-patent references cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims

What is claimed:

1. An antibody-drug conjugate, comprising an antibody and one or more branched linkers covalently coupled to the antibody, wherein
   i) each branched linker comprises a branching unit (BR) covalently coupled to the antibody by a primary linker (PL);
   ii) each branched linker comprises a first branch (B1), in which a first active agent is covalently coupled to the branching unit by a secondary linker (SL) and a cleavage group (CG); and
   iii) each branched linker further comprises a second branch (B2), in which either a) a second active agent is covalently coupled to the branching unit by a secondary linker (SL) and a cleavage group (CG) or b) a polyethylene glycol moiety is covalently coupled to the branching unit; wherein each cleavage group has a structure represented by Formula I:

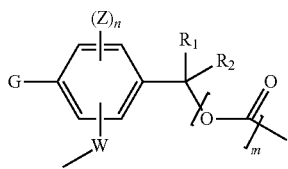

wherein:
G represents

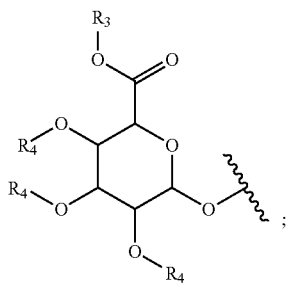

W represents —C(O)—, —C(O)NR'—, —C(O)O—, —S(O)$_2$NR'—, —P(O)R"NR'—, —S(O)NR'—, or —PO$_2$NR'—, wherein the C(O), S, or P is directly bound to the phenyl ring and W is coupled the branching unit;

R' and R" are each independently hydrogen, ($C_1$-$C_8$) alkyl, mono- or di-carboxyl($C_1$-$C_8$)alkyl, ($C_3$-$C_8$) cycloalkyl, ($C_1$-$C_8$)alkoxy, ($C_1$-$C_8$)alkylthio, mono- or di-($C_1$-$C_8$)alkylamino, ($C_3$-$C_{20}$)heteroaryl, or ($C_6$-$C_{20}$)aryl;

each Z independently represents hydrogen, ($C_1$-$C_8$) alkyl, or an electron-withdrawing group;

n is an integer from 1 to 3;

m is 0 or 1;

$R_1$ and $R_2$ are each independently hydrogen, ($C_1$-$C_8$) alkyl, or ($C_3$-$C_8$)cycloalkyl, or $R_1$ and $R_2$ taken together with the carbon atom to which they are attached form a ($C_3$-$C_8$)cycloalkyl ring;

$R_3$ is hydrogen or a carboxyl-protecting group;

each $R_4$ is independently hydrogen or a hydroxyl-protecting group; and the primary linker and each secondary linker comprise, independently, an alkylene having 1 to 100 carbon atoms.

2. The antibody-drug conjugate of claim 1, wherein W is —C(O)NR'—.

3. The antibody-drug conjugate of claim 1, wherein each Z independently represents hydrogen, ($C_1$-$C_8$)alkyl, halogen, cyano, or nitro.

4. The antibody-drug conjugate of claim 1, wherein:
G is

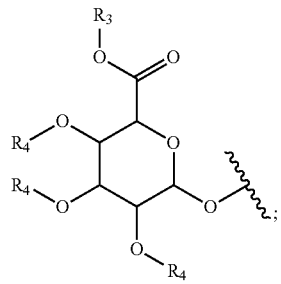

$R_3$ is hydrogen; and
each $R_4$ is independently hydrogen.

5. The antibody-drug conjugate of claim 1, wherein at least one primary or secondary linker has the structure —(CH$_2$)$_r$(V(CH$_2$)$_p$)$_q$—, —((CH$_2$)$_p$V)$_q$—, —(CH$_2$)$_r$(V (CH$_2$)$_p$)$_q$Y—, —((CH$_2$)$_p$V)$_q$(CH$_2$)$_r$—, —Y(((CH$_2$)$_p$V)$_q$— or —(CH$_2$)$_r$(V(CH$_2$)$_p$)$_q$YCH$_2$— wherein:

r is an integer from 0 to 10;

p is an integer from 1 to 10;

q is an integer from 1 to 20;

V and Y are each independently a single bond, —O—, —S—, —NR$_{21}$—, —C(O)NR$_{22}$—, —NR$_{23}$C(O)—, —NR$_{24}$SO$_2$—, or —SO$_2$NR$_{25}$—; and $R_{21}$ to $R_{25}$ are each independently hydrogen, ($C_1$-$C_6$) alkyl, ($C_1$-$C_6$)alkyl($C_6$-$C_{20}$)aryl or ($C_1$-$C_6$)alkyl($C_3$-$C_{20}$)heteroaryl.

6. The antibody-drug conjugate of claim 1, wherein at least one branching unit has the structure

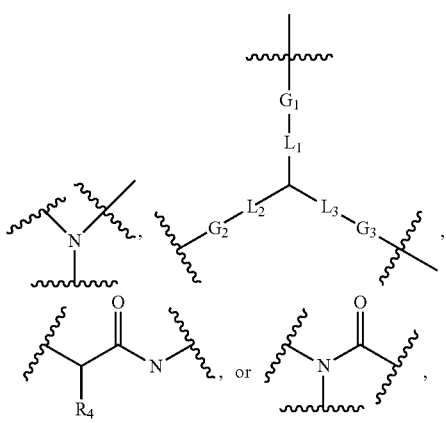

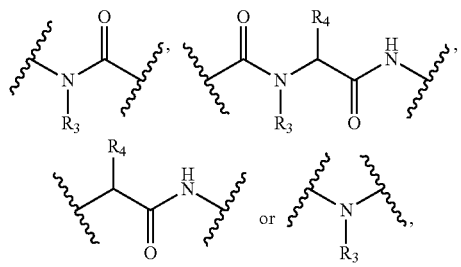

wherein L₁, L₂, L₃ is each independently a direct bond or —$C_nH_{2n}$— where n is a integer of 1 to 30,
wherein G1, G2, G3 is each independently a bond, wherein $R_3$ is hydrogen or $C_1$-$C_{30}$ alkyl;
wherein $R_4$ is hydrogen or -$L_4$-COOR₅, wherein $L_4$ is a direct bond or —$C_nH_{2n}$— wherein n is a integer of 1 to 10, and $R_5$ is hydrogen or $C_1$-$C_{30}$ alkyl.

7. The antibody-drug conjugate of claim 1, wherein the ligand is an antibody.

8. The antibody-drug conjugate of claim 1, wherein the branching unit is a nitrogen atom.

9. The antibody-drug conjugate of claim 1, wherein the primary linker comprises an alkylene having 1 to 100 carbon atoms, and either:
the alkylene includes at least one unsaturated bond;
the alkylene includes at least one heteroarylene;
a carbon atom of the alkylene is replaced by one or more heteroatoms selected from nitrogen (N), oxygen (O), and sulfur (S); or
the alkylene is further substituted with one or more alkyls having 1 to 20 carbon atoms.

10. The antibody-drug conjugate of claim 1, wherein at least one branching unit is a hydrophilic amino acid.

11. The antibody-drug conjugate of claim 1, wherein the primary linker comprises an amino acid, and the amino acid comprises a side chain having a moiety that bears a charge at neutral pH in aqueous solution.

12. The antibody-drug conjugate of claim 1, wherein the primary linker is covalently bound to the antibody by a thioether bond, and wherein
the antibody comprises a C-terminal amino acid motif that is recognized by an isoprenoid transferase; and
the thioether bond comprises a sulfur atom of a cysteine of the amino acid motif.

13. The antibody-drug conjugate of claim 12, wherein the thioether bond comprises a carbon atom of at least one isoprenyl unit, represented by

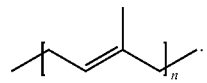

14. The antibody-drug conjugate of claim 13, wherein the at least one isoprenyl unit is a substrate for or product of an isoprenoid transferase.

15. The antibody-drug conjugate of claim 13, wherein the primary linker comprises an oxime, and the at least one isoprenyl unit covalently links the oxime to the antibody.

16. The antibody-drug conjugate of claim 15, wherein the primary linker comprises:

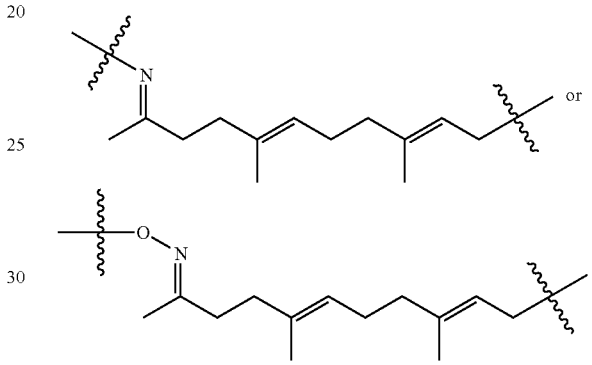

17. The antibody-drug conjugate of claim 1, wherein the primary linker comprises a binding unit, and the binding unit is represented by any one of Formulas A, B, C, or D:

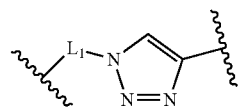

(A)

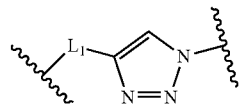

(B)

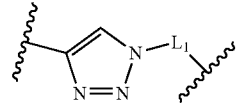

(C)

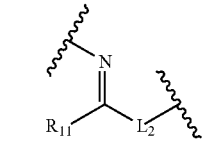

(D)

wherein:
$L_1$ is a single bond or alkylene having 1 to 30 carbon atoms;
$R_{11}$ is hydrogen or alkyl having 1 to 10 carbon atoms; and
$L_2$ is alkylene having 1 to 30 carbon atoms.

18. The antibody-drug conjugate of claim 1, comprising the structure:

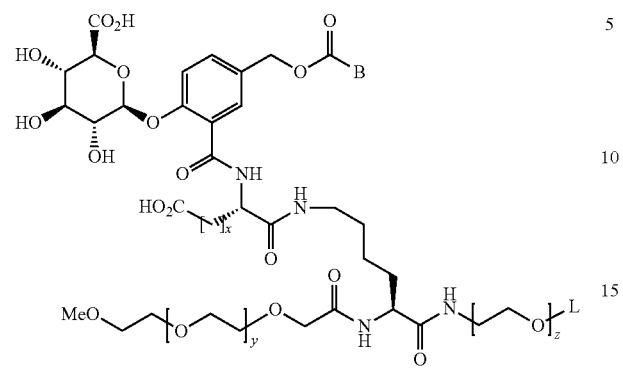

wherein:
B represents an active agent,
x represents an integer from 1 to 3;
y represents an integer from 0 to 20;
z represents an integer from 1 to 20; and
L represents a linkage to the antibody.

19. The antibody-drug conjugate of claim 1, wherein the antibody is selected from muromonab-CD3 abciximab, rituximab, daclizumab, palivizumab, infliximab, trastuzumab, etanercept, basiliximab, gemtuzumab, alemtuzumab, ibritumomab, adalimumab, alefacept, omalizumab, efalizumab, tositumomab, cetuximab, ABT-806, bevacizumab, natalizumab, ranibizumab, panitumumab, eculizumab, rilonacept, certolizumab, romiplostim, AMG-531, golimumab, ustekinumab, ABT-874, belatacept, belimumab, atacicept, an anti-CD20 antibody, canakinumab, tocilizumab, atlizumab, mepolizumab, pertuzumab, HuMax CD20, tremelimumab, ticilimumab, ipilimumab, IDEC-114, inotuzumab, HuMax EGFR, aflibercept, HuMax-CD4, teplizumab, otelixizumab, catumaxomab, the anti-EpCAM antibody IGN101, adecatumomab, oregovomab, dinutuximab, girentuximab, denosumab, bapineuzumab, motavizumab, efumgumab, raxibacumab, LY2469298, and veltuzumab.

20. The antibody-drug conjugate of claim 1, wherein at least one active agent is selected from:
(a) erlotinib, bortezomib, fulvestrant, sutent, letrozole, imatinib mesylate, PTK787/ZK 222584, oxaliplatin, 5-fluorouracil, leucovorin, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethylenimine, altretamine, triethylenemelamine, triethylenephosphoramide, triethiylenethiophosphoramide, trimethylolomelamine, bullatacin, bullatacinone, camptothecin, topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, melphalan, novembichin, phenesterine, prednimustine, trofosfamide, uracil mustard, carmustine, chlorozotocin, fotemustine, lomustine, nimustine, ranimnustine, calicheamicin, calicheamicin gamma 1, calicheamicin omega 1, dynemicin, dynemicin A, clodronate, esperamicin, neocarzinostatin chromophore, aclacinomysins, actinomycin, anthramycin, azaserine, bleomycins, cactinomycin, carabicin, carninomycin, carzinophilin, chromomycins, dactinomycin, daunorubicin, detorubucin, 6-diazo-5-oxo-L-norleucine, doxorubicin, morpholino-doxorubicin, cyanomorpholino-doxorubicin, 2-pyrrolino-doxorubucin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, thiguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaziquone, 2,2',2"-trichlorotriethylamine, T-2 toxin, verracurin A, roridin A, and anguidine, urethane, vindesine, dacarbazine, mannomustine, mitobronitol, mitolactol, pipobroman, gacytosine, arabinoside, cyclophosphamide, thiotepa, paclitaxel, albumin-engineered nanoparticle formulation of paclitaxel, doxetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, xeloda, ibandronate, CPT-11, topoisomerase inhibitor RFS 2000, difluoromethylornithine, retinoic acid, capecitabine, or pharmaceutically acceptable salts, solvates or acids of any of the foregoing;
(b) monokine, a lymphokine, a traditional polypeptide hormone, parathyroid hormone, thyroxine, relaxin, prorelaxin, a glycoprotein hormone, follicle stimulating hormone, thyroid stimulating hormone, luteinizing hormone, hepatic growth factor fibroblast growth factor, prolactin, placental lactogen, tumor necrosis factor-α, tumor necrosis factor-β, mullerian-inhibiting substance, mouse gonadotropin-associated peptide, inhibin, activin, vascular endothelial growth factor, thrombopoietin, erythropoietin, an osteoinductive factor, an interferon, interferon-α, interferon-β, interferon-γ, a colony stimulating factor ("CSF"), macrophage-CSF, granulocyte-macrophage-CSF, granulocyte-CSF, an interleukin ("IL"), IL-1, IL-1α, IL-2, IL-3, IL-4, IL-5, IL-6, IL-7, IL-8, IL-9, IL-10, IL-11, IL-12, a tumor necrosis factor, TNF-α, TNF-β, a polypeptide factor, LIF, kit ligand, or a combination of any of the foregoing;
(c) diphtheria toxin, botulium toxin, tetanus toxin, dysentery toxin, cholera toxin, amanitin, amanitin derivatives, α-amanitin, pyrrolobenzodiazepine, pyrrolobenzodiazepine derivatives, tetrodotoxin, brevetoxin, ciguatoxin, ricin, AM toxin, tubulysin, geldanamycin, maytansinoid, calicheamicin, daunomycin, doxorubicin, methotrexate, vindesine, SG2285, dolastatin, a dolastatin analog, auristatin, cryptophycin, camptothecin, camptothecin derivatives and metabolites, rhizoxin, a rhizoxin derivative, CC-1065, a CC-1065 analogue or derivative, duocarmycin, an enediyne antibiotic, esperamicin, epothilone, azonafide, aplidine, a toxoid, or a combination of any of the foregoing;

(d) an affinity ligand, wherein the affinity ligand is a substrate, an inhibitor, a stimulating agent, a neurotransmitter, a radioisotope, or a combination of any of the foregoing;

(e) a radioactive label, $^{32}P$, $^{35}S$, a fluorescent dye, an electron dense reagent, an enzyme, biotin, streptavidin, dioxigenin, a hapten, an immunogenic protein, a nucleic acid molecule with a sequence complementary to a target, or a combination of any of the foregoing;

(f) an immunomodulatory compound, an anti-cancer agent, an anti-viral agent, an anti-bacterial agent, an anti-fungal agent, and an anti-parasitic agent, or a combination of any of the foregoing;

(g) tamoxifen, raloxifene, droloxifene, 4-hydroxytamoxifen, trioxifene, keoxifene, LY117018, onapristone, or toremifene;

(h) 4(5)-imidazoles, aminoglutethimide, megestrol acetate, exemestane, letrozole, or anastrozole;

(i) flutamide, nilutamide, bicalutamide, leuprolide, goserelin, or troxacitabine;

(j) an aromatase inhibitor;

(k) a protein kinase inhibitor;

(l) a lipid kinase inhibitor;

(m) an antisense oligonucleotide;

(n) a ribozyme;

(o) a vaccine; and (p) an anti-angiogenic agent.

21. A pharmaceutical composition comprising the antibody-drug conjugate of claim 1.

22. A method of treating cancer in a subject, comprising administering the antibody-drug conjugate of claim 1 to the subject.

* * * * *

UNITED STATES PATENT AND TRADEMARK OFFICE
CERTIFICATE OF CORRECTION

PATENT NO. : 11,173,214 B2  Page 1 of 1
APPLICATION NO. : 15/779444
DATED : November 16, 2021
INVENTOR(S) : Yong Zu Kim et al.

It is certified that error appears in the above-identified patent and that said Letters Patent is hereby corrected as shown below:

In the Claims

In Claim 6, appearing at Column 349, Line 15, please replace:

"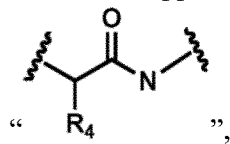",

With:

-- 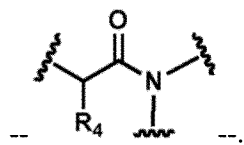 --.

In Claim 13, appearing at Column 350, Line 5, please replace:

"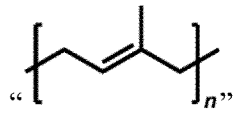",

With:

-- 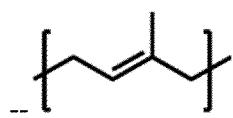 --.

Signed and Sealed this
Ninth Day of May, 2023

Katherine Kelly Vidal
*Director of the United States Patent and Trademark Office*